US011173151B2

(12) United States Patent
Collin-Kroepelin et al.

(10) Patent No.: US 11,173,151 B2
(45) Date of Patent: Nov. 16, 2021

(54) SUBSTITUTED TRIAZOLE DERIVATIVES AND USES THEREOF

(71) Applicants: BAYER AKTIENGESELLSCHAFT, Leverkusen (DE); BAYER PHARMA AKTIENGESELLSCHAFT, Berlin (DE)

(72) Inventors: Marie-Pierre Collin-Kroepelin, Wuppertal (DE); Peter Kolkhof, Wuppertal (DE); Thomas Neubauer, Wuppertal (DE); Chantal Fuerstner, Muelheim/Ruhr (DE); Elisabeth Pook, Wuppertal (DE); Matthias Beat Wittwer, Riehen (CH); Klemens Lustig, Wuppertal (DE); Hanna Tinel, Wuppertal (DE); Niels Lindner, Wuppertal (DE); Heiko Schirmer, Solingen (DE)

(73) Assignees: Bayer Aktiengesellschaft, Leverkusen (DE); Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 16/756,623

(22) PCT Filed: Oct. 17, 2018

(86) PCT No.: PCT/EP2018/078419
§ 371 (c)(1),
(2) Date: Apr. 16, 2020

(87) PCT Pub. No.: WO2019/081307
PCT Pub. Date: May 2, 2019

(65) Prior Publication Data
US 2020/0316045 A1 Oct. 8, 2020

(30) Foreign Application Priority Data
Oct. 24, 2017 (DE) .................................. 17197954.5

(51) Int. Cl.
| | |
|---|---|
| A61K 31/4439 | (2006.01) |
| A61K 31/4188 | (2006.01) |
| A61K 31/4196 | (2006.01) |
| A61K 31/496 | (2006.01) |
| A61K 31/5377 | (2006.01) |
| A61K 31/541 | (2006.01) |
| A61K 31/551 | (2006.01) |
| A61K 45/06 | (2006.01) |
| C07D 401/14 | (2006.01) |
| C07D 403/06 | (2006.01) |
| C07D 403/14 | (2006.01) |
| C07D 405/14 | (2006.01) |
| C07D 409/14 | (2006.01) |
| C07D 413/14 | (2006.01) |
| C07D 417/14 | (2006.01) |
| C07D 487/10 | (2006.01) |

(52) U.S. Cl.
CPC ...... *A61K 31/4439* (2013.01); *A61K 31/4188* (2013.01); *A61K 31/4196* (2013.01); *A61K 31/496* (2013.01); *A61K 31/5377* (2013.01); *A61K 31/541* (2013.01); *A61K 31/551* (2013.01); *A61K 45/06* (2013.01); *C07D 401/14* (2013.01); *C07D 403/06* (2013.01); *C07D 403/14* (2013.01); *C07D 405/14* (2013.01); *C07D 409/14* (2013.01); *C07D 413/14* (2013.01); *C07D 417/14* (2013.01); *C07D 487/10* (2013.01)

(58) Field of Classification Search
CPC combination set(s) only.
See application file for complete search history.

(56) References Cited

U.S. PATENT DOCUMENTS

| | | | |
|---|---|---|---|
| 3,966,781 | A | 6/1976 | Atkinson et al. |
| 6,693,102 | B2 | 2/2004 | Stasch et al. |
| 6,743,798 | B1 | 6/2004 | Straub et al. |
| 6,833,364 | B1 | 12/2004 | Straub et al. |
| 6,864,287 | B1 | 3/2005 | Alonso-Alija et al. |
| 7,087,644 | B1 | 8/2006 | Alonso-Alija et al. |
| 7,173,037 | B2 | 2/2007 | Alonso-Alija et al. |
| 7,517,896 | B2 | 4/2009 | Alonso-Alija et al. |
| 7,674,825 | B2 | 3/2010 | Alonso-Alija et al. |
| 7,705,043 | B2 | 4/2010 | Alonso-Alija et al. |
| 7,781,470 | B2 | 8/2010 | Alonso-Alija et al. |
| 8,202,895 | B2 | 6/2012 | Brueggemeier et al. |
| 8,420,656 | B2 | 4/2013 | Follmann et al. |
| 8,796,324 | B2 | 8/2014 | Brueggemeier et al. |
| 8,921,377 | B2 | 12/2014 | Follmann et al. |
| 9,096,592 | B2 | 8/2015 | Follmann et al. |
| 9,187,466 | B2 | 11/2015 | Furstner et al. |
| 9,216,978 | B2 | 12/2015 | Follmann et al. |

(Continued)

FOREIGN PATENT DOCUMENTS

| | | | |
|---|---|---|---|
| WO | 00/06568 | A1 | 2/2000 |
| WO | 00/06569 | A1 | 2/2000 |

(Continued)

OTHER PUBLICATIONS

Schrier, Robert W. and William T. Abraham, "Hormones and Hemodynamics in Heart Failure", The New England Journal of Medicine, Aug. 19, 1999, pp. 577-585, vol. 341.

(Continued)

*Primary Examiner* — Heidi Reese
(74) *Attorney, Agent, or Firm* — McBee Moore & Vanik IP, LLC

(57) ABSTRACT

The present invention relates to novel substituted 1,2,4-triazole derivatives, to processes for the preparation of such compounds, to pharmaceutical compositions containing such compounds, and to the use of such compounds or compositions for the treatment and/or prevention of diseases, in particular for the treatment and/or prevention of renal and cardiovascular diseases.

13 Claims, No Drawings

(56) References Cited

U.S. PATENT DOCUMENTS

| | | | |
|---|---|---|---|
| 9,266,885 | B2 | 2/2016 | Follmann et al. |
| 9,309,239 | B2 | 4/2016 | Follmann et al. |
| 9,687,476 | B2 | 6/2017 | Furstner et al. |
| 9,771,352 | B2 | 9/2017 | Schmeck et al. |
| 9,988,367 | B2 | 6/2018 | Collin et al. |
| 9,993,476 | B2 | 6/2018 | Follmann et al. |
| 10,472,348 | B2 | 11/2019 | Collin et al. |
| 10,525,041 | B2 | 1/2020 | Neubauer et al. |
| 10,526,314 | B2 | 1/2020 | Collin-Kroepelin et al. |
| 2004/0082798 | A1 | 4/2004 | Alonso-Alija et al. |
| 2004/0176446 | A1 | 9/2004 | Alonso-Alija et al. |
| 2004/0224945 | A1 | 11/2004 | Straub et al. |
| 2010/0317854 | A1 | 12/2010 | Alonso-Alija et al. |
| 2016/0122325 | A1 | 5/2016 | Schmeck et al. |
| 2016/0129004 | A1 | 5/2016 | Follmann et al. |
| 2017/0313665 | A1 | 11/2017 | Schmeck et al. |
| 2018/0263981 | A1 | 9/2018 | Follmann et al. |
| 2019/0119251 | A1 | 4/2019 | Collin-Kroepelin et al. |
| 2019/0144423 | A1 | 5/2019 | Collin-Kroepelin et al. |
| 2019/0161453 | A1 | 5/2019 | Schmeck et al. |
| 2019/0161454 | A1 | 5/2019 | Collin-Kroepelin et al. |
| 2019/0315720 | A1 | 10/2019 | Fuerstner et al. |
| 2020/0017473 | A1 | 1/2020 | Collin et al. |

FOREIGN PATENT DOCUMENTS

| | | |
|---|---|---|
| WO | 01/19355 A2 | 3/2001 |
| WO | 01/19776 A1 | 3/2001 |
| WO | 01/19778 A1 | 3/2001 |
| WO | 01/19780 A2 | 3/2001 |
| WO | 02/42301 A1 | 5/2002 |
| WO | 02/070462 A1 | 9/2002 |
| WO | 02/070510 A2 | 9/2002 |
| WO | 03/095451 A1 | 11/2003 |
| WO | 2005/063754 A1 | 7/2005 |
| WO | 2005/105779 A1 | 11/2005 |
| WO | 2010/105770 A1 | 9/2010 |
| WO | 2011/104322 A1 | 9/2011 |
| WO | 2011/147809 A1 | 12/2011 |
| WO | 2012/004258 A1 | 1/2012 |
| WO | 2012/028647 A1 | 3/2012 |
| WO | 2012/059549 A1 | 5/2012 |
| WO | 2012/112363 A1 | 8/2012 |
| WO | 2016/071212 A1 | 5/2016 |
| WO | 2017/191102 A1 | 9/2017 |
| WO | 2017/191105 A1 | 9/2017 |
| WO | 2017/191112 A1 | 9/2017 |
| WO | 2017/191114 A1 | 9/2017 |
| WO | 2017/191115 A1 | 9/2017 |
| WO | 2017/191107 A1 | 11/2017 |
| WO | 2018/073144 A1 | 4/2018 |

OTHER PUBLICATIONS

De Luca, Leonardo et al., "Hyponatremia in Patients with Heart Failure", Dec. 19, 2005, pp. 19-23, vol. 96, No. 12, Supplement 1.
Francis, Gary S. et al., "Comparison of Neuroendocrine Activation in Patients With Left Ventricular Dysfunction With and Without Congestive Heart Failure: A Substudy of the Studies of Left Ventricular Dysfunction (SOLVD)", Circulation, Nov. 1, 1990, pp. 1724-1729, vol. 82.
Sanghi, Pramod et al., "Vasopressin antagonism: a future treatment option in heart failure", European Heart Journal, 2005, pp. 538-543, vol. 26.
Wasilewski, Melissa A. et al., "Arginine Vasopressin Receptor Signaling and Functional Outcomes in Heart Failure", Cell Signal, Mar. 2016, pp. 224-233, vol. 28, No. 3.
Li, Xue et al., "Controlled and Cardiac-Restricted Overexpression of the Arginine Vasopressin V1A Receptor Causes Reversible Left Ventricular Dysfunction Through Gαq-Mediated Cell Signaling", Circulation, Jul. 11, 2011, pp. 572-581, vol. 124.
Thibonnier, Marc and James M. Roberts, "Characterization of Human Platelet Vasopressin Receptors", Journal of Clinical Investigation, Nov. 1985, pp. 1857-1864, vol. 76.
Taveau, Christopher et al., "Vasopressin and hydration play a major role in the development of glucose intolerance and hepatic steatosis in obese rats", Diabetologia, 2015, pp. 1081-1090, vol. 58.
Santillan, Mark K. et al., "Vasopressin in Preeclampsia: A Novel Very-Early Human Pregnancy Biomarker and Clinically-Relevant Mouse Model", Hypertension, Oct. 2014, pp. 852-859, vol. 64, No. 4.
International Search Report of International Patent Application No. PCT/EP2018/078419 dated Dec. 20, 2018.
"Isotopic Compositions of the Elements 1997," Pure Appl. Chem., (1998), vol. 70, No. 1: 217-235.
Leis, et al., "Stable Isotope Label:ed Targ,et Compounds: Prep,aration and Use as Internal Standards in Quantitative Mass Spectrometry," Curr. Org. Chem., (1998), vol. 2: 131-144.
Esaki, et al., "General method of obtaining deuterium-labeled heterocyclic compounds using neutral D2O with heterogeneous Pd/C," Tetrahedron, (2006), vol. 62: 10954-10961.
Esaki, et al., "Efficient H/D Exchange Reactions of Alkyl-Substituted Benzene Derivatives by Means of the Pd/C-H2-D2O System," Chem. Eur. J., (2007), vol. 13, 4052-4063.
Morandi, et al., "Homogeneous Catalytic Deuteration of Olefinic Double Bonds," J. Org. Chem., (1969), vol. 34, No. 6: 1889-1891.
Khan, N.A., "Preparation of Deuterized Raney Nickel and Selective Deuteration of the Triple Bond," J. Am. Chem. Soc., (1952), vol. 74, No. 12: 3018-3022.
Chandrasekhar, et al., "Flow chemistry approach for partial deuteration of alkynes: synthesis of deuterated taxol side chain," Tetrahedron Letters, (2011), vol. 52, 3865-3867.
Hanzlik, et al., "Active Site Dynamics of Toluene Hydroxylation by Cytochrome P-450," J. Org. Chem., (1990), vol. 55: 3992-3997.
Hanzlik, et al., "Deuterium Isotope Effects on Toluene Metabolism. Product Release as a Rate-Limiting Step in Cytochrome P-450 Catalysis," Biochem. Biophys. Res. Commun., (1989), vol. 160, No. 2: 844-849.
Reider, et al., "Synthesis of (R)-Serine-2-d and Its Conversion to the Broad Spectrum Antibiotic Fludalanine," J. Org. Chem., (1987), vol. 52: 3326-3334.
Jarman, et al., "The deuterium isotope effect for the a-hydroxylation of tamoxifen by rat liver microsomes accounts for the reduced genotoxicity of [d5-ethyl]tamoxifen," (1995), Carcinogenesis, vol. 16, No. 4: 683-688.
Atzrodt, et al., "Th Renaissance of H/D Exchange," Angew. Chem. Int. Ed., (2007), vol. 46: 7744-4465.
Matoishi, et al., "The first synthesis of both enantiomers of [a-2H]phenylacetic acid in high enantiomeric excess," Chem. Commun., (2000): 1519-1520.
Perrin, et al, "Secondary Deuterium Isotope Effects on the Acidity of Carboxylic Acids and Phenols," J. Am. Chem. Soc., (2007), vol. 129: 4490-4497.
Streitwieser, et al., "Isotope Effects on Acidity of Eeuterate Formic, Acetic, Pivalic, and Benzoic Acids," J. Am. Chem. Soc., (1963), vol. 85: 2759-2763.
Perrin, et al., "Stereochemistry of B-Deuterium Isotope Effects on Amine Basicity," J. Am. Chem. Soc., (2005), vol. 127: 9641-9647.
Perrin, et al., "B-Deuterium Isotope Effects on Amine Basicity, "Inductive" and Stereochemical," J. Am. Chem. Soc., (2003), vol. 125: 15008-15009.
Perrin, C.L., "Secondary equilibrium isotope effects on acidity," Advances in Physical Organic Chemistry, (2010), vol. 44, 144-146.
Testa, et al., "The lipophilicity of deuterium atoms. A comparison of shake-flask and HPLC methods," Int. J. Pharm., (1984), vol. 19, No. 3: 271-281. Abstract Only.
Mutlib, et al., "The Species-Dependent Metabolism of Efavirenz Produces a Nephrotoxic Glutathione Conjugate in Rats," Toxicol. Appl. Pharmacol., (2000), vol. 169: 102-113.
Kushner, et al., "Pharmacological uses and perspectives of heavy water and deuterated compounds," Can. J. Physiol. Pharmacol., (1999), vol. 77: 79-88. Abstract Only.
Sharma, et al., "Nevirapine Bioactivation and Covalent Binding in the Skin," Chem. Res. Toxicol., (2013), vol. 26: 410-421.

(56) References Cited

OTHER PUBLICATIONS

Wenthur, et al., "Discovery of (R)-(2-Fluoro-4-((-4-methoxyphenyl)ethynyl)phenyl)(3-Hydroxypiperidin-1-yl)methanone (ML337), an mGlu3 Selective and CNS Penetrant Negative Allosteric Modulator (NAM)," J. Med. Chem., (2013), vol. 56: 5208-5212.

Schneider, et al., "Enhanced Plasma Concentration by Selective Deuteration of Rofecoxib in Rats," Arzneim. Forsch. / Drug. Res., (2006), vol. 56, No. 4: 295-300.

Maltais, et al., "In Vitro and In Vivo Isotope Effects with Hepatitis C Protease Inhibitors: Enhanced Plasma Exposure of Deuterated Telaprevir versus Telaprevir in Rats," J. Med. Chem., (2009), vol. 52: 7993-8001.

"Rules for the Nomenclature of Organic Chemistry Section E: Stereochemistry," Pure Appl. Chem., (1976), Vo. 45: 11-30.

Berge, et al., "Pharmaceutical Salts," J. Pharm. Sci., (1977), vol. 66, No. 1: 1-19.

Kahn, et al., "Management of cardiovascular disease in patients with kidney disease," Nature Rev. Cardiol., (2013), vol. 10: 261-273.

Rizzuto, et al., "Rapid changes of mitochondrial Ca2+ revealed by specifically targeted recombinant aequorin," Nature, (1992), vol. 358: 325-327.

Illarionov, "Sequence of the cDNA encoding the Ca2+-activated photoprotein obelin from the hydroid polyp Obelia longissima," Gene, (1995), vol. 153: 273-274.

Milligan, "G16 as a universal G protein adapter: implications for agonist screening strategies," Trends in Pharmacological Sciences, (1996), vol. 17, 235-237.

Cheng, et al., "Relationship Between the Inhibition Constant (K1) and the Concentration of Inhibitor Which Causes 50 Per Cent Inhibition (/so) of an Enzymatic Reaction," Biochem. Pharmacol., (1973), vol. 22: 3099-3108.

SUBSTITUTED TRIAZOLE DERIVATIVES AND USES THEREOF

CROSS-REFERENCE TO RELATED APPLICATIONS

This application is a National Stage entry of International Application No. PCT/EP2018/078419, filed 17 Oct. 2018, which claims priority to European Patent Application No. 17197954.5, filed 24 Oct. 2017.

BACKGROUND

Field

The present invention relates to novel substituted 1,2,4-triazole derivatives, to processes for the preparation of such compounds, to pharmaceutical compositions containing such compounds, and to the use of such compounds or compositions for the treatment and/or prevention of diseases, in particular for the treatment and/or prevention of renal and cardiovascular diseases.

Description of Related Art

The liquid content of the human body is subject to various physiological control mechanisms, the purpose of which is to keep it constant (volume homeostasis). In the process, both the volume filling of the vascular system and also the osmolarity of the plasma are continuously recorded by appropriate sensors (baroreceptors and osmoreceptors). The information which these sensors supply to the relevant centers in the brain regulates drinking behaviour and controls fluid excretion via the kidneys by means of humoral and neural signals. The peptide hormone vasopressin is of central importance in this [Schrier R. W., Abraham W. T., *New Engl. J. Med.* 341, 577-585 (1999)].

Vasopressin is produced in specialized endocrine neurons in the Nucleus supraopticus and *N. para-ventricularis* in the wall of the third ventricle (hypothalamus) and is transported from there along the neural processes into the posterior lobes of the hypophysis (neurohypophysis). There the hormone is released into the bloodstream in response to stimulus. A loss of volume, e.g. as a result of acute bleeding, heavy sweating, prolonged thirst or diarrhoea, is a stimulus for intensified release of the hormone. Conversely, the secretion of vasopressin is inhibited by an increase in the intravascular volume, e.g. as a result of increased fluid intake.

Vasopressin exerts its action mainly via binding to three receptors, which are classified as V1a, V1b and V2 receptors and which belong to the family of G protein-coupled receptors. V1a receptors are mainly located on the cells of the vascular smooth musculature. Their activation gives rise to vasoconstriction, as a result of which the peripheral resistance and blood pressure rise. Apart from this, V1a receptors are also detectable in the liver. V1b receptors (also named V3 receptors) are detectable in the central nervous system. Together with corticotropin-releasing hormone (CRH), vasopressin regulates the basal and stress-induced secretion of adrenocorticotropic hormone (ACTH) via the V1b receptor. V2 receptors are located in the distal tubular epithelium and the epithelium of the collecting tubules in the kidney. Their activation renders these epithelia permeable to water. This phenomenon is due to the incorporation of aquaporins (special water channels) in the luminal membrane of the epithelial cells.

The importance of vasopressin for the reabsorption of water from the urine in the kidney becomes clear from the clinical picture of diabetes insipidus, which is caused by a deficiency of the hormone, e.g. owing to hypophysis damage. Patients who suffer from this disease excrete up to 20 liters of urine per 24 hours if they are not given replacement hormone. This volume corresponds to about 10% of the primary urine. Because of its great importance for the reabsorption of water from the urine, vasopressin is also synonymously referred to as antidiuretic hormone (ADH). Consequently, pharmacological inhibition of the action of vasopressin/ADH on the V2 receptor results in increased urine excretion. In contrast to the action of other diuretics (thiazides and loop diuretics), however, V2 receptor antagonists cause increased water excretion, without substantially increasing the excretion of electrolytes. This means that with V2 antagonist drugs, volume homeostasis can be restored without affecting electrolyte homeostasis. Hence, drugs with V2 antagonistic activity appear particularly suitable for the treatment of all disease conditions which are associated with an overloading of the body with water, without the electrolytes being adequately increased in parallel.

A significant electrolyte abnormality is measurable in clinical chemistry as hyponatremia (sodium concentration <135 mmol/L); it is the most important electrolyte abnormality in hospital patients, with an incidence of about 5% or 250 000 cases per year in the US alone. If the plasma sodium concentration falls below 115 mmol/L, comatose states and death are imminent. Depending on the underlying cause, a distinction is made between hypovolemic, euvolemic and hypervolemic hyponatremia. The forms of hypervolemia with edema formation are clinically significant. Typical examples of these are the syndrome of inappropriate ADH/vasopressin secretion (SIADH) (e.g. after craniocerebral trauma or as paraneoplasia in carcinomas) and hypervolemic hyponatremia in liver cirrhosis, various renal diseases and heart failure [De Luca L. et al., *Am. J. Cardiol.* 96 (suppl.), 19L-23L (2005)]. In particular, patients with heart failure, in spite of their relative hyponatremia and hypervolemia, often display elevated vasopressin levels, which are seen as the consequence of a generally disturbed neurohumoral regulation in heart failure [Francis G. S. et al., *Circulation* 82, 1724-1729 (1990)].

The disturbed neurohormonal regulation essentially manifests itself in an elevation of the sympathetic tone and inappropriate activation of the renin-angiotensin-aldosterone system. While the inhibition of these components by beta-receptor blockers on the one hand and by ACE inhibitors or angiotensin-receptor blockers on the other is now an inherent part of the pharmacological treatment of heart failure, the inappropriate elevation of vasopressin secretion in advanced heart failure is at present still not adequately treatable. Apart from the retention of water mediated by V2 receptors and the unfavourable hemodynamic consequences associated therewith in terms of increased backload, the emptying of the left ventricle, the pressure in the pulmonary blood vessels and cardiac output are also adversely affected by V1a-mediated vasoconstriction. Furthermore, on the basis of experimental data in animals, a direct hypertrophy-promoting action on the heart muscle is also attributed to vasopressin. In contrast to the renal effect of volume expansion, which is mediated by activation of V2 receptors, the direct action on the heart muscle is triggered by activation of V1a receptors.

For these reasons, agents which inhibit the action of vasopressin on the V2 and/or the V1a receptor appear suitable for the treatment of heart failure. In particular, compounds with combined activity on both vasopressin receptors (V1a and V2) should have both desirable renal as well as hemodynamic effects and thus offer an especially ideal profile for the treatment of patients with heart failure. The provision of such combined vasopressin antagonists also appears to make sense inasmuch as a volume diminution mediated solely via V2 receptor blockade can entail the stimulation of osmoreceptors and, as a result, may lead to a further compensatory increase in vasopressin release. Through this, in the absence of a component simultaneously blocking the V1a receptor, the harmful effects of vasopressin, such as for example vasoconstriction and heart muscle hypertrophy, could be further intensified [Saghi P. et al., *Europ. Heart J.* 26, 538-543 (2005)].

V1a receptors are mainly located on vascular smooth muscle cells (VSMC) but also on cardiomyocytes, fibroblasts and specialized renal cells like glomerular mesangial cells or cells of the macula densa which control the release of renin [Wasilewski M A, Myers V D, Recchia F A, Feldman A M, Tilley D G, Cell Signal., 28(3), 224-233, (2016)]. The activation of VSMC V1a receptor by vasopressin gives rise to intracellular calcium release and according vasoconstriction. Therefore, stimulation of VSMC V1a receptors causes increased vascular resistance and increased cardiac afterload. Cardiac output is adversely affected by V1a-mediated vasoconstriction. The increase in afterload and direct stimulation of V1a receptors on cardiomyocytes can lead to cardiac hypertrophy and remodeling including fibrosis. Mice with cardiac-specific overexpression of V1a receptor develop cardiac hypertrophy leading to dilation and left ventricular dysfunction, suggesting an essential role for V1a receptor in the development of heart failure [Li X, Chan T O, Myers V, Chowdhury I, Zhang X Q, Song J, Zhang J, Andrel J, Funakoshi H, Robbins J, Koch W J, Hyslop T, Cheung J Y, Feldman A M, Circulation.; 124, 572-581 (2011)].

V1a receptor is also expressed in the renal cortical and medullary vasculature, where it mediates vasoconstriction of renal vessels and affecting overall renal blood flow. Thus, the activation of V1a receptor can decrease renal medullary blood flow inducing further pathological processes as tissue hypoxia, reduced oxygen and accordingly energy supply for tubular transport processes as well as direct damages of mesangial and macula densa cells. It has been demonstrated that mesangial V1a receptor activation mediates TGFβ signaling and causes an increase in production of collagen IV. While this signaling contributes extracellular matrix accumulation and remodeling in the kidney, similar signaling pathways are believed to occur in cardiac cells especially after myocardial infarction, which emphasizes the central role of V1a receptor in the development of hypertrophic and fibrotic processes in response to pathophysiological elevated vasopressin levels [Wasilewski M A, Myers V D, Recchia F A, Feldman A M, Tilley D G. Arginine vasopressin receptor signaling and functional outcomes in heart failure. Cell Signal., 28(3), 224-233 (2016)].

Since V1a receptors are mainly expressed on VSMCs and thus participating in vascular function, a link to vascular diseases as peripheral arterial disease (PAD) including claudication and critical limb ischemia as well as coronary microvascular dysfunction (CMD) is conceivable.

Apart from this, V1a receptors are also expressed on human platelets and in the liver. The meaning of platelet V1a receptors is not fully understood although vasopressin induces aggregation of human platelets via V1a receptor at high concentrations ex vivo. Therefore, inhibition of vasopressin-induced platelet aggregation by V1a receptor antagonists is a useful pharmacological ex vivo assay making use of human tissue endogenously expressing the V1a receptor [Thibonnier M, Roberts J M, J Clin Invest.; 76:1857-1864, (1985)].

Vasopressin stimulates gluconeogenesis and glycogenolysis via activation of the hepatic V1a receptor. Animal studies have shown that vasopressin impairs glucose tolerance which could be inhibited by a V1a receptor antagonist thereby providing a link of vasopressin receptor V1a to diabetes mellitus. [Taveau C, Chollet C, Waeckel L, Desposito D, Bichet D G, Arthus M F, Magnan C, Philippe E, Paradis V, Foufelle F, Hainault I, Enhorning S, Velho G, Roussel R, Bankir L, Melander O, Bouby N. Vasopressin and hydration play a major role in the development of glucose intolerance and hepatic steatosis in obese rats. Diabetologia., 58(5), 1081-1090, (2015)]. Vasopressin was shown to contribute to the development of albuminuria and to diabetes-induced nephropathy in animal models which is consistent with epidemiological findings in humans.

It was found recently that vasopressin also seems to play a causal role in the development of preeclampsia. Chronic infusion of vasopressin during pregnancy in mice is sufficient to induce all of the major maternal and fetal phenotypes associated with human preeclampsia, including pregnancy-specific hypertension [Santillan M K, Santillan D A, Scroggins S M, Min J Y, Sandgren J A, Pearson N A, Leslie K K, Hunter S K, Zamba G K, Gibson-Corley K N, Grobe J L. Vasopressin in preeclampsia: a novel very early human pregnancy biomarker and clinically relevant mouse model. Hypertension. 64(4), 852-859, (2014)].

Vasopressin levels can be elevated in women with dysmenorrhoea (a gynecological disorder which is characterised by cyclical cramping pelvic pain) during menstruation, which appear to increase myometrial smooth muscle contraction. It was found recently that a selective vasopressin V1a receptor antagonist (relcovaptan/SR-49059) can reduce intrauterine contractions elicited by vasopressin.

For these reasons, agents which inhibit the action of vasopressin on the V1a receptor appear suitable for the treatment of several cardiovascular diseases. In particular, agents which inhibit the action of vasopressin selectively on the V1a receptor offer an especially ideal profile for the treatment of otherwise normovolemic patients, i.e. those which are not eligible for decongestion by e.g. high doses of loop diuretics or V2 antagonists, and where induced aquaresis via V2 inhibition may be undesired.

Certain 4-phenyl-1,2,4-triazol-3-yl derivatives have been described in WO 2005/063754-A1 and WO 2005/105779-A1 to act as vasopressin V1a receptor antagonists that are useful for the treatment of gynecological disorders, notably menstrual disorders such as dysmenorrhea.

In WO 2011/104322-A1, a particular group of bis-aryl-bonded 1,2,4-triazol-3-ones, including 5-phenyl-1,2,4-triazol-3-yl and 1-phenyl-1,2,3-triazol-4-yl derivatives thereof, has been disclosed as antagonists of vasopressin V1a and/or V2 receptors being useful for the treatment and/or prevention of cardiovascular diseases.

In WO 2016/071212-A1 certain 5-(hydroxyalkyl)-1-phenyl-1,2,4-triazole derivatives have been disclosed, which act as potent antagonists of both vasopressin V1a and V2 receptors and, in addition, exhibit significantly enhanced aquaretic potency in vivo after oral application.

In WO 2017/191107-A1 and WO 2017/191102-A1 certain 5-(carboxamide)-1-phenyl-1,2,4-triazole derivatives as well as in WO 2017/191114-A1 specific 5-(hydroxyalkyl)-1-heteroaryl-1,2,4-triazole derivatives have been described, which represent highly potent and selective antagonists of the V1a receptor and are particularly useful for the treatment and/or prevention of renal and cardiovascular diseases in subjects which do not suffer from fluid overload and who therefore should not be decongested.

Further novel 5-(carboxamide)-substituted, 5-(fluoroalkyl)-substituted and 3-(hydroxyalkyl)-substituted 1,2,4-triazole derivatives have been disclosed as antagonists of vasopressin V2 and/or V1a receptors in WO 2017/191105-A1, WO 2017/191112-A1, WO 2017/191115-A1 and WO 2018/073144-A1.

SUMMARY

It was an object of the present invention to provide novel compounds which act as potent selective or dual V1a/V2 receptor antagonists and as such are suitable for the treatment and/or prevention of diseases, more particularly for the treatment and/or prevention of renal and cardiovascular disorders.

The compounds of the present invention have valuable pharmacological properties and can be used for the prevention and/or treatment of various diseases and disease-induced states in humans and other mammals.

The invention provides compounds of the general formula (I)

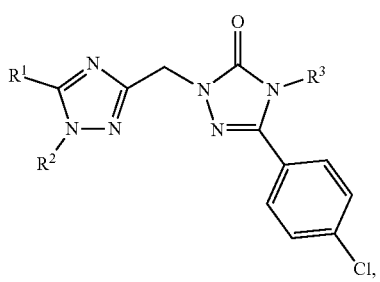

in which
$R^1$ represents hydrogen, 1,1-dioxidothiomorpholin-4-yl, 3-oxopiperazin-1-yl, (1,1-dioxidothiomorpholin-4-yl)carbonyl, (3-oxopiperazin-1-yl)carbonyl or 2-amino-2-methyl-propylaminocarbonyl,
$R^2$ represents a group of the formula

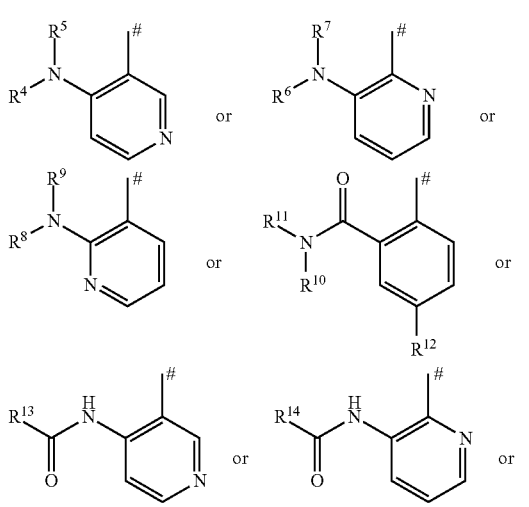

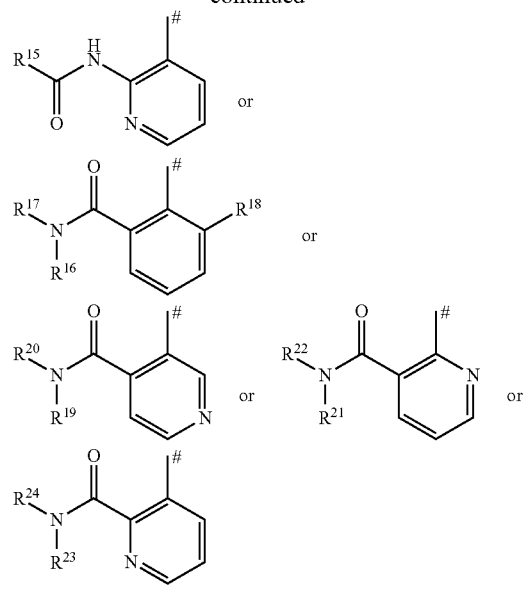

in which
\# represents the point of attachment to the 1,2,4-triazolyl-ring,
$R^4$ represents hydrogen,
$R^5$ represents $C_1$-$C_5$-alkyl or $C_3$-$C_6$-cycloalkyl,
  where alkyl may be substituted by 1 to 2 substituents independently of one another selected from the group consisting of fluorine, hydroxy, amino, hydroxycarbonyl, aminocarbonyl, trifluoromethyl, $C_3$-$C_6$-cycloalkyl, 4- to 7-membered heterocyclyl and $C_1$-$C_4$-alkoxycarbonyl,
    wherein cycloalkyl may be substituted by one substituent hydroxy and amino,
    and
    wherein heterocyclyl may be substituted by 1 to 3 substituents independently of one another selected from the group consisting of oxo, chlorine, fluorine, hydroxy, aminocarbonyl, trifluoromethyl, methyl and methoxy,
  where cycloalkyl may be substituted by 1 to 3 substituents independently of one another selected from the group consisting of fluorine, cyano, hydroxy, amino, trifluoromethyl and methyl,
or
$R^4$ and $R^5$ together with the nitrogen atom to which they are attached form a 4- to 6-membered heterocyclyl,
  where heterocyclyl may be substituted by 1 to 3 substituents independently of one another selected from the group consisting of oxo, chlorine, fluorine, hydroxy, aminocarbonyl, trifluoromethyl, methyl, methoxy and methoxymethyl,
$R^6$ represents hydrogen,
$R^7$ represents $C_1$-$C_5$-alkyl or $C_3$-$C_6$-cycloalkyl,
  where alkyl may be substituted by 1 to 2 substituents independently of one another selected from the group consisting of fluorine, hydroxy, amino, hydroxycarbonyl, aminocarbonyl, trifluoromethyl, $C_3$-$C_6$-cycloalkyl, 4- to 7-membered heterocyclyl and $C_1$-$C_4$-alkoxycarbonyl,
    wherein cycloalkyl may be substituted by one substituent hydroxy and amino,
    and
    wherein heterocyclyl may be substituted by 1 to 3 substituents independently of one another selected from the group consisting of oxo, chlorine, fluorine, hydroxy, aminocarbonyl, trifluoromethyl, methyl and methoxy,
where cycloalkyl may be substituted by 1 to 3 substituents independently of one another selected from the group consisting of fluorine, cyano, hydroxy, amino, trifluoromethyl and methyl, or $R^6$ and $R^7$ together with the nitrogen atom to which they are attached form a 4- to 6-membered heterocyclyl,
where heterocyclyl may be substituted by 1 to 3 substituents independently of one another selected from the group consisting of oxo, chlorine, fluorine, hydroxy, aminocarbonyl, trifluoromethyl, methyl, methoxy and methoxymethyl, $R^8$ represents hydrogen, $R^9$ represents $C_1$-$C_5$-alkyl or $C_3$-$C_6$-cycloalkyl,
where alkyl may be substituted by 1 to 2 substituents independently of one another selected from the group consisting of fluorine, hydroxy, amino, hydroxycarbonyl, aminocarbonyl, trifluoromethyl, $C_3$-$C_6$-cycloalkyl, 4- to 7-membered heterocyclyl and $C_1$-$C_4$-alkoxycarbonyl,
wherein cycloalkyl may be substituted by one substituent fluorine, hydroxy and amino,
and
wherein heterocyclyl may be substituted by 1 to 3 substituents independently of one another selected from the group consisting of oxo, chlorine, fluorine, hydroxy, aminocarbonyl, trifluoromethyl, methyl and methoxy,
where cycloalkyl may be substituted by 1 to 3 substituents independently of one another selected from the group consisting of fluorine, cyano, hydroxy, amino, trifluoromethyl and methyl, or $R^8$ and $R^9$ together with the nitrogen atom to which they are attached form a 4- to 6-membered heterocyclyl,
where heterocyclyl may be substituted by 1 to 3 substituents independently of one another selected from the group consisting of oxo, chlorine, fluorine, hydroxy, aminocarbonyl, trifluoromethyl, methyl, methoxy and methoxymethyl, $R^{10}$ represents hydrogen, methyl, ethyl or propan-2-yl, $R^{11}$ represents $C_1$-$C_5$-alkyl, prop-2-en-1-yl, 3-methylbut-2-en-1-yl, methoxy, $C_3$-$C_7$-cycloalkyl, phenyl, 4- to 6-membered heterocyclyl or 5- or 6-membered heteroaryl,
where alkyl may be substituted by 1 to 2 substituents independently of one another selected from the group consisting of fluorine, cyano, hydroxy, amino, aminocarbonyl, trifluoromethyl, 1,1,2,2-tetrafluoroethyl, $C_3$-$C_6$-cycloalkyl, phenyl, 4- to 7-membered heterocyclyl, 5- or 6-membered heteroaryl and $C_1$-$C_4$-alkoxycarbonyl,
wherein cycloalkyl may be substituted by 1 to 3 substituents independently of one another selected from the group consisting of fluorine, cyano, hydroxyl and methyl,
and
wherein phenyl may be substituted by 1 to 3 substituents independently of one another selected from the group consisting of fluorine, cyano, hydroxyl and methyl,
and
wherein heterocyclyl may be substituted by 1 to 3 substituents independently of one another selected from the group consisting of oxo, chlorine, fluorine, hydroxy, aminocarbonyl, trifluoromethyl, methyl and methoxy,
and
wherein heteroaryl may be substituted by 1 to 3 substituents independently of one another selected from the group consisting of fluorine, trifluoromethyl and methyl,
where cycloalkyl may be substituted by 1 to 3 substituents independently of one another selected from the group consisting of fluorine, cyano, hydroxy, amino and methyl,
and
where phenyl may be substituted by 1 to 3 substituents independently of one another selected from the group consisting of chlorine, fluorine, cyano, hydroxy, amino and methyl,
and
where heterocyclyl may be substituted by 1 to 3 substituents of oxo,
and
where heteroaryl may be substituted by 1 to 3 substituents independently of one another selected from the group consisting of chlorine, fluorine, hydroxy, amino, trifluoromethyl, methyl and ethyl, or $R^{10}$ and $R^{11}$ together with the nitrogen atom to which they are attached form a 4- to 7-membered heterocyclyl, 6-oxo-2,5,7-triazaspiro[3.4]octan-2-yl, 2-oxa-5-azabicyclo[2.2.1]hept-5-yl or 5-methyl-2,5-diazabicyclo[2.2.1]hept-2-yl, where heterocyclyl may be substituted by 1 to 3 substituents independently of one another selected from the group consisting of oxo, chlorine, fluorine, hydroxy, formyl, aminocarbonyl, trifluoromethyl, methyl, ethyl, methoxy, methoxymethyl, dimethylamino and methylcarbonylamino, $R^{12}$ represents hydrogen, chlorine or fluorine, $R^{13}$ represents methyl, methoxy or $C_3$-$C_6$-cycloalkyl,
where methyl and methoxy may be substituted by one substituent independently of one another selected from the group consisting of fluorine, hydroxy, trifluoromethyl, methoxy, $C_3$-$C_6$-cycloalkyl, 4- to 7-membered heterocyclyl, methylsulfonyl and methylsulfonylamino,
and
where cycloalkyl may be substituted by 1 to 3 substituents independently of one another selected from the group consisting of fluorine and trifluoromethyl, $R^{14}$ represents trifluoromethyl, methyl, methoxy, 2,2,2-trifluoroethylamino, $C_3$-$C_6$-cycloalkyl or 4- to 6-membered heterocyclyl,
where methyl and methoxy may be substituted by one substituent independently of one another selected from the group consisting of fluorine, hydroxy, trifluoromethyl, methoxy, $C_3$-$C_6$-cycloalkyl, 4- to 7-membered heterocyclyl, methylsulfonyl and methylsulfonylamino,
and
where cycloalkyl may be substituted by 1 to 3 substituents independently of one another selected from the group consisting of fluorine and trifluoromethyl,
and
where heterocyclyl may be substituted by 1 to 3 substituents of oxo, $R^{15}$ represents $C_1$-$C_5$-alkyl, methoxy, 2,2,2-trifluoroethoxy, prop-2-en-1-yl, but-3-en-2-yl, $C_3$-$C_7$-cycloalkyl, phenyl, 4- to 6-membered heterocyclyl or 5- or 6-membered heteroaryl, where alkyl and methoxy may be substituted by one substituent independently of one another selected from the group consisting of fluorine, hydroxy, trifluoromethyl, methoxy, methylsulfanyl, methylamino, $C_3$-$C_6$-cycloalkyl, phenyl, 4- to 7-membered heterocyclyl, 5- or 6-membered heteroaryl, methylsulfonyl and methylsulfonylamino, wherein heterocyclyl may be substituted by 1 to 3 substituents independently of one another selected from the group consisting of oxo and methyl, and wherein heteroaryl may be substituted by 1 to 3 substituents independently of one another selected from the group consisting of fluorine, trifluoromethyl and methyl, and where cycloalkyl may be substituted by 1 to 3 substituents independently of one another selected from the group consisting of fluorine, aminocarbonyl, trifluoromethyl and methyl, and where phenyl may be substituted by 1 to 3 substituents independently of one another selected from the group consisting of fluorine, cyano, hydroxyl and methyl, and where heterocyclyl may be substituted by 1 to 3 substituents independently of one another selected from the group consisting of oxo and methyl, and where heteroaryl may be substituted by 1 to 3 substituents independently of one another selected from the group consisting of fluorine, trifluoromethyl, methyl and ethyl, $R^{16}$ represents hydrogen or methyl, $R^{17}$ represents $C_1$-$C_5$-alkyl, prop-2-en-1-yl, 3-methylbut-2-en-1-yl or $C_3$-$C_7$-cycloalkyl, where alkyl may be substituted by 1 to 2 substituents independently of one another selected from the group consisting of fluorine, cyano, hydroxy, amino, aminocarbonyl, trifluoromethyl, 1,1,2,2-tetrafluoroethyl, $C_3$-$C_6$-cycloalkyl and $C_1$-$C_4$-alkoxycarbonyl, wherein cycloalkyl may be substituted by 1 to 3 substituents independently of one another selected from the group consisting of fluorine, cyano, hydroxyl and methyl, and where cycloalkyl may be substituted by 1 to 3 substituents independently of one another selected from the group consisting of fluorine, cyano, hydroxy, amino, trifluoromethyl and methyl, or $R^{16}$ and $R^{17}$ together with the nitrogen atom to which they are attached form a 4- to 7-membered heterocyclyl or 2-oxa-6-azaspiro[3.3]hept-6-yl, where heterocyclyl may be substituted by 1 to 3 substituents independently of one another selected from the group consisting of oxo, chlorine, fluorine, hydroxy, formyl, aminocarbonyl, trifluoromethyl, methyl, ethyl, methoxy, methoxymethyl, dimethylamino and methylcarbonylamino, $R^{18}$ represents chlorine or trifluoromethyl, $R^{19}$ represents hydrogen or methyl, $R^{20}$ represents $C_1$-$C_5$-alkyl or $C_3$-$C_6$-cycloalkyl, where alkyl may be substituted by 1 to 2 substituents independently of one another selected from the group consisting of fluorine, hydroxy, amino, trifluoromethyl and $C_3$-$C_6$-cycloalkyl, wherein cycloalkyl may be substituted by one substituent fluorine, hydroxy and amino, and where cycloalkyl may be substituted by 1 to 3 substituents independently of one another selected from the group consisting of fluorine, cyano, hydroxy, amino, trifluoromethyl and methyl, or $R^{19}$ and $R^{20}$ together with the nitrogen atom to which they are attached form a 4- to 6-membered heterocyclyl, where heterocyclyl may be substituted by 1 to 3 substituents independently of one another selected from the group consisting of oxo, chlorine, fluorine, hydroxy, aminocarbonyl, trifluoromethyl, methyl, methoxy and methoxymethyl, $R^{21}$ represents hydrogen or methyl, $R^{22}$ represents $C_1$-$C_5$-alkyl or $C_3$-$C_6$-cycloalkyl, where alkyl may be substituted by 1 to 2 substituents independently of one another selected from the group consisting of fluorine, hydroxy, amino, trifluoromethyl and $C_3$-$C_6$-cycloalkyl, wherein cycloalkyl may be substituted by one substituent fluorine, hydroxy and amino, and where cycloalkyl may be substituted by 1 to 3 substituents independently of one another selected from the group consisting of fluorine, cyano, hydroxy, amino, trifluoromethyl and methyl, or $R^{21}$ and $R^{22}$ together with the nitrogen atom to which they are attached form a 4- to 6-membered heterocyclyl, where heterocyclyl may be substituted by 1 to 3 substituents independently of one another selected from the group consisting of oxo, chlorine, fluorine, hydroxy, aminocarbonyl, trifluoromethyl, methyl, methoxy and methoxymethyl, $R^{23}$ represents hydrogen or methyl, $R^{24}$ represents $C_1$-$C_5$-alkyl or $C_3$-$C_6$-cycloalkyl, where alkyl may be substituted by 1 to 2 substituents independently of one another selected from the group consisting of fluorine, hydroxy, amino, trifluoromethyl and $C_3$-$C_6$-cycloalkyl, wherein cycloalkyl may be substituted by one substituent fluorine, hydroxy and amino, and where cycloalkyl may be substituted by 1 to 3 substituents independently of one another selected from the group consisting of fluorine, cyano, hydroxy, amino, trifluoromethyl and methyl, or $R^{23}$ and $R^{24}$ together with the nitrogen atom to which they are attached form a 4- to 6-membered heterocyclyl, where heterocyclyl may be substituted by 1 to 3 substituents independently of one another selected from the group consisting of oxo, chlorine, fluorine, hydroxy, aminocarbonyl, trifluoromethyl, methyl, methoxy and methoxymethyl, $R^3$ represents a group of the formula

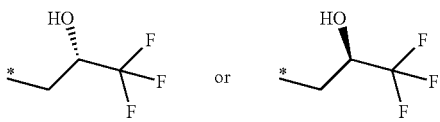

in which
* represents the point of attachment to the 2,4-dihydro-3H-1,2,4-triazolyl-ring, and pharmaceutically acceptable salts thereof, solvates thereof and the solvates of the salts thereof.

DETAILED DESCRIPTION OF A PREFERRED EMBODIMENT

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "optionally substituted" means that the number of substituents can be equal to or different from zero. Unless otherwise indicated, it is possible that optionally substituted groups are substituted with as many optional substituents as can be accommodated by replacing a hydrogen atom with a non-hydrogen substituent on any available carbon atom or heteroatom.

When groups in the compounds according to the invention are substituted, it is possible for said groups to be mono-substituted or poly-substituted with substituent(s), unless otherwise specified. Within the scope of the present invention, the meanings of all groups which occur repeatedly are independent from one another. It is possible that groups in the compounds according to the invention are substituted with one, two or three identical or different substituents.

The term "comprising" when used in the specification includes "consisting of".

If within the present text any item is referred to as "as mentioned herein", it means that it may be mentioned anywhere in the present text.

The terms as mentioned in the present text have the following meanings:

$C_1$-$C_5$-Alkyl represents a straight-chain or branched alkyl radical having 1 to 5 carbon atoms, preferably 1 to 3 carbon atoms ($C_1$-$C_3$-alkyl), by way of example and with preference methyl, ethyl, n-propyl, isopropyl, 2-methylprop-1-yl, n-butyl, tert-butyl and 2,2-dimethylprop-1-yl.

4- to 6-membered heterocyclyl in the definition of the combination of the radicals $R^4$ and $R^5$ represents a saturated or partially unsaturated monocyclic radical having 4 to 6 ring atoms which is bound via a nitrogen atom and which may contain one additional heteroatom from the group consisting of S, O and N, where a nitrogen atom may also form an N-oxide, by way of example and with preference azetidinyl, pyrrolidinyl, pyrazolidinyl, 1,3-oxazolidinyl, piperidinyl, piperazinyl, morpholinyl and thiomorpholinyl, preferred are pyrrolidinyl, piperidinyl, piperazinyl, morpholinyl and thiomorpholinyl.

4- to 7-membered heterocyclyl as a substituent on alkyl in the definition of the radical R represents a saturated or partially unsaturated monocyclic radical having 4 to 7 ring atoms and up to 2 heteroatoms from the group consisting of S, O and N, where a nitrogen atom may also form an N-oxide, by way of example and with preference azetidinyl, oxetanyl, thietanyl, pyrrolidinyl, pyrazolidinyl, tetrahydrofuranyl, tetrahydrothiophenyl, 1,3-oxazolidinyl, imidazolidinyl, piperidinyl, piperazinyl, tetrahydropyranyl, tetrahydrothiopyranyl, 1,3-dioxanyl, 1,4-dioxanyl, morpholinyl, thiomorpholinyl, 1,2-thiazinanyl, azepanyl, hexahydroazepinyl and hexahydro-1,4-diazepinyl, preferred are thietanyl, pyrrolidinyl and imidazolidinyl.

4- to 6-membered heterocyclyl in the definition of the combination of the radicals $R^6$ and $R^7$ represents a saturated or partially unsaturated monocyclic radical having 4 to 6 ring atoms which is bound via a nitrogen atom and which may contain one additional heteroatom from the group consisting of S, O and N, where a nitrogen atom may also form an N-oxide, by way of example and with preference azetidinyl, pyrrolidinyl, pyrazolidinyl, 1,3-oxazolidinyl, piperidinyl, piperazinyl, morpholinyl and thiomorpholinyl.

4- to 7-membered heterocyclyl as a substituent on alkyl in the definition of the radical $R^7$ represents a saturated or partially unsaturated monocyclic radical having 4 to 7 ring atoms and up to 2 heteroatoms from the group consisting of S, O and N, where a nitrogen atom may also form an N-oxide, by way of example and with preference azetidinyl, oxetanyl, thietanyl, pyrrolidinyl, pyrazolidinyl, tetrahydrofuranyl, tetrahydrothiophenyl, 1,3-oxazolidinyl, imidazolidinyl, piperidinyl, piperazinyl, tetrahydropyranyl, tetrahydrothiopyranyl, 1,3-dioxanyl, 1,4-dioxanyl, morpholinyl, thiomorpholinyl, 1,2-thiazinanyl, azepanyl, hexahydroazepinyl and hexahydro-1,4-diazepinyl.

4- to 6-membered heterocyclyl in the definition of the combination of the radicals $R^8$ and $R^9$ represents a saturated or partially unsaturated monocyclic radical having 4 to 6 ring atoms which is bound via a nitrogen atom and which may contain one additional heteroatom from the group consisting of S, O and N, where a nitrogen atom may also form an N-oxide, by way of example and with preference azetidinyl, pyrrolidinyl, pyrazolidinyl, 1,3-oxazolidinyl, piperidinyl, piperazinyl, morpholinyl and thiomorpholinyl, preferred are pyrrolidinyl and morpholinyl.

4- to 7-membered heterocyclyl as a substituent on alkyl in the definition of the radical $R^9$ represents a saturated or partially unsaturated monocyclic radical having 4 to 7 ring atoms and up to 2 heteroatoms from the group consisting of S, O and N, where a nitrogen atom may also form an N-oxide, by way of example and with preference azetidinyl, oxetanyl, thietanyl, pyrrolidinyl, pyrazolidinyl, tetrahydrofuranyl, tetrahydrothiophenyl, 1,3-oxazolidinyl, imidazolidinyl, piperidinyl, piperazinyl, tetrahydropyranyl, tetrahydrothiopyranyl, 1,3-dioxanyl, 1,4-dioxanyl, morpholinyl, thiomorpholinyl, 1,2-thiazinanyl, azepanyl, hexahydroazepinyl and hexahydro-1,4-diazepinyl, preferred are thietanyl and pyrrolidinyl.

4- or 6-membered heterocyclyl in the definition of the radical $R^{11}$ represents a saturated or partially unsaturated monocyclic radical having 4 to 6 ring atoms and up to 2 heteroatoms from the group consisting of S, O and N, where a nitrogen atom may also form an N-oxide, by way of example and with preference azetidinyl, oxetanyl, thietanyl, pyrrolidinyl, pyrazolidinyl, tetrahydrofuranyl, tetrahydrothiophenyl, 1,3-oxazolidinyl, imidazolidinyl, piperidinyl, piperazinyl, tetrahydropyranyl, tetrahydrothiopyranyl, 1,3-dioxanyl, 1,4-dioxanyl, morpholinyl and thiomorpholinyl, preferred are thietanyl, tetrahydrofuranyl, piperidinyl and morpholinyl.

4- to 7-membered heterocyclyl as a substituent on alkyl in the definition of the radical $R^{11}$ represents a saturated or partially unsaturated monocyclic radical having 4 to 7 ring atoms and up to 2 heteroatoms from the group consisting of S, O and N, where a nitrogen atom may also form an N-oxide, by way of example and with preference azetidinyl, oxetanyl, thietanyl, pyrrolidinyl, pyrazolidinyl, tetrahydrofuranyl, tetrahydrothiophenyl, 1,3-oxazolidinyl, imidazolidinyl, piperidinyl, piperazinyl, tetrahydropyranyl, tetrahydrothiopyranyl, 1,3-dioxanyl, 1,4-dioxanyl, morpholinyl, thiomorpholinyl, 1,2-thiazinanyl, azepanyl, hexahydroazepinyl and hexahydro-1,4-diazepinyl, preferred are oxetanyl, thietanyl, pyrrolidinyl, tetrahydrofuranyl and imidazolidinyl.

4- to 7-membered heterocyclyl in the definition of the combination of the radicals $R^{10}$ and $R^{11}$ represents a saturated or partially unsaturated monocyclic radical having 4 to 7 ring atoms which is bound via a nitrogen atom and which may contain one additional heteroatom from the group consisting of S, O and N, where a nitrogen atom may also form an N-oxide, by way of example and with preference azetidinyl, pyrrolidinyl, 2,5-dihydro-1H-pyrrol-1-yl, pyrazolidinyl, 1,2-oxazolidinyl, 1,3-oxazolidinyl, 1,3-thiazolidinyl, imidazolidinyl, piperidinyl, piperazinyl, morpholinyl, thiomorpholinyl, 3,6-dihydropyridin-1(2H)-yl, azepanyl, 1,2-oxazinan-2-yl, 1,4-oxazepan-4-yl and 1,4-diazepanyl, preferred are azetidinyl, pyrrolidinyl, 2,5-dihydro-1H-pyrrol-1-yl, 1,2-oxazolidinyl, 1,3-thiazolidinyl, imidazolidinyl, piperidinyl, piperazinyl, morpholinyl, thiomorpholinyl, 3,6-dihydropyridin-1(2H)-yl, azepanyl, 1,2-oxazinan-2-yl, 1,4-oxazepan-4-yl and 1,4-diazepanyl.

5- or 6-membered heteroaryl in the definition of the radical $R^{11}$ represents an aromatic monocyclic radical having generally 5 or 6 ring atoms and up to 4 heteroatoms from the group consisting of S, O and N, where one nitrogen atom may also form an N-oxide, by way of example and with preference thienyl, furyl, pyrrolyl, thiazolyl, oxazolyl, isoxazolyl, oxadiazolyl, thiadiazolyl, pyrazolyl, imidazolyl, triazolyl, pyridyl, pyrimidyl, pyridazinyl and pyrazinyl, preferred are oxazolyl, thiadiazolyl, pyrazolyl, triazolyl, pyridyl and pyrimidyl.

5- or 6-membered heteroaryl as a substituent on alkyl in the definition of the radical $R^{11}$ represents an aromatic monocyclic radical having generally 5 or 6 ring atoms and up to 4 heteroatoms from the group consisting of S, O and N, where one nitrogen atom may also form an N-oxide, by way of example and with preference thienyl, furyl, pyrrolyl, thiazolyl, oxazolyl, isoxazolyl, oxadiazolyl, pyrazolyl, imidazolyl, triazolyl, pyridyl, pyrimidyl, pyridazinyl and pyrazinyl, preferred are thienyl, furyl, oxazolyl and pyrazolyl.

4- to 7-membered heterocyclyl as a substituent on methyl and methoxy in the definition of the radical $R^{13}$ represents a saturated or partially unsaturated monocyclic radical having 4 to 7 ring atoms and up to 2 heteroatoms from the group consisting of S, O and N, where a nitrogen atom may also form an N-oxide, by way of example and with preference azetidinyl, oxetanyl, thietanyl, pyrrolidinyl, pyrazolidinyl, tetrahydrofuranyl, tetrahydrothiophenyl, 1,3-oxazolidinyl, imidazolidinyl, piperidinyl, piperazinyl, tetrahydropyranyl, tetrahydrothiopyranyl, 1,3-dioxanyl, 1,4-dioxanyl, morpholinyl, thiomorpholinyl, 1,2-thiazinanyl, azepanyl, hexahydroazepinyl and hexahydro-1,4-diazepinyl.

4- to 6-membered heterocyclyl in the definition of the radical $R^{14}$ represents a saturated or partially unsaturated monocyclic radical having 4 to 6 ring atoms and up to 2 heteroatoms from the group consisting of S, O and N, where a nitrogen atom may also form an N-oxide, by way of example and with preference azetidinyl, oxetanyl, thietanyl, pyrrolidinyl, pyrazolidinyl, tetrahydrofuranyl, tetrahydrothiophenyl, 1,3-oxazolidinyl, imidazolidinyl, piperidinyl, piperazinyl, tetrahydropyranyl, tetrahydrothiopyranyl, 1,3-dioxanyl, 1,4-dioxanyl, morpholinyl and thiomorpholinyl, preferred are thietanyl and tetrahydrothiophenyl.

4- to 7-membered heterocyclyl as a substituent on methyl and methoxy in the definition of the radical $R^{14}$ represents a saturated or partially unsaturated monocyclic radical having 4 to 7 ring atoms and up to 2 heteroatoms from the group consisting of S, O and N, where a nitrogen atom may also form an N-oxide, by way of example and with preference azetidinyl, oxetanyl, thietanyl, pyrrolidinyl, pyrazolidinyl, tetrahydrofuranyl, tetrahydrothiophenyl, 1,3-oxazolidinyl, imidazolidinyl, piperidinyl, piperazinyl, tetrahydropyranyl, tetrahydrothiopyranyl, 1,3-dioxanyl, 1,4-dioxanyl, morpholinyl, thiomorpholinyl, 1,2-thiazinanyl, azepanyl, hexahydroazepinyl and hexahydro-1,4-diazepinyl.

4- to 6-membered heterocyclyl in the definition of the radical $R^{15}$ represents a saturated or partially unsaturated monocyclic radical having 4 to 6 ring atoms and up to 2 heteroatoms from the group consisting of S, O and N, where a nitrogen atom may also form an N-oxide, by way of example and with preference azetidinyl, oxetanyl, thietanyl, pyrrolidinyl, pyrazolidinyl, tetrahydrofuranyl, tetrahydrothiophenyl, 1,3-oxazolidinyl, imidazolidinyl, piperidinyl, piperazinyl, tetrahydropyranyl, tetrahydrothiopyranyl, 1,3-dioxanyl, 1,4-dioxanyl, morpholinyl and thiomorpholinyl, preferred are oxetanyl, pyrrolidinyl, tetrahydrofuranyl, tetrahydrothiophenyl, piperidinyl and tetrahydropyranyl.

4- to 7-membered heterocyclyl as a substituent on alkyl and methoxy in the definition of the radical $R^{15}$ represents a saturated or partially unsaturated monocyclic radical having 4 to 7 ring atoms and up to 2 heteroatoms from the group consisting of S, O and N, where a nitrogen atom may also form an N-oxide, by way of example and with preference azetidinyl, oxetanyl, thietanyl, pyrrolidinyl, pyrazolidinyl, tetrahydrofuranyl, tetrahydrothiophenyl, 1,3-oxazolidinyl, imidazolidinyl, piperidinyl, piperazinyl, tetrahydropyranyl, tetrahydrothiopyranyl, 1,3-dioxanyl, 1,4-dioxanyl, morpholinyl, thiomorpholinyl, 1,2-thiazinanyl, azepanyl, hexahydroazepinyl and hexahydro-1,4-diazepinyl, preferred are pyrrolidinyl, tetrahydrofuranyl, piperidinyl and tetrahydropyranyl.

5- or 6-membered heteroaryl in the definition of the radical $R^{15}$ represents an aromatic monocyclic radical having generally 5 or 6 ring atoms and up to 4 heteroatoms from the group consisting of S, O and N, where one nitrogen atom may also form an N-oxide, by way of example and with preference thienyl, furyl, pyrrolyl, thiazolyl, oxazolyl, isoxazolyl, oxadiazolyl, thiadiazolyl, pyrazolyl, imidazolyl, triazolyl, pyridyl, pyrimidyl, pyridazinyl and pyrazinyl, preferred are oxazolyl, oxadiazolyl, thiadiazolyl, imidazolyl, pyridyl, pyrimidyl and pyrazinyl.

5- or 6-membered heteroaryl as a substituent on alkyl in the definition of the radical $R^{15}$ represents an aromatic monocyclic radical having generally 5 or 6 ring atoms and up to 4 heteroatoms from the group consisting of S, O and N, where one nitrogen atom may also form an N-oxide, by way of example and with preference thienyl, furyl, pyrrolyl, thiazolyl, oxazolyl, isoxazolyl, oxadiazolyl, pyrazolyl, imidazolyl, triazolyl, pyridyl, pyrimidyl, pyridazinyl and pyrazinyl, preferred are oxazolyl, oxadiazolyl, pyrazolyl, imidazolyl, triazolyl and pyridyl.

4- to 7-membered heterocyclyl in the definition of the combination of the radicals $R^{16}$ and $R^{17}$ represents a saturated or partially unsaturated monocyclic radical having 4 to 7 ring atoms which is bound via a nitrogen atom and which may contain one additional heteroatom from the group consisting of S, O and N, where a nitrogen atom may also form an N-oxide, by way of example and with preference azetidinyl, pyrrolidinyl, pyrazolidinyl, 1,3-oxazolidinyl, piperidinyl, piperazinyl, morpholinyl, thiomorpholinyl and azepanyl, preferred are pyrrolidinyl, piperidinyl, morpholinyl and thiomorpholinyl.

4- to 6-membered heterocyclyl in the definition of the combination of the radicals $R^{19}$ and $R^{20}$ represents a saturated or partially unsaturated monocyclic radical having 4 to 6 ring atoms which is bound via a nitrogen atom and which may contain one additional heteroatom from the group consisting of S, O and N, where a nitrogen atom may also form an N-oxide, by way of example and with preference azetidinyl, pyrrolidinyl, pyrazolidinyl, 1,3-oxazolidinyl, piperidinyl, piperazinyl, morpholinyl and thiomorpholinyl, preferred is pyrrolidinyl.

4- to 6-membered heterocyclyl in the definition of the combination of the radicals $R^{21}$ and $R^{22}$ represents a saturated or partially unsaturated monocyclic radical having 4 to 6 ring atoms which is bound via a nitrogen atom and which may contain one additional heteroatom from the group consisting of S, O and N, where a nitrogen atom may also form an N-oxide, by way of example and with preference azetidinyl, pyrrolidinyl, pyrazolidinyl, 1,3-oxazolidinyl, piperidinyl, piperazinyl, morpholinyl and thiomorpholinyl, preferred is pyrrolidinyl.

4- to 6-membered heterocyclyl in the definition of the combination of the radicals $R^{23}$ and $R^{24}$ represents a saturated or partially unsaturated monocyclic radical having 4 to 6 ring atoms which is bound via a nitrogen atom and which may contain one additional heteroatom from the group consisting of S, O and N, where a nitrogen atom may also form an N-oxide, by way of example and with preference azetidinyl, pyrrolidinyl, pyrazolidinyl, 1,3-oxazolidinyl, piperidinyl, piperazinyl, morpholinyl and thiomorpholinyl, preferred are pyrrolidinyl, piperidinyl, piperazinyl, morpholinyl and thiomorpholinyl.

$C_1$-$C_4$-alkoxycarbonyl represents a straight-chain or branched alkoxy radical having 1 to 4 carbon atoms, preferably 1 to 3 carbon atoms ($C_1$-$C_3$-alkoxy) which is linked via a carbonyl group, by way of example and with preference methoxycarbonyl, ethoxycarbonyl, n-propoxycarbonyl, iso-propoxycarbonyl, n-butoxycarbonyl and tert-butoxycarbonyl.

$C_3$-$C_6$-cycloalkyl represents a monocyclic cycloalkyl group having 3 to 6 carbon atoms, cycloalkyl which may be mentioned by way of example and with preference being cyclopropyl, cyclobutyl, cyclopentyl and cyclohexyl.

$C_3$-$C_7$-cycloalkyl in the definition of the radical $R^{15}$ represents a monocyclic cycloalkyl group having 3 to 7 carbon atoms, cycloalkyl which may be mentioned by way of example and with preference being cyclopropyl, cyclobutyl, cyclopentyl, cyclohexyl and cycloheptyl.

In the formulae of the group which represent $R^2$, the end point of the line marked by # does not represent a carbon atom or a $CH_2$ group, but is part of the bond to the atom to which $R^2$ is attached.

In the formulae of the group which represent $R^3$, the end point of the line marked by * does not represent a carbon atom or a $CH_2$ group, but is part of the bond to the atom to which $R^3$ is attached.

It is possible for the compounds of general formula (I) to exist as isotopic variants. The invention therefore includes one or more isotopic variant(s) of the compounds of general formula (I), particularly deuterium-containing compounds of general formula (I).

The term "Isotopic variant" of a compound or a reagent is defined as a compound exhibiting an unnatural proportion of one or more of the isotopes that constitute such a compound.

The term "Isotopic variant of the compound of general formula (I)" is defined as a compound of general formula (I) exhibiting an unnatural proportion of one or more of the isotopes that constitute such a compound.

The expression "unnatural proportion" means a proportion of such isotope which is higher than its natural abundance. The natural abundances of isotopes to be applied in this context are described in "Isotopic Compositions of the Elements 1997", Pure Appl. Chem., 70(1), 217-235, 1998.

Examples of such isotopes include stable and radioactive isotopes of hydrogen, carbon, nitrogen, oxygen, phosphorus, sulfur, fluorine, chlorine, bromine and iodine, such as $^2H$ (deuterium), $^3H$ (tritium), $^{11}C$, $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{125}I$, $^{129}I$ and $^{131}I$ respectively.

With respect to the treatment and/or prevention of the disorders specified herein the isotopic variant(s) of the compounds of general formula (I) preferably contain deuterium ("deuterium-containing compounds of general formula (I)"). Isotopic variants of the compounds of general formula (I) in which one or more radioactive isotopes, such as $^3H$ or $^{14}C$, are incorporated are useful e.g. in drug and/or substrate tissue distribution studies. These isotopes are particularly preferred for the ease of their incorporation and detectability. Positron emitting isotopes such as $^{18}F$ or $^{11}C$ may be incorporated into a compound of general formula (I). These isotopic variants of the compounds of general formula (I) are useful for in vivo imaging applications. Deuterium-containing and $^{13}C$-containing compounds of general formula (I) can be used in mass spectrometry analyses (H. J. Leis et al., Curr. Org. Chem., 1998, 2, 131) in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, preferably for a deuterium-containing reagent. Depending on the desired sites of deuteration, in some cases deuterium from $D_2O$ can be incorporated either directly into the compounds or into reagents that are useful for synthesizing such compounds (Esaki et al., Tetrahedron, 2006, 62, 10954; Esaki et al., Chem. Eur. J., 2007, 13, 4052). Deuterium gas is also a useful reagent for incorporating deuterium into molecules. Catalytic deuteration of olefinic bonds (H. J. Leis et al., Curr. Org. Chem., 1998, 2, 131; J. R. Morandi et al., J. Org. Chem., 1969, 34 (6), 1889) and acetylenic bonds (N. H. Khan, J. Am. Chem. Soc., 1952, 74 (12), 3018; S. Chandrasekhar et al., Tetrahedron Letters, 2011, 52, 3865) is a direct route for incorporation of deuterium. Metal catalysts (i.e. Pd, Pt, and Rh) in the presence of deuterium gas can be used to directly exchange deuterium for hydrogen in functional groups containing hydrocarbons (J. G. Atkinson et al., U.S. Pat. No. 3,966,781). A variety of deuterated reagents and synthetic building blocks are commercially available from companies such as for example C/D/N Isotopes, Quebec, Canada; Cambridge Isotope Laboratories Inc., Andover, Mass., USA; and CombiPhos Catalysts, Inc., Princeton, N.J., USA. Further information on the state of the art with respect to deuterium-hydrogen exchange is given for example in Hanzlik et al., J. Org. Chem. 55, 3992-3997, 1990; R. P. Hanzlik et al., Biochem. Biophys. Res. Commun. 160, 844, 1989; P. J. Reider et al., J. Org. Chem. 52, 3326-3334, 1987; M. Jarman et al., Carcinogenesis 16(4), 683-688, 1995; J.

Atzrodt et al., Angew. Chem., Int. Ed. 2007, 46, 7744; K. Matoishi et al., Chem. Commun. 2000, 1519-1520; K. Kassahun et al., WO2012/112363.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [C. L. Perrin, et al., J. Am. Chem. Soc., 2007, 129, 4490; A. Streitwieser et al., J. Am. Chem. Soc., 1963, 85, 2759;], basicity [C. L. Perrin et al., J. Am. Chem. Soc., 2005, 127, 9641; C. L. Perrin, et al., J. Am. Chem. Soc., 2003, 125, 15008; C. L. Perrin in Advances in Physical Organic Chemistry, 44, 144], lipophilicity [B. Testa et al., Int. J. Pharm., 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (A. E. Mutlib et al., Toxicol. Appl. Pharmacol., 2000, 169, 102; D. J. Kushner et al., Can. J. Physiol. Pharmacol., 1999, 77, 79). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and enhances the formation of a desired metabolite (e.g. Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. ML-337 (C. J. Wenthur et al., J. Med. Chem., 2013, 56, 5208) and Odanacatib (K. Kassahun et al., WO2012/112363) are examples for this deuterium effect. Still other cases have been reported in which reduced rates of metabolism result in an increase in exposure of the drug without changing the rate of systemic clearance (e.g. Rofecoxib: F. Schneider et al., Arzneim. Forsch./Drug. Res., 2006, 56, 295; Telaprevir: F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome $P_{450}$.

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

The compounds of the present invention optionally contain one asymmetric centre, depending upon the location and nature of the various substituents desired. It is possible that one asymmetric carbon atom is present in the (R) or (S) configuration, which can result in racemic mixtures. In certain instances, it is possible that asymmetry also be present due to restricted rotation about a given bond, for example, the central bond adjoining two substituted aromatic rings of the specified compounds. Preferred compounds are those which produce the more desirable biological activity. Separated, pure or partially purified isomers and stereoisomers or racemic mixtures of the compounds of the present invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials. In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. (R)- or (S)-isomers, in any ratio. Isolation of a single stereoisomer, e.g. a single enantiomer or a single diastereomer, of a compound of the present invention is achieved by any suitable state of the art method, such as chromatography, especially chiral chromatography, for example.

In the context of the present invention, the term "enantiomerically pure" is to be understood as meaning that the compound in question with respect to the absolute configuration of the chiral centre is present in an enantiomeric excess of more than 95%, preferably more than 97%. The enantiomeric excess, ee, is calculated here by evaluating of the corresponding HPLC chromatogram on a chiral phase using the formula below:

$$ee = [E^A \text{ (area \%)} - E^B \text{ (area \%)}] \times 100\% / [E^A \text{ (area \%)} + E^B \text{ (area \%)}]$$

($E^A$: major enantiomer, $E^B$: minor enantiomer)

Further, it is possible for the compounds of the present invention to exist as tautomers. The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also covers useful forms of the compounds of the present invention, such as metabolites, hydrates, solvates, salts, in particular pharmaceutically acceptable salts, and/or co-precipitates.

The compounds of the present invention can exist as a hydrate, or as a solvate, wherein the compounds of the present invention contain polar solvents, in particular water, methanol or ethanol for example, as structural element of the crystal lattice of the compounds. It is possible for the amount of polar solvents, in particular water, to exist in a stoichiometric or non-stoichiometric ratio. In the case of stoichiometric solvates, e.g. a hydrate, hemi-, (semi-), mono-, sesqui-, di-, tri-, tetra-, penta-etc. solvates or hydrates, respectively, are possible. The present invention includes all such hydrates or solvates. Hydrates are preferred solvates in the context of the present invention.

Further, it is possible for the compounds of the present invention to exist in free form, e.g. as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, or "mineral acid", such as hydrochloric, hydrobromic, hydroiodic, sulfuric, sulfamic, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, 3-phenylpropionic, pivalic, 2-hydroxyethanesulfonic, itaconic, trifluoromethanesulfonic, dodecylsulfuric, ethanesulfonic, benzenesulfonic, para-toluenesulfonic, methanesulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium, magnesium or strontium salt, or an aluminium or a zinc salt, or an ammonium salt derived from ammonia or from an organic primary, secondary or tertiary amine having 1 to 20 carbon atoms, such as ethylamine, diethylamine, triethylamine, ethyldiisopropylamine, monoethanolamine, diethanolamine, triethanolamine, dicyclohexylamine, dimethylaminoethanol, diethylaminoethanol, tris(hydroxymethyl)aminomethane, procaine, dibenzylamine, N-methylmorpholine, arginine, lysine, 1,2-ethylenediamine, N-methylpiperidine, N-methyl-glucamine, N,N-dimethylglucamine, N-ethyl-glucamine, 1,6-hexanediamine, glucosamine, sarcosine, serinol, 2-amino-1,3-propanediol, 3-amino-1,2-propanediol, 4-amino-1,2,3-butanetriol, or a salt with a quarternary ammonium ion having 1 to 20 carbon atoms, such as tetramethylammonium, tetraethylammonium, tetra(n-propyl)ammonium, tetra(n-butyl)ammonium, N-benzyl-N,N,N-trimethylammonium, choline or benzalkonium.

Those skilled in the art will further recognise that it is possible for acid addition salts of the claimed compounds to be prepared by reaction of the compounds with the appropriate inorganic or organic acid via any of a number of known methods. Alternatively, alkali and alkaline earth metal salts of acidic compounds of the present invention are prepared by reacting the compounds of the present invention with the appropriate base via a variety of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae relating to salts, such as "hydrochloride", "trifluoroacetate", "sodium salt", or "x HCl", "x CF$_3$COOH", "x Na", for example, mean a salt form, the stoichiometry of which salt form not being specified.

This applies analogously to cases in which synthesis intermediates or example compounds or salts thereof have been obtained, by the preparation and/or purification processes described, as solvates, such as hydrates, with (if defined) unknown stoichiometric composition.

Furthermore, the present invention includes all possible crystalline forms, or polymorphs, of the compounds of the present invention, either as single polymorph, or as a mixture of more than one polymorph, in any ratio.

Furthermore, the present invention also embraces prodrugs of the compounds of the invention. The term "prodrugs" denotes compounds which may themselves be biologically active or inactive but which during their residence time in the body are converted (metabolically or by hydrolysis, for example) into compounds of the invention.

Preference is given to compounds of the general formula (I) in which

R¹ represents hydrogen, 1,1-dioxidothiomorpholin-4-yl, 3-oxopiperazin-1-yl, (1,1-dioxidothiomorpholin-4-yl)carbonyl, (3-oxopiperazin-1-yl)carbonyl or 2-amino-2-methyl-propylaminocarbonyl, R² represents a group of the formula

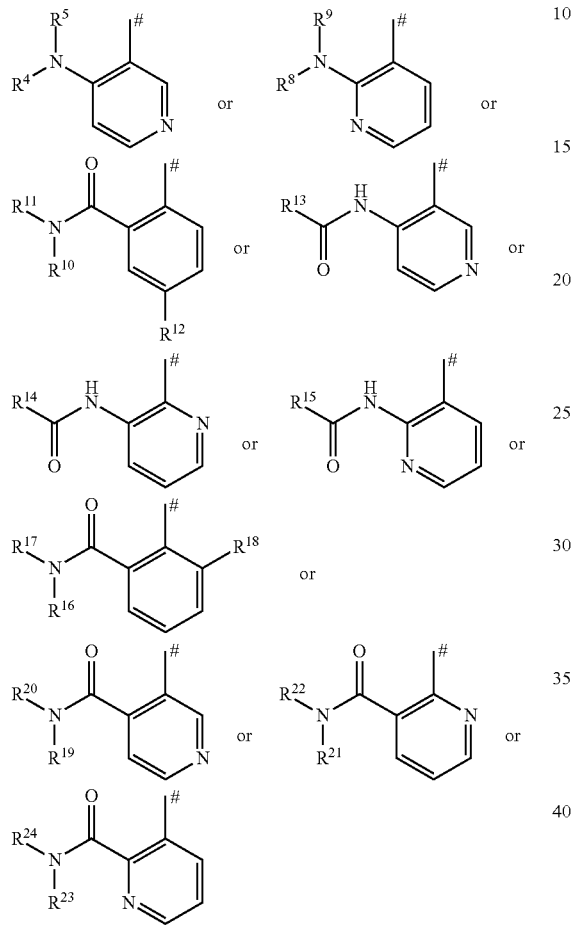

in which
# represents the point of attachment to the 1,2,4-triazolyl-ring,

R⁴ represents hydrogen,
R⁵ represents $C_1$-$C_5$-alkyl,
  where alkyl may be substituted by 1 to 2 substituents independently of one another selected from the group consisting of fluorine, hydroxy, amino, hydroxycarbonyl, aminocarbonyl, trifluoromethyl, $C_3$-$C_6$-cycloalkyl, 4- to 7-membered heterocyclyl and $C_1$-$C_4$-alkoxycarbonyl,
    wherein cycloalkyl may be substituted by one substituent hydroxy and amino,
    and
    wherein heterocyclyl may be substituted by 1 to 3 substituents of oxo,
or
R⁴ and R⁵ together with the nitrogen atom to which they are attached form a 4- to 6-membered heterocyclyl,
  where heterocyclyl may be substituted by 1 to 3 substituents independently of one another selected from the group consisting of oxo, chlorine, fluorine, hydroxy, aminocarbonyl and methyl, R⁸ represents hydrogen,
R⁹ represents $C_1$-$C_5$-alkyl or $C_3$-$C_6$-cycloalkyl,
  where alkyl may be substituted by 1 to 2 substituents independently of one another selected from the group consisting of fluorine, hydroxy, amino, trifluoromethyl, $C_3$-$C_6$-cycloalkyl and 4- to 7-membered heterocyclyl,
    wherein heterocyclyl may be substituted by 1 to 3 substituents of oxo,
  where cycloalkyl may be substituted by 1 to 3 substituents independently of one another selected from the group consisting of fluorine, trifluoromethyl and methyl,
or
R⁸ and R⁹ together with the nitrogen atom to which they are attached form a 4- to 6-membered heterocyclyl,
  where heterocyclyl may be substituted by 1 to 3 substituents independently of one another selected from the group consisting of oxo, chlorine, fluorine, hydroxy, aminocarbonyl, trifluoromethyl and methyl, R¹⁰ represents hydrogen, methyl, ethyl or propan-2-yl,
R¹¹ represents $C_1$-$C_5$-alkyl, prop-2-en-1-yl, 3-methylbut-2-en-1-yl, methoxy, $C_3$-$C_7$-cycloalkyl, phenyl, 4- to 6-membered heterocyclyl or 5- or 6-membered heteroaryl,
  where alkyl may be substituted by 1 to 2 substituents independently of one another selected from the group consisting of fluorine, cyano, hydroxy, amino, aminocarbonyl, trifluoromethyl, 1,1,2,2-tetrafluoroethyl, $C_3$-$C_6$-cycloalkyl, phenyl, 4- to 7-membered heterocyclyl and 5- or 6-membered heteroaryl,
    wherein phenyl may be substituted by 1 to 3 of fluorine,
    and
    wherein heterocyclyl may be substituted by 1 to 3 substituents independently of one another selected from the group consisting of oxo and methyl,
    and
    wherein heteroaryl may be substituted by 1 to 3 substituents of methyl,
  where cycloalkyl may be substituted by 1 to 3 substituents independently of one another selected from the group consisting of fluorine, hydroxy, amino and methyl,
  and
  where phenyl may be substituted by 1 to 3 substituents independently of one another selected from the group consisting of chlorine, fluorine, hydroxy, amino and methyl,
  and
  where heterocyclyl may be substituted by 1 to 3 substituents of oxo,
  and
  where heteroaryl may be substituted by 1 to 3 substituents independently of one another selected from the group consisting of chlorine, fluorine, hydroxy, amino, methyl and ethyl,
or
R¹⁰ and R¹¹ together with the nitrogen atom to which they are attached form a 4- to 7-membered heterocyclyl, 6-oxo-2,5,7-triazaspiro[3.4]octan-2-yl, 2-oxa-5-azabicyclo[2.2.1]hept-5-yl or 5-methyl-2,5-diazabicyclo[2.2.1]hept-2-yl, where heterocyclyl may be substituted by 1 to 3 substituents independently of one another selected from the group consisting of oxo, chlorine, fluorine, hydroxy, formyl, aminocarbonyl, methyl, ethyl, methoxy, methoxymethyl, dimethylamino and methylcarbonylamino, $R^{12}$ represents hydrogen, chlorine or fluorine, $R^{13}$ represents methyl, methoxy or $C_3$-$C_6$-cycloalkyl, where methyl and methoxy may be substituted by one substituent independently of one another selected from the group consisting of trifluoromethyl and $C_3$-$C_6$-cycloalkyl, and where cycloalkyl may be substituted by 1 to 3 substituents independently of one another selected from the group consisting of fluorine and trifluoromethyl, $R^{14}$ represents trifluoromethyl, methyl, methoxy, 2,2,2-trifluoroethylamino, $C_3$-$C_6$-cycloalkyl or 4- to 6-membered heterocyclyl, where methyl and methoxy may be substituted by one substituent independently of one another selected from the group consisting of fluorine, trifluoromethyl, methoxy, $C_3$-$C_6$-cycloalkyl, methylsulfonyl and methylsulfonylamino, and where cycloalkyl may be substituted by 1 to 3 substituents independently of one another selected from the group consisting of fluorine and trifluoromethyl, and where heterocyclyl may be substituted by 1 to 3 substituents of oxo, $R^{15}$ represents $C_1$-$C_5$-alkyl, 2,2,2-trifluoroethoxy, prop-2-en-1-yl, but-3-en-2-yl, $C_3$-$C_7$-cycloalkyl, phenyl, 4- to 6-membered heterocyclyl or 5- or 6-membered heteroaryl, where alkyl may be substituted by one substituent selected from the group consisting of hydroxy, trifluoromethyl, methoxy, methylsulfanyl, methylamino, $C_3$-$C_6$-cycloalkyl, phenyl, 4- to 7-membered heterocyclyl and 5- or 6-membered heteroaryl, wherein heterocyclyl may be substituted by 1 to 3 substituents of oxo, and wherein heteroaryl may be substituted by 1 to 3 substituents of methyl, and where cycloalkyl may be substituted by 1 to 3 substituents independently of one another selected from the group consisting of fluorine, aminocarbonyl, trifluoromethyl and methyl, and where phenyl may be substituted by 1 to 3 substituents independently of one another selected from the group consisting of fluorine, cyano, hydroxyl and methyl, and where heterocyclyl may be substituted by 1 to 3 substituents independently of one another selected from the group consisting of oxo and methyl, and where heteroaryl may be substituted by 1 to 3 substituents independently of one another selected from the group consisting of fluorine, methyl and ethyl, $R^{16}$ represents hydrogen or methyl, $R^{17}$ represents $C_1$-$C_5$-alkyl or $C_3$-$C_7$-cycloalkyl, where alkyl may be substituted by 1 to 2 substituents independently of one another selected from the group consisting of hydroxy, amino, trifluoromethyl and $C_3$-$C_6$-cycloalkyl, and where cycloalkyl may be substituted by 1 to 3 substituents independently of one another selected from the group consisting of fluorine, trifluoromethyl and methyl, or $R^{16}$ and $R^{17}$ together with the nitrogen atom to which they are attached form a 4- to 7-membered heterocyclyl or 2-oxa-6-azaspiro[3.3]hept-6-yl, where heterocyclyl may be substituted by 1 to 3 substituents independently of one another selected from the group consisting of oxo, chlorine, fluorine, hydroxy, aminocarbonyl, trifluoromethyl, methyl, ethyl and methoxymethyl, $R^{18}$ represents chlorine or trifluoromethyl, $R^{19}$ represents hydrogen, $R^{20}$ represents $C_1$-$C_5$-alkyl or $C_3$-$C_6$-cycloalkyl, where alkyl may be substituted by 1 to 2 substituents of trifluoromethyl, and where cycloalkyl may be substituted by 1 to 3 substituents independently of one another selected from the group consisting of fluorine and methyl, or $R^{19}$ and $R^{20}$ together with the nitrogen atom to which they are attached form a 4- to 6-membered heterocyclyl, where heterocyclyl may be substituted by one substituent of methoxymethyl, $R^{21}$ represents hydrogen, $R^{22}$ represents $C_1$-$C_5$-alkyl or $C_3$-$C_6$-cycloalkyl, where alkyl may be substituted by 1 to 2 substituents independently of one another selected from the group consisting of trifluoromethyl and $C_3$-$C_6$-cycloalkyl, and where cycloalkyl may be substituted by 1 to 3 substituents independently of one another selected from the group consisting of fluorine, cyano and methyl, or $R^{21}$ and $R^{22}$ together with the nitrogen atom to which they are attached form a 4- to 6-membered heterocyclyl, where heterocyclyl may be substituted by one substituent of methoxymethyl, $R^{23}$ represents hydrogen or methyl, $R^{24}$ represents $C_1$-$C_5$-alkyl or $C_3$-$C_6$-cycloalkyl, where alkyl may be substituted by 1 to 2 substituents independently of one another selected from the group consisting of hydroxy, amino, trifluoromethyl and $C_3$-$C_6$-cycloalkyl, and where cycloalkyl may be substituted by 1 to 3 substituents independently of one another selected from the group consisting of fluorine, trifluoromethyl and methyl, or $R^{23}$ and $R^{24}$ together with the nitrogen atom to which they are attached form a 4- to 6-membered heterocyclyl, where heterocyclyl may be substituted by 1 to 3 substituents independently of one another selected from the group consisting of oxo, chlorine, fluorine, hydroxy, aminocarbonyl, trifluoromethyl and methyl, $R^3$ represents a group of the formula

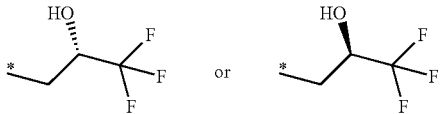

in which

* represents the point of attachment to the 2,4-dihydro-3H-1,2,4-triazolyl-ring, and pharmaceutically acceptable salts thereof, solvates thereof and the solvates of the salts thereof.

Preference is also given to compounds of the general formula (I) in which $R^1$ represents hydrogen, $R^2$ represents a group of the formula

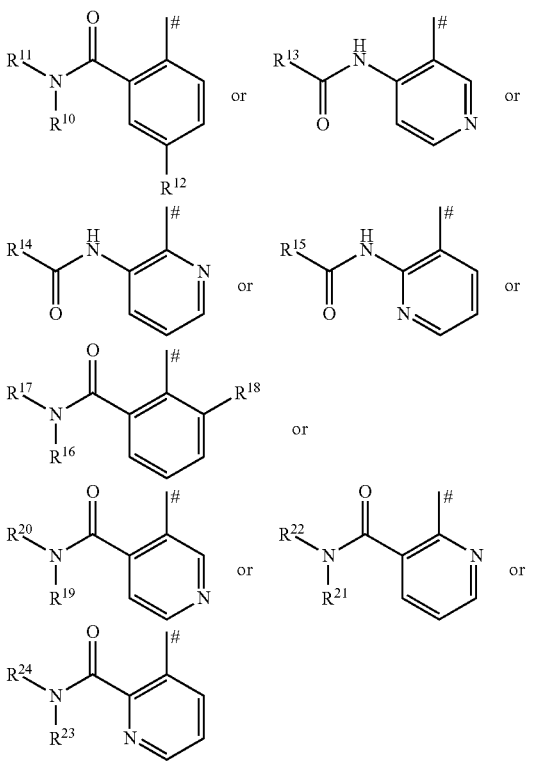

in which # represents the point of attachment to the 1,2,4-triazolyl-ring, $R^{10}$ represents hydrogen, methyl, ethyl or propan-2-yl, $R^{11}$ represents $C_1$-$C_5$-alkyl, prop-2-en-1-yl, 3-methylbut-2-en-1-yl, methoxy, $C_3$-$C_7$-cycloalkyl, phenyl, 4- to 6-membered heterocyclyl or 5- or 6-membered heteroaryl, where alkyl may be substituted by 1 to 2 substituents independently of one another selected from the group consisting of fluorine, cyano, hydroxy, amino, aminocarbonyl, trifluoromethyl, 1,1,2,2-tetrafluoroethyl, $C_3$-$C_6$-cycloalkyl, phenyl, 4- to 7-membered heterocyclyl and 5- or 6-membered heteroaryl, wherein phenyl may be substituted by 1 to 3 of fluorine, and wherein heterocyclyl may be substituted by 1 to 3 substituents independently of one another selected from the group consisting of oxo and methyl, and wherein heteroaryl may be substituted by 1 to 3 substituents of methyl, where cycloalkyl may be substituted by 1 to 3 substituents independently of one another selected from the group consisting of fluorine, hydroxy, amino and methyl, and where phenyl may be substituted by 1 to 3 substituents independently of one another selected from the group consisting of chlorine, fluorine, hydroxy, amino and methyl, and where heterocyclyl may be substituted by 1 to 3 substituents of oxo, and where heteroaryl may be substituted by 1 to 3 substituents independently of one another selected from the group consisting of chlorine, fluorine, hydroxy, amino, methyl and ethyl, or $R^{10}$ and $R^{11}$ together with the nitrogen atom to which they are attached form a 4- to 7-membered heterocyclyl, 6-oxo-2,5,7-triazaspiro[3.4]octan-2-yl, 2-oxa-5-azabicyclo[2.2.1]hept-5-yl or 5-methyl-2,5-diazabicyclo[2.2.1]hept-2-yl, where heterocyclyl may be substituted by 1 to 3 substituents independently of one another selected from the group consisting of oxo, chlorine, fluorine, hydroxy, formyl, aminocarbonyl, methyl, ethyl, methoxy, methoxymethyl, dimethylamino and methylcarbonylamino, $R^{12}$ represents hydrogen, chlorine or fluorine, $R^{13}$ represents methyl, methoxy or $C_3$-$C_6$-cycloalkyl, where methyl and methoxy may be substituted by one substituent independently of one another selected from the group consisting of trifluoromethyl and $C_3$-$C_6$-cycloalkyl, and where cycloalkyl may be substituted by 1 to 3 substituents independently of one another selected from the group consisting of fluorine and trifluoromethyl, $R^{14}$ represents trifluoromethyl, methyl, methoxy, 2,2,2-trifluoroethylamino, $C_3$-$C_6$-cycloalkyl or 4- to 6-membered heterocyclyl, where methyl and methoxy may be substituted by one substituent independently of one another selected from the group consisting of fluorine, trifluoromethyl, methoxy, $C_3$-$C_6$-cycloalkyl, methylsulfonyl and methylsulfonylamino, and where cycloalkyl may be substituted by 1 to 3 substituents independently of one another selected from the group consisting of fluorine and trifluoromethyl, and where heterocyclyl may be substituted by 1 to 3 substituents of oxo, $R^{15}$ represents $C_1$-$C_5$-alkyl, 2,2,2-trifluoroethoxy, prop-2-en-1-yl, but-3-en-2-yl, $C_3$-$C_7$-cycloalkyl, phenyl, 4- to 6-membered heterocyclyl or 5- or 6-membered heteroaryl, where alkyl may be substituted by one substituent selected from the group consisting of hydroxy, trifluoromethyl, methoxy, methylsulfanyl, methylamino, $C_3$-$C_6$-cycloalkyl, phenyl, 4- to 7-membered heterocyclyl and 5- or 6-membered heteroaryl,
   wherein heterocyclyl may be substituted by 1 to 3 substituents of oxo,
   and
   wherein heteroaryl may be substituted by 1 to 3 substituents of methyl,
and
where cycloalkyl may be substituted by 1 to 3 substituents independently of one another selected from the group consisting of fluorine, aminocarbonyl, trifluoromethyl and methyl,
and
where phenyl may be substituted by 1 to 3 substituents independently of one another selected from the group consisting of fluorine, cyano, hydroxyl and methyl,
and
where heterocyclyl may be substituted by 1 to 3 substituents independently of one another selected from the group consisting of oxo and methyl,
and
where heteroaryl may be substituted by 1 to 3 substituents independently of one another selected from the group consisting of fluorine, methyl and ethyl, $R^{16}$ represents hydrogen or methyl,
$R^{17}$ represents $C_1$-$C_5$-alkyl or $C_3$-$C_7$-cycloalkyl,
   where alkyl may be substituted by 1 to 2 substituents independently of one another selected from the group consisting of hydroxy, amino, trifluoromethyl and $C_3$-$C_6$-cycloalkyl,
   and
   where cycloalkyl may be substituted by 1 to 3 substituents independently of one another selected from the group consisting of fluorine, trifluoromethyl and methyl,
or
$R^{16}$ and $R^{17}$ together with the nitrogen atom to which they are attached form a 4- to 7-membered heterocyclyl or 2-oxa-6-azaspiro[3.3]hept-6-yl,
   where heterocyclyl may be substituted by 1 to 3 substituents independently of one another selected from the group consisting of oxo, chlorine, fluorine, hydroxy, aminocarbonyl, trifluoromethyl, methyl, ethyl and methoxymethyl,
$R^{18}$ represents chlorine or trifluoromethyl,
$R^{19}$ represents hydrogen,
$R^{20}$ represents $C_1$-$C_5$-alkyl or $C_3$-$C_6$-cycloalkyl,
   where alkyl may be substituted by 1 to 2 substituents of trifluoromethyl,
   and
   where cycloalkyl may be substituted by 1 to 3 substituents independently of one another selected from the group consisting of fluorine and methyl,
or
$R^{19}$ and $R^{20}$ together with the nitrogen atom to which they are attached form a 4- to 6-membered heterocyclyl,
   where heterocyclyl may be substituted by one substituent of methoxymethyl,
$R^{21}$ represents hydrogen,
$R^{22}$ represents $C_1$-$C_5$-alkyl or $C_3$-$C_6$-cycloalkyl,
   where alkyl may be substituted by 1 to 2 substituents independently of one another selected from the group consisting of trifluoromethyl and $C_3$-$C_6$-cycloalkyl,
   and
   where cycloalkyl may be substituted by 1 to 3 substituents independently of one another selected from the group consisting of fluorine, cyano and methyl,
or
$R^{21}$ and $R^{22}$ together with the nitrogen atom to which they are attached form a 4- to 6-membered heterocyclyl,
   where heterocyclyl may be substituted by one substituent of methoxymethyl,
$R^{23}$ represents hydrogen or methyl,
$R^{24}$ represents $C_1$-$C_5$-alkyl or $C_3$-$C_6$-cycloalkyl,
   where alkyl may be substituted by 1 to 2 substituents independently of one another selected from the group consisting of hydroxy, amino, trifluoromethyl and $C_3$-$C_6$-cycloalkyl,
   and
   where cycloalkyl may be substituted by 1 to 3 substituents independently of one another selected from the group consisting of fluorine, trifluoromethyl and methyl,
or
$R^{23}$ and $R^{24}$ together with the nitrogen atom to which they are attached form a 4- to 6-membered heterocyclyl,
   where heterocyclyl may be substituted by 1 to 3 substituents independently of one another selected from the group consisting of oxo, chlorine, fluorine, hydroxy, aminocarbonyl, trifluoromethyl and methyl,
$R^3$ represents a group of the formula

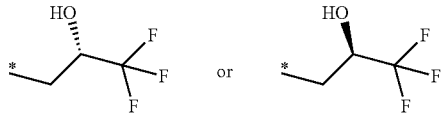

in which
* represents the point of attachment to the 2,4-dihydro-3H-1,2,4-triazolyl-ring,
and pharmaceutically acceptable salts thereof, solvates thereof and the solvates of the salts thereof.

Preference is also given to compounds of the general formula (I) in which
$R^1$ represents hydrogen,
$R^2$ represents a group of the formula

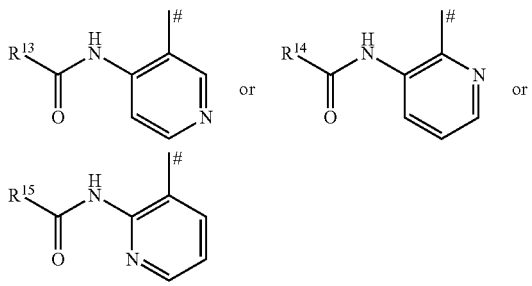

in which
# represents the point of attachment to the 1,2,4-triazolyl-ring, $R^{13}$ represents methyl, methoxy or $C_3$-$C_6$-cycloalkyl,
  where methyl and methoxy may be substituted by one substituent independently of one another selected from the group consisting of trifluoromethyl and $C_3$-$C_6$-cycloalkyl,
  and
  where cycloalkyl may be substituted by 1 to 3 substituents independently of one another selected from the group consisting of fluorine and trifluoromethyl,
$R^{14}$ represents trifluoromethyl, methyl, methoxy, 2,2,2-trifluoroethylamino, $C_3$-$C_6$-cycloalkyl or 4- to 6-membered heterocyclyl,
  where methyl and methoxy may be substituted by one substituent independently of one another selected from the group consisting of fluorine, trifluoromethyl, methoxy, $C_3$-$C_6$-cycloalkyl, methylsulfonyl and methylsulfonylamino,
  and
  where cycloalkyl may be substituted by 1 to 3 substituents independently of one another selected from the group consisting of fluorine and trifluoromethyl,
  and
  where heterocyclyl may be substituted by 1 to 3 substituents of oxo,
$R^{15}$ represents $C_1$-$C_5$-alkyl, 2,2,2-trifluoroethoxy, prop-2-en-1-yl, but-3-en-2-yl, $C_3$-$C_7$-cycloalkyl, phenyl, 4- to 6-membered heterocyclyl or 5- or 6-membered heteroaryl,
  where alkyl may be substituted by one substituent selected from the group consisting of hydroxy, trifluoromethyl, methoxy, methylsulfanyl, methylamino, $C_3$-$C_6$-cycloalkyl, phenyl, 4- to 7-membered heterocyclyl and 5- or 6-membered heteroaryl,
    wherein heterocyclyl may be substituted by 1 to 3 substituents of oxo,
    and
    wherein heteroaryl may be substituted by 1 to 3 substituents of methyl,
  and
  where cycloalkyl may be substituted by 1 to 3 substituents independently of one another selected from the group consisting of fluorine, aminocarbonyl, trifluoromethyl and methyl,
  and
  where phenyl may be substituted by 1 to 3 substituents independently of one another selected from the group consisting of fluorine, cyano, hydroxyl and methyl,
  and
  where heterocyclyl may be substituted by 1 to 3 substituents independently of one another selected from the group consisting of oxo and methyl,
  and
  where heteroaryl may be substituted by 1 to 3 substituents independently of one another selected from the group consisting of fluorine, methyl and ethyl,
$R^3$ represents a group of the formula

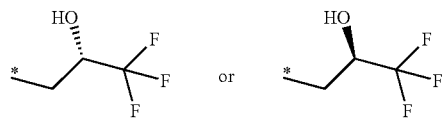

in which
* represents the point of attachment to the 2,4-dihydro-3H-1,2,4-triazolyl-ring,
and pharmaceutically acceptable salts thereof, solvates thereof and the solvates of the salts thereof.

Preference is also given to compounds of the general formula (I) in which
$R^1$ represents hydrogen,
$R^2$ represents a group of the formula

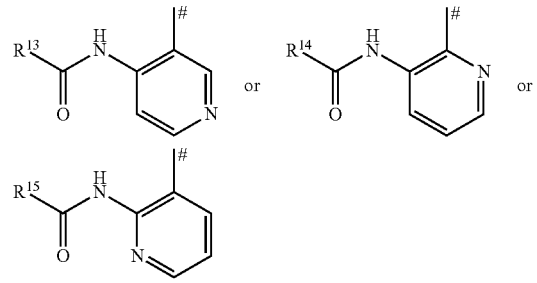

in which
# represents the point of attachment to the 1,2,4-triazolyl-ring,
$R^{13}$ represents methyl or cyclopropyl,
  where methyl is substituted by one substituent independently of one another selected from the group consisting of trifluoromethyl and cyclopropyl,
  and
  where cyclopropyl may be substituted by 1 to 3 substituents independently of one another selected from the group consisting of fluorine and trifluoromethyl,
$R^{14}$ represents methyl, cyclopropyl, thietanyl or tetrahydrothiophenyl,
  where methyl is substituted by one substituent selected from the group consisting of trifluoromethyl, cyclopropyl, methylsulfonyl and methylsulfonylamino,
  and
  where cyclopropyl may be substituted by 1 to 3 substituents independently of one another selected from the group consisting of fluorine and trifluoromethyl,
  and
  where thietanyl and tetrahydrothiophenyl are substituted by 2 substituents of oxo,
$R^{15}$ represents methyl, 2,2-dimethyl-prop-1-yl, cyclopropyl, cyclobutyl, tetrahydrothiophenyl, imidazolyl, pyridyl or pyrazinyl,
  where methyl is substituted by one substituent selected from the group consisting of trifluoromethyl, methylsulfanyl and cyclopropyl,
  and
  where cyclopropyl and cyclobutyl may be substituted by 1 to 3 substituents independently of one another selected from the group consisting of fluorine, trifluoromethyl and methyl,
  and
  where tetrahydrothiophenyl is substituted by 2 substituents of oxo,
  and
  where imidazolyl, pyridyl and pyrazinyl may be substituted by one substituent selected from the group consisting of methyl and ethyl,
$R^3$ represents a group of the formula

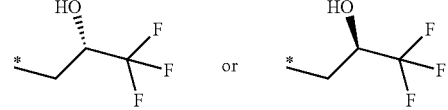

in which
* represents the point of attachment to the 2,4-dihydro-3H-1,2,4-triazolyl-ring,
and pharmaceutically acceptable salts thereof, solvates thereof and the solvates of the salts thereof.

Preference is also given to compounds of the general formula (I) in which
$R^1$ represents hydrogen,
$R^2$ represents a group of the formula

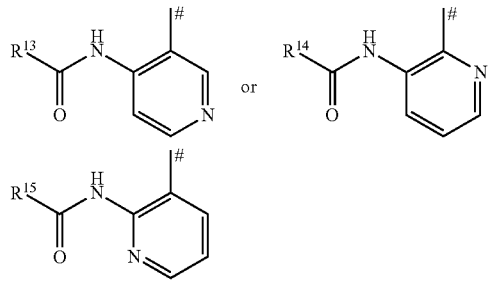

in which
# represents the point of attachment to the 1,2,4-triazolyl-ring,
$R^{13}$ represents methyl or cyclopropyl,
  where methyl is substituted by one substituent independently of one another selected from the group consisting of trifluoromethyl and cyclopropyl,
  and
  where cyclopropyl may be substituted by 1 to 3 substituents independently of one another selected from the group consisting of fluorine and trifluoromethyl,
$R^{14}$ represents methyl, cyclopropyl, thietanyl or tetrahydrothiophenyl,
  where methyl is substituted by one substituent selected from the group consisting of trifluoromethyl, cyclopropyl and methylsulfonyl,
  and
  where cyclopropyl may be substituted by 1 to 3 substituents independently of one another selected from the group consisting of fluorine and trifluoromethyl,
  and
  where thietanyl and tetrahydrothiophenyl are substituted by 2 substituents of oxo,
$R^{15}$ represents methyl, cyclopropyl, cyclobutyl or tetrahydrothiophenyl,
  where methyl is substituted by one substituent selected from the group consisting of trifluoromethyl, methylsulfanyl and cyclopropyl,
  and
  where cyclopropyl and cyclobutyl may be substituted by 1 to 3 substituents independently of one another selected from the group consisting of fluorine, trifluoromethyl and methyl,
  and
  where tetrahydrothiophenyl is substituted by 2 substituents of oxo,
$R^3$ represents a group of the formula

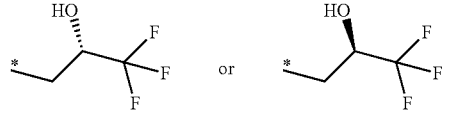

in which
* represents the point of attachment to the 2,4-dihydro-3H-1,2,4-triazolyl-ring,
and pharmaceutically acceptable salts thereof, solvates thereof and the solvates of the salts thereof.

Preference is also given to compounds of the general formula (I) in which
$R^1$ represents hydrogen,
$R^2$ represents a group of the formula

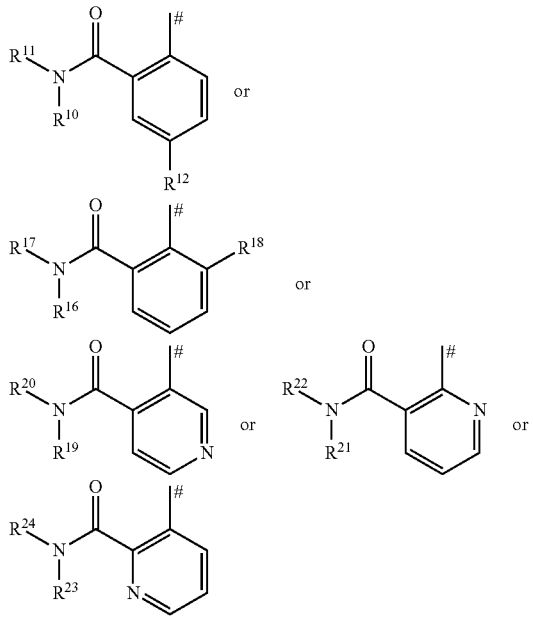

in which
# represents the point of attachment to the 1,2,4-triazolyl-ring,
$R^{10}$ represents hydrogen, methyl, ethyl or propan-2-yl,
$R^{11}$ represents $C_1$-$C_5$-alkyl, prop-2-en-1-yl, 3-methylbut-2-en-1-yl, methoxy, $C_3$-$C_7$-cycloalkyl, phenyl, 4- to 6-membered heterocyclyl or 5- or 6-membered heteroaryl,
  where alkyl may be substituted by 1 to 2 substituents independently of one another selected from the group consisting of fluorine, cyano, hydroxy, amino, aminocarbonyl, trifluoromethyl, 1,1,2,2-tetrafluoroethyl, $C_3$-$C_6$-cycloalkyl, phenyl, 4- to 7-membered heterocyclyl and 5- or 6-membered heteroaryl,
    wherein phenyl may be substituted by 1 to 3 of fluorine,
    and
    wherein heterocyclyl may be substituted by 1 to 3 substituents independently of one another selected from the group consisting of oxo and methyl,
    and
    wherein heteroaryl may be substituted by 1 to 3 substituents of methyl,
  where cycloalkyl may be substituted by 1 to 3 substituents independently of one another selected from the group consisting of fluorine, hydroxy, amino and methyl,
  and
  where phenyl may be substituted by 1 to 3 substituents independently of one another selected from the group consisting of chlorine, fluorine, hydroxy, amino and methyl,
  and
  where heterocyclyl may be substituted by 1 to 3 substituents of oxo,
  and
  where heteroaryl may be substituted by 1 to 3 substituents independently of one another selected from the group consisting of chlorine, fluorine, hydroxy, amino, methyl and ethyl, or $R^{10}$ and $R^{11}$ together with the nitrogen atom to which they are attached form a 4- to 7-membered heterocyclyl, 6-oxo-2,5,7-triazaspiro[3.4]octan-2-yl, 2-oxa-5-azabicyclo[2.2.1]hept-5-yl or 5-methyl-2,5-diazabicyclo[2.2.1]hept-2-yl, where heterocyclyl may be substituted by 1 to 3 substituents independently of one another selected from the group consisting of oxo, chlorine, fluorine, hydroxy, formyl, aminocarbonyl, methyl, ethyl, methoxy, methoxymethyl, dimethylamino and methylcarbonylamino, $R^{12}$ represents hydrogen, chlorine or fluorine, $R^{16}$ represents hydrogen or methyl, $R^{17}$ represents $C_1$-$C_5$-alkyl or $C_3$-$C_7$-cycloalkyl, where alkyl may be substituted by 1 to 2 substituents independently of one another selected from the group consisting of hydroxy, amino, trifluoromethyl and $C_3$-$C_6$-cycloalkyl, and where cycloalkyl may be substituted by 1 to 3 substituents independently of one another selected from the group consisting of fluorine, trifluoromethyl and methyl, or $R^{16}$ and $R^{17}$ together with the nitrogen atom to which they are attached form a 4- to 7-membered heterocyclyl or 2-oxa-6-azaspiro[3.3]hept-6-yl, where heterocyclyl may be substituted by 1 to 3 substituents independently of one another selected from the group consisting of oxo, chlorine, fluorine, hydroxy, aminocarbonyl, trifluoromethyl, methyl, ethyl and methoxymethyl, $R^{18}$ represents chlorine or trifluoromethyl, $R^{19}$ represents hydrogen, $R^{20}$ represents $C_1$-$C_5$-alkyl or $C_3$-$C_6$-cycloalkyl, where alkyl may be substituted by 1 to 2 substituents of trifluoromethyl, and where cycloalkyl may be substituted by 1 to 3 substituents independently of one another selected from the group consisting of fluorine and methyl, or $R^{19}$ and $R^{20}$ together with the nitrogen atom to which they are attached form a 4- to 6-membered heterocyclyl, where heterocyclyl may be substituted by one substituent of methoxymethyl, $R^{21}$ represents hydrogen, $R^{22}$ represents $C_1$-$C_5$-alkyl or $C_3$-$C_6$-cycloalkyl, where alkyl may be substituted by 1 to 2 substituents independently of one another selected from the group consisting of trifluoromethyl and $C_3$-$C_6$-cycloalkyl, and where cycloalkyl may be substituted by 1 to 3 substituents independently of one another selected from the group consisting of fluorine, cyano and methyl, or $R^{21}$ and $R^{22}$ together with the nitrogen atom to which they are attached form a 4- to 6-membered heterocyclyl, where heterocyclyl may be substituted by one substituent of methoxymethyl, $R^{23}$ represents hydrogen or methyl, $R^{24}$ represents $C_1$-$C_5$-alkyl or $C_3$-$C_6$-cycloalkyl, where alkyl may be substituted by 1 to 2 substituents independently of one another selected from the group consisting of hydroxy, amino, trifluoromethyl and $C_3$-$C_6$-cycloalkyl, and where cycloalkyl may be substituted by 1 to 3 substituents independently of one another selected from the group consisting of fluorine, trifluoromethyl and methyl, or $R^{23}$ and $R^{24}$ together with the nitrogen atom to which they are attached form a 4- to 6-membered heterocyclyl, where heterocyclyl may be substituted by 1 to 3 substituents independently of one another selected from the group consisting of oxo, chlorine, fluorine, hydroxy, aminocarbonyl, trifluoromethyl and methyl, $R^3$ represents a group of the formula

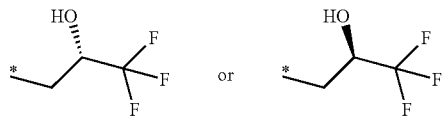

in which

* represents the point of attachment to the 2,4-dihydro-3H-1,2,4-triazolyl-ring, and pharmaceutically acceptable salts thereof, solvates thereof and the solvates of the salts thereof.

Preference is also given to compounds of the general formula (I) in which $R^1$ represents hydrogen, $R^2$ represents a group of the formula

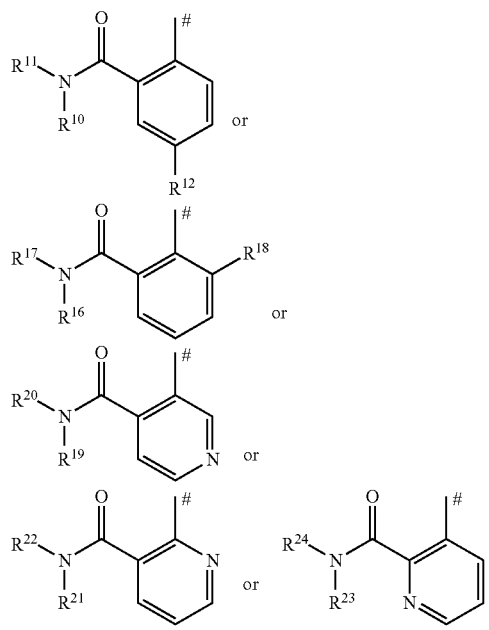

in which # represents the point of attachment to the 1,2,4-triazolyl-ring, $R^{10}$ represents hydrogen or methyl, $R^{11}$ represents methyl, ethyl, 2-methyl-prop-1-yl, 2-amino-2-methyl-prop-1-yl, cyclopropyl, cyclobutyl, cyclopentyl, phenyl, pyrazolyl or pyridyl,
  where methyl and ethyl may be substituted by one substituent selected from the group consisting of trifluoromethyl, cyclopropyl and pyrazolyl,
    wherein pyrazolyl is substituted by one substituent of methyl,
  where cyclopropyl and cyclobutyl may be substituted by 1 to 3 substituents independently of one another selected from the group consisting of fluorine and methyl,
  and
  where phenyl is substituted by 1 to 3 substituents of fluorine,
  and
  where pyrazolyl and pyridyl may be substituted by 1 to 3 substituents independently of one another selected from the group consisting of fluorine and methyl,
or
$R^{10}$ and $R^{11}$ together with the nitrogen atom to which they are attached form a pyrrolidinyl, piperidinyl or morpholinyl,
  where pyrrolidinyl, piperidinyl and morpholinyl may be substituted by 1 to 3 substituents independently of one another selected from the group consisting of fluorine, hydroxy, methyl, methoxy, methoxymethyl and dimethylamino,
$R^{12}$ represents hydrogen,
$R^{16}$ represents hydrogen or methyl,
$R^{17}$ represents methyl, ethyl, 2-methyl-prop-1-yl, 2-amino-2-methyl-prop-1-yl, cyclopropyl, cyclobutyl or cyclopentyl,
  where methyl and ethyl may be substituted by one substituent selected from the group consisting of trifluoromethyl and cyclopropyl,
  and
  where cyclopropyl and cyclobutyl may be substituted by 1 to 3 substituents independently of one another selected from the group consisting of fluorine and methyl,
or
$R^{16}$ and $R^{17}$ together with the nitrogen atom to which they are attached form a pyrrolidinyl, piperidinyl or morpholinyl,
  where pyrrolidinyl, piperidinyl and morpholinyl may be substituted by 1 to 3 substituents independently of one another selected from the group consisting of fluorine, hydroxy, methyl and methoxymethyl,
$R^{18}$ represents chlorine or trifluoromethyl,
$R^{19}$ represents hydrogen,
$R^{20}$ represents methyl, ethyl, 2-methyl-prop-1-yl or cyclopropyl,
  where methyl and ethyl may be substituted by one substituent of trifluoromethyl,
  and
  where cyclopropyl may be substituted by 1 to 3 substituents independently of one another selected from the group consisting of fluorine and methyl,
or
$R^{19}$ and $R^{20}$ together with the nitrogen atom to which they are attached form a pyrrolidinyl,
  where pyrrolidinyl may be substituted by one substituent of methoxymethyl,
$R^{21}$ represents hydrogen,
$R^{22}$ represents methyl, ethyl, 2-methyl-prop-1-yl, cyclopropyl, cyclobutyl or cyclopentyl,
  where methyl and ethyl may be substituted by one substituent from the group consisting of trifluoromethyl and cyclopropyl,
  and
  where cyclopropyl and cyclobutyl may be substituted by 1 to 3 substituents independently of one another selected from the group consisting of fluorine, cyano and methyl,
or
$R^{21}$ and $R^{22}$ together with the nitrogen atom to which they are attached form a pyrrolidinyl,
  where pyrrolidinyl may be substituted by one substituent of methoxymethyl,
$R^{23}$ represents hydrogen or methyl,
$R^{24}$ represents methyl, ethyl, 2-methyl-prop-1-yl, 2-amino-2-methyl-prop-1-yl, cyclopropyl, cyclobutyl or cyclopentyl,
  where methyl and ethyl may be substituted by one substituent selected from the group consisting of trifluoromethyl and cyclopropyl,
  and
  where cyclopropyl and cyclobutyl may be substituted by 1 to 3 substituents independently of one another selected from the group consisting of fluorine, trifluoromethyl and methyl,
or
$R^{23}$ and $R^{24}$ together with the nitrogen atom to which they are attached form a pyrrolidinyl, piperidinyl and morpholinyl,
  where pyrrolidinyl, piperidinyl and morpholinyl may be substituted by 1 to 3 substituents independently of one another selected from the group consisting of fluorine, hydroxyl and methyl,
$R^3$ represents a group of the formula

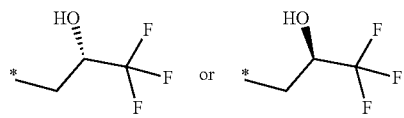

in which
  * represents the point of attachment to the 2,4-dihydro-3H-1,2,4-triazolyl-ring,
and pharmaceutically acceptable salts thereof, solvates thereof and the solvates of the salts thereof.

Preference is also given to compounds of the general formula (I) in which
$R^1$ represents hydrogen,
$R^2$ represents a group of the formula

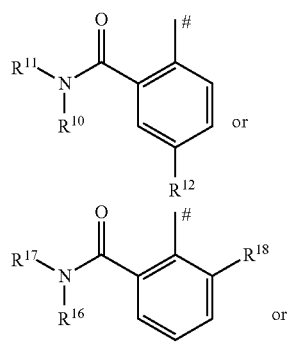

-continued

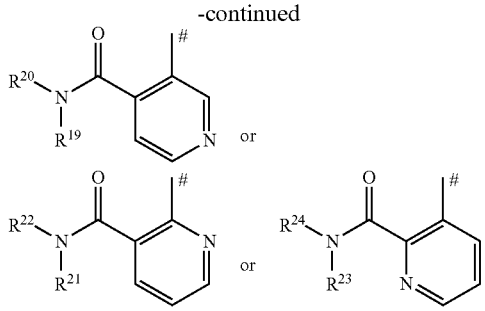

in which
# represents the point of attachment to the 1,2,4-triazolyl-ring,
$R^{10}$ represents hydrogen or methyl,
$R^{11}$ represents methyl, ethyl, 2-methyl-prop-1-yl, 2-amino-2-methyl-prop-1-yl, cyclopropyl, cyclobutyl or cyclopentyl,
where methyl and ethyl may be substituted by one substituent selected from the group consisting of trifluoromethyl and cyclopropyl,
and
where cyclopropyl and cyclobutyl may be substituted by 1 to 3 substituents independently of one another selected from the group consisting of fluorine and methyl,
or
$R^{10}$ and $R^{11}$ together with the nitrogen atom to which they are attached form a pyrrolidinyl, piperidinyl or morpholinyl,
where pyrrolidinyl, piperidinyl and morpholinyl may be substituted by 1 to 3 substituents independently of one another selected from the group consisting of fluorine, hydroxy, methyl, methoxy, methoxymethyl and dimethylamino,
$R^{12}$ represents hydrogen,
$R^{16}$ represents hydrogen or methyl,
$R^{17}$ represents methyl, ethyl, 2-methyl-prop-1-yl, 2-amino-2-methyl-prop-1-yl, cyclopropyl, cyclobutyl or cyclopentyl,
where methyl and ethyl may be substituted by one substituent selected from the group consisting of trifluoromethyl and cyclopropyl,
and
where cyclopropyl and cyclobutyl may be substituted by 1 to 3 substituents independently of one another selected from the group consisting of fluorine and methyl,
or
$R^{16}$ and $R^{17}$ together with the nitrogen atom to which they are attached form a pyrrolidinyl, piperidinyl or morpholinyl,
where pyrrolidinyl, piperidinyl and morpholinyl may be substituted by 1 to 3 substituents independently of one another selected from the group consisting of fluorine, hydroxy, methyl and methoxymethyl,
$R^{18}$ represents chlorine or trifluoromethyl,
$R^{19}$ represents hydrogen,
$R^{20}$ represents methyl, ethyl, 2-methyl-prop-1-yl or cyclopropyl,
where methyl and ethyl may be substituted by one substituent of trifluoromethyl,
and
where cyclopropyl may be substituted by 1 to 3 substituents independently of one another selected from the group consisting of fluorine and methyl,
or
$R^{19}$ and $R^{20}$ together with the nitrogen atom to which they are attached form a pyrrolidinyl,
where pyrrolidinyl may be substituted by one substituent of methoxymethyl,
$R^{21}$ represents hydrogen,
$R^{22}$ represents methyl, ethyl, 2-methyl-prop-1-yl, cyclopropyl, cyclobutyl or cyclopentyl,
where methyl and ethyl may be substituted by one substituent from the group consisting of trifluoromethyl and cyclopropyl,
and
where cyclopropyl and cyclobutyl may be substituted by 1 to 3 substituents independently of one another selected from the group consisting of fluorine, cyano and methyl,
or
$R^{21}$ and $R^{22}$ together with the nitrogen atom to which they are attached form a pyrrolidinyl,
where pyrrolidinyl may be substituted by one substituent of methoxymethyl,
$R^{23}$ represents hydrogen or methyl,
$R^{24}$ represents methyl, ethyl, 2-methyl-prop-1-yl, 2-amino-2-methyl-prop-1-yl, cyclopropyl, cyclobutyl or cyclopentyl,
where methyl and ethyl may be substituted by one substituent selected from the group consisting of trifluoromethyl and cyclopropyl,
and
where cyclopropyl and cyclobutyl may be substituted by 1 to 3 substituents independently of one another selected from the group consisting of fluorine, trifluoromethyl and methyl,
or
$R^{23}$ and $R^{24}$ together with the nitrogen atom to which they are attached form a pyrrolidinyl, piperidinyl and morpholinyl,
where pyrrolidinyl, piperidinyl and morpholinyl may be substituted by 1 to 3 substituents independently of one another selected from the group consisting of fluorine, hydroxyl and methyl,
$R^3$ represents a group of the formula

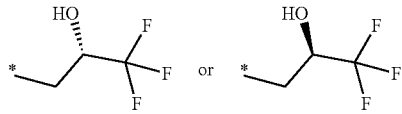

in which
* represents the point of attachment to the 2,4-dihydro-3H-1,2,4-triazolyl-ring,
and pharmaceutically acceptable salts thereof, solvates thereof and the solvates of the salts thereof.
Preference is also given to compounds of the general formula (I) in which
$R^1$ represents hydrogen,
$R^2$ represents a group of the formula

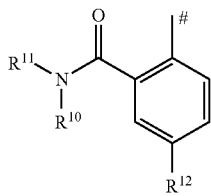

in which
# represents the point of attachment to the 1,2,4-triazolyl-ring,
$R^{10}$ represents hydrogen or methyl,
$R^{11}$ represents methyl, ethyl, 2-methyl-prop-1-yl, 2-amino-2-methyl-prop-1-yl, cyclopropyl, cyclobutyl or cyclopentyl,
  where methyl and ethyl may be substituted by one substituent selected from the group consisting of trifluoromethyl and cyclopropyl,
  and
  where cyclopropyl and cyclobutyl may be substituted by 1 to 3 substituents independently of one another selected from the group consisting of fluorine and methyl,
or
$R^{10}$ and $R^{11}$ together with the nitrogen atom to which they are attached form a pyrrolidinyl, piperidinyl or morpholinyl,
  where pyrrolidinyl, piperidinyl and morpholinyl may be substituted by 1 to 3 substituents independently of one another selected from the group consisting of fluorine, hydroxy, methyl, methoxy, methoxymethyl and dimethylamino,
$R^{12}$ represents hydrogen,
$R^3$ represents a group of the formula

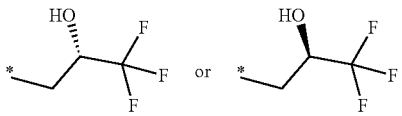

in which
* represents the point of attachment to the 2,4-dihydro-3H-1,2,4-triazolyl-ring,
and pharmaceutically acceptable salts thereof, solvates thereof and the solvates of the salts thereof.

Preference is also given to compounds of the general formula (I) in which
$R^1$ represents hydrogen,
$R^2$ represents a group of the formula

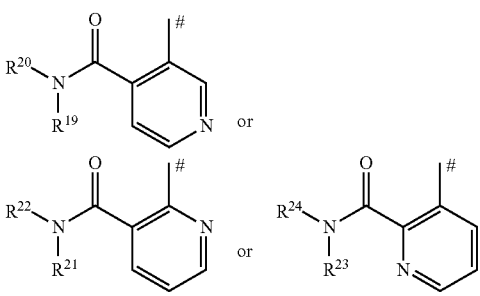

in which
# represents the point of attachment to the 1,2,4-triazolyl-ring,
$R^{19}$ represents hydrogen,
$R^{20}$ represents methyl, ethyl, 2-methyl-prop-1-yl or cyclopropyl,
  where methyl and ethyl may be substituted by one substituent of trifluoromethyl,
  and
  where cyclopropyl may be substituted by 1 to 3 substituents independently of one another selected from the group consisting of fluorine and methyl,
or
$R^{19}$ and $R^{20}$ together with the nitrogen atom to which they are attached form a pyrrolidinyl,
  where pyrrolidinyl may be substituted by one substituent of methoxymethyl,
$R^{21}$ represents hydrogen,
$R^{22}$ represents methyl, ethyl, 2-methyl-prop-1-yl, cyclopropyl, cyclobutyl or cyclopentyl,
  where methyl and ethyl may be substituted by one substituent from the group consisting of trifluoromethyl and cyclopropyl,
  and
  where cyclopropyl and cyclobutyl may be substituted by 1 to 3 substituents independently of one another selected from the group consisting of fluorine, cyano and methyl,
or
$R^{21}$ and $R^{22}$ together with the nitrogen atom to which they are attached form a pyrrolidinyl,
  where pyrrolidinyl may be substituted by one substituent of methoxymethyl,
$R^{23}$ represents hydrogen or methyl,
$R^{24}$ represents methyl, ethyl, 2-methyl-prop-1-yl, 2-amino-2-methyl-prop-1-yl, cyclopropyl, cyclobutyl or cyclopentyl,
  where methyl and ethyl may be substituted by one substituent selected from the group consisting of trifluoromethyl and cyclopropyl,
  and
  where cyclopropyl and cyclobutyl may be substituted by 1 to 3 substituents independently of one another selected from the group consisting of fluorine, trifluoromethyl and methyl,
or
$R^{23}$ and $R^{24}$ together with the nitrogen atom to which they are attached form a pyrrolidinyl, piperidinyl and morpholinyl,
  where pyrrolidinyl, piperidinyl and morpholinyl may be substituted by 1 to 3 substituents independently of one another selected from the group consisting of fluorine, hydroxyl and methyl,
$R^3$ represents a group of the formula

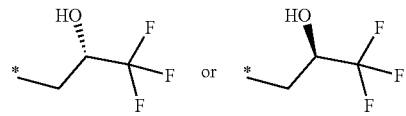

in which
* represents the point of attachment to the 2,4-dihydro-3H-1,2,4-triazolyl-ring, and pharmaceutically acceptable salts thereof, solvates thereof and the solvates of the salts thereof.

Preference is also given to compounds of the general formula (I) in which
$R^3$ represents a group of the formula

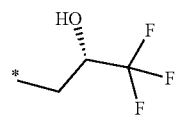

in which
* represents the point of attachment to the 2,4-dihydro-3H-1,2,4-triazolyl-ring.

In a particular further embodiment of the first aspect, the present invention covers combinations of two or more of the above mentioned embodiments under the heading "further embodiments of the first aspect of the present invention".

The present invention covers any sub-combination within any embodiment or aspect of the present invention of compounds of general formula (I).

The present invention covers the compounds of general formula (I) which are disclosed in the Example Section of this text, infra.

The present invention covers methods of preparing compounds of the present invention of general formula (I), said methods comprising the steps as described in the Experimental Section herein.

The schemes and procedures described below illustrate synthetic routes to the compounds of general formula (I) of the invention and are not intended to be limiting. It is clear to the person skilled in the art that the order of transformations as exemplified in schemes 1 to 12 can be modified in various ways. The order of transformations exemplified in these schemes is therefore not intended to be limiting. In addition, interconversion of any of the substituents R to $R^2$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis,* 3rd edition, Wiley 1999). Specific examples are described in the subsequent paragraphs.

The preparation of the compounds of the invention may be illustrated by means of the following synthetic schemes:

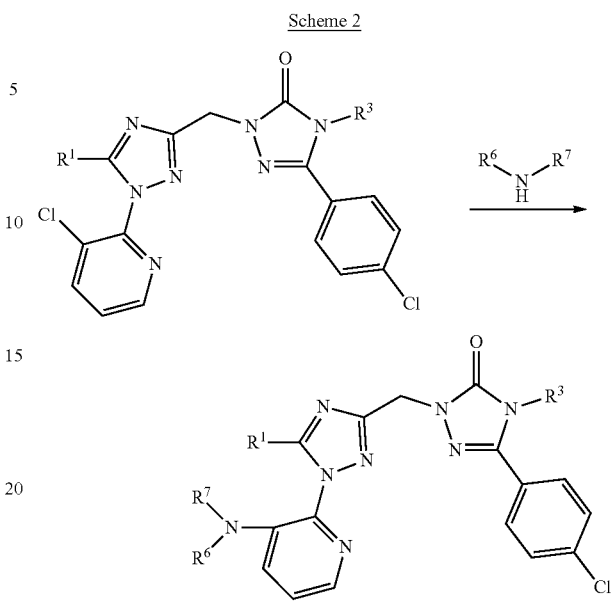

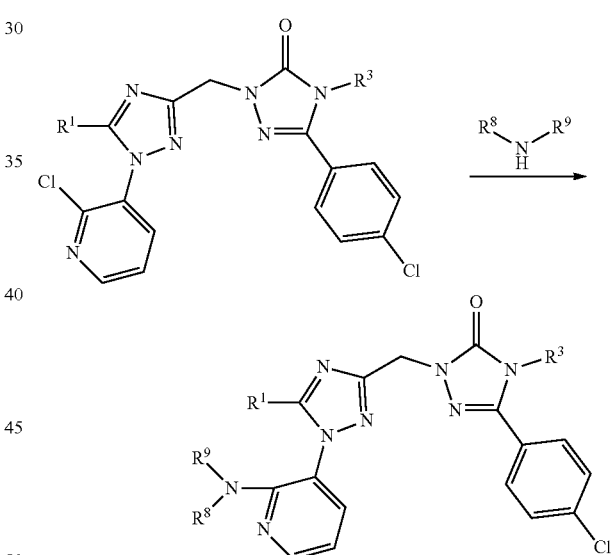

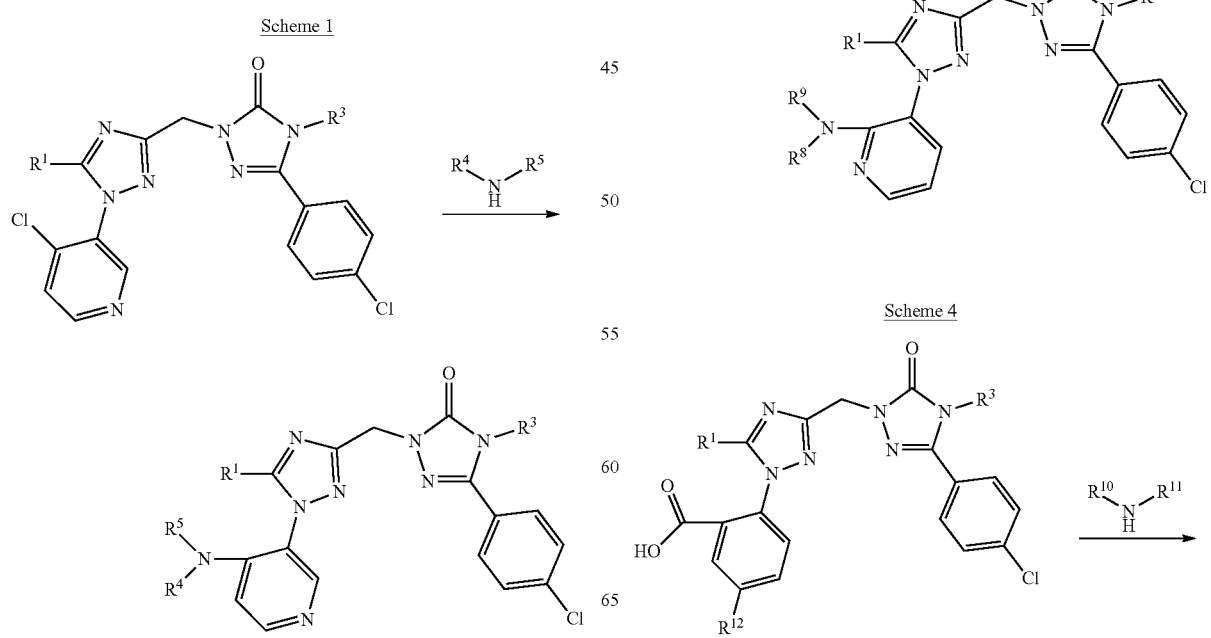

43
-continued
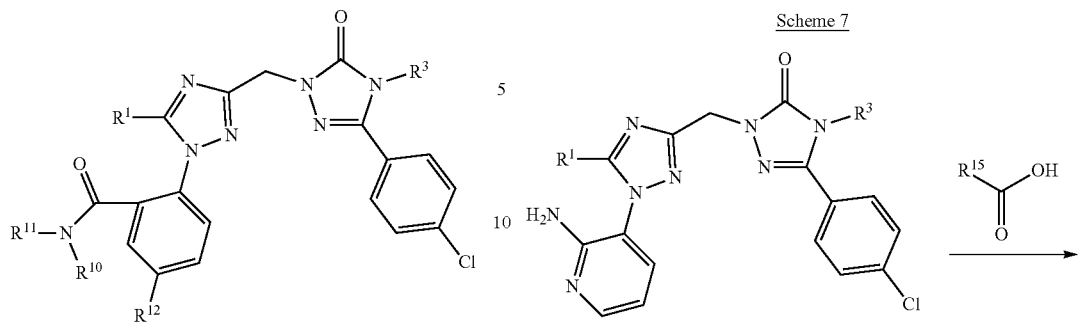
Scheme 5
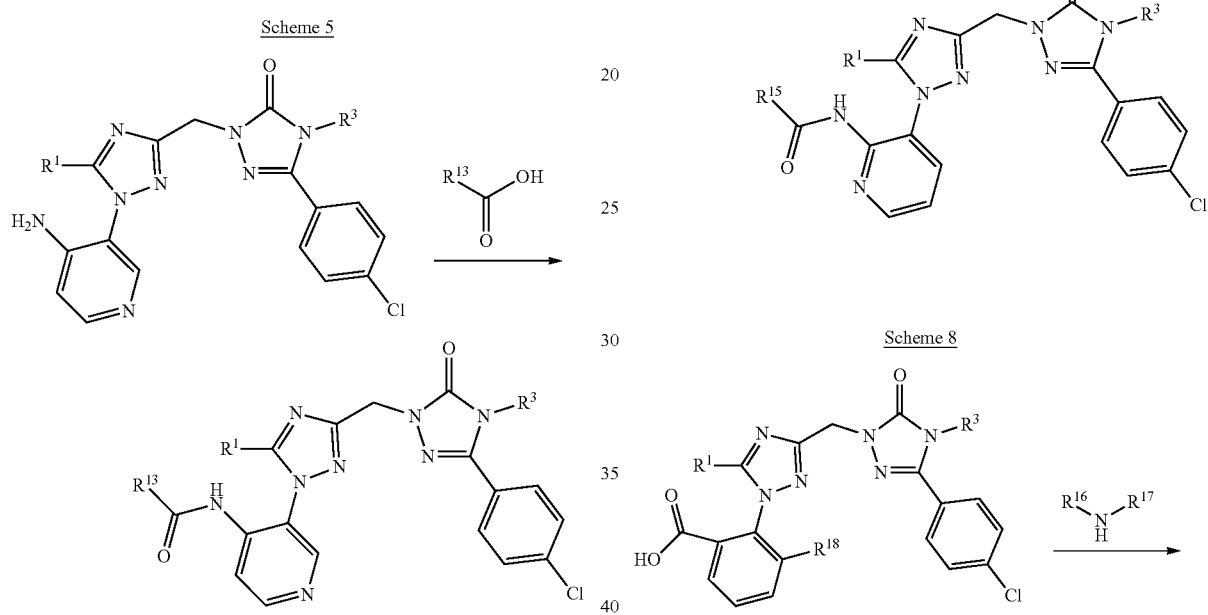
Scheme 6
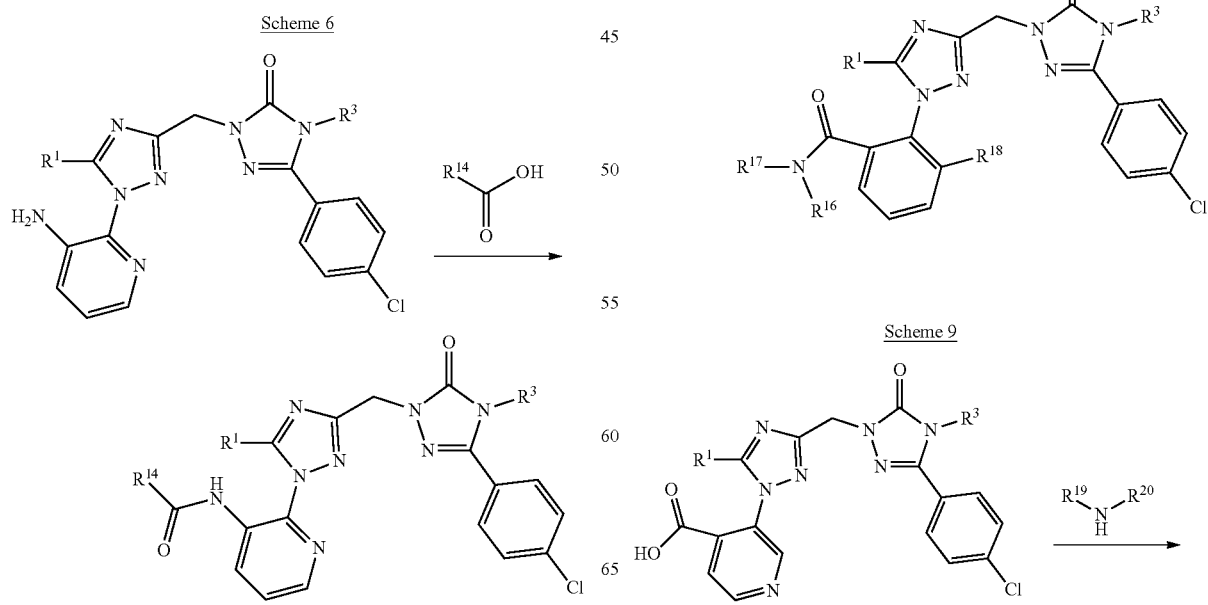
44
Scheme 7
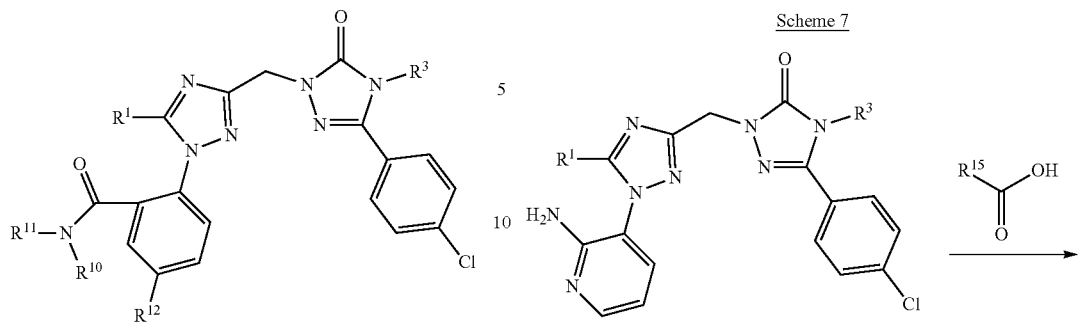
Scheme 8
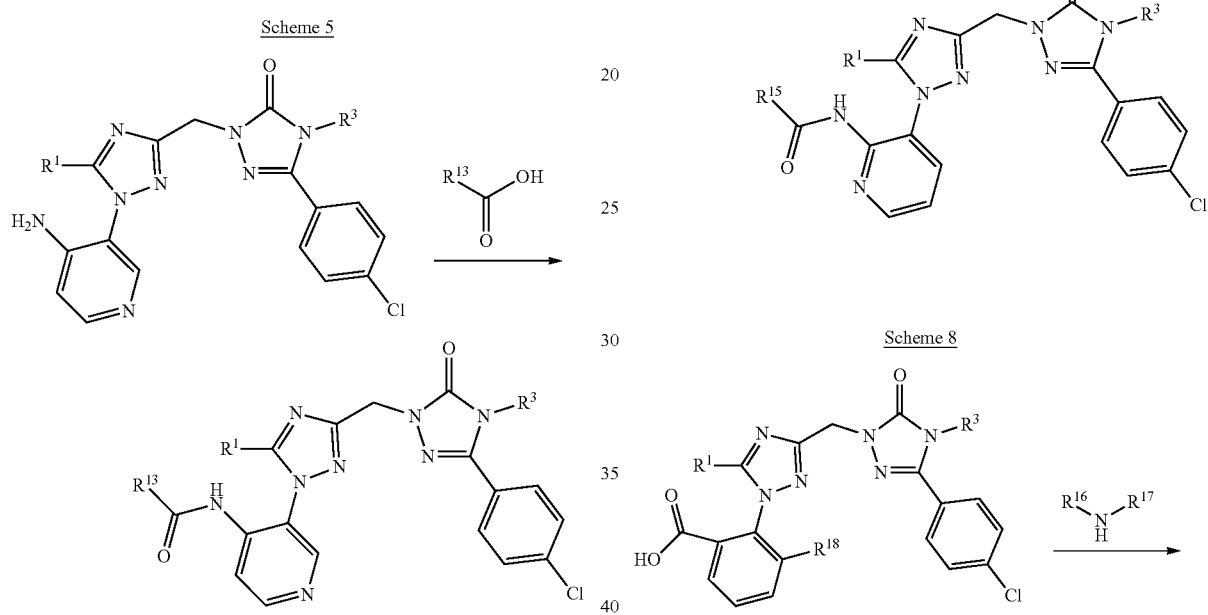
Scheme 9
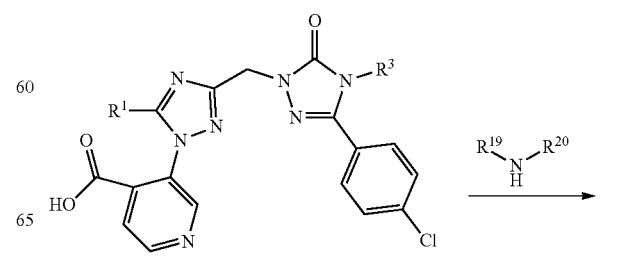

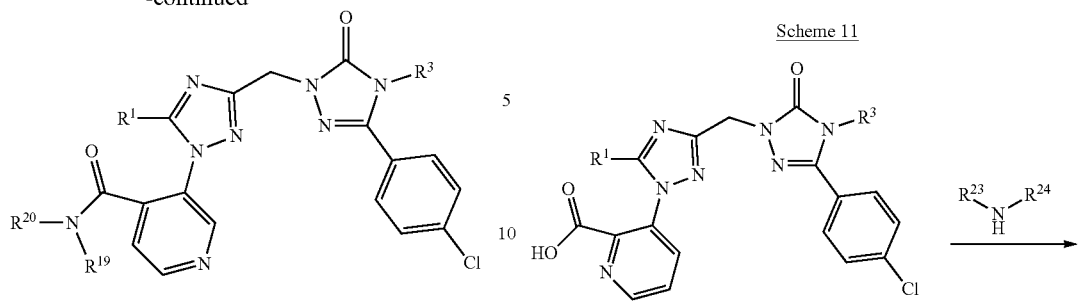
Scheme 10
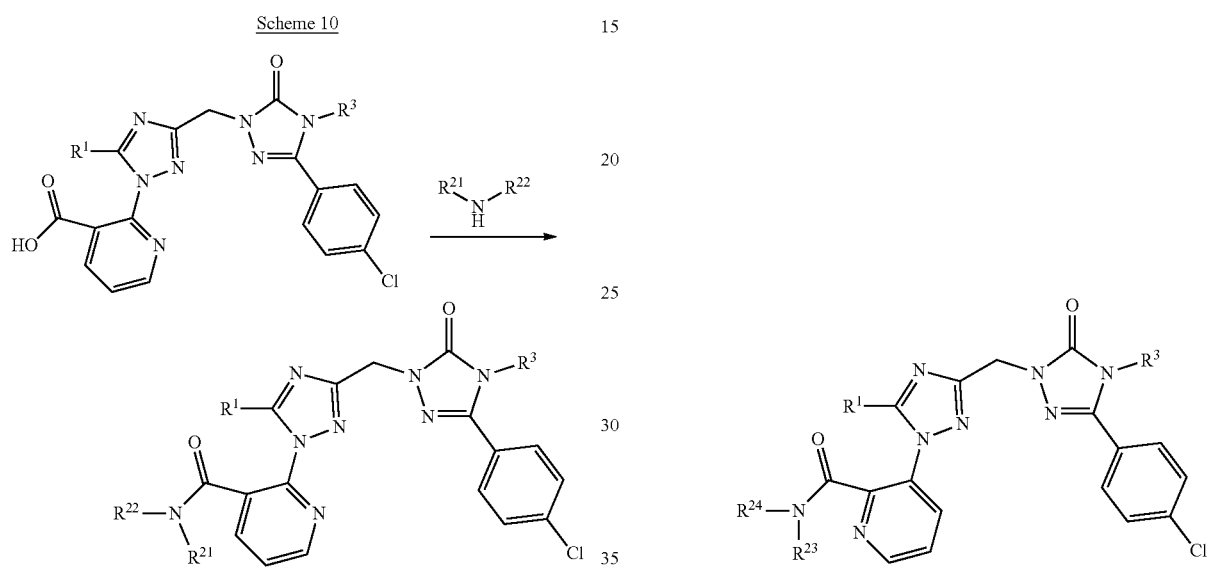
Scheme 11
Scheme 12
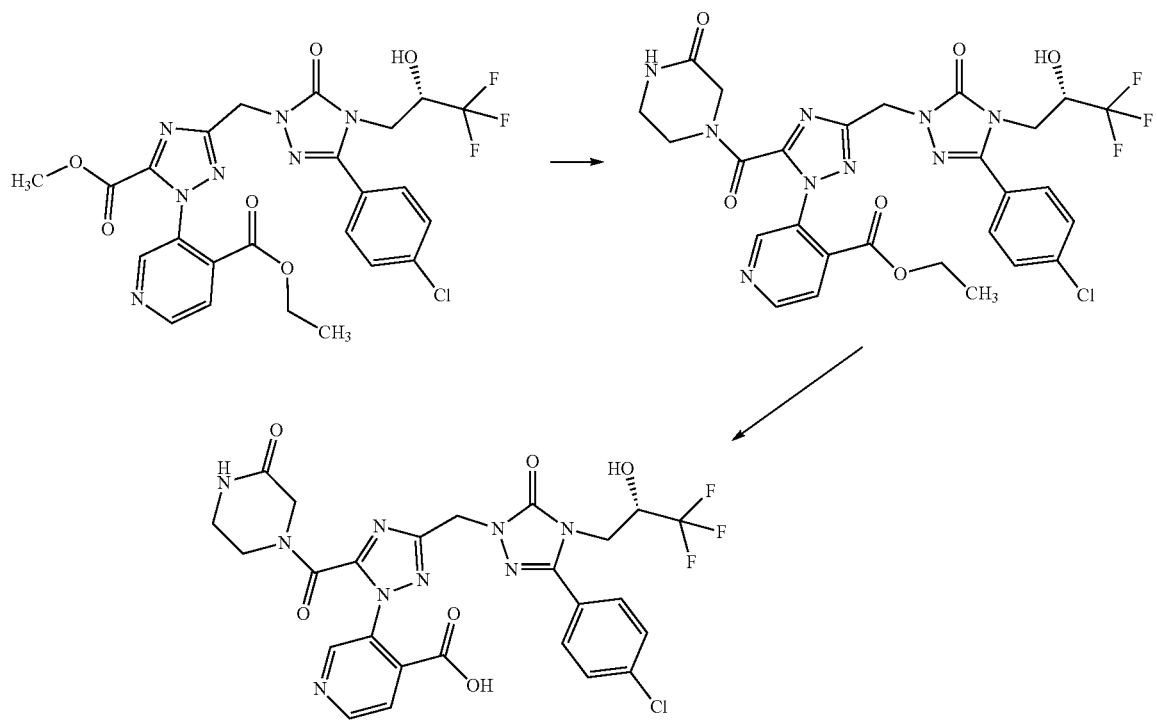

The starting materials are either commercially available, known from the literature, or can be prepared from readily available starting materials by adaptation of standard methods described in the literature. Detailed procedures and literature references for preparing the starting materials can also be found in the Experimental Part in the section on the preparation of the starting materials and intermediates.

The compounds of general formula (I) of the present invention can be converted to any salt, preferably pharmaceutically acceptable salts, as described herein, by any method which is known to the person skilled in the art. Similarly, any salt of a compound of general formula (I) of the present invention can be converted into the free compound, by any method which is known to the person skilled in the art.

The compounds of the present invention have valuable pharmacological properties and can be used for the prevention and/or treatment of various diseases and disease-induced states in humans and other mammals. Compounds of general formula (I) of the present invention demonstrate a valuable pharmacological spectrum of action and pharmacokinetic profile, both of which could not have been predicted. Compounds of the present invention have surprisingly been found to effectively inhibit the vasopressin V1a receptor and it is possible therefore that said compounds be used for the treatment and/or prevention of diseases, preferably renal and cardiovascular diseases in humans and animals.

In the context of the present invention, the term "treatment" or "treating" includes inhibiting, delaying, relieving, mitigating, arresting, reducing, or causing the regression of a disease, disorder, condition, or state, the development and/or progression thereof, and/or the symptoms thereof. The term "prevention" or "preventing" includes reducing the risk of having, contracting, or experiencing a disease, disorder, condition, or state, the development and/or progression thereof, and/or the symptoms thereof. The term prevention includes prophylaxis. Treatment or prevention of a disorder, disease, condition, or state may be partial or complete.

Throughout this document, for the sake of simplicity, the use of singular language is given preference over plural language, but is generally meant to include the plural language if not otherwise stated. For example, the expression "A method of treating a disease in a patient, comprising administering to a patient an effective amount of a compound of the general formula (I)" is meant to include the simultaneous treatment of more than one disease as well as the administration of more than one compound of the general formula (I).

The compounds of the present invention are potent selective or dual antagonists of vasopressin V1a and V2 receptors. The compounds of the invention are therefore expected to be highly valuable as therapeutic agents for the treatment and/or prevention of diseases, in particular for the treatment and/or prevention of cardiovascular and renal diseases.

The compounds according to the invention are suitable for the treatment and/or prevention of renal diseases, in particular of acute and chronic kidney diseases, diabetic kidney diseases, and of acute and chronic renal failure. The general terms 'renal disease' or 'kidney disease' describe a class of conditions in which the kidneys fail to filter and remove waste products from the blood. There are two major forms of kidney disease: acute kidney disease (acute kidney injury, AKI) and chronic kidney disease (CKD). The compounds according to the invention may further be used for the treatment and/or prevention of sequelae of acute kidney injury arising from multiple insults such as ischemia-reperfusion injury, radiocontrast administration, cardiopulmonary bypass surgery, shock and sepsis. In the sense of the present invention, the term renal failure or renal insufficiency comprises both acute and chronic manifestations of renal insufficiency, as well as underlying or related kidney diseases such as renal hypoperfusion, intradialytic hypotension, obstructive uropathy, glomerulopathies, IgA nephropathy, glomerulonephritis, acute glomerulonephritis, glomerulosclerosis, tubulointerstitial diseases, nephropathic diseases such as primary and congenital kidney disease, nephritis, Alport syndrome, kidney inflammation, immunological kidney diseases such as kidney transplant rejection, immune complex-induced kidney diseases, nephropathy induced by toxic substances, contrast medium-induced nephropathy; minimal change glomerulonephritis (lipoid); Membranous glomerulonephritis; focal segmental glomerulosclerosis (FSGS); hemolytic uremic syndrome (HUS), amyloidosis, Goodpasture's syndrome, Wegener's granulomatosis, Purpura Schanlein-Henoch, diabetic and non-diabetic nephropathy, pyelonephritis, renal cysts, nephrosclerosis, hypertensive nephrosclerosis and nephrotic syndrome, which can be characterized diagnostically, for example, by abnormally reduced creatinine and/or water excretion, abnormally increased blood concentrations of urea, nitrogen, potassium and/or creatinine, altered activity of renal enzymes such as, for example, glutamyl synthetase, altered urine osmolarity or urine volume, increased microalbuminuria, macroalbuminuria, lesions of glomeruli and arterioles, tubular dilatation, hyperphosphataemia and/or the need for dialysis. The present invention also comprises the use of the compounds according to the invention for the treatment and/or prevention of sequelae of renal insufficiency, for example pulmonary edema, heart failure, uraemia, anaemia, electrolyte disturbances (e.g. hyperkalaemia, hyponatraemia) and disturbances in bone and carbohydrate metabolism. The compounds according to the invention are also suitable for the treatment and/or prevention of polycystic kidney disease (PCKD) and of the syndrome of inadequate ADH secretion (SIADH).

Cardiovascular diseases in this context that may be treated and/or prevented with the compounds of the invention include, but are not limited to, the following: acute and chronic heart failure including worsening chronic heart failure (or hospitalization for heart failure) and including congestive heart failure, arterial hypertension, resistant hypertension, arterial pulmonary hypertension, coronary heart disease, stable and unstable angina pectoris, atrial and ventricular arrhythmias, disturbances of atrial and ventricular rhythm and conduction disturbances, for example atrioventricular blocks of degree I-III (AVB I-III), supraventricular tachyarrhythmia, atrial fibrillation, atrial flutter, ventricular fibrillation, ventricular flutter, ventricular tachyarrhythmia, torsade-de-pointes tachycardia, atrial and ventricular extrasystoles, AV-junction extrasystoles, sick-sinus syndrome, syncopes, AV-node re-entry tachycardia and Wolff-Parkinson-White syndrome, acute coronary syndrome (ACS), autoimmune heart diseases (pericarditis, endocarditis, valvulitis, aortitis, cardiomyopathies), shock such as cardiogenic shock, septic shock and anaphylactic shock, aneurysms, Boxer cardiomyopathy (premature ventricular contraction), furthermore thromboembolic diseases and ischaemias such as peripheral perfusion disturbances, reperfusion injury, arterial and venous thromboses, myocardial insufficiency, endothelial dysfunction, micro- and macrovascular damage (vasculitis) and for preventing restenoses such as after thrombolysis therapies, percutaneous transluminal angioplasty (PTA), percutaneous transluminal coronary angioplasty (PTCA), heart transplantation and bypass operations, arteriosclerosis, disturbances of lipid metabolism, hypolipoproteinaemias, dyslipidemias, hypertriglyceridemias, hyperlipidemias and combined hyperlipidemias, hypercholesterolaemias, abetalipoproteinaemia, sitosterolemia, xanthomatosis, Tangier disease, adipositas, obesity, metabolic syndrome, transitory and ischemic attacks, stroke, inflammatory cardiovascular diseases, peripheral and cardiac vascular diseases, peripheral circulation disorders, spasms of the coronary arteries and peripheral arteries, and edema such as, for example, pulmonary edema, cerebral edema, renal edema and heart failure-related edema.

In the sense of the present invention, the term heart failure also includes more specific or related disease forms such as right heart failure, left heart failure, global insufficiency, ischemic cardiomyopathy, dilatative cardiomyopathy, congenital heart defects, heart valve defects, heart failure with heart valve defects, mitral valve stenosis, mitral valve insufficiency, aortic valve stenosis, aortic valve insufficiency, tricuspidal stenosis, tricuspidal insufficiency, pulmonary valve stenosis, pulmonary valve insufficiency, combined heart valve defects, heart muscle inflammation (myocarditis), chronic myocarditis, acute myocarditis, viral myocarditis, diabetic heart failure, alcohol-toxic cardiomyopathy, cardiac storage diseases, heart failure with preserved ejection fraction (HFpEF or diastolic heart failure), and heart failure with reduced ejection fraction (HFrEF or systolic heart failure).

The compounds of the present invention may be particularly useful for the treatment and/or prevention of the cardiorenal syndrome (CRS) and its various subtypes. This term embraces certain disorders of the heart and kidneys whereby acute or chronic dysfunction in one organ may induce acute or chronic dysfunction of the other. CRS has been sub-classified into five types based upon the organ that initiated the insult as well as the acuity and chronicity of the disease (type 1: development of renal insufficiency resulting from acute decompensated heart failure; type 2: chronic congestive heart failure resulting in progressive renal dysfunction; type 3: acute cardiac dysfunction resulting from an abrupt fall in renal function; type 4: chronic kidney disease leading to cardiac remodeling; type 5: systemic disease involving both the heart and the kidneys) [see, for example, M. R. Kahn et al., Nature Rev. Cardiol. 10, 261-273 (2013)].

The compounds according to the invention are also suitable for the treatment and/or prevention of polycystic kidney disease (PCKD) and of the syndrome of inadequate ADH secretion (SIADH). Furthermore, the compounds of the invention are suitable for use as a diuretic for the treatment of edemas and in electrolyte disorders, in particular in hypervolemic and euvolemic hyponatremia.

Moreover, the compounds according to the invention may be used for the treatment and/or prevention of peripheral arterial disease (PAD) including claudication and including critical limb ischemia coronary microvascular dysfunction (CMD) including CMD type 1-4, primary and secondary Raynaud's phenomenon, microcirculation disturbances, claudication, peripheral and autonomic neuropathies, diabetic microangiopathies, diabetic retinopathy, diabetic limb ulcers, gangrene, CREST syndrome, erythematous disorders, rheumatic diseases and for promoting wound healing.

Furthermore, the compounds of the invention are suitable for treating urological diseases and diseases of the male and female urogenital system such as, for example, benign prostatic syndrome (BPS), benign prostatic hyperplasia (BPH), benign prostatic enlargement (BPE), bladder outlet obstruction (BOO), lower urinary tract syndromes (LUTS), neurogenic overactive bladder (OAB), interstitial cystitis (IC), urinary incontinence (UI) such as, for example, mixed, urge, stress and overflow incontinence (MUI, UUI, SUI, OUI), pelvic pains, erectile dysfunction, dysmenorrhea and endometriosis.

The compounds according to the invention may also be used for the treatment and/or prevention of inflammatory diseases, asthmatic diseases, chronic obstructive pulmonary disease (COPD), acute respiratory distress syndrome (ARDS), acute lung injury (ALI), alpha-1-antitrypsin deficiency (AATD), pulmonary fibrosis, pulmonary emphysema (e.g. smoking-induced pulmonary emphysema) and cystic fibrosis (CF). In addition, the compounds of the invention may be used for the treatment and/or prevention of pulmonary arterial hypertension (PAH) and other forms of pulmonary hypertension (PH), including pulmonary hypertension associated with left ventricular disease, HIV infection, sickle cell anaemia, thromboembolism (CTEPH), sarcoidosis, chronic obstructive pulmonary disease (COPD) or pulmonary fibrosis.

Additionally, the compounds according to the invention may be used for the treatment and/or prevention of liver cirrhosis, ascites, diabetes mellitus and diabetic complications such as, for example, neuropathy and nephropathy.

Further, the compounds of the invention are suitable for the treatment and/or prevention of central nervous disorders such as anxiety states, depression, glaucoma, cancer such as in particular pulmonary tumors, and circadian rhythm misalignment such as jet lag and shift work.

Furthermore, the compounds according to the invention may be useful for the treatment and/or prevention of pain conditions, diseases of the adrenals such as, for example, pheochromocytoma and adrenal apoplexy, diseases of the intestine such as, for example, Crohn's disease and diarrhea, menstrual disorders such as, for example, dysmenorrhea, endometriosis, preterm labor and tocolysis.

Due to their activity and selectivity profile, the compounds of the present invention are believed to be particularly suitable for the treatment and/or prevention of acute and chronic kidney diseases including diabetic nephropathy, acute and chronic heart failure, preeclampsia, peripheral arterial disease (PAD), coronary microvascular dysfunction (CMD), Raynaud's syndrome, dysmenorrhea, cardiorenal syndrome, hypervolemic and euvolemic hyponatremia, liver cirrhosis, ascites, edema and the syndrome of inadequate ADH secretion (SIADH).

The diseases mentioned above have been well characterized in humans, but also exist with a com-parable etiology in other mammals, and may be treated in those with the compounds and methods of the present invention.

Thus, the present invention further relates to the use of the compounds according to the invention for the treatment and/or prevention of diseases, especially of the aforementioned diseases.

The present invention further relates to the use of the compounds according to the invention for preparing a pharmaceutical composition for the treatment and/or prevention of diseases, especially of the aforementioned diseases.

The present invention further relates to the use of the compounds according to the invention in a method for the treatment and/or prevention of diseases, especially of the aforementioned diseases.

The present invention further relates to a method for the treatment and/or prevention of diseases, especially of the aforementioned diseases, by using an effective amount of at least one of the compounds according to the invention.

In accordance with another aspect, the present invention covers pharmaceutical combinations, in particular medicaments, comprising at least one compound of general formula (I) of the present invention and at least one or more further active ingredients, in particular for the treatment and/or prevention of diseases, especially of the aforementioned diseases.

Particularly, the present invention covers a pharmaceutical combination, which comprises:
- one or more first active ingredients, in particular compounds of general formula (I) as defined aforementioned, and
- one or more further active ingredients, in particular for the treatment and/or prevention of diseases, especially of the aforementioned diseases.

The term "combination" in the present invention is used as known to persons skilled in the art, it being possible for said combination to be a fixed combination, a non-fixed combination or a kit-of-parts.

A "fixed combination" in the present invention is used as known to persons skilled in the art and is defined as a combination wherein, for example, a first active ingredient, such as one or more compounds of general formula (I) of the present invention, and a further active ingredient are present together in one unit dosage or in one single entity. One example of a "fixed combination" is a pharmaceutical composition wherein a first active ingredient and a further active ingredient are present in admixture for simultaneous administration, such as in a formulation. Another example of a "fixed combination" is a pharmaceutical combination wherein a first active ingredient and a further active ingredient are present in one unit without being in admixture.

A non-fixed combination or "kit-of-parts" in the present invention is used as known to persons skilled in the art and is defined as a combination wherein a first active ingredient and a further active ingredient are present in more than one unit. One example of a non-fixed combination or kit-of-parts is a combination wherein the first active ingredient and the further active ingredient are present separately. It is possible for the components of the non-fixed combination or kit-of-parts to be administered separately, sequentially, simultaneously, concurrently or chronologically staggered.

The compounds of the present invention can be administered as the sole pharmaceutical agent or in combination with one or more other pharmaceutically active ingredients where the combination causes no unacceptable adverse effects. The present invention also covers such pharmaceutical combinations. For example, the compounds of the present invention can be combined with known agents for the treatment and/or prevention of diseases, especially of the aforementioned diseases.

In particular, the compounds of the present invention may be used in fixed or separate combination with
- antithrombotic agents, for example and preferably from the group of platelet aggregation inhibitors, anticoagulants and profibrinolytic substances;
- blood pressure lowering agents, for example and preferably from the group of calcium antagonists, angiotensin AII antagonists, ACE inhibitors, NEP inhibitors, vasopeptidase inhibitors, endothelin antagonists, renin inhibitors, alpha-blockers, beta-blockers, mineralocorticoid receptor antagonists and diuretics;
- antidiabetic agents (hypoglycemic or antihyperglycemic agents), such as for example and preferably insulin and derivatives, sulfonylureas, biguanides, thiazolidinediones, acarbose, DPP4 inhibitors, GLP-1 analogues, or SGLT inhibitors (gliflozins).
- organic nitrates and NO-donors, for example sodium nitroprusside, nitroglycerin, isosorbide mononitrate, isosorbide dinitrate, molsidomine or SIN-1, and inhalational NO;
- compounds that inhibit the degradation of cyclic guanosine monophosphate (cGMP), for example inhibitors of phosphodiesterases (PDE) 1, 2, 5 and/or 9, in particular PDE-5 inhibitors such as sildenafil, vardenafil, tadalafil, udenafil, dasantafil, avanafil, mirodenafil, lodenafil, CTP-499 or PF-00489791;
- positive-inotropic agents, such as for example cardiac glycosides (digoxin) and beta-adrenergic and dopaminergic agonists such as isoproterenol, adrenalin, noradrenalin, dopamine or dobut-amine;
- natriuretic peptides, such as for example atrial natriuretic peptide (ANP, anaritide), B-type natriuretic peptide or brain natriuretic peptide (BNP, nesiritide), C-type natriuretic peptide (CNP) or urodilatin;
- calcium sensitizers, such as for example and preferably levosimendan;
- NO- and heme-independent activators of soluble guanylate cyclase (sGC for example and with preference the compounds described in WO 01/19355, WO 01/19776, WO 01/19778, WO 01/19780, WO 02/070462 and WO 02/070510;
- NO-independent, but heme-dependent stimulators of guanylate cyclase (sGC), for example and with preference the compounds described in WO 00/06568, WO 00/06569, WO 02/42301, WO 03/095451, WO 2011/147809, WO 2012/004258, WO 2012/028647 and WO 2012/059549;
- agents, that stimulates the synthesis of cGMP, for example and with preference sGC modulators, for example and with preference riociguat, cinaciguat, vericiguat or BAY 1101042;
- inhibitors of human neutrophil elastase (HNE), such as for example sivelestat or DX-890 (reltran);
- compounds inhibiting the signal transduction cascade, in particular tyrosine and/or serine/threo-nine kinase inhibitors, such as for example nintedanib, dasatinib, nilotinib, bosutinib, regorafenib, sorafenib, sunitinib, cediranib, axitinib, telatinib, imatinib, brivanib, pazopanib, vatalanib, gefitinib, erlotinib, lapatinib, canertinib, lestaurtinib, pelitinib, semaxanib or tandutinib;
- compounds influencing the energy metabolism of the heart, such as for example and preferably etomoxir, dichloroacetate, ranolazine or trimetazidine, or full or partial adenosine A1 receptor agonists as GS-9667 (previously known as CVT-3619), capadenoson and neladenoson bialanate (BAY 1067197);
- compounds influencing the heart rate, such as for example and preferably ivabradine;
- cardiac myosin activators, such as for example and preferably omecamtiv mecarbil (CK-1827452);
- anti-inflammatory drugs such as non-steroidal anti-inflammatory drugs (NSAIDs) including acetylsalicylic acid (aspirin), ibuprofen and naproxen, glucocorticoids, NEP inhibitors, 5-aminosalicylic acid derivatives, leukotriene antagonists, TNF-alpha inhibitors and chemokine receptor antagonists such as CCR1, 2 and/or 5 inhibitors;
- fat metabolism altering agents, for example and preferably from the group of thyroid receptor agonists, cholesterol synthesis inhibitors, such as for example and preferably HMG-CoA-reductase or squalene synthesis inhibitors, ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbers, bile acid reabsorption inhibitors and lipoprotein(a) antagonists.

Antithrombotic agents are preferably to be understood as compounds from the group of platelet aggregation inhibitors, anticoagulants and profibrinolytic substances.

In a preferred embodiment of the invention, the compounds according to the invention are administered in combination with a platelet aggregation inhibitor, for example and preferably aspirin, clopi-dogrel, ticlopidine or dipyridamole.

In a preferred embodiment of the invention, the compounds according to the invention are administered in combination with a thrombin inhibitor, for example and preferably ximelagatran, dabigatran, melagatran, bivalirudin or enoxaparin.

In a preferred embodiment of the invention, the compounds according to the invention are administered in combination with a GPIIb/IIIa antagonist, for example and preferably tirofiban or abciximab.

In a preferred embodiment of the invention, the compounds according to the invention are administered in combination with a factor Xa inhibitor, for example and preferably rivaroxaban, apixaban, otamixaban, fidexaban, razaxaban, fondaparinux, idraparinux, DU-176b, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist, for example and preferably coumarin.

Blood pressure lowering agents are preferably to be understood as compounds from the group of calcium antagonists, angiotensin AII antagonists, ACE inhibitors, NEP inhibitors, vasopeptidase inhibitors, endothelin antagonists, renin inhibitors, alpha-blockers, beta-blockers, mineralocorticoid receptor antagonists and diuretics.

In a preferred embodiment of the invention, the compounds according to the invention are administered in combination with a calcium antagonist, for example and preferably nifedipine, amlodipine, verapamil or diltiazem.

In a preferred embodiment of the invention, the compounds according to the invention are administered in combination with an alpha-1-receptor blocker, for example and preferably prazosin or tam-sulosin.

In a preferred embodiment of the invention, the compounds according to the invention are administered in combination with a beta-blocker, for example and preferably propranolol, atenolol, timolol, pindolol, alprenolol, oxprenolol, penbutolol, bupranolol, metipranolol, nadolol, mepindolol, carazolol, sotalol, metoprolol, betaxolol, celiprolol, bisoprolol, carteolol, esmolol, labetalol, carve-dilol, adaprolol, landiolol, nebivolol, epanolol or bucindolol.

In a preferred embodiment of the invention, the compounds according to the invention are administered in combination with an angiotensin AII receptor antagonist, for example and preferably losar-tan, candesartan, valsartan, telmisartan, irbesartan, olmesartan, eprosartan, embursartan or azilsartan.

In a preferred embodiment of the invention, the compounds according to the invention are administered in combination with a vasopeptidase inhibitor or inhibitor of neutral endopeptidase (NEP), such as for example and preferably sacubitril, omapatrilat or AVE-7688.

In a preferred embodiment of the invention, the compounds according to the invention are administered in combination with a dual angiotensin AII receptor antagonist/NEP inhibitor (ARNI), for example and preferably LCZ696.

In a preferred embodiment of the invention, the compounds according to the invention are administered in combination with an ACE inhibitor, for example and preferably enalapril, captopril, lisino-pril, ramipril, delapril, fosinopril, quinopril, perindopril, benazepril or trandopril.

In a preferred embodiment of the invention, the compounds according to the invention are administered in combination with an endothelin antagonist, for example and preferably bosentan, darusentan, ambrisentan, tezosentan, sitaxsentan, avosentan, macitentan or atrasentan.

In a preferred embodiment of the invention, the compounds according to the invention are administered in combination with a renin inhibitor, for example and preferably aliskiren, SPP-600 or SPP-800.

In a preferred embodiment of the invention, the compounds according to the invention are administered in combination with a mineralocorticoid receptor antagonist, for example and preferably fine-renone, spironolactone, canrenone, potassium canrenoate, eplerenone, esaxerenone (CS-3150), or apararenone (MT-3995), CS-3150, or MT-3995.

In a preferred embodiment of the invention, the compounds according to the invention are administered in combination with a diuretic, such as for example and preferably furosemide, bumetanide, piretanide, torsemide, bendroflumethiazide, chlorothiazide, hydrochlorothiazide, xipamide, indapa-mide, hydroflumethiazide, methyclothiazide, polythiazide, trichloromethiazide, chlorothalidone, metolazone, quinethazone, acetazolamide, dichlorophenamide, methazolamide, glycerine, isosorbide, mannitol, amiloride or triamterene.

Fat metabolism altering agents are preferably to be understood as compounds from the group of CETP inhibitors, thyroid receptor agonists, cholesterol synthesis inhibitors such as HMG-CoA-reductase or squalene synthesis inhibitors, ACAT inhibitors, MTP inhibitors, PPAR-alpha, PPAR-gamma and/or PPAR-delta agonists, cholesterol absorption inhibitors, polymeric bile acid adsorbers, bile acid reabsorption inhibitors, lipase inhibitors and lipoprotein(a) antagonists.

In a preferred embodiment of the invention, the compounds according to the invention are administered in combination with a CETP inhibitor, for example and preferably dalcetrapib, anacetrapib, BAY 60-5521 or CETP-vaccine (Avant).

In a preferred embodiment of the invention, the compounds according to the invention are administered in combination with a thyroid receptor agonist, for example and preferably D-thyroxin, 3,5,3'-triiodothyronin (T3), CGS 23425 or axitirome (CGS 26214).

In a preferred embodiment of the invention, the compounds according to the invention are administered in combination with an HMG-CoA-reductase inhibitor from the class of statins, for example and preferably lovastatin, simvastatin, pravastatin, fluvastatin, atorvastatin, rosuvastatin or pitava-statin.

In a preferred embodiment of the invention, the compounds according to the invention are administered in combination with a squalene synthesis inhibitor, for example and preferably BMS-188494 or TAK-475.

In a preferred embodiment of the invention, the compounds according to the invention are administered in combination with an ACAT inhibitor, for example and preferably avasimibe, melinamide, pactimibe, eflucimibe or SMP-797.

In a preferred embodiment of the invention, the compounds according to the invention are administered in combination with an MTP inhibitor, for example and preferably implitapide, R-103757, BMS-201038 or JTT-130.

In a preferred embodiment of the invention, the compounds according to the invention are administered in combination with a PPAR-gamma agonist, for example and preferably pioglitazone or rosiglitazone.

In a preferred embodiment of the invention, the compounds according to the invention are administered in combination with a PPAR-delta agonist, for example and preferably GW 501516 or BAY 68-5042.

In a preferred embodiment of the invention, the compounds according to the invention are administered in combination with a cholesterol absorption inhibitor, for example and preferably ezetimibe, tiqueside or pamaqueside.

In a preferred embodiment of the invention, the compounds according to the invention are administered in combination with a lipase inhibitor, for example and preferably orlistat.

In a preferred embodiment of the invention, the compounds according to the invention are administered in combination with a polymeric bile acid adsorber, for example and preferably cholestyramine, colestipol, colesolvam, CholestaGel or colestimide.

In a preferred embodiment of the invention, the compounds according to the invention are administered in combination with a bile acid reabsorption inhibitor, for example and preferably ASBT (=IBAT) inhibitors such as AZD-7806, S-8921, AK-105, BARI-1741, SC-435 or SC-635.

In a preferred embodiment of the invention, the compounds according to the invention are administered in combination with a lipoprotein(a) antagonist, for example and preferably gemcabene calcium (CI-1027) or nicotinic acid.

In a preferred embodiment of the invention, the compounds according to the invention are administered in combination with a TGFbeta antagonist, by way of example and with preference pirfenidone or fresolimumab.

In a preferred embodiment of the invention, the compounds according to the invention are administered in combination with HIF-PH inhibitors, by way of example and with preference molidustat or roxadustat.

In a preferred embodiment of the invention, the compounds according to the invention are administered in combination with a CCR2 antagonist, by way of example and with preference CCX-140.

In a preferred embodiment of the invention, the compounds according to the invention are administered in combination with a TNFalpha antagonist, by way of example and with preference adalimumab.

In a preferred embodiment of the invention, the compounds according to the invention are administered in combination with a galectin-3 inhibitor, by way of example and with preference GCS-100.

In a preferred embodiment of the invention, the compounds according to the invention are administered in combination with a BMP-7 agonist, by way of example and with preference THR-184.

In a preferred embodiment of the invention, the compounds according to the invention are administered in combination with a NOX1/4 inhibitor, by way of example and with preference GKT-137831.

In a preferred embodiment of the invention, the compounds according to the invention are administered in combination with a medicament which affects the vitamin D metabolism, by way of example and with preference cholecalciferol or paracalcitol.

In a preferred embodiment of the invention, the compounds according to the invention are administered in combination with a cytostatic agent, by way of example and with preference cyclophosphamide.

In a preferred embodiment of the invention, the compounds according to the invention are administered in combination with an immunosuppressive agent, by way of example and with preference ciclosporin.

In a preferred embodiment of the invention, the compounds according to the invention are administered in combination with a phosphate binder, by way of example and with preference sevelamer or lanthanum carbonate.

In a preferred embodiment of the invention, the compounds according to the invention are administered in combination with a calcimimetic for therapy of hyperparathyroidism.

In a preferred embodiment of the invention, the compounds according to the invention are administered in combination with agents for iron deficit therapy, by way of example and with preference iron products.

In a preferred embodiment of the invention, the compounds according to the invention are administered in combination with agents for the therapy of hyperurikaemia, by way of example and with preference allopurinol or rasburicase.

In a preferred embodiment of the invention, the compounds according to the invention are administered in combination with glycoprotein hormone for the therapy of anaemia, by way of example and with preference erythropoietin.

In a preferred embodiment of the invention, the compounds according to the invention are administered in combination with biologics for immune therapy, by way of example and with preference abatacept, rituximab, eculizumab or belimumab.

In a preferred embodiment of the invention, the compounds according to the invention are administered in combination with Jak inhibitors, by way of example and with preference ruxolitinib, tofacitinib, baricitinib, CYT387, GSK2586184, lestaurtinib, pacritinib (SB1518) or TG101348.

In a preferred embodiment of the invention, the compounds according to the invention are administered in combination with prostacyclin analogs for therapy of microthrombi.

In a preferred embodiment of the invention, the compounds according to the invention are administered in combination with an alkali therapy, by way of example and with preference sodium bicarbonate.

In a preferred embodiment of the invention, the compounds according to the invention are administered in combination with an mTOR inhibitor, by way of example and with preference everolimus or rapamycin.

In a preferred embodiment of the invention, the compounds according to the invention are administered in combination with an NHE3 inhibitor, by way of example and with preference AZD1722.

In a preferred embodiment of the invention, the compounds according to the invention are administered in combination with an eNOS modulator, by way of example and with preference sapropterin.

In a preferred embodiment of the invention, the compounds according to the invention are administered in combination with a CTGF inhibitor, by way of example and with preference FG-3019.

In a preferred embodiment of the invention, the compounds according to the invention are administered in combination with antidiabetics (hypoglycemic or antihyperglycemic agents), such as for example and preferably insulin and derivatives, sulfonylureas such as tolbutamide, carbutamide, acetohexamide, chlorpropamide, glipizide, gliclazide, glibenclamide, glyburide, glibornuride, gliquidone, glisoxepide, glyclopyramide, glimepiride, JB253 and JB558, meglitinides such as repaglinide and nateglinide, biguanides such as metformin and buformin, thiazolidinediones such as rosiglitazone and pioglitazone, alpha-glucosidase inhibitors such as miglitol, acarbose and voglibose, DPP4 inhibitors such as vildagliptin, sitagliptin, saxagliptin, linagliptin, alogliptin, septagliptin and teneligliptin, GLP-1 analogues such as exenatide (also exendin-4, liraglutide, lixisenatide and taspoglutide, or SGLT inhibitors (gliflozins) such as canagliflozin, dapagliflozin and empagliflozin.

In a particularly preferred embodiment, the compounds of the present invention are administered in combination with one or more additional therapeutic agents selected from the group consisting of diuretics, angiotensin AII antagonists, ACE inhibitors, beta-receptor blockers, mineralocorticoid receptor antagonists, antidiabetics, organic nitrates and NO donors, activators and stimulators of the soluble guanylate cyclase (sGC), and positive-inotropic agents.

In a further particularly preferred embodiment, the compounds of the present invention are administered in combination with one or more additional therapeutic agents selected from the group consisting of diuretics, angiotensin AII antagonists, ACE inhibitors, beta-receptor blockers, mineralocorticoid receptor antagonists, antidiabetics, organic nitrates and NO donors, activators and stimulators of the soluble guanylate cyclase (sGC), positive-inotropic agents, antiinflammatory agents, immunosuppressive agents, phosphate binders and/or compounds which modulate vitamin D metabolism.

Thus, in a further embodiment, the present invention relates to pharmaceutical compositions comprising at least one of the compounds according to the invention and one or more additional therapeutic agents for the treatment and/or prevention of diseases, especially of the aforementioned diseases.

Furthermore, the compounds of the present invention may be utilized, as such or in compositions, in research and diagnostics, or as analytical reference standards and the like, which are well known in the art.

When the compounds of the present invention are administered as pharmaceuticals, to humans and other mammals, they can be given per se or as a pharmaceutical composition containing, for example, 0.1% to 99.5% (more preferably, 0.5% to 90%) of active ingredient in combination with one or more pharmaceutically acceptable excipients.

Thus, in another aspect, the present invention relates to pharmaceutical compositions comprising at least one of the compounds according to the invention, conventionally together with one or more inert, non-toxic, pharmaceutically acceptable excipients, and to the use thereof for the treatment and/or prevention of diseases, especially of the aforementioned diseases.

It is possible for the compounds according to the invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent.

For these administration routes, it is possible for the compounds according to the invention to be administered in suitable administration forms.

For oral administration, it is possible to formulate the compounds according to the invention to dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, powders, emulsions, suspensions, aerosols or solutions. It is possible to incorporate the compounds according to the invention in crystalline and/or amorphised and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, dusting powders, implants or stents.

The compounds according to the invention can be incorporated into the stated administration forms. This can be effected in a manner known per se by mixing with pharmaceutically suitable excipients. Pharmaceutically suitable excipients include, inter alia,

- fillers and carriers (for example cellulose, microcrystalline cellulose (such as, for example, Avicel®), lactose, mannitol, starch, calcium phosphate (such as, for example, Di-Cafos®)),
- ointment bases (for example petroleum jelly, paraffins, triglycerides, waxes, wool wax, wool wax alcohols, lanolin, hydrophilic ointment, polyethylene glycols),
- bases for suppositories (for example polyethylene glycols, cacao butter, hard fat),
- solvents (for example water, ethanol, iso-propanol, glycerol, propylene glycol, medium chain-length triglycerides fatty oils, liquid polyethylene glycols, paraffins),
- surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxyethylene fatty acid esters, polyoxyethylene fatty alcohol ethers, glycerol fatty acid esters, poloxamers (such as, for example, Pluronic®), buffers, acids and bases (for example phosphates, carbonates, citric acid, acetic acid, hydrochloric acid, sodium hydroxide solution, ammonium carbonate, trometamol, triethanolamine), isotonicity agents (for example glucose, sodium chloride), adsorbents (for example highly-disperse silicas), viscosity-increasing agents, gel formers, thickeners and/or binders (for example polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®); alginates, gelatine), disintegrants (for example modified starch, carboxymethylcellulose-sodium, sodium starch glycolate (such as, for example, Explotab®), cross-linked polyvinylpyrrolidone, croscarmellose-sodium (such as, for example, AcDiSol®)), flow regulators, lubricants, glidants and mould release agents (for example magnesium stearate, stearic acid, talc, highly-disperse silicas (such as, for example, Aerosil®)), coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)), capsule materials (for example gelatine, hydroxypropylmethylcellulose), synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers), plasticizers (for example polyethylene glycols, propylene glycol, glycerol, triacetine, triacetyl citrate, dibutyl phthalate), penetration enhancers, stabilisers (for example antioxidants such as, for example, ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), colourants (for example inorganic pigments such as, for example, iron oxides, titanium dioxide), flavourings, sweeteners, flavour- and/or odour-masking agents.

The present invention furthermore relates to a pharmaceutical composition which comprise at least one compound according to the invention, conventionally together with one or more pharmaceutically suitable excipient(s), and to their use according to the present invention.

Based upon standard laboratory techniques known to evaluate compounds useful for the treatment of cardiovascular and renal disorders, by standard toxicity tests and by standard pharmacological assays for the determination of treatment of the conditions identified above in mammals, and by comparison of these results with the results of known active ingredients or medicaments that are used to treat these conditions, the effective dosage of the compounds of the present invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, it is possible for "drug holidays", in which a patient is not dosed with a drug for a certain period of time, to be beneficial to the overall balance between pharmacological effect and tolerability. It is possible for a unit dosage to contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. Illustratively, the compound of the present invention may be administered parenterally at a dose of about 0.001 mg/kg to about 10 mg/kg, preferably of about 0.01 mg/kg to about 1 mg/kg of body weight. In oral administration, an exemplary dose range is about 0.01 to 100 mg/kg, preferably about 0.01 to 20 mg/kg, and more preferably about 0.1 to 10 mg/kg of body weight. Ranges intermediate to the above-recited values are also intended to be part of the invention.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

The following exemplary embodiments illustrate the invention. The invention is not restricted to the examples.

The percentages in the following tests and examples are, unless stated otherwise, by weight; parts are by weight. Solvent ratios, dilution ratios and concentrations reported for liquid/liquid solutions are each based on volume.

EXPERIMENTAL SECTION

Experimental Section—General Part

NMR peak forms are stated as they appear in the spectra, possible higher order effects have not been considered.

Chemical names were generated using the ACD/Name software from ACD/Labs. In some cases generally accepted names of commercially available reagents were used in place of ACD/Name generated names.

The following table 1 lists the abbreviations used in this paragraph and in the Examples section as far as they are not explained within the text body. Other abbreviations have their meanings customary per se to the skilled person.

TABLE 1

Abbreviations
The following table lists the abbreviations used herein.

| Abbreviation | Meaning |
| --- | --- |
| abs | absolut |
| br | broad ($^1$H-NMR signal) |
| conc. | concentrated |
| CI | chemical ionisation |
| d | doublet ($^1$H-NMR signal) |
| d | day(s) |
| DAD | diode array detector |
| DCM | dichloromethane |
| dd | double-doublet |
| DMSO | dimethylsulfoxide |
| ESI | electrospray (ES) ionisation |
| h | hour(s) |
| HPLC | high performance liquid chromatography |
| LC-MS | liquid chromatography mass spectrometry |
| m | multiplet ($^1$H-NMR signal) |
| min | minute(s) |
| MS | mass spectrometry |
| MTBE | methyl-tert-butylether |
| NMR | nuclear magnetic resonance spectroscopy: chemical shifts (δ) are given in ppm. The chemical shifts were corrected by setting the DMSO signal to 2.50 ppm unless otherwise stated. |
| of th. | of theory |
| PDA | Photo Diode Array |
| Rt | retention time (as measured either with HPLC or UPLC) in minutes |
| s | singlet ($^1$H-NMR signal) |
| SFC | Supercritical Fluid Chromatography |
| SQD | Single-Quadrupole-Detector |
| t | triplet ($^1$H-NMR signal) |
| td | triple-doublet ($^1$H-NMR signal) |
| TFA | trifluoroacetic acid |
| THF | tetrahydrofuran |
| UPLC | ultra performance liquid chromatography |

The various aspects of the invention described in this application are illustrated by the following examples which are not meant to limit the invention in any way.

The example testing experiments described herein serve to illustrate the present invention and the invention is not limited to the examples given.

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. Biotage SNAP cartidges KP-Sil® or KP-NH® in combination with a Biotage autopurifier system (SP4® or Isolera Four®) and eluents such as gradients of hexane/ethyl acetate or DCM/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

In the case of the synthesis intermediates and working examples of the invention described hereinafter, any compound specified in the form of a salt of the corresponding base or acid is generally a salt of unknown exact stoichiometric composition, as obtained by the respective preparation and/or purification process. Unless specified in more detail, additions to names and structural formulae, such as "hydrochloride", "trifluoroacetate", "sodium salt" or "x HCl", "x CF$_3$COOH", "x Na$^+$" should not therefore be understood in a stoichiometric sense in the case of such salts, but have merely descriptive character with regard to the salt-forming components present therein.

This applies correspondingly if synthesis intermediates or working examples or salts thereof were obtained in the form of solvates, for example hydrates, of unknown stoichiometric composition (if they are of a defined type) by the preparation and/or purification processes described.

HPLC and LC-MS Methods:

Method 1 (LC-MS):

Instrument: Waters ACQUITY SQD UPLC System; Column: Waters Acquity UPLC HSS T3 1.8µ 50×1 mm; eluent A: 1 l water+0.25 ml 99% formic acid, eluent B: 1 l acetonitrile+0.25 ml 99% formic acid; gradient: 0.0 min 90% A→1.2 min 5% A→2.0 min 5% A; oven: 50° C.; flow rate: 0.40 ml/min; UV detection: 208-400 nm.

Method 2 (LC-MS)

Instrument MS: Thermo Scientific FT-MS; Instrument type UHPLC+: Thermo Scientific UltiMate 3000; Column: Waters, HSST3, 2.1×75 mm, C18 1.8 µm; eluent A: 1 l water+0.01% formic acid; eluent B: 1 l acetonitrile+0.01% formic acid; gradient: 0.0 min 10% B→2.5 min 95% B→3.5 min 95% B; oven: 50° C.; flow rate: 0.90 ml/min; UV detection: 210 nm/optimum integration path 210-300 nm.

Method 3 (LC-MS)

Instrument: Waters ACQUITY SQD UPLC System; Column: Waters Acquity UPLC HSS T3 1.8µ 50×1 mm; eluent A: 1 l water+0.25 ml 99% formic acid, Eluent B: 1 l acetonitrile+0.25 ml 99% formic acid; gradient: 0.0 min 95% A→6.0 min 5% A→7.5 min 5% A; oven: 50° C.; flow rate: 0.35 ml/min; UV detection: 210-400 nm.

Method 4 (Preparative HPLC)

Column: Chromatorex or Reprosil C18 10 µm; 125×30 mm, eluent A: water+0.1% formic acid, eluent B: acetonitrile+0.1% formic acid; gradient: 3 min 10% B; 17.5 min 95% B; 19.5 min 100% B, 20 min 10% B, flow: 75 ml/min, run time: 20 min, Detection at 210 nm.

or

Instrument: Waters Prep LC/MS System, Column: Phenomenex Kinetex C18 5 µm 100×30 mm; eluent A: water, eluent B: acetonitrile, flow: 65 ml/min under addition of 0.1% formic acid in water, gradient: 0.0 min 10% B, 2 min 20% B, 2.2 min 60% B, 7 min 92% B, 7.5 min 92% B, room temperature, UV detection: 200-400 nm.

Method 5 (LC-MS)

Instrument MS: Waters (Micromass) Quattro Micro; Instrument Waters UPLC Acquity; Column: Waters BEH C18 1.7µ 50×2.1 mm; eluent A: 1 l water+0.01 mol ammonium formiat, eluent B: 1 l acetonitrile; gradient: 0.0 min 95% A, 0.1 min 95% A, 2.0 min 15% A, 2.5 min 15% A, 2.51 min 10% A, 3.0 min 10% A; oven: 40° C.; flow rate: 0.5 ml/min; UV-detection: 210 nm.

Method 6 (LC-MS)

Instrument: Agilent MS Quad 6150; HPLC: Agilent 1290; Column: Waters Acquity UPLC HSS T3 1.8µ 50×2.1 mm; eluent A: 1 l water+0.25 ml 99% ige formic acid, eluent B: 1 l acetonitrile+0.25 ml 99% ige formic acid; gradient: 0.0 min 90% A→0.3 min 90% A→1.7 min 5% A→3.0 min 5% A; oven: 50° C.; flow rate: 1.20 ml/min; UV-detection: 205-305 nm.

Method 7 (Preparative HPLC)

Instrument MS: Waters, Instrument HPLC: Waters (column Phenomenex Luna 5µ C18(2) 100 A, AXIA Tech. 50×21.2 mm, eluent A: water, eluent B: acetonitrile (ULC), gradient; flow: 38.5 ml/min under addition of 1.5 ml/min modifier (10% aq. formic acid); UV-detection: DAD; 210-400 nm.

or

Instrument MS: Waters, Instrument HPLC: Waters (column Phenomenex Luna 5µ C18(2) 100 A, AXIA Tech. 50×21.2 mm, eluent A: water, eluent B: methanol (ULC), gradient; flow: 38.5 ml/min under addition of 1.5 ml/min modifier (10% ammonia in water), UV-detection: DAD; 210-400 nm.

Method 8 (LC-MS)

Instrument MS: Waters SQD2; Instrument HPLC: Waters UPLC; column: Zorbax SB-Aq (Agilent), 50 mm×2.1 mm, 1.8 µm; eluent A: water+0.025% formic acid, eluent B: acetonitrile (ULC)+0.025% formic acid; gradient: 0.0 min 98% A-0.9 min 25% A-1.0 min 5% A-1.4 min 5% A-1.41 min 98% A-1.5 min 98% A; oven: 40° C.; flow: 0.600 ml/min; UV-detection: DAD; 210 nm.

Method 9 (LC-MS)

Instrument MS: Waters SQD; Instrument HPLC: Waters UPLC; column: Zorbax SB-Aq (Agilent), 50 mm×2.1 mm, 1.8 µm; eluent A: water+0.025% formic acid, eluent B: acetonitrile (ULC)+0.025% formic acid; gradient: 0.0 min 98% A-0.9 min 25% A-1.0 min 5% A-1.4 min 5% A-1.41 min 98% A-1.5 min 98% A; oven: 40° C.; flow: 0.600 ml/min; UV-detection: DAD; 210 nm.

Microwave:

The microwave reactor used was an Initiator+ microwave system with robot sixty from Biotage®.

EXPERIMENTAL SECTION—STARTING MATERIALS AND INTERMEDIATES

Example 1A

{3-(4-Chlorophenyl)-5-oxo-4-[(2S)-3,3,3-trifluoro-2-hydroxypropyl]-4,5-dihydro-1H-1,2,4-triazol-1-yl}acetonitrile

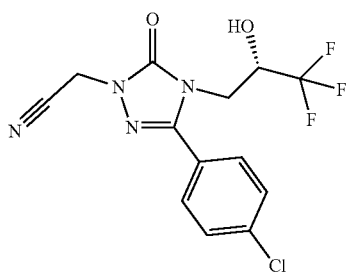 [SMILES: N#CCn1nc(-c2ccc(Cl)cc2)n(C[C@H](O)C(F)(F)F)c1=O]

In a 2 L reaction vessel, 100 g (273 mmol) of {3-(4-chlorophenyl)-5-oxo-4-[(2S)-3,3,3-trifluoro-2-hydroxypropyl]-4,5-dihydro-1H-1,2,4-triazol-1-yl}acetic acid (synthesis described as Example 8A in WO 2010/105770-A1), 43.3 g (547 mmol) of pyridine and 33 mg (0.3 mmol) of 4-dimethylaminopyridine were dissolved in 300 ml THF. The resulting solution was treated at 5° C. with 52.8 g (438 mmol) of 2,2-dimethylpropanoylchloride over 15 minutes and the resulting mixture was stirred at room temperature for 2.5 hours. After cooling to 0° C., 183 ml of 28% aqueous ammonia solution was added over 1 h while the solution temperature was kept between 10° C. and 20° C. and at the resulting mixture then stirred at 5° C. for an additional time period of 1 h. 500 ml methyl tert-butylether and 300 ml 20% aqueous citric acid were then added while keeping the internal temperature between 10° C. and 20° C. The phases were the separated and the organic phase was washed with 300 ml of 20% aqueous citric acid followed by 300 ml saturated aqueous sodium hydrogencarbonate solution and finally with 300 ml of 10% aqueous sodium chloride solution. The organic phase was evaporated at 60° C. under reduced pressure until an oily residue was obtained. 300 ml THF was then added and the solution was evaporated again until an oily solution was obtained. This operation was repeated a second time. The oil residue was retaken in 360 ml THF and treated with 172 g (820 mmol) trifluoroacetic acid anhydride over 20 min at a temperature between 10° C. and 20° C. The resulting solution was then stirred at room temperature for 1 h. 720 ml 4-methyl-2-pentanone and 650 ml 7.5% aqueous sodium hydroxide solution were added at a temperature between 10° C. and 20° C. Finally the pH-value was adjusted to pH=9.5 using 7.5% aqueous sodium hydroxide solution. After phase separation, the organic phase was washed twice with 450 ml 10% aqueous sodium chloride solution. The organic phase was evaporated at a temperature of 80° C. under reduced pressure while 1200 ml n-heptane was added. The formed suspension was cooled to 20° C. and a solid formed which was filtered off and washed with 200 ml n-heptane and then dried under reduced pressure (50° C., 30 mbar) affording 88 g (93% of th.) of {3-(4-chlorophenyl)-5-oxo-4-[(2S)-3,3,3-trifluoro-2-hydroxypropyl]-4,5-dihydro-1H-1,2,4-triazol-1-yl}acetonitrile as a solid.

$^1$H-NMR (400 MHz, DMSO-d6): δ [ppm]=7.78 (d, 2H), 7.55 (d, 2H), 6.91 (d, 1H), 5.17 (s, 2H), 4.34-4.23 (m, 1H), 3.98 (dd, 1H), 3.81 (dd, 1H).

Example 2A

Methyl-2-{3-(4-chlorophenyl)-5-oxo-4-[(2S)-3,3,3-trifluor-2-hydroxypropyl]-4,5-dihydro-1H-1,2,4-triazol-1-yl}ethanimidate

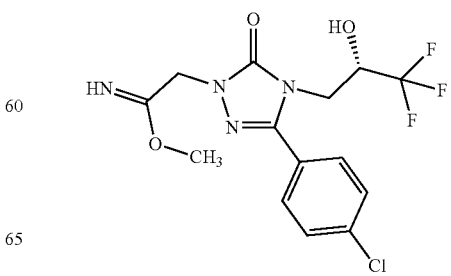

In a 4 L reaction vessel, 200 g (576.9 mmol) of {3-(4-chlorophenyl)-5-oxo-4-[(2S)-3,3,3-trifluoro-2-hydroxypropyl]-4,5-dihydro-1H-1,2,4-triazol-1-yl}acetonitrile (Example 1A) in 1600 ml methanol was treated with 5.2 g (28 mmol) sodium methanolate (30% in methanol) and the resulting mixture was stirred at 50° C. for 2.5 hours. The solution was then evaporated at 50° C. under reduced pressure until an oily solution was obtained. 2000 ml methyl tert-butylether was added and the solution was concentrated until a volume of 800 ml was achieved. 3000 ml n-heptane was then added and a suspension was formed. After cooling at 20° C., the solid was filtered and washed with 500 ml n-heptane and then dried under reduced pressure (50° C., 30 mbar) affording 175 g (80% of th.) of methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate as a solid.

$^1$H-NMR (400 MHz, DMSO-d6): δ [ppm]=8.01 (s, 1H), 7.78 (d, 2H), 7.62 (d, 2H), 6.93 (br. s, 1H), 4.50 (s, 2H), 4.35-4.23 (m, 1H), 3.96 (dd, 1H), 3.81 (dd, 1H), 3.67 (s, 3H).

Example 3A 5-(4-Chlorophenyl)-4-[(2R)-3,3,3-trifluoro-2-hydroxypropyl]-2,4-dihydro-3H-1,2,4-triazol-3-one

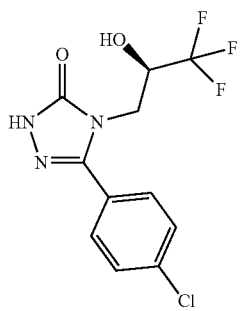 [SMILES: O=c1[nH]nc(-c2ccc(Cl)cc2)n1C[C@@H](O)C(F)(F)F]

A solution of 5-(4-chlorophenyl)-4-(3,3,3-trifluoro-2,2-dihydroxypropyl)-2,4-dihydro-3H-1,2,4-triazol-3-one (synthesis described as Example 4A in WO 2010/105770-A1) (10.0 g, 30.9 mmol), N-[(1R,2R)-2-amino-1,2-diphenylethyl]-4-methylbenzenesulfonamide (56.6 mg, 154 μmol) and 1-methyl-4-(propan-2-yl)benzene-dichlororuthenium (47.3 mg, 77.2 μmol) in ethyl acetate was treated with triethylamine (8.6 ml, 62 mmol) followed by addition of formic acid (5.8 ml, 150 mmol). The resulting mixture was heated under reflux for 3 h and then cooled down to room temperature. The reaction mixture was diluted with hydrochloric acid (70 ml, 1N). The organic phase was washed twice with hydrochloric acid (1N). The aqueous phase was extracted twice with ethyl acetate. The combined organic phases were evaporated. The residue was retaken in methanol (22.5 ml) and the resulting suspension was heated to 60° C. until the solid was completely dissolved. Hydrochloric acid (22.5 ml, 1N) was added and the resulting suspension was heated at 78° C. for 10 min and cooled down to room temperature. The solid was filtered off and dried under vacuum. The solid was retaken in hydrochloric acid (30 ml, 1N), heated at 35° C. The resulting suspension was treated with methanol (30 ml), heated 4 h at 35° C. and filtered off at 35° C. The filtrate solution was evaporated affording 4.9 g (ee=99.6%, 51% of th.) of 5-(4-chlorophenyl)-4-[(2R)-3,3,3-trifluoro-2-hydroxypropyl]-2,4-dihydro-3H-1,2,4-triazol-3-one.

$^1$H-NMR (400 MHz, DMSO): δ [ppm]=12.10 (s, 1H), 7.52-7.79 (m, 4H), 6.84 (d, 1H), 3.54-4.52 (m 3H).

Example 4A

{3-(4-Chlorophenyl)-5-oxo-4-[(2R)-3,3,3-trifluoro-2-hydroxypropyl]-4,5-dihydro-1H-1,2,4-triazol-1-yl}acetonitrile

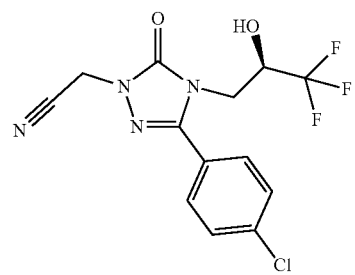 [SMILES: N#CCn1nc(-c2ccc(Cl)cc2)n(C[C@@H](O)C(F)(F)F)c1=O]

A solution of 40 g (130 mmol) 5-(4-Chlorophenyl)-4-[(2R)-3,3,3-trifluor-2-hydroxypropyl]-2,4-dihydro-3H-1,2,4-triazol-3-one (Example 3A) in 400 ml methylisobutyl ketone was treated with 17.9 g (143 mmol) bromoacetonitrile and 53.9 g (390 mmol) potassium carbonate and stirred for 4 hours at 60° C. After cooling to 20° C., 200 ml water was added and the mixture was stirred for 10 min.

After phase separation, the organic phase was washed with 200 ml water. The organic phase was evaporated at 80° C. under reduced pressure while 300 ml n-heptane was added. The formed suspension was cooled to 20° C. and a solid formed which was filtered off and washed with 50 ml n-heptane and then dried under reduced pressure (50° C., 30 mbar) affording 25.2 g (56% of th.) of {3-(4-chlorophenyl)-5-oxo-4-[(2R)-3,3,3-trifluoro-2-hydroxypropyl]-4,5-dihydro-1H-1,2,4-triazol-1-yl}acetonitrile.

$^1$H-NMR (400 MHz, DMSO-d6): δ [ppm]=7.78 (d, 2H), 7.65 (d, 2H), 6.91 (d, 1H), 5.17 (s, 2H), 4.34-4.23 (m, 1H), 3.98 (dd, 1H), 3.81 (dd, 1H).

Example 5A

Methyl-2-{3-(4-chlorophenyl)-5-oxo-4-[(2R)-3,3,3-trifluor-2-hydroxypropyl]-4,5-dihydro-1H-1,2,4-triazol-1-yl}ethanimidate

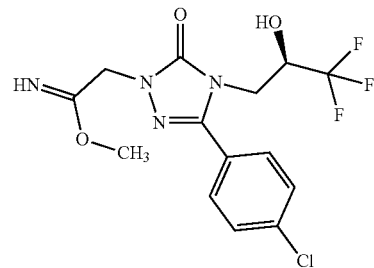 [SMILES: COC(=N)Cn1nc(-c2ccc(Cl)cc2)n(C[C@@H](O)C(F)(F)F)c1=O]

A solution 8.58 g (24.7 mmol) of {3-(4-chlorophenyl)-5-oxo-4-[(2R)-3,3,3-trifluoro-2-hydroxypropyl]-4,5-dihydro-1H-1,2,4-triazol-1-yl}acetonitrile (Example 4A) in methanol (43 ml) was treated with 229 μl (1.24 mmol) of a sodium methoxide solution (30% in methanol). The resulting mixture was stirred overnight at room temperature and then evaporated affording 9.31 g (99% of th.) of the title compound.

$^1$H NMR (DMSO-$d_6$, 400 MHz): δ [ppm]=8.01 (s, 1H), 7.81-7.58 (m, 4H), 7.00-6.84 (m, 1H), 4.50 (s, 2H), 4.40-4.23 (m, 1H), 4.04-3.74 (m, 2H), 3.66 (s, 3H).

Example 6A 5-(4-Chlorophenyl)-2-{[1-(4-chloropyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one

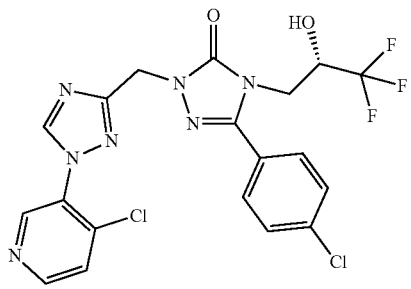 [SMILES: O=c1n(Cc2ncn(-c3cnccc3Cl)n2)nc(-c2ccc(Cl)cc2)n1C[C@H](O)C(F)(F)F]

At room temperature, a solution of methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate (Example 2A, 2.00 g, 5.28 mmol) in tetrahydrofuran (33 ml) was treated with 4-chloro-3-hydrazinylpyridine hydrochloride (1:1) (1.05 g, 5.81 mmol) and N,N-diisopropylethylamine (2.0 ml, 12 mmol). After stirring 1 h, (diethoxymethoxy)ethane (33 ml) was then added. The resulting mixture was heated at reflux overnight and diluted with ethyl acetate. The organic layer was first washed twice with water, followed by a saturated solution of sodium hydrogenocarbonate and finally with a saturated solution of sodium chloride. The organic layer was dried over magnesium sulfate and evaporated. The residue was purified by flash chromatography (isolera, silica gel, ethyl acetate/methanol gradient) affording 1.98 g (70% of th.) of the title compound.

LC-MS (Method 1): $R_t$=0.88 min; MS (ESIpos): m/z=500.1 [M+H]$^+$ $^1$H-NMR (400 MHz, DMSO-d6) δ [ppm]: 9.01 (s, 1H), 8.83 (s, 1H), 8.70 (d, 1H), 7.88 (d, 1H), 7.81-7.55 (m, 4H), 6.91 (d, 1H), 5.15 (s, 2H), 4.41-4.22 (m, 1H), 4.14-3.77 (m, 2H).

Example 7A

4-[(2S)-2-{[Tert-butyl(dimethyl)silyl]oxy}-3,3,3-trifluoropropyl]-5-(4-chlorophenyl)-2-{[1-(4-chloropyridin-3-yl)-1H-1,2,4-triazol-3-yl]methyl}-2,4-dihydro-3H-1,2,4-triazol-3-one

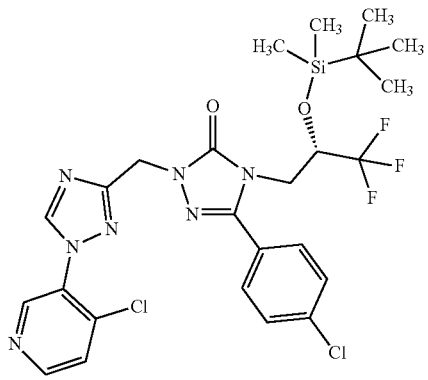

A solution of 5-(4-chlorophenyl)-2-{[1-(4-chloropyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Example 6A, 1.00 g, 2.00 mmol) in N,N-dimethylformamide (10 ml) was treated with imidazole (177 mg, 2.60 mmol) followed by tert-butyl(chloro)dimethylsilane (331 mg, 2.20 mmol) and stirred overnight at 65° C. The reaction mixture was evaporated and the residue purified by flash chromatography (Biotage, silica gel, ethylacetate/methanol gradient) affording 490 mg (40% of th.) of the title compound.

LC-MS (Method 2): R&=2.54 min; MS (ESIpos): m/z=614.1 [M+H]$^+$ $^1$H-NMR (400 MHz, DMSO-d6) δ [ppm]: 9.01 (s, 1H), 8.80 (s, 1H), 8.70 (d, 1H), 7.88 (d, 1H), 7.78-7.60 (m, 4H), 5.26-4.99 (m, 2H), 4.68-4.48 (m, 1H), 4.23-3.84 (m, 2H), 0.71 (s, 9H), −0.01–−0.05 (s, 3H), −0.23 (s, 3H).

Example 8A

2-[(1-{4-[(2-Amino-2-methylpropyl)amino]pyridin-3-yl}-1H-1,2,4-triazol-3-yl)methyl]-4-[(2S)-2-{[tert-butyl(dimethyl)silyl]oxy}-3,3,3-trifluoropropyl]-5-(4-chlorophenyl)-2,4-dihydro-3H-1,2,4-triazol-3-one

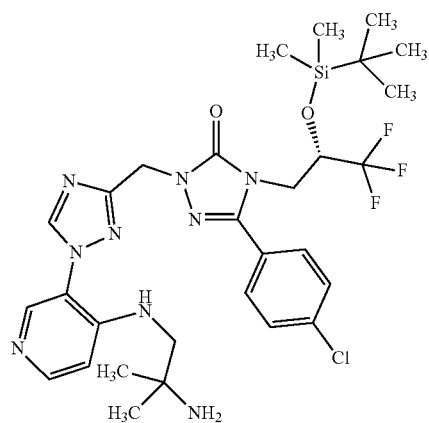

A solution of 4-[(2S)-2-{[tert-butyl(dimethyl)silyl]oxy}-3,3,3-trifluoropropyl]-5-(4-chlorophenyl)-2-{[1-(4-chloropyridin-3-yl)-1H-1,2,4-triazol-3-yl]methyl}-2,4-dihydro-3H-1,2,4-triazol-3-one (Example 7A, 50.0 mg, 81.4 μmol) in ethanol (200 μl, 3.4 mmol) was treated with 2-methylpropane-1,2-diamine (71.7 mg, 814 μmol) The resulting mixture was heated at refluxed overnight and purified over preparative HPLC (Method 4) affording 39.2 mg (72% of th.) of the title compound.

LC-MS (Method 2): $R_t$=1.38 min; MS (ESIneg): m/z=664.2 [M−H]$^−$

Example 9A

2-{[1-(4-Aminopyridin-3-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one

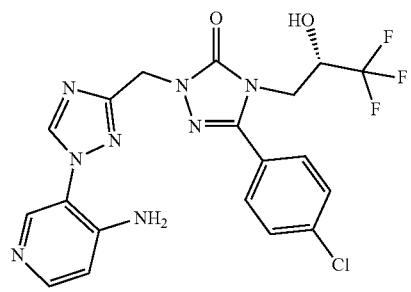 [SMILES: Nc1ccncc1-n1cnc(Cn2nc(-c3ccc(Cl)cc3)n(C[C@H](O)C(F)(F)F)c2=O)n1]

5-(4-chlorophenyl)-2-{[1-(4-chloropyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Example 6A, 2.11 g, 4.22 mmol) was dissolved in a solution of ammonia in methanol (16 ml, 7.0 M, 110 mmol) and heated 18 h at 140° C. under microwave irradiation. The reaction mixture was evaporated and purified by preparative HPLC (Method 4) affording 1.37 g (67% of th.) of the title compound.

LC-MS (Method 1): $R_t$=0.68 min; MS (ESIpos): m/z=481.1 [M+H]$^+$ $^1$H-NMR (400 MHz, DMSO-d6) δ [ppm]: 8.85 (s, 1H), 8.29 (s, 1H), 8.18-7.99 (m, 1H), 7.84-7.52 (m, 4H), 7.05-6.73 (m, 2H), 6.57 (br s, 2H), 5.13 (s, 2H), 4.40-4.20 (br m, 1H), 4.07-3.74 (m, 2H).

Example 10A

3-Hydrazinylpyridine-2-carboxylic acid hydrochloride

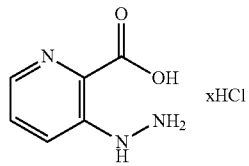 [SMILES: NNc1cccnc1C(=O)O]

At 0° C., a concentrated hydrochloric acid solution (81 ml) was added to a suspension of 3-aminopyridine-2-carboxylic acid (10.0 g, 72.4 mmol) in water (80 ml). A solution of sodium nitrite (5.00 g, 72.4 mmol) in water (50 ml) was then added dropewisely within 10 minutes. The resulting mixture was stirred at 0° C. for 15 min.

A solution of an aqueous sulfurous acid cooled at 0° C. (6%, 560 ml) was added in 4 portions within 20 minutes to the reaction mixture and the resulting mixture was warmed to room temperature within 1 h, stirred 1.5 h at room temperature and cooled down to +4° C. The solid was filtered off and washed with a small volume of concentrated hydrochloric acid.

The solid was retaken in concentrated hydrochloric acid (100 ml) and heated 4 h at 60° C. The solid was filtered off and washed with a small volume of concentrated hydrochloric acid affording 10.0 g (73% of th.) of the title compound.

LC-MS (Method 1): $R_t$=0.16 min; MS (ESIpos): m/z=154.0 [M+H]$^+$

Example 11A

3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid

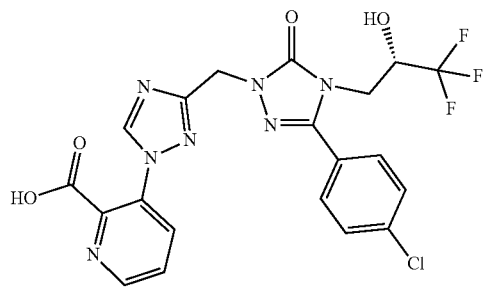 [SMILES: O=C(O)c1ncccc1-n1cnc(Cn2nc(-c3ccc(Cl)cc3)n(C[C@H](O)C(F)(F)F)c2=O)n1]

To a suspension of 3-hydrazinylpyridine-2-carboxylic acid hydrochloride (1:1) (Example 11A, 3.99 g, 21.0 mmol) in tetrahydrofuran (80 ml) was added methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate (Example 2A, 7.24 g, 19.1 mmol) and N,N-diisopropylethylamine (10 ml, 57 mmol). The resulting solution was stirred 1.5 h at room temperature and evaporated. The residue was retaken in (diethoxymethoxy)ethane (160 ml, 960 mmol). The resulting mixture was stirred 84 h at 50° C. and evaporated. The residue was purified by preparative flash chromatography (silica gel, eluent dichloromethane/methanol/0.1% aq. ammonia) followed by a purification by preparative HPLC (Column Chromatorex C18, 10 μm, Spring column, 370× 100 mm, flow: 250 ml/min, detection 210 nm, temperature 22° C., 8.9 g of compound was dissolved in 100 ml THF and 18 ml portion were injected) affording 4.53 g (44% of th.) of the title compound.

LC-MS (Method 1): $R_t$=0.73 min; MS (ESIpos): m/z=510.0 [M+H]$^+$ $^1$H-NMR (400 MHz, DMSO-d6) δ [ppm]: 13.63 (br s, 1H), 8.96 (s, 1H), 8.74 (dd, 1H), 8.17 (dd, 1H), 7.85-7.55 (m, 5H), 7.04-6.81 (m, 1H), 5.16-4.95 (m, 2H), 4.41-4.21 (m, 1H), 4.09-3.71 (m, 2H).

Example 12A

3-[3-({3-(4-Chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid

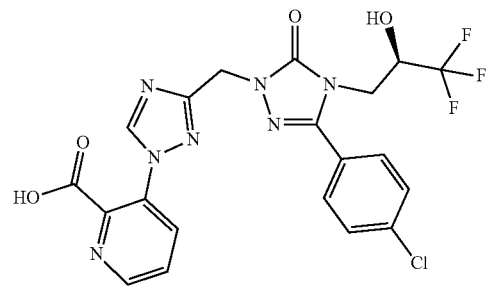 [SMILES: O=C(O)c1ncccc1-n1cnc(Cn2nc(-c3ccc(Cl)cc3)n(C[C@@H](O)C(F)(F)F)c2=O)n1]

To a suspension of 3-hydrazinylpyridine-2-carboxylic acid hydrochloride (1:1) (Example 10A, 5.02 g, 26.5 mmol) in tetrahydrofuran (100 ml) was added methyl 2-{3-(4-chlorophenyl)-5-oxo-4-[(2R)-3,3,3-trifluoro-2-hydroxypropyl]-4,5-dihydro-1H-1,2,4-triazol-1-yl}ethanimidate (Example 5A, 9.11 g, 24.1 mmol) and N,N-diisopropylethylamine (13 ml, 72 mmol). The resulting solution was stirred 130 minutes at room temperature and evaporated. The residue was retaken in (diethoxymethoxy)ethane (200 ml, 1.2 mol). The resulting mixture was stirred 70 h at 50° C. and 72 h followed by 40° C. and evaporated. The residue was purified by preparative flash chromatography (silica gel, eluent dichloromethane/methanol/0.1% aq. ammonia) affording 8.9 g (57% of th.) of the title compound.

LC-MS (Method 1): $R_t$=0.73 min; MS (ESIpos): m/z=510.0 [M+H]$^+$

Example 13A

Ethyl 3-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridine-2-carboxylate

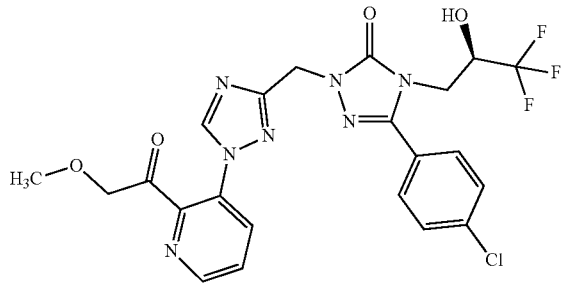 [SMILES: COCC(=O)c1ncccc1-n1cnc(Cn2nc(-c3ccc(Cl)cc3)n(C[C@@H](O)C(F)(F)F)c2=O)n1]

A solution of 3-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 12A, 2.00 g, 3.92 mmol) in dichloromethane (20 ml) was treated with 1-chloro-N,N,2-trimethylprop-1-en-1-amine (780 µl, 5.9 mmol) and stirred 1 h at room temperature. Ethanol (20 ml, 350 mmol) was then added. The resulting mixture was stirred overnight at room temperature and evaporated. The residue was purified by preparative HPLC (Method 4) affording 236 mg (11% of th.) of the title compound LC-MS (Method 2): R$_t$=1.69 min MS (ESIpos): m/z=538.1 [M+H]$^+$ $^1$H-NMR (400 MHz, DMSO-d6) δ [ppm]: 9.07 (s, 1H), 8.75 (dd, 1H), 8.27 (dd, 1H), 7.89-7.51 (m, 5H), 6.91 (d, 1H), 5.09 (s, 2H), 4.42-3.74 (m, 5H), 1.01 (t, 3H).

Example 14A

Ethyl 3-[5-bromo-3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridine-2-carboxylate

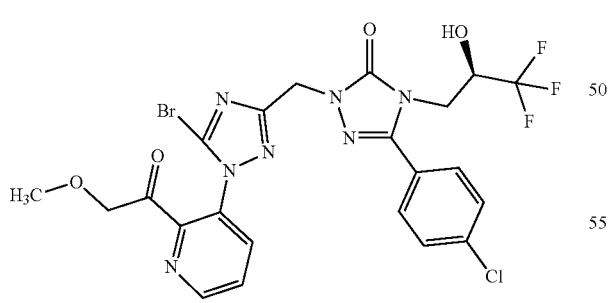

A solution of ethyl 3-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridine-2-carboxylate (Example 13A, 209 mg, 389 µmol) in acetonitrile was treated with 1-bromopyrrolidine-2,5-dione (346 mg, 1.94 mmol) and 2,2'-(E)-diazene-1,2-diylbis(2-methylpropanenitrile) (12.8 mg, 77.7 µmol). The resulting mixture was stirred 17 h at reflux and evaporated. The residue was purified by preparative HPLC (Method 4) affording 141 mg (59% of th.) of the title compound.

LC-MS (Method 1): R$_t$=0.94 min; MS (ESIpos): m/z=616.0 [M+H]$^+$ $^1$H-NMR (400 MHz, DMSO-d6) δ [ppm]: 8.90 (dd, 1H), 8.31 (dd, 1H), 7.99-7.49 (m, 5H), 6.91 (d, 1H), 5.09 (s, 2H), 4.44-3.76 (m, 5H), 0.97 (t, 3H).

Example 15A

Ethyl 3-[3-({3-(4-chlorophenyl)-5-oxo-4-[(2R)-3,3,3-trifluoro-2-hydroxypropyl]-4,5-dihydro-1H-1,2,4-triazol-1-yl}methyl)-5-(1,1-dioxidothiomorpholin-4-yl)-1H-1,2,4-triazol-1-yl]pyridine-2-carboxylate

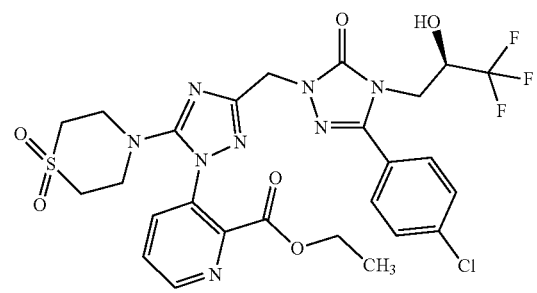 [SMILES: CCOC(=O)c1ncccc1-n1nc(Cn2nc(-c3ccc(Cl)cc3)n(C[C@@H](O)C(F)(F)F)c2=O)nc1N1CCS(=O)(=O)CC1]

A solution of ethyl 3-[5-bromo-3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridine-2-carboxylate (Example 14A, 124 mg, 201 µmol) in acetonitrile were treated with thiomorpholine 1,1-dioxide (544 mg, 4.02 mmol) and N,N-diisopropylethylamine (74 µl, 420 µmol). The resulting mixture was stirred 4 h at 180° C. under microwave irradiation. Formic acid was added to the reaction mixture and a solid precipitated out which was filtered off. The filtrate was purified by preparative HPLC (Method 4) affording 50.0 mg (37% of th.) of the title compound LC-MS (Method 2): R$_t$=1.65 min; MS (ESIpos): m/z=671.1 [M+H]$^+$ $^1$H-NMR (400 MHz, DMSO-d6) δ [ppm]: 8.79 (dd, 1H), 8.26 (dd, 1H), 7.90-7.56 (m, 5H), 6.87 (d, 1H), 4.94 (d, 2H), 4.40-3.69 (m, 5H), 3.61-3.38 (m, 4H), 3.14 (br s, 4H), 1.09-0.88 (m, 3H).

Example 16A

3-[3-({3-(4-Chlorophenyl)-5-oxo-4-[(2R)-3,3,3-trifluoro-2-hydroxypropyl]-4,5-dihydro-1H-1,2,4-triazol-1-yl}methyl)-5-(1,1-dioxidothiomorpholin-4-yl)-1H-1,2,4-triazol-1-yl]pyridine-2-carboxylic acid

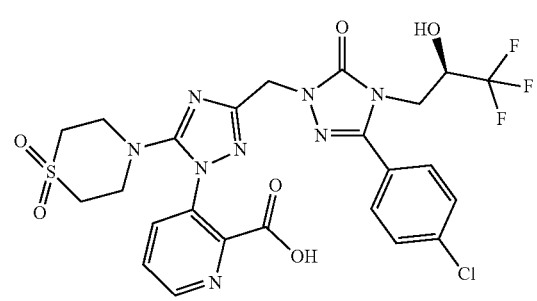 [SMILES: O=C(O)c1ncccc1-n1nc(Cn2nc(-c3ccc(Cl)cc3)n(C[C@@H](O)C(F)(F)F)c2=O)nc1N1CCS(=O)(=O)CC1]

A solution of ethyl 3-[3-({3-(4-chlorophenyl)-5-oxo-4-[(2R)-3,3,3-trifluoro-2-hydroxypropyl]-4,5-dihydro-1H-1,2,4-triazol-1-yl}methyl)-5-(1,1-dioxidothiomorpholin-4-yl)-1H-1,2,4-triazol-1-yl]pyridine-2-carboxylate (Example 15A; 45.0 mg, 67.1 µmol) in tetrahydrofuran (1.0 ml) and water (100 µl) was treated with lithium hydroxide monohydrate (3.10 mg, 73.8 µmol) and stirred overnight at room temperature. The reaction mixture was purified by preparative HPLC (Method 4) affording 36.5 mg (85% of th.) of the title compound.

LC-MS (Method 2): $R_t$=1.44 min; MS (ESIpos): m/z=643.1 [M+H]$^+$ $^1$H-NMR (400 MHz, DMSO-d6) δ [ppm]: 13.68 (br s, 1H), 8.74 (d, 1H), 8.15 (br d, 1H), 7.87-7.50 (m, 5H), 7.25-6.68 (m, 1H), 5.02-4.80 (m, 2H), 4.39-4.20 (br m, 1H), 4.10-3.70 (m, 2H), 3.45 (br s, 4H), 3.14 (br s, 4H).

Example 17A

Ethyl 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-2-carboxylate

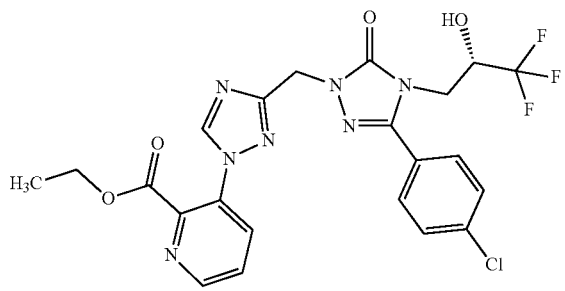 [SMILES: CCOC(=O)c1ncccc1-n1cnc(Cn2nc(-c3ccc(Cl)cc3)n(C[C@H](O)C(F)(F)F)c2=O)n1]

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 11A, 1.35 g, 2.65 mmol) in tetrahydrofuran (13 ml) was treated with HATU (1.51 g, 3.97 mmol) and stirred 15 minutes at room temperature. Ethanol (13 ml) and N,N-diisopropylethylamine (1.4 ml, 7.9 mmol) were then added. The resulting mixture was stirred 2 h at room temperature and evaporated. The residue was purified by flash chromatography (silica gel, eluent cyclohexane/ethyl acetate) and evaporated. The residue was retaken in ethyl acetate and the resulting solution was washed with water followed by a saturated sodium chloride solution. The organic layer was dryed over magnesium sulfate and evaporated affording 943 mg (60% of th.) of the title compound LC-MS (Method 1): $R_t$=0.87 min; MS (ESIpos): m/z=538.1 [M+H]$^+$ $^1$H-NMR (400 MHz, DMSO-d6) δ [ppm]: 9.07 (s, 1H), 8.75 (dd, 1H), 8.27 (dd, 1H), 7.89-7.51 (m, 5H), 6.91 (d, 1H), 5.09 (s, 2H), 4.41-3.74 (m, 5H), 1.01 (t, 3H).

Example 18A

Ethyl 3-[5-bromo-3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-2-carboxylate

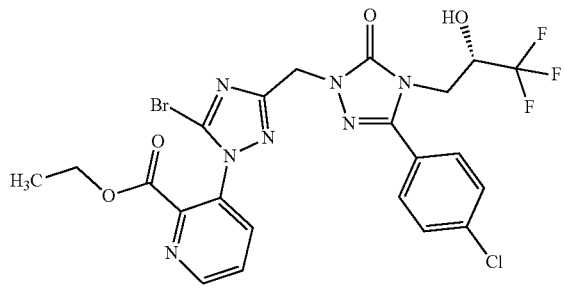 [SMILES: CCOC(=O)c1ncccc1-n1nc(Cn2nc(-c3ccc(Cl)cc3)n(C[C@H](O)C(F)(F)F)c2=O)nc1Br]

A solution of ethyl 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-2-carboxylate (Example 17A, 930 mg, 1.73 mmol) in acetonitrile was treated with 1-bromopyrrolidine-2,5-dione (1.54 g, 8.64 mmol) and 2,2'-(E)-diazene-1,2-diylbis(2-methylpropanenitrile) (56.8 mg, 346 µmol). The resulting mixture was stirred 18 h at reflux. The reaction mixture was diluted with ethyl acetate and washed with water followed by a saturated solution of sodium chloride. The organic layer was dried over magnesium sulfate and evaporated. The residue was purified by flash chromatography (silica gel, petrol ether/ethyl acetate) affording 624 mg (55% of th.) of the title compound.

LC-MS (Method 2): $R_t$=1.86 min; MS (ESIpos): m/z=616.0 [M+H]$^+$ $^1$H-NMR (400 MHz, DMSO-d6) δ [ppm]: 8.90 (dd, 1H), 8.38-8.20 (m, 1H), 7.97-7.53 (m, 5H), 6.90 (d, 1H), 5.20-4.97 (m, 2H), 4.44-3.70 (m, 6H), 0.97 (t, 3H).

Example 19A

Ethyl 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-5-(3-oxopiperazin-1-yl)-1H-1,2,4-triazol-1-yl]pyridine-2-carboxylate

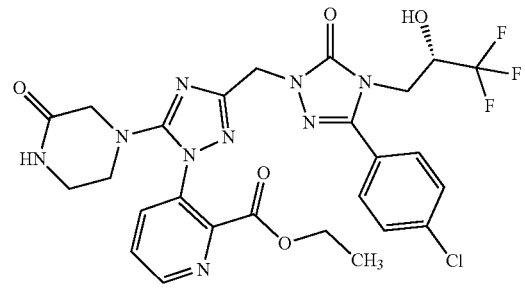 [SMILES: CCOC(=O)c1ncccc1-n1nc(Cn2nc(-c3ccc(Cl)cc3)n(C[C@H](O)C(F)(F)F)c2=O)nc1N1CCNC(=O)C1]

A solution of ethyl 3-[5-bromo-3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-2-carboxylate (Example 18A, 267 mg, 433 µmol) in acetonitrile (2.5 ml) was treated with piperazin-2-one (867 mg, 8.66 mmol) and N,N-diisopropylethylamine (160 µl, 910 µmol). The resulting mixture was stirred 8 h at 100° C. under microwave irradiation. The reaction mixture was diluted with water and extracted with ethyl acetate. The combined organic layers were evaporated and the residue purified by preparative HPLC (Method 4) affording 196 mg (71% of th.) of the title compound.

LC-MS (Method 2): $R_t$=1.47 min; MS (ESIpos): m/z=636.2 [M+H]$^+$ $^1$H-NMR (400 MHz, DMSO-d6) δ [ppm]: 8.80-8.76 (m, 1H), 8.20 (dd, 1H), 8.07-7.94 (m, 1H), 7.87-7.55 (m, 5H), 6.88 (d, 1H), 4.98-4.86 (m, 2H), 4.37-4.21 (m, 1H), 4.15-3.78 (m, 4H), 3.58 (s, 2H), 3.21-3.05 (m, 4H), 0.99 (t, 3H).

Example 20A

3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-5-(3-oxopiperazin-1-yl)-1H-1,2,4-triazol-1-yl]pyridine-2-carboxylic acid

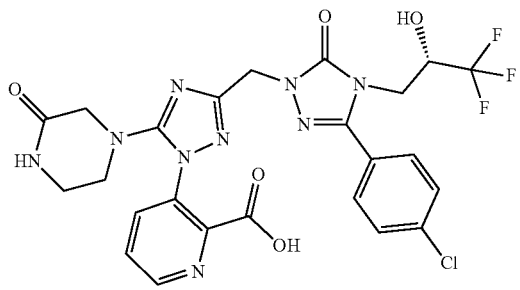 [SMILES: O=C1CN(c2nc(Cn3nc(-c4ccc(Cl)cc4)n(C[C@H](O)C(F)(F)F)c3=O)nn2-c2cccnc2C(=O)O)CCN1]

A solution of ethyl 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-5-(3-oxopiperazin-1-yl)-1H-1,2,4-triazol-1-yl]pyridine-2-carboxylate (Example 19A, 190 mg, 299 µmol) in tetrahydrofuran (4.5 ml) and in water (450 µl) was treated with lithium hydroxide monohydrate (13.8 mg, 329 µmol). The resulting mixture was stirred 5 h at room temperature and evaporated. The residue was purified by preparative HPLC (Method 4) affording 139 mg (77% of th.) of the title compound.

LC-MS (Method 2): $R_t$=1.27 min; MS (ESIpos): m/z=608.1 [M+H]$^+$ $^1$H-NMR (400 MHz, DMSO-d6) δ [ppm]: 13.57 (br s, 1H), 8.75 (dd, 1H), 8.18-7.93 (m, 2H), 7.83-7.54 (m, 5H), 6.91 (br d, 1H), 4.99-4.83 (m, 2H), 4.38-4.22 (m, 1H), 4.06-3.76 (m, 2H), 3.57 (s, 2H), 3.20-3.04 (m, 4H).

Example 21A

Ethyl 3-hydrazinylpyridine-4-carboxylate

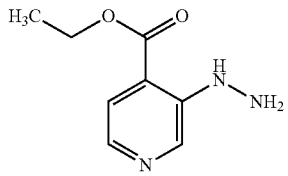

At −20° C., a solution of ethyl 3-aminopyridine-4-carboxylate (1.50 g, 9.03 mmol) in a concentrated solution of hydrochloric acid (8 ml) was treated dropwisely with a solution of sodium nitrite (685 mg, 9.93 mmol) in water (7.0 ml). The resulting mixture was stirred 1 h at −15° C. A solution of tin chloride dihydrate (6.11 g, 27.1 mmol) in a concentrated solution of hydrochloric acid (4 ml) cooled at −15 C was added dropwisely and the resulting mixture was stirred 1 h at −15° C. The pH of the reaction was brought to pH=10-11 with aqueous potassium hydroxide solution (40%) while the temperature is kept at −15° C. The reaction mixture was brought to room temperature and extracted twice with ethyl acetate. The combined organic layers were filtered over celite. The filtrate was washed with a saturated sodium chloride solution, dried over magnesium sulfate and evaporated affording 939 mg (49% of th.) of the title compound which was used as such without further purification.

LC-MS (Method 5): $R_t$=1.09 min; MS (ESIpos): m/z=182 [M+H]$^+$ $^1$H-NMR (400 MHz, DMSO-d6) δ [ppm]: 1.293 (7.65), 1.311 (16.00), 1.329 (7.95), 1.334 (1.32), 3.832 (1.57), 4.268 (2.50), 4.286 (7.65), 4.304 (7.59), 4.321 (2.46), 4.486 (6.80), 7.486 (3.27), 7.499 (3.60), 7.810 (4.82), 7.823 (4.56), 8.110 (3.04), 8.778 (6.23).

Example 22A

Ethyl 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-5-(methoxycarbonyl)-1H-1,2,4-triazol-1-yl]pyridine-4-carboxylate

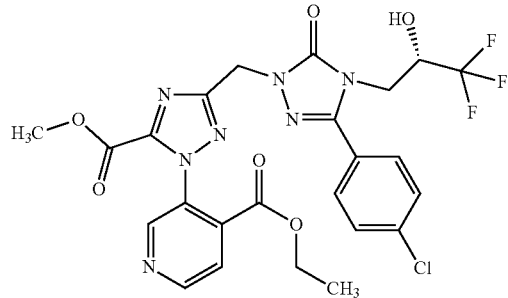 [SMILES: CCOC(=O)c1ccncc1-n1nc(Cn2nc(-c3ccc(Cl)cc3)n(C[C@H](O)C(F)(F)F)c2=O)nc1C(=O)OC]

At 0° C., a solution of methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate (Example 2A, 500 mg, 1.32 mmol) in tetrahydrofuran (10 ml) was treated with N,N-diisopropylethylamine (250 µl, 1.5 mmol) and methyl chloro(oxo)acetate (130 µl, 1.5 mmol) and stirred 30 min at 0° C. Ethyl 3-hydrazinylpyridine-4-carboxylate (Example 21A, 310 mg, 85% purity, 1.45 mmol) was then added and the resulting mixture was stirred at room temperature overnight and 10.5 h at reflux. The reaction mixture was purified by preparative HPLC (Method 4) affording 417 mg (48% of th.) of the title compound.

LC-MS (Method 2): $R_t$=1.83 min; MS (ESIpos): m/z=596.1 [M+H]$^+$ $^1$H-NMR (400 MHz, DMSO-d6) δ [ppm]: 9.03-8.84 (m, 2H), 8.01-7.56 (m, 5H), 6.91 (d, 1H), 5.17 (s, 2H), 4.45-4.21 (m, 1H), 4.07-3.97 (m, 3H), 3.90-3.73 (m, 4H), 0.93 (t, 3H).

Example 23A

3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-4-carboxylic acid

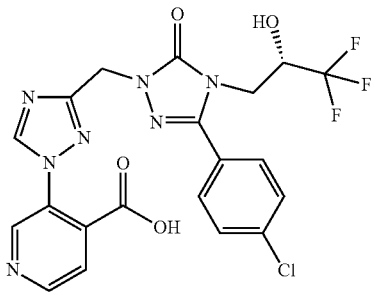 [SMILES: O=C(O)c1ccncc1-n1cnc(Cn2nc(-c3ccc(Cl)cc3)n(C[C@H](O)C(F)(F)F)c2=O)n1]

A solution of ethyl 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-5-(methoxycarbonyl)-1H-1,2,4-triazol-1-yl]pyridine-4-carboxylate (Example 22A, 187 mg, 313 µmol) in tetrahydrofuran (5.0 ml) was treated with an aqueous solution of sodium hydroxide (940 µl, 1.0 M, 940 µmol) and stirred 10 min at room temperature. The reaction mixture was brought to pH=1 with a concentrated solution of hydrochloric acid and stirred overnight at room temperature. The resulting mixture was purified by preparative HPLC (Method 4) affording 126 mg (79% of th.) of the title compound.

LC-MS (Method 2): $R_t$=1.24 min; MS (ESIpos): m/z=510.1 [M+H]$^+$ $^1$H-NMR (400 MHz, DMSO-d6) δ [ppm]: 14.41-13.43 (m, 1H), 9.05-8.78 (m, 3H), 7.93-7.51 (m, 5H), 6.95 (br s, 1H), 5.22-5.00 (m, 2H), 4.46-4.20 (m, 1H), 4.10-3.75 (m, 2H).

Example 24A

3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-4-carbonyl chloride

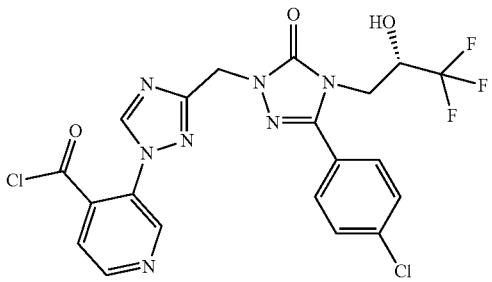 [SMILES: O=C(Cl)c1ccncc1-n1cnc(Cn2nc(-c3ccc(Cl)cc3)n(C[C@H](O)C(F)(F)F)c2=O)n1]

A solution of 3-[3-({3-(4-chlorophenyl)-5-oxo-4-[(2S)-3,3,3-trifluoro-2-hydroxypropy]-4,5-dihydro-1H-1,2,4-triazol-1-yl}methyl)-1H-1,2,4-triazol-1-yl]pyridine-4-carboxylic acid (Example 23A, 60.0 mg, 118 µmol) in dichloromethane (2.0 ml) was treated with 1-chloro-N,N,2-trimethylprop-1-en-1-amine (46 µl, 360 µmol) and stirred 1 h at room temperature. The solution was used as such in the next step.

Example 25A ethyl 3-{3-({3-(4-chlorophenyl)-5-oxo-4-[(2S)-3,3,3-trifluoro-2-hydroxypropyl]-4,5-dihydro-1H-1,2,4-triazol-1-yl}methyl)-5-[(3-oxopiperazin-1-yl)carbonyl]-1H-1,2,4-triazol-1-yl}pyridine-4-carboxylate

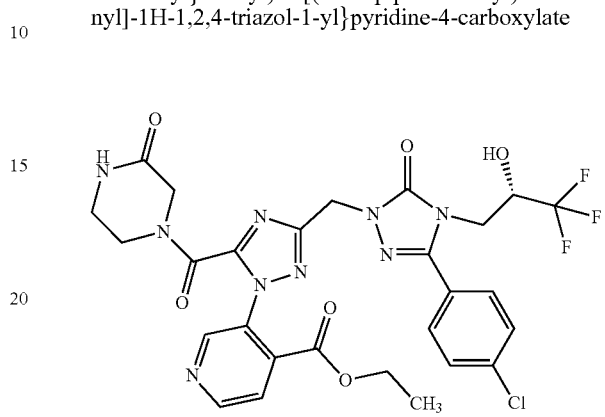

A solution of ethyl 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-5-(methoxycarbonyl)-1H-1,2,4-triazol-1-yl]pyridine-4-carboxylate (Example 22A, 1.00 g, 1.68 mmol) in N,N-dimethylformamide (7.0 ml) was treated with an aqueous solution of sodium hydroxide (880 µl, 2.0 M, 1.8 mmol) and stirred 5 min at room temperature. HATU (1.28 g, 3.36 mmol) was added to the reaction mixture and stirred 5 min. Piperazin-2-one (336 mg, 3.36 mmol) and N,N-diisopropylethylamine (880 µl, 5.0 mmol) were then added and the resulting mixture stirred overnight at room temperature. Purification by preparative HPLC (Method 4) afforded 636 mg (54% of th.) of the title compound.

LC-MS (Method 1): $R_t$=0.84 min; MS (ESIpos): m/z=664.1 [M+H]$^+$ $^1$H-NMR (400 MHz, DMSO-d6) δ [ppm]: 8.96-8.79 (m, 2H), 8.28-8.10 (m, 1H), 7.97-7.52 (m, 5H), 7.03-6.82 (m, 1H), 5.27-5.14 (m, 2H), 4.60-4.20 (m, 2H), 4.13-3.94 (m, 5H), 3.92-3.57 (m, 2H), 3.29-3.07 (m, 2H), 1.04-0.89 (m, 3H).

Example 26A

3-{3-({3-(4-chlorophenyl)-5-oxo-4-[(2S)-3,3,3-trifluoro-2-hydroxypropyl]-4,5-dihydro-1H-1,2,4-triazol-1-yl}methyl)-5-[(3-oxopiperazin-1-yl)carbonyl]-1H-1,2,4-triazol-1-yl}pyridine-4-carboxylic acid

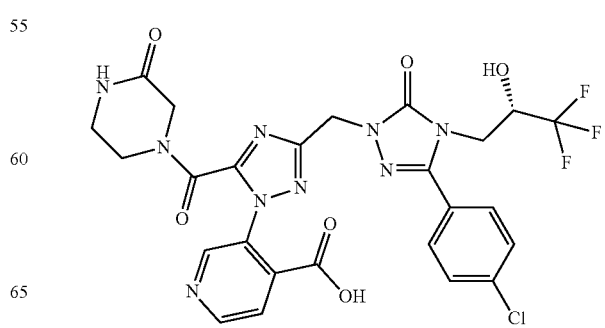

A solution of ethyl 3-{3-({3-(4-chlorophenyl)-5-oxo-4-[(2S)-3,3,3-trifluoro-2-hydroxypropyl]-4,5-dihydro-1H-1,2,4-triazol-1-yl}methyl)-5-[(3-oxopiperazin-1-yl)carbonyl]-1H-1,2,4-triazol-1-yl}pyridine-4-carboxylate (Example 25A, 630 mg, 949 μmol) in tetrahydrofuran (19 ml, 230 mmol) was treated with an aqueous solution of lithium hydroxide (950 μl, 1.0 M, 950 μmol) and stirred overnight at room temperature. The reaction mixture was brought to pH=4 with an aqueous solution of hydrogen chloride (1N) and evaporated. The residue was purified by preparative HPLC (Method 4) affording 466 mg (75% of th.) of the title compound.

LC-MS (Method 6): $R_t$=0.96 min; MS (ESIpos): m/z=636.0 [M+H]$^+$ $^1$H-NMR (400 MHz, DMSO-d6) δ [ppm]: 14.10 (br s, 1H), 8.97-8.70 (m, 2H), 8.01-7.49 (m, 5H), 7.01-6.76 (m, 1H), 5.29-5.02 (m, 2H), 4.49-4.19 (m, 3H), 4.10-3.72 (m, 4H), 3.24-3.07 (m, 2H, overlap with HDO peak), NH not visible.

Example 27A

Ethyl 3-{3-({3-(4-chlorophenyl)-5-oxo-4-[(2S)-3,3,3-trifluoro-2-hydroxypropyl]-4,5-dihydro-1H-1,2,4-triazol-1-yl}methyl)-5-[(1,1-dioxidothiomorpholin-4-yl)carbonyl]-1H-1,2,4-triazol-1-yl}pyridine-4-carboxylate

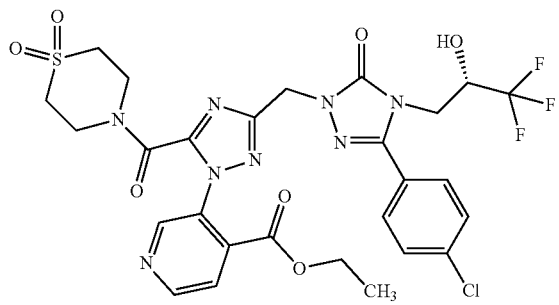 [SMILES: CCOC(=O)c1ccncc1-n1nc(Cn2nc(-c3ccc(Cl)cc3)n(C[C@H](O)C(F)(F)F)c2=O)nc1C(=O)N1CCS(=O)(=O)CC1]

A solution of ethyl 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-5-(methoxycarbonyl)-1H-1,2,4-triazol-1-yl]pyridine-4-carboxylate (Example 22A, 1.50 g, 2.52 mmol) in N,N-dimethylformamide (10 ml) was treated with an aqueous solution of sodium hydroxide (1.3 ml, 2.0 M, 2.6 mmol) and stirred 5 min at room temperature. HATU (1.91 g, 5.03 mmol) was added to the reaction mixture and stirred 5 min. Thiomorpholine 1,1-dioxide (681 mg, 5.03 mmol) and N,N-diisopropylethylamine (1.3 ml, 7.6 mmol) were then added and the resulting mixture stirred overnight at room temperature. Purification by preparative HPLC (Method 4) afforded 1.15 g (63% of th.) of the title compound.

LC-MS (Method 1): $R_t$=0.90 min; MS (ESIpos): m/z=699.1 [M+H]$^+$ $^1$H-NMR (400 MHz, DMSO-d6) δ [ppm]: 9.00-8.82 (m, 2H), 7.98-7.55 (m, 5H), 6.93-6.83 (m, 1H), 5.26-5.07 (m, 2H), 4.44-4.20 (m, 3H), 4.14-3.73 (m, 6H), 3.41-3.10 (m, 4H, overlap with HDO peak), 1.07-0.90 (m, 3H).

Example 28A

3-{3-({3-(4-Chlorophenyl)-5-oxo-4-[(2S)-3,3,3-trifluoro-2-hydroxypropyl]-4,5-dihydro-1H-1,2,4-triazol-1-yl}methyl)-5-[(1,1-dioxidothiomorpholin-4-yl)carbonyl]-1H-1,2,4-triazol-1-yl}pyridine-4-carboxylic acid

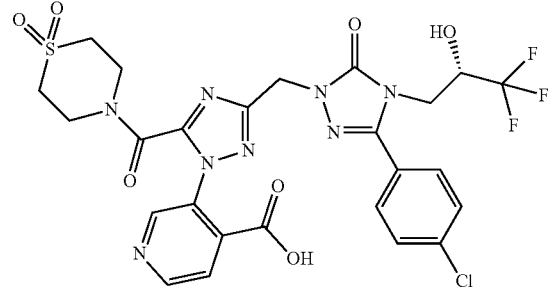 [SMILES: O=C(O)c1ccncc1-n1nc(Cn2nc(-c3ccc(Cl)cc3)n(C[C@H](O)C(F)(F)F)c2=O)nc1C(=O)N1CCS(=O)(=O)CC1]

A solution of ethyl 3-{3-({3-(4-chlorophenyl)-5-oxo-4-[(2S)-3,3,3-trifluoro-2-hydroxypropyl]-4,5-dihydro-1H-1,2,4-triazol-1-yl}methyl)-5-[(1,1-dioxidothiomorpholin-4-yl)carbonyl]-1H-1,2,4-triazol-1-yl}pyridine-4-carboxylate (Example 27A, 1.10 g, 1.57 mmol) in tetrahydrofuran (31 ml) was treated with an aqueous solution of lithium hydroxide (1.6 ml, 1.0 M, 1.6 mmol) and stirred overnight at room temperature. The reaction mixture was brought to pH=4 with an aqueous solution of hydrogen chloride (1N) and evaporated. The residue was purified by preparative HPLC (Method 4) affording 891 mg (84% of th.) of the title compound.
Mixture of Rotamers LC-MS (Method 6): $R_t$=1.02 min; MS (ESIpos): m/z=671.0 [M+H]$^+$ Example 29A Ethyl 3-{5-[(2-amino-2-methylpropyl)carbamoyl]-3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl}pyridine-4-carboxylate

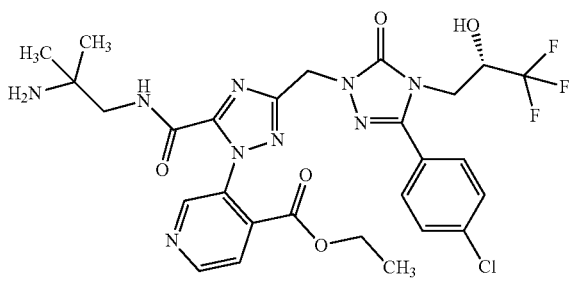 [SMILES: CCOC(=O)c1ccncc1-n1nc(Cn2nc(-c3ccc(Cl)cc3)n(C[C@H](O)C(F)(F)F)c2=O)nc1C(=O)NCC(C)(C)N]

A solution of ethyl 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-5-(methoxycarbonyl)-1H-1,2,4-triazol-1-yl]pyridine-4-carboxylate (Example 22A, 1.50 g, 2.52 mmol) in dichloromethane (15 ml, 230 mmol) was treated with an aqueous solution of sodium hydroxide (1.3 ml, 2.0 M, 2.6 mmol) and stirred 15 min at room temperature. The reaction mixture was cooled to 0° C. and 1-chloro-N,N-2-trimethylpropenylamine (370 μl, 2.8 mmol) was added to the reaction mixture and stirred 1 h at room temperature. 2-methylpropane-1,2-diamine (290 μl, 2.8 mmol), N,N-diisopropylethylamine (880 µl, 5.0 mmol) and 4-dimethylaminopyridine (61.5 mg, 503 µmol) were then added and the resulting mixture stirred overnight at room temperature. The reaction mixture was evaporated and the residue purified by preparative HPLC (Method 4) afforded 292 mg (18% of th.) of the title compound LC-MS (Method 5): $R_t$=1.76 min; MS (ESIpos): m/z=652.3 [M+H]$^+$ Example 30A 3-{5-[(2-Amino-2-methylpropyl)carbamoyl]-3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl}pyridine-4-carboxylic acid

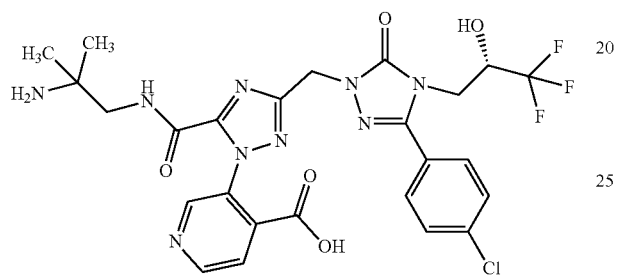

A solution of ethyl 3-{5-[(2-amino-2-methylpropyl)carbamoyl]-3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl}pyridine-4-carboxylate (Example 29A, 275 mg, 422 µmol) in tetrahydrofuran (7.0 ml) was treated with an aqueous solution of lithium hydroxide (1.3 ml, 1.0 M, 1.3 mmol) and stirred 2 h at room temperature. The reaction mixture was evaporated and the residue was purified by preparative HPLC (Method 4) affording 219 mg (83% of th.) of the title compound.

LC-MS (Method 2): $R_t$=1.16 min; MS (ESIpos): m/z=624.2 [M+H]$^+$ $^1$H-NMR (400 MHz, DMSO-d6) δ [ppm]: 9.38-9.19 (m, 1H), 8.63-8.46 (m, 2H), 8.03-7.42 (m, 8H), 7.16-6.98 (m, 1H), 5.26-4.96 (m, 2H), 4.42-4.21 (m, 1H), 4.11-3.67 (m, 2H), 3.31-3.08 (m, 2H, overlap with HDO peak), 1.28-1.08 (m, 6H).

Example 31A

Ethyl 2-hydrazinylpyridine-3-carboxylate

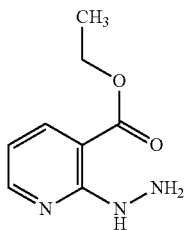

Ethyl 2-chloropyridine-3-carboxylate (2.00 g, 10.8 mmol) was added to a solution of hydrazine in tetrahydrofuran (21 ml, 1.0 M, 32 mmol) and stirred 16 h at room temperature. More of the solution of hydrazine in tetrahydrofuran (11 ml, 1.0 M, 32 mmol) was then added and stirred 16 h at room temperature. The reaction mixture was evaporated. The residue was retaken in chloroform/methanol solution (9/1) and washed twice with a potassium carbonate solution (40%). The combined aqueous layer were washed with chloroform/methanol solution (9/1). The combined organic layers were dried over magnesium sulfate and evaporated affording 1.87 g (68% of th., purity 72%) of the title compound which was used in the next step without further purification.

LC-MS (Method 5): $R_t$=1.21 min; MS (ESIpos): m/z=181.1 [M+H]$^+$

Example 32A

Ethyl 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-5-(methoxycarbonyl)-1H-1,2,4-triazol-1-yl]pyridine-3-carboxylate

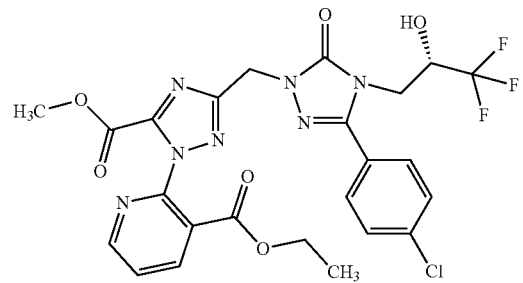 [SMILES: CCOC(=O)c1cccnc1-n1nc(Cn2nc(-c3ccc(Cl)cc3)n(C[C@H](O)C(F)(F)F)c2=O)nc1C(=O)OC]

At 0° C., a solution of methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate (Example 2A, 2.35 g, 6.19 mmol) in dioxane (47 ml) was treated with methyl chloro(oxo)acetate (680 µl, 7.4 mmol) and N,N-diisopropylethylamine (1.3 ml, 7.4 mmol) and stirred 15 min. A pre-mixed solution of ethyl 2-hydrazinylpyridine-3-carboxylate (Example 31A, 1.87 g, 72% purity, 7.43 mmol), in dioxane (23 ml) was then added and the resulting mixture was stirred 3 days at room temperature. The reaction mixture was evaporated and the residue purified by flash chromatography (silicagel, eluent dichloromethane/methanol) followed by a preparative HPLC (Method 4) affording 833 mg (23% of th.) of the title compound.

LC-MS (Method 1): $R_t$=0.98 min; MS (ESIpos): m/z=596.2 [M+H]$^+$ $^1$H-NMR (400 MHz, DMSO-d6) δ [ppm]: 8.88-8.42 (m, 2H), 7.95-7.54 (m, 5H), 6.91 (d, 1H), 5.17 (s, 2H), 4.40-4.19 (m, 1H), 4.10-3.80 (m, 4H), 3.77 (s, 3H), 0.97 (t, 3H).

Example 33A

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-3-carboxylic acid

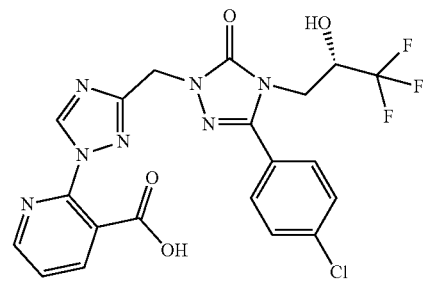 [SMILES: O=C(O)c1cccnc1-n1cnc(Cn2nc(-c3ccc(Cl)cc3)n(C[C@H](O)C(F)(F)F)c2=O)n1]

A solution of ethyl 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-5-(methoxycarbonyl)-1H-1,2,4-triazol-1-yl]pyridine-3-carboxylate (Example 32A, 600 mg, 1.01 mmol) in tetrahydrofuran THF (60 ml) was treated with an aqueous sodium hydroxide solution (12 ml, 5.0 M, 60 mmol) and stirred 1 h at room temperature. The reaction mixture was acidified to pH=1 with a concentrated solution of hydrochloric acid. Tetrahydrofuran was then evaporated. The resulting solution was extracted twice with ethyl acetate. The combined organic layers were evaporated and the residue purified by preparative HPLC (Method 4) affording 388 mg (75% of th.) of the title compound.

LC-MS (Method 6): $R_t$=1.05 min; MS (ESIpos): m/z=510.0 [M+H]$^+$ $^1$H-NMR (400 MHz, DMSO-d6) δ [ppm]: 13.56 (br s, 1H), 9.14 (s, 1H), 8.68 (dd, 1H), 8.27 (dd, 1H), 7.87-7.49 (m, 5H), 7.09-6.75 (m, 1H), 5.20-4.98 (m, 2H), 4.41-4.22 (br m, 1H), 4.09-3.72 (m, 2H)

Example 34A

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-3-carbonylchloride

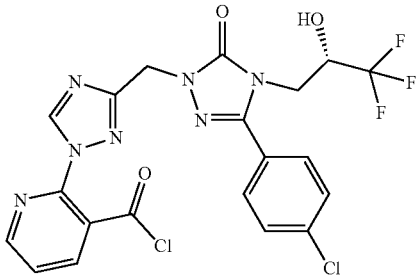 [SMILES: O=C(Cl)c1cccnc1-n1cnc(Cn2nc(-c3ccc(Cl)cc3)n(C[C@H](O)C(F)(F)F)c2=O)n1]

A solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-3-carboxylic acid (Example 33A, 291 mg, 571 μmol) in dichloromethane (6.0 ml, 93 mmol) was treated with 1-chloro-N,N,2-trimethylprop-1-en-1-amine (400 μl, 3 mmol) and stirred 1 h at room temperature. The solution was used as such in the next step without further purification.

Example 35A

Ethyl 2-{3-({3-(4-chlorophenyl)-5-oxo-4-[(2S)-3,3,3-trifluoro-2-hydroxypropyl]-4,5-dihydro-1H-1,2,4-triazol-1-yl}methyl)-5-[(3-oxopiperazin-1-yl)carbonyl]-1H-1,2,4-triazol-1-yl}pyridine-3-carboxylate

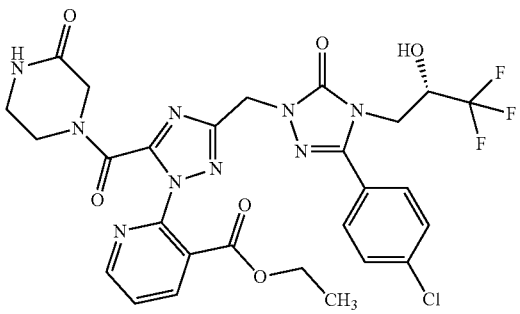 [SMILES: CCOC(=O)c1cccnc1-n1nc(Cn2nc(-c3ccc(Cl)cc3)n(C[C@H](O)C(F)(F)F)c2=O)nc1C(=O)N1CCNC(=O)C1]

A solution of ethyl 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-5-(methoxycarbonyl)-1H-1,2,4-triazol-1-yl]pyridine-3-carboxylate (Example 34A, 500 mg, 839 μmol) in N,N-dimethylformamide (3.5 ml) was treated with an aqueous solution of sodium hydroxide (440 μl, 2.0 M, 880 μmol) and stirred 5 min at room temperature. HATU (638 mg, 1.68 mmol) was added to the reaction mixture and stirred 20 min. Piperazin-2-one (168 mg, 1.68 mmol) and N,N-diisopropylethylamine (440 μl, 2.5 mmol) were then added and the resulting mixture stirred overnight at room temperature. Purification by preparative HPLC (Method 4) afforded 447 mg (80% of th.) of the title compound As a Mixture of Conformers LC-MS (Method 2): $R_t$=1.61 min; MS (ESIpos): m/z=664.2 [M+H]$^+$ $^1$H-NMR (400 MHz, DMSO-d6) δ [ppm]: 8.79-8.61 (m, 1H), 8.49-8.30 (m, 1H), 8.28-8.10 (m, 1H), 7.87-7.52 (m, 5H), 6.99-6.83 (m, 1H), 5.27-5.07 (m, 2H), 4.44-3.65 (m, 9H), 3.27-3.15 (m, 2H), 1.08-0.92 (m, 3H).

Example 36A

2-{3-({3-(4-chlorophenyl)-5-oxo-4-[(2S)-3,3,3-trifluoro-2-hydroxypropyl]-4,5-dihydro-1H-1,2,4-triazol-1-yl}methyl)-5-[(3-oxopiperazin-1-yl)carbonyl]-1H-1,2,4-triazol-1-yl}pyridine-3-carboxylic acid

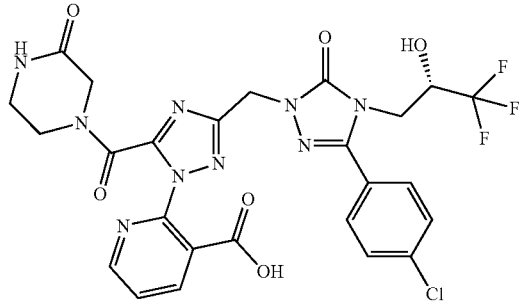 [SMILES: O=C1CN(C(=O)c2nc(Cn3nc(-c4ccc(Cl)cc4)n(C[C@H](O)C(F)(F)F)c3=O)nn2-c2ncccc2C(=O)O)CCN1]

A solution of ethyl 2-{3-({3-(4-chlorophenyl)-5-oxo-4-[(2S)-3,3,3-trifluoro-2-hydroxypropyl]-4,5-dihydro-1H-1,2,4-triazol-1-yl}methyl)-5-[(3-oxopiperazin-1-yl)carbonyl]-1H-1,2,4-triazol-1-yl}pyridine-3-carboxylate (Example 35A, 370 mg, 557 μmol) in tetrahydrofuran (11 ml) was treated with an aqueous solution of lithium hydroxide (610 μl, 1.0 M, 610 μmol) and stirred overnight at room temperature. The reaction mixture was brought to pH=4 with an aqueous solution of hydrogen chloride (1N) and evaporated. The residue was purified by preparative HPLC (Method 4) affording 216 mg (49% of th.) of the title compound.

LC-MS (Method 2): $R_t$=1.35 min; MS (ESIpos): m/z=636.1 [M+H]$^+$

Example 37A

Ethyl 2-{3-({3-(4-chlorophenyl)-5-oxo-4-[(2S)-3,3,3-trifluoro-2-hydroxypropyl]-4,5-dihydro-1H-1,2,4-triazol-1-yl}methyl)-5-[(1,1-dioxidothiomorpholin-4-yl)carbonyl]-1H-1,2,4-triazol-1-yl}pyridine-3-carboxylate

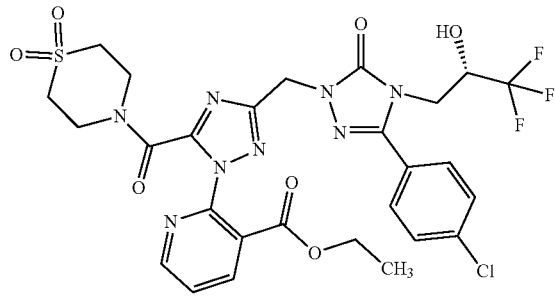 [SMILES: CCOC(=O)c1cccnc1-n1nc(Cn2nc(-c3ccc(Cl)cc3)n(C[C@H](O)C(F)(F)F)c2=O)nc1C(=O)N1CCS(=O)(=O)CC1]

A solution of ethyl 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-5-(methoxycarbonyl)-1H-1,2,4-triazol-1-yl]pyridine-3-carboxylate (Example 34A, 1.15 g, 1.93 mmol) in N,N-dimethylformamide (8.0 ml) was treated with an aqueous solution of sodium hydroxide (1.0 ml, 2.0 M, 2.0 mmol) and stirred 5 min at room temperature. HATU (1.47 g, 3.86 mmol) was added to the reaction mixture and stirred 5 min. Thiomorpholine 1,1-dioxide (522 mg, 3.86 mmol) and N,N-diisopropylethylamine (1.0 ml, 5.8 mmol) were then added and the resulting mixture stirred 3 h at room temperature. Purification by preparative HPLC (Method 4) afforded 1.09 g (81% of th.) of the title compound.

LC-MS (Method 2): $R_t$=1.77 min; MS (ESIpos): m/z=699.1 [M+H]$^+$ $^1$H-NMR (400 MHz, DMSO-d6) δ [ppm]: 8.70 (dd, 1H), 8.38 (dd, 1H), 7.84-7.54 (m, 5H), 6.90 (d, 1H), 5.25-5.03 (m, 2H), 4.42-4.21 (m, 1H), 4.19-3.74 (m, 8H), 3.40-3.11 (m, 4H, overlap with HDO peak), 1.11-0.95 (m, 3H).

Example 38A

2-{3-({3-(4-chlorophenyl)-5-oxo-4-[(2S)-3,3,3-trifluoro-2-hydroxypropyl]-4,5-dihydro-1H-1,2,4-triazol-1-yl}methyl)-5-[(1,1-dioxidothiomorpholin-4-yl)carbonyl]-1H-1,2,4-triazol-1-yl}pyridine-3-carboxylic acid

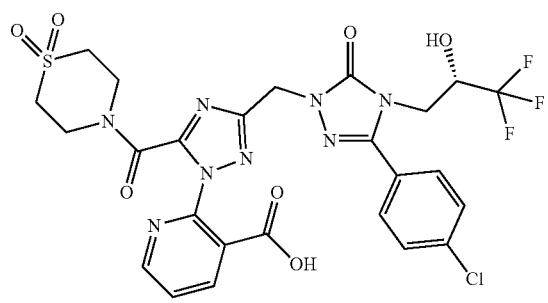 [SMILES: O=C(O)c1cccnc1-n1nc(Cn2nc(-c3ccc(Cl)cc3)n(C[C@H](O)C(F)(F)F)c2=O)nc1C(=O)N1CCS(=O)(=O)CC1]

A solution of ethyl 2-{3-({3-(4-chlorophenyl)-5-oxo-4-[(2S)-3,3,3-trifluoro-2-hydroxypropyl]-4,5-dihydro-1H-1,2,4-triazol-1-yl}methyl)-5-[(1,1-dioxidothiomorpholin-4-yl)carbonyl]-1H-1,2,4-triazol-1-yl}pyridine-3-carboxylate (Example 37A, 1.08 g, 1.54 mmol) in tetrahydrofuran (31 ml) was treated with an aqueous solution of lithium hydroxide (1.7 ml, 1.0 M, 1.7 mmol) and stirred overnight at room temperature. The reaction mixture was brought to pH=4 with an aqueous solution of hydrogen chloride (1N) and evaporated. The residue was purified by preparative HPLC (Method 4) affording 706 mg (60% of th.) of the title compound.

LC-MS (Method 2): $R_t$=1.49 min; MS (ESIpos): m/z=671.1 [M+H]$^+$ $^1$H-NMR (400 MHz, DMSO-d6) δ [ppm]: 13.76 (br s, 1H), 8.71 (dd, 1H), 8.41 (dd, 1H), 7.83-7.55 (m, 5H), 6.91 (br s, 1H), 5.31-5.01 (m, 2H), 4.44-3.75 (m, 7H), 3.35-3.06 (m, 4H).

Example 39A 5-(4-Chlorophenyl)-2-{[1-(3-nitropyridin-2-yl)-1H-1,2,4-triazol-3-yl]methyl}-4-[(2S)-3,3,3-trifluoro-2-hydroxypropyl]-2,4-dihydro-3H-1,2,4-triazol-3-one

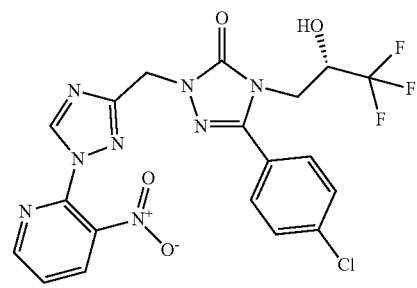 [SMILES: O=c1n(Cc2ncn(-c3ncccc3[N+](=O)[O-])n2)nc(-c2ccc(Cl)cc2)n1C[C@H](O)C(F)(F)F]

A solution of methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate (Example 2A, 2.00 g, 5.28 mmol) in tetrahydrofuran (33 ml) was treated with 2-hydrazinyl-3-nitropyridine (895 mg, 5.81 mmol) and N,N-diisopropylethylamine (2.0 ml, 12 mmol) and stirred 1 h at room temperature. (Diethoxymethoxy)ethane (33 ml) was added and the resulting mixture was stirred overnight at reflux and 4 h at 120° C. under microwave irradiation. The reaction mixture was evaporated and the residue was purified by preparative HPLC (Method 4) affording 464 mg (17% of th.) of the title compound.

LC-MS (Method 2): $R_t$=1.70 min; MS (ESIpos): m/z=511.1 [M+H]$^+$ $^1$H-NMR (400 MHz, DMSO-d6) δ [ppm]: 9.35 (s, 1H), 8.84 (dd, 1H), 8.62 (dd, 1H), 7.89-7.56 (m, 5H), 6.92 (d, 1H), 5.11 (d, 2H), 4.40-4.23 (m, 1H), 4.04-3.76 (m, 2H).

Example 40A

2-{[1-(3-Aminopyridin-2-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one

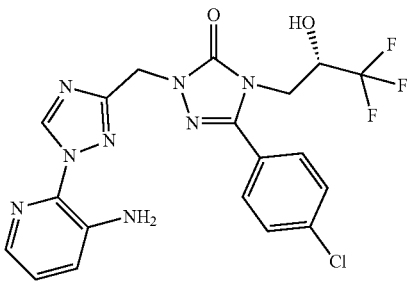 [SMILES: Nc1cccnc1-n1cnc(Cn2nc(-c3ccc(Cl)cc3)n(C[C@H](O)C(F)(F)F)c2=O)n1]

A solution of 5-(4-chlorophenyl)-2-{[1-(3-nitropyridin-2-yl)-1H-1,2,4-triazol-3-yl]methyl}-4-[(2S)-3,3,3-trifluoro-2-hydroxypropyl]-2,4-dihydro-3H-1,2,4-triazol-3-one (Example 39A, 4.35 g, 8.52 mmol) in an ethanol/ethyl acetate mixture (1:1, 1060 ml) was treated with 1% Pt/C (Vanadium doped) (603 mg, 3.09 mmol). The reaction mixture was stirred 36 h at room temperature under an atmosphere of hydrogen (1 atm). The reaction mixture was filtered over celite and rinsed with an ethanol/ethyl acetate mixture (1:1) affording 4.37 g (quant.) of the title compound which was used in the next step without further purification.

LC-MS (Method 2): $R_t$=1.64 min; MS (ESIpos): m/z=481.1 [M+H]$^+$ $^1$H-NMR (400 MHz, DMSO-d6) δ [ppm]: 9.13 (s, 1H), 7.78-7.56 (m, 5H), 7.38-7.14 (m, 2H), 6.92 (d, 1H), 6.12 (s, 2H), 5.22-5.10 (m, 2H), 4.36-4.23 (m, 1H), 4.08-3.75 (m, 2H).

Example 41A

4-[(2S)-2-{[Tert-butyl(dimethyl)silyl]oxy}-3,3,3-trifluoropropyl]-5-(4-chlorophenyl)-2-{[1-(3-nitropyridin-2-yl)-1H-1,2,4-triazol-3-yl]methyl}-2,4-dihydro-3H-1,2,4-triazol-3-one

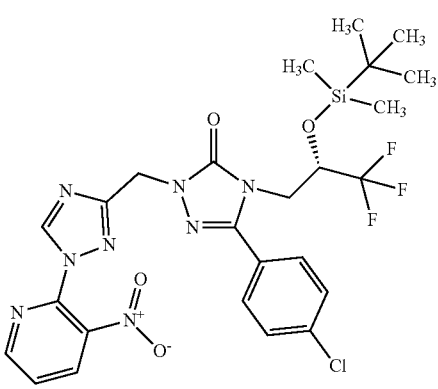 [SMILES: CC(C)(C)[Si](C)(C)O[C@@H](Cn1c(-c2ccc(Cl)cc2)nn(Cc2ncn(-c3ncccc3[N+](=O)[O-])n2)c1=O)C(F)(F)F]

A solution of 5-(4-chlorophenyl)-2-{[1-(3-nitropyridin-2-yl)-1H-1,2,4-triazol-3-yl]methyl}-4-[(2S)-3,3,3-trifluoro-2-hydroxypropyl]-2,4-dihydro-3H-1,2,4-triazol-3-one (Example 39A, 460 mg, 901 μmol) in N,N-dimethylformamide was treated with tert-butyl(chloro)dimethylsilane (271 mg, 1.80 mmol) and 1H-imidazole (184 mg, 2.70 mmol) and stirred overnight at room temperature. Additional tert-butyl(chloro)dimethylsilane (136 mg, 901 μmol) and 1H-imidazole (92.0 mg, 1.35 mmol) and 4-dimethylaminopyridine (110 mg, 901 μmol) were added and the resulting mixture was stirred 24 h at room temperature. The reaction mixture was diluted with ethyl acetate and washed three times with water and once with brine. The organic layer was dried over magnesium sulfate and evaporated. The residue was purified by flash chromatography (silica gel, eluent petrol ether/ethyl acetate) affording 419 mg (74% of th.) of the title compound.

LC-MS (Method 2): R&=2.56 min; MS (ESIpos): m/z=625.2 [M+H]$^+$ $^1$H-NMR (400 MHz, DMSO-d6) δ [ppm]: 9.34 (s, 1H), 8.84 (dd, 1H), 8.63 (dd, 1H), 7.90-7.55 (m, 5H), 5.17-5.04 (m, 2H), 4.65-4.51 (m, 1H), 4.16-3.84 (m, 2H), 0.72 (s, 9H), 0.03--0.06 (m, 3H), -0.23 (s, 3H).

Example 42A

2-{[1-(3-Aminopyridin-2-yl)-1H-1,2,4-triazol-3-yl]methyl}-4-[(2S)-2-{[tert-butyl(dimethyl)silyl]oxy}-3,3,3-trifluoropropyl]-5-(4-chlorophenyl)-2,4-dihydro-3H-1,2,4-triazol-3-one

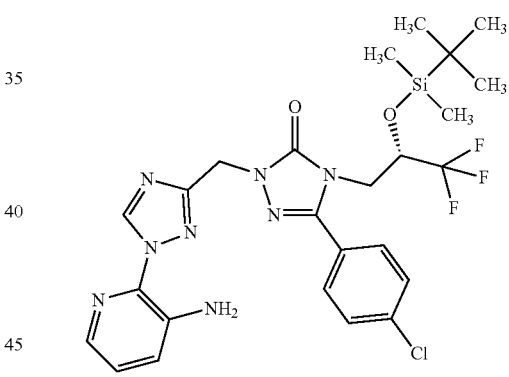

A solution of 4-[(2S)-2-{[tert-butyl(dimethyl)silyl]oxy}-3,3,3-trifluoropropyl]-5-(4-chlorophenyl)-2-{[1-(3-nitropyridin-2-yl)-1H-1,2,4-triazol-3-yl]methyl}-2,4-dihydro-3H-1,2,4-triazol-3-one (Example 41A, 415 mg, 664 μmol) in an ethanol/ethyl acetate mixture (1:1, 82 ml) was treated with 1% Pt/C (Vanadium doped) (47.0 mg, 241 μmol). The reaction mixture was stirred overnight at room temperature under an atmosphere of hydrogen (1 atm). The reaction mixture was filtered over celite and rinsed with an ethanol/ethyl acetate mixture (1:1) affording 396 mg (quant.) of the title compound which was used in the next step without further purification.

LC-MS (Method 2): $R_t$=2.53 min; MS (ESIpos): m/z=595.2 [M+H]$^+$ $^1$H-NMR (400 MHz, DMSO-d6) δ [ppm]: 9.11 (s, 1H), 7.80-7.55 (m, 5H), 7.39-7.14 (m, 2H), 6.13 (s, 2H), 5.16 (d, 2H), 4.67-4.46 (m, 1H), 4.19-3.87 (m, 2H), 0.72 (s, 9H), 0.07--0.07 (m, 3H), -0.19--0.30 (m, 3H).

Example 43A

1-{2-[3-({4-[(2S)-2-{[Tert-butyl(dimethyl)silyl]oxy}-3,3,3-trifluoropropyl]-3-(4-chlorophenyl)-5-oxo-4,5-dihydro-1H-1,2,4-triazol-1-yl}methyl)-1H-1,2,4-triazol-1-yl]pyridin-3-yl}-3-(2,2,2-trifluoroethyl)urea

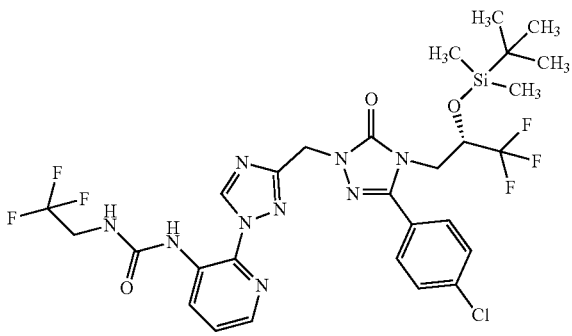 [SMILES: CC(C)(C)[Si](C)(C)O[C@@H](Cn1c(-c2ccc(Cl)cc2)nn(Cc2ncn(-c3ncccc3NC(=O)NCC(F)(F)F)n2)c1=O)C(F)(F)F]

A solution of 2-{[1-(3-aminopyridin-2-yl)-1H-1,2,4-triazol-3-yl]methyl}-4-[(2S)-2-{[tert-butyl(dimethyl)silyl]oxy}-3,3,3-trifluoropropyl]-5-(4-chlorophenyl)-2,4-dihydro-3H-1,2,4-triazol-3-one (Example 42A, 145 mg, 244 µmol) in tetrahydrofuran (1.4 ml) was treated with 4-nitrophenyl carbonochloridate (73.7 mg, 365 µmol), 4-dimethylaminopyridine (29.8 mg, 244 µmol) and N,N-diisopropylethylamine (47 µl, 270 µmol), heated 6 h at reflux and cooled to room temperature. 2,2,2-trifluoroethanamine (500 µl, 4.9 mmol) was added and the resulting mixture was stirred overnight at room temperature. 2,2,2-trifluoroethanamine (0.5 ml) was added and the resulting mixture was stirred 1 h at 60° C. under microwave irradiation. 1 ml of 2,2,2-trifluoroethanamine (1 ml) was added and the reaction heated 12 h at 100° C. under microwave irradiation and evaporated.

The residue was evaporated and purified by preparative HPLC (Method 4) affording 57.6 mg (33% of th.) of the title compound.

LC-MS (Method 2): $R_t$=2.70 min; MS (ESIneg): m/z=718 [M–H]⁻

¹H-NMR (400 MHz, DMSO-d6) δ [ppm]: –0.234 (5.58), –0.013 (5.14), 0.715 (16.00), 3.947 (0.78), 3.969 (0.69), 5.243 (2.83), 7.622 (1.31), 7.642 (1.94), 7.724 (1.90), 7.746 (1.29), 7.874 (0.62), 8.167 (0.84), 8.179 (0.83), 8.687 (0.84), 8.708 (0.83), 9.175 (1.97), 9.232 (1.24).

Example 44A 5-(4-Chlorophenyl)-2-{[1-(2-chloropyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one

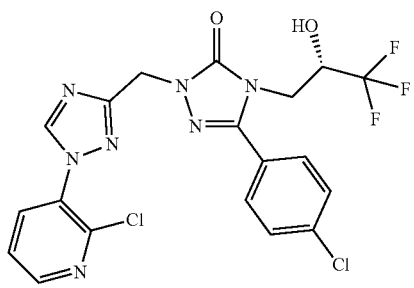 [SMILES: O=c1n(Cc2ncn(-c3cccnc3Cl)n2)nc(-c2ccc(Cl)cc2)n1C[C@H](O)C(F)(F)F]

A solution of methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate (Example 2A; 30.0 g, 79.2 mmol) in tetrahydrofuran (450 ml) was treated with 2-chloro-3-hydrazinylpyridine hydrochloride (1:1) (15.7 g, 87.1 mmol) followed by N,N-diisopropylethylamine (30 ml, 170 mmol) and stirred overnight at room temperature. (Diethoxymethoxy)ethane (450 ml) was added and the resulting mixture was stirred 5 h at reflux. The reaction mixture was evaporated. The residue was retaken in ethyl acetate, washed with a saturated solution of sodium hydrogenocarbonate followed by brine, dried over magnesium sulfate and evaporated. The residue was purified by flash chromatography (silica gel, eluent cyclohexane/ethyl acetate to ethyl acetate/methanol) affording 18.8 g (43% of th.) of the title compound.

LC-MS (Method 2): $R_t$=1.66 min; MS (ESIpos): m/z=500.1 [M+H]⁺

¹H-NMR (400 MHz, DMSO-d6) δ [ppm]: 9.01 (s, 1H), 8.60 (dd, 1H), 8.17 (dd, 1H), 7.82-7.58 (m, 5H), 6.91 (d, 1H), 5.19-5.09 (m, 2H), 4.39-4.20 (m, 1H), 4.09-3.78 (m, 2H).

Example 45A

2-{[1-(2-Aminopyridin-3-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one

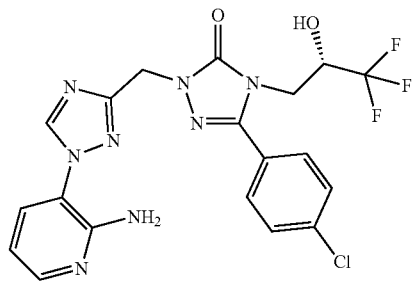 [SMILES: Nc1ncccc1-n1cnc(Cn2nc(-c3ccc(Cl)cc3)n(C[C@H](O)C(F)(F)F)c2=O)n1]

5-(4-chlorophenyl)-2-{[1-(2-chloropyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Example 44A, 17.7 g, 35.3 mmol) in a solution of ammonia in methanol (130 ml, 7.0 M, 910 mmol) was heated 25 h at 140° C. under microwave irradiation and evaporated. Purification by flash chromatography (silica gel, eluent ethyl acetate/methanol) afforded 8.70 g (49% of th.) of the title compound.

LC-MS (Method 2): $R_t$=1.37 min; MS (ESIpos): m/z=481.1 [M+H]⁺

¹H-NMR (400 MHz, DMSO-d6) δ [ppm]: 8.88 (s, 1H), 8.08 (dd, 1H), 7.83-7.54 (m, 5H), 6.98-6.60 (m, 2H), 6.30 (s, 2H), 5.13 (s, 2H), 4.41-4.21 (m, 1H), 4.10-3.73 (m, 2H).

Example 46A

4-[(2S)-2-{Tert-butyl(dimethyl)silyl]oxy}-3,3,3-trifluoropropyl]-5-(4-chlorophenyl)-2-{[1-(2-chloropyridin-3-yl)-1H-1,2,4-triazol-3-yl]methyl}-2,4-dihydro-3H-1,2,4-triazol-3-one

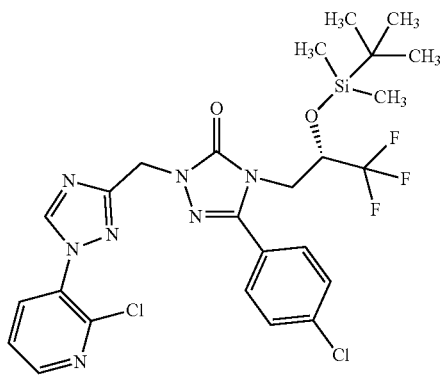 [SMILES: CC(C)(C)[Si](C)(C)O[C@@H](Cn1c(-c2ccc(Cl)cc2)nn(Cc2ncn(-c3cccnc3Cl)n2)c1=O)C(F)(F)F]

A solution of 5-(4-chlorophenyl)-2-{[1-(2-chloropyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Example 44A; 1.00 g, 2.00 mmol) in N,N-dimethylformamide (3.1 ml) was treated with tert-butyl(chloro)dimethylsilane (603 mg, 4.00 mmol) followed by 1H-imidazole (544 mg, 8.00 mmol) and stirred overnight at room temperature. The reaction mixture was diluted with a saturated solution of sodium hydrogenocarbonate and stirred 2 h at room temperature. The reaction mixture was brought to pH=7 with an aqueous hydrochloric acid solution (1N). The aqueous layer was extracted with ethyl acetate. The combined organic layers were washed with water followed by brine, dried over magnesium sulfate and evaporated. Purification by flash chromatography (silica gel, eluent petrol ether/ethyl acetate) afforded 989 mg (80% of th.) of the title compound.

LC-MS (Method 1): $R_t$=1.35 min; MS (ESIpos): m/z=614.3 [M+H]$^+$ $^1$H-NMR (400 MHz, DMSO-d6) δ [ppm]: 9.04-8.98 (m, 1H), 8.59 (dd, 1H), 8.14 (dd, 1H), 7.79-7.58 (m, 5H), 5.21-5.08 (m, 2H), 4.67-4.49 (m, 1H), 4.16-3.88 (m, 2H), 0.71 (s, 9H), 0.02--0.05 (m, 3H), -0.23 (s, 3H).

Example 47A

2-{[1-(2-Aminopyridin-3-yl)-1H-1,2,4-triazol-3-yl]methyl}-4-[(2S)-2-{[tert-butyl(dimethyl)silyl]oxy}-3,3,3-trifluoropropyl]-5-(4-chlorophenyl)-2,4-dihydro-3H-1,2,4-triazol-3-one

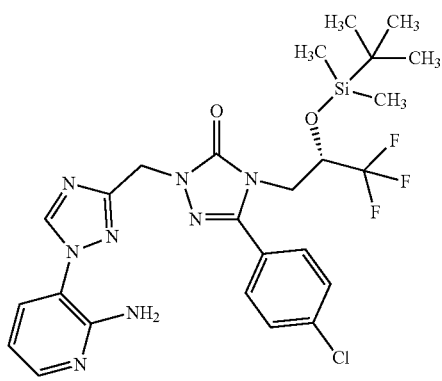 [SMILES: CC(C)(C)[Si](C)(C)O[C@@H](Cn1c(-c2ccc(Cl)cc2)nn(Cc2ncn(-c3cccnc3N)n2)c1=O)C(F)(F)F]

4-[(2S)-2-{[tert-butyl(dimethyl)silyl]oxy}-3,3,3-trifluoropropyl]-5-(4-chlorophenyl)-2-{[1-(2-chloropyridin-3-yl)-1H-1,2,4-triazol-3-yl]methyl}-2,4-dihydro-3H-1,2,4-triazol-3-one (Example 46A, 985 mg, 1.60 mmol) in a solution of ammonia in methanol (15 ml, 7.0 M, 110 mmol) was heated 18 h at 140° C. under microwave irradiation, followed by 18 h at 120° C. under microwave irradiation. The reaction mixture was evaporated and purified by preparative HPLC (Method 4) affording 335 mg (34% of th.) of the title compound.

LC-MS (Method 2): $R_t$=2.32 min; MS (ESIpos): m/z=595.2 [M+H]$^+$ $^1$H-NMR (400 MHz, DMSO-d6) δ [ppm]: 8.88 (s, 1H), 8.07 (dd, 1H), 7.81-7.56 (m, 5H), 6.70 (dd, 1H), 6.29 (s, 2H), 5.13 (d, 2H), 4.70-4.47 (m, 1H), 4.21-3.87 (m, 2H), 0.72 (s, 9H), 0.00 (s, 3H), -0.22 (s, 3H).

Example 48A 2,2,2-Trifluoroethyl{3-[3-({4-[(2S)-2-{[tert-butyl(dimethyl)silyl]oxy}-3,3,3-trifluoropropyl]-3-(4-chlorophenyl)-5-oxo-4,5-dihydro-1H-1,2,4-triazol-1-yl}methyl)-1H-1,2,4-triazol-1-yl]pyridin-2-yl}carbamate

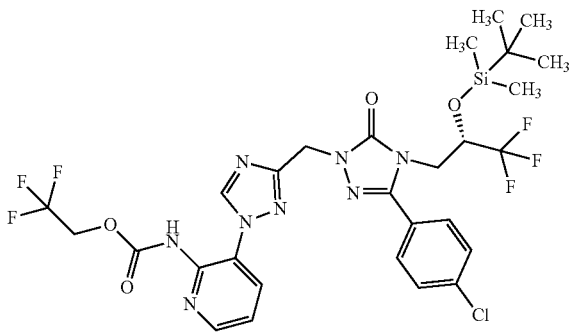 [SMILES: CC(C)(C)[Si](C)(C)O[C@@H](Cn1c(-c2ccc(Cl)cc2)nn(Cc2ncn(-c3cccnc3NC(=O)OCC(F)(F)F)n2)c1=O)C(F)(F)F]

At 0° C., a solution of 2-{[1-(2-aminopyridin-3-yl)-1H-1,2,4-triazol-3-yl]methyl}-4-[(2S)-2-{[tert-butyl(dimethyl)silyl]oxy}-3,3,3-trifluoropropyl]-5-(4-chlorophenyl)-2,4-dihydro-3H-1,2,4-triazol-3-one (Example 47A, 160 mg, 269 μmol) in dichloromethane (1.3 ml) was treated with 2,2,2-trifluoroethyl carbonochloridate (87.4 mg, 538 μmol), N,N-diisopropylethylamine (94 μl, 540 μmol) and 4-dimethylaminopyridine (32.8 mg, 269 μmol) and stirred 72 h at room temperature. 2,2,2-trifluoroethyl carbonochloridate (74.3 mg, 457 μmol), N,N-diisopropylethylamine (94 μl, 540 μmol) and 4-dimethylaminopyridine (32.8 mg, 269 μmol) were added at 0° C. and stirred 4 h at room temperature. The reaction mixture was evaporated and purified by preparative HPLC (Method 4) affording 24.1 mg (12% of th.) of the title compound.

LC-MS (Method 2): R&=2.50 min; MS (ESIpos): m/z=721.2 [M+H]$^+$ $^1$H-NMR (400 MHz, DMSO-d6) δ [ppm]: 10.41 (br s, 1H), 8.86 (s, 1H), 8.53 (dd, 1H), 8.05 (dd, 1H), 7.79-7.41 (m, 5H), 5.06 (s, 2H), 4.67-4.46 (m, 3H), 4.16-3.89 (m, 2H), 0.73 (s, 9H), 0.00 (s, 3H), -0.20 (s, 3H).

Example 49A

2-[3-({3-(4-Chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]benzoic acid

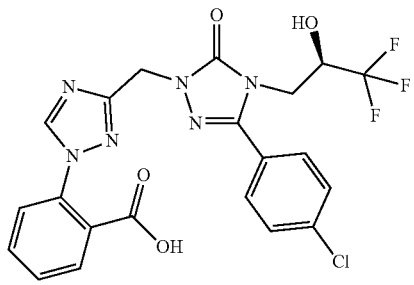 [SMILES: O=C(O)c1ccccc1-n1cnc(Cn2nc(-c3ccc(Cl)cc3)n(C[C@@H](O)C(F)(F)F)c2=O)n1]

A solution of methyl 2-{3-(4-chlorophenyl)-5-oxo-4-[(2R)-3,3,3-trifluoro-2-hydroxypropyl]-4,5-dihydro-1H-1,2,4-triazol-1-yl}ethanimidate (Example 5A, 328 mg, 865 µmol) in tetrahydrofuran (2.7 ml) was treated with 2-hydrazinylbenzoic acid hydrochloride (1:1) (179 mg, 952 µmol) and N,N-diisopropylethylamine (330 µl, 1.9 mmol) and stirred 10 min at room temperature. The reaction mixture was concentrated to 0.5 ml. (Diethoxymethoxy)ethane (1.8 ml, 11 mmol) was added and the resulting mixture was stirred 6 h at 60° C. Purification by preparative HPLC (Method 4) afforded 202 mg (46% of th.) of the title compound.

LC-MS (Method 2): $R_t$=1.62 min; MS (ESIpos): m/z=509.1 [M+H]$^+$ $^1$H-NMR (400 MHz, DMSO-d6) δ [ppm]: 13.54-12.59 (m, 1H), 8.83 (s, 1H), 7.96-7.53 (m, 8H), 6.92 (br d, 1H), 5.16-4.99 (m, 2H), 4.39-4.20 (br m, 1H), 4.08-3.75 (m, 2H).

Example 50A

3-Chloro-2-hydrazinylbenzoic acid hydrochloride

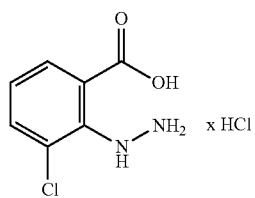 [SMILES: NNc1c(Cl)cccc1C(=O)O]

At 0° C., a solution of 2-amino-3-chlorobenzoic acid (16.6 g, 96.7 mmol) in water (60 ml) and in concentrated hydrochloric acid (60 ml) was treated dropwisely with a solution of sodium nitrite (7.34 g, 106 mmol) in water (50 ml). The resulting mixture was stirred 20 min at 10° C. and cooled to 0° C. A solution of tin chloride dihydrate (43.7 g, 193 mmol) in concentrated hydrochloric acid (50 ml) was added dropwisely within 20 min and the resulting mixture was stirred 1 h at room temperature. The reaction mixture was cooled to 0° C. The solid was filtered off, washed with a small volume of concentrated hydrochloric acid followed by a small volume of tert-butylmethylether affording 19.3 g (66% purity, 59% of th.) of the title compound.

LC-MS (Method 1): $R_t$=0.21 min; MS (ESIpos): m/z=187.0 [M+H]$^+$

Example 51A

3-Chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoic acid

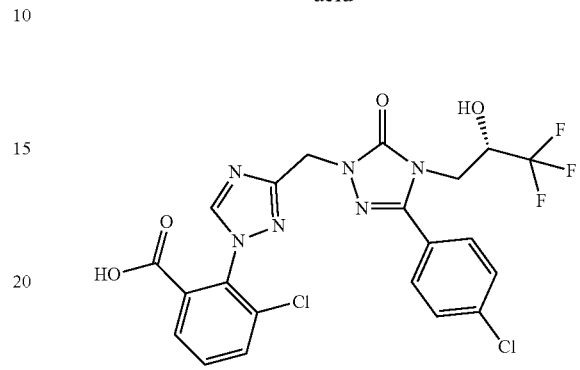

A suspension of 3-chloro-2-hydrazinylbenzoic acid hydrochloride (Example 50A, 3.24 g, 14.5 mmol) in tetrahydrofuran (55 ml) was treated with methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate (Example 2A, 5.00 g, 13.2 mmol) and N,N-diisopropylethylamine (6.9 ml, 40 mmol) and stirred 1 h at room temperature. The reaction mixture was evaporated and the residue was retaken in (diethoxymethoxy)ethane (100 ml, 600 mmol). The resulting mixture was stirred 18 h at 60° C. and 24 h at 70° C. Tetrahydrofuran (100 ml) was added and the resulting mixture was stirred 5 h at reflux. Evaporation and purification of the residue by flash chromatography (silica gel, eluent petrol ether/ethyl acetate to ethyl acetate/methanol) afforded 6.2 g (86% of th.) of the title compound.

LC-MS (Method 2): $R_t$=1.66 min; MS (ESIpos): m/z=543.1 [M+H]$^+$ $^1$H-NMR (400 MHz, DMSO-d6) δ [ppm]: 13.40 (br s, 1H), 8.81 (s, 1H), 8.00-7.55 (m, 7H), 6.96 (br d, 1H), 5.16-5.00 (m, 2H), 4.39-4.21 (br m, 1H), 4.08-3.75 (m, 2H).

Example 52A 5-(4-Chlorophenyl)-2-(4H-1,2,4-triazol-3-ylmethyl)-4-[(2S)-3,3,3-trifluoro-2-hydroxypropyl]-2,4-dihydro-3H-1,2,4-triazol-3-one

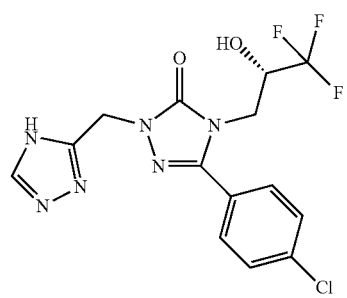 [SMILES: O=c1n(Cc2nnc[nH]2)nc(-c2ccc(Cl)cc2)n1C[C@H](O)C(F)(F)F]

A solution of 2-{3-(4-chlorophenyl)-5-oxo-4-[(2S)-3,3,3-trifluoro-2-hydroxypropyl]-4,5-dihydro-1H-1,2,4-triazol-1-yl}acetohydrazide (synthesis described as Example 2A in WO 2016/01222325-A1, 5.00 g, 13.2 mmol) in (50 ml) was treated with imidoformamide acetate (1:1) (1.51 g, 14.5 mmol) and stirred 24 h at 65° C. The reaction mixture was evaporated and purified by preparative HPLC (Method 4) affording 2.57 g (44% of th.) of the title compound.

LC-MS (Method 2): $R_t$=1.36 min; MS (ESIpos): m/z=389.1 [M+H]$^+$ $^1$H-NMR (400 MHz, DMSO-d6) δ [ppm]: 13.96 (br s, 1H), 8.76-8.13 (m, 1H), 7.83-7.53 (m, 4H), 7.00-6.71 (m, 1H), 5.18-4.85 (m, 2H), 4.44-4.17 (m, 1H), 4.05-3.68 (m, 2H).

Example 53A

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-3-(trifluoromethyl)benzonitrile

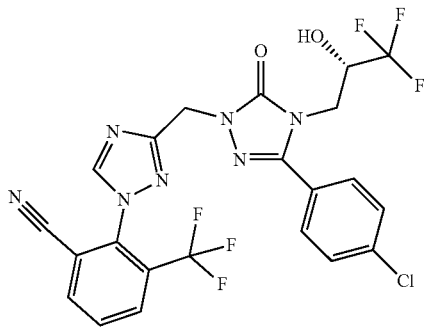 [SMILES: N#Cc1cccc(C(F)(F)F)c1-n1cnc(Cn2nc(-c3ccc(Cl)cc3)n(C[C@H](O)C(F)(F)F)c2=O)n1]

A solution of 5-(4-chlorophenyl)-2-(1H-1,2,4-triazol-3-ylmethyl)-4-[(2S)-3,3,3-trifluoro-2-hydroxypropyl]-2,4-dihydro-3H-1,2,4-triazol-3-one (Example 52A, 1.52 g, 3.91 mmol) in N,N-dimethylformamide (20 ml) was treated with 2-fluoro-3-(trifluoromethyl)benzonitrile (610 μl, 4.3 mmol) and potassium carbonate (567 mg, 4.11 mmol) and stirred overnight at room temperature. The reaction mixture was diluted with ethyl acetate and washed three times with water, once with an aqueous citric acid solution (10%) and twice with brine. The organic layer was dried over magnesium sulfate and evaporated. The residue was purified by flash chromatography (silica gel, eluent cyclohexane/ethyl acetate) affording 1.52 g (50% of th.) of the title compound.

LC-MS (Method 2): $R_t$=1.83 min; MS (ESIpos): m/z=558.1 [M+H]$^+$ $^1$H-NMR (400 MHz, DMSO-d6) δ [ppm]: 9.03 (s, 1H), 8.50-8.00 (m, 3H), 7.79-7.52 (m, 4H), 6.92 (d, 1H), 5.27-5.02 (m, 2H), 4.39-4.20 (br m, 1H), 4.07-3.79 (m, 2H).

Example 54A

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-3-(trifluoromethyl)benzoic acid

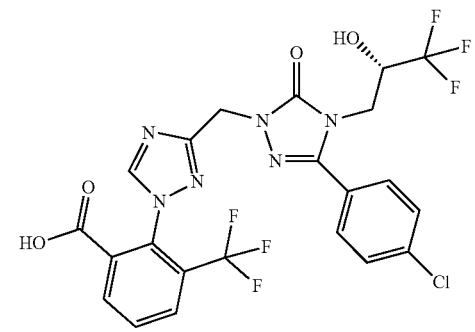 [SMILES: O=C(O)c1cccc(C(F)(F)F)c1-n1cnc(Cn2nc(-c3ccc(Cl)cc3)n(C[C@H](O)C(F)(F)F)c2=O)n1]

A solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-3-(trifluoromethyl)benzonitrile (Example 53A, 1.52 g, 2.72 mmol) in methanol (5.1 ml) was treated with an aqueous solution of sodium hydroxide (3.4 ml, 4.0 M, 14 mmol) and stirred 10 h at 70° C. The reaction mixture was cooled to room temperature and brought to pH=1 with formic acid. Purification by preparative HPLC (Method 4) afforded 541 mg (35% of th.) of the title compound.

LC-MS (Method 1): $R_t$=0.91 min; MS (ESIpos): m/z=577.1 [M+H]$^+$ $^1$H-NMR (400 MHz, DMSO-d6) δ [ppm]: 13.54 (br s, 1H), 8.80 (s, 1H), 8.30-8.10 (m, 2H), 8.00-7.89 (m, 1H), 7.80-7.55 (m, 4H), 6.94 (br s, 1H), 5.16-4.98 (m, 2H), 4.39-4.21 (br m, 1H), 4.07-3.78 (m, 2H).

Example 55A

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoic acid

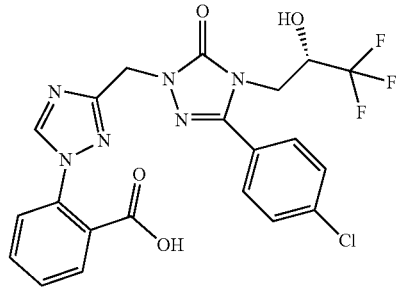 [SMILES: O=C(O)c1ccccc1-n1cnc(Cn2nc(-c3ccc(Cl)cc3)n(C[C@H](O)C(F)(F)F)c2=O)n1]

To a solution of methyl 2-{3-(4-chlorophenyl)-5-oxo-4-[(2S)-3,3,3-trifluoro-2-hydroxypropy]-4,5-dihydro-1H-1,2,4-triazol-1-yl}ethanimidate (Example 2A; 200 mg, 528 μmol) in tetrahydrofuran (2.0 ml), 2-hydrazinylbenzoic acid hydrochloride (110 mg, 581 μmol) and N,N-diisopropylethylamine (200 μl, 1.2 mmol) were added. The reaction mixture was stirred over night at room temperature. The reaction mixture was acidified with formic acid (2.0 ml) and heated under reflux for 1 h. Trimethyl orthoformate (2.0 ml) was added and the reaction mixture was stirred over night at room temperature A second portion of trimethyl orthoformate (2.0 ml) was added and stirred was continued overnight. The organic solvent was removed in vacuo. The crude product was purified by preparative HPLC (Method 4). Lyophilisation of the product containing fractions afforded 131 mg (49% of th.) of the title compound LC-MS (Method 2): $R_t$=1.60 min; MS (ESIpos): m/z=509 [M+H]$^+$ $^1$H-NMR (400 MHz, DMSO-d6) δ [ppm]: −0.008 (1.26), 3.815 (1.79), 3.839 (2.10), 3.852 (2.47), 3.876 (2.59), 3.980 (2.79), 3.989 (3.02), 4.017 (1.99), 4.025 (1.77), 4.312 (1.44), 5.082 (16.00), 6.925 (1.39), 7.585 (4.13), 7.588 (4.59), 7.607 (15.74), 7.625 (8.68), 7.628 (15.24), 7.635 (2.36), 7.644 (3.08), 7.647 (2.61), 7.706 (2.98), 7.711 (3.17), 7.726 (4.12), 7.730 (4.19), 7.745 (4.18), 7.750 (12.88), 7.755 (4.39), 7.767 (3.68), 7.772 (8.66), 7.778 (1.28), 7.899 (4.20), 7.903 (4.01), 7.918 (3.65), 7.922 (3.32), 8.830 (12.82), 13.204 (0.92).

Example 56A

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-5-fluorobenzoic acid

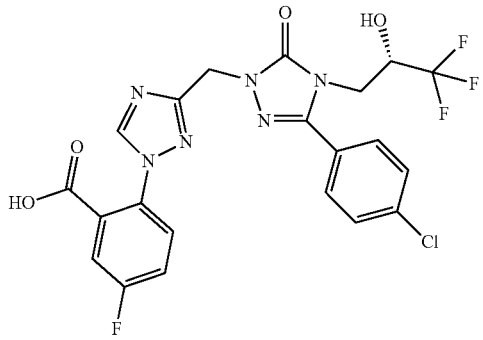 [SMILES: O=C(O)c1cc(F)ccc1-n1cnc(Cn2nc(-c3ccc(Cl)cc3)n(C[C@H](O)C(F)(F)F)c2=O)n1]

To a solution of methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate (Example 2A, 1.00 g, 2.64 mmol) in tetrahydrofuran (10 ml), 5-fluoro-2-hydrazinylbenzoic acid hydrochloride (1:1) (600 mg, 2.90 mmol) and N,N-diisopropylethylamine (1.5 ml, 8.7 mmol) were added. The reaction mixture was stirred for 20 min at room temperature. Triethyl orthoformate (5.5 ml, 33 mmol) was added and the reaction mixture was stirred for 4.5 h at 60° C. and 80 h at room temperature. A second portion of triethyl orthoformate (3.0 ml, 18 mmol) was added and stirred was continued for 20 h at 60° C. The reaction mixture was diluted with ethyl acetate and washed with an aqueous solution of citric acid (5%) and brine. The organic phase was separated and dried over Magnesium sulfate. The organic solvent was removed in vacuo. The crude product was purified by preparative HPLC (Method 4). Lyophilisation of the product containing fractions afforded 600 mg (42% of th.) of the title compound LC-MS (Method 2): $R_t$=1.59 min; MS (ESIpos): m/z=527 [M+H]$^+$ $^1$H-NMR (400 MHz, DMSO-d6) δ [ppm]: 2.211 (1.27), 3.815 (1.74), 3.839 (2.00), 3.851 (2.45), 3.876 (2.68), 3.979 (2.69), 3.987 (3.10), 4.015 (2.00), 4.024 (1.87), 4.311 (1.31), 5.075 (15.87), 5.754 (4.65), 7.579 (1.16), 7.587 (1.47), 7.601 (3.59), 7.607 (12.20), 7.612 (4.33), 7.621 (3.39), 7.624 (4.82), 7.629 (15.91), 7.635 (2.28), 7.660 (4.20), 7.673 (4.38), 7.682 (2.65), 7.695 (2.48), 7.702 (3.44), 7.710 (3.33), 7.724 (3.44), 7.732 (3.28), 7.743 (1.94), 7.749 (13.21), 7.754 (4.47), 7.766 (3.49), 7.771 (9.75), 7.777 (1.64), 8.818 (16.00).

Example 57A

5-Chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoic acid

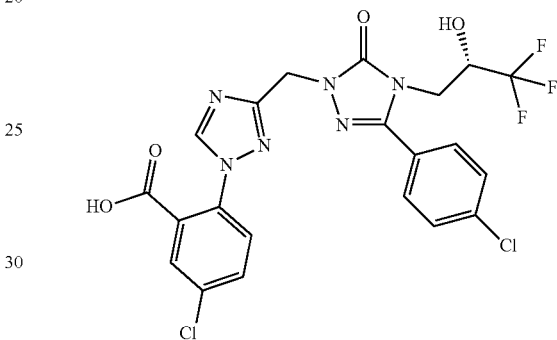

To a solution of methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate (Example 2A, 1.00 g, 2.64 mmol) in tetrahydrofuran (10 ml), 5-chloro-2-hydrazinylbenzoic acid hydrochloride (1:1) (648 mg, 2.90 mmol) and N,N-diisopropylethylamine (1.5 ml, 8.7 mmol) were added. The reaction mixture was stirred for 20 min at room temperature. Triethyl orthoformate (5.5 ml, 33 mmol) was added and the reaction mixture was stirred for 4.5 h at 60° C. and 80 h at room temperature. A second portion of triethyl orthoformate (5.5 ml, 33 mmol) was added and stirred was continued for 20 h at 60° C. The reaction mixture was diluted with ethyl acetate and washed with an aqueous solution of citric acid (5%) and brine. The organic phase was separated and dried over Magnesium sulfate. The organic solvent was removed in vacuo. The crude product was purified by preparative HPLC (sample preparation: 1.4 g dissolved in 15 ml acetonitrile/methanol; injection volume: 250 μl; column: Kinetix 5 μm C18, 100×21.2 mm; eluent: water/acetonitrile+0.1% formic acid gradient; flow rate: 50 ml/min; temperature: 40° C.; UV detection: 210 nm). Lyophilisation of the product containing fractions afforded 600 mg (42% of th.) of the title compound $^1$H-NMR (400 MHz, DMSO-d6) δ [ppm]: −0.008 (1.12), 0.008 (0.99), 1.217 (0.65), 2.073 (1.16), 3.814 (1.68), 3.838 (1.95), 3.851 (2.45), 3.874 (2.65), 3.978 (2.69), 3.987 (3.07), 4.015 (1.96), 4.024 (1.86), 4.309 (1.39), 4.689 (0.57), 5.080 (16.00), 6.929 (1.07), 7.600 (1.29), 7.607 (8.61), 7.611 (3.46), 7.623 (3.93), 7.628 (11.89), 7.634 (2.18), 7.646 (6.21), 7.668 (7.72), 7.741 (2.01), 7.747 (11.85), 7.752 (4.25), 7.764 (3.48), 7.768 (8.78), 7.775 (1.61), 7.799 (4.08), 7.805 (4.41), 7.820 (3.10), 7.826 (3.51), 7.910 (6.43), 7.916 (5.82), 8.858 (12.51).

Example 58A

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl chloride

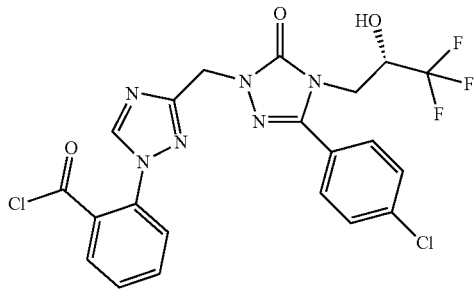 [SMILES: O=C(Cl)c1ccccc1-n1cnc(Cn2nc(-c3ccc(Cl)cc3)n(C[C@H](O)C(F)(F)F)c2=O)n1]

To a solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoic acid (Example 55A, 2.00 g, 3.62 mmol) in dichloromethane (48 ml), 1-chloro-N,N,2-trimethylprop-1-en-1-amine (720 µl, 5.4 mmol) was added and stirred for 20 min at room temperature. This crude solution was directly used in the next step without further purification.

Example 59A

5-Chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl chloride

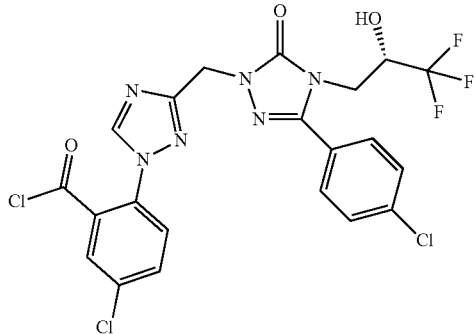 [SMILES: O=C(Cl)c1cc(Cl)ccc1-n1cnc(Cn2nc(-c3ccc(Cl)cc3)n(C[C@H](O)C(F)(F)F)c2=O)n1]

To a solution of 5-chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoic acid (Example 57A, 600 mg, 1.10 mmol) in dichloromethane (15 ml), 1-chloro-N,N,2-trimethylprop-1-en-1-amine (220 µl, 1.7 mmol) was added and stirred for 20 min at room temperature. This crude solution was directly used in the next step without further purification.

Example 60A

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-5-fluorobenzoyl chloride

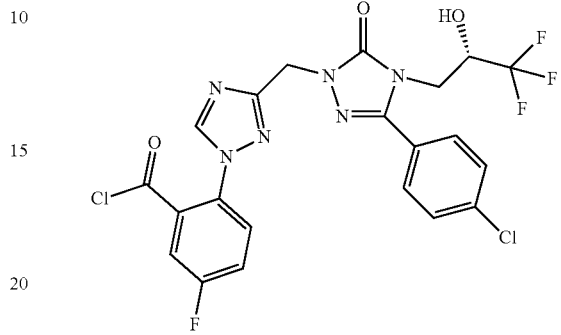

To a solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-5-fluorobenzoic acid (Example 56A, 150 mg, 285 µmol) in dichloromethane (3.7 ml), 1-chloro-N,N,2-trimethylprop-1-en-1-amine (57 µl, 430 µmol) was added and stirred for 20 min at room temperature. This crude solution was directly used in the next step without further purification.

Example 61A

3-Chloro-2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]benzoic acid

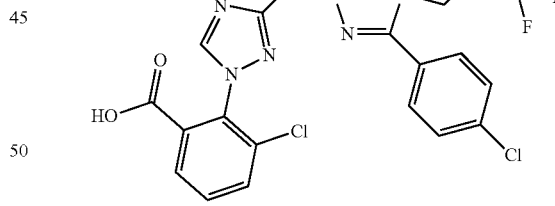

A suspension of 3-chloro-2-hydrazinylbenzoic acid hydrochloride (Example 50A, 3.24 g, 14.5 mmol) in tetrahydrofuran (100 ml) was treated with methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate (Example 5A, 5.00 g, 13.2 mmol) and N,N-diisopropylethylamine (6.9 ml, 40 mmol) and stirred 1 h at room temperature. The reaction mixture was evaporated and the residue was retaken in (diethoxymethoxy)ethane (100 ml, 600 mmol). The resulting mixture was stirred 18 h at 60° C., 24 h at 70° C. and 5 h at reflux. Evaporation and purification of the residue by flash chromatography (silica gel, eluent petrol ether/ethyl acetate to ethyl acetate/methanol) afforded 5.2 g (62% of th.) of the title compound.

LC-MS (Method 2): $R_t$=1.66 min; MS (ESIpos): m/z=543. [M+H]⁺

¹H-NMR (400 MHz, DMSO-d6) δ [ppm]: 13.40 (br s, 1H), 8.81 (s, 1H), 7.93 (dd, 2H), 7.80-7.58 (m, 5H), 6.94 (br s, 1H), 5.15-5.02 (m 2H), 4.38-4.24 (m 1H), 4.06-3.79 (m 2H).

Example 62A

2-[2-(Tert-butoxycarbonyl)hydrazinyl]benzoic acid

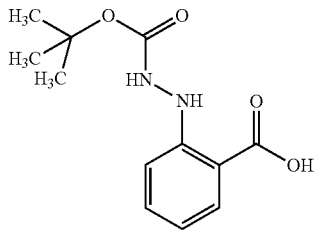 [SMILES: CC(C)(C)OC(=O)NNc1ccccc1C(=O)O]

A solution of 2-hydrazinobenzoic acid hydrochloride (1:1) (3.00 g, 15.9 mmol) in dioxane (55 ml) was treated with a solution of di-tert-butyl dicarbonate (3.8 g, 17 mmol) in dioxane (7 ml). The resulting solution was cooled to 0° C. and the solution was adjust to pH 8-9 with an aqueous solution of sodium carbonate (5% w/w). The reaction mixture was stirred 24 h at room temperature. The dioxane was evaporated, the residue was retaken in water. The solution was brought to pH=1 with an aqueous solution of hydrogenchloride (1N). The mixture was extracted three times with ethyl acetate. The combined organic phases were dried over sodium sulfate and evaporated. The resulting solid was triturated with petroleum ether, filtered off and dried under high vacuum affording 3.75 g (93% of th.) of the title compound.

LC-MS (Method 6): $R_t$=1.07 min; MS (ESIneg): m/z=251.2. [M–H]⁻

Example 63A

2-Hydrazinyl-N-methylbenzamide trifluoroacetate

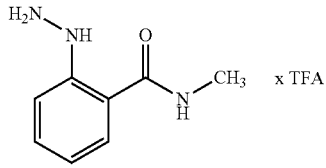

A solution of 2-[2-(tert-butoxycarbonyl)hydrazinyl]benzoic acid (Example 62A, 300 mg, 1.19 mmol) and 4-Methylmorpholine (160 µl, 1.4 mmol) in tetrahydrofuran (6 ml) was cooled at −30° C., treated with 2-methylpropyl carbonochloridate (170 µl, 1.3 mmol) and stirred 5 min. A solution of methanamine in tetrahydrofuran (890 µl, 2.0 M, 1.8 mmol) was then added dropwisely. The resulting mixture was brought slowly to room temperature and the resulting mixture was stirred overnight at room temperature. The reaction mixture was quenched with a saturated solution of sodium hydrogenocarbonate and extracted twice with ethyl acetate. The combined organic layers were dried over magnesium sulfate and evaporated.

The residue was retaken in dichloromethane (4.4 ml) and treated with trifluoroacetic acid (2.2 ml). The resulting mixture was stirred 30 min at room temperature and evaporated affording the title compound which was used in the next steps without further purification.

Example 64A

Methyl 3-({3-(4-chlorophenyl)-5-oxo-4-[(2S)-3,3,3-trifluoro-2-hydroxypropyl]-4,5-dihydro-1H-1,2,4-triazol-1-yl}methyl)-1-[2-(methylcarbamoyl)phenyl]-1H-1,2,4-triazole-5-carboxylate

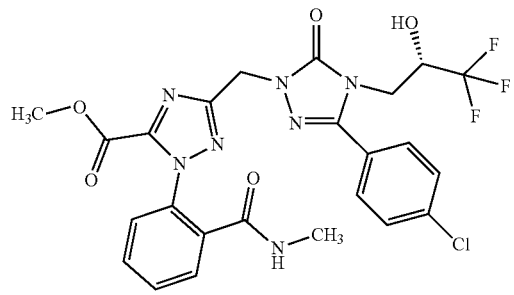 [SMILES: CNC(=O)c1ccccc1-n1nc(Cn2nc(-c3ccc(Cl)cc3)n(C[C@H](O)C(F)(F)F)c2=O)nc1C(=O)OC]

At 0° C., a solution of methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate (Example 2A, 315 mg, 832 µmol) in tetrahydrofuran (6.5 ml) was treated with N,N-diisopropylethylamine (580 µl, 3.3 mmol) and methyl chloro(oxo)acetate (92 µl, 1000 µmol). The resulting mixture was stirred 1 h at room temperature and cooled to 0° C. 2-Hydrazinyl-N-methylbenzamide trifluoroacetate (Example 63A, 360 mg, 915 µmol) was added and the resulting mixture was stirred 1 h at room temperature and 1 h at 120° C. under microwave irradiation. Purification by preparative HPLC (Method 4) afforded 101 mg (69% purity, 14% of th.) of the title compound.

LC-MS (Method 3): $R_t$=2.71 min; MS (ESIpos): m/z=580.3 [M+H]⁺

EXPERIMENTAL SECTION—EXAMPLES

Example 1

2-[(1-{4-[(2-Amino-2-methylpropyl)amino]pyridin-3-yl}-1H-1,2,4-triazol-3-yl)methyl]-5-(4-chlorophenyl)-4-[(2S)-3,3,3-trifluoro-2-hydroxypropyl]-2,4-dihydro-3H-1,2,4-triazol-3-one

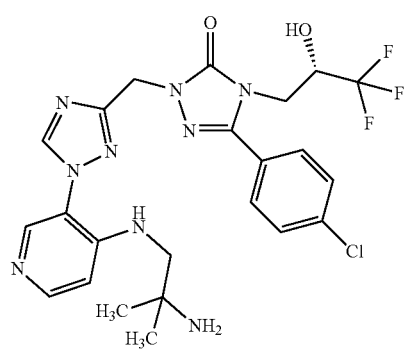 [SMILES: CC(C)(N)CNc1ccncc1-n1cnc(Cn2nc(-c3ccc(Cl)cc3)n(C[C@H](O)C(F)(F)F)c2=O)n1]

2-[(1-{4-[(2-amino-2-methylpropyl)amino]pyridin-3-yl}-1H-1,2,4-triazol-3-yl)methyl]-4-[(2S)-2-{[tert-butyl(dimethyl)silyl]oxy}-3,3,3-trifluoropropyl]-5-(4-chlorophenyl)-2,4-dihydro-3H-1,2,4-triazol-3-one (Example 8A, 39.0 mg, 58.5 µmol) was dissolved in a tetra-n-butylammoniumfluoride solution (1.0 ml, 1.0 M, 1.0 mmol) and stirred overnight at room temperature. The resulting mixture was mixed with 10 mg and 50 mg test runs and evaporated. The crude was purified by preparative HPLC (Method 4) and evaporated. The residue was retaken water and purified a second time by preparative HPLC affording 64 mg (78% of th.) of the title compound.

LC-MS (Method 2): $R_t$=0.75 min; MS (ESIneg): m/z=550 [M−H]−

$^1$H-NMR (400 MHz, DMSO-d6) δ [ppm]: 8.93 (s, 1H), 8.32-8.13 (m, 3H), 7.82-7.54 (m, 4H), 6.91 (d, 1H), 6.36 (br t, 1H), 5.26-4.98 (m, 2H), 4.40-4.23 (br m, 1H), 4.08-3.71 (m, 2H), 3.15 (br s, 2H, overlapping with HDO peak), 1.07 (s, 3H), 1.06 (s, 3H), $NH_2$ not visible.

Example 2

5-(4-Chlorophenyl)-2-[(1-{4-[(2-hydroxy-2-methylpropyl)amino]pyridin-3-yl}-1H-1,2,4-triazol-3-yl) methyl]-4-[(2S)-3,3,3-trifluoro-2-hydroxypropyl]-2,4-dihydro-3H-1,2,4-triazol-3-one

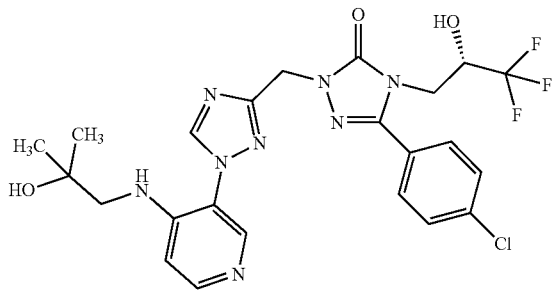 [SMILES: CC(C)(O)CNc1ccncc1-n1cnc(Cn2nc(-c3ccc(Cl)cc3)n(C[C@H](O)C(F)(F)F)c2=O)n1]

A solution of 5-(4-chlorophenyl)-2-{[1-(4-chloropyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Example 6A, 150 mg, 300 μmol) in ethanol (600 μl) was treated with 1-amino-2-methylpropan-2-ol (267 mg, 3.00 mmol) and heated at reflux overnight. The reaction mixture was purified by preparative HPLC (Method 4) affording 104 mg (63% of th.) of the title compound.

LC-MS (Method 2): $R_t$=1.10 min MS (ESIpos): m/z=553.2 [M+H]+

$^1$H-NMR (400 MHz, DMSO-d6) δ [ppm]: 8.95 (s, 1H), 8.48-8.14 (m, 2H), 7.85-7.49 (m, 4H), 7.12-6.69 (m, 2H), 6.26 (t, 1H), 5.27-4.99 (m, 2H), 4.71-4.17 (m, 2H), 4.09-3.66 (m, 2H), 3.07 (d, 2H), 1.24-0.94 (m, 6H).

Example 3

2-{[1-(4-{[(1-Aminocyclopropyl)methyl] amino}pyridin-3-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one

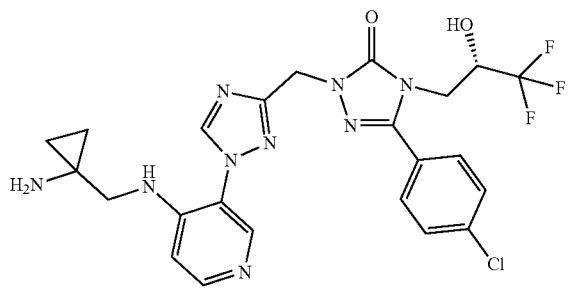 [SMILES: NC1(CNc2ccncc2-n2cnc(Cn3nc(-c4ccc(Cl)cc4)n(C[C@H](O)C(F)(F)F)c3=O)n2)CC1]

A solution of 5-(4-chlorophenyl)-2-{[1-(4-chloropyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Example 6A, 150 mg, 300 μmol) in ethanol (200 μl) was treated with 1-(aminomethyl)cyclopropan-1-amine dihydrochloride (429 mg, 2.70 mmol) followed by N,N-diisopropylethylamine (130 μl, 750 μmol) and the resulting mixture was heated at reflux overnight. N,N-diisopropylethylamine (100 μl, 600 μmol) was added. The resulting mixture was diluted with methanol (200 μl) and heated at reflux for 72 h. The reaction mixture was purified by preparative HPLC (Method 4) affording 47.8 mg (29% of th.) of the title compound.

LC-MS (Method 2): $R_t$=0.77 min; MS (ESIpos): m/z=550.2 [M+H]+

$^1$H-NMR (400 MHz, DMSO-d6) δ [ppm]: 8.90 (s, 1H), 8.27-8.16 (m, 2H), 7.82-7.51 (m, 4H), 7.30-6.72 (m, 2H), 6.35 (br t, 1H), 5.14 (s, 2H), 4.40-4.17 (m, 1H), 4.11-3.72 (m, 2H), 3.28-3.17 (m, 2H, overlapping with HDO peak), 0.53 (s, 4H), $NH_2$ not visible.

Example 4

5-(4-Chlorophenyl)-2-{[1-(4-{[(1-hydroxycyclopropyl)methyl]amino}pyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one

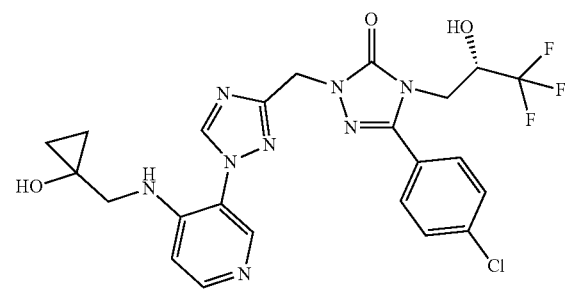 [SMILES: O=c1n(Cc2ncn(-c3cnccc3NCC3(O)CC3)n2)nc(-c2ccc(Cl)cc2)n1C[C@H](O)C(F)(F)F]

A solution of 5-(4-chlorophenyl)-2-{[1-(4-chloropyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Example 6A, 150 mg, 300 μmol) in ethanol (600 μl) was treated with 1-(aminomethyl)cyclopropanol (78.4 mg, 900 μmol) and heated at reflux 48 h. The reaction mixture was purified by preparative HPLC (Method 4) affording 107 mg (65% of th.) of the title compound.

LC-MS (Method 2): $R_t$=1.12 min; MS (ESIpos): m/z=551.2 [M+H]+

$^1$H-NMR (400 MHz, DMSO-d6) δ [ppm]: 8.90 (s, 1H), 8.33-8.03 (m, 2H), 7.85-7.49 (m, 4H), 6.98-6.80 (m, 2H), 6.40 (br t, 1H), 5.47 (s, 1H), 5.14 (s, 2H), 4.43-4.17 (br m, 1H), 4.11-3.73 (m, 2H), 3.26 (d, 2H), 0.63-0.36 (m, 4H).

Example 5

4-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-4-yl}piperazin-2-one

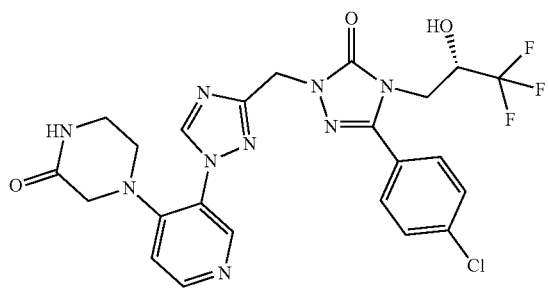 [SMILES: O=C1CN(c2ccncc2-n2cnc(Cn3nc(-c4ccc(Cl)cc4)n(C[C@H](O)C(F)(F)F)c3=O)n2)CCN1]

A solution of 5-(4-chlorophenyl)-2-{[1-(4-chloropyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Example 6A, 150 mg, 300 μmol) in ethanol (600 μl) was treated with piperazin-e-one (300 mg, 3.00 mmol) and heated at reflux overnight. The reaction mixture was purified by preparative HPLC (Method 4) affording 143 mg (85% of th.) of the title compound.

LC-MS (Method 2): $R_t$=1.03 min; MS (ESIpos): m/z=564.1 [M+H]$^+$ $^1$H-NMR (400 MHz, DMSO-d6) δ [ppm]: 8.88 (s, 1H), 8.49-8.20 (m, 2H), 8.06 (br s, 1H), 7.80-7.53 (m, 4H), 7.08 (d, 1H), 6.91 (d, 1H), 5.22-4.97 (m, 2H), 4.39-4.23 (br m, 1H), 4.10-3.70 (m, 2H), 3.51 (s, 2H), 3.12-2.82 (m, 4H).

Example 6

5-(4-Chlorophenyl)-2-({1-[4-(1,1-dioxidothiomorpholin-4-yl)pyridin-3-yl]-1H-1,2,4-triazol-3-yl}methyl)-4-[(2S)-3,3,3-trifluoro-2-hydroxypropyl]-2,4-dihydro-3H-1,2,4-triazol-3-one

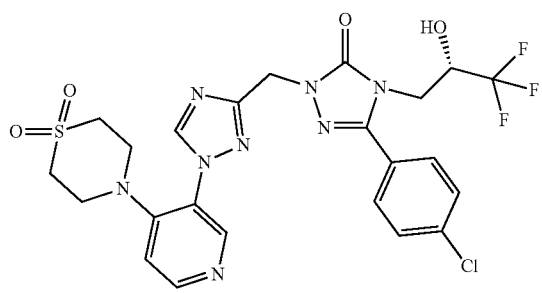 [SMILES: O=c1n(Cc2ncn(-c3cnccc3N3CCS(=O)(=O)CC3)n2)nc(-c2ccc(Cl)cc2)n1C[C@H](O)C(F)(F)F]

A solution of 5-(4-chlorophenyl)-2-{[1-(4-chloropyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Example 6A, 150 mg, 300 μmol) in ethanol (600 μl) was treated with thiomorpholine-1,1-dioxide (405 mg, 3.00 mmol) and heated at reflux 48 h. The reaction mixture was purified by preparative HPLC (Method 4) affording 122 mg (68% of th.) of the title compound.

LC-MS (Method 2): $R_t$=1.34 min; MS (ESIpos): m/z=599.1 [M+H]$^+$ $^1$H-NMR (400 MHz, DMSO-d6) δ [ppm]: 8.98 (s, 1H), 8.51-8.36 (m, 2H), 7.84-7.50 (m, 4H), 7.24 (d, 1H), 6.90 (br s, 1H), 5.22-5.04 (m, 2H), 4.35-4.21 (br m, 1H), 4.11-3.74 (m, 2H), 3.32-3.24 (br m, 4H, overlapping with DMSO peak), 3.08-2.97 (br m, 4H).

Example 7

5-(4-Chlorophenyl)-2-({1-[4-({[5-oxopyrrolidin-2-yl]methyl}amino)pyridin-3-yl]-1H-1,2,4-triazol-3-yl}methyl)-4-[(2S)-3,3,3-trifluoro-2-hydroxypropyl]-2,4-dihydro-3H-1,2,4-triazol-3-one (Diastereomeric Mixture)

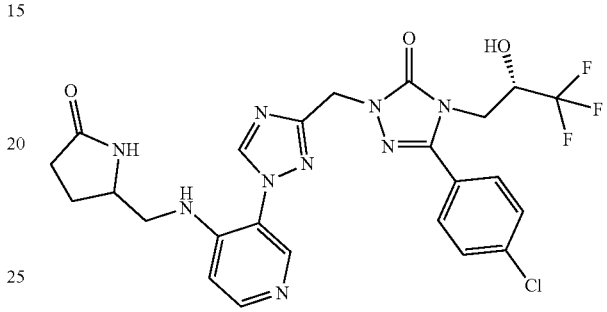

A solution of 5-(4-chlorophenyl)-2-{[1-(4-chloropyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Example 6A, 150 mg, 300 μmol) in ethanol (600 μl) was treated with 5-aminomethyl-pyrrolidin-2-one (229 mg, 2.01 mmol) and heated at reflux overnight. The reaction mixture was purified by preparative HPLC (Method 4) affording 133 mg (77% of th.) of the title compound.

LC-MS (Method 2): $R_t$=1.00 min: MS (ESIpos): m/z=578.2 [M+H]$^+$

Example 8

5-(4-Chlorophenyl)-2-{[1-(4-{[2-(2-oxoimidazolidin-1-yl)ethyl]amino}pyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one

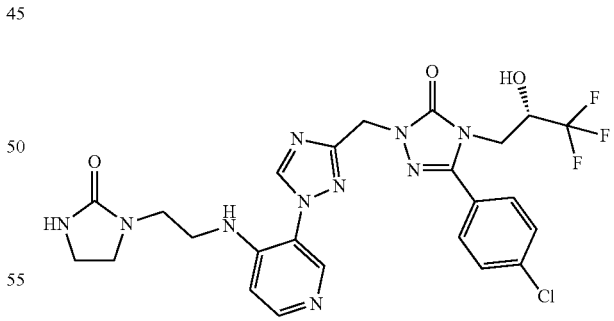

A solution of 5-(4-chlorophenyl)-2-{[1-(4-chloropyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Example 6A, 150 mg, 300 μmol) in ethanol (600 μl) was treated with 1-(2-aminoethyl)imidazolidin-2-one (387 mg, 3.00 mmol) and heated at reflux overnight. The reaction mixture was purified by preparative HPLC (Method 4) affording 167 mg (94% of th.) of the title compound.

LC-MS (Method 2): $R_t$=1.02 min; MS (ESIpos): m/z=593.2 [M+H]$^+$

¹H-NMR (400 MHz, DMSO-d6) δ [ppm]: 8.83 (s, 1H), 8.31-8.17 (m, 2H), 7.88-7.51 (m, 4H), 7.02-6.75 (m, 2H), 6.55-6.25 (m, 2H), 5.13 (s, 2H), 4.39-4.21 (br m, 1H), 4.12-3.71 (m, 2H), 3.48-3.07 (m, 8H).

Example 9

5-(4-Chlorophenyl)-2-({1-[4-(4,4-difluoropiperidin-1-yl)pyridin-3-yl]-1H-1,2,4-triazol-3-yl}methyl)-4-[(2S)-3,3,3-trifluoro-2-hydroxypropyl]-2,4-dihydro-3H-1,2,4-triazol-3-one

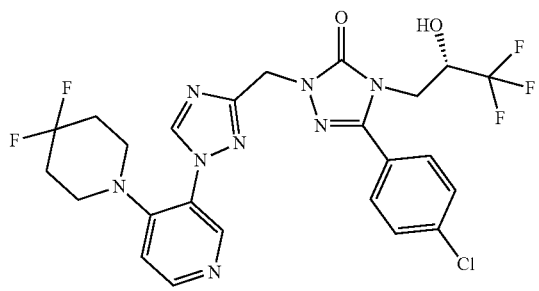 [SMILES: O=c1n(Cc2ncn(-c3cnccc3N3CCC(F)(F)CC3)n2)nc(-c2ccc(Cl)cc2)n1C[C@H](O)C(F)(F)F]

A solution of 5-(4-chlorophenyl)-2-{[1-(4-chloropyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Example 6A, 150 mg, 300 μmol) in ethanol (600 μl) was treated with 4,4-difluoropiperidine (473 mg, 3.00 mmol) and heated at reflux overnight. The reaction mixture was purified by preparative HPLC (Method 4) affording 49.0 mg (28% of th.) of the title compound.

LC-MS (Method 2): R$_t$=1.46 min; MS (ESIpos): m/z=585.2 [M+H]⁺

¹H-NMR (400 MHz, DMSO-d6) δ [ppm]: 8.93 (s, 1H), 8.50-8.24 (m, 2H), 7.84-7.50 (m, 4H), 7.16 (d, 1H), 6.90 (d, 1H), 5.14 (s, 2H), 4.43-4.19 (m, 1H), 4.09-3.74 (m, 2H), 3.00-2.76 (m, 4H), 1.98-1.68 (m, 4H).

Example 10

5-(4-Chlorophenyl)-2-[(1-{4-[(2,2,2-trifluoroethyl)amino]pyridin-3-yl}-1H-1,2,4-triazol-3-yl)methyl]-4-[(2S)-3,3,3-trifluoro-2-hydroxypropyl]-2,4-dihydro-3H-1,2,4-triazol-3-one

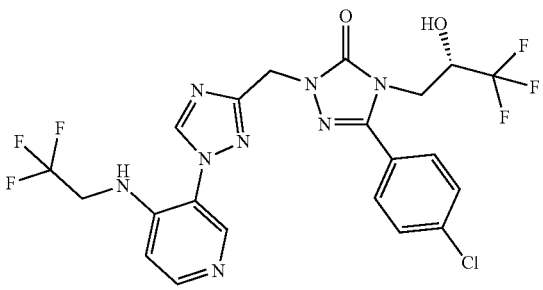 [SMILES: O=c1n(Cc2ncn(-c3cnccc3NCC(F)(F)F)n2)nc(-c2ccc(Cl)cc2)n1C[C@H](O)C(F)(F)F]

A solution of 5-(4-chlorophenyl)-2-{[1-(4-chloropyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Example 6A, 150 mg, 300 μmol) in ethanol (600 μl) was treated with 2,2,2-trifluoroethylamine (297 mg, 3.00 mmol) and heated at reflux 48 h. 2,2,2-trifluoroethylamine (297 mg, 3.00 mmol) was added and the resulting mixture was stirred 16 h at 100° C. under microwave irradiation. The reaction mixture was purified by preparative HPLC (Method 4) affording 28.5 mg (17% of th.) of the title compound.

LC-MS (Method 2): R$_t$=1.30 min; MS (ESIpos): m/z=563.1 [M+H]⁺

¹H-NMR (400 MHz, DMSO-d6) δ [ppm]: 8.87 (s, 1H), 8.45-8.23 (m, 2H), 7.86-7.49 (m, 4H), 7.10 (d, 1H), 7.00-6.70 (m, 2H), 5.14 (s, 2H), 4.40-4.23 (br m, 1H), 4.18-3.95 (m, 3H), 3.93-3.75 (m, 1H).

Example 11

5-(4-Chlorophenyl)-4-[(2S)-3,3,3-trifluoro-2-hydroxypropyl]-2-[(1-{4-[(3,3,3-trifluoropropyl)amino]pyridin-3-yl}-1H-1,2,4-triazol-3-yl)methyl]-2,4-dihydro-3H-1,2,4-triazol-3-one

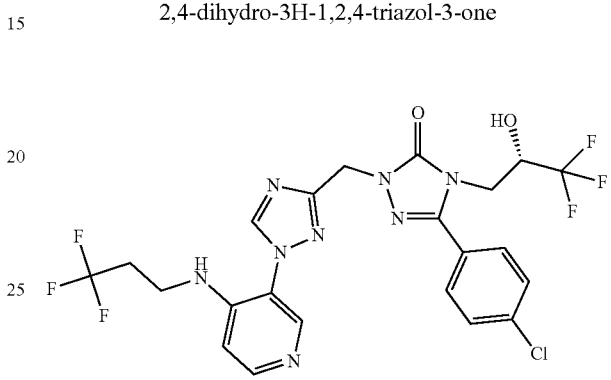

A solution of 5-(4-chlorophenyl)-2-{[1-(4-chloropyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Example 6A, 150 mg, 300 μmol) in ethanol (600 μl) was treated with 3,3,3-trifluoropropylamine (339 mg, 3.00 mmol) and heated at reflux overnight. The reaction mixture was purified by preparative HPLC (Method 4) affording 94.3 mg (55% of th.) of the title compound.

LC-MS (Method 2): R$_t$=1.27 min; MS (ESIpos): m/z=577.1 [M+H]⁺

¹H-NMR (400 MHz, DMSO-d6) δ [ppm]: 8.84 (s, 1H), 8.35-8.13 (m, 2H), 7.86-7.50 (m, 4H), 6.97-6.80 (m, 2H), 6.43 (br t, 1H), 5.13 (s, 2H), 4.40-4.20 (br m, 1H), 4.11-3.73 (m, 2H), 3.42 (q, 2H), 2.62-2.50 (m, 2H, overlapping with DMSO peak).

Example 12

5-(4-Chlorophenyl)-2-[(1-{4-[(2,2-difluoropropyl)amino]pyridin-3-yl}-1H-1,2,4-triazol-3-yl)methyl]-4-[(2S)-3,3,3-trifluoro-2-hydroxypropyl]-2,4-dihydro-3H-1,2,4-triazol-3-one

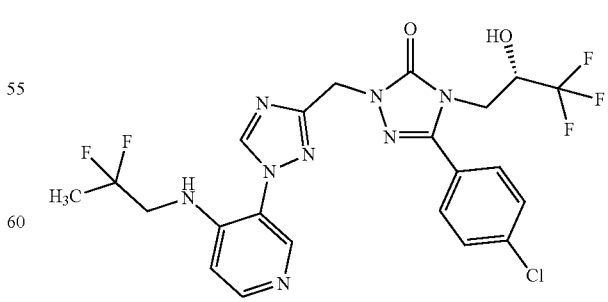

A solution of 5-(4-chlorophenyl)-2-{[1-(4-chloropyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Example 6A, 150 mg, 300 μmol) in ethanol (600 μl) was treated with 2,2-difluoropropan-1-amine (394 mg, 3.00 mmol) and heated at reflux overnight. The reaction mixture was purified by preparative HPLC (Method 4) affording 131 mg (78% of th.) of the title compound.

LC-MS (Method 2): $R_t$=1.22 min; MS (ESIpos): m/z=559.1 [M+H]$^+$ $^1$H-NMR (400 MHz, DMSO-d6) δ [ppm]: 8.88 (s, 1H), 8.36-8.11 (m, 2H), 7.84-7.49 (m, 4H), 7.11-6.81 (m, 2H), 6.59 (br t, 1H), 5.14 (s, 2H), 4.40-4.20 (br m, 1H), 4.12-3.76 (m, 2H), 3.67 (td, 2H), 1.58 (t, 3H).

Example 13

5-(4-Chlorophenyl)-2-[(1-{4-[3-hydroxy-3-methylpyrrolidin-1-yl]pyridin-3-yl}-1H-1,2,4-triazol-3-yl)methyl]-4-[(2S)-3,3,3-trifluoro-2-hydroxypropyl]-2,4-dihydro-3H-1,2,4-triazol-3-one (Diastereomeric Mixture)

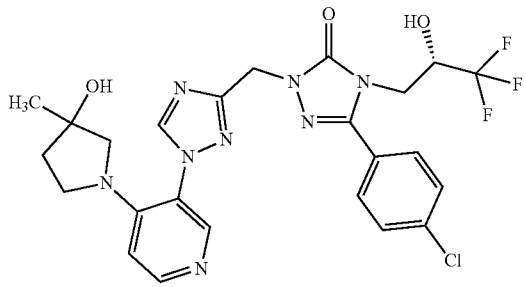 [SMILES: CC1(O)CCN(c2ccncc2-n2cnc(Cn3nc(-c4ccc(Cl)cc4)n(C[C@H](O)C(F)(F)F)c3=O)n2)C1]

A solution of 5-(4-chlorophenyl)-2-{[1-(4-chloropyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Example 6A, 150 mg, 300 µmol) in ethanol (600 µl) was treated with 3-methylpyrrolidin-3-ol (303 mg, 3.00 mmol) and heated at reflux overnight. The reaction mixture was purified by preparative HPLC (Method 4) affording 114 mg (67% of th.) of the title compound.

LC-MS (Method 2): $R_t$=1.03 min; MS (ESIpos): m/z=565.2 [M+H]$^+$

Example 14

5-(4-Chlorophenyl)-2-({1-[4-(3,3-dimethylpiperazin-1-yl)pyridin-3-yl]-1H-1,2,4-triazol-3-yl}methyl)-4-[(2S)-3,3,3-trifluoro-2-hydroxypropyl]-2,4-dihydro-3H-1,2,4-triazol-3-one

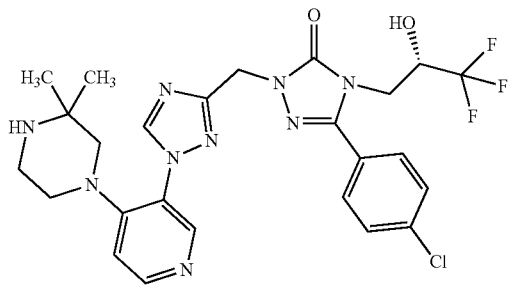 [SMILES: CC1(C)CN(c2ccncc2-n2cnc(Cn3nc(-c4ccc(Cl)cc4)n(C[C@H](O)C(F)(F)F)c3=O)n2)CCN1]

A solution of 5-(4-chlorophenyl)-2-{[1-(4-chloropyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Example 6A, 150 mg, 300 µmol) in ethanol (600 µl) was treated with 2,2-dimethylpiperazine (342 mg, 3.00 mmol) and heated at reflux overnight. The reaction mixture was purified by preparative HPLC (Method 4) affording 131 mg (75% of th.) of the title compound.

LC-MS (Method 2): $R_t$=0.94 min; MS (ESIpos): m/z=578.2 [M+H]$^+$ $^1$H-NMR (400 MHz, DMSO-d6) δ [ppm]: 8.82 (s, 1H), 8.44-8.07 (m, 3H), 7.83-7.52 (m, 4H), 7.05 (d, 1H), 5.28-4.99 (m, 2H), 4.44-4.19 (m, 1H), 4.07-3.72 (m, 2H), 2.81-2.33 (m, 6H, overlapping with DMSO peak), 0.88 (d, 6H), NH not visible.

Example 15

5-(4-Chlorophenyl)-2-({1-[4-(morpholin-4-yl)pyridin-3-yl]-1H-1,2,4-triazol-3-yl}methyl)-4-[(2S)-3,3,3-trifluoro-2-hydroxypropyl]-2,4-dihydro-3H-1,2,4-triazol-3-one

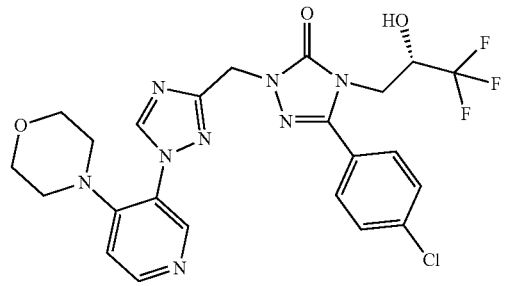 [SMILES: O=c1n(Cc2ncn(-c3cnccc3N3CCOCC3)n2)nc(-c2ccc(Cl)cc2)n1C[C@H](O)C(F)(F)F]

A solution of 5-(4-chlorophenyl)-2-{[1-(4-chloropyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Example 6A, 150 mg, 300 µmol) in ethanol (600 µl) was treated with morpholine (260 µl, 3.0 mmol) and heated at reflux overnight. The reaction mixture was purified by preparative HPLC (Method 4) affording 118 mg (71% of th.) of the title compound.

LC-MS (Method 2): $R_t$=1.17 min; MS (ESIpos): m/z=551.2 [M+H]$^+$ $^1$H-NMR (400 MHz, DMSO-d6) δ [ppm]: 8.89 (s, 1H), 8.49-8.25 (m, 2H), 7.81-7.55 (m, 4H), 7.08 (d, 1H), 6.90 (d, 1H), 5.12 (s, 2H), 4.40-4.20 (br m, 1H), 4.12-3.77 (m, 2H), 3.49-3.42 (m, 4H), 2.75-2.67 (m, 4H).

Example 16

Tert-butyl N-{3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-4-yl}glycinate

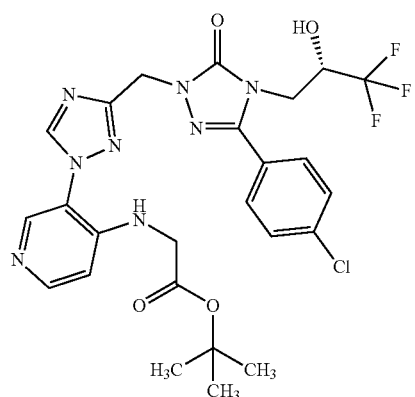

A solution of 5-(4-chlorophenyl)-2-{[1-(4-chloropyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Example 6A, 200 mg, 400 μmol) in ethanol (980 μl) was treated with tert-butyl glycinate (550 μl, 4.0 mmol) and heated at reflux overnight. The reaction mixture was purified by preparative HPLC (Method 4) affording 97.7 mg (41% of th.) of the title compound.

LC-MS (Method 2): $R_t$=1.38 min; MS (ESIpos): m/z=595.2 [M+H]$^+$ $^1$H-NMR (400 MHz, DMSO-d6) δ [ppm]: 8.89 (s, 1H), 8.38-8.16 (m, 2H), 7.87-7.51 (m, 4H), 6.94 (d, 1H), 6.78-6.51 (m, 2H), 5.14 (s, 2H), 4.43-4.20 (m, 1H), 4.09-3.76 (m, 4H), 1.48-1.32 (m, 9H).

Example 17

N$^2$-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-4-yl}glycinamide

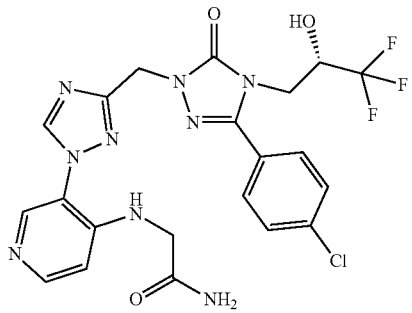 [SMILES: NC(=O)CNc1ccncc1-n1cnc(Cn2nc(-c3ccc(Cl)cc3)n(C[C@H](O)C(F)(F)F)c2=O)n1]

Tert-butyl N-{3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-4-yl}glycinate (Example 16A, 93.7 mg, 157 μmol) was dissolved in a solution of ammonia in methanol (1.0 ml, 7.0 M, 7.0 mmol) and the resulting mixture was heated 3 h at 100° C. under microwave irradiation. Ammonia solution in methanol (1.0 ml, 7.0 M, 7.0 mmol) was added and the resulting mixture was heated 3 h at 100° C. under microwave irradiation. The reaction mixture was purified by preparative HPLC (Method 4) affording 38.4 mg (45% of th.) of the title compound.

LC-MS (Method 2): $R_t$=0.99 min; MS (ESIpos): m/z=538.1 [M+H]$^+$ $^1$H-NMR (400 MHz, DMSO-d6) δ [ppm]: 8.91 (s, 1H), 8.42-8.16 (m, 2H), 7.86-7.53 (m, 4H), 7.49 (br s, 1H), 7.20 (br s, 1H), 6.98-6.73 (m, 2H), 6.63 (d, 1H), 5.20-4.95 (m, 2H), 4.32 (br d, 1H), 4.10-3.65 (m, 4H).

Example 18

5-(4-Chlorophenyl)-2-{[1-(4-{[(1,1-dioxidothietan-3-yl)methyl]amino}pyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one

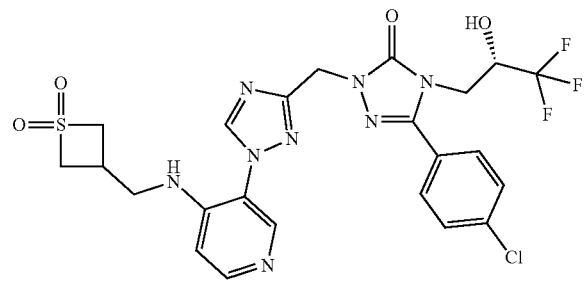 [SMILES: O=c1n(Cc2ncn(-c3cnccc3NCC3CS(=O)(=O)C3)n2)nc(-c2ccc(Cl)cc2)n1C[C@H](O)C(F)(F)F]

A solution of 5-(4-chlorophenyl)-2-{[1-(4-chloropyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Example 6A, 150 mg, 300 μmol) in ethanol (600 μl) was treated with 1-(1,1-dioxidothietan-3-yl)methanamine (405 mg, 3.00 mmol) and heated at reflux overnight. The reaction mixture was purified by preparative HPLC (Method 4) affording 115 mg (64% of th.) of the title compound.

LC-MS (Method 2): $R_t$=1.11 min; MS (ESIpos): m/z=599.1 [M+H]$^+$ $^1$H-NMR (400 MHz, DMSO-d6) δ [ppm]: 8.80 (s, 1H), 8.30-8.13 (m, 2H), 7.85-7.53 (m, 4H), 6.92 (t, 2H), 6.67 (br s, 1H), 5.14 (s, 2H), 4.42-4.23 (m, 1H), 4.17 (dd, 2H), 4.07-3.75 (m, 4H), 3.44 (t, 2H), 2.85-2.67 (m, 1H).

Example 19

Tert-butyl N-{3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-4-yl}-beta-alaninate

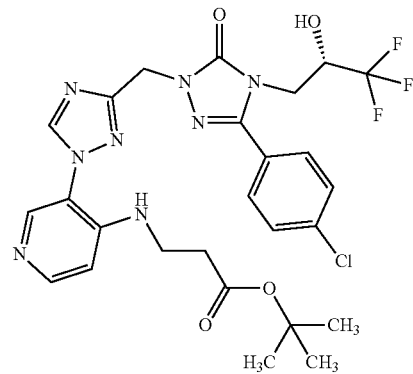 [SMILES: CC(C)(C)OC(=O)CCNc1ccncc1-n1cnc(Cn2nc(-c3ccc(Cl)cc3)n(C[C@H](O)C(F)(F)F)c2=O)n1]

A solution of 5-(4-chlorophenyl)-2-{[1-(4-chloropyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Example 6A, 200 mg, 400 μmol) in ethanol (980 μl) was treated with tert-butyl beta-alaninate (726 mg, 4.00 mmol) followed by N,N-diisopropylethylamine (1.4 ml, 8.0 mmol) and heated at reflux overnight. The reaction mixture was purified by preparative HPLC (Method 4) affording 165 mg (67% of th.) of the title compound.

LC-MS (Method 2): $R_t$=1.37 min MS (ESIpos): m/z=609.2 [M+H]$^+$ $^1$H-NMR (400 MHz, DMSO-d6) δ [ppm]: 8.84 (s, 1H), 8.31-8.14 (m, 2H), 7.86-7.53 (m, 4H), 7.03-6.71 (m, 2H), 6.36 (br t, 1H), 5.12 (s, 2H), 4.44-4.20 (m, 1H), 4.13-3.71 (m, 2H), 3.38 (q, 2H), 2.46 (t, 2H), 1.36 (s, 9H).

Example 20

N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-4-yl}-beta-alanine

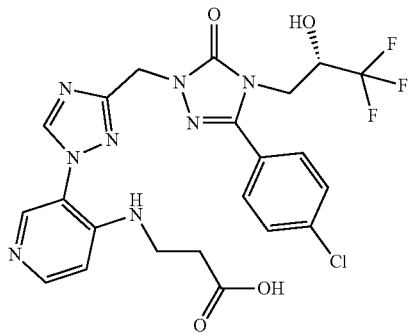 [SMILES: O=C(O)CCNc1ccncc1-n1cnc(Cn2nc(-c3ccc(Cl)cc3)n(C[C@H](O)C(F)(F)F)c2=O)n1]

Tert-butyl N-{3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-4-yl}-beta-alaninate (Example 19A, 145 mg, 238 μmol) was dissolved in a hydrogen chloride solution in dioxane (2.5 ml, 4.0 M, 10 mmol). The resulting mixture was stirred overnight at room temperarture and purified by preparative HPLC (Method 4) affording 111 mg (85% of th.) of the title compound.

LC-MS (Method 2): $R_t$=1.04 min; MS (ESIpos): m/z=553.1 [M+H]$^+$ $^1$H-NMR (400 MHz, DMSO-d6) δ [ppm]: 12.32 (br s, 1H), 8.84 (s, 1H), 8.32-8.15 (m, 2H), 7.87-7.45 (m, 4H), 7.05-6.74 (m, 2H), 6.41 (t, 1H), 5.13 (s, 2H), 4.40-4.21 (br m, 1H), 4.11-3.70 (m, 2H), 3.38 (q, 2H), 2.49-2.44 (m, 2H, overlapping with DMSO peak).

Example 21

N$^3$-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-4-yl}-beta-alaninamide

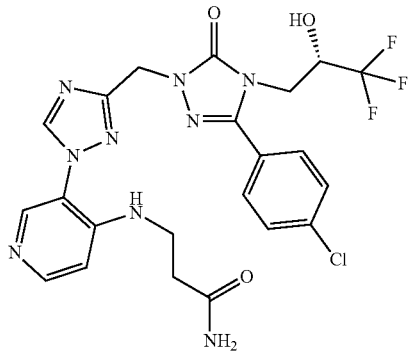 [SMILES: NC(=O)CCNc1ccncc1-n1cnc(Cn2nc(-c3ccc(Cl)cc3)n(C[C@H](O)C(F)(F)F)c2=O)n1]

At 0° C., a solution of N-{3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-4-yl}-beta-alanine (Example 20A, 107 mg, 194 μmol), pyridine (31 μl, 390 μmol) and 4-dimethylaminopyridine (24 μg, 0.19 μmol) in tetrahydrofuran (920 μl) was treated with 2,2-dimethylpropanoylchloride (38 μl, 310 μmol) dropewisely. The resulting suspension was stirred at room temperature for 2 h and cooled down to 0° C. A solution of ammonia in methanol (280 μl, 7.0 M, 1.9 mmol) was then added, the resulting mixture was stirred overnight at room temperature and evaporated. The residue was purified by preparative HPLC (Method 4) and evaporated. The residue was submitted to a second purification [sample preparation: 62 mg dissolved in 3 ml DMSO; column: Kinetex C18 5 μm, 100×30 mm; Eluent A: Water, Eluent B: Acetonitrile+0.07% formic acid; gradient: 0.0 min 10% B, 2 min 10% B, 2.2 min 20% B, 7 min 60% B, 7.5 min 92% B; flow rate: 70 ml/min; temperature: 25° C.; UV detection: 210 nm] affording 15.0 mg (14% of th.) of the title compound.

LC-MS (Method 1): $R_t$=0.61 min; MS (ESIpos): m/z=552.2 [M+H]$^+$ $^1$H-NMR (400 MHz, DMSO-d6) δ [ppm]: 8.84 (s, 1H), 8.31-8.16 (m, 2H), 7.86-7.54 (m, 4H), 7.38 (br s, 1H), 7.03-6.77 (m, 3H), 6.47 (br t, 1H), 5.12 (s, 2H), 4.40-4.20 (br m, 1H), 4.12-3.73 (m, 2H), 3.37 (q, 2H, overlapping with HDO peak), 2.38-2.21 (m, 2H).

Example 22

1-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-4-yl}-D-prolinamide

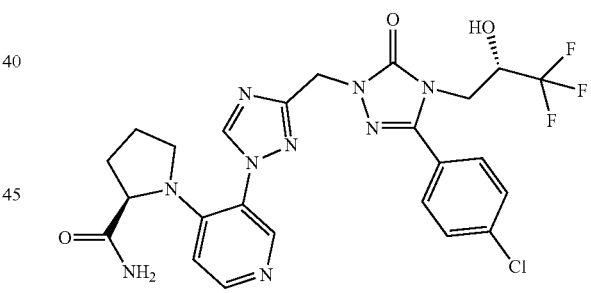

A solution of 5-(4-chlorophenyl)-2-{[1-(4-chloropyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Example 6A, 150 mg, 300 μmol) in ethanol (600 μl) was treated with D-prolinamide (342 mg, 3.00 mmol) and heated at reflux overnight. The reaction mixture was purified by preparative HPLC (Method 4) affording 137 mg (79% of th.) of the title compound.

LC-MS (Method 2): $R_t$=1.03 min; MS (ESIpos): m/z=578.2 [M+H]$^+$ $^1$H-NMR (400 MHz, DMSO-d6) δ [ppm]: 8.73 (s, 1H), 8.27-8.00 (m, 2H), 7.80-7.50 (m, 4H), 7.30 (s, 1H), 7.10 (s, 1H), 6.91 (d, 1H), 6.52 (d, 1H), 5.19-4.99 (m, 2H), 4.40-4.20 (br m, 1H), 4.16-3.76 (m 3H), 2.93-2.66 (m 2H), 2.11-1.91 (m 1H), 1.85-1.44 (m 3H).

Example 23

1-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-4-yl}-L-prolinamide

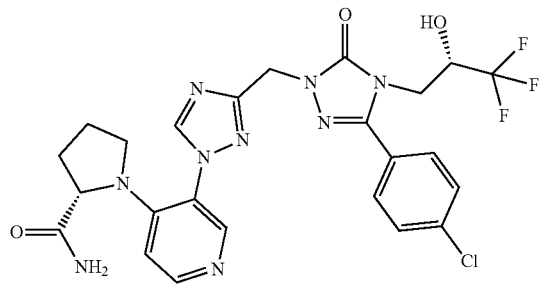 [SMILES: NC(=O)[C@@H]1CCCN1c1ccncc1-n1cnc(Cn2nc(-c3ccc(Cl)cc3)n(C[C@H](O)C(F)(F)F)c2=O)n1]

A solution of 5-(4-chlorophenyl)-2-{[1-(4-chloropyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Example 6A, 150 mg, 300 μmol) in ethanol (600 μl) was treated with L-prolinamide (342 mg, 3.00 mmol) and heated at reflux overnight. The reaction mixture was purified by preparative HPLC (Method 4) affording 139 mg (80% of th.) of the title compound.

LC-MS (Method 2): $R_t$=1.06 min; MS (ESIpos): m/z=578.2 [M+H]$^+$ $^1$H-NMR (400 MHz, DMSO-d6) δ [ppm]: 8.72 (s, 1H), 8.30-7.98 (m, 2H), 7.84-7.54 (m, 4H), 7.29 (s, 1H), 7.09 (s, 1H), 6.91 (d, 1H), 6.53 (d, 1H), 5.11 (s, 2H), 4.40-4.20 (br m, 1H), 4.13-3.72 (m, 3H), 2.95-2.70 (m, 2H), 2.02 (dq, 1H), 1.84-1.43 (m, 3H).

Example 24

1-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-4-yl}-4,4-difluoro-D-prolinamide

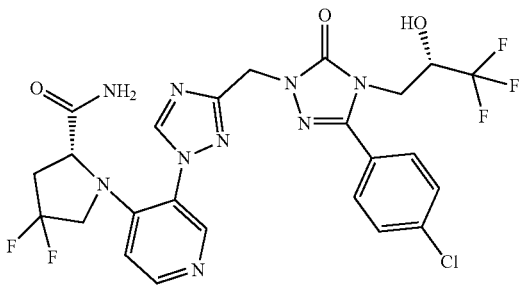 [SMILES: NC(=O)[C@H]1CC(F)(F)CN1c1ccncc1-n1cnc(Cn2nc(-c3ccc(Cl)cc3)n(C[C@H](O)C(F)(F)F)c2=O)n1]

A solution of 5-(4-chlorophenyl)-2-{[1-(4-chloropyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Example 6A, 100 mg, 200 μmol) in ethanol (400 μl) was treated with (R)-4,4-difluoropyrrolidine-2-carboxamide hydrochloride (186 mg, 999 μmol) and heated at reflux overnight. The reaction mixture was purified by preparative HPLC (Method 4) affording 36.0 mg (29% of th.) of the title compound.

LC-MS (Method 2): $R_t$=1.25 min; MS (ESIpos): m/z=614.1 [M+H]$^+$ $^1$H-NMR (400 MHz, DMSO-d6) δ [ppm]: 8.76 (s, 1H), 8.44-8.08 (m, 2H), 7.83-7.49 (m, 4H), 7.42 (s, 1H), 7.29 (s, 1H), 6.92 (d, 1H), 6.71 (d, 1H), 5.14 (s, 2H), 4.45-4.23 (br m, 2H), 4.09-3.73 (m, 2H), 3.48-3.07 (m, 2H, overlapping with HDO peak), 2.90-2.12 (m, 2H, overlapping with DMSO peak).

Example 25

1-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-4-yl}-4,4-difluoro-L-prolinamide

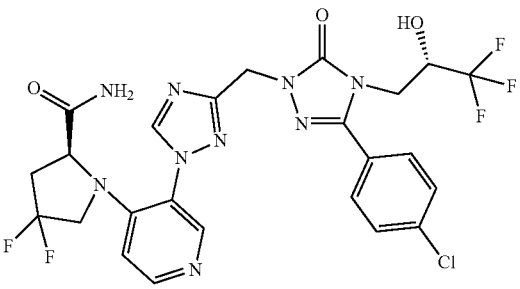 [SMILES: NC(=O)[C@@H]1CC(F)(F)CN1c1ccncc1-n1cnc(Cn2nc(-c3ccc(Cl)cc3)n(C[C@H](O)C(F)(F)F)c2=O)n1]

A solution of 5-(4-chlorophenyl)-2-{[1-(4-chloropyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Example 6A, 100 mg, 200 μmol) in ethanol (400 μl) was treated with (S)-4,4-difluoropyrrolidine-2-carboxamide hydrochloride (186 mg, 999 μmol) and heated at reflux overnight. The reaction mixture was purified by preparative HPLC (Method 4) affording 37.6 mg (31% of th.) of the title compound.

LC-MS (Method 2): $R_t$=1.25 min; MS (ESIpos): m/z=614.1 [M+H]$^+$ $^1$H-NMR (400 MHz, DMSO-d6) δ [ppm]: 8.76 (s, 1H), 8.41-8.07 (m, 2H), 7.83-7.54 (m, 4H), 7.43 (s, 1H), 7.30 (s, 1H), 6.90 (d, 1H), 6.71 (d, 1H), 5.22-5.01 (m, 2H), 4.50-4.18 (m, 2H), 4.10-3.72 (m, 2H), 3.43-3.11 (m, 2H, overlapping with HDO peak), 2.90-2.60 (m, 1H), 2.40-2.13 (m, 1H).

Example 26

2,2,2-Trifluoroethyl {3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-4-yl}carbamate

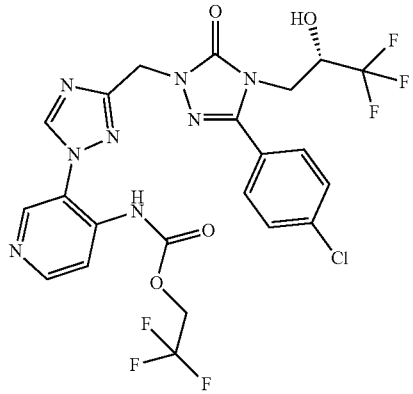 [SMILES: O=C(Nc1ccncc1-n1cnc(Cn2nc(-c3ccc(Cl)cc3)n(C[C@H](O)C(F)(F)F)c2=O)n1)OCC(F)(F)F]

A solution of 2-{[1-(4-aminopyridin-3-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 9A, 100 mg, 208 µmol) in dichloromethane (980 µl) was treated with 2,2,2-trifluoroethyl carbonochloridate (67.6 mg, 416 µmol), N,N-diisopropylethylamine (72 µl, 420 µmol) and 4-dimethylaminopyridine (25.4 mg, 208 µmol). The resulting mixture was stirred 3 h at room temperature and purified by preparative HPLC (Method 4) affording 51.0 mg (38% of th.) of the title compound.

LC-MS (Method 2): $R_t$=1.83 min; MS (ESIpos): m/z=607.1 [M+H]$^+$ $^1$H-NMR (400 MHz, DMSO-d6) δ [ppm]: 10.12 (br s, 1H), 8.94 (s, 1H), 8.69-8.52 (m, 2H), 7.93 (d, 1H), 7.83-7.46 (m, 4H), 6.92 (d, 1H), 5.26-4.99 (m, 2H), 4.76 (q, 2H), 4.40-4.21 (br m, 1H), 4.10-3.72 (m, 2H).

Example 27

N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-4-yl}-3,3,3-trifluoropropanamide

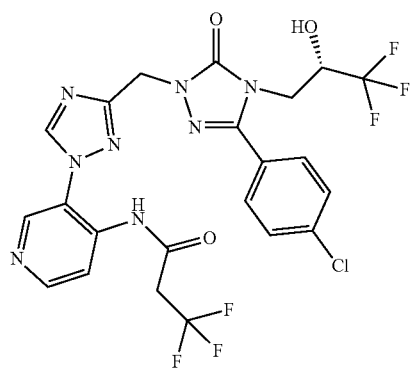 [SMILES: O=C(CC(F)(F)F)Nc1ccncc1-n1cnc(Cn2nc(-c3ccc(Cl)cc3)n(C[C@H](O)C(F)(F)F)c2=O)n1]

At 0° C., a solution of 3,3,3-trifluoropropanoic acid (92 µl, 1.0 mmol) in dichloromethane (4.5 ml) was treated with 1-chloro-N,N,2-trimethylprop-1-en-1-amine (220 µl, 1.7 mmol) and stirred 1 h at room temperature. The solution was cooled to 0° C., 2-{[1-(4-aminopyridin-3-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 9A, 100 mg, 208 µmol) was then added followed by N,N-diisopropylethylamine (250 µl, 1.5 mmol) and 4-dimethylaminopyridine (127 mg, 1.04 mmol) and stirred 72 h at room temperature. A solution of ammonia in methanol (1.8 ml, 7N, 12.6 mmol) was then added. The resulting mixture was stirred 2 h at room temperature and evaporated. The residue was purified by preparative HPLC (Method 4) affording 23.7 mg (19% of th.) of the title compound.

LC-MS (Method 2): $R_t$=1.73 min; MS (ESIpos): m/z=591.1 [M+H]$^+$ $^1$H-NMR (400 MHz, DMSO-d6) δ [ppm]: 10.08 (s, 1H), 9.00 (s, 1H), 8.80-8.51 (m, 2H), 8.10 (d, 1H), 7.92-7.47 (m, 4H), 6.91 (d, 1H), 5.24-5.06 (m, 2H), 4.40-4.20 (br m, 1H), 4.10-3.77 (m, 2H), 3.59 (q, 2H).

Example 28

N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-4-yl}acetamide

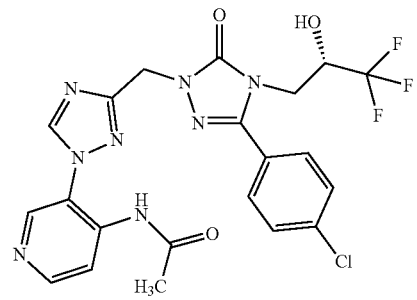 [SMILES: CC(=O)Nc1ccncc1-n1cnc(Cn2nc(-c3ccc(Cl)cc3)n(C[C@H](O)C(F)(F)F)c2=O)n1]

A solution of 2-{[1-(4-aminopyridin-3-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 9A, 100 mg, 208 µmol) in dichloromethane (4.5 ml) was treated with acetyl chloride (44 µl, 620 µmol) and 4-dimethylaminopyridine (76.2 mg, 624 µmol) and stirred 72 h at room temperature. A solution of ammonia in methanol (1.5 ml, 7N, 10.5 mmol) was then added. The resulting mixture was stirred overnight at room temperature and evaporated. The residue was purified by preparative HPLC (Method 4) affording 54.4 mg (49% of th.) of the title compound.

LC-MS (Method 2): $R_t$=1.49 min; MS (ESIpos): m/z=523.1 [M+H]$^+$ $^1$H-NMR (400 MHz, DMSO-d6) δ [ppm]: 9.76 (s, 1H), 9.00 (s, 1H), 8.73-8.47 (m, 2H), 8.17 (d, 1H), 7.84-7.57 (m, 4H), 6.92 (d, 1H), 5.16 (s, 2H), 4.40-4.20 (br m, 1H), 4.11-3.73 (m, 2H), 2.00 (s, 3H).

Example 29

N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-4-yl}-2,2-difluorocyclopropanecarboxamide (Diastereomeric Mixture)

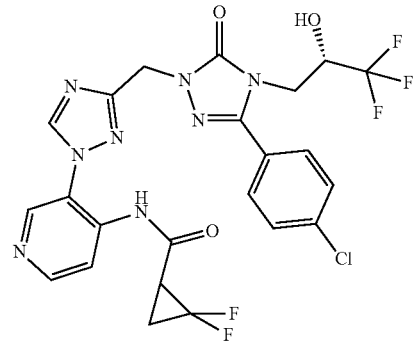 [SMILES: O=C(Nc1ccncc1-n1cnc(Cn2nc(-c3ccc(Cl)cc3)n(C[C@H](O)C(F)(F)F)c2=O)n1)C1CC1(F)F]

At 0° C., a solution of 2,2-difluorocyclopropanecarboxylic acid (63.5 mg, 520 µmol) in dichloromethane (2.3 ml)

was treated with 1-chloro-N,N,2-trimethylprop-1-en-1-amine (110 μl, 830 μmol) and stirred 1 h at room temperature. The solution was cooled to 0° C., 2-{[1-(4-aminopyridin-3-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 9A, 50.0 mg, 104 μmol) was then added followed by N,N-diisopropylethylamine (130 μl, 730 μmol) and 4-dimethylaminopyridine (63.5 mg, 520 μmol) and stirred 24 h at room temperature. A solution of ammonia in methanol (1.8 ml, 7N, 12.6 mmol) was then added. The resulting mixture was stirred 2 h at room temperature and evaporated. The residue was purified by preparative HPLC (Method 4) affording 44.7 mg (66% of th.) of the title compound.

LC-MS (Method 1): $R_t$=0.93 min; MS (ESIpos): m/z=585.1 [M+H]$^+$ $^1$H-NMR (400 MHz, DMSO-d6) δ [ppm]: 10.19 (s, 1H), 9.06-8.90 (m, 1H), 8.72-8.50 (m, 2H), 8.23-8.05 (m, 1H), 7.82-7.53 (m, 4H), 6.98-6.85 (m, 1H), 5.16 (s, 2H), 4.40-4.19 (br m, 1H), 4.10-3.73 (m, 2H), 3.02-2.84 (m, 1H), 2.11-1.79 (m, 2H).

Example 30

N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-4-yl}-2-cyclopropylacetamide

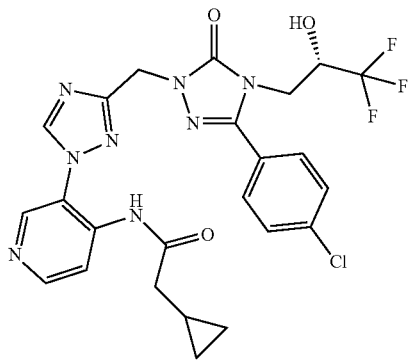 [SMILES: O=C(CC1CC1)Nc1ccncc1-n1cnc(Cn2nc(-c3ccc(Cl)cc3)n(C[C@H](O)C(F)(F)F)c2=O)n1]

At 0° C., a solution of 1-chloro-N,N,2-trimethylprop-1-en-1-amine (110 μl, 830 μmol) in dichloromethane (2.3 ml) was treated with cyclopropylacetic acid (52.1 mg, 520 μmol) and stirred 1 h at room temperature. The solution was cooled to 0° C., 2-{[1-(4-aminopyridin-3-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 9A, 50.0 mg, 104 μmol) was then added followed by N,N-diisopropylethylamine (130 μl, 730 μmol) and 4-dimethylaminopyridine (63.5 mg, 520 μmol) and stirred 24 h at room temperature. A solution of ammonia in methanol (1.8 ml, 7N, 12.6 mmol) was then added. The resulting mixture was stirred 2 h at room temperature and evaporated. The residue was purified by preparative HPLC (Method 4) and evaporated. The residue was submitted to a second purification [sample preparation: 40 mg dissolved in 3 ml 2-propanol and 3 ml n-heptane; injection volume: 1 ml; column: Daicel Chiralpak IA 5 μm, 250×20 mm; eluent: n-heptane/2-propanol 70:30; flow rate: 15 ml/min; temperature: 30° C.; UV detection: 220 nm] affording 7.40 mg (13% of th.) of the title compound.

LC-MS (Method 2): $R_t$=1.77 min; MS (ESIpos): m/z=563.2 [M+H]$^+$ $^1$H-NMR (400 MHz, DMSO-d6) δ [ppm]: 9.69 (s, 1H), 9.04 (s, 1H), 8.71 (s, 1H), 8.57 (d, 1H), 8.26 (d, 1H), 7.93-7.38 (m, 4H), 6.90 (d, 1H), 5.36-4.92 (m, 2H), 4.40-4.19 (br m, 1H), 4.09-3.75 (m, 2H), 2.21 (d, 2H), 1.02-0.87 (m, 1H), 0.53-0.30 (m, 2H), 0.21-0.03 (m, 2H).

Example 31

N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-4-yl}-3,3-difluorocyclobutanecarboxamide

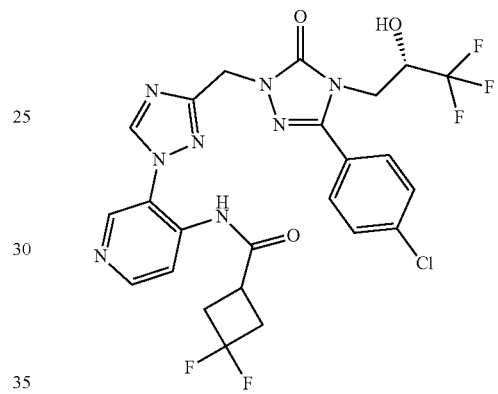

At 0° C., a solution of 1-chloro-N,N,2-trimethylprop-1-en-1-amine (110 μl, 830 μmol) in dichloromethane (2.3 ml) was treated with 3,3-difluorocyclobutanecarboxylic acid (70.8 mg, 520 μmol) and stirred 1 h at room temperature. The solution was cooled to 0° C., 2-{[1-(4-aminopyridin-3-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 9A, 50.0 mg, 104 μmol) was then added followed by N,N-diisopropylethylamine (130 μl, 730 μmol) and 4-dimethylaminopyridine (63.5 mg, 520 μmol) and stirred 24 h at room temperature. A solution of ammonia in methanol (1.8 ml, 7N, 12.6 mmol) was then added. The resulting mixture was stirred 2 h at room temperature and evaporated. The residue was purified by preparative HPLC (Method 4) and evaporated. The residue was submitted to a second purification [sample preparation: 28 mg dissolved in 3 ml 2-propanol and 1 ml dichloromethane; injection volume: 2 ml; column: Daicel Chiralpak IA 5 μm, 250×20 mm; eluent: n-heptane/2-propanol 80:20; flow rate: 15 ml/min; temperature: 30° C.; UV detection: 220 nm] affording 7.50 mg (12% of th.) of the title compound.

LC-MS (Method 2): $R_t$=1.78 min; MS (ESIpos): m/z=599.1 [M+H]$^+$ $^1$H-NMR (400 MHz, DMSO-d6) δ [ppm]: 9.92 (br s, 1H), 9.03 (s, 1H), 8.81-8.41 (m, 2H), 8.14 (d, 1H), 7.86-7.47 (m, 4H), 6.91 (d, 1H), 5.15 (s, 2H), 4.40-4.20 (br m, 1H), 4.13-3.74 (m, 2H), 3.21-3.00 (br m, 1H), 2.89-2.61 (m, 4H).

Example 32

N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-4-yl}-1-(trifluoromethyl)cyclopropanecarboxamide

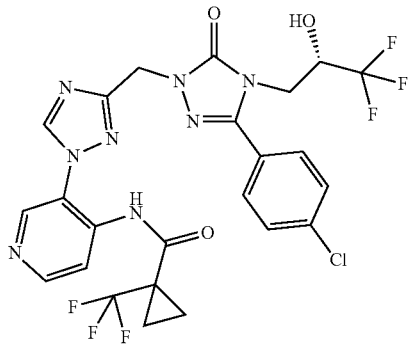 [SMILES: O=C(Nc1ccncc1-n1cnc(Cn2nc(-c3ccc(Cl)cc3)n(C[C@H](O)C(F)(F)F)c2=O)n1)C1(C(F)(F)F)CC1]

At 0° C., a solution of 1-chloro-N,N,2-trimethylprop-1-en-1-amine (110 µl, 830 µmol) in dichloromethane (2.3 ml) was treated with 1-(trifluoromethyl)cyclopropanecarboxylic acid (80.1 mg, 520 µmol) and stirred 1 h at room temperature. The solution was cooled to 0° C., 2-{[1-(4-aminopyridin-3-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 9A, 50.0 mg, 104 µmol) was then added followed by N,N-diisopropylethylamine (130 µl, 730 µmol) and 4-dimethylaminopyridine (63.5 mg, 520 µmol) and stirred 24 h at room temperature. A solution of ammonia in methanol (1.8 ml) was then added. The resulting mixture was stirred 2 h at room temperature and evaporated. The residue was purified by preparative HPLC (Method 4) and evaporated. The residue was submitted to a second purification [sample preparation: 28 mg dissolved in 1 ml ethanol and 2 ml acetonitrile; injection volume: 400 µl; column: Daicel Chiralpak IC 5 µm, 250×20 mm; eluent: n-heptane/ethanol 50:50; flow rate: 15 ml/min; temperature: 25° C.; UV detection: 220 nm] affording 21.2 mg (33% of th.) of the title compound.

LC-MS (Method 2): $R_t$=1.90 min: MS (ESIpos): m/z=617.1 [M+H]$^+$ $^1$H-NMR (400 MHz, DMSO-d6) δ [ppm]: 10.04 (s, 1H), 9.12 (s, 1H), 8.86 (s, 1H), 8.60 (d, 1H), 8.06 (d, 1H), 7.84-7.51 (m, 4H), 6.91 (d, 1H), 5.26-4.99 (m, 2H), 4.40-4.21 (br m, 1H), 4.10-3.72 (m, 2H), 1.66-1.23 (m, 4H).

Example 33

N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-4-yl}-2-fluorocyclopropanecarboxamide
(Diastereomeric Mixture Cis Configured)

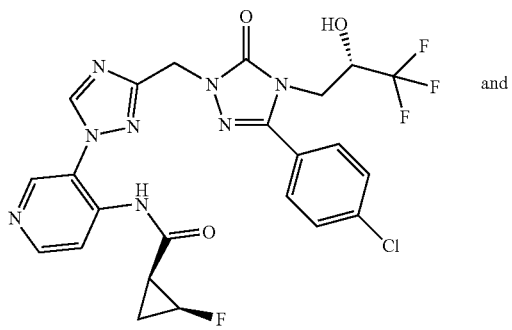

and

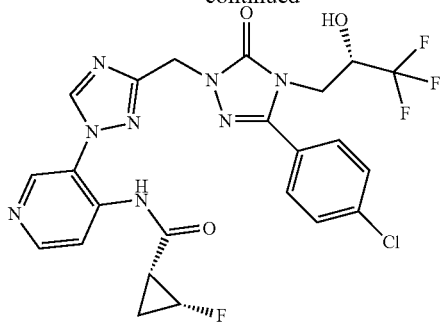

At 0° C., a solution of 1-chloro-N,N,2-trimethylprop-1-en-1-amine (110 µl, 830 µmol) in dichloromethane (2.3 ml) was treated with 2-fluorocyclopropanecarboxylic acid (cis configured, 54.1 mg, 520 µmol) and stirred 1 h at room temperature. The solution was cooled to 0° C., 2-{[1-(4-aminopyridin-3-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 9A, 50.0 mg, 104 µmol) was then added followed by N,N-diisopropylethylamine (130 µl, 730 µmol) and 4-dimethylaminopyridine (63.5 mg, 520 µmol) and stirred 24 h at room temperature. A solution of ammonia in methanol (1.8 ml, 7N, 12.6 mmol) was then added. The resulting mixture was stirred 2 h at room temperature and evaporated. The residue was purified by preparative HPLC (Method 4) affording 11.7 mg of diastereomer 1 (Example 42) (17% of th.) and 12 mg of diastereoisomer 2 (Example 34) which was submitted to a second purification [sample preparation: 12 mg dissolved in 1 ml ethanol and 2 ml acetonitrile; injection volume: 250 µl; column: Daicel Chiralpak IB 5 µm, 250×20 mm; eluent: n-heptane/ethanol 50:50; flow rate: 15 ml/min; temperature: 25° C.; UV detection: 210 nm] affording 9.3 mg (15% of th.) of diastereomer 2 (Example 35).

Example 34

(1S,2S)—N-{t3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-4-yl}-2-fluorocyclopropanecarboxamide
(diastereomer 1)

LC-MS (Method 1): $R_t$=0.90 min: MS (ESIpos): m/z=567.2 [M+H]$^+$ $^1$H-NMR (400 MHz, DMSO-d6) δ [ppm]: 10.13 (s, 1H), 9.01 (s, 1H), 8.80-8.38 (m, 2H), 8.17 (d, 1H), 7.91-7.45 (m, 4H), 7.04-6.78 (m, 1H), 5.17 (s, 2H), 5.03-4.66 (m, 1H), 4.40-4.20 (br m, 1H), 4.10-3.70 (m, 2H), 1.60-1.03 (m, 3H).

Example 35

(1S,2S)—N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-4-yl}-2-fluorocyclopropanecarboxamide
(diastereomer 2)

LC-MS (Method 2): $R_t$=1.61 min; MS (ESIpos): m/z=567.1 [M+H]$^+$ $^1$H-NMR (400 MHz, DMSO-d6) δ [ppm]: 10.05 (br s, 1H), 9.00 (d, 1H), 8.77-8.47 (m, 2H), 8.22 (d, 1H), 7.87-7.52

(m, 4H), 6.91 (d, 1H), 5.16 (s, 2H), 5.01-4.61 (m, 1H), 4.40-4.19 (br m, 1H), 4.11-3.71 (m, 2H), 2.22-0.74 (m, 3H).

Example 36

N-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-3-yl}-2,2,2-trifluoroacetamide

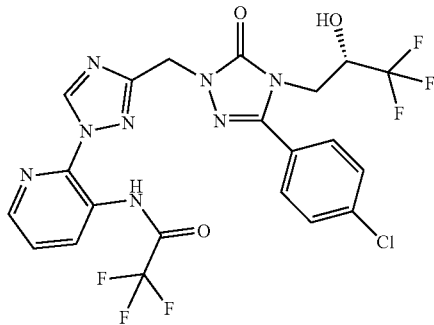 [SMILES: O=C(Nc1cccnc1-n1cnc(Cn2nc(-c3ccc(Cl)cc3)n(C[C@H](O)C(F)(F)F)c2=O)n1)C(F)(F)F]

A solution of 2-{[1-(3-aminopyridin-2-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 40A, 20.4 mg, 42.4 µmol) in dichloromethane (200 µl) was treated with N,N-diisopropylethylamine (15 µl, 85 µmol), 4-dimethylaminopyridine (5.18 mg, 42.4 µmol) and trifluoroacetic anhydride (12 µl, 85 µmol). The resulting mixture was stirred overnight at room temperature and evaporated. The residue was purified by preparative HPLC (Method 4) affording 10.2 mg (42% of th.) of the title compound.

LC-MS (Method 2): $R_t$=1.99 min; MS (ESIpos): m/z=577.1 [M+H]$^+$ $^1$H-NMR (400 MHz, DMSO-d6) δ [ppm]: 11.60 (s, 1H), 9.26 (s, 1H), 8.61-8.25 (m, 2H), 7.81-7.53 (m, 5H), 6.92 (d, 1H), 5.22-4.98 (m 2H), 4.39-4.21 (br m, 1H), 4.08-3.73 (m 2H).

Example 37

N-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-3-yl}-3,3,3-trifluoropropanamide

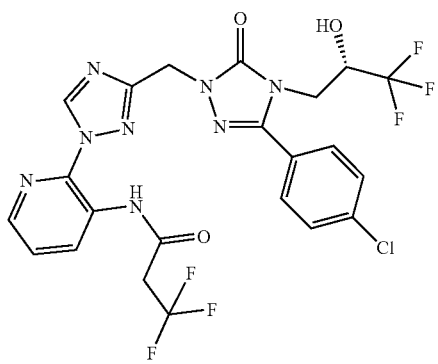 [SMILES: O=C(CC(F)(F)F)Nc1cccnc1-n1cnc(Cn2nc(-c3ccc(Cl)cc3)n(C[C@H](O)C(F)(F)F)c2=O)n1]

A solution of 2-{[1-(3-aminopyridin-2-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 40A, 114 mg, 237 µmol) in dichloromethane (1.1 ml) was treated with N,N-diisopropylethylamine (83 µl, 470 µmol), 4-dimethylaminopyridine (29.0 mg, 237 µmol) and 3,3,3-trifluoropropanoyl chloride (69.5 mg, 474 µmol). The resulting mixture stirred overnight at room temperature and evaporated. The residue was purified by preparative HPLC (Method 4) affording 32.8 mg (22% of th.) of the title compound.

LC-MS (Method 2): $R_t$=1.92 min; MS (ESIpos): m/z=591.1 [M+H]$^+$ $^1$H-NMR (400 MHz, DMSO-d6) δ [ppm]: 10.39 (s, 1H), 9.18 (s, 1H), 8.53-8.29 (m, 2H), 7.84-7.49 (m, 5H), 6.91 (d, 1H), 5.32-5.03 (m, 2H), 4.39-4.20 (br m, 1H), 4.10-3.70 (m, 2H), 3.58 (q, 2H).

Example 38

N-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-3-yl}acetamide

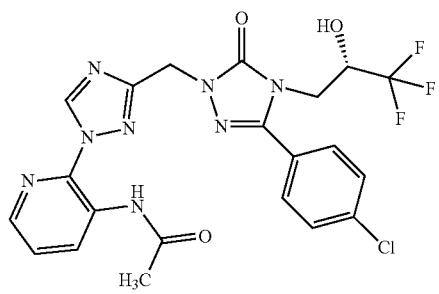 [SMILES: CC(=O)Nc1cccnc1-n1cnc(Cn2nc(-c3ccc(Cl)cc3)n(C[C@H](O)C(F)(F)F)c2=O)n1]

A solution of 2-{[1-(3-aminopyridin-2-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 40A, 100 mg, 208 µmol) in dichloromethane (980 µl) was treated with N,N-diisopropylethylamine (140 µl, 830 µmol), 4-dimethylaminopyridine (25.4 mg, 208 µmol) and acetyl chloride (44 µl, 620 µmol). The resulting mixture stirred 2 h at room temperature. Dichloroethane (0.5 ml) was added and the resulting mixture was stirred 1 h at 65° C. and evaporated. The residue was retaken in a solution of ammonia in methanol (1 ml, 7N), stirred 1 h at room temperature and evaporated. The residue was purified by preparative HPLC (Method 4) followed by flash chromatography (silica gel, eluent cyclohexane/ethyl acetate) affording 41.3 mg (38% of th.) of the title compound.

LC-MS (Method 1): $R_t$=0.89 min; MS (ESIpos): m/z=523.1 [M+H]$^+$ $^1$H-NMR (400 MHz, DMSO-d6) δ [ppm]: 10.13 (s, 1H), 9.20 (s, 1H), 8.55 (d, 1H), 8.30 (dd, 1H), 7.81-7.47 (m, 5H), 6.92 (d, 1H), 5.28-5.09 (m, 2H), 4.40-4.21 (br m, 1H), 4.09-3.77 (m, 2H), 1.98 (s, 3H).

Example 39

N-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-3-yl}-2-fluoroacetamide

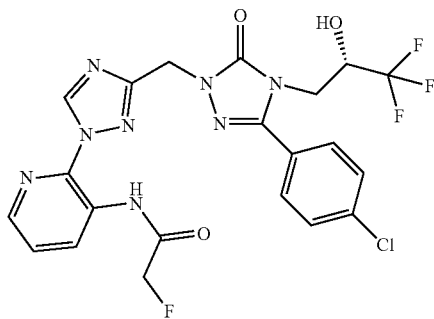 [SMILES: O=C(CF)Nc1cccnc1-n1cnc(Cn2nc(-c3ccc(Cl)cc3)n(C[C@H](O)C(F)(F)F)c2=O)n1]

A solution of 2-{[1-(3-aminopyridin-2-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 40A, 100 mg, 208 μmol) in dichloromethane (980 μl) was treated with N,N-diisopropylethylamine (140 μl, 830 μmol), 4-dimethylaminopyridine (25.4 mg, 208 μmol) and fluoroacetyl chloride (44 μl, 620 μmol). The resulting mixture stirred overnight at room temperature and evaporated. The residue was retaken in a solution of ammonia in methanol (1 ml, 7N) and stirred 3 h at room temperature. Purification by preparative HPLC (Method 4) afforded 46.4 mg (41% of th.) of the title compound.

LC-MS (Method 1): $R_t$=0.93 min; MS (ESIpos): m/z=541.1 [M+H]$^+$ $^1$H-NMR (400 MHz, DMSO-d6) δ [ppm]: 10.90 (br s, 1H), 9.32 (s, 1H), 8.72 (dd, 1H), 8.36 (dd, 1H), 7.83-7.47 (m 5H), 6.97-6.84 (m, 1H), 5.26-4.78 (m 4H), 4.40-4.19 (m, 1H), 4.05-3.73 (m 2H).

Example 40

N-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-3-yl}-2-methoxyacetamide

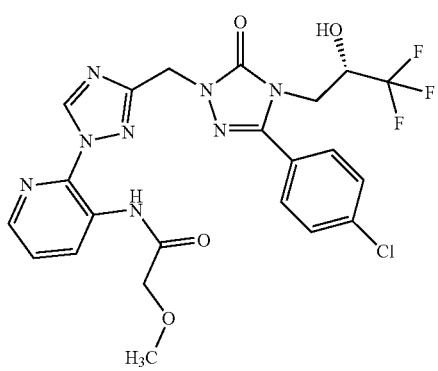 [SMILES: COCC(=O)Nc1cccnc1-n1cnc(Cn2nc(-c3ccc(Cl)cc3)n(C[C@H](O)C(F)(F)F)c2=O)n1]

A solution of 2-{[1-(3-aminopyridin-2-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 40A, 72.0 mg, 150 μmol) in dichloromethane (710 μl) was treated with N,N-diisopropylethylamine (100 μl, 600 μmol), 4-dimethylaminopyridine (18.3 mg, 150 μmol) and methoxyacetyl chloride (42 μl, 450 μmol). The resulting mixture stirred 4 h at room temperature. Dichloroethane (0.5 ml) was added and the resulting mixture was stirred overnight at 70° C. methoxyacetyl chloride (14 μl, 150 μmol) and N,N-diisopropylethylamine (50 μl, 300 μmol) were added and the reaction mixture was stirred overnight at 70° C. and evaporated. The residue was retaken in a solution of ammonia in methanol (1 ml, 7N), stirred 4 h at room temperature and evaporated. The residue was purified by preparative HPLC (Method 4) affording 13.0 mg (16% of th.) of the title compound.

LC-MS (Method 2): $R_t$=1.81 min; MS (ESIpos): m/z=553.1 [M+H]$^+$ $^1$H-NMR (400 MHz, DMSO-d6) δ [ppm]: 11.14 (s, 1H), 9.33 (s, 1H), 8.91 (dd, 1H), 8.31 (dd, 1H), 7.84-7.40 (m, 5H), 6.92 (d, 1H), 5.18 (s, 2H), 4.39-4.20 (br m, 1H), 4.11-3.73 (m, 4H), 3.47 (s, 3H).

Example 41

N-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-3-yl}-2,2-difluorocyclopropanecarboxamide
(Diastereomeric Mixture)

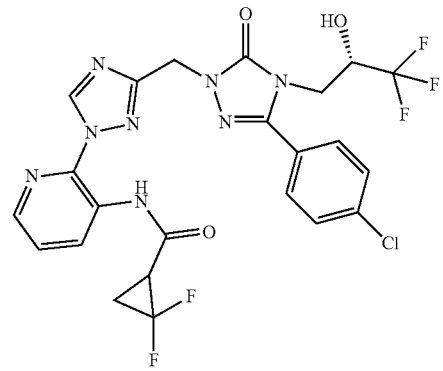 [SMILES: O=C(Nc1cccnc1-n1cnc(Cn2nc(-c3ccc(Cl)cc3)n(C[C@H](O)C(F)(F)F)c2=O)n1)C1CC1(F)F]

A solution of 2-{[1-(3-aminopyridin-2-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 40A, 400 mg, 832 μmol) in dichloromethane (3.9 ml) was treated with N,N-diisopropylethylamine (580 μl, 3.3 mmol), 4-dimethylaminopyridine (102 mg, 832 μmol) and 2,2-difluorocyclopropanecarbonyl chloride (351 mg, 2.50 mmol). The resulting mixture stirred overnight at room temperature and evaporated. The residue was retaken in a solution of ammonia in methanol (1 ml, 7N) and stirred 2 h at room temperature and evaporated. The residue was purified by preparative HPLC (Method 4) affording 397 mg (78% of th.) of the title compound.

The two diastereomers were separated by preparative chiral HPLC [sample preparation: 366 mg dissolved in 20 ml methanol; injection volume: 1 ml; column: Chiralpak AD SFC, 250×20 mm; eluent: CO$_2$/methanol 75:25; flow rate: 80 ml/min; temperature: 40° C.; UV detection: 210 nm]. After separation, 159 mg of diastereomer 1 (Example 42), which eluted first, and 161 mg of diastereomer 2 (Example 43), which eluted later, were isolated.

LC-MS (Method 1): R$_t$=1.01 min; MS (ESIpos): m/z=585.1 [M+H]$^+$ $^1$H-NMR (400 MHz, DMSO-d6) δ [ppm]: 10.51 (br d, 1H), 9.17 (d, 1H), 8.61-8.20 (m, 2H), 7.84-7.43 (m, 5H), 6.91 (2 d, 1H), 5.18 (d, 2H), 4.38-4.19 (br m, 1H), 4.07-3.72 (m, 2H), 3.02-2.79 (m, 1H), 2.14-1.66 (m, 2H).

Example 42

N-{2-[3-({3-(4-chlorophenyl)-5-oxo-4-[(2S)-3,3,3-trifluoro-2-hydroxypropyl]-4,5-dihydro-H-1,2,4-triazol-1-yl}methyl)-1H-1,2,4-triazol-1-yl]pyridin-3-yl}-2,2-difluorocyclopropanecarboxamide (diastereomer 1)

Analytical chiral HPLC: R$_t$=0.79 min, e.e.=100% [column: SFC Daicel AD, 10×4.6 mm; eluent: CO$_2$/methanol 70:30; flow rate: 3.0 ml/min; temperature: 23° C.; UV detection: 210 nm].

LC-MS (MS-M1): R$_t$=1.89 min: MS (ESIpos): m/z=585.1 [M+H]$^+$ $^1$H-NMR (400 MHz, DMSO-d6) δ [ppm]: 10.50 (s, 1H), 9.17 (s, 1H), 8.59-8.22 (m, 2H), 7.84-7.43 (m, 5H), 6.90 (d, 1H), 5.31-5.00 (m, 2H), 4.43-4.18 (m, 1H), 4.13-3.73 (m, 2H), 2.91 (ddd, 1H), 2.10-1.72 (m, 2H).

Example 43

N-{2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-3-yl}-2,2-difluorocyclopropanecarboxamide (diastereomer 2)

Analytical chiral HPLC: R$_t$=1.37 min, e.e.=99.6% [column: SFC Daicel AD, 10×4.6 mm; eluent: CO$_2$/methanol 70:30; flow rate: 3.0 ml/min; temperature: 23° C.; UV detection: 210 nm].

LC-MS (MCW_SQ-HSST3): R$_t$=1.01 min; MS (ESIpos): m/z=585.2 [M+H]$^+$ $^1$H-NMR (400 MHz, DMSO-d6) δ [ppm]: 10.51 (s, 1H), 9.17 (s, 1H), 8.62-8.22 (m, 2H), 7.87-7.46 (m, 5H), 6.92 (d, 1H), 5.27-5.05 (m, 2H), 4.46-4.13 (m, 1H), 4.08-3.71 (m, 2H), 2.91 (ddd, 1H), 2.13-1.72 (m, 2H).

Example 44

N-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-3-yl}cyclopropanecarboxamide

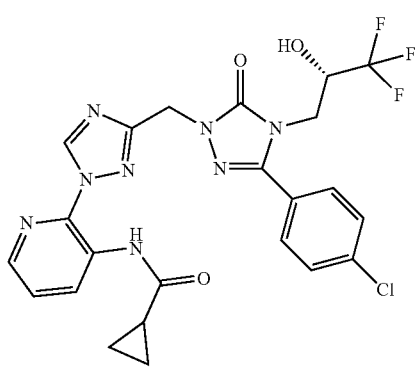 [SMILES: O=C(Nc1cccnc1-n1cnc(Cn2nc(-c3ccc(Cl)cc3)n(C[C@H](O)C(F)(F)F)c2=O)n1)C1CC1]

A solution of cyclopropanecarboxylic acid (83 µl, 1.0 mmol) in N,N-dimethylformamide DMF (1.2 ml) was treated with HATU (395 mg, 1.04 mmol) and stirred 30 min at room temperature. 2-{[1-(3-aminopyridin-2-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 40A, 100 mg, 208 µmol) was added followed by and N,N-diisopropylethylamine (250 µl, 1.5 mmol). The resulting mixture was stirred overnight at room temperature, 24 h at 60° C. and evaporated. A solution of ammonia in methanol (1.2 ml, 7N) was added and the resulting mixture was stirred 1.5 h at room temperature Purification by prep HPLC (Method 4) afforded 65.5 mg (57% of th.) of the title compound.

LC-MS (Method 11: R$_t$=0.99 min: MS (ESIpos): m/z=549.2 [M+H]$^+$ $^1$H-NMR (400 MHz, DMSO-d6) δ [ppm]: 10.48 (s, 1H), 9.24 (s, 1H), 8.66 (dd, 1H), 8.28 (dd, 1H), 7.91-7.35 (m, 5H), 6.93 (d, 1H), 5.34-5.04 (m, 2H), 4.40-4.21 (br m, 1H), 4.10-3.75 (m, 2H), 1.85-1.57 (m, 1H), 0.90-0.40 (m, 4H).

Example 45

N-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-3-yl}-2-(trifluoromethyl)cyclopropanecarboxamide (Diastereomeric Mixture Cis Configured)

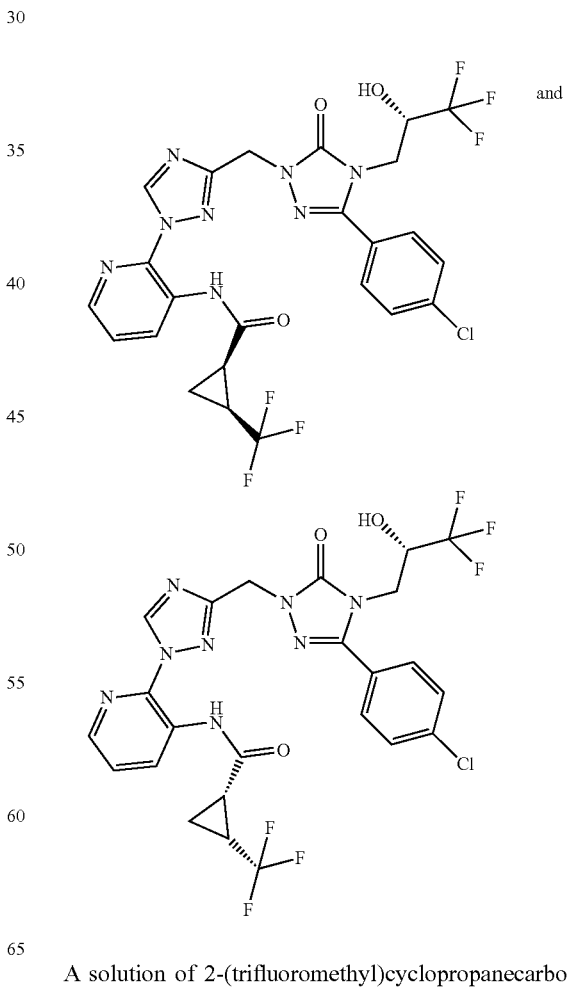

A solution of 2-(trifluoromethyl)cyclopropanecarboxylic acid (cis configured, 76.9 mg, 499 µmol) in N,N-dimethylformamide (1 ml) was treated with HATU (190 mg, 499 μmol) and stirred 30 min at room temperature. 2-{[1-(3-aminopyridin-2-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 40A, 80.0 mg, 166 μmol) was added followed by N,N-diisopropylethylamine (140 μl, 830 μmol). The resulting mixture was stirred overnight at room temperature and 2 h at 60° C. A pre-stirred (30 min) solution of 2-(trifluoromethyl)cyclopropanecarboxylic acid (51 mg, 332 μmol), N,N-diisopropylethylamine (56 μl, 332 μmol) and HATU (127 mg, 332 μmol) in N,N-dimethylformamid (1 ml) was added to the reaction mixture and stirred 72 h at room temperature. A solution of ammonia in methanol (2 ml, 7N) was added and the resulting mixture was stirred overnight at room temperature Purification by preparative HPLC (Method 4) affording 23.0 mg (22% of th.) of the title compound.

LC-MS (Method 1): $R_t$=1.08 min; MS (ESIpos): m/z=617.2 [M+H]$^+$ $^1$H-NMR (400 MHz, DMSO-d6) δ [ppm]: 10.53 (s, 1H), 9.16 (d, 1H), 8.58-8.17 (m, 2H), 7.94-7.42 (m, 5H), 6.91 (2 d, 1H), 5.35-4.99 (m, 2H), 4.38-4.19 (br m, 1H), 4.09-3.71 (m, 2H), 2.47-2.11 (m, 2H), 1.33-1.03 (m 2H).

Example 46

N-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-3-yl}-2-cyclopropylacetamide

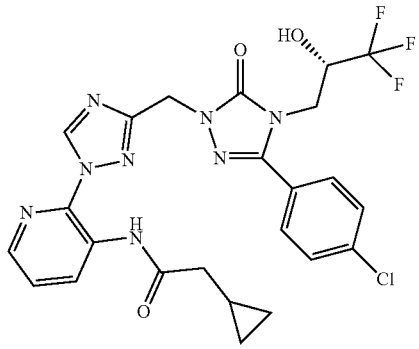 [SMILES: O=C(CC1CC1)Nc1cccnc1-n1cnc(Cn2nc(-c3ccc(Cl)cc3)n(C[C@H](O)C(F)(F)F)c2=O)n1]

A solution of cyclopropylacetic acid (44 μl, 500 μmol) in N,N-dimethylformamide (1.0 ml) was treated with HATU (190 mg, 499 μmol) and stirred 30 min at room temperature. 2-{[1-(3-aminopyridin-2-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 40A; 80.0 mg, 166 μmol) was then added followed by N,N-diisopropylethylamine (140 μl, 830 μmol). The resulting mixture was stirred 72 h at room temperature. A pre-stirred (30 min) solution of cyclopropylacetic acid (44 μl, 500 μmol), N,N-diisopropylethylamine (140 μl, 830 μmol) and HATU (190 mg, 499 μmol) in N,N-dimethylformamide (1.0 ml, 13 mmol) was added to the reaction mixture and stirred 48 h at room temperature. A solution of ammonia in methanol (1.2 ml, 7N) was added and the resulting mixture was stirred 80 min at room temperature. Purification by preparative HPLC (Method 4) afforded 20.5 mg (22% of th.) of the title compound.

LC-MS (Method 2): $R_t$=1.90 min; MS (ESIpos): m/z=563.2 [M+H]$^+$ $^1$H-NMR (400 MHz, DMSO-d6) δ [ppm]: 10.23 (s, 1H), 9.24 (s, 1H), 8.69 (dd, 1H), 8.30 (dd, 1H), 7.91-7.43 (m, 5H), 6.92 (d, 1H), 5.29-5.03 (m, 2H), 4.41-4.16 (m, 1H), 4.10-3.69 (m, 2H), 2.23 (d, 2H), 1.10-0.89 (m, 1H), 0.65-0.37 (m, 2H), 0.26-0.06 (m, 2H).

Example 47

N-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-3-yl}-1-(trifluoromethyl)cyclopropanecarboxamide

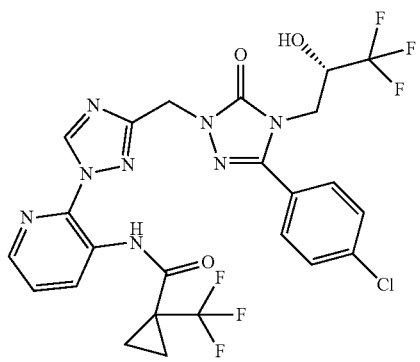 [SMILES: O=C(Nc1cccnc1-n1cnc(Cn2nc(-c3ccc(Cl)cc3)n(C[C@H](O)C(F)(F)F)c2=O)n1)C1(C(F)(F)F)CC1]

A solution of 1-(trifluoromethyl)cyclopropanecarboxylic acid (100 mg, 649 μmol) in N,N-dimethylformamide (1.2 ml, 16 mmol) was treated with HATU (247 mg, 649 μmol) and stirred 30 min at room temperature. 2-{[1-(3-aminopyridin-2-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 40A, 62.4 mg, 130 μmol) was then added followed by and N,N-diisopropylethylamine (160 μl, 910 μmol). The resulting mixture was stirred overnight at room temperature. A pre-stirred (30 min) solution of 1-(trifluoromethyl)cyclopropanecarboxylic acid (40.0 mg, 260 μmol), N,N-diisopropylethylamine (160 μl, 910 μmol), HATU (98.7 mg, 260 μmol) in N,N-dimethylformamide (500 μl, 6.5 mmol) was added and the resulting mixture was stirred overnight at room temperature.

A solution of ammonia in methanol (1.2 ml, 7N) was added and the resulting mixture was stirred overnight at room temperature. Purification by preparative HPLC (Method 4) afforded 62.8 mg (78% of th.) of the title compound.

LC-MS (Method 1): $R_t$=1.10 min; MS (ESIpos): m/z=617.2 [M+H]$^+$ $^1$H-NMR (400 MHz, DMSO-d6) δ [ppm]: 10.42 (s, 1H), 9.28 (s, 1H), 8.63-8.25 (m, 2H), 7.86-7.35 (m, 5H), 6.92 (d, 1H), 5.25-5.04 (m, 2H), 4.43-4.20 (m, 1H), 4.08-3.74 (m, 2H), 1.61-1.25 (m, 4H).

Example 48

N-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-3-yl}-3,3-difluorocyclobutanecarboxamide

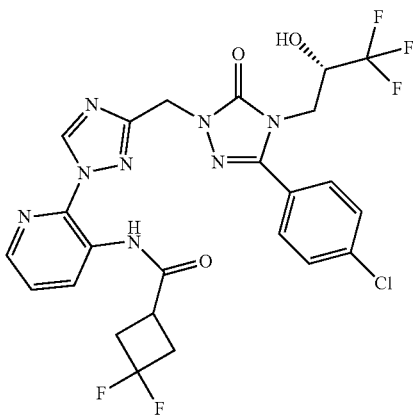 [SMILES: O=C(Nc1cccnc1-n1cnc(Cn2nc(-c3ccc(Cl)cc3)n(C[C@H](O)C(F)(F)F)c2=O)n1)C1CC(F)(F)C1]

A solution of 3,3-difluorocyclobutanecarboxylic acid (142 mg, 1.04 mmol) in N,N-dimethylformamide (1.2 ml) was treated with HATU (395 mg, 1.04 mmol) and stirred 30 min at room temperature. 2-{[1-(3-aminopyridin-2-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 40A, 100 mg, 208 µmol) was then added followed by N,N-diisopropylethylamine (250 µl, 1.5 mmol). The resulting mixture was stirred overnight at room temperature. A solution of ammonia in methanol (1.2 ml, 7N) was added and the resulting mixture was stirred overnight at room temperature. Purification by preparative HPLC (Method 4) afforded 102 mg (82% of th.) of the title compound.

LC-MS (Method 1): $R_t$=1.03 min; MS (ESIpos): m/z=599.2 [M+H]$^+$ $^1$H-NMR (400 MHz, DMSO-d6) δ [ppm]: 10.25 (s, 1H), 9.20 (s, 1H), 8.60-8.25 (m, 2H), 7.84-7.48 (m, 5H), 6.92 (d, 1H), 5.29-5.04 (m, 2H), 4.46-4.18 (m, 1H), 4.11-3.75 (m, 2H), 3.22-3.00 (m, 1H), 2.88-2.65 (m, 4H).

Example 49

N-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-3-yl}-2-(methylsulfonyl)acetamide

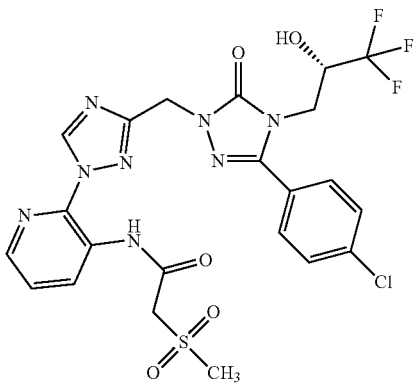 [SMILES: CS(=O)(=O)CC(=O)Nc1cccnc1-n1cnc(Cn2nc(-c3ccc(Cl)cc3)n(C[C@H](O)C(F)(F)F)c2=O)n1]

At 0° C., a solution of (methylsulfonyl)acetic acid (144 mg, 1.04 mmol) in dichloromethane (3.0 ml) was treated with 1-chloro-N,N,2-trimethylprop-1-en-1-amine (220 µl, 1.7 mmol) and stirred 1 h at room temperature. 2-{[1-(3-aminopyridin-2-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 40A; 100 mg, 208 µmol), N,N-diisopropylethylamine (180 µl, 1.0 mmol) and 4-dimethylaminopyridine (127 mg, 1.04 mmol) were added at 0° C. The resulting mixture was stirred overnight at room temperature. A solution of ammonia in methanol (1.5 ml, 7N) was added. The resulting mixture was stirred overnight at room temperature and evaporated. The residue was purified by preparative HPLC (Method 4) affording 88.0 mg (69% of th.) of the title compound.

LC-MS (Method 2): $R_t$=1.59 min; MS (ESIpos): m/z=601.1 [M+H]$^+$ $^1$H-NMR (400 MHz, DMSO-d6) δ [ppm]: 10.52 (s, 1H), 9.16 (s, 1H), 8.54-8.29 (m, 2H), 7.86-7.51 (m, 5H), 6.91 (d, 1H), 5.27-5.06 (m, 2H), 4.43-4.17 (m, 3H), 4.10-3.75 (m, 2H), 3.14 (s, 3H).

Example 50

N-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-3-yl}tetrahydrothiophene-3-carboxamide 1,1-dioxide (Diastereomeric Mixture)

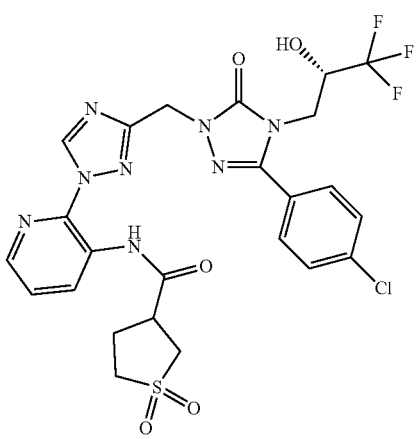 [SMILES: O=C(Nc1cccnc1-n1cnc(Cn2nc(-c3ccc(Cl)cc3)n(C[C@H](O)C(F)(F)F)c2=O)n1)C1CCS(=O)(=O)C1]

A solution of tetrahydrothiophene-3-carboxylic acid 1,1-dioxide (171 mg, 1.04 mmol) in N,N-dimethylformamide (1.2 ml) was treated with HATU (395 mg, 1.04 mmol) and stirred 30 min at room temperature. 2-{[1-(3-aminopyridin-2-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 40A, 100 mg, 208 µmol) was added followed by N,N-diisopropylethylamine (250 µl, 1.5 mmol). The resulting mixture was stirred overnight at room temperature. A solution of ammonia in methanol (1.2 ml, 7N) was added and the resulting mixture was stirred overnight at room temperature. Purification by preparative HPLC (Method 4) afforded 104 mg (80% of th.) of the title compound.

The two diastereomers were separated by preparative chiral HPLC [sample preparation: 130 mg dissolved in 7 ml warm ethanol+3 ml warm acetonitrile; injection volume: 500 µl; column: Daicel Chiralpak IB 5 µm, 250×20 mm; eluent: n-heptane/ethanol 20:80; flow rate: 15 ml/min; temperature: 25° C.; UV detection: 210 nm]. After separation, 66 mg of diastereomer 1 (Example 51), which eluted first, and 64 mg of diastereomer 2 (Example 52), which eluted later, were isolated.

LC-MS (Method 1): $R_t$=0.88 min; MS (ESIpos): m/z=627.2 [M+H]$^+$

¹H-NMR (400 MHz, DMSO-d6) δ [ppm]: 10.30 (s, 1H), 9.17 (s, 1H), 8.49-8.26 (m, 2H), 7.82-7.49 (m, 5H), 6.90 (d, 1H), 5.29-5.02 (m, 2H), 4.38-4.19 (br m, 1H), 4.08-3.71 (m, 2H), 3.55-2.97 (m, 5H, overlap with HDO peak), 2.50-2.38 (m, 1H, overlap with DMSO peak), 2.28-2.11 (m, 1H).

Example 51

N-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-3-yl}tetrahydrothiophene-3-carboxamide 1,1-dioxide
(Diastereomer 1)

Analytical chiral HPLC: $R_t$=2.36 min, e.e.=100% [column: Daicel Chiralpak IB-3 3 µm, 50×4.6 mm; eluent: iso-hexane/ethanol 50:50; flow rate: 1.0 ml/min; temperature: 23° C.; UV detection: 220 nm].

LC-MS (Method 2): $R_t$=1.65 min; MS (ESIpos): m/z=627.1 [M+H]⁺

¹H-NMR (400 MHz, DMSO-d6) δ [ppm]: 10.30 (s, 1H), 9.17 (s, 1H), 8.44-8.31 (m, 2H), 7.82-7.52 (m, 5H), 6.90 (d, 1H), 5.17 (d, 2H), 4.37-4.21 (m, 1H), 4.08-3.79 (m, 2H), 3.54-2.98 (m, 5H, overlap with HDO peak), 2.51-2.37 (m, 1H, overlap with DMSO peak), 2.28-2.10 (m, 1H).

Example 52

N-{2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-3-yl}tetrahydrothiophene-3-carboxamide 1,1-dioxide
(Diastereomer 2)

Analytical chiral HPLC: $R_t$=3.51 min, e.e.=100% [column: Daicel Chiralpak IB-3 3 µm, 50×4.6 mm; eluent: iso-hexane/ethanol 50:50; flow rate: 1.0 ml/min; temperature: 23° C.; UV detection: 220 nm].

LC-MS (Method 2): $R_t$=1.65 min; MS (ESIpos): m/z=627.1 [M+H]⁺

¹H-NMR (400 MHz, DMSO-d6) δ [ppm]: 10.30 (s, 1H), 9.17 (s, 1H), 8.48-8.24 (m, 2H), 7.85-7.46 (m, 5H), 6.91 (d, 1H), 5.17 (s, 2H), 4.39-4.20 (br m, 1H), 4.10-3.72 (m, 2H), 3.55-2.98 (m, 5H, overlap with HDO peak), 2.51-2.38 (m 1H, overlap with DMSO peak), 2.27-2.12 (m, 1H).

Example 53

N-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-3-yl}-N²-(methylsulfonyl)glycinamide

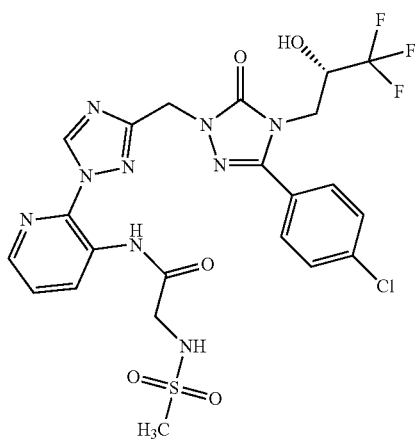 [SMILES: CS(=O)(=O)NCC(=O)Nc1cccnc1-n1cnc(Cn2nc(-c3ccc(Cl)cc3)n(C[C@H](O)C(F)(F)F)c2=O)n1]

At 0° C., a solution of N-(methylsulfonyl)glycine (159 mg, 1.04 mmol) in dichloromethane (3.0 ml) was treated with 1-chloro-N,N,2-trimethylprop-1-en-1-amine (222 mg, 1.66 mmol) and stirred 1 h at room temperature. 2-{[1-(3-aminopyridin-2-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 40A, 100 mg, 208 µmol), N,N-diisopropylethylamine (180 µl, 1.0 mmol) and 4-dimethylaminopyridine (127 mg, 1.04 mmol) were added at 0° C. The resulting mixture was stirred overnight at room temperature. A solution of ammonia in methanol (1.5 ml, 7N) was added and the resulting mixture was stirred overnight at room temperature. The residue was purified by preparative HPLC (Method 4) affording 63.0 mg (49% of th.) of the title compound.

LC-MS (Method 2): $R_t$=1.61 min; MS (ESIpos): m/z=616.1 [M+H]⁺

¹H-NMR (400 MHz, DMSO-d6) δ [ppm]: 11.20 (s, 1H), 9.30 (s, 1H), 8.86 (dd, 1H), 8.32 (dd, 1H), 8.02-7.48 (m, 6H), 6.93 (d, 1H), 5.37-5.12 (m, 2H), 4.41-4.20 (m, 1H), 4.12-3.73 (m, 4H), 3.03 (s, 3H).

Example 54

N-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-3-yl}-2-fluorocyclopropanecarboxamide
(Diastereomeric Mixture Cis Configured)

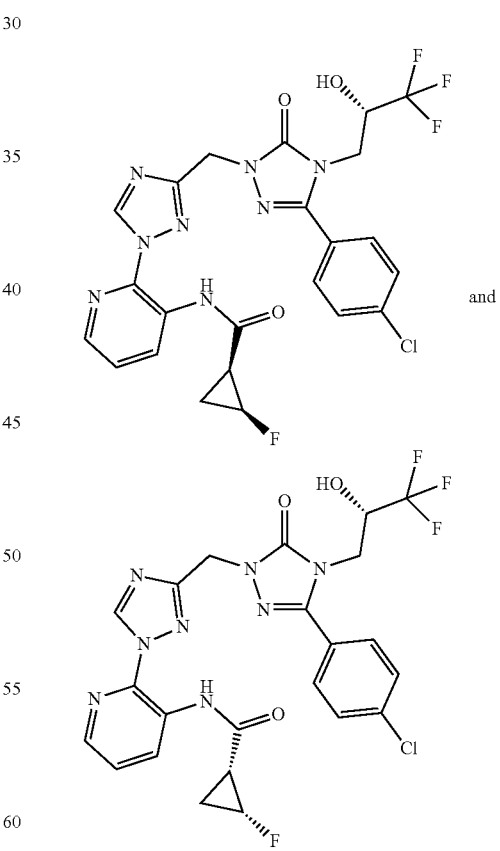

A solution of 2-fluorocyclopropanecarboxylic acid (cis configured, 108 mg, 1.04 mmol) in N,N-dimethylformamide (1.2 ml) was treated with HATU (395 mg, 1.04 mmol) and stirred 1 h at room temperature. 2-{[1-(3-aminopyridin-2-yl)-1H-1,2,4-triazol-3-yl]methyl}-5-(4-chlorophenyl)-4-[(2S)-3,3,3-trifluoro-2-hydroxypropyl]-2,4-dihydro-3H-1,2, 4-triazol-3-one (Example 40A, 100 mg, 208 μmol) was added followed by N,N-diisopropylethylamine (250 μl, 1.5 mmol). The resulting mixture was stirred overnight at room temperature. 4-Dimethylaminopyridine (25.4 mg, 208 μmol) was added and the reaction mixture was stirred 72 h at room temperature. A solution of ammonia in methanol (1.2 ml, 7N) was added and the resulting mixture was stirred overnight at room temperature. Purification by preparative HPLC (Method 4) afforded 42.2 mg (36% of th.) of the title compound.

The two diastereomers were separated by preparative chiral HPLC [sample preparation: 45 mg dissolved in 6 ml warm 2-propanol; injection volume: 400 μl; column: Daicel Chiralpak IE 5 μm, 250×20 mm; eluent: n-heptane/isopropanol 73:27; flow rate: 15 ml/min; temperature: 50° C.; UV detection: 220 nm]. After separation, 17 mg of diastereomer 1 (Example 55), which eluted first, and 13 mg of diastereomer 2 (Example 56), which eluted later, were isolated.

LC-MS (Method 2): $R_t$=1.78 min; MS (ESIpos): m/z=567.1 [M+H]$^+$ $^1$H-NMR (400 MHz, DMSO-d6) δ [ppm]: 10.48 (d, 1H), 9.21 (d, 1H), 8.75-8.53 (m, 1H), 8.31 (dd, 1H), 7.83-7.45 (m, 5H), 6.91 (dd, 1H), 5.30-5.08 (m, 2H), 4.95-4.58 (m, 1H), 4.41-4.17 (m, 1H), 4.08-3.67 (m, 2H), 2.10-1.88 (m, 1H), 1.71-1.42 (m, 1H), 1.12-0.88 (m, 1H).

Example 55

N-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-3-yl}-2-fluorocyclopropanecarboxamide
(Diastereomer 1, Cis Configured)

Analytical chiral HPLC: $R_t$=7.607 min, e.e.=99.7% [column: Daicel Chiralpak IE-3 5 μm, 250×4.6 mm; eluent: iso-hexane/2-propanol 70:30; flow rate: 1.0 ml/min; temperature: 50° C.; UV detection: 220 nm].

LC-MS (Method 2): $R_t$=1.81 min; MS (ESIpos): m/z=567.1 [M+H]$^+$ $^1$H-NMR (400 MHz, DMSO-d6) δ [ppm]: 10.48 (s, 1H), 9.21 (s, 1H), 8.62 (dd, 1H), 8.30 (dd, 1H), 7.81-7.48 (m, 5H), 6.91 (br d, 1H), 5.29-5.13 (m, 2H), 4.91-4.62 (m, 1H), 4.38-4.19 (br m, 1H), 4.08-3.77 (m, 2H), 2.08-1.91 (m, 1H), 1.68-1.50 (m, 1H), 1.08-0.93 (m, 1H).

Example 56

N-{2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-3-yl}-2-fluorocyclopropanecarboxamide
(Diastereomer 2, Cis Configured)

Analytical chiral HPLC: $R_t$=8.43 min, e.e.=97.6% [column: Daicel Chiralpak IE-3 5 μm, 250×4.6 mm; eluent: iso-hexane/2-propanol 70:30; flow rate: 1.0 ml/min; temperature: 50° C.; UV detection: 220 nm].

LC-MS (Method 2): $R_t$=1.81 min; MS (ESIpos): m/z=567 [M+H]$^+$ $^1$H-NMR (400 MHz, DMSO-d6) δ [ppm]: 10.49 (s, 1H), 9.22 (s, 1H), 8.63 (dd, 1H), 8.30 (dd, 1H), 7.81-7.49 (m, 5H), 6.92 (br s, 1H), 5.25-5.13 (m, 2H), 4.92-4.62 (m, 1H), 4.39-4.20 (br m, 1H), 4.07-3.76 (m, 2H), 2.11-1.92 (m, 1H), 1.68-1.49 (m, 1H), 1.08-0.93 (m, 1H).

Example 57

N-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-3-yl}-1-fluorocyclopropanecarboxamide

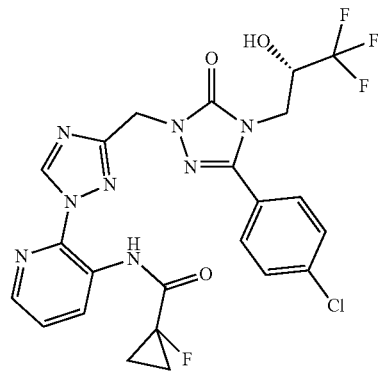

A solution of 1-fluorocyclopropanecarboxylic acid (108 mg, 1.04 mmol) in N,N-dimethylformamide (1.2 ml) was treated with HATU (395 mg, 1.04 mmol) and stirred 1 h at room temperature. 2-{[1-(3-aminopyridin-2-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 40A, 100 mg, 208 μmol) was then added followed by N,N-diisopropylethylamine (250 μl, 1.5 mmol). The resulting mixture was stirred overnight at room temperature. A solution of ammonia in methanol (1.2 ml, 7N) was added and the resulting mixture was stirred 1.5 h at room temperature. Purification by prep HPLC (Method 4) affording 96.6 mg (82% of th.) of the title compound.

LC-MS (Method 1): $R_t$=1.03 min; MS (ESIpos): m/z=567.2 [M+H]$^+$ $^1$H-NMR (400 MHz, DMSO-d6) δ [ppm]: 11.33 (d, 1H), 9.36 (s, 1H), 8.79 (dd, 1H), 8.34 (dd, 1H), 7.85-7.45 (m, 5H), 6.92 (d, 1H), 5.17 (d, 2H), 4.40-4.22 (br m, 1H), 4.04-3.67 (m, 2H), 1.53-1.20 (m, 4H).

Example 58

N-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-3-yl}thietane-3-carboxamide 1,1-dioxide

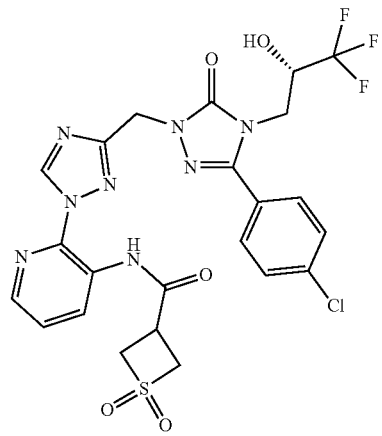

A solution of thietane-3-carboxylic acid 1,1-dioxide (156 mg, 1.04 mmol) in N,N-dimethylformamide (1.2 ml) was treated with HATU (395 mg, 1.04 mmol) and stirred 1 h at room temperature. 2-{[1-(3-aminopyridin-2-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 40A, 100 mg, 208 μmol) was then added followed by and N,N-diisopropylethylamine (250 μl, 1.5 mmol). The resulting mixture was stirred overnight at room temperature. A solution of ammonia in methanol (1.2 ml, 7N) was added and the resulting mixture was stirred 1.5 h at room temperature. Purification by preparative HPLC (Method 4) afforded 98.8 mg (78% of th.) of the title compound.

LC-MS (Method 1): $R_t$=0.89 min; MS (ESIpos): m/z=613.2 [M+H]$^+$ $^1$H-NMR (400 MHz, DMSO-d6) δ [ppm]: 10.37 (s, 1H), 9.18 (s, 1H), 8.43-8.33 (m, 2H), 7.81-7.54 (m, 5H), 6.91 (d, 1H), 5.24-5.11 (m, 2H), 4.44-4.22 (m, 5H), 4.08-3.78 (m, 2H), 3.55 (quin, 1H).

Example 59

N-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-3-yl}-2-fluorocyclopropanecarboxamide
(Diastereomeric Mixture Trans Configured)

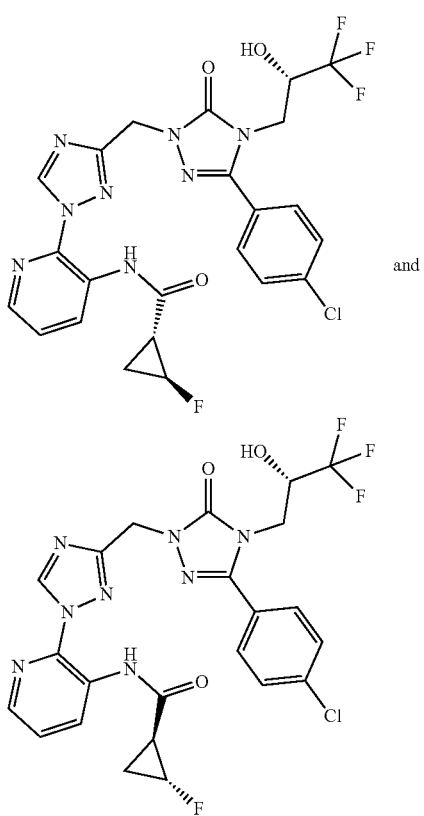

At 0° C., a solution of 2-fluorocyclopropanecarboxylic acid (trans configured, 162 mg, 1.56 mmol) in dichloromethane (4.5 ml) was treated with 1-chloro-N,N,2-trimethylprop-1-en-1-amine (330 μl, 2.5 mmol) and stirred 1 h at room temperature. 2-{[1-(3-aminopyridin-2-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 40A, 150 mg, 312 μmol), N,N-diisopropylethylamine (270 μl, 1.6 mmol) and 4-dimethylaminopyridine (191 mg, 1.56 mmol) were then added to the reaction mixture at 0° C. The resulting mixture was stirred overnight at room temperature. A solution of ammonia in methanol (4.5 ml, 7N) was added and the resulting mixture was stirred 2 h at room temperature and evaporated. The residue was purified by preparative HPLC (Method 4) afforded 58.2 mg (32% of th.) of the title compound.

The two diastereomers were separated by preparative chiral HPLC [sample preparation: 58 mg dissolved in 5 ml warm ethanol; injection volume: 500 μl; column: Daicel Chiralpak IE 5 μm, 250×20 mm; eluent: n-heptane/ethanol 50:50; flow rate: 15 ml/min; temperature: 25° C.; UV detection: 210 nm]. After separation, 45 mg of diastereomer 1 (Example 60), which eluted first, and 49 mg of diastereomer 2 (Example 61), which eluted later, were isolated.

LC-MS (Method 2): $R_t$=1.86 min; MS (ESIpos): m/z=567.1 [M+H]$^+$ $^1$H-NMR (400 MHz, DMSO-d6) δ [ppm]: 10.51 (br d, 1H), 9.19 (2 s, 1H), 8.62-8.24 (m, 2H), 7.81-7.47 (m, 5H), 6.92 (2 d, 1H), 5.22 (s, 2H), 4.99-4.69 (m, 1H), 4.40-4.18 (m, 1H), 4.08-3.75 (m, 2H), 2.48-2.28 (m, 1H), 1.47-1.12 (m, 2H).

Example 60

N-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-3-yl}-2-fluorocyclopropanecarboxamide
(Diastereomer 1, Trans Configured)

Analytical chiral HPLC: $R_t$=2.924 min, e.e.=100% [column: Daicel Chiralpak IE-3 3 μm, 50×4.6 mm; eluent: iso-hexane/ethanol 50:50; flow rate: 1.0 ml/min; temperature: 23° C.; UV detection: 220 nm].

LC-MS (Method 2): $R_t$=1.87 min; MS (ESIpos): m/z=567.1 [M+H]$^+$ $^1$H-NMR (400 MHz, DMSO-d6) δ [ppm]: 10.50 (s, 1H), 9.19 (s, 1H), 8.53 (dd, 1H), 8.30 (d, 1H), 7.79-7.44 (m, 5H), 6.92 (br s, 1H), 5.29-5.13 (m, 2H), 4.96-4.71 (m, 1H), 4.39-4.20 (br m, 1H), 4.08-3.75 (m, 2H), 2.47-2.29 (m, 1H), 1.49-1.08 (m, 2H).

Example 61

N-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-3-yl}-2-fluorocyclopropanecarboxamide
(Diastereomer 2, Trans Configured)

Analytical chiral HPLC: $R_t$=3.426 min, e.e.=97% [column: Daicel Chiralpak IE-3 3 μm, 50×4.6 mm; eluent: iso-hexane/ethanol 50:50; flow rate: 1.0 ml/min; temperature: 23° C.; UV detection: 220 nm].

LC-MS (Method 2): $R_t$=1.88 min; MS (ESIpos): m/z=567.1 [M+H]$^+$ $^1$H-NMR (400 MHz, DMSO-d6) δ [ppm]: 10.51 (s, 1H), 9.20 (s, 1H), 8.54 (dd, 1H), 8.30 (d, 1H), 7.85-7.44 (m, 5H), 6.93 (s, 1H), 5.21 (s, 2H), 5.01-4.65 (m, 1H), 4.39-4.21 (br m, 1H), 4.08-3.79 (m, 2H), 2.46-2.27 (m, 1H), 1.49-1.09 (m, 2H).

Example 62

2,2,2-trifluoroethyl {2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-3-yl}carbamate

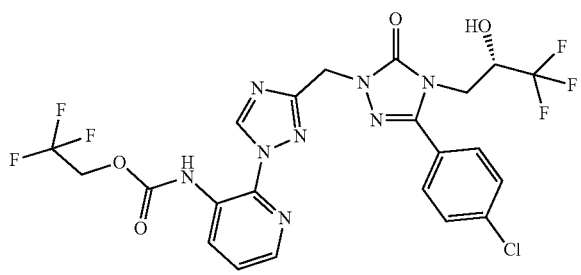

A solution of 2,2,2-trifluoroethyl {2-[3-({4-[(2S)-2-{[tert-butyl(dimethyl)silyl]oxy}-3,3,3-trifluoropropyl]-3-(4-chlorophenyl)-5-oxo-4,5-dihydro-1H-1,2,4-triazol-1-yl}methyl)-1H-1,2,4-triazol-1-yl]pyridin-3-yl}carbamate (Example 43A, 160 mg, 222 µmol) in tetrahydrofuran (3.0 ml) was treated with a tetrabutyl ammonium fluoride solution in tetrahydrofuran (440 µl, 1.0 M, 440 µmol) and stirred 30 min at room temperature. Purification by preparative HPLC (Method 4) afforded 27.4 mg (20% of th.) of the title compound.

LC-MS (Method 3): $R_t$=3.44 min; MS (ESIpos): m/z=607.2 [M+H]$^+$ $^1$H-NMR (400 MHz, DMSO-d6) δ [ppm]: 10.05 (br s, 1H), 9.27-9.06 (m, 1H), 8.47-8.16 (m, 2H), 7.84-7.47 (m, 5H), 6.93 (d, 1H), 5.25-4.99 (m, 2H), 4.70 (q, 2H), 4.40-4.21 (br m, 1H), 4.09-3.73 (m, 2H).

Example 63

1-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-3-yl}-3-(2,2,2-trifluoroethyl)urea

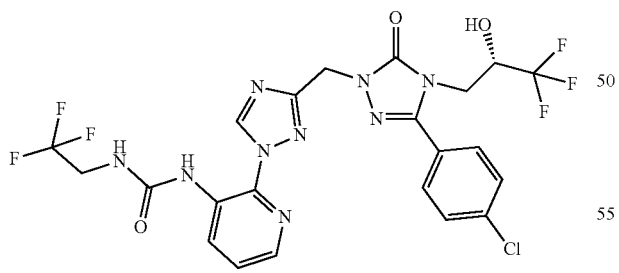

A solution of 1-{2-[3-({4-[(2S)-2-{[tert-butyl(dimethyl)silyl]oxy}-3,3,3-trifluoropropyl]-3-(4-chlorophenyl)-5-oxo-4,5-dihydro-1H-1,2,4-triazol-1-yl}methyl)-1H-1,2,4-triazol-1-yl]pyridin-3-yl}-3-(2,2,2-trifluoroethyl)urea (Example 43A, 50.0 mg, 69.4 µmol) in tetrahydrofuran (500 µl) was treated with a tetrabutyl ammonium fluoride solution in tetrahydrofuran (140 µl, 1.0 M, 140 µmol) and stirred 30 min at room temperature. Purification by preparative HPLC (Method 4) afforded 38.8 mg (92% of th.) of the title compound.

LC-MS (Method 2): $R_t$=1.91 min; MS (ESIpos): m/z=606.1 [M+H]$^+$ $^1$H-NMR (400 MHz, DMSO-d6) δ [ppm]: 9.31-9.08 (m, 2H), 8.69 (dd, 1H), 8.18 (dd, 1H), 7.95-7.43 (m, 6H), 6.93 (d, 1H), 5.24 (s, 2H), 4.39-4.19 (m, 1H), 4.12-3.75 (m, 4H).

Example 64

5-(4-Chlorophenyl)-2-({1-[2-(morpholin-4-yl)pyridin-3-yl]-1H-1,2,4-triazol-3-yl}methyl)-4-[(2S)-3,3,3-trifluoro-2-hydroxypropyl]-2,4-dihydro-3H-1,2,4-triazol-3-one

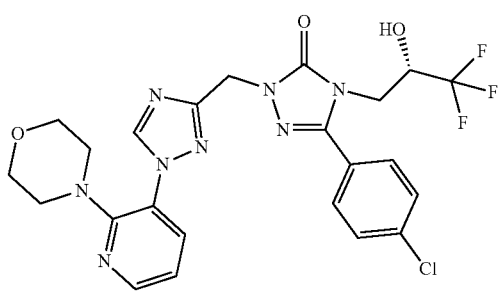

A solution of 5-(4-chlorophenyl)-2-{[1-(2-chloropyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Example 44A; 70.0 mg, 140 µmol) in ethanol (280 µl) was treated with morpholine (120 µl, 1.4 mmol) and stirred overnight at reflux. The reaction mixture was diluted with methanol and purified by preparative HPLC (Method 4) affording 67.0 mg (87% of th.) of the title compound.

LC-MS (Method 1): $R_t$=0.91 min; MS (ESIpos): m/z=551.1 [M+H]$^+$ $^1$H-NMR (500 MHz, DMSO-d6) δ [ppm]: 8.94 (s, 1H), 8.35 (dd, 1H), 7.82-7.57 (m, 5H), 7.09 (dd, 1H), 6.90 (d, 1H), 5.18-5.05 (m, 2H), 4.38-4.19 (br m, 1H), 4.06-3.80 (m, 2H), 3.52-3.41 (m, 4H), 2.87-2.77 (m, 4H).

Example 65

2-[(1-{2-[(2-Amino-2-methylpropyl)amino]pyridin-3-yl}-1H-1,2,4-triazol-3-yl)methyl]-5-(4-chlorophenyl)-4-[(2S)-3,3,3-trifluoro-2-hydroxypropyl]-2,4-dihydro-3H-1,2,4-triazol-3-one

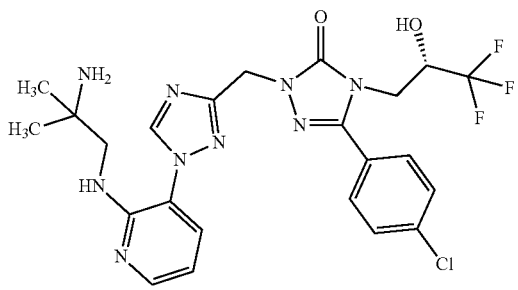

A solution of 5-(4-chlorophenyl)-2-{[1-(2-chloropyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Example 44A; 70.0 mg, 140 µmol) in ethanol (280 µl) was treated with 2-methylpropane-1,2-diamine (123 mg, 1.40 mmol) and stirred overnight at reflux. The reaction mixture was diluted with methanol and purified by preparative HPLC (Method 4) affording 48.8 mg (63% of th.) of the title compound.

LC-MS (Method 1): R$_t$=0.69 min; MS (ESIpos): m/z=552.1 [M+H]$^+$
$^1$H-NMR (400 MHz, DMSO-d6) δ [ppm]: 8.95 (s, 1H), 8.36 (br s, 1H), 8.13 (dd, 1H), 7.82-7.54 (m, 5H), 6.79-6.60 (m, 2H), 5.21-5.06 (m, 2H), 4.40-4.22 (m, 1H), 4.06-3.77 (m, 2H), 3.43 (br d, 2H), 4.56-2.87 (br s, 2H), 1.08 (s, 3H), 1.07 (s, 3H).

Example 66

1-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-D-prolinamide

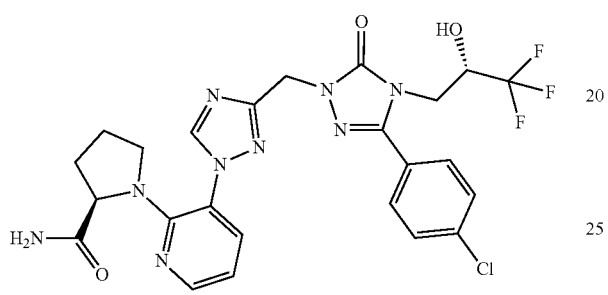

A solution of 5-(4-chlorophenyl)-2-{[1-(2-chloropyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Example 44A; 70.0 mg, 140 μmol) in ethanol (280 μl) was treated with D-prolinamide (160 mg, 1.40 mmol) and stirred overnight at reflux. The reaction mixture was diluted with methanol and purified by preparative HPLC (Method 4) affording 56.3 mg (70% of th.) of the title compound.
LC-MS (Method 2): R$_t$=1.52 min; MS (ESIpos): m/z=578.2 [M+H]$^+$
$^1$H-NMR (400 MHz, DMSO-d6) δ [ppm]: 8.80 (s, 1H), 8.19 (dd, 1H), 7.79-7.52 (m, 5H), 7.06 (br s, 1H), 6.95-6.71 (m, 3H), 5.18-5.02 (m, 2H), 4.48-4.21 (m, 2H), 4.06-3.78 (m, 2H), 2.77-2.58 (m, 2H), 2.04-1.87 (m, 1H), 1.75-1.42 (m, 3H).

Example 67

5-(4-Chlorophenyl)-2-[(1-{2-[(2-hydroxy-2-methylpropyl)amino]pyridin-3-yl}-1H-1,2,4-triazol-3-yl)methyl]-4-[(2S)-3,3,3-trifluoro-2-hydroxypropyl]-2,4-dihydro-3H-1,2,4-triazol-3-one

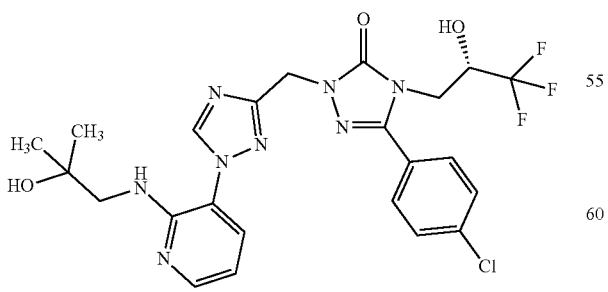

A solution of 5-(4-chlorophenyl)-2-{[1-(2-chloropyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Example 44A; 70.0 mg, 140 μmol) in ethanol (280 μl) was treated with 1-amino-2-methylpropan-2-ol (125 mg, 1.40 mmol), stirred overnight at reflux and 2 h at 120° C. under microwave irradiation. The reaction mixture was diluted with methanol and purified by preparative HPLC (Method 4) affording 38.6 mg (50% of th.) of the title compound.
LC-MS (Method 1): R$_t$=0.87 min: MS (ESIpos): m/z=553.1 [M+H]$^+$
$^1$H-NMR (400 MHz, DMSO-d6) δ [ppm]: 8.96 (s, 1H), 8.12 (dd, 1H), 7.83-7.55 (m, 5H), 6.92 (br d, 1H), 6.74-6.46 (m, 2H), 5.23-5.07 (m, 2H), 4.59 (br s, 1H), 4.39-4.21 (br s, 1H), 4.08-3.77 (m, 2H), 3.44-3.19 (m, 2H, overlap with HDO peak). 1.05 (s, 3H), 1.04 (s, 3H).

Example 68

1-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-L-prolinamide

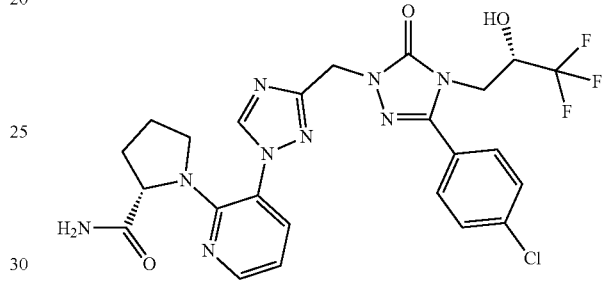

A solution of 5-(4-chlorophenyl)-2-{[1-(2-chloropyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Example 44A; 70.0 mg, 140 μmol) in ethanol (280 μl) was treated with L-prolinamide and stirred overnight at reflux. The reaction mixture was diluted with methanol and purified by preparative HPLC (Method 4) affording 64.1 mg (79% of th.) of the title compound.
LC-MS (Method 2): R$_t$=1.52 min; MS (ESIpos): m/z=578.2 [M+H]$^+$
$^1$H-NMR (400 MHz, DMSO-d6) δ [ppm]: 8.81 (s, 1H), 8.19 (dd, 1H), 7.78-7.53 (m, 5H), 7.07 (s, 1H), 6.95-6.72 (m, 3H), 5.15-5.05 (m, 2H), 4.49-4.19 (m, 2H), 4.06-3.78 (m, 2H), 2.77-2.60 (m, 2H), 2.03-1.89 (m, 1H), 1.73-1.45 (m, 3H).

Example 69

5-(4-Chlorophenyl)-4-[(2S)-3,3,3-trifluoro-2-hydroxypropyl]-2-[(1-{2-[(3,3,3-trifluoropropyl)amino]pyridin-3-yl}-1H-1,2,4-triazol-3-yl)methyl]-2,4-dihydro-3H-1,2,4-triazol-3-one

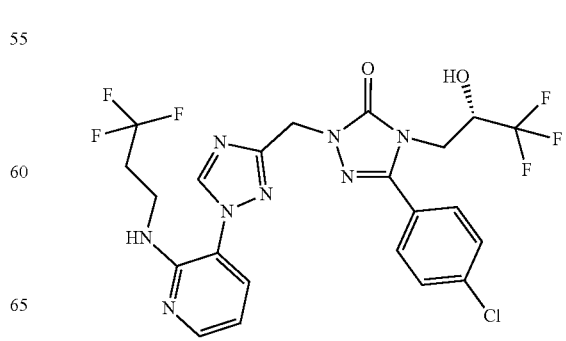

A solution of 5-(4-chlorophenyl)-2-{[1-(2-chloropyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Example 44A; 70.0 mg, 140 µmol) in ethanol (280 µl) was treated with 3,3,3-trifluoropropan-1-amine (158 mg, 1.40 mmol), stirred 4 h at 150° C. under microwave irradiation. The reaction mixture was diluted with methanol and purified by preparative HPLC (Method 4) affording 35.7 mg (44% of th.) of the title compound.

LC-MS (Method 2): $R_t$=1.99 min; MS (ESIpos): m/z=577.1 [M+H]$^+$ $^1$H-NMR (400 MHz, DMSO-d6) δ [ppm]: 8.86 (s, 1H), 8.19 (dd, 1H), 7.79-7.58 (m, 5H), 6.92 (d, 1H), 6.81-6.62 (m, 2H), 5.14 (s, 2H), 4.36-4.23 (m, 1H), 4.05-3.78 (m, 2H), 3.62-3.52 (m, 2H), 2.61-2.43 (m, 2H, overlap with DMSO peak).

Example 70

5-(4-Chlorophenyl)-2-{[1-(2-{[(5-oxopyrrolidin-2-yl)methyl]amino}pyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Diastereomeric Mixture)

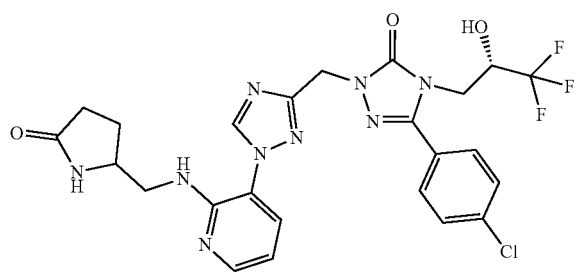

A solution of 5-(4-chlorophenyl)-2-{[1-(2-chloropyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Example 44A, 70.0 mg, 140 µmol) in ethanol (280 µl) was treated with 5-(aminomethyl)pyrrolidin-2-one (160 mg, 1.40 mmol), stirred 16 h at 150° C. under microwave irradiation. The reaction mixture was diluted with methanol and purified by preparative HPLC (Method 4) affording 41.7 mg (50% of th.) of the title compound.

LC-MS (Method 2): $R_t$=1.51 min; MS (ESIpos): m/z=578.2 [M+H]$^+$ $^1$H-NMR (400 MHz, DMSO-d6) δ [ppm]: 8.91 (s, 1H), 8.14 (dd, 1H), 7.80-7.58 (m, 6H), 6.92 (d, 1H), 6.76-6.56 (m, 2H), 5.14 (s, 2H), 4.39-4.20 (br m, 1H), 4.09-3.65 (m, 3H), 3.49-3.22 (m, 2H, overlap with HDO peak), 2.19-1.94 (m, 3H), 1.74-1.57 (m, 1H).

Example 71

5-(4-Chlorophenyl)-2-[(1-{2-[(2,2,2-trifluoroethyl)amino]pyridin-3-yl}-1H-1,2,4-triazol-3-yl)methyl]-4-[(2S)-3,3,3-trifluoro-2-hydroxypropyl]-2,4-dihydro-3H-1,2,4-triazol-3-one

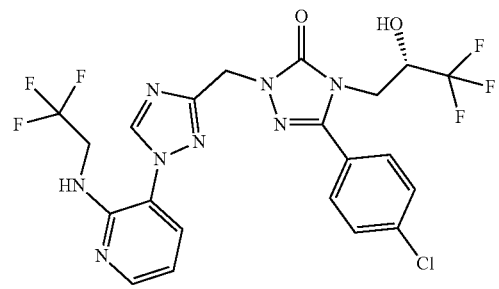

A solution of 5-(4-chlorophenyl)-2-{[1-(2-chloropyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Example 44A; 70.0 mg, 140 µmol) in ethanol (280 µl) was treated with 2,2,2-trifluoroethanamine (139 mg, 1.40 mmol) and stirred 100 h at 185° C. under microwave irradiation. The reaction mixture was diluted with methanol and purified by preparative HPLC (Method 4) affording 26.8 mg (34% of th.) of the title compound.

LC-MS (MS-M1): $R_t$=1.92 min; MS (ESIpos): m/z=563 [M+H]$^+$ $^1$H-NMR (400 MHz, DMSO-d6) δ [ppm]: 8.91 (s, 1H), 8.22 (dd, 1H), 7.84-7.56 (m, 5H), 7.04-6.80 (m, 3H), 5.15 (s, 2H), 4.41-4.10 (m, 3H), 4.07-3.78 (m, 2H).

Example 72

5-(4-Chlorophenyl)-2-{[1-(2-{[(1,1-dioxidothietan-3-yl)methyl]amino}pyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one

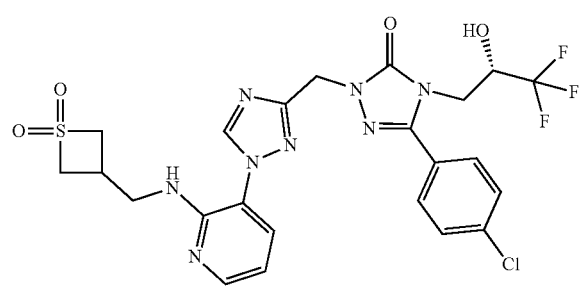

A solution of 5-(4-chlorophenyl)-2-{[1-(2-chloropyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Example 44A; 70.0 mg, 140 µmol) in ethanol (280 µl) was treated with 1-(1,1-dioxidothietan-3-yl)methanamine (189 mg, 1.40 mmol) and stirred 6 h at 150° C. under microwave irradiation. The reaction mixture was diluted with methanol and purified by preparative HPLC (Method 4) affording 34.5 mg (41% of th.) of the title compound.

LC-MS (Method 1): R$_t$=0.65 min; MS (ESIpos): m/z=599.1 [M+H]$^+$ $^1$H-NMR (400 MHz, DMSO-d6) δ [ppm]: 9.02-8.37 (m, 2H), 8.20-7.45 (m, 6H), 7.28-6.75 (m, 2H), 5.15 (s, 2H), 4.67-3.51 (m, 6H), 3.46-3.12 (m, 1H, overlap with HDO peak), 2.78-2.59 (m, 1H), 1.96-1.77 (m 2H).

Example 73

N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}acetamide

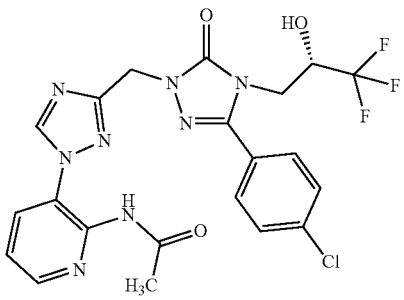 [SMILES: CC(=O)Nc1ncccc1-n1cnc(Cn2nc(-c3ccc(Cl)cc3)n(C[C@H](O)C(F)(F)F)c2=O)n1]

A solution of 2-{[1-(2-aminopyridin-3-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 45A; 60.0 mg, 125 μmol) in dichloromethane (1.5 ml) was treated with acetyl chloride (27 μl, 370 μmol) and N,N-diisopropylethylamine (110 μl, 620 μmol), stirred overnight at room temperature and evaporated. The residue was retaken in a solution of ammonia in methanol (1 ml, 7N), stirred 3 h at room temperature and evaporated. The residue was purified by preparative HPLC (Method 4) affording 19.9 mg (31% of th.) of the title compound.

LC-MS (Method 1): R$_t$=0.77 min; MS (ESIpos): m/z=523.2 [M+H]$^+$ $^1$H-NMR (400 MHz, DMSO-d6) δ [ppm]: 10.31 (s, 1H), 8.81 (s, 1H), 8.51 (dd, 1H), 8.03 (dd, 1H), 7.83-7.56 (m, 4H), 7.45 (dd, 1H), 6.92 (d, 1H), 5.07 (s, 2H), 4.39-4.23 (m, 1H), 4.09-3.72 (m, 2H), 1.86 (s, 3H).

Example 74

N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-3,3,3-trifluoropropanamide

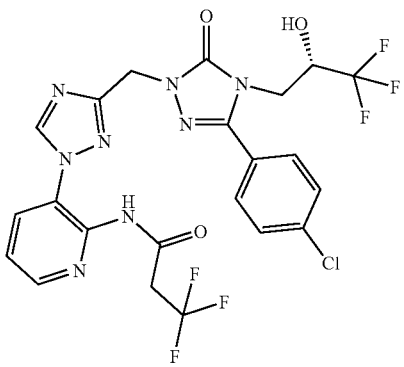 [SMILES: O=C(CC(F)(F)F)Nc1ncccc1-n1cnc(Cn2nc(-c3ccc(Cl)cc3)n(C[C@H](O)C(F)(F)F)c2=O)n1]

A solution of 2-{[1-(2-aminopyridin-3-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 45A; 80.0 mg, 166 μmol) in dichloromethane (1.0 ml) was treated with 3,3,3-trifluoropropanoyl chloride (73.1 mg, 499 μmol) and N,N-diisopropylethylamine (140 μl, 830 μmol), stirred overnight at room temperature and evaporated. The residue was retaken in a solution of ammonia in methanol (1 ml, 7N), stirred 3 h at room temperature and evaporated. The residue was purified by preparative HPLC (Method 4) affording 28.0 mg (27% of th.) of the title compound.

LC-MS (Method 1): R$_t$=0.88 min; MS (ESIpos): m/z=591.2 [M+H]$^+$ $^1$H-NMR (400 MHz, DMSO-d6) δ [ppm]: 10.76 (s, 1H), 8.84 (s, 1H), 8.55 (dd, 1H), 8.09 (dd, 1H), 7.80-7.46 (m, 5H), 6.91 (d, 1H), 5.05 (s, 2H), 4.38-4.19 (br m, 1H), 4.05-3.76 (m, 2H), 3.39 (q, 2H, overlap with HDO peak).

Example 75

N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2,2-difluorocyclopropanecarboxamide (Diastereomeric Mixture)

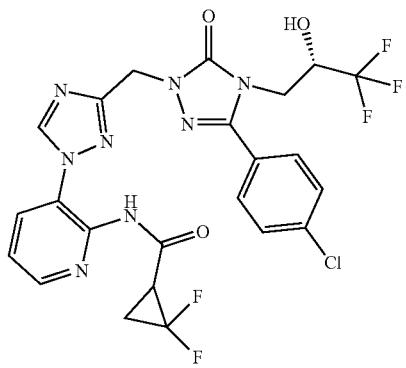 [SMILES: O=C(Nc1ncccc1-n1cnc(Cn2nc(-c3ccc(Cl)cc3)n(C[C@H](O)C(F)(F)F)c2=O)n1)C1CC1(F)F]

A solution of 2-{[1-(2-aminopyridin-3-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 45A; 80.0 mg, 166 μmol) in dichloromethane (1 ml) was treated with 2,2-difluorocyclopropanecarbonyl chloride (70.1 mg, 499 μmol) and N,N-diisopropylethylamine (140 μl, 830 μmol), stirred overnight at room temperature and evaporated. The residue was retaken in a solution of ammonia in methanol (1 ml, 7N), stirred 3 h at room temperature and evaporated. The residue was purified by preparative HPLC (Method 4) affording 69.7 mg (72% of th.) of the title compound.

LC-MS (Method 1): R$_t$=0.87 min; MS (ESIpos): m/z=585.2 [M+H]$^+$ $^1$H-NMR (400 MHz, DMSO-d6) δ [ppm]: 10.85 (s, 1H), 8.80 (s, 1H), 8.58-8.48 (m, 1H), 8.10-8.01 (m, 1H), 7.83-7.37 (m, 5H), 6.91 (2 d, 1H), 5.12-4.95 (m, 2H), 4.44-3.66 (m, 3H), 2.88-2.64 (m, 1H), 1.94-1.65 (m 2H).

Example 76

N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-fluorocyclopropanecarboxamide (Diastereomeric Mixture Cis Configured)

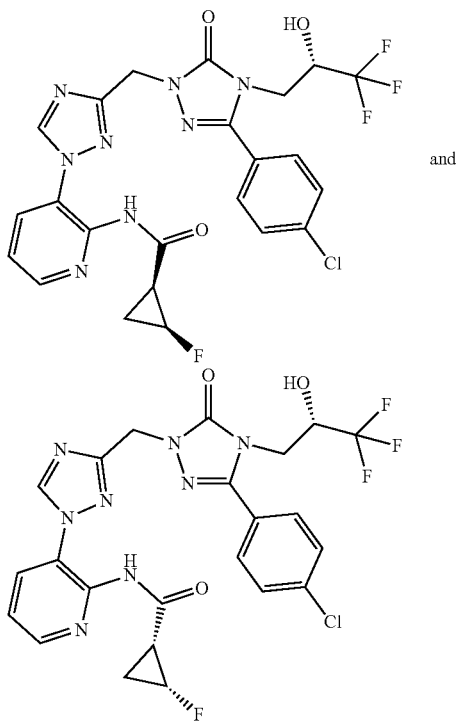

and

At 0° C., a solution of 2-fluorocyclopropanecarboxylic acid (cis configured, 162 mg, 1.56 mmol) in dichloromethane (4.5 ml) was treated with 1-chloro-N,N,2-trimethylprop-1-en-1-amine (330 µl, 2.5 mmol) and stirred 1 h at room temperature. 2-{[1-(2-aminopyridin-3-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 45A, 150 mg, 312 µmol), N,N-diisopropylethylamine (270 µl, 1.6 mmol), 4-dimethylaminopyridine (191 mg, 1.56 mmol) were added and the resulting mixture stirred overnight at room temperature. A solution of ammonia in methanol (4.5 ml, 7N) was added. The resulting mixture was stirred overnight at room temperature and evaporated. The residue was purified by preparative HPLC (Method 4) affording 96 mg (54% of th.) of the title compound.

The two diastereomers were separated by preparative chiral HPLC [sample preparation: 96 mg dissolved in 3.55 ml ethanol; injection volume: 100 µl; column: Daicel Chiralpak IC 5 µm, 250×20 mm; eluent: n-heptane/ethanol 80:20; flow rate: 20 ml/min; temperature: 23° C.; UV detection: 220 nm]. After separation, 20 mg of diastereomer 1 (Example 77), which eluted first, and 22 mg of diastereomer 2 (Example 78), which eluted later, were isolated.

LC-MS (Method 2): $R_t$=1.56 min; MS (ESIpos): m/z=567.1 [M+H]$^+$

H-NMR (400 MHz, DMSO-d6) δ [ppm]: 10.80 (s, 1H), 8.78 (s, 1H), 8.53 (dd, 1H), 8.04 (dd, 1H), 7.86-7.44 (m, 5H), 6.95 (br d, 1H), 5.18-4.93 (m, 2H), 4.76-4.14 (m, 2H), 4.09-3.77 (m, 2H), 2.40-2.24 (m, 1H), 1.48-1.25 (m, 1H), 1.05-0.84 (m, 1H).

Example 77

N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-fluorocyclopropanecarboxamide (Diastereomer 1, Cis Configured)

Analytical chiral HPLC: $R_t$=2.849 min, e.e.=100% [column: Daicel Chiralpak IC-3 3 µm, 50×4.6 mm; eluent: n-heptane/ethanol 80:20; flow rate: 1.0 ml/min; temperature: 30° C.; UV detection: 220 nm].

LC-MS (Method 2): $R_t$=1.57 min; MS (ESIpos): m/z=567.1 [M+H]$^+$ $^1$H-NMR (400 MHz, DMSO-d6) δ [ppm]: 10.78 (s, 1H), 8.78 (s, 1H), 8.53 (dd, 1H), 8.04 (dd, 1H), 7.80-7.41 (m, 5H), 6.92 (d, 1H), 5.06 (s, 2H), 4.74-4.19 (m, 2H), 4.07-3.75 (m, 2H), 2.39-2.23 (m, 1H), 1.47-1.26 (m, 1H), 0.95 (dq, 1H)

Example 78

N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-fluorocyclopropanecarboxamide (Diastereomer 2, Cis Configured)

Analytical chiral HPLC: $R_t$=3.502 min, e.e.=100% [column: Daicel Chiralpak IC-3 3 µm, 50×4.6 mm; eluent: n-heptane/ethanol 80:20; flow rate: 1.0 ml/min; temperature: 30° C.; UV detection: 220 nm].

LC-MS (Method 2): $R_t$=1.57 min; MS (ESIpos): m/z=567.1 [M+H]$^+$ $^1$H-NMR (400 MHz, DMSO-d6) δ [ppm]: 10.78 (s, 1H), 8.83-8.70 (m, 1H), 8.53 (dd, 1H), 8.04 (dd, 1H), 7.82-7.40 (m, 5H), 6.92 (d, 1H), 5.14-4.94 (m, 2H), 4.75-4.21 (m, 2H), 4.09-3.71 (m, 2H), 2.39-2.22 (m, 1H), 1.45-1.27 (m, 1H), 0.95 (dq, 1H).

Example 79

N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-(trifluoromethyl)cyclopropanecarboxamide (Diastereoisomeric Mixture Cis Configured)

and

-continued

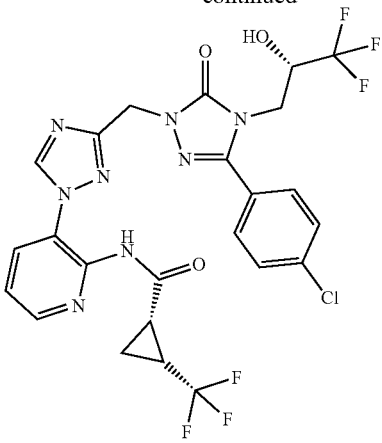

At 0° C., a solution of 2-(trifluoromethyl)cyclopropanecarboxylic acid (cis configured, 160 mg, 1.04 mmol) in dichloromethane (3.0 ml) was treated with 1-chloro-N,N,2-trimethylprop-1-en-1-amine (220 µl, 1.7 mmol) and stirred 1 h at room temperature. A solution of 2-{[1-(2-aminopyridin-3-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 45A, 100 mg, 208 µmol), N,N-diisopropylethylamine (180 µl, 1.0 mmol), 4-dimethylaminopyridine (127 mg, 1.04 mmol) in dichloromethane (500 µl) was added dropwisely and the resulting mixture stirred 48 h at room temperature. A solution of ammonia in methanol (1.5 ml, 7N) was added. The resulting mixture was stirred overnight at room temperature and evaporated. The residue was purified by preparative HPLC (Method 4) affording 48.4 mg (38% of th.) of the title compound.

LC-MS (Method 2): $R_t$=1.76 min; MS (ESIpos): m/z=617.1 [M+H]$^+$ $^1$H-NMR (500 MHz, DMSO-d6) δ [ppm]: 10.90 (s, 1H), 8.79 (s, 1H), 8.54 (dd, 1H), 8.06 (dd, 1H), 7.80-7.44 (m, 5H), 6.92 (2d, 1H), 5.11-4.96 (m, 2H), 4.39-4.21 (br m, 1H), 4.06-3.76 (m, 2H), 2.33-2.25 (m, 1H), 2.08-1.93 (m, 1H), 1.21-0.94 (m, 2H).

Example 80

N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-3,3-difluorocyclobutanecarboxamide

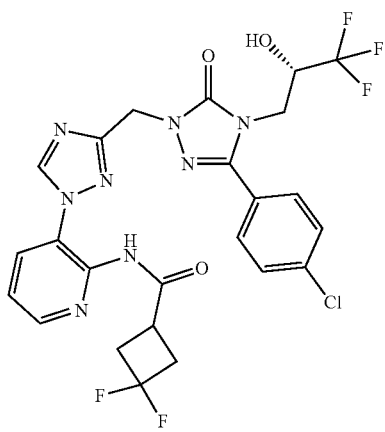 [SMILES: O=C(Nc1ncccc1-n1cnc(Cn2nc(-c3ccc(Cl)cc3)n(C[C@H](O)C(F)(F)F)c2=O)n1)C1CC(F)(F)C1]

At 0° C., a solution of 3,3-difluorocyclobutanecarboxylic acid (142 mg, 1.04 mmol) in dichloromethane (3.0 ml) was treated with 1-chloro-N,N,2-trimethylprop-1-en-1-amine (220 µl, 1.7 mmol) and stirred 1 h at room temperature. A solution of 2-{[1-(2-aminopyridin-3-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 45A, 100 mg, 208 µmol), N,N-diisopropylethylamine (180 µl, 1.0 mmol), 4-dimethylaminopyridine (127 mg, 1.04 mmol) in dichloromethane (500 µl) was added dropwisely and the resulting mixture stirred overnight at room temperature. A solution of ammonia in methanol (1.5 ml, 7N) was added. The resulting mixture was stirred overnight at room temperature and evaporated. The residue was purified by preparative HPLC (Method 4) affording 47.7 mg (38% of th.) of the title compound.

LC-MS (Method 1): $R_t$=0.89 min; MS (ESIpos): m/z=599.2 [M+H]$^+$ $^1$H-NMR (400 MHz, DMSO-d6) δ [ppm]: 10.56 (s, 1H), 8.84 (s, 1H), 8.54 (dd, 1H), 8.05 (dd, 1H), 7.79-7.44 (m, 5H), 6.92 (d, 1H), 5.04 (s, 2H), 4.39-4.20 (br m, 1H), 4.08-3.76 (m, 2H), 3.15-2.94 (m, 1H), 2.78-2.45 (m, 4H, overlap with DMSO peak).

Example 81

N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-1-(trifluoromethyl)cyclopropanecarboxamide

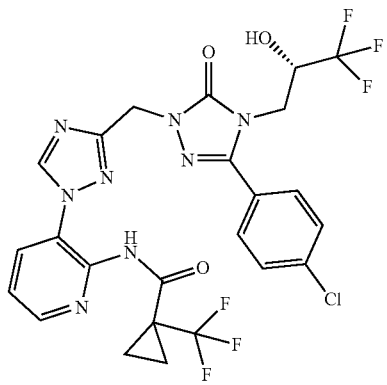 [SMILES: O=C(Nc1ncccc1-n1cnc(Cn2nc(-c3ccc(Cl)cc3)n(C[C@H](O)C(F)(F)F)c2=O)n1)C1(C(F)(F)F)CC1]

At 0° C., a solution of 1-(trifluoromethyl)cyclopropanecarboxylic acid (160 mg, 1.04 mmol) in dichloromethane (3.0 ml) was treated with 1-chloro-N,N,2-trimethylprop-1-en-1-amine (220 µl, 1.7 mmol) and stirred 1 h at room temperature. A solution of 2-{[1-(2-aminopyridin-3-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 45A, 100 mg, 208 µmol), N,N-diisopropylethylamine (180 µl, 1.0 mmol), 4-dimethylaminopyridine (127 mg, 1.04 mmol) in dichloromethane (500 µl, 39 mmol) was added dropwisely and the resulting mixture stirred overnight at room temperature. A solution of ammonia in methanol (1.5 ml, 7N) was added. The resulting mixture was stirred overnight at room temperature and evaporated. The residue was purified by preparative HPLC (Method 4) affording 46.7 mg (36% of th.) of the title compound.

LC-MS (Method 2): $R_t$=1.75 min; MS (ESIpos): m/z=617.1 [M+H]⁺

¹H-NMR (500 MHz, DMSO-d6) δ [ppm]: 10.27 (br s, 1H), 8.83 (s, 1H), 8.55 (br d, 1H), 8.19-7.95 (m, 1H), 7.79-7.43 (m, 5H), 6.91 (br d, 1H), 5.14-4.93 (m, 2H), 4.39-4.20 (br m, 1H), 4.10-3.75 (m 2H), 1.49-1.13 (m 4H).

Example 82

N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}tetrahydrothiophene-3-carboxamide 1,1-dioxide (Diastereomeric Mixture)

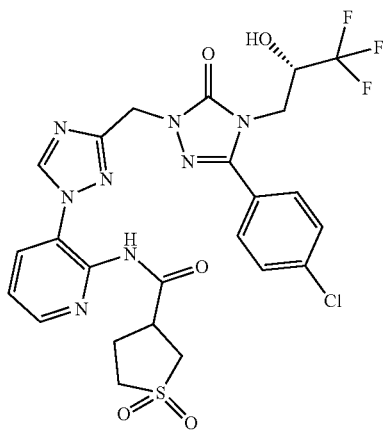 [SMILES: O=C(Nc1ncccc1-n1cnc(Cn2nc(-c3ccc(Cl)cc3)n(C[C@H](O)C(F)(F)F)c2=O)n1)C1CCS(=O)(=O)C1]

A solution of tetrahydrothiophene-3-carboxylic acid 1,1-dioxide (81.9 mg, 499 µmol) in N,N-dimethylformamide DMF (1.0 ml) was treated with HATU (190 mg, 499 µmol) and stirred 15 min at room temperature. A solution of 2-{[1-(2-aminopyridin-3-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 45A, 80.0 mg, 166 µmol) and N,N-diisopropylethylamine (140 µl, 830 µmol) were added and the resulting mixture stirred overnight at room temperature and 1 h at 80° C.

A solution of (3R)-tetrahydrothiophene-3-carboxylic acid 1,1-dioxide (54.6 mg, 333 µmol) and of thionyl chloride (24 µl, 330 µmol) in dichloromethane (0.5 ml) and 2 drops of N,N-dimethylformamide was stirred overnight at room temperature and evaporated. The residue was retaken in DMF and added to the reaction mixture together with 4-dimethylaminopyridine (40.6 mg, 333 µmol). The resulting mixture was stirred overnight at room temperature and evaporated. The residue was retaken in a solution of ammonia in methanol (1.5 ml, 7N). The resulting mixture was stirred overnight at room temperature and evaporated. The residue was purified by preparative HPLC (Method 4) affording 17.9 mg (17% of th.) of the title compound.

LC-MS (Method 2): $R_t$=1.42 min; MS (ESIpos): m/z=627.1 [M+H]⁺

¹H-NMR (400 MHz, DMSO-d6) δ [ppm]: 10.70 (s, 1H), 8.86 (s, 1H), 8.55 (dd, 1H), 8.06 (dd, 1H), 7.82-7.41 (m, 5H), 6.99-6.83 (m, 1H), 5.19-4.93 (m, 2H), 4.39-4.20 (br m, 1H), 4.09-3.76 (m, 2H), 3.52-2.85 (m, 5H, overlap with HDO peak), 2.45-1.89 (m 2H).

Example 83

N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}cyclopropanecarboxamide

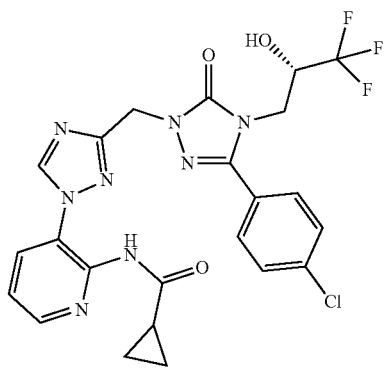 [SMILES: O=C(Nc1ncccc1-n1cnc(Cn2nc(-c3ccc(Cl)cc3)n(C[C@H](O)C(F)(F)F)c2=O)n1)C1CC1]

At 0° C., a solution of cyclopropanecarboxylic acid (83 µl, 1.0 mmol) in dichloromethane (3.0 ml) was treated with 1-chloro-N,N,2-trimethylprop-1-en-1-amine (220 µl, 1.7 mmol) and stirred 1 h at room temperature. A solution of 2-{[1-(2-aminopyridin-3-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 45A, 100 mg, 208 µmol), N,N-diisopropylethylamine (180 µl, 1.0 mmol), 4-dimethylaminopyridine (127 mg, 1.04 mmol) in dichloromethane (500 µl) was added and the resulting mixture stirred overnight at room temperature. A solution of ammonia in methanol (1.5 ml, 7N) was added. The resulting mixture was stirred overnight at room temperature and evaporated. The residue was purified by preparative HPLC (Method 4). The compound containing fractions were evaporated and the residue purified by preparative HPLC (Method 4) affording 38.7 mg (33% of th.) of the title compound.

LC-MS (Method 2): $R_t$=1.54 min; MS (ESIpos): m/z=549.1 [M+H]⁺

¹H-NMR (400 MHz, DMSO-d6) δ [ppm]: 10.59 (s, 1H), 8.73 (s, 1H), 8.52 (dd, 1H), 8.02 (dd, 1H), 7.82-7.55 (m, 4H), 7.45 (dd, 1H), 6.93 (d, 1H), 5.06 (s, 2H), 4.39-4.21 (br m, 1H), 4.07-3.74 (m, 2H), 1.85-1.66 (m, 1H), 0.71-0.47 (m, 4H).

Example 84

N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-fluorocyclopropanecarboxamide (Diastereomeric Mixture Trans Configured)

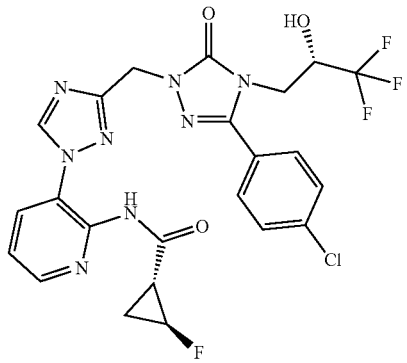

and

-continued

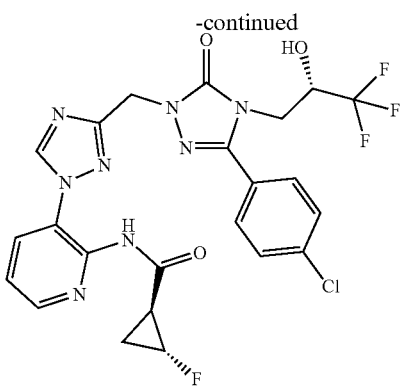

At 0° C., a solution of 2-fluorocyclopropanecarboxylic acid (trans configured, 162 mg, 1.56 mmol) in dichloromethane (4.5 ml) was treated with 1-chloro-N,N,2-trimethylprop-1-en-1-amine (330 µl, 2.5 mmol) and stirred 1 h at room temperature. 2-{[1-(2-aminopyridin-3-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 45A, 150 mg, 312 µmol), N,N-diisopropylethylamine (270 µl, 1.6 mmol), 4-dimethylaminopyridine (191 mg, 1.56 mmol) were added and the resulting mixture stirred overnight at room temperature. A solution of ammonia in methanol (4.5 ml, 7N) was added. The resulting mixture was stirred 2 h at room temperature and evaporated. The residue was purified by preparative HPLC (Method 4) affording 90.0 mg (47% of th.) of the title compound.

The two diastereomers were separated by preparative chiral HPLC [sample preparation: 90 mg dissolved in 0.5 ml methanol and 3.5 ml tert-butylmethylether; injection volume: 300 µl; column: Daicel Chiralpak IB 5 µm, 250×20 mm; eluent: tert-butylmethylether/methanol 90:10; flow rate: 15 ml/min; temperature: 25° C.; UV detection: 220 nm]. After separation, 45 mg of diastereomer 1 (Example 85), which eluted first, and 44 mg of diastereomer 2 (Example 86), which eluted later, were isolated.

LC-MS (Method 2): $R_t$=1.56 min; MS (ESIpos): m/z=567.1 [M+H]$^+$ $^1$H-NMR (400 MHz, DMSO-d6) δ [ppm]: 10.79 (s, 1H), 8.78 (s, 1H), 8.53 (dd, 1H), 8.04 (dd, 1H), 7.83-7.38 (m, 5H), 7.02-6.87 (m, 1H), 5.20-4.96 (m, 2H), 4.73-4.15 (m, 2H), 4.08-3.75 (m, 2H), 2.40-2.20 (m, 1H), 1.46-1.26 (m, 1H), 1.03-0.84 (m, 1H).

Example 85

N-{3-[3-({3-(4-Chlorophenyl)-5-oxo-4-[(2S)-3,3,3-trifluoro-2-hydrxypropyl]-4,5-dihydro-1H-1,2,4-triazol-1-yl}methyl)-1H-1,2,4-triazol-1-yl]pyridin-2-yl}-2-fluorocyclopropanecarboxamide (diastereomer 1, trans configured)

Analytical chiral HPLC: $R_t$=5.606 min, e.e.=100% [column: Daicel Chiralpak IB 3 µm, 250×4.6 mm; eluent: tert-butylmethyleter/methanol 90:10; flow rate: 1.0 ml/min; temperature: 25° C.; UV detection: 220 nm].

LC-MS (Method 2): $R_t$=1.58 min: MS (ESIpos): m/z=567.1 [M+H]$^+$ $^1$H-NMR (400 MHz, DMSO-d6) δ [ppm]: 10.79 (s, 1H), 8.78 (s, 1H), 8.53 (dd, 1H), 8.04 (dd, 1H), 7.80-7.42 (m, 5H), 6.93 (d, 1H), 5.06 (s, 2H), 4.74-4.44 (m, 1H), 4.39-4.21 (br m, 1H), 4.06-3.78 (m, 2H), 2.39-2.22 (m, 1H), 1.46-1.27 (m, 1H), 0.95 (dq, 1H).

Example 86

N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-fluorocyclopropanecarboxamide (diastereomer 2, trans configured)

Analytical chiral HPLC: $R_t$=6.543 min, e.e.=100% [column: Daicel Chiralpak IB 3 µm, 250×4.6 mm; eluent: tert-butylmethyleter/methanol 90:10; flow rate: 1.0 ml/min; temperature: 25° C.; UV detection: 220 nm].

LC-MS (Method 2): $R_t$=1.57 min; MS (ESIpos): m/z=567.1 [M+H]$^+$ $^1$H-NMR (400 MHz, DMSO-d6) δ [ppm]: 10.78 (s, 1H), 8.78 (s, 1H), 8.53 (dd, 1H), 8.04 (dd, 1H), 7.81-7.39 (m, 5H), 6.92 (d, 1H), 5.17-4.96 (m, 2H), 4.77-4.18 (m, 2H), 4.07-3.76 (m, 2H), 2.41-2.21 (m, 1H), 1.45-1.27 (m, 1H), 0.95 (dq, 1H)

Example 87

N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-cyclopropylacetamide

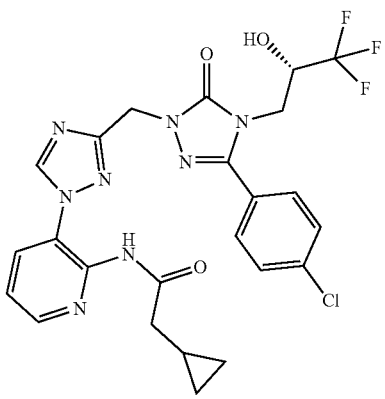 [SMILES: O=C(CC1CC1)Nc1ncccc1-n1cnc(Cn2nc(-c3ccc(Cl)cc3)n(C[C@H](O)C(F)(F)F)c2=O)n1]

At 0° C., a solution of cyclopropylacetic acid (91 µl, 1.0 mmol) in dichloromethane (3.0 ml) was treated with 1-chloro-N,N,2-trimethylprop-1-en-1-amine (220 µl, 1.7 mmol) and stirred 1 h at room temperature. A solution of 2-{[1-(2-aminopyridin-3-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 45A, 100 mg, 208 µmol), N,N-diisopropylethylamine (180 µl, 1.0 mmol), 4-dimethylaminopyridine (127 mg, 1.04 mmol) in dichloromethane (500 µl) was added and the resulting mixture stirred overnight at room temperature. A solution of ammonia in methanol (0.5 ml, 7N) was added. The resulting mixture was stirred overnight at room temperature and evaporated. The residue was purified by preparative HPLC (Method 4). The product containing fractions were evaporated and purified by preparative HPLC (Method 4) affording 44.9 mg (38% of th.) of the title compound.

LC-MS (Method 2): $R_t$=1.57 min; MS (ESIpos): m/z=563.1 [M+H]$^+$ $^1$H-NMR (400 MHz, DMSO-d6) δ [ppm]: 10.21 (s, 1H), 8.79 (s, 1H), 8.52 (dd, 1H), 8.03 (dd, 1H), 7.79-7.36 (m, 5H), 6.92 (d, 1H), 5.06 (s, 2H), 4.39-4.20 (br m, 1H), 4.09-3.74 (m, 2H), 2.06 (d, 2H), 0.91-0.72 (m, 1H), 0.41-0.27 (m, 2H), 0.05--0.03 (m, 2H).

Example 88

N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-(1H-1,2,4-triazol-1-yl)acetamide

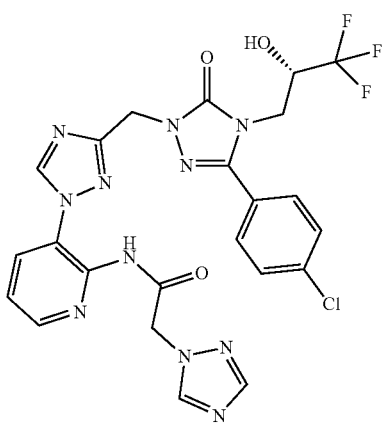 [SMILES: O=C(Cn1cncn1)Nc1ncccc1-n1cnc(Cn2nc(-c3ccc(Cl)cc3)n(C[C@H](O)C(F)(F)F)c2=O)n1]

1H-1,2,4-triazol-1-ylacetic acid (12.7 mg, 0.1 mmol) was dissolved in 1,2-Dichloroethane (0.4 ml) in one well of a 96 deep well plate. Then 1-Chloro-N,N,2-trimethyl-1-propenylamine (26.7 mg, 0.2 mmol) was added and the plate was shaken at room temperature for 10 minutes. Then a solution of 2-{[1-(2-aminopyridin-3-yl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 45A, 48.1 mg, 0.1 mmol) and 4-Dimethylaminopyridine (36.7 mg, 0.3 mmol) in 1,2-Dichloroethane (400 µl) was added and the plate was sealed and shaken over night at room temperature. Then a solution of ammonia in methanol (50 µl, 7N) was added to the reaction mixture and the plate was shaken for additional 3 hours before the solvent was completely removed in vacuo by a centrifugal dryer. The residue was taken up in N,N-dimethylformamide (0.6 ml), filtered and the filtrate was purified by preparative LC-MS (Method 7). The product containing fractions were evaporated in vacuo with a centrifugal dryer, dissolved in 0.6 ml DMSO then pooled and evaporated again affording 6.3 mg (11% of th.) of the title compound.

LC/MS (Method 9): $R_t$=0.9 min, MS (ESIpos): m/z=590 [M+H]$^+$

The examples shown in Table 2 were synthesized in analogy to the protocol of Example 88:

TABLE 2

| Example No | Structure IUPAC-Name | Quantity (yield) Analytic |
|---|---|---|
| Example 89 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-(pyridin-3-yl)acetamide | 17.0 mg (27% of th.) LC-MS (Method 9): $R_t$ = 0.79 min MS (ESIpos): m/z = 600 [M + H]$^+$ |

TABLE 2-continued

| Example No | Structure IUPAC-Name | Quantity (yield) Analytic |
|---|---|---|
| Example 90 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-1-methyl-5-oxopyrrolidine-3-carboxamide (diastereomeric mixture) | 12.9 mg (21% of th.) LC-MS (Method 9): $R_t$ = 0.89 min MS (ESIpos): m/z = 606 [M + H]$^+$ |
| Example 91 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-(2-oxopyrrolidin-1-yl)acetamide | 15.7 mg (25% of th.) LC-MS (METHOD 9): $R_t$ = 0.92 min MS (ESIpos): m/z = 606 [M + H]$^+$ |

TABLE 2-continued

| Example No | Structure IUPAC-Name | Quantity (yield) Analytic |
|---|---|---|
| Example 92 | 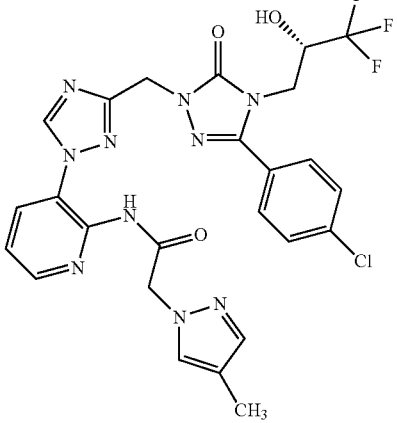<br>N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-(4-methyl-1H-pyrazol-1-yl)acetamide | 11.0 mg (16% of th.)<br>LC-MS (Method 9):<br>$R_t$ = 1.00 min<br>MS (ESIpos): m/z = 603<br>$[M + H]^+$ |
| Example 93 | 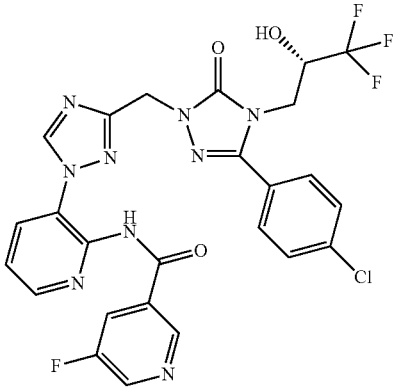<br>N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-5-fluoropyridine-3-carboxamide | 3.10 mg (5% of th.)<br>LC-MS (Method 9):<br>$R_t$ = 0.99 min<br>MS (ESIpos): m/z = 604<br>$[M + H]^+$ |
| Example 94 | 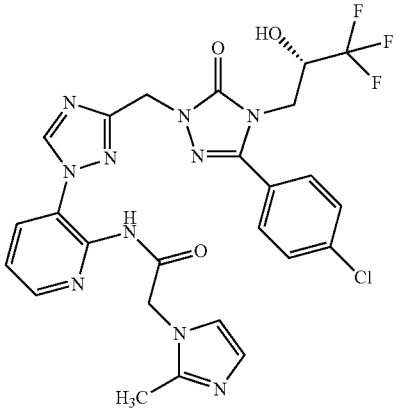<br>N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-(2-methyl-1H-pyrazol-1-yl)acetamide | 2.90 mg (5% of th.)<br>LC-MS (Method 9):<br>$R_t$ = 0.71 min<br>MS ( ): m/z = 603<br>$[M + H]^+$ |

TABLE 2-continued

| Example No | Structure IUPAC-Name | Quantity (yield) Analytic |
|---|---|---|
| Example 95 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}benzamide | 2.40 mg (4% of th.) LC-MS (Method 9): $R_t$ = 1.09 min MS (ESIpos): m/z = 585 $[M + H]^+$ |
| Example 96 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-$N^2$-methylglycinamide | 1.20 mg (2% of th.) LC-MS (Method 9): $R_t$ = 0.77 min MS (ESIpos): m/z = 552 $[M + H]^+$ |
| Example 97 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-phenylacetamide | 3.90 mg (6% of th.) LC-MS (Method 9): $R_t$ = 1.05 min MS (ESIpos): m/z = 599 $[M + H]^+$ |

TABLE 2-continued

| Example No | Structure IUPAC-Name | Quantity (yield) Analytic |
|---|---|---|
| Example 98 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-methyltetrahydrofuran-2-carboxamide (diastereomeric mixture) | 9.80 mg (16% of th.) LC-MS (Method 9): $R_t$ = 1.03 min MS (ESIpos): m/z = 593 $[M + H]^+$ |
| Example 99 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-3-methyl-5-oxoprolinamide (mixture of stereoisomers) | 9.50 mg (15% of th.) LC-MS (Method 9): $R_t$ = 0.90 min MS (ESIpos): m/z = 606 $[M + H]^+$ |
| Example 100 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-1,2,3-thiadiazole-4-carboxamide | 4.70 mg (8% of th.) LC-MS (Method 9): $R_t$ = 0.99 min MS (ESIpos): m/z = 593 $[M + H]^+$ |

TABLE 2-continued

| Example No | Structure IUPAC-Name | Quantity (yield) Analytic |
|---|---|---|
| Example 101 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-hydroxybenzamide | 4.90 mg (8% of th.) LC-MS (Method 9): $R_t$ = 1.08 min MS (ESIpos): m/z = 601 [M + H]$^+$ |
| Example 102 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-3-methyl-1,2-oxazole-5-carboxamide | 10.9 mg (18% of th.) LC-MS (Method 9): $R_t$ = 1.00 min MS (ESIpos): m/z = 590 [M + H]$^+$ |
| Example 103 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-(piperidin-1-yl)acetamide | 9.60 mg (16% of th.) LC-MS (Method 9): $R_t$ = 0.74 min MS (ESIpos): m/z = 606 [M + H]$^+$ |

TABLE 2-continued

| Example No | Structure IUPAC-Name | Quantity (yield) Analytic |
|---|---|---|
| Example 104 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}pyrazine-2-carboxamide | 8.30 mg (14% of th.) LC-MS (Method 9): $R_t$ = 0.99 min MS (ESIpos): m/z = 587 [M + H]$^+$ |
| Example 105 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-cyclohexylacetamide | 7.80 mg (12% of th.) LC-MS (Method 9): $R_t$ = 1.10 min MS (ESIpos): m/z = 605 [M + H]$^+$ |
| Example 106 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-1-methyl-1,2-oxazole-5-carboxamide | 1.20 mg (2% of th.) LC-MS (Method 9): $R_t$ = 0.98 min MS (ESIpos): m/z = 589 [M + H]$^+$ |

TABLE 2-continued

| Example No | Structure<br>IUPAC-Name | Quantity (yield)<br>Analytic |
|---|---|---|
| Example 107 | 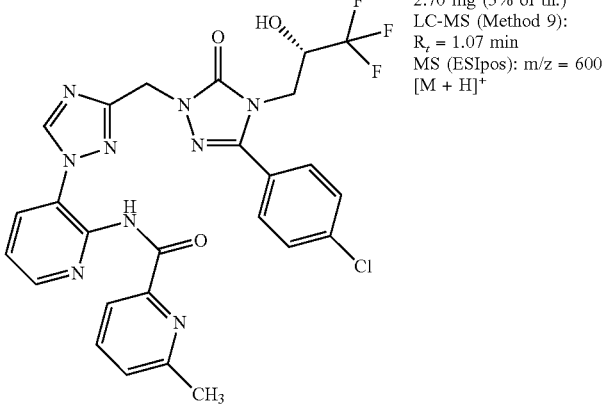<br>N-{3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-6-methylpyridine-2-carboxamide | 2.70 mg (5% of th.)<br>LC-MS (Method 9):<br>$R_t$ = 1.07 min<br>MS (ESIpos): m/z = 600<br>$[M + H]^+$ |
| Example 108 | 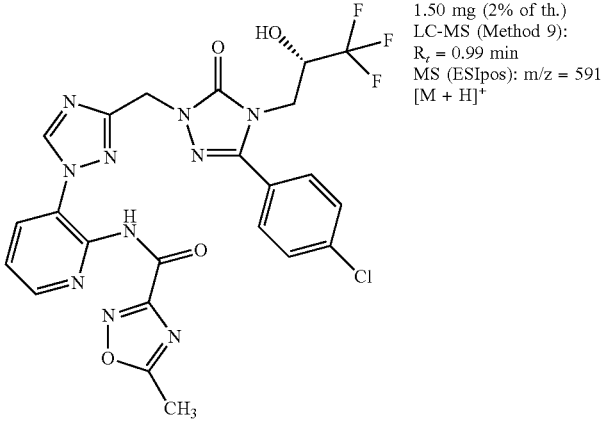<br>N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-5-methyl-1,2,4-oxadiazole-3-carboxamide | 1.50 mg (2% of th.)<br>LC-MS (Method 9):<br>$R_t$ = 0.99 min<br>MS (ESIpos): m/z = 591<br>$[M + H]^+$ |

TABLE 2-continued

| Example No | Structure IUPAC-Name | Quantity (yield) Analytic |
|---|---|---|
| Example 109 | 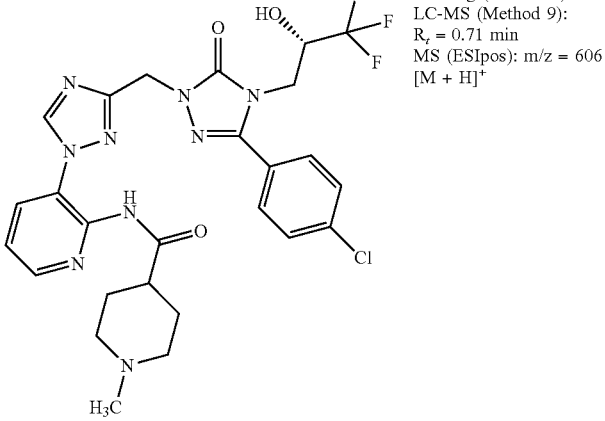<br>N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-1-methylpiperidine-4-carboxamide | 3.30 mg (5% of th.)<br>LC-MS (Method 9):<br>$R_t$ = 0.71 min<br>MS (ESIpos): m/z = 606 $[M + H]^+$ |
| Example 110 | 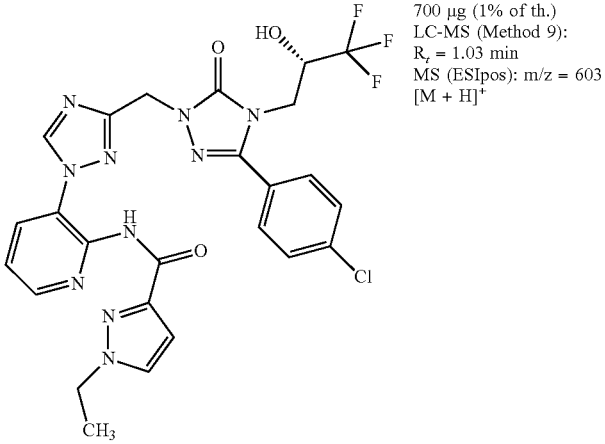<br>N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-1-ethyl-1H-pyrazole-3-carboxamide | 700 μg (1% of th.)<br>LC-MS (Method 9):<br>$R_t$ = 1.03 min<br>MS (ESIpos): m/z = 603 $[M + H]^+$ |
| Example 111 | 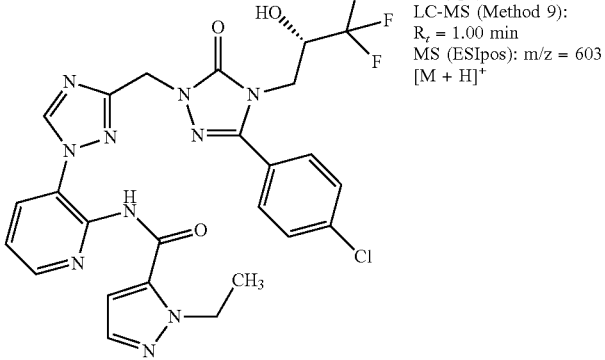<br>N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-1-ethyl-1H-pyrazole-5-carboxamide | 800 μg (1% of th.)<br>LC-MS (Method 9):<br>$R_t$ = 1.00 min<br>MS (ESIpos): m/z = 603 $[M + H]^+$ |

TABLE 2-continued

| Example No | Structure IUPAC-Name | Quantity (yield) Analytic |
|---|---|---|
| Example 112 | 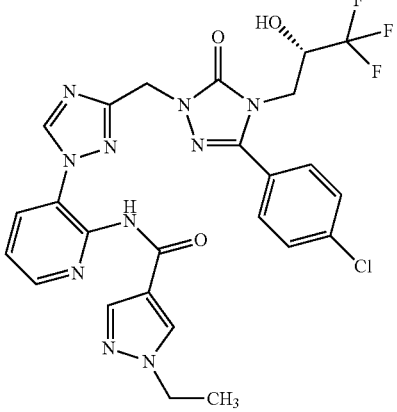<br>N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-1-ethyl-1H-pyrazole-4-carboxamide | 35.1 mg (54% of th.)<br>LC-MS (Method 9):<br>$R_t$ = 0.99 min<br>MS (ESIpos): m/z = 603 $[M + H]^+$ |
| Example 113 | 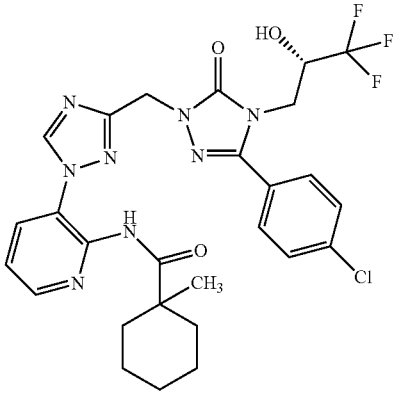<br>N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-1-methylcyclohexanecarboxamide | 16.7 mg (28% of th.)<br>LC-MS (Method 9):<br>$R_t$ = 1.19 min<br>MS (ESIpos): m/z = 605 $[M + H]^+$ |
| Example 114 | 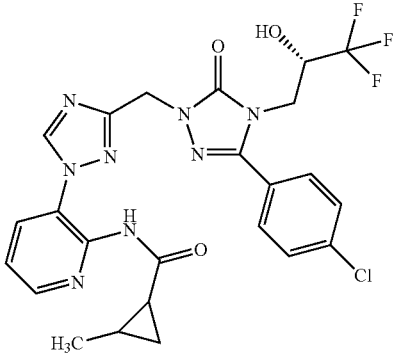<br>N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-methylcyclopropanecarboxamide<br>(diastereomeric mixture) | 25.0 mg (44% of th.)<br>LC-MS (Method 9):<br>$R_t$ = 1.07 min<br>MS (ESIpos): m/z = 563 $[M + H]^+$ |

TABLE 2-continued

| Example No | Structure IUPAC-Name | Quantity (yield) Analytic |
|---|---|---|
| Example 115 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}cyclobutanecarboxamide | 24.2 mg (41% of th.) LC-MS (Method 9): $R_t$ = 1.08 min MS (ESIpos): m/z = 561 [M − H]$^-$ |
| Example 116 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-fluorobenzamide | 32.5 mg (53% of th.) LC-MS (Method 9): $R_t$ = 1.08 min MS (ESIpos): m/z = 603 [M + H]$^+$ |
| Example 117 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2,2-dimethylpropanamide | 9.10 mg (16% of th.) LC-MS (Method 9): $R_t$ = 1.11 min MS (ESIpos): m/z = 565 [M + H]$^+$ |

TABLE 2-continued

| Example No | Structure IUPAC-Name | Quantity (yield) Analytic |
|---|---|---|
| Example 118 | 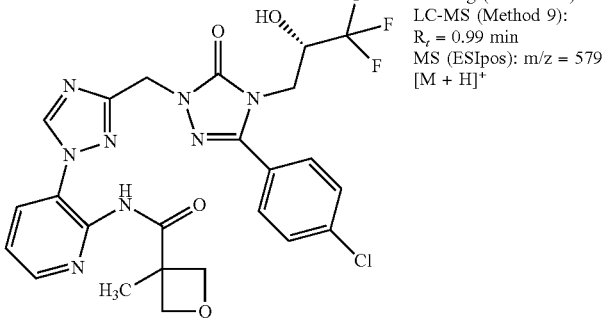<br>N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-3-methyloxetane-3-carboxamide | 12.6 mg (20% of th.)<br>LC-MS (Method 9):<br>$R_t$ = 0.99 min<br>MS (ESIpos): m/z = 579 [M + H]$^+$ |
| Example 119 | 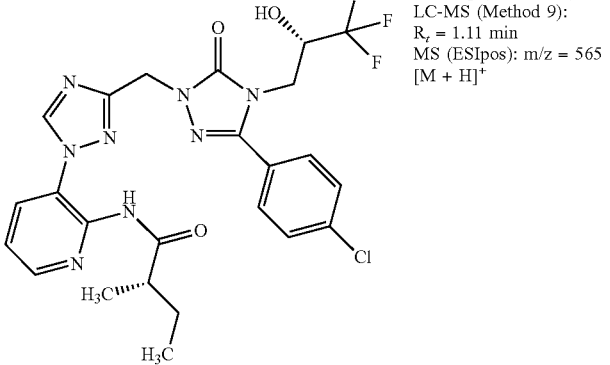<br>(2S)-N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-methylbutanamide | 34.9 mg (61% of th.)<br>LC-MS (Method 9):<br>$R_t$ = 1.11 min<br>MS (ESIpos): m/z = 565 [M + H]$^+$ |
| Example 120 | 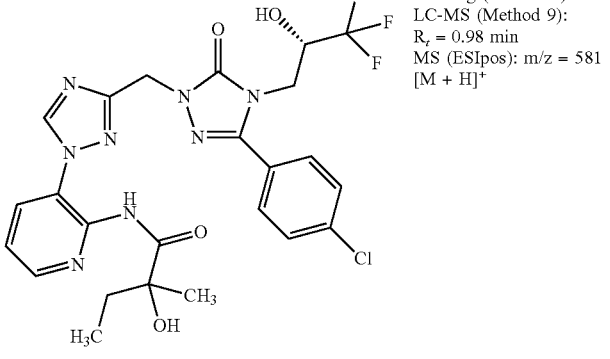<br>N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-hydroxy-2-methylbutanamide | 1.50 mg (2% of th.)<br>LC-MS (Method 9):<br>$R_t$ = 0.98 min<br>MS (ESIpos): m/z = 581 [M + H]$^+$ |

TABLE 2-continued

| Example No | Structure IUPAC-Name | Quantity (yield) Analytic |
|---|---|---|
| Example 121 | 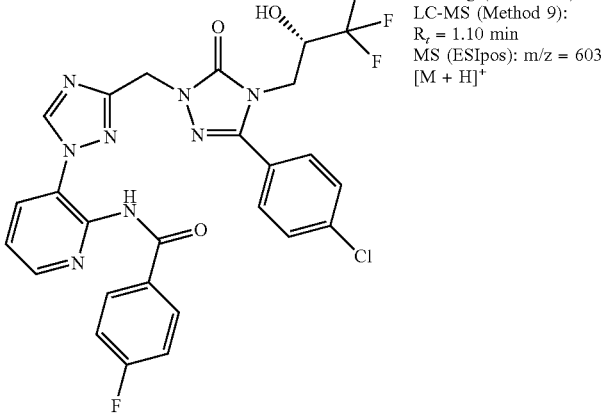<br>N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-4-fluorobenzamide | 22.2 mg (36% of th.)<br>LC-MS (Method 9):<br>$R_t$ = 1.10 min<br>MS (ESIpos): m/z = 603 [M + H]$^+$ |
| Example 122 | 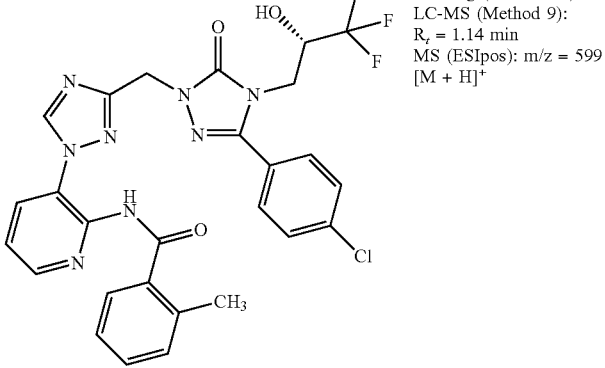<br>N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-methylbenzamide | 45.0 mg (73% of th.)<br>LC-MS (Method 9):<br>$R_t$ = 1.14 min<br>MS (ESIpos): m/z = 599 [M + H]$^+$ |
| Example 123 | 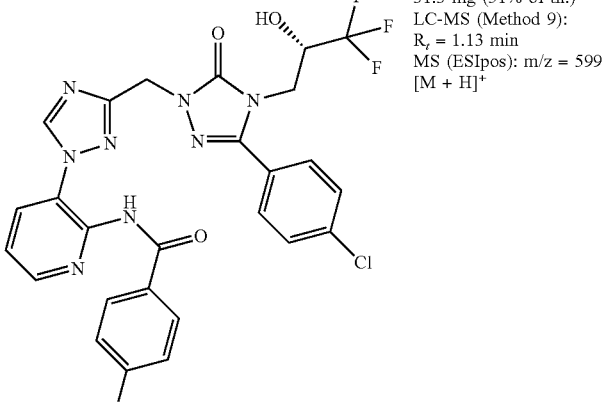<br>N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-4-methylbenzamide | 31.3 mg (51% of th.)<br>LC-MS (Method 9):<br>$R_t$ = 1.13 min<br>MS (ESIpos): m/z = 599 [M + H]$^+$ |

TABLE 2-continued

| Example No | Structure IUPAC-Name | Quantity (yield) Analytic |
|---|---|---|
| Example 124 | 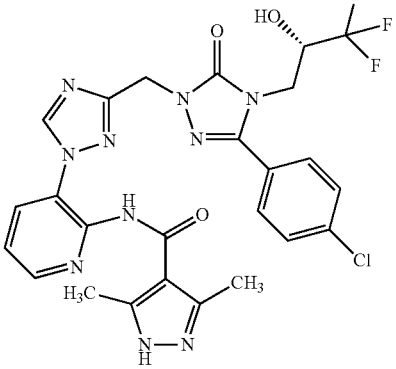<br>N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-3,5-dimethyl-1H-pyrazole-4-carboxamide | 1.60 mg (3% of th.)<br>LC-MS (Method 9):<br>$R_t$ = 0.91 min<br>MS (ESIpos): m/z = 603 $[M + H]^+$ |
| Example 125 | 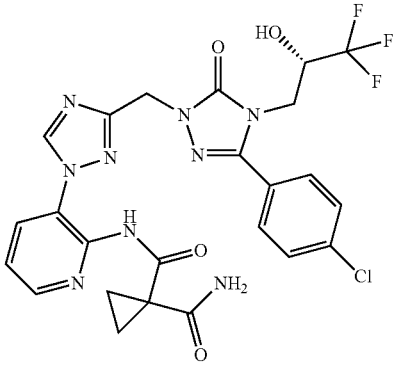<br>N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}cyclopropane-1,1-dicarboxamide | 27.1 mg (45% of th.)<br>LC-MS (Method 9):<br>$R_t$ = 0.90 min<br>MS (ESIpos): m/z = 592 $[M + H]^+$ |
| Example 126 | 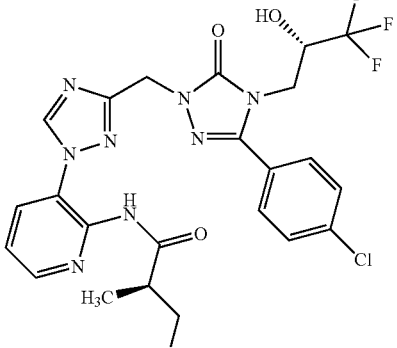<br>N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-methylbutanamide (diastereomeric mixture) | 27.3 mg (48% of th.)<br>LC-MS (Method 9):<br>$R_t$ = 1.11 min<br>MS (ESIpos): m/z = 565 $[M + H]^+$ |

TABLE 2-continued

| Example No | Structure IUPAC-Name | Quantity (yield) Analytic |
|---|---|---|
| Example 127 | 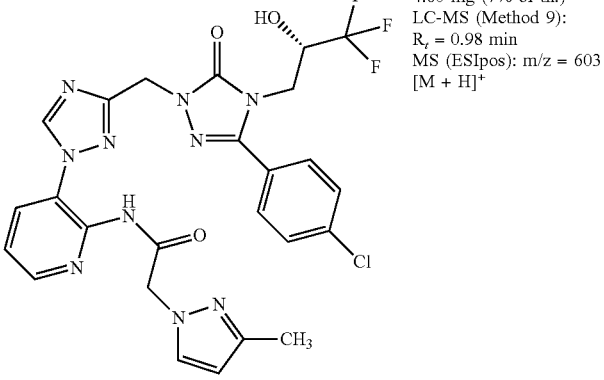<br>N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-(3-methyl-1H-pyrazol-1-yl)acetamide | 4.60 mg (7% of th.)<br>LC-MS (Method 9):<br>$R_t$ = 0.98 min<br>MS (ESIpos): m/z = 603 $[M + H]^+$ |
| Example 128 | 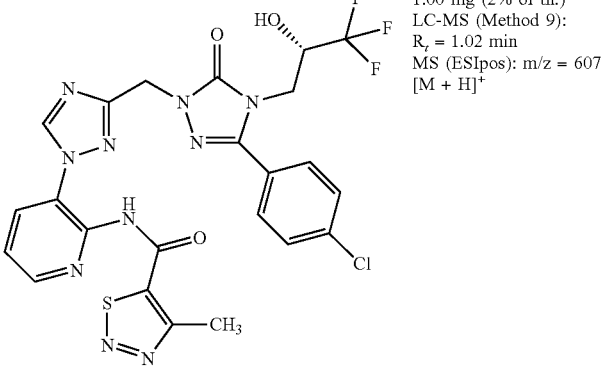<br>N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-4-methyl-1,2,3-thiadiazole-5-carboxamide | 1.00 mg (2% of th.)<br>LC-MS (Method 9):<br>$R_t$ = 1.02 min<br>MS (ESIpos): m/z = 607 $[M + H]^+$ |
| Example 129 | 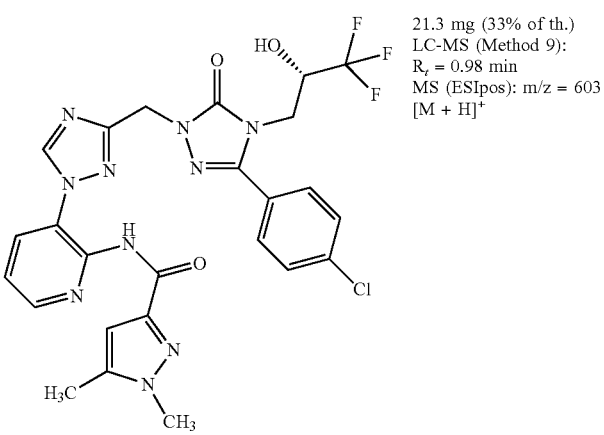<br>N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-1,5-dimethyl-1H-pyrazole-3-carboxamide | 21.3 mg (33% of th.)<br>LC-MS (Method 9):<br>$R_t$ = 0.98 min<br>MS (ESIpos): m/z = 603 $[M + H]^+$ |

TABLE 2-continued

| Example No | Structure IUPAC-Name | Quantity (yield) Analytic |
|---|---|---|
| Example 130 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-5-methyl-1H-pyrazole-4-carboxamide | 2.50 mg (4% of th.) LC-MS (Method 9): $R_t$ = 0.90 min MS (ESIpos): m/z = 589 [M + H]$^+$ |
| Example 131 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-(1H-imidazol-1-yl)propanamide (diastereomeric mixture) | 2.40 mg (4% of th.) LC-MS (Method 9): $R_t$ = 0.72 min MS (ESIpos): m/z = 603 [M + H]$^+$ |
| Example 132 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-1-methyl-1H-imidazole-5-carboxamide | 2.90 mg (4% of th.) LC-MS (Method 9): $R_t$ = 0.90 min MS (ESIpos): m/z = 589 [M + H]$^+$ |

TABLE 2-continued

| Example No | Structure IUPAC-Name | Quantity (yield) Analytic |
|---|---|---|
| Example 133 | 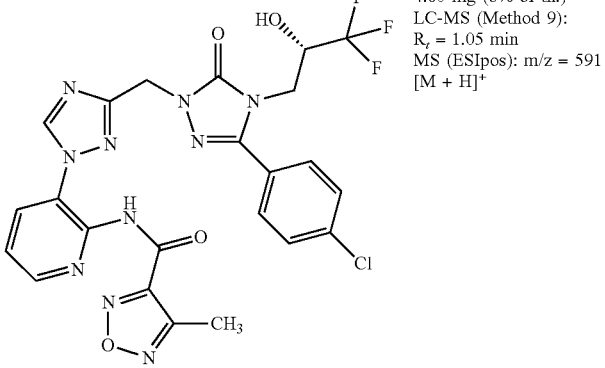<br>N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-4-methyl-1,2,5-oxadiazole-3-carboxamide | 4.60 mg (8% of th.)<br>LC-MS (Method 9):<br>$R_t$ = 1.05 min<br>MS (ESIpos): m/z = 591 [M + H]$^+$ |
| Example 134 | 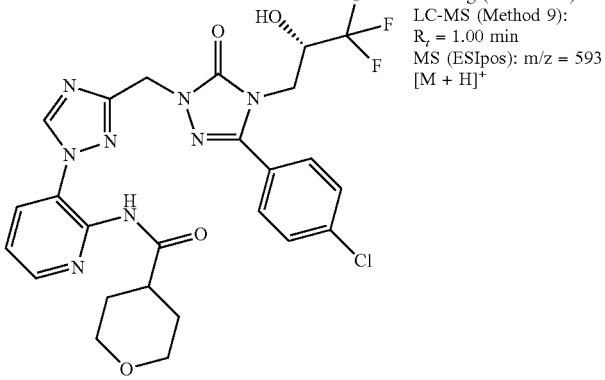<br>N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}tetrahydro-2H-pyran-4-carboxamide | 16.0 mg (27% of th.)<br>LC-MS (Method 9):<br>$R_t$ = 1.00 min<br>MS (ESIpos): m/z = 593 [M + H]$^+$ |
| Example 135 | 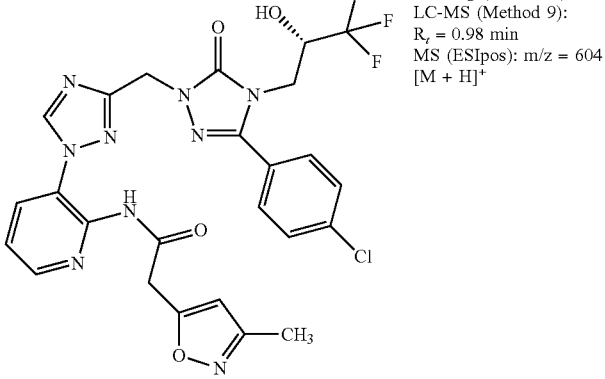<br>N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-(3-methyl-1,2-oxazol-5-yl)acetamide | 5.90 mg (9% of th.)<br>LC-MS (Method 9):<br>$R_t$ = 0.98 min<br>MS (ESIpos): m/z = 604 [M + H]$^+$ |

TABLE 2-continued

| Example No | Structure IUPAC-Name | Quantity (yield) Analytic |
|---|---|---|
| Example 136 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-cyclobutylacetamide | 42.8 mg (73% of th.) LC-MS (Method 9): R$_t$ = 1.13 min MS (ESIpos): m/z = 577 [M + H]$^+$ |
| Example 137 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-methoxy-2-methylpropanamide | 7.70 mg (13% of th.) LC-MS (Method 9): R$_t$ = 1.04 min MS (ESIpos): m/z = 581 [M + H]$^+$ |
| Example 138 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-(4-methyl-1,2,5-oxadiazol-3-yl)acetamide | 6.30 mg (10% of th.) LC-MS (Method 9): R$_t$ = 1.01 min MS (ESIpos): m/z = 605 [M + H]$^+$ |

TABLE 2-continued

| Example No | Structure IUPAC-Name | Quantity (yield) Analytic |
|---|---|---|
| Example 139 | 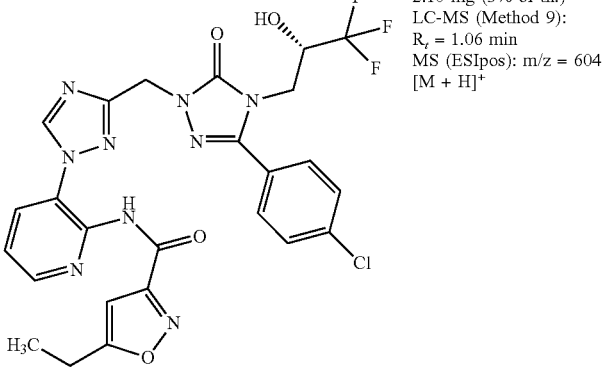<br>N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-5-ethyl-1,2-oxazole-3-carboxamide | 2.10 mg (3% of th.)<br>LC-MS (Method 9):<br>$R_t$ = 1.06 min<br>MS (ESIpos): m/z = 604 [M + H]$^+$ |
| Example 140 | 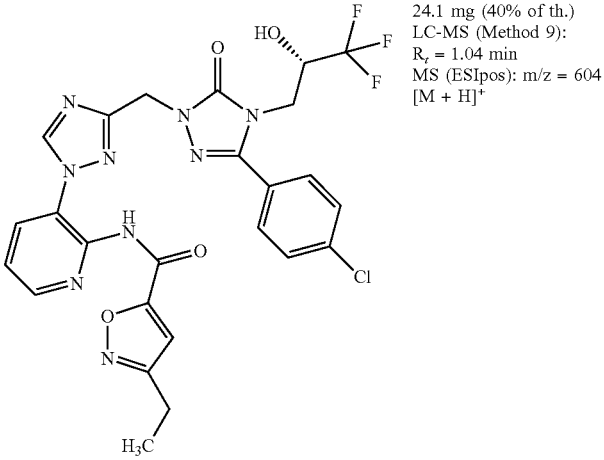<br>N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-3-ethyl-1,2-oxazole-5-carboxamide | 24.1 mg (40% of th.)<br>LC-MS (Method 9):<br>$R_t$ = 1.04 min<br>MS (ESIpos): m/z = 604 [M + H]$^+$ |
| Example 141 | 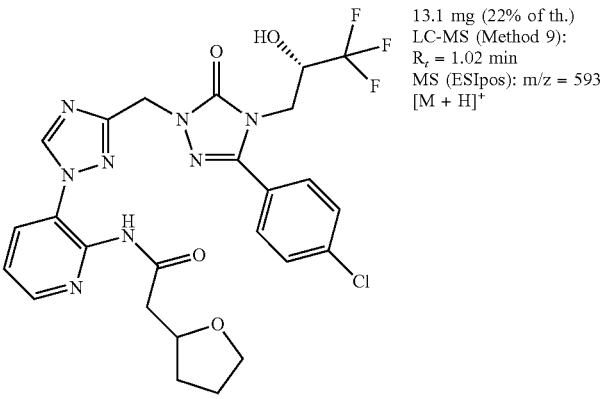<br>N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-[(tetrahydrofuran-2-yl]acetamide (diastereomeric mixture) | 13.1 mg (22% of th.)<br>LC-MS (Method 9):<br>$R_t$ = 1.02 min<br>MS (ESIpos): m/z = 593 [M + H]$^+$ |

TABLE 2-continued

| Example No | Structure IUPAC-Name | Quantity (yield) Analytic |
|---|---|---|
| Example 142 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-3,5-dimethyl-4,5-dihydro-1,2-oxazole-5-carboxamide (diastereomeric mixture) | 10.6 mg (17% of th.) LC-MS (Method 9): $R_t$ = 0.99 min MS (ESIpos): m/z = 606 [M + H]$^+$ |
| Example 143 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}pyrimidine-4-carboxamide | 1.90 mg (3% of th.) LC-MS (Method 9): $R_t$ = 0.99 min MS (ESIpos): m/z = 587 [M + H]$^+$ |
| Example 144 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-methylbut-3-enamide (diastereomeric mixture) | 28.3 mg (50% of th.) LC-MS (Method 9): $R_t$ = 1.08 min MS (ESIpos): m/z = 563 [M + H]$^+$ |

TABLE 2-continued

| Example No | Structure IUPAC-Name | Quantity (yield) Analytic |
|---|---|---|
| Example 145 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-hydroxy-2-methylpropanamide | 700 µg (1% of th.) LC-MS (Method 9): R$_t$ = 1.04 min MS (ESIpos): m/z = 567 [M + H]$^+$ |
| Example 146 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}butanamide | 17.1 mg (31% of th.) LC-MS (Method 9): R$_t$ = 1.07 min MS (ESIpos): m/z = 551 [M + H]$^+$ |
| Example 147 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}propanamide | 9.90 mg (18% of th.) LC-MS (Method 9): R$_t$ = 1.02 min MS (ESIpos): m/z = 537 [M + H]$^+$ |

TABLE 2-continued

| Example No | Structure IUPAC-Name | Quantity (yield) Analytic |
|---|---|---|
| Example 148 | 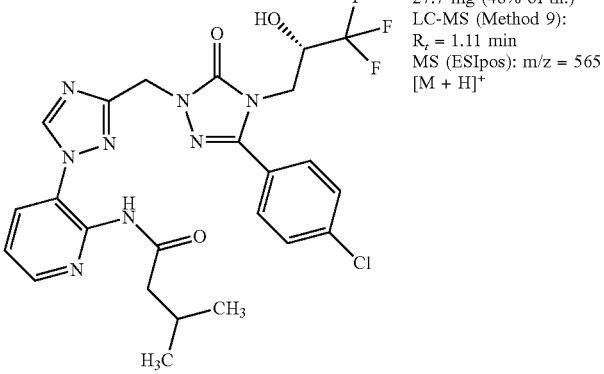<br>N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-3-methylbutanamide | 27.7 mg (48% of th.)<br>LC-MS (Method 9):<br>$R_t$ = 1.11 min<br>MS (ESIpos): m/z = 565 [M + H]$^+$ |
| Example 149 | 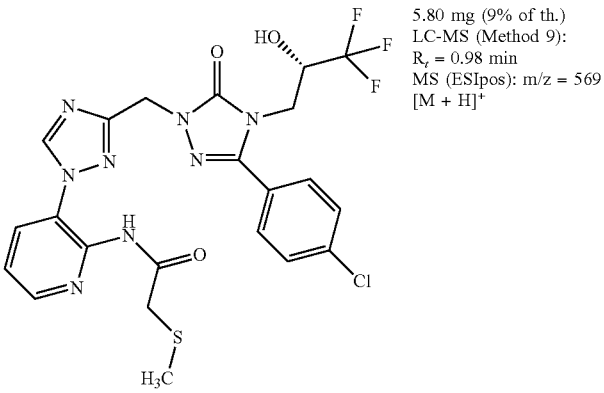<br>N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-(methylsulfanyl)acetamide | 5.80 mg (9% of th.)<br>LC-MS (Method 9):<br>$R_t$ = 0.98 min<br>MS (ESIpos): m/z = 569 [M + H]$^+$ |
| Example 150 | 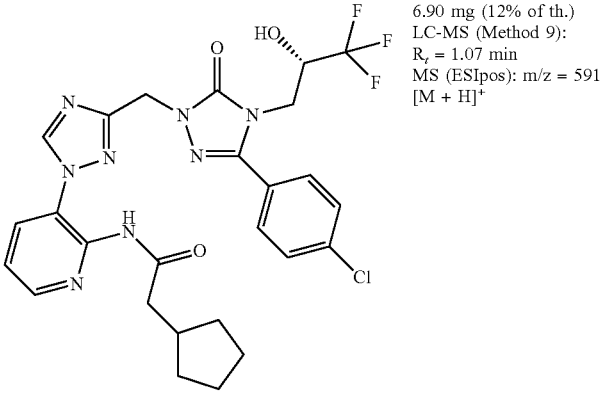<br>N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-cyclopentylacetamide | 6.90 mg (12% of th.)<br>LC-MS (Method 9):<br>$R_t$ = 1.07 min<br>MS (ESIpos): m/z = 591 [M + H]$^+$ |

TABLE 2-continued

| Example No | Structure / IUPAC-Name | Quantity (yield) Analytic |
|---|---|---|
| Example 151 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-methylpropanamide | 19.1 mg (34% of th.) LC-MS (Method 9): $R_t$ = 1.07 min MS (ESIpos): m/z = 551 [M + H]$^+$ |
| Example 152 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}but-3-enamide | 16.4 mg (29% of th.) LC-MS (Method 9): $R_t$ = 1.04 min MS (ESIpos): m/z = 549 [M + H]$^+$ |
| Example 153 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-3-cyanobenzamide | 10.7 mg (16% of th.) LC-MS (Method 9): $R_t$ = 1.06 min MS (ESIpos): m/z = 610 [M + H]$^+$ |

TABLE 2-continued

| Example No | Structure IUPAC-Name | Quantity (yield) Analytic |
|---|---|---|
| Example 154 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-1-methylcyclopropanecarboxamide | 5.90 mg (9% of th.)<br>LC-MS (Method 9):<br>$R_t$ = 1.00 min<br>MS (ESIpos): m/z = 563 [M + H]$^+$ |
| Example 155 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-(1H-1,2,4-triazol-1-yl)propanamide (diastereomeric mixture) | 5.90 mg (9% of th.)<br>LC-MS (Method 9):<br>$R_t$ = 0.93 min<br>MS (ESIpos): m/z = 604 [M + H]$^+$ |
| Example 156 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}cycloheptanecarboxamide | 800 µg (9% of th.)<br>LC-MS (Method 9):<br>$R_t$ = 1.09 min<br>MS (ESIpos): m/z = 605 [M + H]$^+$ |

TABLE 2-continued

| Example No | Structure IUPAC-Name | Quantity (yield) Analytic |
|---|---|---|
| Example 157 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}pyridine-4-carboxamide | 7.10 mg (12% of th.) LC-MS (Method 9): $R_t$ = 0.93 min MS (ESIpos): m/z = 586 $[M + H]^+$ |
| Example 158 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-3,3-dimethylbutanamide | 4.10 mg (7% of th.) LC-MS (Method 9): $R_t$ = 1.05 min MS (ESIpos): m/z = 579 $[M + H]^+$ |
| Example 159 | N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}cyclohexanecarboxamide | 2.80 mg (5% of th.) LC-MS (Method 9): $R_t$ = 1.06 min MS (ESIpos): m/z = 591 $[M + H]^+$ |

TABLE 2-continued

| Example No | Structure<br>IUPAC-Name | Quantity (yield)<br>Analytic |
|---|---|---|
| Example 160 | 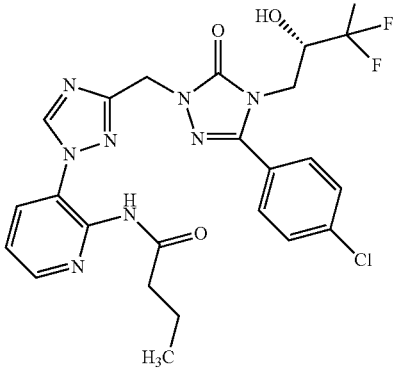<br>N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-methoxyacetamide | 7.70 mg (5% of th.)<br>LC-MS (Method 9):<br>$R_t$ = 0.96 min<br>MS (ESIpos): m/z = 553 $[M + H]^+$ |
| Example 161 | 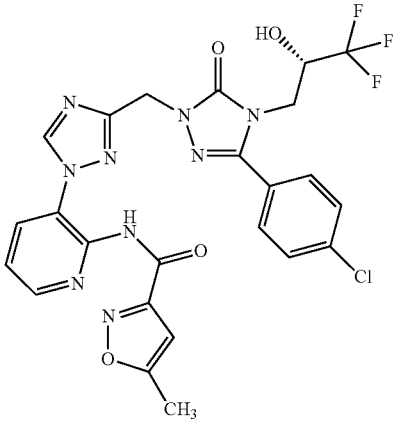<br>N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-5-methyl-1,2-oxazole-3-carboxamide | 600 µg (1% of th.)<br>LC-MS (Method 9):<br>$R_t$ = 1.02 min<br>MS (ESIpos): m/z = 590 $[M + H]^+$ |
| Example 162 | 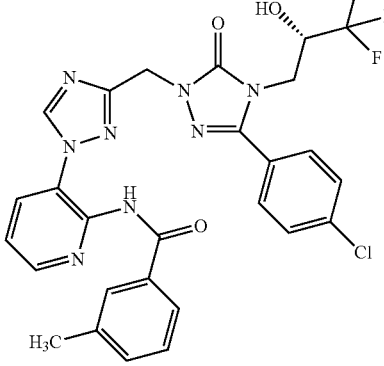<br>N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-3-methylbenzamide | 9.90 mg (15% of th.)<br>LC-MS (Method 9):<br>$R_t$ = 1.13 min<br>MS (ESIpos): m/z = 599 $[M + H]^+$ |

TABLE 2-continued

| Example No | Structure IUPAC-Name | Quantity (yield) Analytic |
|---|---|---|
| Example 163 | 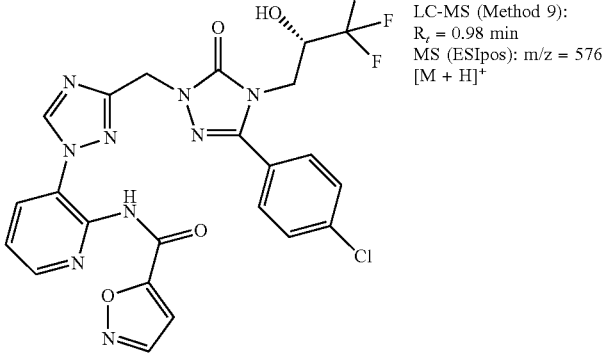<br>N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-1,2-oxazole-5-carboxamide | 2.20 mg (4% of th.)<br>LC-MS (Method 9):<br>$R_t$ = 0.98 min<br>MS (ESIpos): m/z = 576 [M + H]$^+$ |
| Example 164 | 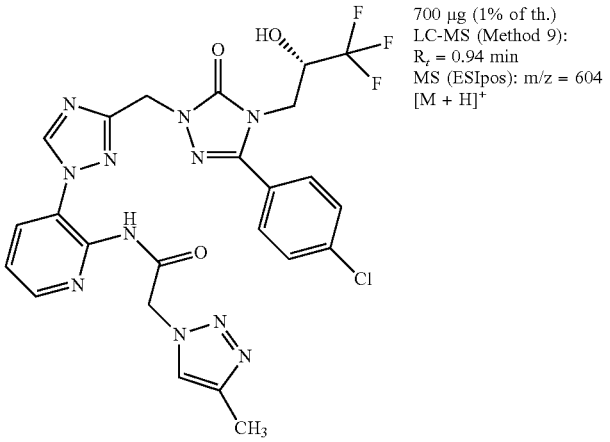<br>N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-(4-methyl-1H-1,2,3-triazol-1-yl)acetamide | 700 µg (1% of th.)<br>LC-MS (Method 9):<br>$R_t$ = 0.94 min<br>MS (ESIpos): m/z = 604 [M + H]$^+$ |
| Example 165 | 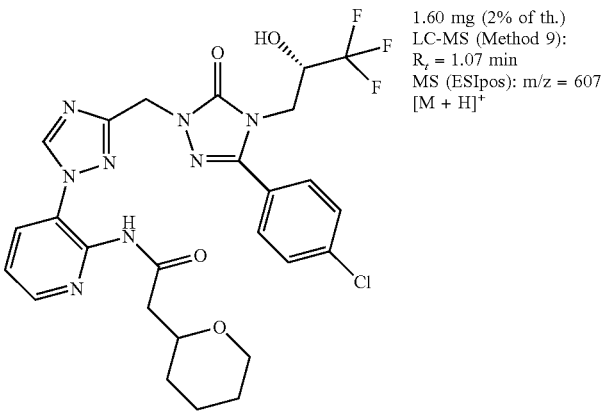<br>N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}-2-[(tetrahydro-2H-pyran-2-yl]acetamide<br>(diastereomeric mixture) | 1.60 mg (2% of th.)<br>LC-MS (Method 9):<br>$R_t$ = 1.07 min<br>MS (ESIpos): m/z = 607 [M + H]$^+$ |

TABLE 2-continued

| Example No | Structure IUPAC-Name | Quantity (yield) Analytic |
|---|---|---|
| Example 166 | 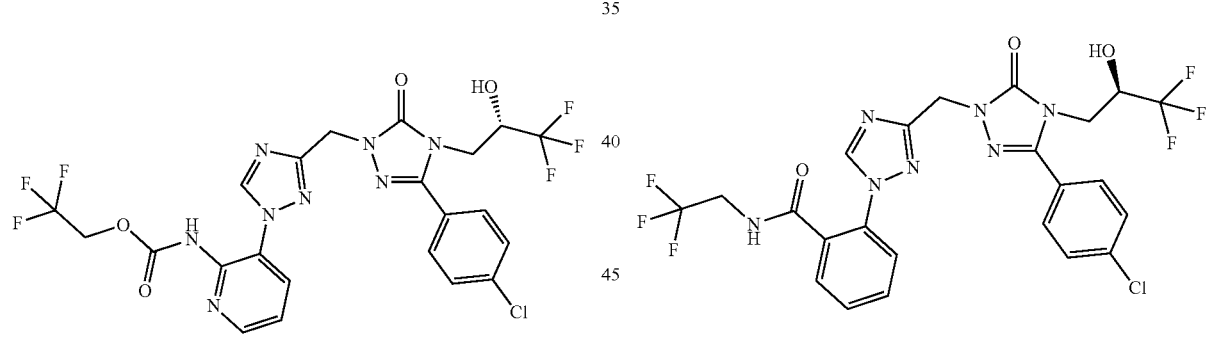<br>N-{3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}tetrahydro-2H-pyran-2-carboxamide<br>(diastereomeric mixture) | 2.30 mg (4% of th.)<br>LC-MS (Method 9):<br>$R_t$ = 1.04 min<br>MS (ESIpos): m/z = 593 [M + H]$^+$ |

Example 167

2,2,2-Trifluoroethyl {3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}carbamate A solution of 2,2,2-trifluoroethyl {3-[3-({4-[(2S)-2-{([tert-butyl(dimethyl)silyl]oxy}-3,3,3-trifluoropropyl]-3-(4-chlorophenyl)-5-oxo-4,5-dihydro-1H-1,2,4-triazol-1-yl}methyl)-1H-1,2,4-triazol-1-yl]pyridin-2-yl}carbamate (Example 48A, 20.0 mg, 27.7 µmol) in tetrahydrofuran (500 µl) was treated with N,N,N-tributylbutan-1-aminium fluoride (55 µl, 1.0 M, 55 µmol) and stirred 1 h at room temperature. The reaction mixture was purified by preparative HPLC (Method 4) affording 1.30 mg (8% of th.) of the title compound.

LC-MS (Method 2): $R_t$=1.73 min; MS (ESIpos): m/z=607.1 [M+H]$^+$ $^1$H-NMR (500 MHz, CHLOROFORM-d) δ [ppm]: 9.17 (s, 1H), 8.55 (br d, 1H), 8.47-8.33 (m, 1H), 7.84-7.02 (m, 6H), 5.52-5.11 (m, 3H), 4.72-4.45 (m, 3H), 4.06-3.87 (m, 2H).

Example 168

2-[3-({3-(4-Chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]-N-(2,2,2-trifluoroethyl)benzamide

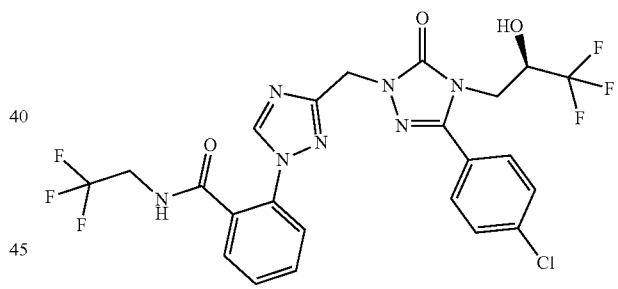

A solution of 2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]benzoic acid (Example 49A, 190 mg, 373 µmol) in dichloromethane (5.0 ml) was treated with 1-chloro-N,N,2-trimethylprop-1-en-1-amine (74 µl, 560 µmol) and stirred 30 min at room temperature. Evaporation afforded crude 2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]benzoyl chloride.

A solution of the residue in tetrahydrofuran (5.0 ml) was treated with 2,2,2-trifluoroethanamine (73 µl, 930 µmol) and N,N-diisopropylethylamine (97 µl, 560 µmol). The resulting mixture was stirred overnight at room temperature and evaporated. Purification of the residue by preparative HPLC (Method 4) afforded 170 mg (77% of th.) of the title compound.

LC-MS (Method 2): $R_t$=1.74 min; MS (ESIpos): m/z=590.1 [M+H]$^+$

¹H-NMR (400 MHz, DMSO-d6) δ [ppm]: 8.97 (t, 1H), 8.75 (s, 1H), 7.80-7.52 (m, 8H), 6.91 (d, 1H), 5.03 (s, 2H), 4.39-4.21 (br m, 1H), 4.06-3.78 (m, 4H).

Example 169

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-methylbenzamide

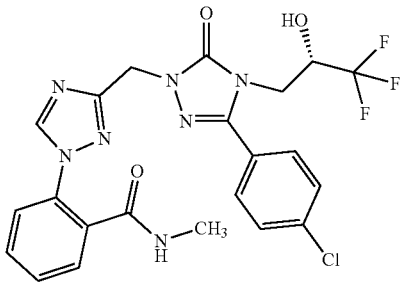 [SMILES: CNC(=O)c1ccccc1-n1cnc(Cn2nc(-c3ccc(Cl)cc3)n(C[C@H](O)C(F)(F)F)c2=O)n1]

To a solution of methyl 3-({3-(4-chlorophenyl)-5-oxo-4-[(2S)-3,3,3-trifluoro-2-hydroxypropyl]-4,5-dihydro-1H-1,2,4-triazol-1-yl}methyl)-1-[2-(methylcarbamoyl)phenyl]-1H-1,2,4-triazole-5-carboxylate (Example 64A, 60.0 mg, 70% purity, 72.4 µmol) in tetrahydrofuran (1.0 ml), lithium hydroxide (17.3 mg, 724 µmol) in water (1.0 ml) was added and stirred over night at room temperature. The organic solvent was removed in vacuo. The crude product was purified by preparative HPLC (Method 4). Lyophilisation of the product containing fractions afforded 6.30 mg (17% of th.) of the title compound LC-MS (Method 1): R$_t$=0.83 min; MS (ESIpos): m/z=522 [M+H]$^+$ ¹H-NMR (400 MHz, DMSO-d6) δ [ppm]: –0.008 (2.87), 0.008 (1.55), 2.585 (16.00), 2.597 (15.58), 3.814 (1.55), 3.838 (1.78), 3.851 (2.20), 3.875 (2.34), 3.975 (2.28), 3.984 (2.38), 4.013 (1.55), 4.021 (1.42), 4.309 (1.29), 4.326 (1.19), 5.072 (14.47), 6.917 (4.31), 6.932 (4.22), 7.536 (3.69), 7.540 (4.80), 7.542 (6.83), 7.547 (7.67), 7.551 (8.09), 7.558 (1.21), 7.583 (1.61), 7.586 (2.15), 7.598 (8.67), 7.602 (8.28), 7.606 (8.66), 7.608 (11.10), 7.613 (4.12), 7.617 (3.29), 7.625 (4.13), 7.630 (10.85), 7.636 (1.93), 7.746 (2.19), 7.752 (10.63), 7.757 (3.50), 7.768 (3.18), 7.773 (7.66), 7.780 (1.15), 8.230 (2.57), 8.242 (2.47), 8.707 (12.43).

Example 170

N-[(3R)-1-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl}pyrrolidin-3-yl]acetamide

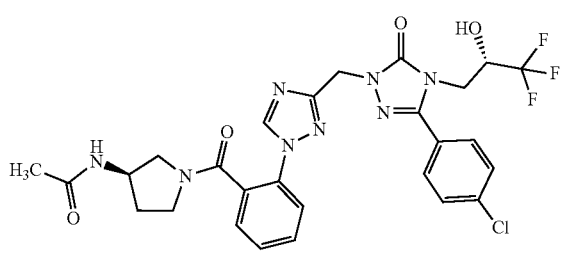 [SMILES: CC(=O)N[C@@H]1CCN(C(=O)c2ccccc2-n2cnc(Cn3nc(-c4ccc(Cl)cc4)n(C[C@H](O)C(F)(F)F)c3=O)n2)C1]

N-[(3R)-pyrrolidin-3-yl]acetamide (32.0 mg, 250 µmol) was added to a solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl chloride (Example 58A, 52.7 mg, 100 µmol) in tetrahydrofuran (1.5 ml). This reaction mixture was stirred for 1 h at room temperature. The crude product was purified by preparative HPLC (Method 4). Lyophilisation of the product containing fractions afforded 43.4 mg (70% of th.) of the title compound as mixture of rotamers.

LC-MS (Method 1): R$_t$=0.86 min; MS (ESIpos): m/z=619 [M+H]$^+$

¹H-NMR (400 MHz, DMSO-d6) δ [ppm]: –0.008 (0.99), 1.638 (1.06), 1.654 (1.33), 1.670 (1.18), 1.751 (16.00), 1.778 (0.77), 1.805 (0.96), 1.816 (13.17), 1.904 (1.00), 1.920 (1.04), 2.274 (0.81), 2.846 (0.78), 2.859 (0.76), 3.151 (0.74), 3.164 (0.86), 3.187 (1.28), 3.194 (1.44), 3.205 (1.11), 3.213 (1.06), 3.231 (0.92), 3.290 (1.32), 3.378 (0.95), 3.445 (0.86), 3.495 (0.92), 3.512 (0.79), 3.821 (1.17), 3.845 (1.39), 3.858 (1.80), 3.882 (1.94), 3.976 (1.58), 3.984 (2.10), 4.018 (2.08), 4.293 (0.96), 4.303 (1.06), 4.318 (0.92), 5.081 (10.06), 6.913 (3.84), 6.929 (3.83), 7.476 (1.17), 7.480 (1.32), 7.495 (2.26), 7.498 (2.91), 7.502 (1.47), 7.516 (1.73), 7.520 (1.86), 7.533 (1.06), 7.536 (1.11), 7.546 (1.06), 7.552 (2.17), 7.555 (2.03), 7.564 (1.75), 7.568 (1.78), 7.570 (1.50), 7.574 (1.17), 7.583 (0.98), 7.586 (1.03), 7.592 (1.58), 7.599 (4.67), 7.605 (5.50), 7.611 (3.75), 7.616 (4.49), 7.621 (7.26), 7.627 (6.50), 7.633 (2.05), 7.640 (0.87), 7.691 (2.56), 7.695 (3.65), 7.711 (1.81), 7.715 (2.48), 7.718 (1.35), 7.744 (5.64), 7.748 (7.07), 7.753 (2.10), 7.761 (1.71), 7.765 (5.02), 7.770 (4.66), 7.963 (1.28), 7.978 (1.26), 8.017 (1.00), 8.033 (0.97), 8.833 (4.75), 8.851 (5.50).

Example 171

4-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl}piperazin-2-one

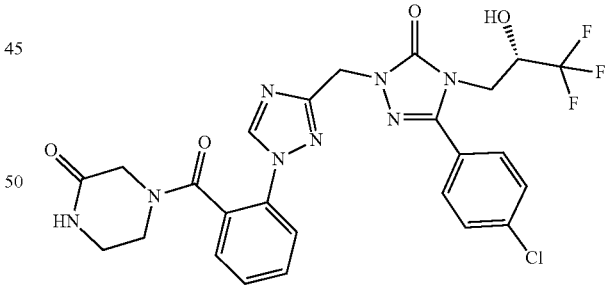

Piperazin-2-one (20.0 mg, 200 µmol) was added to a solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl chloride (Example 58A, 42.2 mg, 80.0 µmol) in tetrahydrofuran (1.0 ml). This reaction mixture was stirred for 1 h at room temperature. N,N-diisopropylethylamine (35 µl, 200 µmol) was added and stirring was continued over night at room temperature. The crude product was purified by preparative HPLC (Method 4). Lyophilisation of the product containing fractions afforded 22.0 mg (47% of th.) of the title compound.

LC-MS (Method 1): R$_t$=0.83 min: MS (ESIpos): m/z=591 [M+H]$^+$ $^1$H-NMR (400 MHz, DMSO-d6) δ [ppm]: −0.008 (4.21), 0.008 (3.38), 0.068 (1.04), 0.964 (1.14), 0.981 (1.11), 1.148 (0.63), 2.302 (1.14), 2.320 (1.43), 2.366 (0.75), 2.709 (0.82), 2.731 (0.77), 2.798 (0.63), 2.890 (0.99), 2.996 (1.33), 3.134 (1.74), 3.217 (1.84), 3.288 (5.73), 3.559 (1.21), 3.728 (2.03), 3.806 (2.13), 3.830 (2.39), 3.843 (3.38), 3.858 (1.89), 3.867 (3.05), 3.881 (1.64), 3.980 (4.33), 3.988 (4.69), 4.016 (3.31), 4.024 (3.26), 4.067 (0.89), 4.298 (2.25), 5.048 (11.07), 5.065 (2.88), 5.085 (7.40), 5.125 (1.62), 6.902 (5.70), 6.918 (4.30), 7.473 (2.18), 7.477 (2.34), 7.492 (3.31), 7.495 (3.38), 7.506 (2.01), 7.510 (2.37), 7.525 (5.22), 7.529 (5.10), 7.542 (2.92), 7.558 (5.63), 7.577 (4.93), 7.579 (5.00), 7.595 (9.86), 7.600 (9.38), 7.606 (3.84), 7.617 (14.21), 7.622 (10.85), 7.632 (4.62), 7.637 (4.01), 7.646 (3.29), 7.650 (4.18), 7.655 (2.56), 7.664 (1.79), 7.668 (1.60), 7.731 (12.54), 7.735 (16.00), 7.752 (15.59), 7.757 (10.85), 7.769 (4.25), 8.084 (5.53), 8.982 (13.17).

Example 172

5-(4-Chlorophenyl)-2-({1-[2-(morpholin-4-ylcarbonyl)phenyl]-1H-1,2,4-triazol-3-yl}methyl)-4-[(2S)-3,3,3-trifluoro-2-hydroxypropyl]-2,4-dihydro-3H-1,2,4-triazol-3-one

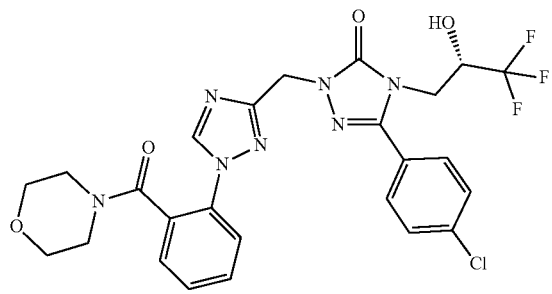 [SMILES: O=C(c1ccccc1-n1cnc(Cn2nc(-c3ccc(Cl)cc3)n(C[C@H](O)C(F)(F)F)c2=O)n1)N1CCOCC1]

Morpholine (17 μl, 200 μmol) was added to a solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl chloride (Example 58A, 41.4 mg, 78.5 μmol) in tetrahydrofuran (1.0 ml). This reaction mixture was stirred for 30 min at room temperature. The crude product was purified by preparative HPLC (Method 4). Lyophilisation of the product containing fractions afforded 44.8 mg (99% of th.) of the title compound.

LC-MS (Method 6): R$_t$=1.16 min; MS (ESIpos): m/z=579 [M+H]$^+$ $^1$H-NMR (400 MHz, DMSO-d6) δ [ppm]: −0.008 (1.74), 0.008 (1.45), 2.938 (1.41), 3.107 (1.45), 3.289 (2.83), 3.390 (1.80), 3.442 (6.92), 3.454 (6.00), 3.485 (2.70), 3.851 (1.64), 3.871 (1.39), 3.979 (2.66), 3.987 (2.95), 4.015 (1.85), 4.023 (1.75), 4.325 (1.36), 5.056 (0.92), 5.096 (11.91), 6.900 (3.63), 6.915 (3.59), 7.457 (3.39), 7.461 (3.71), 7.476 (5.09), 7.480 (5.27), 7.542 (2.31), 7.545 (2.41), 7.560 (5.07), 7.563 (5.04), 7.579 (3.08), 7.582 (3.22), 7.594 (10.26), 7.610 (5.23), 7.615 (16.00), 7.621 (6.86), 7.636 (2.54), 7.639 (2.24), 7.689 (6.25), 7.692 (6.07), 7.709 (4.18), 7.712 (3.75), 7.738 (10.52), 7.759 (7.95), 8.896 (10.20).

Example 173

N-(2-Amino-2-methylpropyl)-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzamide

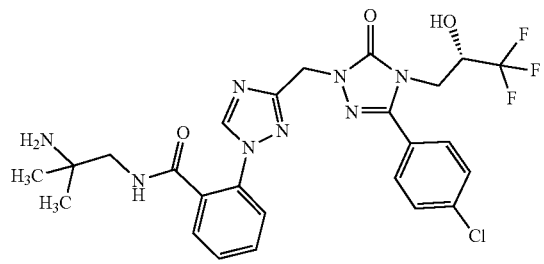 [SMILES: CC(C)(N)CNC(=O)c1ccccc1-n1cnc(Cn2nc(-c3ccc(Cl)cc3)n(C[C@H](O)C(F)(F)F)c2=O)n1]

2-Methylpropane-1,2-diamine (1.5 ml, 15 mmol) was added to a solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl chloride (Example 58A, 3.11 g, 5.90 mmol) in tetrahydrofuran (75 ml). This reaction mixture was stirred for 30 min at room temperature. The crude product was purified by preparative HPLC (Method 4). Lyophilisation of the product containing fractions afforded 2.45 g (72% of th.) of the title compound.

LC-MS (Method 6): R$_t$=0.85 min; MS (ESIpos): m/z=579 [M+H]$^+$ $^1$H-NMR (400 MHz, DMSO-d6) δ [ppm]: 1.050 (15.92), 1.070 (16.00), 3.169 (3.36), 3.184 (3.32), 3.807 (1.04), 3.831 (1.19), 3.844 (1.55), 3.868 (1.66), 3.967 (1.68), 3.975 (1.96), 4.003 (1.24), 4.011 (1.18), 4.304 (0.77), 4.320 (1.05), 4.337 (0.72), 5.040 (5.72), 5.046 (5.86), 5.086 (0.60), 7.558 (0.57), 7.571 (1.49), 7.575 (1.90), 7.592 (2.95), 7.608 (8.60), 7.614 (4.48), 7.619 (3.41), 7.625 (2.66), 7.630 (7.92), 7.637 (2.77), 7.650 (3.45), 7.654 (3.16), 7.669 (2.07), 7.672 (1.98), 7.757 (0.93), 7.763 (7.28), 7.768 (2.62), 7.779 (2.05), 7.784 (5.68), 7.790 (1.09), 8.328 (1.21), 8.758 (1.48), 8.775 (9.08).

Example 174

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(2,2,2-trifluoroethyl)benzamide

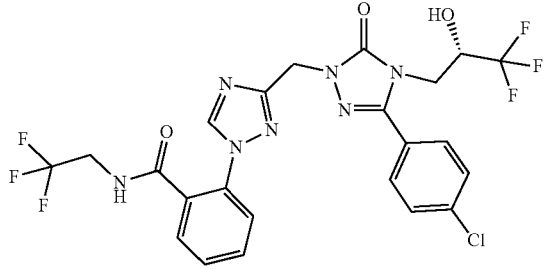 [SMILES: O=C(NCC(F)(F)F)c1ccccc1-n1cnc(Cn2nc(-c3ccc(Cl)cc3)n(C[C@H](O)C(F)(F)F)c2=O)n1]

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl chloride (Example 58A, 417 mg, 790 μmol) and N,N- diisopropylethylamine (210 µl, 1.2 mmol) were dissolved in tetrahydrofuran (10 ml) and 2,2,2-trifluoroethanamine (160 µl, 2.0 mmol) was added. This reaction mixture was stirred for 1 h at room temperature. The crude product was purified by preparative HPLC (Method 4). Lyophilisation of the product containing fractions afforded 355 mg (76% of th.) of the title compound.

LC-MS (Method 5): $R_t$=1.74 min; MS (ESIpos): m/z=590 [M+H]$^+$ $^1$H-NMR (400 MHz, DMSO-d6) δ [ppm]: 2.273 (1.31), 3.291 (1.49), 3.814 (2.04), 3.833 (1.78), 3.838 (2.80), 3.851 (4.12), 3.856 (3.97), 3.874 (5.57), 3.881 (3.75), 3.897 (3.03), 3.921 (0.97), 3.975 (2.65), 3.984 (2.84), 4.012 (1.83), 4.021 (1.66), 4.288 (0.98), 4.304 (1.52), 4.321 (1.40), 4.928 (0.73), 5.034 (16.00), 6.906 (5.07), 6.921 (4.96), 7.551 (1.18), 7.555 (1.88), 7.567 (7.51), 7.574 (7.54), 7.580 (3.88), 7.587 (3.83), 7.594 (2.24), 7.601 (9.06), 7.617 (4.09), 7.622 (11.28), 7.628 (2.64), 7.639 (2.31), 7.650 (9.51), 7.658 (7.09), 7.662 (3.70), 7.669 (2.60), 7.688 (0.67), 7.738 (2.16), 7.744 (11.17), 7.749 (4.22), 7.761 (3.46), 7.766 (8.39), 7.772 (1.53), 8.750 (11.86), 8.954 (2.04), 8.969 (4.04), 8.985 (1.91).

Example 175

5-(4-Chlorophenyl)-2-[(1-{2-[(4,4-difluoropiperidin-1-yl)carbonyl]phenyl}-1H-1,2,4-triazol-3-yl)methyl]-4-[(2S)-3,3,3-trifluoro-2-hydroxypropyl]-2,4-dihydro-3H-1,2,4-triazol-3-one

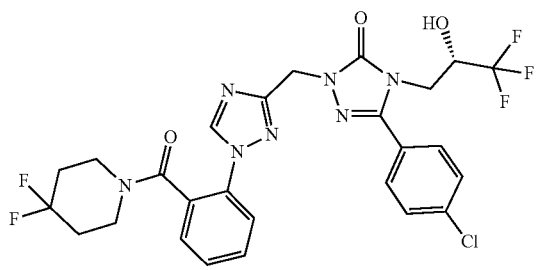 [SMILES: O=C(c1ccccc1-n1cnc(Cn2nc(-c3ccc(Cl)cc3)n(C[C@H](O)C(F)(F)F)c2=O)n1)N1CCC(F)(F)CC1]

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl chloride (Example 58A, 45.0 mg, 85.3 µmol) and N,N-diisopropylethylamine (45 µl, 260 µmol) were dissolved in tetrahydrofuran (2.0 ml) and 4,4-difluoropiperidine hydrochloride (33.6 mg, 213 µmol) was added. This reaction mixture was stirred for 30 min at room temperature. The crude product was purified by preparative HPLC (Method 4). Lyophilisation of the product containing fractions afforded 14.3 mg (25% of th.) of the title compound.

LC-MS (Method 6): $R_t$=1.31 min; MS (ESIpos): m/z=612 [M+H]$^+$ $^1$H-NMR (400 MHz, DMSO-d6) δ [ppm]: −0.008 (3.27), 0.008 (2.96), 1.948 (2.92), 2.073 (0.60), 2.299 (6.27), 3.208 (1.40), 3.273 (2.47), 3.288 (4.29), 3.577 (1.73), 3.613 (1.10), 3.649 (1.12), 3.835 (1.60), 3.864 (1.27), 3.960 (3.01), 3.968 (3.33), 3.996 (2.07), 4.004 (1.95), 4.308 (1.39), 4.994 (0.97), 5.034 (10.12), 5.040 (7.94), 5.080 (0.69), 6.885 (1.22), 6.901 (2.52), 6.909 (2.58), 6.923 (1.60), 7.521 (1.86), 7.525 (2.34), 7.540 (5.14), 7.544 (5.39), 7.553 (3.10), 7.556 (2.97), 7.561 (1.17), 7.571 (4.77), 7.574 (4.90), 7.590 (2.15), 7.593 (2.33), 7.604 (7.43), 7.610 (6.54), 7.615 (4.46), 7.625 (11.85), 7.632 (8.28), 7.639 (3.48), 7.648 (2.60), 7.652 (2.18), 7.709 (5.17), 7.712 (5.29), 7.721 (2.74), 7.728 (16.00), 7.732 (7.19), 7.744 (4.18), 7.749 (9.89), 7.755 (1.28), 8.925 (8.47).

Example 176

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(1,1-dioxidothietan-3-yl)benzamide

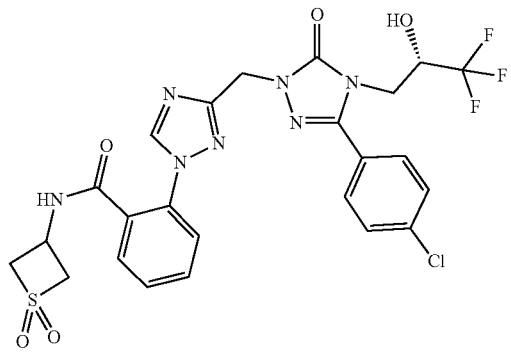 [SMILES: O=C(NC1CS(=O)(=O)C1)c1ccccc1-n1cnc(Cn2nc(-c3ccc(Cl)cc3)n(C[C@H](O)C(F)(F)F)c2=O)n1]

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl chloride (Example 58A, 52.7 mg, 100 µmol) and thietan-3-amine 1,1-dioxide hydrochloride (39.4 mg, 250 µmol) were dissolved in tetrahydrofuran. N,N-diisopropylethylamine (44 µl, 250 µmol) and thietan-3-amine 1,1-dioxide hydrochloride (39.4 mg, 250 µmol) was added. This reaction mixture was stirred for 1 h at room temperature. The crude product was purified by preparative HPLC (Method 4). Lyophilisation of the product containing fractions afforded 44.0 mg (72% of th.) of the title compound.

LC-MS (Method 1): $R_t$=0.89 min; MS (ESIpos): m/z=612 [M+H]$^+$ $^1$H-NMR (400 MHz, DMSO-d6) δ [ppm]: −0.008 (1.59), 0.008 (1.51), 0.069 (0.72), 2.287 (1.48), 3.289 (1.73), 3.813 (1.90), 3.836 (2.16), 3.849 (2.70), 3.873 (2.89), 3.982 (2.73), 3.991 (3.03), 4.019 (1.98), 4.027 (1.88), 4.092 (3.76), 4.103 (4.41), 4.109 (2.40), 4.120 (1.59), 4.128 (4.29), 4.141 (5.11), 4.286 (0.96), 4.295 (1.25), 4.303 (1.60), 4.321 (1.69), 4.334 (1.59), 4.346 (1.66), 4.356 (2.04), 4.368 (1.85), 4.378 (1.85), 4.390 (1.75), 4.401 (0.80), 4.436 (5.01), 4.443 (2.01), 4.454 (2.14), 4.459 (2.84), 4.464 (2.56), 4.471 (3.98), 4.484 (1.13), 4.493 (2.60), 4.968 (0.73), 5.073 (16.00), 6.904 (5.45), 6.920 (5.47), 7.557 (0.83), 7.566 (1.15), 7.576 (2.89), 7.584 (4.07), 7.586 (4.42), 7.591 (5.57), 7.595 (11.41), 7.601 (12.32), 7.606 (5.11), 7.610 (2.74), 7.613 (2.57), 7.617 (4.77), 7.622 (13.26), 7.628 (2.32), 7.644 (1.69), 7.652 (8.75), 7.655 (9.44), 7.661 (8.20), 7.739 (2.09), 7.745 (13.36), 7.750 (4.31), 7.762 (3.86), 7.767 (9.97), 7.773 (1.38), 8.848 (14.55), 9.116 (4.61), 9.129 (4.43).

Example 177

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-[2-(2-oxopyrrolidin-1-yl)ethyl]benzamide

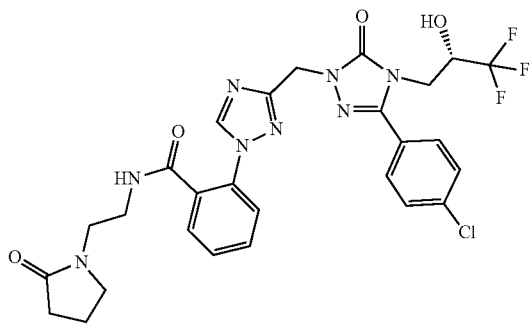 [SMILES: O=C(NCCN1CCCC1=O)c1ccccc1-n1cnc(Cn2nc(-c3ccc(Cl)cc3)n(C[C@H](O)C(F)(F)F)c2=O)n1]

1-(2-Aminoethyl)pyrrolidin-2-one (32.0 mg, 250 µmol) was added to a solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl chloride (Example 58A, 52.7 mg, 100 µmol) in tetrahydrofuran (1.5 ml). This reaction mixture was stirred for 1 h at room temperature. The crude product was purified by preparative HPLC (Method 4). Lyophilisation of the product containing fractions afforded 44.5 mg (72% of th.) of the title compound.

LC-MS (Method 1): $R_t$=0.87 min; MS (ESIpos): m/z=619 [M+H]$^+$ $^1$H-NMR (400 MHz, DMSO-d6) δ [ppm]: 1.838 (0.95), 1.857 (1.46), 1.876 (1.08), 2.141 (1.59), 2.162 (2.37), 2.182 (1.18), 3.291 (1.80), 3.313 (16.00), 3.327 (1.79), 3.836 (0.61), 3.848 (0.76), 3.873 (0.83), 3.973 (0.76), 3.981 (0.85), 5.071 (4.94), 6.916 (1.36), 6.932 (1.32), 7.538 (2.23), 7.543 (2.47), 7.552 (1.12), 7.557 (1.22), 7.576 (0.68), 7.598 (2.14), 7.603 (2.71), 7.608 (3.64), 7.613 (1.39), 7.618 (1.04), 7.624 (1.98), 7.629 (4.14), 7.750 (3.92), 7.755 (1.22), 7.767 (1.08), 7.772 (2.82), 8.491 (0.96), 8.747 (4.47).

Example 178

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-{[(2S)-5-oxopyrrolidin-2-yl]methyl}benzamide

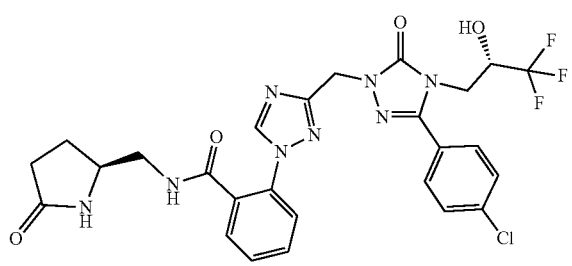 [SMILES: O=C1CC[C@@H](CNC(=O)c2ccccc2-n2cnc(Cn3nc(-c4ccc(Cl)cc4)n(C[C@H](O)C(F)(F)F)c3=O)n2)N1]

(5S)-5-(Aminomethyl)pyrrolidin-2-one (22.8 mg, 200 µmol) was added to a solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl chloride (Example 58A, 42.2 mg, 80.0 µmol) in tetrahydrofuran (1.0 ml). This reaction mixture was stirred for 1 h at room temperature. N,N-diisopropylethylamine (35 µl, 200 µmol) was added and stirring was continued over night at room temperature. The crude product was purified by preparative HPLC (Method 4). Lyophilisation of the product containing fractions afforded 23.9 mg (49% of th.) of the title compound.

LC-MS (Method 1): $R_t$=0.83 min; MS (ESIpos): m/z=605 [M+H]$^+$ $^1$H-NMR (400 MHz, DMSO-d6) δ [ppm]: −0.008 (1.68), 0.008 (1.43), 1.560 (0.76), 1.574 (1.56), 1.590 (1.08), 1.599 (1.28), 1.609 (1.05), 1.971 (0.82), 1.976 (0.78), 1.994 (1.34), 2.006 (0.95), 2.012 (1.73), 2.018 (1.49), 2.023 (2.48), 2.049 (2.76), 2.064 (3.02), 2.070 (2.50), 2.082 (1.15), 2.087 (1.64), 2.094 (1.90), 2.100 (2.00), 2.117 (2.07), 2.141 (0.83), 2.256 (0.97), 3.043 (0.66), 3.058 (1.23), 3.076 (1.61), 3.092 (2.41), 3.107 (1.30), 3.133 (1.24), 3.148 (2.44), 3.163 (1.70), 3.181 (1.25), 3.196 (0.69), 3.289 (1.56), 3.549 (1.29), 3.564 (1.87), 3.580 (1.41), 3.815 (1.50), 3.839 (1.68), 3.851 (2.16), 3.875 (2.35), 3.975 (2.17), 3.983 (2.48), 4.011 (1.50), 4.020 (1.45), 4.299 (1.20), 4.316 (1.16), 5.063 (14.11), 6.909 (4.38), 6.924 (4.30), 7.528 (5.13), 7.544 (1.37), 7.549 (1.43), 7.558 (1.44), 7.565 (2.81), 7.578 (2.09), 7.584 (3.42), 7.592 (2.12), 7.599 (2.11), 7.606 (12.17), 7.612 (16.00), 7.622 (4.78), 7.627 (13.69), 7.632 (5.62), 7.647 (0.83), 7.652 (0.69), 7.738 (1.72), 7.744 (10.88), 7.749 (3.39), 7.761 (3.06), 7.766 (7.95), 7.772 (1.10), 8.456 (1.64), 8.471 (3.24), 8.485 (1.52), 8.731 (0.76), 8.740 (12.42).

Example 179

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-{[(2R)-5-oxopyrrolidin-2-yl]methyl}benzamide

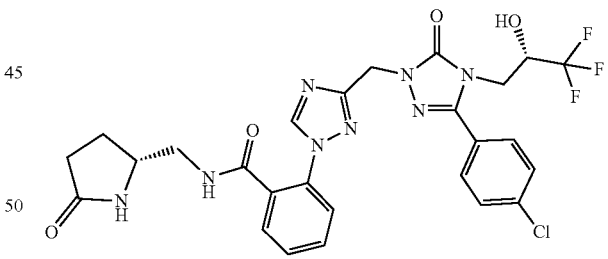

(5R)-5-(Aminomethyl)pyrrolidin-2-one (22.8 mg, 200 µmol) was added to a solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl chloride (Example 58A, 42.2 mg, 80.0 µmol) in tetrahydrofuran (1.0 ml). This reaction mixture was stirred for 1 h at room temperature. N,N-diisopropylethylamine (35 µl, 200 µmol) was added and stirring was continued over night at room temperature. The crude product was purified by preparative HPLC (Method 4). Lyophilisation of the product containing fractions afforded 12.8 mg (26% of th.) of the title compound.

LC-MS (Method 1): $R_t$=0.83 min; MS (ESIpos): m/z=605 [M+H]$^+$

¹H-NMR (400 MHz, DMSO-d6) δ [ppm]: −0.008 (1.43), 0.008 (1.44), 0.068 (0.69), 1.559 (0.77), 1.575 (1.58), 1.592 (1.05), 1.600 (1.35), 1.611 (1.06), 1.972 (0.87), 1.977 (0.82), 1.990 (0.85), 1.995 (1.38), 2.007 (0.93), 2.013 (1.78), 2.019 (1.48), 2.025 (2.39), 2.050 (2.89), 2.065 (3.17), 2.071 (2.18), 2.079 (1.09), 2.088 (1.95), 2.092 (2.15), 2.098 (2.15), 2.115 (2.05), 2.139 (0.94), 2.256 (1.46), 2.731 (0.99), 2.890 (1.36), 3.047 (0.62), 3.062 (1.16), 3.080 (1.70), 3.096 (2.53), 3.111 (1.38), 3.124 (1.34), 3.139 (2.53), 3.154 (1.70), 3.172 (1.16), 3.187 (0.66), 3.289 (1.81), 3.550 (1.32), 3.565 (1.87), 3.582 (1.41), 3.813 (1.52), 3.837 (1.72), 3.850 (2.22), 3.873 (2.36), 3.976 (2.36), 3.984 (2.64), 4.013 (1.62), 4.021 (1.53), 4.286 (0.77), 4.302 (1.30), 4.320 (1.22), 4.953 (0.71), 5.062 (14.48), 6.914 (4.18), 6.930 (4.20), 7.522 (5.10), 7.544 (1.52), 7.549 (1.70), 7.553 (1.04), 7.558 (1.69), 7.565 (2.82), 7.568 (2.37), 7.578 (2.03), 7.584 (3.51), 7.593 (2.21), 7.601 (2.63), 7.605 (10.90), 7.612 (16.00), 7.621 (5.12), 7.627 (13.66), 7.632 (5.89), 7.647 (0.86), 7.652 (0.71), 7.739 (1.68), 7.745 (10.74), 7.750 (3.91), 7.762 (3.03), 7.767 (8.10), 7.773 (1.38), 8.459 (1.61), 8.473 (3.23), 8.488 (1.51), 8.728 (1.10), 8.743 (11.72).

Example 180

N-[(3S)-1-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl}pyrrolidin-3-yl]acetamide

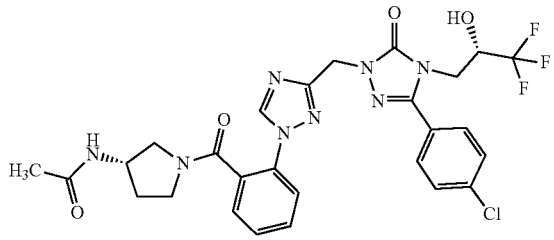 [SMILES: CC(=O)N[C@H]1CCN(C(=O)c2ccccc2-n2cnc(Cn3nc(-c4ccc(Cl)cc4)n(C[C@H](O)C(F)(F)F)c3=O)n2)C1]

N-[(3S)-Pyrrolidin-3-yl]acetamide (32.0 mg, 250 µmol) was added to a solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl chloride (Example 58A, 52.7 mg, 100 µmol) in tetrahydrofuran (1.5 ml). This reaction mixture was stirred for 1 h at room temperature. The crude product was purified by preparative HPLC (Method 4). Lyophilisation of the product containing fractions afforded 46.9 mg (76% of th.) of the title compound as mixture of rotamers.

LC-MS (Method 1): $R_t$=0.86 min; MS (ESIpos): m/z=619 [M+H]⁺

¹H-NMR (400 MHz, DMSO-d6) δ [ppm]: −0.008 (1.48), 0.008 (1.32), 1.638 (1.00), 1.655 (1.23), 1.670 (1.10), 1.754 (16.00), 1.780 (0.73), 1.806 (1.06), 1.816 (13.25), 1.886 (0.80), 1.903 (0.95), 1.918 (0.88), 2.271 (0.66), 2.857 (0.75), 3.169 (0.94), 3.188 (1.52), 3.199 (1.30), 3.215 (1.24), 3.232 (0.92), 3.289 (1.72), 3.517 (0.73), 3.534 (0.82), 3.548 (0.70), 3.820 (1.18), 3.844 (1.37), 3.856 (1.77), 3.880 (1.92), 3.982 (2.02), 3.990 (2.27), 4.019 (1.74), 4.026 (2.18), 4.040 (0.96), 4.294 (1.12), 4.311 (1.05), 5.079 (8.88), 5.083 (7.75), 6.904 (2.16), 6.910 (2.53), 6.920 (2.20), 6.926 (2.45), 7.476 (1.15), 7.480 (1.30), 7.495 (2.24), 7.499 (2.84), 7.516 (1.74), 7.520 (1.85), 7.534 (1.02), 7.537 (1.08), 7.546 (0.98), 7.549 (1.20), 7.552 (2.06), 7.555 (1.99), 7.564 (1.69), 7.567 (1.69), 7.571 (1.33), 7.574 (1.16), 7.582 (0.93), 7.586 (1.00), 7.592 (1.69), 7.598 (4.69), 7.607 (5.08), 7.612 (4.35), 7.615 (4.81), 7.620 (6.47), 7.629 (6.46), 7.635 (2.38), 7.639 (0.97), 7.691 (2.45), 7.694 (3.44), 7.710 (1.66), 7.714 (2.33), 7.718 (1.31), 7.744 (5.57), 7.748 (7.08), 7.753 (2.11), 7.760 (1.63), 7.765 (4.96), 7.770 (4.65), 7.963 (1.23), 7.979 (1.16), 8.018 (0.97), 8.034 (0.93), 8.833 (5.12), 8.847 (5.84).

Example 181

5-(4-Chlorophenyl)-2-[(1-{2-[(3,3-dimethylpiperazin-1-yl)carbonyl]phenyl}-1H-1,2,4-triazol-3-yl)methyl]-4-[(2S)-3,3,3-trifluoro-2-hydroxypropyl]-2,4-dihydro-3H-1,2,4-triazol-3-one

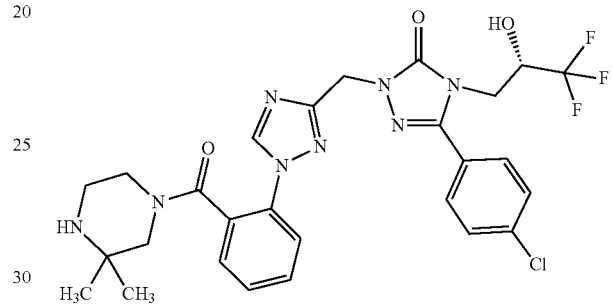

2,2-Dimethylpiperazine (22.8 mg, 200 µmol) was added to a solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl chloride (Example 58A, 42.2 mg, 80.0 µmol) in tetrahydrofuran (1.0 ml). This reaction mixture was stirred for 1 h at room temperature. The crude product was purified by preparative HPLC (Method 4). Lyophilisation of the product containing fractions afforded 37.0 mg (76% of th.) of the title compound as mixture of rotamers.

LC-MS (Method 2): $R_t$=1.09 min; MS (ESIpos): m/z=609 [M+H]⁺

¹H-NMR (400 MHz, DMSO-d6) δ [ppm]: −0.149 (0.64), −0.008 (6.29), 0.008 (4.83), 0.146 (0.58), 0.783 (12.46), 0.813 (10.77), 0.952 (10.43), 0.998 (5.43), 1.017 (8.67), 1.052 (11.09), 1.088 (10.41), 1.147 (0.66), 2.040 (0.74), 2.073 (1.22), 2.277 (0.76), 2.366 (0.80), 2.475 (2.30), 2.670 (3.62), 2.699 (3.36), 2.879 (3.40), 3.059 (2.10), 3.138 (1.70), 3.170 (3.10), 3.201 (3.14), 3.225 (2.96), 3.255 (1.58), 3.283 (2.68), 3.314 (2.16), 3.792 (2.72), 3.817 (3.48), 3.829 (4.35), 3.853 (4.55), 3.965 (5.07), 3.973 (5.23), 4.001 (4.67), 4.009 (4.11), 4.391 (1.28), 4.984 (1.36), 4.998 (1.84), 5.012 (1.52), 5.025 (2.24), 5.039 (3.76), 5.052 (3.88), 5.084 (5.09), 5.103 (3.42), 5.123 (1.46), 5.143 (1.80), 5.160 (2.02), 5.203 (1.26), 7.376 (1.50), 7.396 (2.32), 7.422 (1.28), 7.475 (2.58), 7.490 (3.78), 7.512 (1.22), 7.528 (2.24), 7.546 (2.94), 7.567 (3.62), 7.584 (4.91), 7.598 (12.32), 7.613 (14.48), 7.618 (16.00), 7.633 (10.15), 7.660 (4.55), 7.680 (2.38), 7.709 (2.96), 7.728 (2.18), 7.760 (5.41), 7.780 (9.15), 7.801 (6.51), 7.816 (6.05), 7.838 (3.48), 8.168 (14.96), 8.813 (5.01), 8.886 (4.91), 8.913 (2.00), 8.977 (3.66).

Example 182

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(3,3,3-trifluoropropyl)benzamide

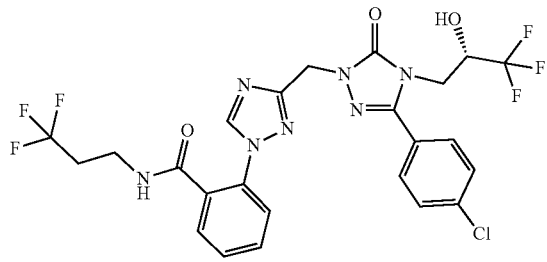 [SMILES: O=C(NCCC(F)(F)F)c1ccccc1-n1cnc(Cn2nc(-c3ccc(Cl)cc3)n(C[C@H](O)C(F)(F)F)c2=O)n1]

3,3,3-Trifluoropropan-1-amine (22.6 mg, 200 µmol) was added to a solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl chloride (Example 58A, 42.2 mg, 80.0 µmol) in tetrahydrofuran (1.0 ml). This reaction mixture was stirred for 1 h at room temperature. The crude product was purified by preparative HPLC (Method 4). Lyophilisation of the product containing fractions afforded 34.0 mg (70% of th.) of the title compound.

LC-MS (Method 2): $R_t$=1.80 min; MS (ESIpos): m/z=604 [M+H]$^+$ $^1$H-NMR (400 MHz, DMSO-d6) δ [ppm]: −0.008 (1.73), 0.008 (1.46), 2.264 (1.26), 2.371 (1.00), 2.382 (1.42), 2.389 (0.86), 2.399 (2.53), 2.410 (1.53), 2.418 (1.80), 2.428 (2.45), 2.446 (1.57), 2.456 (0.85), 3.276 (2.04), 3.290 (3.95), 3.293 (4.33), 3.326 (1.98), 3.810 (1.38), 3.834 (1.57), 3.847 (1.99), 3.870 (2.16), 3.970 (1.95), 3.978 (2.16), 4.006 (1.36), 4.014 (1.28), 4.305 (1.05), 4.322 (1.01), 5.056 (12.34), 6.905 (3.90), 6.921 (3.92), 7.529 (1.15), 7.533 (1.09), 7.547 (4.38), 7.551 (6.31), 7.557 (2.49), 7.564 (2.54), 7.570 (2.95), 7.584 (1.03), 7.589 (1.54), 7.595 (1.16), 7.601 (7.80), 7.606 (4.00), 7.622 (16.00), 7.634 (2.78), 7.639 (2.11), 7.737 (1.53), 7.743 (10.08), 7.749 (2.97), 7.760 (2.70), 7.765 (7.28), 7.771 (0.95), 8.554 (1.48), 8.568 (2.98), 8.582 (1.42), 8.753 (12.05).

Example 183

5-(4-Chlorophenyl)-2-{[1-(2-{[3-hydroxy-3-methylpyrrolidin-1-yl]carbonyl}phenyl)-1H-1,2,4-triazol-3-yl]methyl}-4-[(2S)-3,3,3-trifluoro-2-hydroxypropyl]-2,4-dihydro-3H-1,2,4-triazol-3-one (Diastereomeric Mixture)

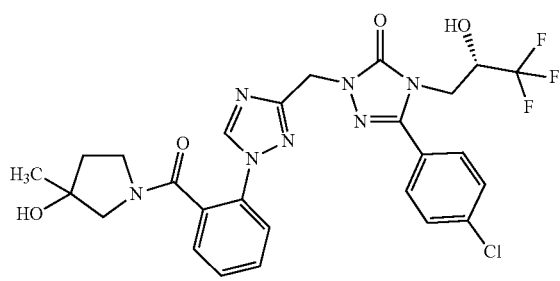 [SMILES: CC1(O)CCN(C(=O)c2ccccc2-n2cnc(Cn3nc(-c4ccc(Cl)cc4)n(C[C@H](O)C(F)(F)F)c3=O)n2)C1]

3-Methylpyrrolidin-3-ol (48.0 mg, 474 µmol) was added to a solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl chloride (Example 58A, 100 mg, 190 µmol) in tetrahydrofuran (2.4 ml). This reaction mixture was stirred for 1 h at room temperature. The crude product was purified by preparative HPLC (Method 4). Lyophilisation of the product containing fractions afforded 79.0 mg (70% of th.) of the title compound.

LC-MS (Method 2): $R_t$=1.57 min; MS (ESIpos): m/z=592 [M+H]$^+$ $^1$H-NMR (400 MHz, DMSO-d6) δ [ppm]: −0.008 (2.63), 0.008 (2.38), 1.085 (7.72), 1.092 (8.31), 1.113 (0.78), 1.123 (0.65), 1.209 (8.30), 1.215 (9.30), 1.656 (2.27), 1.676 (3.88), 1.692 (2.26), 1.734 (1.11), 1.744 (1.15), 2.073 (0.90), 2.266 (1.14), 2.881 (0.80), 2.932 (3.04), 2.958 (1.65), 3.118 (1.01), 3.137 (1.44), 3.167 (1.88), 3.193 (1.80), 3.223 (0.88), 3.233 (0.91), 3.289 (1.64), 3.339 (1.46), 3.398 (0.93), 3.407 (0.76), 3.420 (1.39), 3.430 (1.80), 3.451 (2.00), 3.473 (0.93), 3.807 (1.79), 3.830 (2.04), 3.844 (2.72), 3.868 (2.95), 3.976 (3.26), 4.005 (1.70), 4.011 (2.03), 4.305 (1.73), 4.788 (8.27), 4.798 (6.32), 5.059 (8.93), 5.071 (11.52), 6.910 (3.67), 6.917 (3.74), 6.926 (3.77), 6.932 (3.48), 7.462 (2.09), 7.466 (2.33), 7.481 (5.10), 7.485 (4.02), 7.496 (2.94), 7.501 (3.06), 7.534 (2.87), 7.552 (5.47), 7.572 (2.95), 7.588 (1.60), 7.594 (2.88), 7.599 (3.56), 7.607 (13.51), 7.613 (7.84), 7.618 (4.28), 7.624 (5.74), 7.628 (16.00), 7.633 (5.32), 7.679 (3.95), 7.683 (4.92), 7.687 (3.48), 7.699 (2.64), 7.703 (3.09), 7.707 (2.27), 7.736 (1.72), 7.742 (10.04), 7.746 (10.79), 7.751 (3.23), 7.759 (3.11), 7.764 (8.39), 7.768 (6.93), 7.774 (1.07), 8.765 (7.47), 8.796 (4.92), 8.799 (5.42).

Example 184

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-[(1,1-dioxidothietan-3-yl)methyl]benzamide

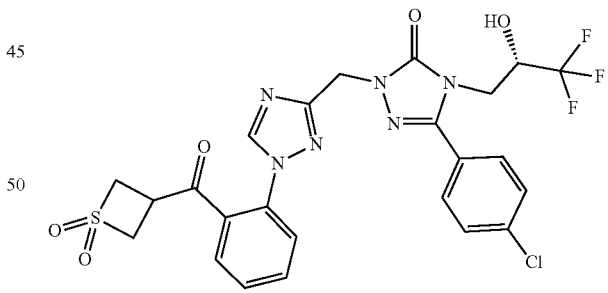

1-(1,1-Dioxidothietan-3-yl)methanamine (33.8 mg, 250 µmol) was added to a solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl chloride (Example 58A, 52.7 mg, 100 µmol) in tetrahydrofuran (1.5 ml). This reaction mixture was stirred for 1 h at room temperature. N,N-diisopropylethylamine (44 µl, 250 µmol) was added and the reaction mixture was stirred for 72 h at room temperature. The crude product was purified by preparative HPLC (Method 4). Lyophilisation of the product containing fractions afforded 29.0 mg (46% of th.) of the title compound.

LC-MS (Method 2): R$_t$=1.55 min; MS (ESIpos): m/z=626 [M+H]$^+$ $^1$H-NMR (400 MHz, DMSO-d6) δ [ppm]: −0.008 (1.79), 0.008 (1.65), 2.267 (1.18), 2.635 (0.98), 2.644 (1.17), 2.650 (1.00), 2.659 (1.76), 2.668 (1.15), 2.674 (1.33), 2.683 (1.02), 3.288 (2.17), 3.341 (4.21), 3.357 (6.78), 3.373 (3.88), 3.815 (2.06), 3.825 (3.52), 3.840 (5.14), 3.851 (3.78), 3.862 (4.45), 3.877 (6.33), 3.982 (2.62), 3.990 (2.92), 4.018 (1.87), 4.026 (1.78), 4.135 (4.02), 4.159 (4.36), 4.168 (3.28), 4.171 (3.63), 4.195 (2.97), 4.287 (0.87), 4.304 (1.47), 4.320 (1.40), 5.081 (16.00), 6.905 (5.22), 6.921 (5.17), 7.554 (0.78), 7.558 (0.76), 7.573 (2.85), 7.578 (2.82), 7.587 (7.92), 7.592 (9.48), 7.608 (10.91), 7.613 (4.78), 7.618 (6.90), 7.624 (11.76), 7.629 (15.94), 7.638 (3.51), 7.643 (2.77), 7.650 (0.91), 7.657 (0.82), 7.663 (0.73), 7.745 (1.95), 7.752 (12.34), 7.757 (4.19), 7.768 (3.52), 7.773 (9.17), 7.779 (1.45), 8.648 (1.94), 8.663 (3.95), 8.678 (1.85), 8.768 (13.70).

Example 185

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-[2-(2-oxoimidazolidin-1-yl)ethyl]benzamide

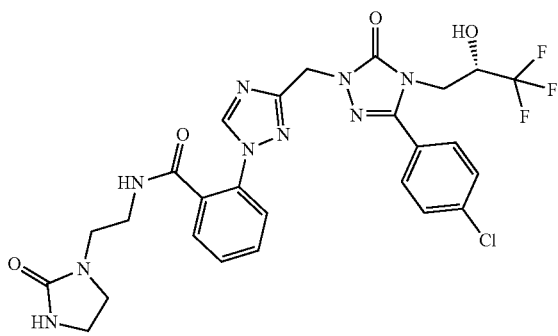 [SMILES: O=C(NCCN1CCNC1=O)c1ccccc1-n1cnc(Cn2nc(-c3ccc(Cl)cc3)n(C[C@H](O)C(F)(F)F)c2=O)n1]

1-(2-Aminoethyl)imidazolidin-2-one (32.3 mg, 250 µmol) was added to a solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl chloride (Example 58A, 52.7 mg, 100 µmol) in tetrahydrofuran (1.5 ml). This reaction mixture was stirred for 1 h at room temperature. The crude product was purified by preparative HPLC (Method 4). Lyophilisation of the product containing fractions afforded 37.9 mg (61% of th.) of the title compound.

LC-MS (Method 2): R$_t$=1.43 min; MS (ESIpos): m/z=620 [M+H]$^+$ $^1$H-NMR (400 MHz, DMSO-d6) δ [ppm]: −0.008 (1.03), 2.251 (1.30), 3.080 (2.44), 3.096 (7.00), 3.111 (4.72), 3.165 (2.82), 3.175 (3.77), 3.184 (7.29), 3.188 (8.81), 3.204 (8.80), 3.220 (1.50), 3.296 (5.74), 3.335 (2.75), 3.812 (1.74), 3.836 (1.97), 3.849 (2.52), 3.873 (2.69), 3.976 (3.50), 3.984 (2.83), 4.013 (1.77), 4.021 (1.67), 4.289 (0.83), 4.305 (1.42), 4.313 (1.20), 4.322 (1.33), 4.962 (0.63), 5.074 (16.00), 6.264 (6.04), 6.917 (5.08), 6.932 (4.92), 7.520 (0.74), 7.525 (0.71), 7.539 (2.60), 7.544 (2.84), 7.553 (7.52), 7.558 (9.18), 7.571 (1.56), 7.579 (1.08), 7.584 (1.99), 7.599 (6.48), 7.602 (10.74), 7.606 (13.57), 7.617 (3.37), 7.623 (6.26), 7.628 (12.38), 7.634 (2.10), 7.643 (0.86), 7.746 (1.88), 7.752 (12.31), 7.757 (3.87), 7.768 (3.45), 7.773 (9.08), 7.780 (1.18), 8.463 (1.76), 8.478 (3.73), 8.492 (1.75), 8.741 (13.34).

Example 186

N-(2-Amino-2-methylpropyl)-5-chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzamide

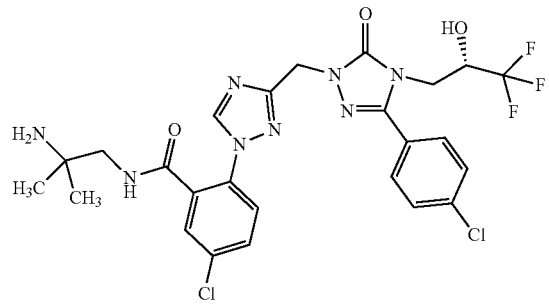 [SMILES: CC(C)(N)CNC(=O)c1cc(Cl)ccc1-n1cnc(Cn2nc(-c3ccc(Cl)cc3)n(C[C@H](O)C(F)(F)F)c2=O)n1]

2-Methylpropane-1,2-diamine (48 µl, 460 µmol) and N,N-diisopropylethylamine (48 µl, 280 µmol) were added to a solution of 5-chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl chloride (Example 59A, 104 mg, 184 µmol) in dichloromethane (3.0 ml). This reaction mixture was stirred for 30 min at room temperature. The crude product was purified by preparative HPLC (Method 4). Lyophilisation of the product containing fractions afforded 74.3 mg (66% of th.) of the title compound.

LC-MS (Method 2): R$_t$=1.19 min MS (ESIpos): m/z=613 [M+H]$^+$ $^1$H-NMR (400 MHz, DMSO-d6) δ [ppm]: −0.008 (1.01), 0.008 (1.09), 1.030 (15.08), 1.052 (16.00), 3.131 (3.30), 3.428 (0.82), 3.807 (1.40), 3.830 (1.52), 3.843 (1.86), 3.867 (1.95), 3.965 (1.92), 3.973 (2.20), 4.001 (1.45), 4.010 (1.35), 4.297 (0.88), 4.313 (1.14), 4.331 (0.76), 4.995 (0.66), 5.034 (5.91), 5.041 (5.86), 5.081 (0.62), 7.609 (5.62), 7.614 (2.32), 7.625 (2.38), 7.630 (7.46), 7.636 (1.31), 7.647 (2.83), 7.669 (5.14), 7.709 (2.56), 7.715 (3.16), 7.730 (1.16), 7.736 (1.97), 7.752 (1.88), 7.758 (10.43), 7.762 (7.05), 7.775 (2.22), 7.780 (6.06), 7.786 (0.93), 8.317 (2.86), 8.788 (1.10), 8.796 (9.97).

Example 187

5-chloro-2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-methylbenzamide

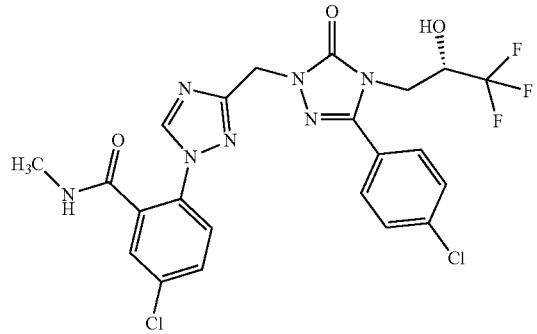 [SMILES: CNC(=O)c1cc(Cl)ccc1-n1cnc(Cn2nc(-c3ccc(Cl)cc3)n(C[C@H](O)C(F)(F)F)c2=O)n1]

Methanamine (230 µl, 2.0 M, 460 µmol) and N,N-diisopropylethylamine (48 µl, 280 µmol) were added to a solution of 5-chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl chloride (Example 59A, 104 mg, 184 µmol) in dichloromethane (3.0 ml). This reaction mixture was stirred for 30 min at room temperature. The crude product was purified by preparative HPLC (Method 4). Lyophilisation of the product containing fractions afforded 77.0 mg (75% of th.) of the title compound.

LC-MS (Method 2): $R_t$=1.69 min; MS (ESIpos): m/z=556 [M+H]$^+$ $^1$H-NMR (500 MHz, DMSO-d6) δ [ppm]: 2.593 (15.34), 2.603 (15.23), 3.295 (1.99), 3.820 (1.57), 3.839 (1.76), 3.849 (2.11), 3.869 (2.25), 3.977 (2.08), 3.984 (2.33), 4.006 (1.58), 4.013 (1.50), 4.305 (1.09), 4.318 (1.04), 5.068 (14.65), 6.917 (3.61), 6.929 (3.63), 7.605 (1.09), 7.610 (8.08), 7.614 (3.03), 7.624 (3.80), 7.628 (16.00), 7.632 (8.26), 7.640 (4.45), 7.657 (7.84), 7.690 (5.08), 7.695 (4.35), 7.708 (2.62), 7.712 (2.42), 7.744 (1.53), 7.750 (10.16), 7.754 (3.24), 7.763 (2.86), 7.767 (7.80), 7.772 (0.99), 8.360 (0.87), 8.370 (2.56), 8.379 (2.56), 8.388 (0.87), 8.731 (12.69).

Example 188

2-[3-({3-(4-Chlorophenyl)-5-oxo-4-[(2S)-3,3,3-trifluoro-2-hydroxypropyl]-4,5-dihydro-1H-1,2,4-triazol-1-yl}ylmethyl)-1H-1,2,4-triazol-1-yl]-N-[(3-methyloxetan-3-yl)methyl]benzamide

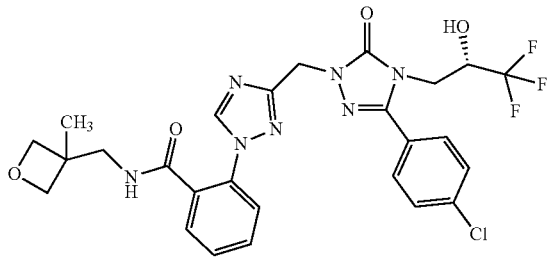 [SMILES: CC1(CNC(=O)c2ccccc2-n2cnc(Cn3nc(-c4ccc(Cl)cc4)n(C[C@H](O)C(F)(F)F)c3=O)n2)COC1]

1-(3-Methyloxetan-3-yl)methanamine (25.3 mg, 250 µmol) was added to a solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl chloride (Example 58A, 52.7 mg, 100 µmol) in tetrahydrofuran (1.5 ml). This reaction mixture was stirred over night at room temperature. The crude product was purified by column chromatography (silica gel, dichloromethane/methanol, 97/3.) to afforded 55.7 mg (94% of th.) of the title compound.

LC-MS (Method 2): $R_t$=1.58 min; MS (ESIpos): m/z=592 [M+H]$^+$ $^1$H-NMR (400 MHz, DMSO-d6) δ [ppm]: 1.113 (16.00), 1.179 (1.00), 1.236 (0.88), 2.261 (0.70), 3.271 (4.22), 3.286 (4.47), 3.815 (0.83), 3.839 (0.95), 3.852 (1.21), 3.876 (1.31), 3.975 (1.23), 3.984 (1.36), 4.012 (0.86), 4.020 (0.83), 4.109 (5.65), 4.123 (6.30), 4.296 (4.16), 4.299 (4.26), 4.310 (3.81), 4.313 (3.78), 5.045 (7.87), 5.754 (2.14), 6.908 (2.43), 6.924 (2.41), 7.568 (2.98), 7.571 (3.50), 7.582 (5.20), 7.598 (3.53), 7.601 (4.65), 7.604 (5.62), 7.610 (3.64), 7.621 (4.26), 7.626 (6.27), 7.630 (2.50), 7.641 (0.84), 7.741 (0.96), 7.747 (5.79), 7.752 (2.08), 7.764 (1.68), 7.769 (4.32), 8.514 (0.92), 8.529 (1.87), 8.544 (0.87), 8.716 (6.56).

Example 189

1-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl}azetidine-3-carboxamide

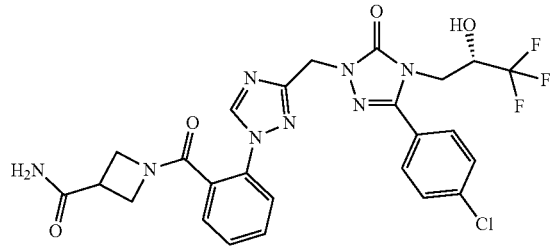 [SMILES: NC(=O)C1CN(C(=O)c2ccccc2-n2cnc(Cn3nc(-c4ccc(Cl)cc4)n(C[C@H](O)C(F)(F)F)c3=O)n2)C1]

Azetidine-3-carboxamide (25.0 mg, 250 µmol) was added to a solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl chloride (Example 58A, 52.7 mg, 100 µmol) in tetrahydrofuran (1.5 ml). This reaction mixture was stirred over night at room temperature. N,N-diisopropylethylamine (44 µl, 250 µmol) was added and stirring was continued for 5 h. The crude product was purified by preparative HPLC (Method 4). Lyophilisation of the product containing fractions afforded 35.0 mg (59% of th.) of the title compound.

LC-MS (Method 2): $R_t$=1.41 min; MS (ESIpos): m/z=591 [M+H]$^+$ $^1$H-NMR (400 MHz, DMSO-d6) δ [ppm]: −0.008 (1.38), 0.008 (1.58), 2.283 (1.32), 3.246 (1.35), 3.252 (1.30), 3.262 (2.04), 3.267 (2.05), 3.276 (1.48), 3.289 (2.56), 3.824 (1.99), 3.836 (1.29), 3.848 (3.24), 3.860 (5.32), 3.884 (5.03), 3.902 (2.79), 3.909 (2.80), 3.930 (2.17), 3.944 (1.64), 3.953 (2.41), 3.959 (2.25), 3.969 (2.06), 3.974 (2.02), 3.989 (3.00), 3.998 (3.57), 4.005 (2.12), 4.027 (4.40), 4.033 (3.83), 4.056 (2.65), 4.080 (0.92), 4.311 (1.57), 4.329 (1.52), 5.128 (16.00), 6.925 (4.59), 6.942 (4.58), 7.052 (3.54), 7.400 (3.50), 7.485 (2.39), 7.490 (2.79), 7.505 (5.62), 7.508 (5.60), 7.526 (3.18), 7.529 (3.19), 7.544 (4.97), 7.547 (4.85), 7.562 (2.11), 7.566 (2.15), 7.593 (1.45), 7.599 (10.45), 7.604 (3.82), 7.621 (14.20), 7.627 (2.63), 7.633 (4.36), 7.638 (3.96), 7.651 (2.56), 7.656 (2.44), 7.694 (6.27), 7.714 (3.68), 7.754 (2.06), 7.761 (12.86), 7.766 (4.18), 7.777 (3.86), 7.782 (9.88), 7.789 (1.39), 8.905 (15.11).

Example 190

2-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl}-2,5,7-triazaspiro[3.4]octan-6-one

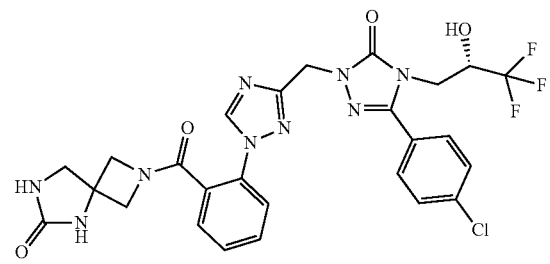 [SMILES: O=C1NCC2(CN(C(=O)c3ccccc3-n3cnc(Cn4nc(-c5ccc(Cl)cc5)n(C[C@H](O)C(F)(F)F)c4=O)n3)C2)N1]

2,5,7-Triazaspiro[3.4]octan-6-one (95.4 mg, 750 µmol) was added to a solution of 2-[3-({3-(4-chlorophenyl)-5-oxo- 4-[(2S)-3,3,3-trifluoro-2-hydroxypropyl]-4,5-dihydro-1H-1,2,4-triazol-1-yl}methyl)-1H-1,2,4-triazol-1-yl]benzoyl chloride (Example 58A, 158 mg, 300 µmol) in tetrahydrofuran (4.5 ml). This reaction mixture was stirred over night at room temperature. N,N-diisopropylethylamine (130 µl, 750 µmol) was added and stirring was continued over night at room temperature. The crude product was purified by preparative HPLC (Method 4). Lyophilisation of the product containing fractions afforded 56.0 mg (30% of th.) of the title compound.

LC-MS (Method 5): $R_t$=1.43 min; MS (ESIpos): m/z=618 [M+H]$^+$ $^1$H-NMR (400 MHz, DMSO-d6) δ [ppm]: −0.008 (1.70), 0.008 (1.48), 2.289 (2.57), 2.565 (1.39), 3.289 (1.69), 3.460 (2.09), 3.486 (3.55), 3.565 (2.98), 3.583 (1.80), 3.589 (1.83), 3.824 (1.77), 3.848 (2.28), 3.861 (3.24), 3.885 (7.72), 3.917 (1.23), 3.961 (2.30), 3.986 (5.08), 4.030 (1.85), 4.045 (2.61), 4.070 (3.43), 4.095 (1.49), 4.317 (1.40), 5.026 (1.07), 5.087 (1.28), 5.126 (7.72), 5.139 (4.58), 5.145 (4.42), 5.178 (0.81), 5.185 (0.95), 6.357 (6.49), 6.907 (3.04), 6.912 (3.14), 6.923 (3.07), 6.928 (2.97), 7.102 (5.05), 7.491 (2.42), 7.495 (2.83), 7.510 (5.22), 7.514 (5.39), 7.536 (2.73), 7.539 (2.92), 7.554 (4.20), 7.557 (4.24), 7.573 (1.99), 7.576 (2.10), 7.599 (1.50), 7.606 (10.15), 7.610 (4.11), 7.615 (3.18), 7.622 (5.45), 7.627 (13.72), 7.635 (5.11), 7.639 (4.25), 7.653 (2.48), 7.657 (2.36), 7.693 (5.72), 7.710 (3.19), 7.754 (1.66), 7.762 (9.14), 7.782 (7.11), 8.890 (16.00).

Example 191

2-[3-({3-(4-Chlorophenyl)-5-oxo-4-[(3,3,3-trifluoro-2-hydroxypropyl]-4,5-dihydro-1H-1,2,4-triazol-1-yl}methyl)-1H-1,2,4-triazol-1-yl]-N-[6-oxopiperidin-3-yl]benzamide (Diastereomeric Mixture)

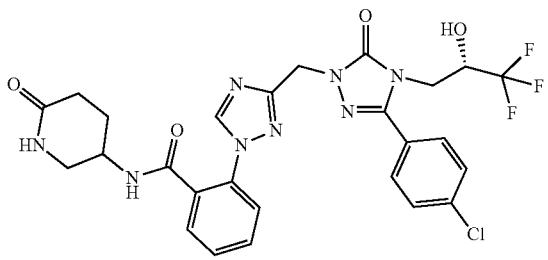 [SMILES: O=C1CCC(NC(=O)c2ccccc2-n2cnc(Cn3nc(-c4ccc(Cl)cc4)n(C[C@H](O)C(F)(F)F)c3=O)n2)CN1]

5-Aminopiperidin-2-one (54.1 mg, 474 µmol) was added to a solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl chloride (Example 58A, 100 mg, 190 µmol) in tetrahydrofuran (2.4 ml). This reaction mixture was stirred for 1 h at room temperature. N,N-diisopropylethylamine (83 µl, 470 µmol) was added and the reaction mixture was stirred over night at room temperature. The crude product was purified by preparative HPLC (Method 4). Lyophilisation of the product containing fractions afforded 62.4 mg (54% of th.) of the title compound.

LC-MS (Method 1): $R_t$=0.81 min; MS (ESIpos): m/z=605 [M+H]$^+$ $^1$H-NMR (400 MHz, DMSO-d6) δ [ppm]: −0.008 (1.83), 0.008 (1.52), 1.613 (0.79), 1.622 (0.99), 1.631 (1.21), 1.641 (1.18), 1.654 (0.99), 1.776 (1.32), 2.121 (1.56), 2.147 (4.44), 2.163 (2.39), 2.272 (1.42), 2.888 (1.26), 2.907 (1.49), 2.912 (1.54), 2.918 (1.61), 2.937 (1.47), 3.241 (1.44), 3.250 (1.11), 3.261 (1.25), 3.289 (1.80), 3.818 (1.38), 3.843 (1.61), 3.855 (2.06), 3.879 (2.27), 3.948 (1.04), 3.955 (1.32), 3.966 (1.66), 3.980 (3.22), 3.987 (3.26), 4.017 (1.52), 4.309 (1.30), 4.965 (0.62), 5.063 (16.00), 6.918 (2.56), 6.934 (2.72), 6.943 (2.50), 6.959 (2.44), 7.326 (2.80), 7.544 (5.77), 7.549 (6.18), 7.553 (8.08), 7.577 (0.91), 7.595 (3.19), 7.600 (9.97), 7.606 (12.88), 7.615 (9.99), 7.622 (13.21), 7.633 (1.27), 7.746 (8.86), 7.768 (7.10), 8.447 (2.10), 8.458 (2.49), 8.465 (2.38), 8.476 (2.07), 8.728 (9.22), 8.731 (8.60).

The two diastereomers were separated by preparative chiral HPLC [sample preparation: 58 mg dissolved in 2.0 ml ethanol; injection volume: 0.5 ml; column: Daicel Chiralcelk® OZ-H 5 µm, 250×20 mm; eluent: iso-hexane/ethanol 40:60; flow rate: 15 ml/min; temperature: 40° C.; UV detection: 220 nm]. After two separations, 22.0 mg of diastereomer 1 (Example 192), which eluted first, and 23.0 mg of diastereomer 2 (Example 193), which eluted later, were isolated.

Example 192

2-[3-({3-(4-Chlorophenyl)-5-oxo-4-[3,3,3-trifluoro-2-hydroxypropyl]-4,5-dihydro-1H-1,2,4-triazol-1-yl}methyl)-1H-1,2,4-triazol-1-yl]-N-[6-oxopiperidin-3-yl]benzamide (diastereomer 1)

Analytical chiral HPLC: $R_t$=3.83 min, d.e.=99% [column: Daicel Chiralcelk® OZ-H 50×4.6 mm; eluent: iso-hexane/ethanol 50:50, flow rate: 1 ml/min; UV detection: 220 nm].

LC-MS (Method 2): $R_t$=1.41 min; MS (ESIpos): m/z=605 [M+H]$^+$ $^1$H-NMR (400 MHz, DMSO-d6) δ [ppm]: 0.008 (2.20), 0.822 (0.86), 0.840 (0.91), 0.865 (0.68), 1.010 (0.61), 1.038 (1.65), 1.087 (2.57), 1.600 (1.12), 1.622 (1.46), 1.636 (1.69), 1.654 (1.57), 1.675 (0.68), 1.770 (1.54), 1.779 (1.64), 1.795 (1.32), 1.812 (1.18), 1.829 (1.10), 2.122 (2.65), 2.131 (2.94), 2.147 (4.82), 2.158 (2.57), 2.163 (2.46), 2.893 (1.50), 2.912 (1.82), 2.919 (1.90), 2.938 (1.71), 3.232 (2.04), 3.254 (1.71), 3.263 (2.14), 3.271 (1.97), 3.821 (1.71), 3.844 (2.01), 3.857 (2.49), 3.881 (2.64), 3.948 (1.34), 3.956 (1.71), 3.967 (2.14), 3.978 (4.17), 3.987 (4.13), 4.015 (2.03), 4.024 (1.83), 4.310 (1.47), 5.063 (16.00), 6.939 (1.72), 7.324 (4.01), 7.544 (6.51), 7.549 (7.05), 7.553 (8.85), 7.559 (6.25), 7.578 (1.41), 7.596 (4.27), 7.601 (10.95), 7.606 (13.11), 7.615 (10.69), 7.622 (13.30), 7.743 (2.62), 7.749 (11.84), 7.754 (4.40), 7.766 (3.83), 7.771 (8.77), 7.777 (1.41), 8.449 (4.09), 8.467 (3.91), 8.729 (13.44).

Example 193

2-[3-({3-(4-Chlorophenyl)-5-oxo-4-[3,3,3-trifluoro-2-hydroxypropyl]-4,5-dihydro-1H-1,2,4-triazol-1-yl}methyl)-1H-1,2,4-triazol-1-yl]-N-[6-oxopiperidin-3-yl]benzamide (diastereomer 2)

Analytical chiral HPLC: $R_t$=4.91 min, d.e.=99% [column: Daicel Chiralcelk® OZ-H 50×4.6 mm; eluent: iso-hexane/ethanol 50:50, flow rate: 1 ml/min; UV detection: 220 nm].

LC-MS (Method 2): $R_t$=1.42 min; MS (ESIpos): m/z=605 [M+H]$^+$ $^1$H-NMR (400 MHz, DMSO-d6) δ [ppm]: −0.008 (2.28), 0.008 (2.10), 1.038 (1.00), 1.087 (1.61), 1.609 (1.02), 1.630 (1.31), 1.643 (1.60), 1.663 (1.55), 1.684 (0.64), 1.765 (1.40), 1.775 (1.52), 1.791 (1.22), 1.799 (1.07), 1.808 (1.01), 2.127 (2.53), 2.134 (2.58), 2.150 (5.10), 2.167 (2.59), 2.888 (1.38), 2.907 (1.61), 2.914 (1.75), 2.933 (1.65), 3.240 (1.84), 3.249 (1.55), 3.261 (1.43), 3.270 (1.87), 3.280 (1.77), 3.818 (1.70), 3.841 (1.91), 3.854 (2.43), 3.878 (2.61), 3.948 (1.09), 3.957 (1.43), 3.967 (1.74), 3.982 (3.55), 3.990 (3.71), 4.018 (1.92), 4.027 (1.81), 4.313 (1.28), 5.063 (16.00), 6.960 (1.71), 6.973 (1.73), 7.333 (3.96), 7.543 (6.13), 7.548 (6.31), 7.552 (8.50), 7.558 (5.97), 7.577 (0.81), 7.595 (3.02), 7.600 (9.74), 7.605 (12.04), 7.615 (10.15), 7.622 (13.32), 7.628 (2.30), 7.740 (1.83), 7.746 (11.74), 7.752 (3.84), 7.763 (3.36), 7.768 (8.88), 7.774 (1.27), 8.460 (3.99), 8.478 (3.88), 8.731 (13.16).

Example 194

1-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl}-D-prolinamide

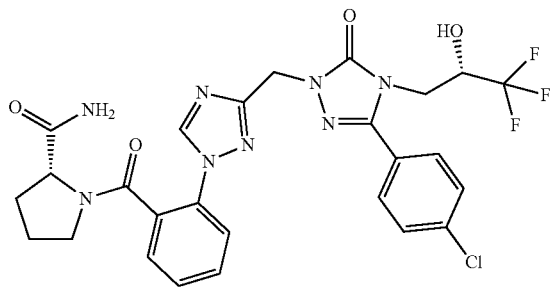 [SMILES: NC(=O)[C@H]1CCCN1C(=O)c1ccccc1-n1cnc(Cn2nc(-c3ccc(Cl)cc3)n(C[C@H](O)C(F)(F)F)c2=O)n1]

D-Prolinamide (42.8 mg, 375 µmol) and N,N-diisopropylethylamine (65 µl, 380 µmol) were added to a solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl chloride (Example 58A, 79.1 mg, 150 µmol) in tetrahydrofuran (2.3 ml). This reaction mixture was stirred for 1 h at room temperature. The crude product was purified by preparative HPLC (Method 4). Lyophilisation of the product containing fractions afforded 53.9 mg (57% of th.) of the title compound.

LC-MS (Method 2): $R_t$=1.53 min; MS (ESIpos): m/z=605 [M+H]$^+$ $^1$H-NMR (400 MHz, DMSO-d6) δ [ppm]: −0.215 (1.05), −0.008 (3.93), 0.008 (3.02), 0.716 (3.19), 1.701 (2.80), 1.716 (2.72), 1.742 (2.33), 1.759 (3.07), 1.776 (3.57), 1.787 (3.15), 1.798 (2.94), 1.812 (1.93), 2.053 (1.59), 2.073 (1.94), 2.709 (0.57), 3.205 (1.74), 3.231 (1.37), 3.247 (2.09), 3.287 (4.72), 3.373 (0.82), 3.441 (1.05), 3.816 (1.83), 3.824 (1.18), 3.840 (2.10), 3.852 (2.94), 3.860 (1.87), 3.877 (2.98), 3.884 (2.00), 3.974 (4.06), 3.982 (4.47), 4.010 (2.84), 4.019 (2.68), 4.217 (1.80), 4.229 (1.82), 4.309 (2.20), 5.021 (1.30), 5.061 (14.55), 5.069 (10.76), 5.109 (1.19), 6.913 (3.15), 6.928 (5.00), 6.958 (4.94), 6.973 (4.86), 7.064 (3.77), 7.297 (2.31), 7.342 (3.89), 7.411 (1.12), 7.472 (1.37), 7.492 (2.44), 7.509 (1.27), 7.539 (1.39), 7.556 (3.82), 7.577 (3.93), 7.601 (12.46), 7.614 (6.91), 7.617 (8.60), 7.622 (16.00), 7.629 (8.66), 7.635 (11.09), 7.648 (3.33), 7.676 (3.24), 7.696 (2.26), 7.723 (5.02), 7.745 (10.67), 7.752 (12.89), 7.767 (6.68), 7.773 (9.27), 8.933 (10.76).

Example 195

1-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl}-L-prolinamide

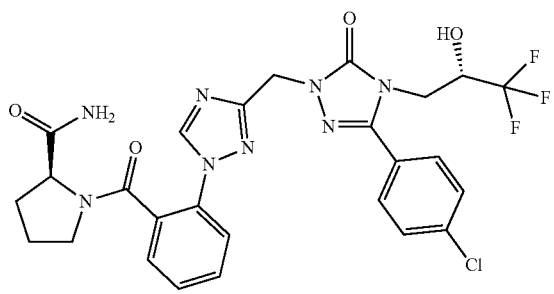 [SMILES: NC(=O)[C@@H]1CCCN1C(=O)c1ccccc1-n1cnc(Cn2nc(-c3ccc(Cl)cc3)n(C[C@H](O)C(F)(F)F)c2=O)n1]

L-Prolinamide (42.8 mg, 375 µmol) and N,N-diisopropylethylamine (65 µl, 380 µmol) were added to a solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl chloride (Example 58A, 79.1 mg, 150 µmol) in tetrahydrofuran (2.3 ml). This reaction mixture was stirred for 1 h at room temperature. The crude product was purified by preparative HPLC (Method 4). Lyophilisation of the product containing fractions afforded 70.0 mg (77% of th.) of the title compound.

LC-MS (Method 2): $R_t$=1.52 min; MS (ESIpos): m/z=605 [M+H]$^+$ $^1$H-NMR (400 MHz, DMSO-d6) δ [ppm]: −0.008 (1.85), 0.008 (1.54), 1.700 (2.38), 1.715 (2.83), 1.737 (2.61), 1.756 (2.97), 1.773 (3.13), 1.784 (2.76), 1.803 (2.22), 1.817 (1.31), 2.045 (1.45), 2.056 (1.17), 2.066 (1.53), 3.188 (1.17), 3.205 (1.61), 3.224 (1.64), 3.240 (2.01), 3.263 (1.16), 3.426 (1.32), 3.443 (1.48), 3.457 (0.95), 3.818 (2.11), 3.842 (2.44), 3.855 (3.20), 3.878 (3.43), 3.972 (1.80), 3.982 (3.54), 3.991 (2.88), 4.008 (1.29), 4.018 (2.37), 4.028 (1.68), 4.198 (1.47), 4.210 (1.49), 4.291 (1.83), 4.300 (1.82), 4.308 (1.82), 5.066 (16.00), 6.903 (2.70), 6.919 (3.55), 6.943 (4.70), 6.959 (4.52), 7.052 (3.14), 7.289 (2.19), 7.316 (3.47), 7.410 (0.98), 7.471 (1.19), 7.474 (1.22), 7.490 (2.24), 7.493 (2.20), 7.508 (1.17), 7.511 (1.13), 7.536 (1.21), 7.539 (1.26), 7.555 (3.49), 7.565 (1.55), 7.573 (3.33), 7.577 (3.47), 7.581 (2.52), 7.584 (2.16), 7.592 (1.62), 7.599 (11.00), 7.603 (6.94), 7.612 (6.64), 7.620 (14.79), 7.628 (7.75), 7.633 (8.58), 7.641 (3.09), 7.646 (3.12), 7.650 (2.36), 7.675 (2.88), 7.695 (2.00), 7.727 (4.52), 7.746 (11.30), 7.751 (13.60), 7.756 (4.09), 7.763 (2.78), 7.768 (7.93), 7.773 (8.97), 7.779 (1.28), 8.932 (10.40).

Example 196

N-[2-Amino-3,3,4,4-tetrafluorobutyl]-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzamide (Diastereomeric Mixture)

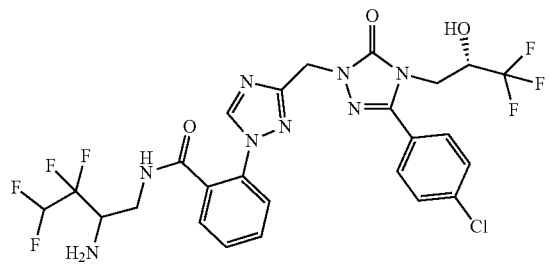 [SMILES: NC(CNC(=O)c1ccccc1-n1cnc(Cn2nc(-c3ccc(Cl)cc3)n(C[C@H](O)C(F)(F)F)c2=O)n1)C(F)(F)C(F)F]

3,3,4,4-Tetrafluorobutane-1,2-diamine dihydrochloride (175 mg, 750 µmol) and N,N-diisopropylethylamine (180 µl, 1.1 mmol) were added to a solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl chloride (Example 58A, 158 mg, 300 µmol) in tetrahydrofuran (4.5 ml). This reaction mixture was stirred for 1 h at room temperature. The crude product was purified by preparative HPLC (Method 4). Lyophilisation of the product containing fractions afforded 45.4 mg (23% of th.) of the title compound.

LC-MS (Method 5): $R_t$=1.71 min; MS (ESIpos): m/z=651 [M+H]$^+$ $^1$H-NMR (400 MHz, DMSO-d6) δ [ppm]: −0.008 (1.30), 0.008 (1.10), 3.136 (1.62), 3.154 (1.32), 3.171 (1.06), 3.470 (1.71), 3.503 (1.42), 3.809 (1.78), 3.833 (2.04), 3.845 (2.60), 3.869 (2.83), 3.971 (2.72), 3.979 (3.04), 4.007 (1.95), 4.015

(1.81), 4.306 (1.43), 5.056 (15.52), 6.554 (1.15), 6.577 (1.23), 6.912 (2.67), 6.917 (2.65), 6.928 (2.85), 7.554 (1.17), 7.562 (1.41), 7.567 (1.43), 7.574 (2.86), 7.580 (2.74), 7.588 (3.25), 7.598 (10.69), 7.603 (3.91), 7.614 (5.31), 7.619 (16.00), 7.625 (10.32), 7.630 (14.00), 7.639 (7.13), 7.644 (6.59), 7.648 (3.42), 7.739 (2.18), 7.745 (12.74), 7.750 (4.16), 7.762 (3.95), 7.767 (9.40), 7.773 (1.43), 8.530 (1.93), 8.544 (3.92), 8.559 (1.89), 8.800 (15.08).

Example 197

1-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl}-4,4-difluoro-L-prolinamide

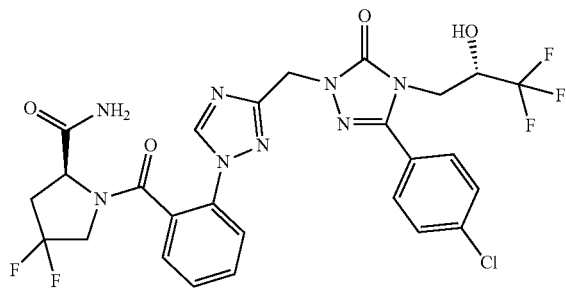 [SMILES: NC(=O)[C@@H]1CC(F)(F)CN1C(=O)c1ccccc1-n1cnc(Cn2nc(-c3ccc(Cl)cc3)n(C[C@H](O)C(F)(F)F)c2=O)n1]

4,4-Difluoro-L-prolinamide hydrochloride (70.0 mg, 375 μmol) and N,N-diisopropylethylamine (100 μl, 600 μmol) were added to a solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl chloride (Example 58A, 79.1 mg, 150 μmol) in tetrahydrofuran (12 ml). This reaction mixture was stirred for 30 min at room temperature. The crude product was purified by preparative HPLC (Method 4). Lyophilisation of the product containing fractions afforded 49.0 mg (51% of th.) of the title compound.

LC-MS (Method 2): $R_t$=1.63 min; MS (ESIpos): m/z=641 [M+H]$^+$ $^1$H-NMR (400 MHz, DMSO-d6) δ [ppm]: −0.008 (2.40), 0.008 (1.67), 1.314 (1.06), 2.366 (0.65), 2.410 (1.56), 2.423 (1.57), 2.443 (2.13), 2.455 (2.18), 2.477 (2.40), 2.524 (1.84), 2.783 (1.03), 2.797 (1.32), 2.821 (1.48), 2.833 (1.25), 2.857 (1.27), 2.896 (0.67), 3.290 (2.76), 3.699 (1.76), 3.730 (2.30), 3.768 (2.26), 3.802 (3.32), 3.814 (2.37), 3.827 (2.87), 3.839 (3.94), 3.851 (2.61), 3.863 (2.60), 3.875 (2.32), 3.960 (2.14), 3.969 (2.43), 3.979 (2.40), 3.987 (2.57), 3.997 (1.68), 4.005 (1.51), 4.016 (1.67), 4.024 (1.54), 4.037 (0.75), 4.070 (1.38), 4.106 (1.23), 4.309 (2.36), 4.554 (1.73), 4.566 (1.85), 4.578 (1.81), 4.590 (1.56), 5.049 (11.37), 5.060 (12.81), 6.908 (3.80), 6.919 (4.76), 6.924 (4.25), 6.935 (3.91), 7.212 (3.00), 7.303 (3.09), 7.468 (3.74), 7.491 (2.35), 7.516 (2.52), 7.534 (4.03), 7.547 (3.91), 7.568 (2.22), 7.587 (5.13), 7.594 (7.88), 7.599 (4.09), 7.606 (5.34), 7.610 (10.35), 7.616 (12.14), 7.621 (4.12), 7.628 (4.11), 7.632 (8.72), 7.639 (4.66), 7.645 (2.85), 7.660 (4.04), 7.664 (3.55), 7.680 (2.14), 7.684 (2.11), 7.694 (3.63), 7.713 (2.95), 7.746 (16.00), 7.762 (8.00), 7.767 (12.76), 7.779 (3.63), 8.982 (8.64), 9.024 (6.39).

Example 198

1-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl}-4,4-difluoro-D-prolinamide

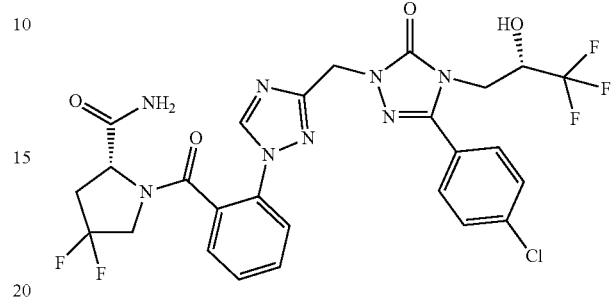

4,4-Difluoro-D-prolinamide hydrochloride (70.0 mg, 375 μmol) and N,N-diisopropylethylamine (100 μl, 600 μmol) were added to a solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl chloride (Example 58A, 79.1 mg, 150 μmol) in tetrahydrofuran (12 ml). This reaction mixture was stirred for 30 min at room temperature. The crude product was purified by preparative HPLC (Method 4). Lyophilisation of the product containing fractions afforded 68.0 mg (71% of th.) of the title compound.

LC-MS (Method 2): $R_t$=1.63 min: MS (ESIpos): m/z=641 [M+H]$^+$ $^1$H-NMR (400 MHz, DMSO-d6) δ [ppm]: 0.981 (0.57), 1.141 (0.72), 2.073 (1.47), 2.439 (2.85), 2.453 (2.78), 2.797 (1.66), 2.823 (1.67), 2.858 (1.49), 3.290 (3.54), 3.696 (1.89), 3.727 (2.42), 3.773 (2.13), 3.807 (3.37), 3.814 (2.93), 3.830 (2.88), 3.839 (3.40), 3.851 (3.11), 3.867 (2.65), 3.875 (2.71), 3.971 (4.35), 3.979 (4.71), 4.007 (3.12), 4.015 (2.95), 4.032 (1.68), 4.068 (1.36), 4.309 (2.87), 4.580 (2.20), 4.593 (2.25), 4.604 (2.21), 4.617 (1.96), 5.005 (1.23), 5.044 (6.57), 5.060 (16.00), 5.095 (1.03), 6.895 (3.79), 6.911 (3.99), 6.922 (4.56), 6.938 (4.35), 7.219 (3.21), 7.312 (3.64), 7.480 (4.22), 7.518 (2.71), 7.537 (4.06), 7.556 (5.16), 7.571 (2.61), 7.594 (9.48), 7.610 (12.27), 7.616 (13.54), 7.631 (9.48), 7.640 (5.20), 7.660 (4.72), 7.683 (2.59), 7.691 (4.17), 7.710 (3.31), 7.739 (11.18), 7.744 (15.46), 7.760 (13.36), 7.765 (11.57), 7.779 (3.77), 8.980 (10.61), 9.024 (7.52).

Example 199

(3R)-1-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl}pyrrolidine-3-carboxamide

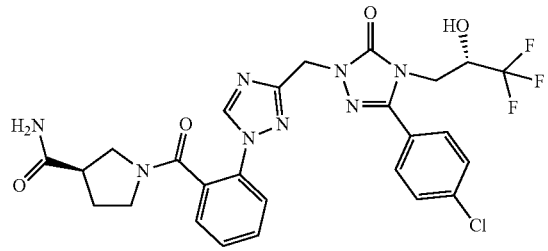 [SMILES: NC(=O)[C@@H]1CCN(C(=O)c2ccccc2-n2cnc(Cn3nc(-c4ccc(Cl)cc4)n(C[C@H](O)C(F)(F)F)c3=O)n2)C1]

(3R)-pyrrolidine-3-carboxamide (61.2 mg, 70% purity, 375 μmol) and N,N-diisopropylethylamine (100 μl, 600 μmol) were added to a solution of 2-[3-({3-(4-chlorophenyl)-5-Oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl chloride (Example 58A, 79.1 mg, 150 μmol) in tetrahydrofuran (12 ml). This reaction mixture was stirred for 30 min at room temperature. The crude product was purified by preparative HPLC (Method 4). Lyophilisation of the product containing fractions afforded 18.0 mg (20% of th.) of the title compound LC-MS (Method 5): R$_t$=1.45 min; MS (ESIpos): m/z=605 [M+H]$^+$ $^1$H-NMR (400 MHz, DMSO-d6) δ [ppm]: −0.008 (3.63), 0.008 (2.97), 1.855 (0.64), 1.876 (1.97), 1.886 (1.80), 1.896 (3.09), 1.916 (2.77), 1.928 (1.25), 1.937 (1.70), 1.958 (0.95), 1.990 (1.20), 2.841 (1.39), 2.860 (2.49), 2.878 (2.20), 2.902 (1.08), 3.078 (0.96), 3.166 (2.09), 3.183 (2.07), 3.191 (2.41), 3.210 (1.69), 3.253 (1.28), 3.277 (1.76), 3.346 (1.74), 3.365 (0.75), 3.382 (1.16), 3.400 (1.16), 3.412 (1.67), 3.430 (2.30), 3.450 (1.34), 3.460 (0.86), 3.481 (0.59), 3.534 (1.08), 3.553 (1.74), 3.563 (1.06), 3.573 (0.72), 3.583 (1.25), 3.820 (1.82), 3.844 (2.16), 3.857 (2.66), 3.881 (2.83), 3.982 (2.86), 3.989 (3.64), 4.018 (1.96), 4.026 (2.23), 4.300 (1.87), 5.083 (16.00), 5.127 (0.76), 6.905 (1.47), 6.918 (5.54), 6.933 (7.10), 6.969 (2.19), 7.352 (2.14), 7.425 (2.14), 7.479 (1.81), 7.483 (2.02), 7.498 (5.18), 7.502 (3.83), 7.512 (3.85), 7.517 (3.82), 7.527 (1.94), 7.530 (2.02), 7.534 (2.39), 7.537 (2.33), 7.545 (3.32), 7.548 (3.45), 7.552 (3.94), 7.555 (3.43), 7.564 (1.87), 7.567 (1.89), 7.571 (1.97), 7.574 (1.77), 7.587 (2.21), 7.591 (2.86), 7.596 (8.66), 7.600 (5.15), 7.606 (10.62), 7.611 (7.28), 7.618 (11.76), 7.628 (10.90), 7.634 (3.20), 7.638 (1.95), 7.693 (6.85), 7.713 (4.64), 7.740 (1.56), 7.747 (9.51), 7.752 (7.11), 7.756 (7.98), 7.763 (3.42), 7.768 (7.70), 7.773 (5.12), 7.778 (5.34), 8.837 (4.81), 8.839 (6.95), 8.878 (9.71).

Example 200

(3S)-1-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl}pyrrolidine-3-carboxamide

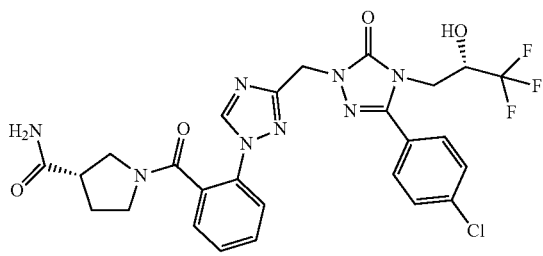 [SMILES: NC(=O)[C@H]1CCN(C(=O)c2ccccc2-n2cnc(Cn3nc(-c4ccc(Cl)cc4)n(C[C@H](O)C(F)(F)F)c3=O)n2)C1]

(3S)-Pyrrolidine-3-carboxamide (61.2 mg, 70% purity, 375 μmol) and N,N-diisopropylethylamine (100 μl, 600 μmol) were added to a solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl chloride (Example 58A, 79.1 mg, 150 μmol) in tetrahydrofuran (12 ml). This reaction mixture was stirred for 30 min at room temperature. The crude product was purified by preparative HPLC (Method 4). Lyophilisation of the product containing fractions afforded 27.5 mg (30% of th.) of the title compound LC-MS (Method 5): R$_t$=1.45 min; MS (ESIpos): m/z=605 [M+H]$^+$ $^1$H-NMR (400 MHz, DMSO-d6) δ [ppm]: −0.008 (4.16), 0.008 (3.57), 1.267 (0.71), 1.857 (0.78), 1.876 (2.28), 1.887 (2.33), 1.896 (3.43), 1.916 (3.11), 1.937 (1.84), 1.985 (1.19), 2.842 (1.62), 2.860 (3.04), 2.879 (2.99), 2.898 (1.53), 3.050 (0.99), 3.070 (1.13), 3.166 (2.43), 3.184 (2.40), 3.191 (2.87), 3.209 (2.07), 3.258 (1.48), 3.276 (2.27), 3.303 (2.61), 3.380 (1.52), 3.398 (1.37), 3.409 (1.90), 3.427 (2.18), 3.451 (1.53), 3.462 (1.00), 3.482 (0.67), 3.534 (0.62), 3.553 (1.84), 3.573 (1.43), 3.583 (1.55), 3.603 (0.94), 3.819 (2.26), 3.844 (2.66), 3.856 (3.31), 3.880 (3.60), 3.982 (3.59), 3.990 (4.26), 4.018 (2.56), 4.027 (2.57), 4.301 (2.05), 5.037 (0.89), 5.077 (7.82), 5.084 (16.00), 5.127 (1.02), 6.905 (2.22), 6.918 (4.67), 6.933 (5.91), 6.970 (2.38), 7.354 (2.37), 7.425 (2.31), 7.479 (1.92), 7.483 (2.19), 7.498 (5.59), 7.502 (4.15), 7.512 (4.20), 7.516 (4.13), 7.527 (2.07), 7.530 (2.24), 7.534 (2.60), 7.537 (2.60), 7.545 (3.61), 7.548 (3.84), 7.552 (4.33), 7.555 (3.85), 7.564 (1.98), 7.567 (2.10), 7.571 (2.15), 7.574 (1.94), 7.587 (2.33), 7.591 (3.16), 7.596 (9.21), 7.600 (5.83), 7.606 (11.38), 7.611 (7.94), 7.618 (12.74), 7.628 (11.78), 7.633 (3.64), 7.638 (2.14), 7.692 (6.93), 7.713 (4.63), 7.741 (1.86), 7.747 (10.53), 7.752 (10.63), 7.756 (6.23), 7.763 (3.63), 7.768 (9.06), 7.774 (7.23), 7.778 (3.69), 8.836 (7.97), 8.839 (4.74), 8.877 (10.74).

Example 201

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(3,5-dimethyl-4H-pyrazol-4-yl)benzamide

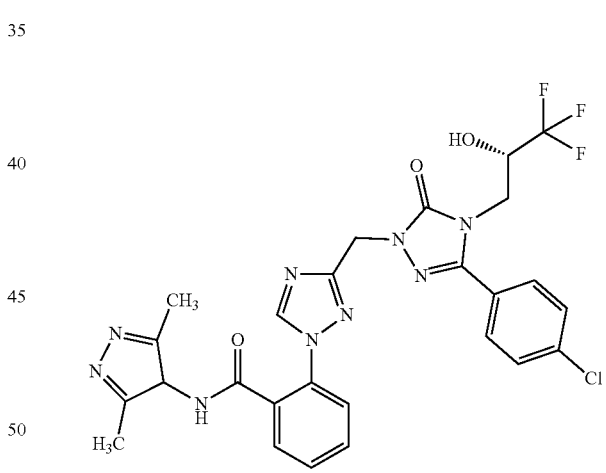

3,5-dimethyl-4H-pyrazol-4-amine (11.1 mg, 0.1 mmol) was placed in one well of a 96 deep well plate. Then a solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoic acid (Example 55A; 50.9 mg, 0.1 mmol) in DMF (0.4 ml) and a solution of HATU (53 mg, 0.14 mmol) in DMF (0.4 ml) were added followed by 4-methylmorpholine (50 μl). The plate was sealed and shaken over 48 h at room temperature. The solid was filtered and the filtrate was purified by preparative LC-MS (Method 7). The product containing fractions were evaporated in vacuo with a centrifugal dryer. The residue was retaken in DMSO (0.6 ml) then pooled and evaporated affording 21.9 mg (35% of th.) of the title compound.

LC/MS (Method 9): $R_t$=0.92 min, MS (ESIpos): m/z=602 [M+H]$^+$

The examples shown in Table 3 were synthesized in analogy to the protocole of Example 201:

TABLE 3

| Example No | Structure IUPAC-Name | Qantity (yield) Analytic |
|---|---|---|
| Example 202 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-{[2-methyltetrahydrofuran-2-yl]methyl}benzamide (diastereomeric mixture) | 13.0 mg (20% of th.) LC-MS (Method 8): $R_t$ = 1.04 min MS (ESIpos): m/z = 606 [M + H]$^+$ |
| Example 203 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(2,3-difluorobenzyl)benzamide | 30.4 mg (47% of th.) LC-MS (Method 8): $R_t$ = 1.11 min MS (ESIpos): m/z = 634 [M + H]$^+$ |
| Example 204 | N-[Butan-2-yl]-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzamide (diastereomeric mixture) | 28.2 mg (50% of th.) LC-MS (Method 8): $R_t$ = 1.06 min MS (ESIpos): m/z = 564 [M + H]$^+$ |

TABLE 3-continued

| Example No | Structure IUPAC-Name | Qantity (yield) Analytic |
|---|---|---|
| Example 205 | N-(4-Aminophenyl)-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzamide | 26.1 mg (41% of th.) LC-MS (Method 8): $R_t$ = 0.87 min MS (ESIpos): m/z = 599 [M + H]$^+$ |
| Example 206 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-[(1-methyl-1H-pyrazol-5-yl)methyl]benzamide | 28.5 mg (46% of th.) LC-MS (Method 8): $R_t$ = 0.98 min MS (ESIpos): m/z = 602 [M + H]$^+$ |
| Example 207 | 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(2,5-difluorobenzyl)benzamide | 28.6 mg (43% of th.) LC-MS (Method 8): $R_t$ = 1.11 min MS (ESIpos): m/z = 634 [M + H]$^+$ |

TABLE 3-continued

| Example No | Structure IUPAC-Name | Qantity (yield) Analytic |
|---|---|---|
| Example 208 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-[tetrahydrofuran-3-yl]benzamide (diastereomeric mixture) | 32.7 mg (55% of th.) LC-MS (Method 8): $R_t$ = 0.97 min MS (ESIpos): m/z = 578 [M + H]$^+$ |
| Example 209 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-[(5-methylfuran-2-yl)methyl]benzamide | 12.8 mg (21% of th.) LC-MS (Method 8): $R_t$ = 1.09 min MS (ESIpos): m/z = 602 [M + H]$^+$ |
| Example 210 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(1-methyl-1H-pyrazol-5-yl)benzamide | 8.90 mg (14% of th.) LC-MS (Method 8): $R_t$ = 0.98 min MS (ESIpos): m/z = 588 [M + H]$^+$ |

TABLE 3-continued

| Example No | Structure IUPAC-Name | Qantity (yield) Analytic |
|---|---|---|
| Example 211 | 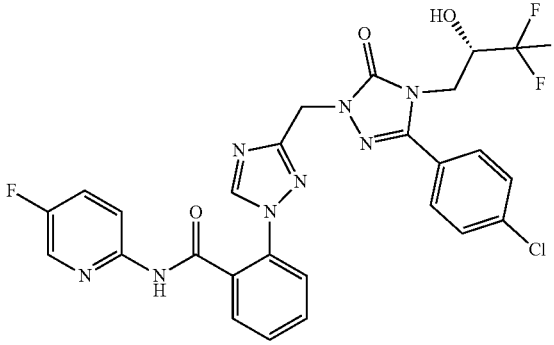 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(5-fluoropyridin-2-yl)benzamide | 10.3 mg (17% of th.) LC-MS (Method 8): $R_t$ = 1.07 min MS (ESIpos): m/z = 603 [M + H]$^+$ |
| Example 212 | 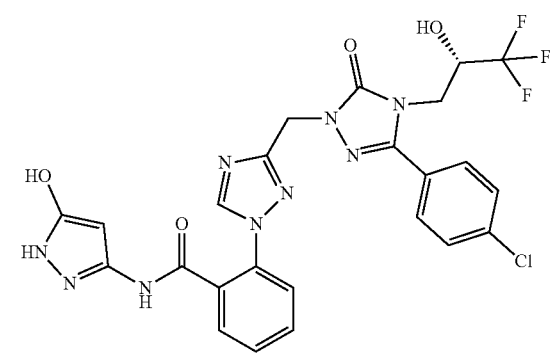 [SMILES: O=C(Nc1cc(O)[nH]n1)c1ccccc1-n1cnc(Cn2nc(-c3ccc(Cl)cc3)n(C[C@H](O)C(F)(F)F)c2=O)n1] 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(5-hydroxy-1H-pyrazol-3-yl)benzamide | 26.0 mg (40% of th.) LC-MS (Method 8): $R_t$ = 0.94 min MS (ESIpos): m/z = 590 [M + H]$^+$ |
| Example 213 | 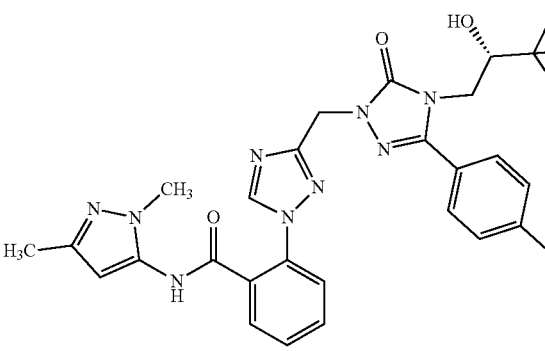 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(1,3-dimethyl-1H-pyrazol-5-yl)benzamide | 14.4 mg (23% of th.) LC-MS (Method 8): $R_t$ = 1.00 min MS (ESIpos): m/z = 602 [M + H]$^+$ |

TABLE 3-continued

| Example No | Structure IUPAC-Name | Qantity (yield) Analytic |
|---|---|---|
| Example 214 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(3,5-dimethyl-1H-pyrazol-4-yl)benzamide | 17.9 mg (94% purity, 28% of th.) LC-MS (Method 8): $R_t$ = 0.92 min; MS (ESIpos): m/z = 602 [M + H]$^+$ |
| Example 215 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(1-ethyl-1H-pyrazol-5-yl)benzamide | 24.3 mg (40% of th.) LC-MS (Method 8): $R_t$ = 1.00 min MS (ESIpos): m/z = 602 [M + H]$^+$ |
| Example 216 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-[1-(1,2-oxazol-3-yl)ethyl]benzamide | 34.5 mg (57% of th.) LC-MS (Method 8): $R_t$ = 1.02 min MS (ESIpos): m/z = 603 [M + H]$^+$ |

TABLE 3-continued

| Example No | Structure IUPAC-Name | Qantity (yield) Analytic |
|---|---|---|
| Example 217 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(4-fluoro-2-hydroxyphenyl)benzamide | 31.0 mg (50% of th.) LC-MS (Method 8): $R_t$ = 1.07 min MS (ESIpos): m/z = 618 [M + H]$^+$ |
| Example 218 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(4-chloro-1H-pyrazol-3-yl)benzamide | 30.2 mg (50% of th.) LC-MS (Method 8): $R_t$ = 1.06 min MS (ESIpos): m/z = 608 [M + H]$^+$ |
| Example 219 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(1-oxidopyridin-2-yl)benzamide | 19.4 mg (32% of th.) LC-MS (Method 8): $R_t$ = 0.99 min MS (ESIpos): m/z = 601 [M + H]$^+$ |

TABLE 3-continued

| Example No | Structure IUPAC-Name | Qantity (yield) Analytic |
|---|---|---|
| Example 220 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(5-methylpyridin-3-yl)benzamide | 23.5 mg (39% of th.) LC-MS (Method 8): $R_t$ = 0.88 min MS (ESIpos): m/z = 599 [M + H]$^+$ |
| Example 221 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(2-methylpyridin-3-yl)benzamide | 12.0 mg (20% of th.) LC-MS (Method 8): $R_t$ = 0.84 min MS (ESIpos): m/z = 599 [M + H]$^+$ |
| Example 222 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(2,5-dimethylcyclopentyl)benzamide (stereomeric mixture) | 35.3 mg (57% of th.) LC-MS (Method 8): $R_t$ = 1.14 min MS (ESIpos): m/z = 604 [M + H]$^+$ |

TABLE 3-continued

| Example No | Structure IUPAC-Name | Qantity (yield) Analytic |
|---|---|---|
| Example 223 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(1,3-thiazol-2-yl)benzamide | 21.7 mg (33% of th.) LC-MS (Method 8): $R_t$ = 1.03 min MS (ESIpos): m/z = 591 [M + H]+ |
| Example 224 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(3-methylcyclohexyl)benzamide (diastereomeric mixture) | 37.2 mg (62% of th.) LC-MS (Method 8): $R_t$ = 1.14 min MS (ESIpos): m/z = 604 [M + H]+ |
| Example 225 | N-(2-Amino-2-oxoethyl)-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzamide | 28.9 mg (46% of th.) LC-MS (Method 8): $R_t$ = 0.89 min MS (ESIpos): m/z = 565 [M + H]+ |

TABLE 3-continued

| Example No | Structure IUPAC-Name | Qantity (yield) Analytic |
|---|---|---|
| Example 226 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(6-chloropyridin-3-yl)benzamide | 29.0 mg (47% of th.) LC-MS (Method 8): $R_t$ = 1.07 min MS (ESIpos): m/z = 619 [M + H]$^+$ |
| Example 227 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(3-hydroxyphenyl)benzamide | 22.1 mg (33% of th.) LC-MS (Method 8): $R_t$ = 1.02 min MS (ESIpos): m/z = 600 [M + H]$^+$ |
| Example 228 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(4-fluoro-3-methylphenyl)benzamide | 37.7 mg (56% of th.) LC-MS (Method 8): $R_t$ = 1.13 min MS (ESIpos): m/z = 616 [M + H]$^+$ |

TABLE 3-continued

| Example No | Structure IUPAC-Name | Qantity (yield) Analytic |
|---|---|---|
| Example 229 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(5-fluoro-2-methylphenyl)benzamide | 30.2 mg (48% of th.) LC-MS (Method 8): $R_t$ = 1.12 min MS (ESIpos): m/z = 616 [M + H]$^+$ |
| Example 230 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(4-methylpyridin-2-yl)benzamide | 4.10 mg (7% of th.) LC-MS (Method 8): $R_t$ = 1.00 min MS (ESIpos): m/z = 599 [M + H]$^+$ |
| Example 231 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-[(3S)-2-oxotetrahydrofuran-3-yl]benzamide (diastereomeric mixture) | 26.1 mg (41% of th.) LC-MS (Method 8): $R_t$ = 0.97 min MS (ESIpos): m/z = 592 [M + H]$^+$ |

TABLE 3-continued

| Example No | Structure IUPAC-Name | Qantity (yield) Analytic |
|---|---|---|
| Example 232 | 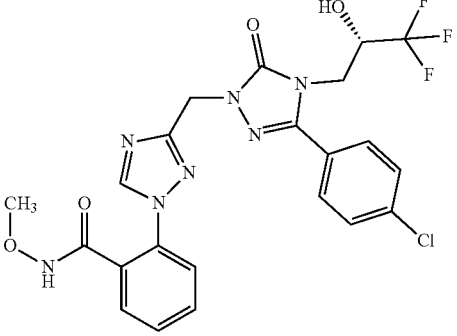 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-methoxybenzamide | 30.7 mg (54% of th.) LC-MS (Method 8): $R_t$ = 0.95 min MS (ESIpos): m/z = 538 [M + H]$^+$ |
| Example 233 | 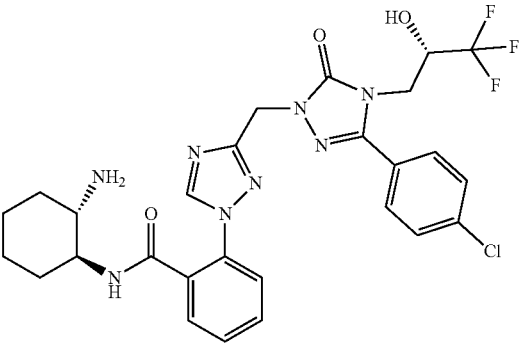 [SMILES: N[C@H]1CCCC[C@@H]1NC(=O)c1ccccc1-n1cnc(Cn2nc(-c3ccc(Cl)cc3)n(C[C@H](O)C(F)(F)F)c2=O)n1] N-[(1S,2S)-2-Aminocyclohexyl]-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzamide | 27.7 mg (46% of th.) LC-MS (Method 8): $R_t$ = 0.77 min MS (ESIpos): m/z = 605 [M + H]$^+$ |
| Example 234 | 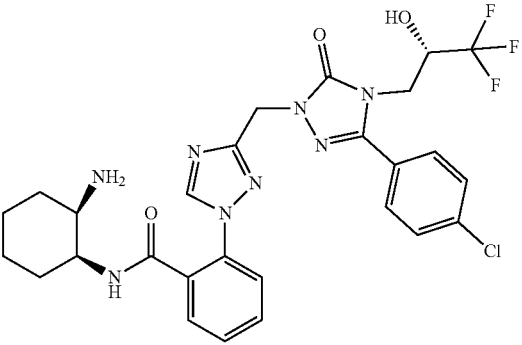 [SMILES: N[C@@H]1CCCC[C@@H]1NC(=O)c1ccccc1-n1cnc(Cn2nc(-c3ccc(Cl)cc3)n(C[C@H](O)C(F)(F)F)c2=O)n1] N-[(1S,2R)-2-Aminocyclohexyl]-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzamide | 16.2 mg (27% of th.) LC-MS (Method 8): $R_t$ = 0.77 min MS (ESIpos): m/z = 605 [M + H]$^+$ |

TABLE 3-continued

| Example No | Structure IUPAC-Name | Qantity (yield) Analytic |
|---|---|---|
| Example 235 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(4-fluorobenzyl)benzamide | 32.1 mg (52% of th.) LC-MS (Method 8): $R_t$ = 1.10 min MS (ESIpos): m/z = 616 [M + H]$^+$ |
| Example 236 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(3-fluorobenzyl)benzamide | 28.3 mg (45% of th.) LC-MS (Method 8): $R_t$ = 1.10 min MS (ESIpos): m/z = 616 [M + H]$^+$ |
| Example 237 | N-[(2S)-1-Amino-1-oxopropan-2-yl]-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzamide | 28.7 mg (50% of th.) LC-MS (Method 8): $R_t$ = 0.91 min MS (ESIpos): m/z = 579 [M + H]$^+$ |

TABLE 3-continued

| Example No | Structure IUPAC-Name | Qantity (yield) Analytic |
|---|---|---|
| Example 238 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(5-methyl-1,3,4-thiadiazol-2-yl)benzamide | 35.5 mg (59% of th.) LC-MS (Method 8): $R_t$ = 1.00 min MS (ESIpos): m/z = 606 [M + H]$^+$ |
| Example 239 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(3,4-difluorobenzyl)benzamide | 23.3 mg (36% of th.) LC-MS (Method 8): $R_t$ = 1.11 min MS (ESIpos): m/z = 634 [M + H]$^+$ |
| Example 240 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(4-methylpyrimidin-2-yl)benzamide | 1.90 mg (3% of th.) LC-MS (Method 8): $R_t$ = 0.99 min MS (ESIpos): m/z = 600 [M + H]$^+$ |

TABLE 3-continued

| Example No | Structure IUPAC-Name | Qantity (yield) Analytic |
|---|---|---|
| Example 241 | 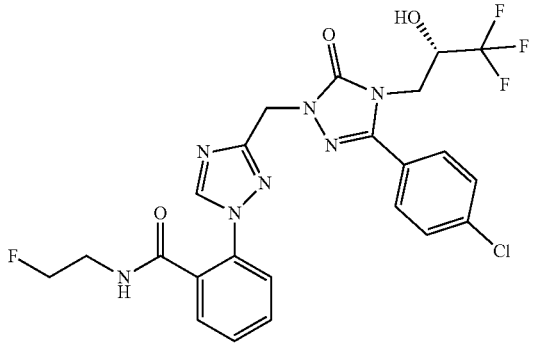 [SMILES: O=C(NCCF)c1ccccc1-n1cnc(Cn2nc(-c3ccc(Cl)cc3)n(C[C@H](O)C(F)(F)F)c2=O)n1]<br>2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(2-fluoroethyl)benzamide | 27.9 mg (50% of th.)<br>LC-MS (Method 8):<br>$R_t$ = 0.99 min<br>MS (ESIpos): m/z = 554 [M + H]$^+$ |
| Example 242 | 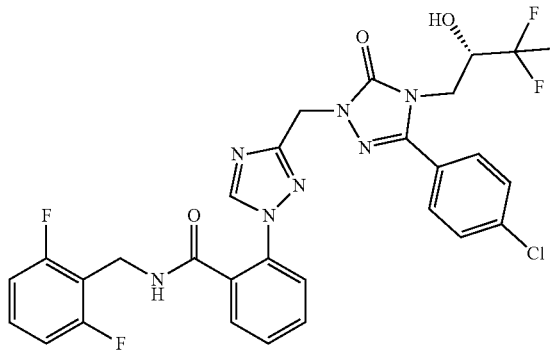<br>2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(2,6-difluorobenzyl)benzamide | 5.30 mg (8% of th.)<br>LC-MS (Method 8):<br>$R_t$ = 1.10 min<br>MS (ESIpos): m/z = 634 [M + H]$^+$ |
| Example 243 | 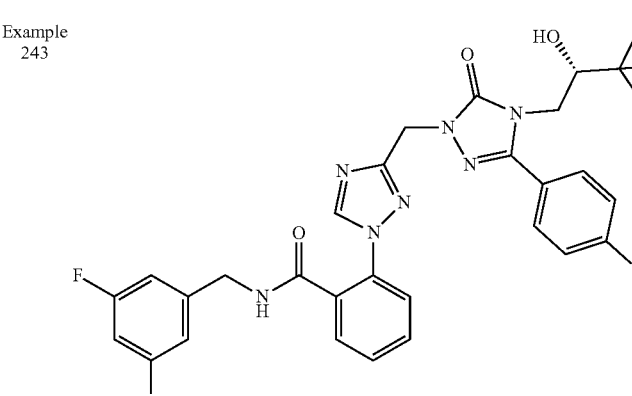<br>2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(3,5-difluorobenzyl)benzamide | 10.5 mg (15% of th.)<br>LC-MS (Method 8):<br>$R_t$ = 1.12 min<br>MS (ESIpos): m/z = 634 [M + H]$^+$ |

TABLE 3-continued

| Example No | Structure IUPAC-Name | Qantity (yield) Analytic |
|---|---|---|
| Example 244 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(3,4-dimethyl-1,2-oxazol-5-yl)benzamide | 900 µg (1% of th.) LC-MS (Method 8): $R_t$ = 1.04 min MS (ESIpos): m/z = 603 [M + H]$^+$ |
| Example 245 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(3-methylbut-2-en-1-yl)benzamide | 12.4 mg (22% of th.) LC-MS (Method 8): $R_t$ = 1.09 min MS (ESIpos): m/z = 576 [M + H]$^+$ |
| Example 246 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(trans-4-hydroxycyclohexyl)benzamide | 34.7 mg (57% of th.) LC-MS (Method 8): $R_t$ = 1.93 min; MS (ESIpos): m/z = 606 [M + H]$^+$ |

TABLE 3-continued

| Example No | Structure IUPAC-Name | Qantity (yield) Analytic |
|---|---|---|
| Example 247 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(2-hydroxyphenyl)benzamide | 22.9 mg (38% of th.) LC-MS (Method 8): $R_t$ = 1.06 min MS (ESIpos): m/z = 600 [M + H]$^+$ |
| Example 248 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(pyridin-3-yl)benzamide | 24.1 mg (41% of th.) LC-MS (Method 8): $R_t$ = 0.89 min MS (ESIpos): m/z = 585 [M + H]$^+$ |
| Example 249 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(6-methylpyridin-3-yl)benzamide | 17.5 mg (29% of th.) LC-MS (Method 8): $R_t$ = 0.83 min MS (ESIpos): m/z = 599 [M + H]$^+$ |

TABLE 3-continued

| Example No | Structure / IUPAC-Name | Qantity (yield) Analytic |
|---|---|---|
| Example 250 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(6-fluoro-5-methylpyridin-3-yl)benzamide | 27.7 mg (40% of th.) LC-MS (Method 8): $R_t$ = 1.07 min MS (ESIpos): m/z = 617 [M + H]$^+$ |
| Example 251 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(1,3,4-thiadiazol-2-yl)benzamide | 9.20 mg (16% of th.) LC-MS (Method 8): $R_t$ = 0.98 min MS (ESIpos): m/z = 592 [M + H]$^+$ |
| Example 252 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(cyanomethyl)benzamide | 28.0 mg (50% of th.) LC-MS (Method 8): $R_t$ = 0.98 min MS (ESIpos): m/z = 547 [M + H]$^+$ |

TABLE 3-continued

| Example No | Structure IUPAC-Name | Qantity (yield) Analytic |
|---|---|---|
| Example 253 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(thiophen-2-ylmethyl)benzamide | 25.6 mg (41% of th.) LC-MS (Method 8): $R_t$ = 1.08 min MS (ESIpos): m/z = 604 [M + H]$^+$ |
| Example 254 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(2-methylpyridin-4-yl)benzamide | 16.9 mg (28% of th.) LC-MS (Method 8): $R_t$ = 0.77 min MS (ESIpos): m/z = 599 [M + H]$^+$ |
| Example 255 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(5-fluoropyridin-3-yl)benzamide | 27.2 mg (43% of th.) LC-MS (Method 8): $R_t$ = 1.04 min MS (ESIpos): m/z = 603 [M + H]$^+$ |

TABLE 3-continued

| Example No | Structure IUPAC-Name | Qantity (yield) Analytic |
|---|---|---|
| Example 256 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(5-methyl-1,3-thiazol-2-yl)benzamide | 29.9 mg (46% of th.) LC-MS (Method 8): R$_t$ = 1.06 min MS (ESIpos): m/z = 605 [M + H]$^+$ |
| Example 257 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(pyrimidin-4-yl)benzamide | 13.7 mg (23% of th.) LC-MS (Method 8): R$_t$ = 1.00 min MS (ESIpos): m/z = 586 [M + H]$^+$ |
| Example 258 | N-(2-Chlorophenyl)-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzamide | 19.0 mg (28% of th.) LC-MS (Method 8): R$_t$ = 1.12 min MS (ESIpos): m/z = 618 [M + H]$^+$ |

TABLE 3-continued

| Example No | Structure IUPAC-Name | Qantity (yield) Analytic |
|---|---|---|
| Example 259 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(4-methyl-1,3-thiazol-2-yl)benzamide | 14.8 mg (96% purity, 23% of th.) LC-MS (Method 8): $R_t$ = 1.06 min; MS (ESIpos): m/z = 605 [M + H]$^+$ |
| Example 260 | 5-(4-Chlorophenyl)-2-[(1-{2-[(4,5-dimethyl-3,6-dihydropyridin-1(2H)-yl)carbonyl]phenyl}-1H-1,2,4-triazol-3-yl)methyl]-4-[(2S)-3,3,3-trifluoro-2-hydroxypropyl]-2,4-dihydro-3H-1,2,4-triazol-3-one | 23.5 mg (37% of th.) LC-MS (Method 8): $R_t$ = 1.14 min MS (ESIpos): m/z = 602 [M + H]$^+$ |
| Example 261 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-ethyl-N-methoxybenzamide | 24.5 mg (42% of th.) LC-MS (Method 8): $R_t$ = 1.06 min MS (ESIpos): m/z = 566 [M + H]$^+$ |

TABLE 3-continued

| Example No | Structure IUPAC-Name | Qantity (yield) Analytic |
|---|---|---|
| Example 262 | 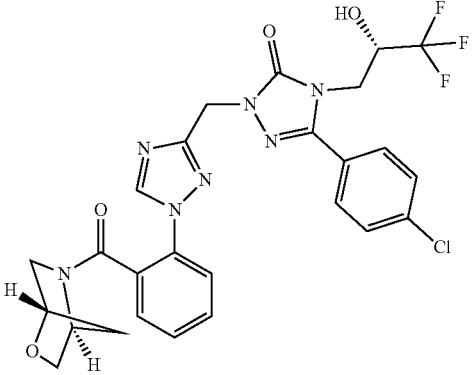 [SMILES: O=C(c1ccccc1-n1cnc(Cn2nc(-c3ccc(Cl)cc3)n(C[C@H](O)C(F)(F)F)c2=O)n1)N1C[C@@H]2C[C@H]1CO2]<br>5-(4-Chlorophenyl)-2-[(1-{2-[(1S,4S)-2-oxa-5-azabicyclo[2.2.1]hept-5-ylcarbonyl]phenyl}-1H-1,2,4-triazol-3-yl)methyl]-4-[(2S)-3,3,3-trifluoro-2-hydroxypropyl]-2,4-dihydro-3H-1,2,4-triazol-3-one | 26.1 mg (44% of th.)<br>LC-MS (Method 8):<br>$R_t$ = 0.99 min<br>MS (ESIpos): m/z = 590 [M + H]$^+$ |
| Example 263 | 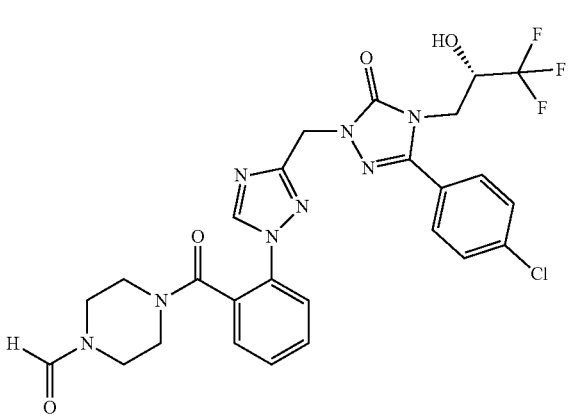 [SMILES: O=CN1CCN(C(=O)c2ccccc2-n2cnc(Cn3nc(-c4ccc(Cl)cc4)n(C[C@H](O)C(F)(F)F)c3=O)n2)CC1]<br>4-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl}piperazine-1-carbaldehyde | 20.9 mg (33% of th.)<br>LC-MS (Method 8):<br>$R_t$ = 0.94 min<br>MS (ESIpos): m/z = 605 [M + H]$^+$ |
| Example 264 | 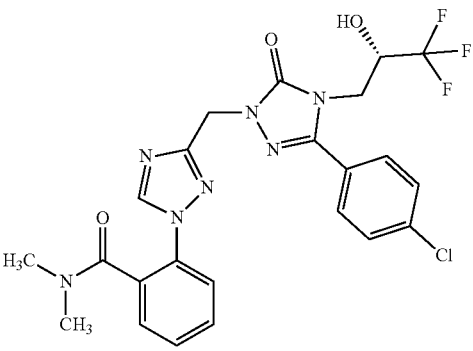 [SMILES: CN(C)C(=O)c1ccccc1-n1cnc(Cn2nc(-c3ccc(Cl)cc3)n(C[C@H](O)C(F)(F)F)c2=O)n1]<br>2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N,N-dimethylbenzamide | 21.4 mg (39% of th.)<br>LC-MS (Method 8):<br>$R_t$ = 1.01 min; MS (ESIpos): m/z = 536 [M + H]$^+$ |

TABLE 3-continued

| Example No | Structure IUPAC-Name | Qantity (yield) Analytic |
|---|---|---|
| Example 265 | 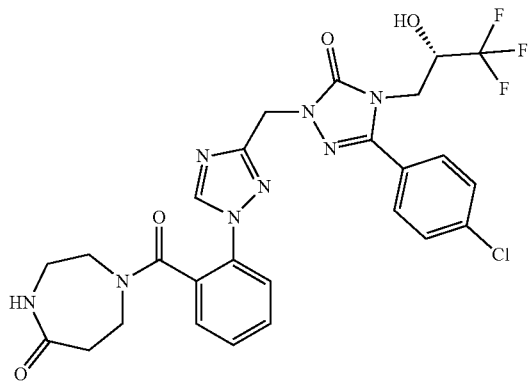 [SMILES: O=C1CCN(C(=O)c2ccccc2-n2cnc(Cn3nc(-c4ccc(Cl)cc4)n(C[C@H](O)C(F)(F)F)c3=O)n2)CCN1]  1-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl}-1,4-diazepan-5-one | 22.2 mg (33% of th.) LC-MS (Method 8): $R_t$ = 0.90 min MS (ESIpos): m/z = 605 [M + H]$^+$ |
| Example 266 | 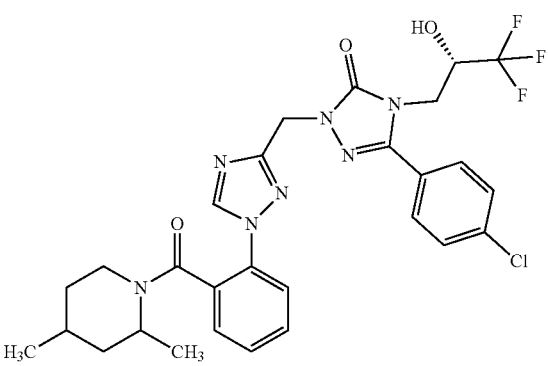 [SMILES: CC1CCN(C(=O)c2ccccc2-n2cnc(Cn3nc(-c4ccc(Cl)cc4)n(C[C@H](O)C(F)(F)F)c3=O)n2)C(C)C1]  5-(4-Chlorophenyl)-2-[(1-{2-[(2,4-dimethylpiperidin-1-yl)carbonyl]phenyl}-1H-1,2,4-triazol-3-yl)methyl]-4-[(2S)-3,3,3-trifluoro-2-hydroxypropyl]-2,4-dihydro-3H-1,2,4-triazol-3-one | 24.0 mg (38% of th.) LC-MS (Method 8): $R_t$ = 1.15 min MS (ESIpos): m/z = 604 [M + H]$^+$ |
| Example 267 | 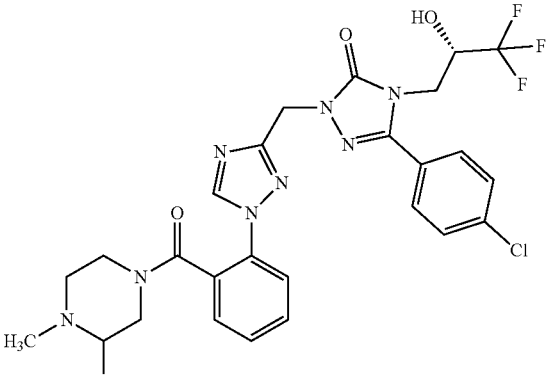  5-(4-Chlorophenyl)-2-{[1-(2-{[(3,4-dimethylpiperazin-1-yl]carbonyl}phenyl)-1H-1,2,4-triazol-3-yl]methyl}-4-[(2S)-3,3,3-trifluoro-2-hydroxypropyl]-2,4-dihydro-3H-1,2,4-triazol-3-one | 20.5 mg (33% of th.) LC-MS (Method 8): $R_t$ = 0.75 min MS (ESIpos): m/z = 605 [M + H]$^+$ |

TABLE 3-continued

| Example No | Structure IUPAC-Name | Qantity (yield) Analytic |
|---|---|---|
| Example 268 | 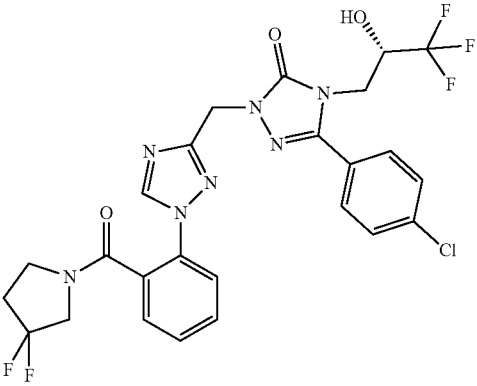 [SMILES: O=C(c1ccccc1-n1cnc(Cn2nc(-c3ccc(Cl)cc3)n(C[C@H](O)C(F)(F)F)c2=O)n1)N1CCC(F)(F)C1]<br>5-(4-Chlorophenyl)-2-[(1-{2-[(3,3-difluoropyrrolidin-1-yl)carbonyl]phenyl}-1H-1,2,4-triazol-3-yl)methyl]-4-[(2S)-3,3,3-trifluoro-2-hydroxypropyl]-2,4-dihydro-3H-1,2,4-triazol-3-one | 35.1 mg (57% of th.)<br>LC-MS (Method 8):<br>$R_t$ = 1.07 min<br>MS (ESIpos): m/z = 598 [M + H]$^+$ |
| Example 269 | 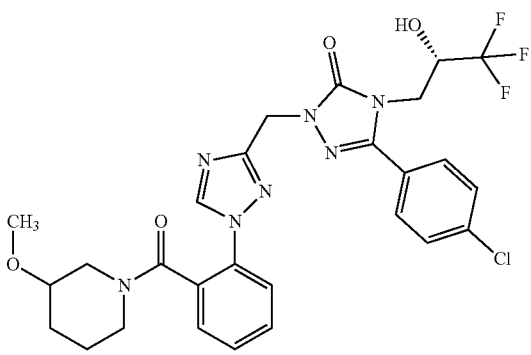 [SMILES: COC1CCCN(C(=O)c2ccccc2-n2cnc(Cn3nc(-c4ccc(Cl)cc4)n(C[C@H](O)C(F)(F)F)c3=O)n2)C1]<br>5-(4-Chlorophenyl)-2-{[1-(2-{[3-methoxypiperidin-1-yl]carbonyl}phenyl)-1H-1,2,4-triazol-3-yl]methyl}-4-[(2S)-3,3,3-trifluoro-2-hydroxypropyl]-2,4-dihydro-3H-1,2,4-triazol-3-one (diastereomeric mixture) | 39.5 mg (61% of th.)<br>LC-MS (Method 8):<br>$R_t$ = 1.05 min<br>MS (ESIpos): m/z = 606 [M + H]$^+$ |
| Example 270 | 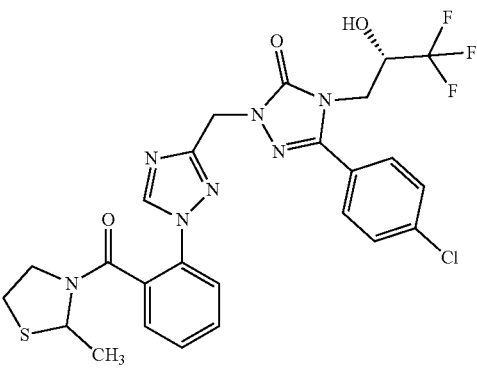 [SMILES: CC1SCCN1C(=O)c1ccccc1-n1cnc(Cn2nc(-c3ccc(Cl)cc3)n(C[C@H](O)C(F)(F)F)c2=O)n1]<br>5-(4-Chlorophenyl)-2-{[1-(2-{[2-methyl-1,3-thiazolidin-3-yl]carbonyl}phenyl)-1H-1,2,4-triazol-3-yl]methyl}-4-[(2S)-3,3,3-trifluoro-2-hydroxypropyl]-2,4-dihydro-3H-1,2,4-triazol-3-one (diastereomeric mixture) | 14.5 mg (24% of th.)<br>LC-MS (Method 8):<br>$R_t$ = 1.09 min<br>MS (ESIpos): m/z = 594 [M + H]$^+$ |

TABLE 3-continued

| Example No | Structure IUPAC-Name | Qantity (yield) Analytic |
|---|---|---|
| Example 271 | 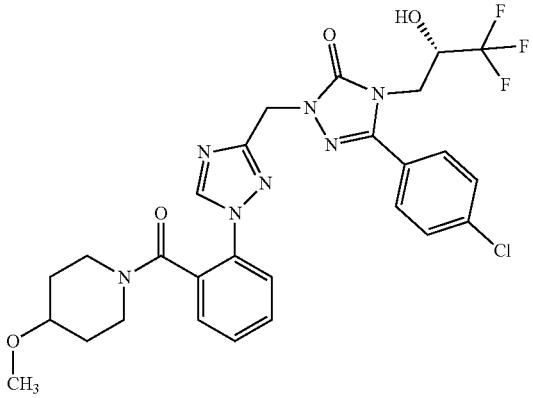 [SMILES: COC1CCN(C(=O)c2ccccc2-n2cnc(Cn3nc(-c4ccc(Cl)cc4)n(C[C@H](O)C(F)(F)F)c3=O)n2)CC1]<br>5-(4-Chlorophenyl)-2-[(1-{2-[(4-methoxypiperidin-1-yl)carbonyl]phenyl}-1H-1,2,4-triazol-3-yl)methyl]-4-[(2S)-3,3,3-trifluoro-2-hydroxypropyl]-2,4-dihydro-3H-1,2,4-triazol-3-one | 28.1 mg (44% of th.)<br>LC-MS (Method 8):<br>$R_t$ = 1.04 min<br>MS (ESIpos): m/z = 606 [M + H]$^+$ |
| Example 272 | 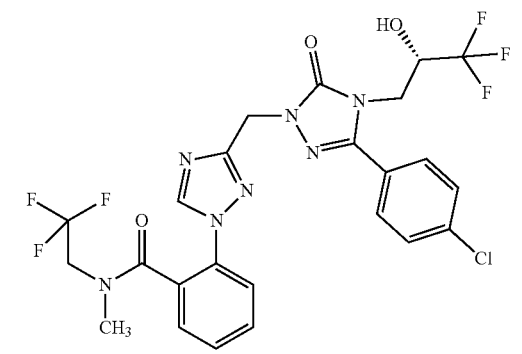 [SMILES: CN(CC(F)(F)F)C(=O)c1ccccc1-n1cnc(Cn2nc(-c3ccc(Cl)cc3)n(C[C@H](O)C(F)(F)F)c2=O)n1]<br>2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-methyl-N-(2,2,2-trifluoroethyl)benzamide | 22.4 mg (37% of th.)<br>LC-MS (Method 8):<br>$R_t$ = 1.10 min<br>MS (ESIpos): m/z = 604 [M + H]$^+$ |
| Example 273 | 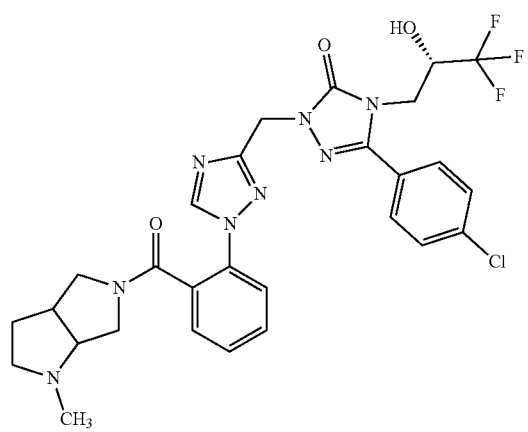<br>5-(4-Chlorophenyl)-2-[(1-{2-[(5-methyl-2,5-diazabicyclo[2.2.1]hept-2-yl)carbonyl]phenyl}-1H-1,2,4-triazol-3-yl)methyl]-4-[(2S)-3,3,3-trifluoro-2-hydroxypropyl]-2,4-dihydro-3H-1,2,4-triazol-3-one {diastereomeric mixture} | 18.3 mg (30% of th.)<br>LC-MS (Method 8):<br>$R_t$ = 0.73 min<br>MS (ESIpos): m/z = 603 [M + H]$^+$ |

TABLE 3-continued

| Example No | Structure IUPAC-Name | Qantity (yield) Analytic |
|---|---|---|
| Example 274 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-methyl-N-[1-methylpyrrolidin-3-yl]benzamide (diastereomeric mixture) | 17.6 mg (29% of th.) LC-MS (Method 8): $R_t$ = 0.76 min MS (ESIpos): m/z = 605 [M + H]$^+$ |
| Example 275 | 5-(4-Chlorophenyl)-2-[(1-{2-[(2,3-dimethylpiperidin-1-yl)carbonyl]phenyl}-1H-1,2,4-triazol-3-yl)methyl]-4-[(2S)-3,3,3-trifluoro-2-hydroxypropyl]-2,4-dihydro-3H-1,2,4-triazol-3-one (mixture of stereoisomers) | 32.1 mg (53% of th.) LC-MS (Method 8): $R_t$ = 1.14 min MS (ESIpos): m/z = 604 [M + H]$^+$ |
| Example 276 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-cyclopentyl-N-methylbenzamide | 24.2 mg (40% of th.) LC-MS (Method 8): $R_t$ = 1.12 min MS (ESIpos): m/z = 590 [M + H]$^+$ |

| Example No | Structure IUPAC-Name | Qantity (yield) Analytic |
|---|---|---|
| Example 277 | 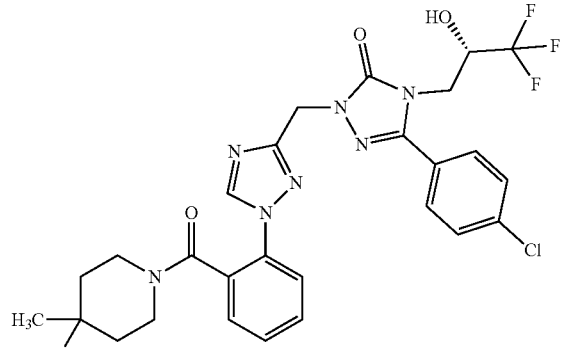<br>5-(4-Chlorophenyl)-2-[(1-{2-[(4,4-dimethylpiperidin-1-yl)carbonyl]phenyl}-1H-1,2,4-triazol-3-yl)methyl]-4-[(2S)-3,3,3-trifluoro-2-hydroxypropyl]-2,4-dihydro-3H-1,2,4-triazol-3-one | 27.2 mg (45% of th.)<br>LC-MS (Method 8):<br>$R_t$ = 1.15 min<br>MS (ESIpos): m/z = 604 [M + H]$^+$ |
| Example 278 | 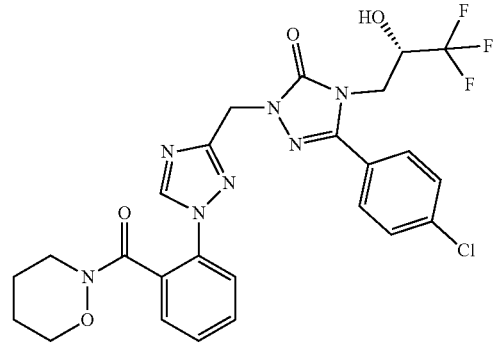 [SMILES: O=C(c1ccccc1-n1cnc(Cn2nc(-c3ccc(Cl)cc3)n(C[C@H](O)C(F)(F)F)c2=O)n1)N1CCCCO1]<br>5-(4-Chlorophenyl)-2-({1-[2-(1,2-oxazinan-2-ylcarbonyl)phenyl]-1H-1,2,4-triazol-3-yl}methyl)-4-[(2S)-3,3,3-trifluoro-2-hydroxypropyl]-2,4-dihydro-3H-1,2,4-triazol-3-one | 8.00 mg (14% of th.)<br>LC-MS (Method 8):<br>$R_t$ = 1.06 min<br>MS (ESIpos): m/z = 578 [M + H]$^+$ |
| Example 279 | 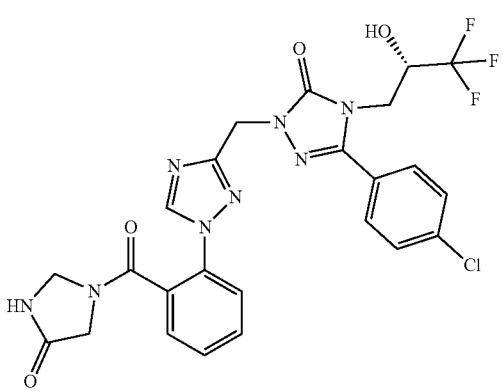 [SMILES: O=C1CN(C(=O)c2ccccc2-n2cnc(Cn3nc(-c4ccc(Cl)cc4)n(C[C@H](O)C(F)(F)F)c3=O)n2)CN1]<br>5-(4-Chlorophenyl)-2-[(1-{2-[(4-oxoimidazolidin-1-yl)carbonyl]phenyl}-1H-1,2,4-triazol-3-yl)methyl]-4-[(2S)-3,3,3-trifluoro-2-hydroxypropyl]-2,4-dihydro-3H-1,2,4-triazol-3-one | 22.9 mg (40% of th.)<br>LC-MS (Method 8):<br>$R_t$ = 0.91 min<br>MS (ESIpos): m/z = 577 [M + H]$^+$ |

TABLE 3-continued

| Example No | Structure IUPAC-Name | Qantity (yield) Analytic |
|---|---|---|
| Example 280 | 4-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl}-3-methylpiperazin-2-one (diastereomeric mixture) | 31.4 mg (52% of th.) LC-MS (Method 8): $R_t$ = 0.93 min MS (ESIpos): m/z = 605 [M + H]$^+$ |
| Example 281 | 5-(4-Chlorophenyl)-2-[(1-{2-[(3,3-dimethylmorpholin-4-yl)carbonyl]phenyl}-1H-1,2,4-triazol-3-yl)methyl]-4-[(2S)-3,3,3-trifluoro-2-hydroxypropyl]-2,4-dihydro-3H-1,2,4-triazol-3-one | 17.8 mg (29% of th.) LC-MS (Method 8): $R_t$ = 1.08 min MS (ESIpos): m/z = 606 [M + H]$^+$ |
| Example 282 | 5-(4-Chlorophenyl)-2-{[1-(2-{[3-methylmorpholin-4-yl]carbonyl}phenyl)-1H-1,2,4-triazol-3-yl]methyl}-4-[(2S)-3,3,3-trifluoro-2-hydroxypropyl]-2,4-dihydro-3H-1,2,4-triazol-3-one (diastereomeric mixture) | 20.9 mg (32% of th.) LC-MS (Method 8): $R_t$ = 1.03 min MS (ESIpos): m/z = 592 [M + H]$^+$ |

TABLE 3-continued

| Example No | Structure IUPAC-Name | Qantity (yield) Analytic |
|---|---|---|
| Example 283 | 5-(4-Chlorophenyl)-2-{[1-(2-{[2-methylmorpholin-4-yl]carbonyl}phenyl]-1H-1,2,4-triazol-3-yl]methyl}-4-[(2S)-3,3,3-trifluoro-2-hydroxypropyl]-2,4-dihydro-3H-1,2,4-triazol-3-one (diastereomeric mixture) | 21.2 mg (34% of th.) LC-MS (Method 8): $R_t$ = 1.03 min MS (ESIpos): m/z = 592 [M + H]$^+$ |
| Example 284 | 5-(4-Chlorophenyl)-2-({1-[2-(1,4-oxazepan-4-ylcarbonyl)phenyl]-1H-1,2,4-triazol-3-yl}methyl)-4-[(2S)-3,3,3-trifluoro-2-hydroxypropyl]-2,4-dihydro-3H-1,2,4-triazol-3-one | 29.2 mg (49% of th.) LC-MS (Method 8): $R_t$ = 1.01 min MS (ESIpos): m/z = 592 [M + H]$^+$ |
| Example 285 | 5-(4-Chlorophenyl)-2-({1-[2-(1,2-oxazolidin-2-ylcarbonyl)phenyl]-1H-1,2,4-triazol-3-yl}methyl)-4-[(2S)-3,3,3-trifluoro-2-hydroxypropyl]-2,4-dihydro-3H-1,2,4-triazol-3-one | 26.4 mg (45% of th.) LC-MS (Method 8): $R_t$ = 1.02 min MS (ESIpos): m/z = 564 [M + H]$^+$ |

TABLE 3-continued

| Example No | Structure IUPAC-Name | Qantity (yield) Analytic |
|---|---|---|
| Example 286 | 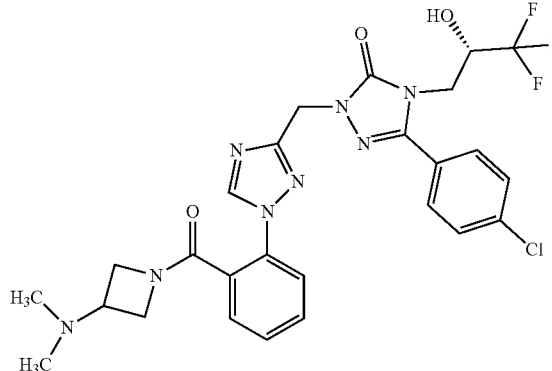<br>5-(4-Chlorophenyl)-2-{[1-(2-{[3-(dimethylamino)azetidin-1-yl]carbonyl}phenyl)-1H-1,2,4-triazol-3-yl]methyl}-4-[(2S)-3,3,3-trifluoro-2-hydroxypropyl]-2,4-dihydro-3H-1,2,4-triazol-3-one | 27.1 mg (46% of th.)<br>LC-MS (Method 8):<br>$R_t$ = 0.74 min<br>MS (ESIpos): m/z = 591 [M + H]$^+$ |
| Example 287 | 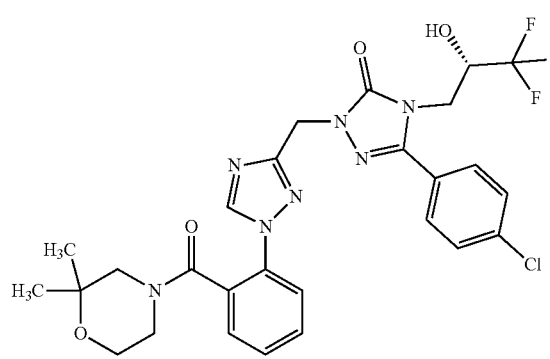<br>5-(4-Chlorophenyl)-2-[(1-{2-[(2,2-dimethylmorpholin-4-yl)carbonyl]phenyl}-1H-1,2,4-triazol-3-yl)methyl]-4-[(2S)-3,3,3-trifluoro-2-hydroxypropyl]-2,4-dihydro-3H-1,2,4-triazol-3-one | 32.6 mg (49% of th.)<br>LC-MS (Method 8):<br>$R_t$ = 1.05 min<br>MS (ESIpos): m/z = 606 [M + H]$^+$ |
| Example 288 | 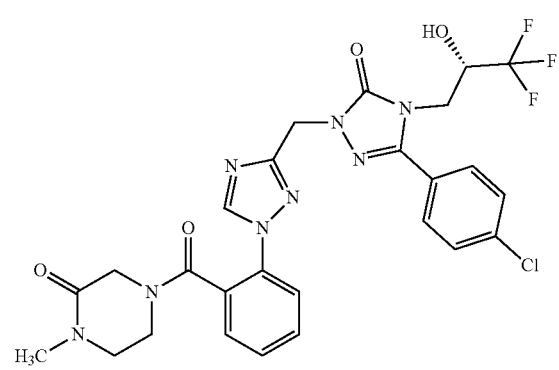 [SMILES: CN1CCN(C(=O)c2ccccc2-n2cnc(Cn3nc(-c4ccc(Cl)cc4)n(C[C@H](O)C(F)(F)F)c3=O)n2)CC1=O]<br>4-{2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl}-1-methylpiperazin-2-one | 32.8 mg (53% of th.)<br>LC-MS (Method 8):<br>$R_t$ = 0.95 min<br>MS (ESIpos): m/z = 605 [M + H]$^+$ |

TABLE 3-continued

| Example No | Structure IUPAC-Name | Qantity (yield) Analytic |
|---|---|---|
| Example 289 | 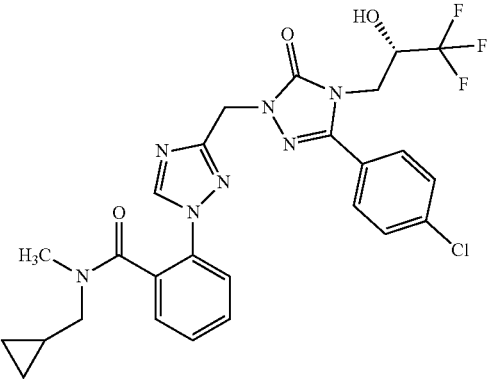 [SMILES: CN(CC1CC1)C(=O)c1ccccc1-n1cnc(Cn2nc(-c3ccc(Cl)cc3)n(C[C@H](O)C(F)(F)F)c2=O)n1]<br>2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(cyclopropylmethyl)-N-methylbenzamide | 29.1 mg (49% of th.)<br>LC-MS (Method 8):<br>$R_t$ = 1.09 min<br>MS (ESIpos): m/z = 576 [M + H]$^+$ |
| Example 290 | 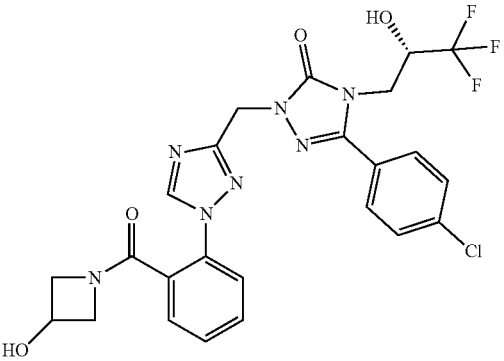 [SMILES: O=C(c1ccccc1-n1cnc(Cn2nc(-c3ccc(Cl)cc3)n(C[C@H](O)C(F)(F)F)c2=O)n1)N1CC(O)C1]<br>5-(4-Chlorophenyl)-2-[(1-{2-[(3-hydroxyazetidin-1-yl)carbonyl]phenyl}-1H-1,2,4-triazol-3-yl)methyl]-4-[(2S)-3,3,3-trifluoro-2-hydroxypropyl]-2,4-dihydro-3H-1,2,4-triazol-3-one | 20.8 mg (35% of th.)<br>LC-MS (Method 8):<br>$R_t$ = 0.93 min<br>MS (ESIpos): m/z = 564 [M + H]$^+$ |
| Example 291 | 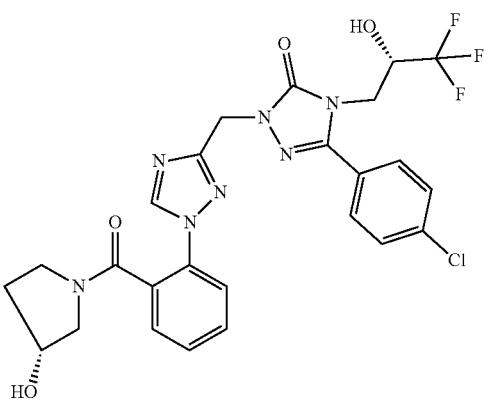 [SMILES: O=C(c1ccccc1-n1cnc(Cn2nc(-c3ccc(Cl)cc3)n(C[C@H](O)C(F)(F)F)c2=O)n1)N1CC[C@@H](O)C1]<br>5-(4-Chlorophenyl)-2-{[1-(2-{[(3R)-3-hydroxypyrrolidin-1-yl]carbonyl}phenyl)-1H-1,2,4-triazol-3-yl]methyl}-4-[(2S)-3,3,3-trifluoro-2-hydroxypropyl]-2,4-dihydro-3H-1,2,4-triazol-3-one | 28.8 mg (48% of th.)<br>LC-MS (Method 8):<br>$R_t$ = 0.94 min<br>MS (ESIpos): m/z = 578 [M + H]$^+$ |

TABLE 3-continued

| Example No | Structure IUPAC-Name | Qantity (yield) Analytic |
|---|---|---|
| Example 292 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-[2-hydroxypropyl]benzamide (diastereomeric mixture) | 5.70 mg (9% of th.) LC-MS (Method 8): $R_t$ = 0.94 min MS (ESIpos): m/z = 566 [M + H]$^+$ |
| Example 293 | 5-(4-Chlorophenyl)-2-[(1-{2-[(2,5-dimethyl-2,5-dihydro-1H-pyrrol-1-yl)carbonyl]phenyl}-1H-1,2,4-triazol-3-yl)methyl]-4-[(2S)-3,3,3-trifluoro-2-hydroxypropyl]-2,4-dihydro-3H-1,2,4-triazol-3-one | 5.70 mg (9% of th.) LC-MS (Method 8): $R_t$ = 1.10 min MS (ESIpos): m/z = 588 [M + H]$^+$ |
| Example 294 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-methyl-N-(prop-2-en-1-yl)benzamide | 23.2 mg (40% of th.) LC-MS (Method 8): $R_t$ = 1.07 min MS (ESIpos): m/z = 562 [M + H]$^+$ |

TABLE 3-continued

| Example No | Structure IUPAC-Name | Qantity (yield) Analytic |
|---|---|---|
| Example 295 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-ethyl-N-methylbenzamide | 700 μg (1% of th.) LC-MS (Method 8): $R_t$ = 1.04 min MS (ESIpos): m/z = 550 [M + H]$^+$ |
| Example 296 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(3-methylpyridin-2-yl)benzamide | 11.6 mg (19% of th.) LC-MS (Method 8): $R_t$ = 0.96 min MS (ESIpos): m/z = 599 [M + H]$^+$ |
| Example 297 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-[2,3-dihydroxypropyl]benzamide (diastereomeric mixture) | 30.5 mg (51% of th.) LC-MS (Method 8): $R_t$ = 0.88 min MS (ESIpos): m/z = 582 [M + H]$^+$ |

TABLE 3-continued

| Example No | Structure IUPAC-Name | Qantity (yield) Analytic |
|---|---|---|
| Example 298 | 5-(4-Chlorophenyl)-2-{[1-(2-{[3-hydroxypyrrolidin-1-yl]carbonyl}phenyl)-1H-1,2,4-triazol-3-yl]methyl}-4-[(2S)-3,3,3-trifluoro-2-hydroxypropyl]-2,4-dihydro-3H-1,2,4-triazol-3-one (diastereomeric mixture) | 21.6 mg (36% of th.) LC-MS (Method 8): $R_t$ = 0.94 min MS (ESIpos): m/z = 578 [M + H]$^+$ |
| Example 299 | N-Benzyl-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzamide | 24.3 mg (41% of th.) LC-MS (Method 8): $R_t$ = 1.09 min MS (ESIpos): m/z = 598 [M + H]$^+$ |
| Example 300 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(pyridin-4-yl)benzamide | 32.9 mg (55% of th.) LC-MS (Method 8): $R_t$ = 0.76 min MS (ESIpos): m/z = 585 [M + H]$^+$ |

TABLE 3-continued

| Example No | Structure  IUPAC-Name | Qantity (yield)  Analytic |
|---|---|---|
| Example 301 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(pyridin-2-ylmethyl)benzamide | 16.1 mg (25% of th.)  LC-MS (Method 8):  $R_t$ = 0.91 min  MS (ESIpos): m/z = 599 [M + H]$^+$ |
| Example 302 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(pyridin-4-ylmethyl)benzamide | 14.8 mg (25% of th.)  LC-MS (Method 8):  $R_t$ = 0.78 min  MS (ESIpos): m/z = 599 [M + H]$^+$ |
| Example 303 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(2,4-difluorophenyl)benzamide | 14.7 mg (23% of th.)  LC-MS (Method 8):  $R_t$ = 1.10 min  MS (ESIpos): m/z = 620 [M + H]$^+$ |

TABLE 3-continued

| Example No | Structure IUPAC-Name | Qantity (yield) Analytic |
|---|---|---|
| Example 304 | 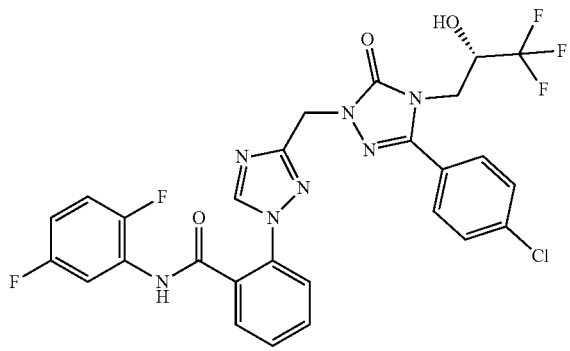 [SMILES: O=C(Nc1cc(F)ccc1F)c1ccccc1-n1cnc(Cn2nc(-c3ccc(Cl)cc3)n(C[C@H](O)C(F)(F)F)c2=O)n1]<br>2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(2,5-difluorophenyl)benzamide | 11.5 mg (17% of th.)<br>LC-MS (Method 8):<br>$R_t$ = 1.12 min<br>MS (ESIpos): m/z = 620 [M + H]$^+$ |
| Example 305 | 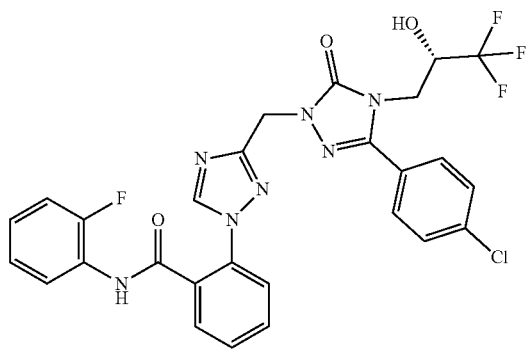 [SMILES: O=C(Nc1ccccc1F)c1ccccc1-n1cnc(Cn2nc(-c3ccc(Cl)cc3)n(C[C@H](O)C(F)(F)F)c2=O)n1]<br>2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(2-fluorophenyl)benzamide | 24.4 mg (41% of th.)<br>LC-MS (Method 8):<br>$R_t$ = 1.10 min<br>MS (ESIpos): m/z = 602 [M + H]$^+$ |
| Example 306 | 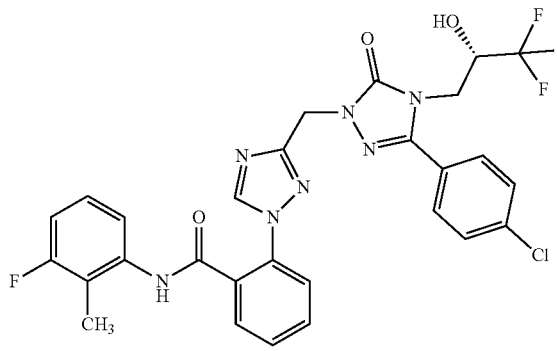<br>2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(3-fluoro-2-methylphenyl)benzamide | 23.7 mg (37% of th.)<br>LC-MS (Method 8):<br>$R_t$ = 1.12 min<br>MS (ESIpos): m/z = 616 [M + H]$^+$ |

TABLE 3-continued

| Example No | Structure IUPAC-Name | Qantity (yield) Analytic |
|---|---|---|
| Example 307 | 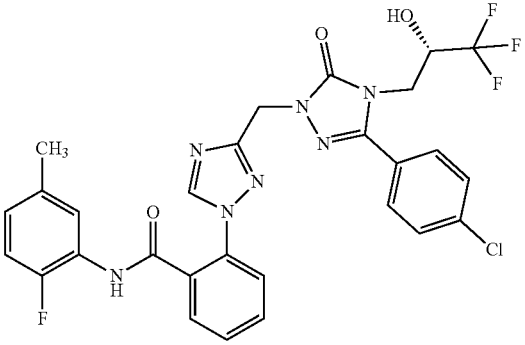 [SMILES: Cc1ccc(F)c(NC(=O)c2ccccc2-n2cnc(Cn3nc(-c4ccc(Cl)cc4)n(C[C@H](O)C(F)(F)F)c3=O)n2)c1]<br>2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(2-fluoro-5-methylphenyl)benzamide | 4.40 mg (7% of th.)<br>LC-MS (Method 8):<br>$R_t$ = 1.13 min<br>MS (ESIpos): m/z = 616 [M + H]$^+$ |
| Example 308 | 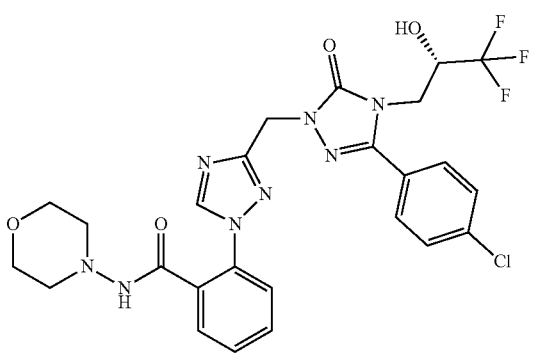 [SMILES: O=C(NN1CCOCC1)c1ccccc1-n1cnc(Cn2nc(-c3ccc(Cl)cc3)n(C[C@H](O)C(F)(F)F)c2=O)n1]<br>2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(morpholin-4-yl)benzamide | 20.7 mg (35% of th.)<br>LC-MS (Method 8):<br>$R_t$ = 0.94 min<br>MS (ESIpos): m/z = 593 [M + H]$^+$ |
| Example 309 | 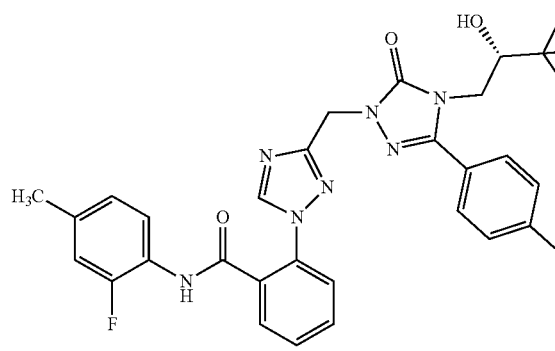<br>2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(2-fluoro-4-methylphenyl)benzamide | 29.7 mg (47% of th.)<br>LC-MS (Method 8):<br>$R_t$ = 1.12 min<br>MS (ESIpos): m/z = 616 [M + H]$^+$ |

TABLE 3-continued

| Example No | Structure IUPAC-Name | Qantity (yield) Analytic |
|---|---|---|
| Example 310 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(4-fluorophenyl)benzamide | 31.7 mg (53% of th.) LC-MS (Method 8): $R_t$ = 1.10 min MS (ESIpos): m/z = 602 [M + H]$^+$ |
| Example 311 | 5-(4-Chlorophenyl)-2-({1-[2-(thiomorpholin-4-ylcarbonyl)phenyl]-1H-1,2,4-triazol-3-yl}methyl)-4-[(2S)-3,3,3-trifluoro-2-hydroxypropyl]-2,4-dihydro-3H-1,2,4-triazol-3-one | 28.8 mg (46% of th.) LC-MS (Method 8): $R_t$ = 1.07 min MS (ESIpos): m/z = 594 [M + H]$^+$ |
| Example 312 | N-(6-Aminopyridin-2-yl)-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzamide | 30.3 mg (48% of th.) LC-MS (Method 8): $R_t$ = 0.87 min MS (ESIpos): m/z = 600 [M + H]$^+$ |

TABLE 3-continued

| Example No | Structure / IUPAC-Name | Qantity (yield) Analytic |
|---|---|---|
| Example 313 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(4-methylpyridin-3-yl)benzamide | 16.7 mg (27% of th.) LC-MS (Method 8): $R_t$ = 0.84 min MS (ESIpos): m/z = 599 [M + H]$^+$ |
| Example 314 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N,N-diethylbenzamide | 5.70 mg (10% of th.) LC-MS (Method 8): $R_t$ = 1.07 min MS (ESIpos): m/z = 564 [M + H]$^+$ |
| Example 315 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(furan-2-ylmethyl)benzamide | 27.9 mg (45% of th.) LC-MS (Method 8): $R_t$ = 1.05 min MS (ESIpos): m/z = 588 [M + H]$^+$ |

TABLE 3-continued

| Example No | Structure IUPAC-Name | Qantity (yield) Analytic |
|---|---|---|
| Example 316 | 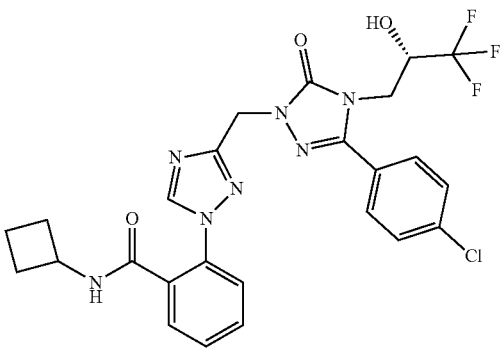 [SMILES: O=C(NC1CCC1)c1ccccc1-n1cnc(Cn2nc(-c3ccc(Cl)cc3)n(C[C@H](O)C(F)(F)F)c2=O)n1]  2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-cyclobutylbenzamide | 31.8 mg (52% of th.) LC-MS (Method 8): $R_t$ = 1.05 min MS (ESIpos): m/z = 562 [M + H]$^+$ |
| Example 317 | 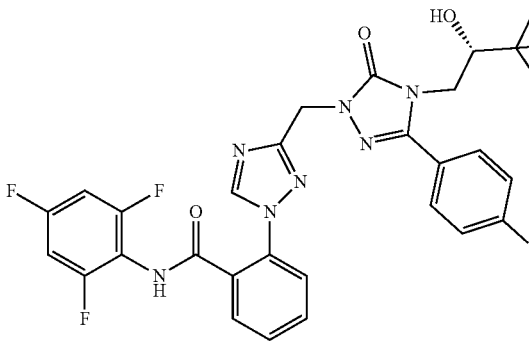  2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(2,4,6-trifluorophenyl)benzamide | 8.10 mg (12% of th.) LC-MS (Method 8): $R_t$ = 1.09 min MS (ESIpos): m/z = 638 [M + H]$^+$ |
| Example 318 | 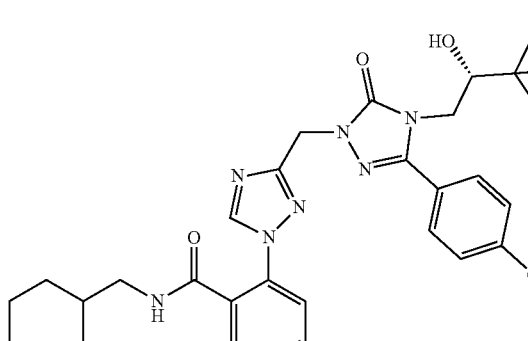  2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(cyclohexylmethyl)benzamide | 26.6 mg (44% of th.) LC-MS (Method 8): $R_t$ = 1.15 min MS (ESIpos): m/z = 604 [M + H]$^+$ |

TABLE 3-continued

| Example No | Structure / IUPAC-Name | Qantity (yield) Analytic |
|---|---|---|
| Example 319 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(2-methylcyclohexyl)benzamide (diastereomeric mixture) | 36.9 mg (60% of th.) LC-MS (Method 8): $R_t$ = 1.14 min MS (ESIpos): m/z = 604 [M + H]$^+$ |
| Example 320 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-propylbenzamide | 28.8 mg (49% of th.) LC-MS (Method 8): $R_t$ = 1.04 min MS (ESIpos): m/z = 550 [M + H]$^+$ |
| Example 321 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(4-methylcyclohexyl)benzamide | 27.8 mg (46% of th.) LC-MS (Method 8): $R_t$ = 1.15 min MS (ESIpos): m/z = 604 [M + H]$^+$ |

TABLE 3-continued

| Example No | Structure / IUPAC-Name | Qantity (yield) Analytic |
|---|---|---|
| Example 322 | 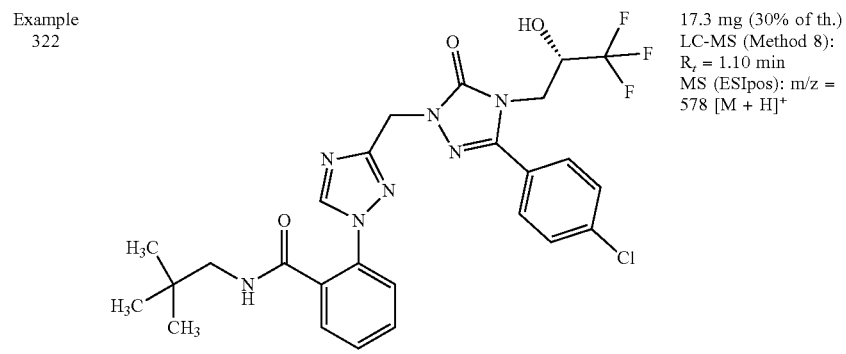<br>2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(2,2-dimethylpropyl)benzamide | 17.3 mg (30% of th.)<br>LC-MS (Method 8):<br>$R_t$ = 1.10 min<br>MS (ESIpos): m/z = 578 [M + H]$^+$ |
| Example 323 | 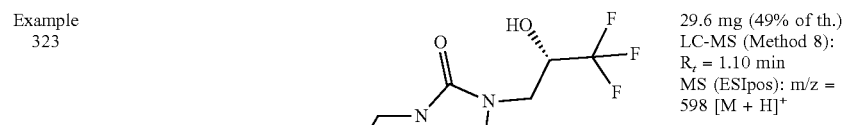<br>2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(2-methylphenyl)benzamide | 29.6 mg (49% of th.)<br>LC-MS (Method 8):<br>$R_t$ = 1.10 min<br>MS (ESIpos): m/z = 598 [M + H]$^+$ |
| Example 324 | 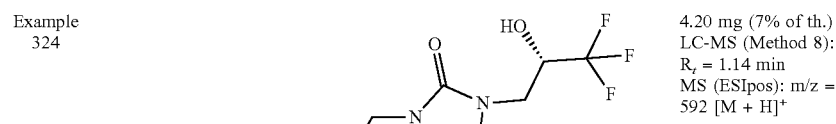<br>2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N,N-di(propan-2-yl)benzamide | 4.20 mg (7% of th.)<br>LC-MS (Method 8):<br>$R_t$ = 1.14 min<br>MS (ESIpos): m/z = 592 [M + H]$^+$ |

TABLE 3-continued

| Example No | Structure IUPAC-Name | Qantity (yield) Analytic |
|---|---|---|
| Example 325 | 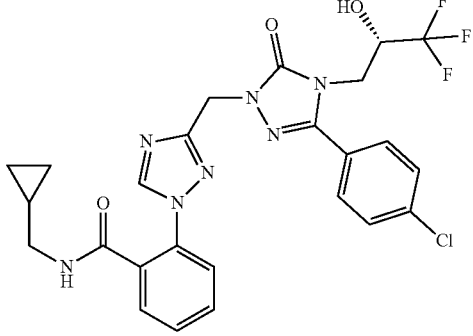<br>2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(cyclopropylmethyl)benzamide | 29.2 mg (48% of th.)<br>LC-MS (Method 8):<br>$R_t$ = 1.05 min<br>MS (ESIpos): m/z = 562 [M + H]$^+$ |
| Example 326 | 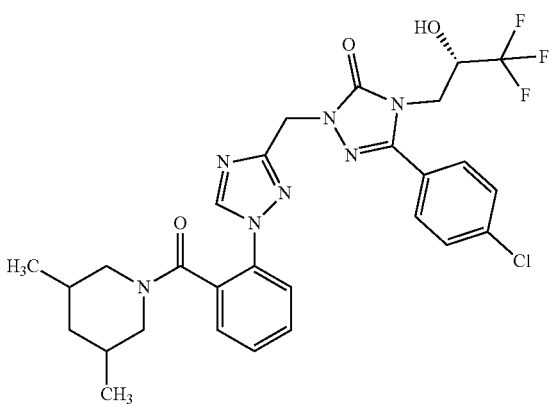 [SMILES: CC1CC(C)CN(C(=O)c2ccccc2-n2cnc(Cn3nc(-c4ccc(Cl)cc4)n(C[C@H](O)C(F)(F)F)c3=O)n2)C1]<br>5-(4-Chlorophenyl)-2-[(1-{2-[(3,5-dimethylpiperidin-1-yl)carbonyl]phenyl}-1H-1,2,4-triazol-3-yl)methyl]-4-[(2S)-3,3,3-trifluoro-2-hydroxypropyl]-2,4-dihydro-3H-1,2,4-triazol-3-one (diastereomeric mixture) | 33.7 mg (53% of th.)<br>LC-MS (Method 8):<br>$R_t$ = 1.16 min<br>MS (ESIpos): m/z = 604 [M + H]$^+$ |
| Example 327 | 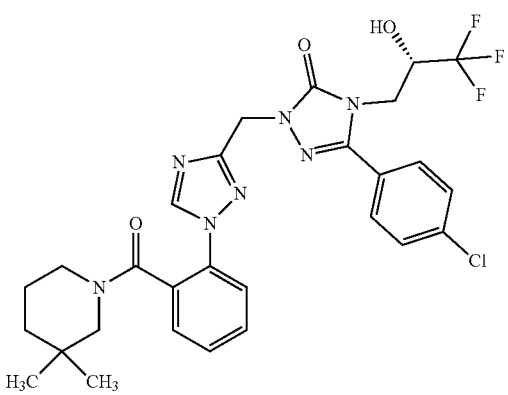 [SMILES: CC1(C)CCCN(C(=O)c2ccccc2-n2cnc(Cn3nc(-c4ccc(Cl)cc4)n(C[C@H](O)C(F)(F)F)c3=O)n2)C1]<br>5-(4-Chlorophenyl)-2-[(1-{2-[(3,3-dimethylpiperidin-1-yl)carbonyl]phenyl}-1H-1,2,4-triazol-3-yl)methyl]-4-[(2S)-3,3,3-trifluoro-2-hydroxypropyl]-2,4-dihydro-3H-1,2,4-triazol-3-one | 35.9 mg (58% of th.)<br>LC-MS (Method 8):<br>$R_t$ = 1.15 min<br>MS (ESIpos): m/z = 604 [M + H]$^+$ |

TABLE 3-continued

| Example No | Structure IUPAC-Name | Qantity (yield) Analytic |
|---|---|---|
| Example 328 | 5-(4-Chlorophenyl)-2-[(1-{2-[(2,5-dimethylpyrrolidin-1-yl)carbonyl]phenyl}-1H-1,2,4-triazol-3-yl)methyl]-4-[(2S)-3,3,3-trifluoro-2-hydroxypropyl]-2,4-dihydro-3H-1,2,4-triazol-3-one (mixture of stereoisomers) | 26.5 mg (44% of th.) LC-MS (Method 8): $R_t$ = 1.13 min MS (ESIpos): m/z = 590 [M + H]$^+$ |
| Example 329 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-cyclohexyl-N-methylbenzamide | 29.5 mg (48% of th.) LC-MS (Method 8): $R_t$ = 1.15 min MS (ESIpos): m/z = 604 [M + H]$^+$ |
| Example 330 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(furan-2-ylmethyl)-N-methylbenzamide | 27.6 mg (44% of th.) LC-MS (Method 8): $R_t$ = 1.10 min MS (ESIpos): m/z = 602 [M + H]$^+$ |

TABLE 3-continued

| Example No | Structure IUPAC-Name | Qantity (yield) Analytic |
|---|---|---|
| Example 331 | 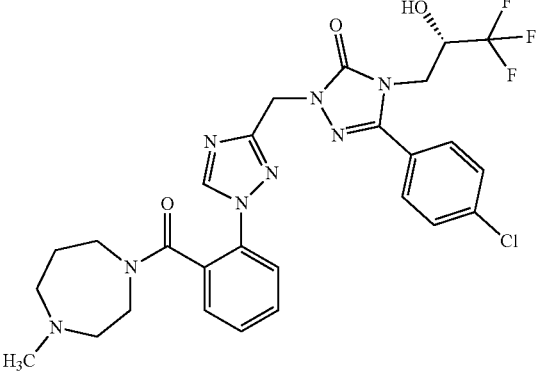<br>5-(4-Chlorophenyl)-2-[(1-{2-[(4-methyl-1,4-diazepan-1-yl)carbonyl]phenyl}-1H-1,2,4-triazol-3-yl)methyl]-4-[(2S)-3,3,3-trifluoro-2-hydroxypropyl]-2,4-dihydro-3H-1,2,4-triazol-3-one | 17.9 mg (30% of th.)<br>LC-MS (Method 8):<br>$R_t$ = 0.74 min<br>MS (ESIpos): m/z = 605 [M + H]$^+$ |
| Example 332 | 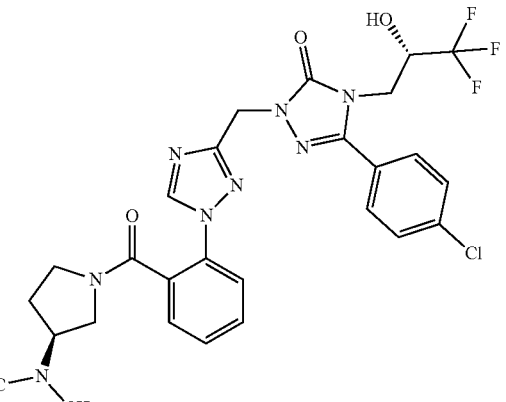<br>5-(4-Chlorophenyl)-2-{[1-(2-{[(3S)-3-(dimethylamino)pyrrolidin-1-yl]carbonyl}phenyl)-1H-1,2,4-triazol-3-yl]methyl}-4-[(2S)-3,3,3-trifluoro-2-hydroxypropyl]-2,4-dihydro-3H-1,2,4-triazol-3-one | 16.8 mg (28% of th.)<br>LC-MS (Method 8):<br>$R_t$ = 0.74 min<br>MS (ESIpos): m/z = 605 [M + H]$^+$ |
| Example 333 | 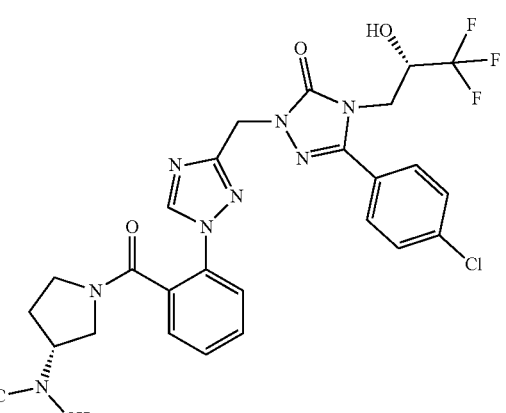<br>5-(4-Chlorophenyl)-2-{[1-(2-{[(3R)-3-(dimethylamino)pyrrolidin-1-yl]carbonyl}phenyl)-1H-1,2,4-triazol-3-yl]methyl}-4-[(2S)-3,3,3-trifluoro-2-hydroxypropyl]-2,4-dihydro-3H-1,2,4-triazol-3-one | 21.1 mg (35% of th.)<br>LC-MS (Method 8):<br>$R_t$ = 0.74 min<br>MS (ESIpos): m/z = 605 [M + H]$^+$ |

TABLE 3-continued

| Example No | Structure IUPAC-Name | Qantity (yield) Analytic |
|---|---|---|
| Example 334 | 5-(4-Chlorophenyl)-2-({1-[2-(1,3-thiazolidin-3-ylcarbonyl)phenyl]-1H-1,2,4-triazol-3-yl}methyl)-4-[(2S)-3,3,3-trifluoro-2-hydroxypropyl]-2,4-dihydro-3H-1,2,4-triazol-3-one | 6.40 mg (11% of th.) LC-MS (Method 8): $R_t$ = 1.05 min MS (ESIpos): m/z = 580 [M + H]$^+$ |
| Example 335 | 5-(4-Chlorophenyl)-2-{[1-(2-{[(2R)-2-(methoxymethyl)pyrrolidin-1-yl]carbonyl}phenyl)-1H-1,2,4-triazol-3-yl]methyl}-4-[(2S)-3,3,3-trifluoro-2-hydroxypropyl]-2,4-dihydro-3H-1,2,4-triazol-3-one | 24.4 mg (38% of th.) LC-MS (Method 8): $R_t$ = 1.07 min MS (ESIpos): m/z = 606 [M + H]$^+$ |
| Example 336 | 5-(4-Chlorophenyl)-2-[(1-{2-[(2,2-dimethylpyrrolidin-1-yl)carbonyl]phenyl}-1H-1,2,4-triazol-3-yl)methyl]-4-[(2S)-3,3,3-trifluoro-2-hydroxypropyl]-2,4-dihydro-3H-1,2,4-triazol-3-one | 22.5 mg (38% of th.) LC-MS (Method 8): $R_t$ = 1.12 min MS (ESIpos): m/z = 590 [M + H]$^+$ |

TABLE 3-continued

| Example No | Structure IUPAC-Name | Qantity (yield) Analytic |
|---|---|---|
| Example 337 | 5-(4-Chlorophenyl)-2-[(1-{2-[(2,6-dimethylpiperidin-1-yl)carbonyl]phenyl}-1H-1,2,4-triazol-3-yl)methyl]-4-[(2S)-3,3,3-trifluoro-2-hydroxypropyl]-2,4-dihydro-3H-1,2,4-triazol-3-one (mixture of stereoisomers) | 9.40 mg (14% of th.) LC-MS (Method 8): R$_t$ = 1.15 min MS (ESIpos): m/z = 604 [M + H]$^+$ |
| Example 338 | 5-(4-Chlorophenyl)-2-({1-[2-(piperidin-1-ylcarbonyl)phenyl]-1H-1,2,4-triazol-3-yl}methyl)-4-[(2S)-3,3,3-trifluoro-2-hydroxypropyl]-2,4-dihydro-3H-1,2,4-triazol-3-one | 21.1 mg (37% of th.) LC-MS (Method 8): R$_t$ = 1.08 min MS (ESIpos): m/z = 576 [M + H]$^+$ |
| Example 339 | 5-(4-Chlorophenyl)-2-{[1-(2-{[(2S)-2-(methoxymethyl)pyrrolidin-1-yl]carbonyl}phenyl)-1H-1,2,4-triazol-3-yl]methyl}-4-[(2S)-3,3,3-trifluoro-2-hydroxypropyl]-2,4-dihydro-3H-1,2,4-triazol-3-one | 22.2 mg (37% of th.) LC-MS (Method 8): R$_t$ = 1.07 min MS (ESIpos): m/z = 606 [M + H]$^+$ |

TABLE 3-continued

| Example No | Structure IUPAC-Name | Qantity (yield) Analytic |
|---|---|---|
| Example 340 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-cyclopropylbenzamide | 12.3 mg (22% of th.) LC-MS (Method 8): $R_t$ = 1.00 min MS (ESIpos): m/z = 548 [M + H]$^+$ |
| Example 341 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(2-methylpropyl)benzamide | 3.30 mg (6% of th.) LC-MS (Method 8): $R_t$ = 1.07 min MS (ESIpos): m/z = 564 [M + H]$^+$ |
| Example 342 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-cycloheptylbenzamide | 29.3 mg (49% of th.) LC-MS (Method 8): $R_t$ = 1.14 min MS (ESIpos): m/z = 604 [M + H]$^+$ |

TABLE 3-continued

| Example No | Structure IUPAC-Name | Qantity (yield) Analytic |
|---|---|---|
| Example 343 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-cyclopentylbenzamide | 20.5 mg (33% of th.) LC-MS (Method 8): R$_t$ = 1.08 min MS (ESIpos): m/z = 576 [M + H]$^+$ |
| Example 344 | N-Tert-butyl-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzamide | 900 μg (2% of th.) LC-MS (Method 8): R$_t$ = 1.07 min MS (ESIpos): m/z = 564 [M + H]$^+$ |
| Example 345 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-[(2R)-3-methylbutan-2-yl]benzamide (diastereomeric mixture) | 26.2 mg (44% of th.) LC-MS (Method 8): R$_t$ = 1.10 min MS (ESIpos): m/z = 578 [M + H]$^+$ |

TABLE 3-continued

| Example No | Structure IUPAC-Name | Qantity (yield) Analytic |
|---|---|---|
| Example 346 | 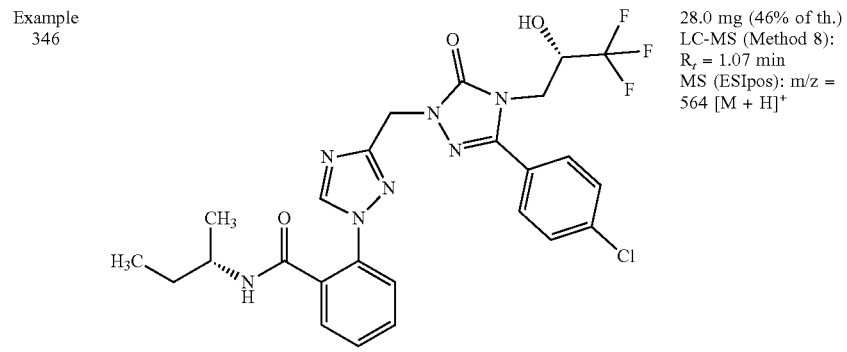<br>N-[(2S)-Butan-2-yl]-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzamide | 28.0 mg (46% of th.)<br>LC-MS (Method 8):<br>R$_t$ = 1.07 min<br>MS (ESIpos): m/z = 564 [M + H]$^+$ |
| Example 347 | 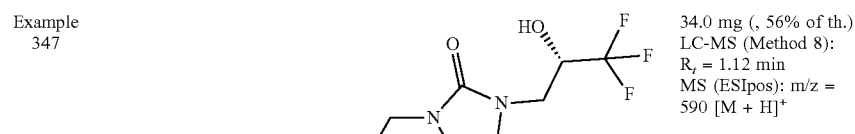<br>5-(4-Chlorophenyl)-2-[(1-{2-[(4-methylpiperidin-1-yl)carbonyl]phenyl}-1H-1,2,4-triazol-3-yl)methyl]-4-[(2S)-3,3,3-trifluoro-2-hydroxypropyl]-2,4-dihydro-3H-1,2,4-triazol-3-one | 34.0 mg (, 56% of th.)<br>LC-MS (Method 8):<br>R$_t$ = 1.12 min<br>MS (ESIpos): m/z = 590 [M + H]$^+$ |
| Example 348 | 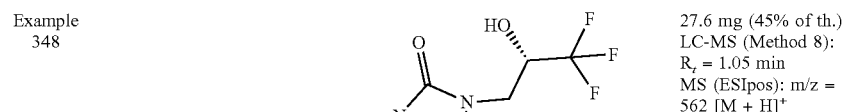<br>5-(4-Chlorophenyl)-2-({1-[2-(pyrrolidin-1-ylcarbonyl)phenyl]-1H-1,2,4-triazol-3-yl}methyl)-4-[(2S)-3,3,3-trifluoro-2-hydroxypropyl]-2,4-dihydro-3H-1,2,4-triazol-3-one | 27.6 mg (45% of th.)<br>LC-MS (Method 8):<br>R$_t$ = 1.05 min<br>MS (ESIpos): m/z = 562 [M + H]$^+$ |

TABLE 3-continued

| Example No | Structure IUPAC-Name | Qantity (yield) Analytic |
|---|---|---|
| Example 349 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-ethyl-N-(propan-2-yl)benzamide | 23.9 mg (40% of th.) LC-MS (Method 8): $R_t$ = 1.10 min MS (ESIpos): m/z = 578 [M + H]$^+$ |
| Example 350 | 2-({1-[2-(Azepan-1-ylcarbonyl)phenyl]-1H-1,2,4-triazol-3-yl}methyl)-5-(4-chlorophenyl)-4-[(2S)-3,3,3-trifluoro-2-hydroxypropyl]-2,4-dihydro-3H-1,2,4-triazol-3-one | 28.4 mg (47% of th.) LC-MS (Method 8): $R_t$ = 1.11 min MS (ESIpos): m/z = 590 [M + H]$^+$ |
| Example 351 | 5-(4-Chlorophenyl)-2-{[1-(2-{[3-methylpiperidin-1-yl]carbonyl}phenyl)-1H-1,2,4-triazol-3-yl]methyl}-4-[(2S)-3,3,3-trifluoro-2-hydroxypropyl]-2,4-dihydro-3H-1,2,4-triazol-3-one (diastereomeric mixture) | 33.1 mg (54% of th.) LC-MS (Method 8): $R_t$ = 1.12 min MS (ESIpos): m/z = 590 [M + H]$^+$ |

TABLE 3-continued

| Example No | Structure IUPAC-Name | Qantity (yield) Analytic |
|---|---|---|
| Example 352 | 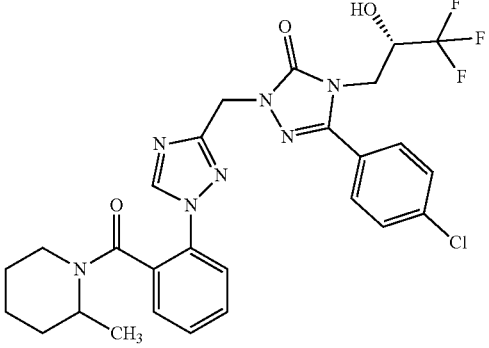 [SMILES: CC1CCCCN1C(=O)c1ccccc1-n1cnc(Cn2nc(-c3ccc(Cl)cc3)n(C[C@H](O)C(F)(F)F)c2=O)n1]<br>5-(4-Chlorophenyl)-2-{[1-(2-{[2-methylpiperidin-1-yl]carbonyl}phenyl)-1H-1,2,4-triazol-3-yl]methyl}-4-[(2S)-3,3,3-trifluoro-2-hydroxypropyl]-2,4-dihydro-3H-1,2,4-triazol-3-one | 35.0 mg (55% of th.)<br>LC-MS (Method 8):<br>$R_t$ = 1.11 min<br>MS (ESIpos): m/z = 590 [M + H]$^+$ |
| Example 353 | 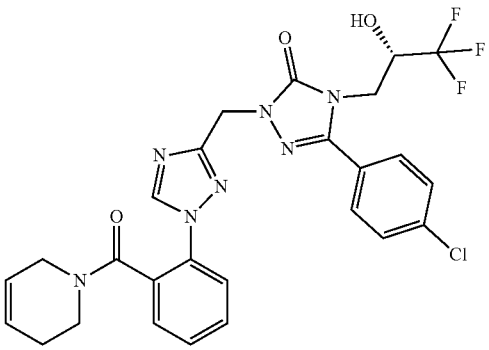 [SMILES: O=C(c1ccccc1-n1cnc(Cn2nc(-c3ccc(Cl)cc3)n(C[C@H](O)C(F)(F)F)c2=O)n1)N1CC=CCC1]<br>5-(4-Chlorophenyl)-2-({1-[2-(3,6-dihydropyridin-1(2H)-ylcarbonyl)phenyl]-1H-1,2,4-triazol-3-yl}methyl)-4-[(2S)-3,3,3-trifluoro-2-hydroxypropyl]-2,4-dihydro-3H-1,2,4-triazol-3-one | 30.0 mg (49% of th.)<br>LC-MS (Method 8):<br>$R_t$ = 1.07 min<br>MS (ESIpos): m/z = 574 [M + H]$^+$ |
| Example 354 | 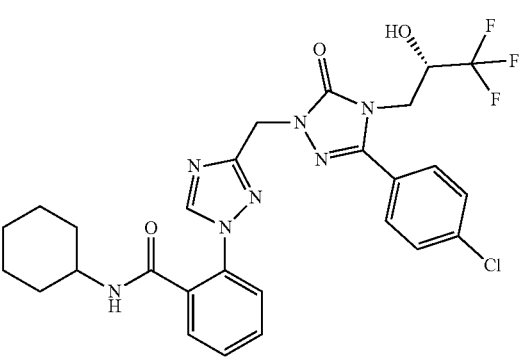 [SMILES: O=C(NC1CCCCC1)c1ccccc1-n1cnc(Cn2nc(-c3ccc(Cl)cc3)n(C[C@H](O)C(F)(F)F)c2=O)n1]<br>2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-cyclohexylbenzamide | 35.1 mg (59% of th.)<br>LC-MS (Method 8):<br>$R_t$ = 1.11 min<br>MS (ESIpos): m/z = 590 [M + H]$^+$ |

TABLE 3-continued

| Example No | Structure IUPAC-Name | Qantity (yield) Analytic |
|---|---|---|
| Example 355 | 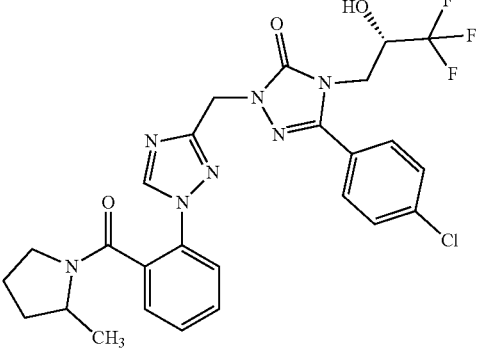<br>5-(4-Chlorophenyl)-2-{[1-(2-{[2-methylpyrrolidin-1-yl]carbonyl}phenyl)-1H-1,2,4-triazol-3-yl]methyl}-4-[(2S)-3,3,3-trifluoro-2-hydroxypropyl]-2,4-dihydro-3H-1,2,4-triazol-3-one (diastereomeric mixture) | 27.5 mg (46% of th.)<br>LC-MS (Method 8):<br>$R_t$ = 1.08 min<br>MS (ESIpos): m/z = 576 [M + H]$^+$ |
| Example 356 | 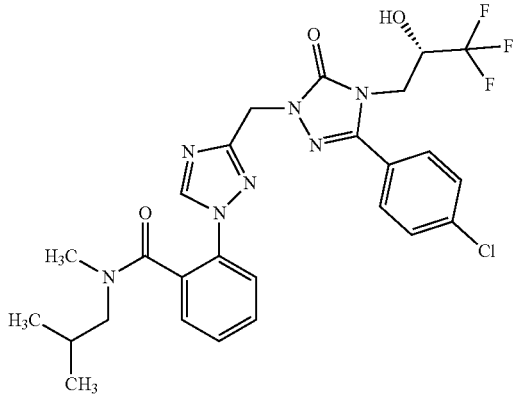 [SMILES: CC(C)CN(C)C(=O)c1ccccc1-n1cnc(Cn2nc(-c3ccc(Cl)cc3)n(C[C@H](O)C(F)(F)F)c2=O)n1]<br>2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-methyl-N-(2-methylpropyl)benzamide | 27.4 mg (47% of th.)<br>LC-MS (Method 8):<br>$R_t$ = 1.11 min<br>MS (ESIpos): m/z = 578 [M + H]$^+$ |
| Example 357 | 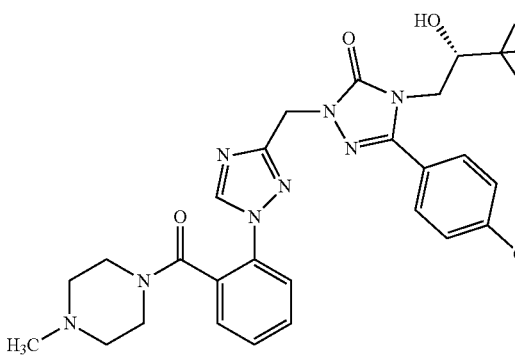<br>5-(4-Chlorophenyl)-2-[(1-{2-[(4-methylpiperazin-1-yl)carbonyl]phenyl}-1H-1,2,4-triazol-3-yl)methyl]-4-[(2S)-3,3,3-trifluoro-2-hydroxypropyl]-2,4-dihydro-3H-1,2,4-triazol-3-one | 21.1 mg (35% of th.)<br>LC-MS (Method 8):<br>$R_t$ = 0.74 min<br>MS (ESIpos): m/z = 591 [M + H]$^+$ |

TABLE 3-continued

| Example No | Structure IUPAC-Name | Qantity (yield) Analytic |
|---|---|---|
| Example 358 | 5-(4-Chlorophenyl)-2-[(1-{2-[(4-ethylpiperazin-1-yl)carbonyl]phenyl}-1H-1,2,4-triazol-3-yl)methyl]-4-[(2S)-3,3,3-trifluoro-2-hydroxypropyl]-2,4-dihydro-3H-1,2,4-triazol-3-one | 20.2 mg (31% of th.) LC-MS (Method 8): $R_t$ = 0.75 min MS (ESIpos): m/z = 605 [M + H]$^+$ |
| Example 359 | 2-({1-[2-(Azocan-1-ylcarbonyl)phenyl]-1H-1,2,4-triazol-3-yl}methyl)-5-(4-chlorophenyl)-4-[(2S)-3,3,3-trifluoro-2-hydroxypropyl]-2,4-dihydro-3H-1,2,4-triazol-3-one | 31.9 mg (50% of th.) LC-MS (Method 8): $R_t$ = 1.14 min MS (ESIpos): m/z = 604 [M + H]$^+$ |
| Example 360 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-phenylbenzamide | 35.4 mg (61% of th.) LC-MS (Method 8): $R_t$ = 1.09 min MS (ESIpos): m/z = 584 [M + H]$^+$ |

TABLE 3-continued

| Example No | Structure IUPAC-Name | Qantity (yield) Analytic |
|---|---|---|
| Example 361 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(3-methylphenyl)benzamide | 35.4 mg (55% of th.) LC-MS (Method 8): $R_t$ = 1.12 min MS (ESIpos): m/z = 598 [M + H]$^+$ |
| Example 362 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(2-cyanoethyl)-N-methylbenzamide | 28.5 mg (50% of th.) LC-MS (Method 8): $R_t$ = 1.01 min MS (ESIpos): m/z = 575 [M + H]$^+$ |
| Example 363 | 2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(2-fluorobenzyl)benzamide | 26.8 mg (42% of th.) LC-MS (Method 8): $R_t$ = 1.10 min MS (ESIpos): m/z = 616 [M + H]$^+$ |

TABLE 3-continued

| Example No | Structure IUPAC-Name | Qantity (yield) Analytic |
|---|---|---|
| Example 364 | <br>2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(2-fluorocyclopropyl)benzamide (diastereomeric mixture) | 25.7 mg (43% of th.)<br>LC-MS (Method 8):<br>$R_t$ = 1.00 min<br>MS (ESIpos): m/z = 566 [M + H]$^+$ |

Example 365

3-Chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(2,2,2-trifluoroethyl)benzamide

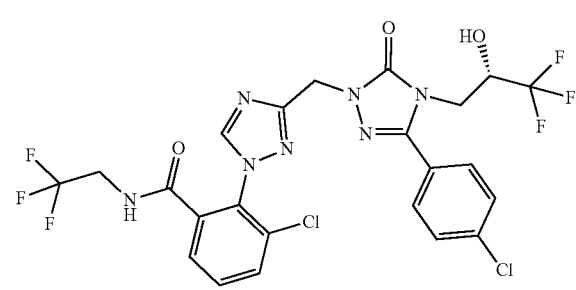 [SMILES: O=C(NCC(F)(F)F)c1cccc(Cl)c1-n1cnc(Cn2nc(-c3ccc(Cl)cc3)n(C[C@H](O)C(F)(F)F)c2=O)n1]

A solution of 3-chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoic acid (Example 51A, 100 mg, 184 µmol) in N,N-dimethylformamide (920 µl) was treated with HATU (105 mg, 276 µmol) and stirred 1.5 h at room temperature. 2,2,2-Trifluoroethanamine (22 µl, 280 µmol) was added followed by N,N-diisopropylethylamine (96 µl, 550 µmol). The resulting mixture was stirred overnight at room temperature. Purification by preparative HPLC (Method 4) afforded 39.4 mg (34% of th.) of the title compound.

LC-MS (Method 2): $R_t$=1.81 min; MS (ESIpos): m/z=624.1 [M+H]$^+$ $^1$H-NMR (400 MHz, DMSO-d6) δ [ppm]: 9.06 (t, 1H), 8.75 (s, 1H), 7.91-7.52 (m, 7H), 6.92 (d, 1H), 5.03 (d, 2H), 4.38-4.23 (m, 1H), 4.07-3.69 (m, 4H).

Example 366

3-Chloro-2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]-N-(2,2,2-trifluoroethyl)benzamide

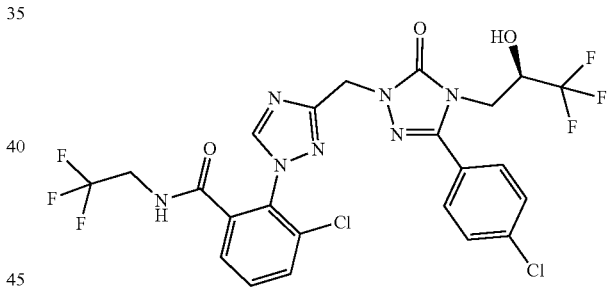

A solution of 3-chloro-2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]benzoic acid (Example 61A, 100 mg, 184 µmol) in N,N-dimethylformamide (940 µl) was treated with HATU (105 mg, 276 µmol) and stirred 1.5 h at room temperature. 2,2,2-trifluoroethanamine (22 µl, 280 µmol) was added followed by N,N-diisopropylethylamine (96 µl, 550 µmol). The resulting mixture was stirred overnight at room temperature. Purification by preparative HPLC (Method 4) afforded 52.8 mg (46% of th.) of the title compound.

LC-MS (Method 2): $R_t$=1.81 min; MS (ESIpos): m/z=624.1 [M+H]$^+$ $^1$H-NMR (400 MHz, DMSO-d6) δ [ppm]: 9.06 (t, 1H), 8.75 (s, 1H), 7.92-7.48 (m, 7H), 6.92 (d, 1H), 5.03 (d, 2H), 4.39-4.20 (br m, 1H), 4.06-3.65 (m, 4H).

Example 367

3-Chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-[3,3,3-trifluoro-2-hydroxypropyl]benzamide
(Diastereomeric Mixture)

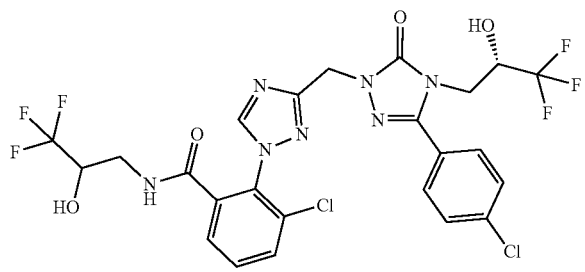 [SMILES: O=C(NCC(O)C(F)(F)F)c1cccc(Cl)c1-n1cnc(Cn2nc(-c3ccc(Cl)cc3)n(C[C@H](O)C(F)(F)F)c2=O)n1]

A solution of 3-chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoic acid (Example 51A, 100 mg, 184 μmol) in N,N-dimethylformamide (940 μl) was treated with HATU (105 mg, 276 μmol) and stirred 1.5 h at room temperature. 3-Amino-1,1,1-trifluoropropan-2-ol hydrochloride (1:1) (45.7 mg, 276 μmol) was added followed by N,N-diisopropylethylamine (130 μl, 740 μmol). The resulting mixture was stirred overnight at room temperature. Purification by preparative HPLC (Method 4) afforded 84.1 mg (70% of th.) of the title compound.

LC-MS (Method 2): $R_t$=1.76 min; MS (ESIpos): m/z=654.1 [M+H]$^+$ $^1$H-NMR (400 MHz, DMSO-d6) δ [ppm]: 8.76-8.58 (m, 2H), 7.89-7.51 (m, 7H), 6.92 (dd, 1H), 6.40 (dd, 1H), 5.15-4.97 (m, 2H), 4.39-4.20 (br m, 1H), 4.10-3.78 (m, 3H), 3.42-3.23 (m, 1H, overlap with DMSO peak), 3.12-2.96 (m, 1H).

Example 368

3-Chloro-2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]-N-[3,3,3-trifluoro-2-hydroxypropyl]benzamide
(Diastereomeric Mixture)

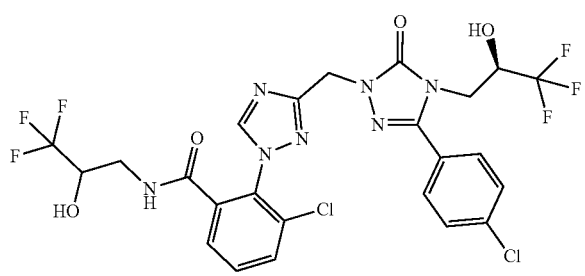 [SMILES: O=C(NCC(O)C(F)(F)F)c1cccc(Cl)c1-n1cnc(Cn2nc(-c3ccc(Cl)cc3)n(C[C@@H](O)C(F)(F)F)c2=O)n1]

A solution of 3-chloro-2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]benzoic acid (Example 61A, 100 mg, 184 μmol) in N,N-dimethylformamide (940 μl) was treated with HATU (105 mg, 276 μmol) and stirred 1.5 h at room temperature. 3-Amino-1,1,1-trifluoropropan-2-ol hydrochloride (1:1) (45.7 mg, 276 μmol) was added followed by N,N-diisopropylethylamine (130 μl, 740 μmol). The resulting mixture was stirred overnight at room temperature. Purification by preparative HPLC (Method 4) afforded 56.3 mg (47% of th.) of the title compound.

LC-MS (Method 2): $R_t$=1.75 min; MS (ESIpos): m/z=654.1 [M+H]$^+$ $^1$H-NMR (400 MHz, DMSO-d6) δ [ppm]: 8.77-8.55 (m, 2H), 7.89-7.49 (m, 7H), 6.92 (dd, 1H), 6.40 (dd, 1H), 5.15-4.99 (m, 2H), 4.39-4.21 (br m, 1H), 4.07-3.73 (m, 3H), 3.42-3.23 (m, 1H, overlap with DMSO peak), 3.12-2.94 (m, 1H).

Example 369

3-Chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-cyclopropylbenzamide

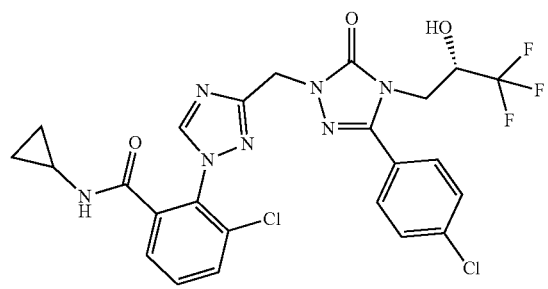 [SMILES: O=C(NC1CC1)c1cccc(Cl)c1-n1cnc(Cn2nc(-c3ccc(Cl)cc3)n(C[C@H](O)C(F)(F)F)c2=O)n1]

A solution of 3-chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoic acid (Example 51A, 120 mg, 221 μmol) in N,N-dimethylformamide (1.2 ml) was treated with HATU (126 mg, 331 μmol) and stirred 1.5 h at room temperature. Cyclopropanamine (23 μl, 330 μmol) was added followed by N,N-diisopropylethylamine (120 μl, 660 μmol). The resulting mixture was stirred overnight at room temperature. Purification by preparative HPLC (Method 4) afforded 35.7 mg (28% of th.) of the title compound.

LC-MS (Method 2): $R_t$=1.70 min; MS (ESIpos): m/z=582.1 [M+H]$^+$ $^1$H-NMR (400 MHz, DMSO-d6) δ [ppm]: 8.69 (s, 1H), 8.34 (d, 1H), 7.84-7.48 (m, 7H), 6.92 (d, 1H), 5.07 (d, 2H), 4.40-4.22 (m, 1H), 4.07-3.77 (m, 2H), 2.53-2.41 (m, 1H, overlap with DMSO peak), 0.49-0.16 (m, 4H).

Example 370

3-Chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(cyclopropylmethyl)benzamide

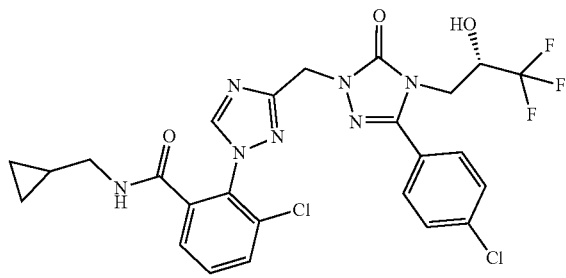 [SMILES: O=C(NCC1CC1)c1cccc(Cl)c1-n1cnc(Cn2nc(-c3ccc(Cl)cc3)n(C[C@H](O)C(F)(F)F)c2=O)n1]

A solution of 3-chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoic acid (Example 51A, 120 mg, 221 µmol) in N,N-dimethylformamide (1.2 ml) was treated with HATU (126 mg, 331 µmol) and stirred 3 h at room temperature. 1-Cyclopropylmethanamine (29 µl, 330 µmol) was added followed by N,N-diisopropylethylamine (120 µl, 660 µmol). The resulting mixture was stirred overnight at room temperature. Purification by preparative HPLC (Method 4) afforded 49.5 mg (38% of th.) of the title compound.

LC-MS (Method 2): $R_t$=1.81 min; MS (ESIpos): m/z=596.1 [M+H]$^+$ $^1$H-NMR (400 MHz, DMSO-d6) δ [ppm]: 8.70 (s, 1H), 8.34 (t, 1H), 7.84-7.50 (m, 7H), 6.91 (d, 1H), 5.12-4.98 (m, 2H), 4.39-4.20 (br m, 1H), 4.06-3.77 (m, 2H), 2.84 (t, 2H), 0.80-0.61 (m, 1H), 0.31-0.19 (m, 2H), 0.03--0.07 (m, 2H).

Example 371

3-Chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-[2,2-difluorocyclopropyl]benzamide (Diastereomeric Mixture)

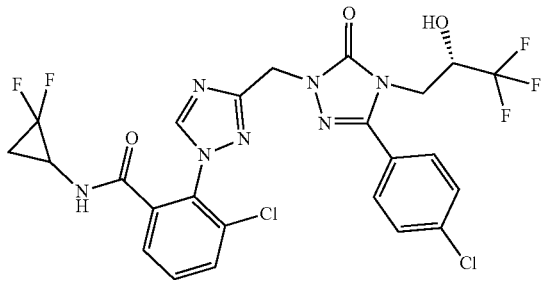 [SMILES: O=C(NC1CC1(F)F)c1cccc(Cl)c1-n1cnc(Cn2nc(-c3ccc(Cl)cc3)n(C[C@H](O)C(F)(F)F)c2=O)n1]

A solution of 3-chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoic acid (Example 51A, 120 mg, 221 µmol) in N,N-dimethylformamide (1.2 ml) was treated with HATU (126 mg, 331 µmol) and stirred 3 h at room temperature. 2,2-Difluorocyclopropanamine hydrochloride (1:1) (42.9 mg, 331 µmol) was added followed by N,N-diisopropylethylamine (150 µl, 880 µmol). The resulting mixture was stirred overnight at room temperature. Purification by preparative HPLC (Method 4) afforded 21.5 mg (16% of th.) of the title compound.

LC-MS (Method 2): $R_t$=1.77 min; MS (ESIpos): m/z=618.1 [M+H]$^+$ $^1$H-NMR (400 MHz, DMSO-d6) δ [ppm]: 8.94-8.61 (m, 2H), 7.99-7.43 (m, 7H), 6.92 (d, 1H), 5.17-4.96 (m, 2H), 4.39-4.21 (br m, 1H), 4.12-3.70 (m, 2H), 3.25-3.04 (br m, 1H), 1.81-1.17 (m, 2H).

Example 372

1-{3-Chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl}-4,4-difluoro-L-prolinamide

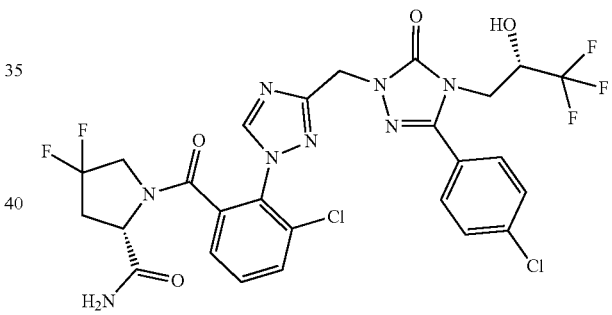

A solution of 3-chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoic acid (Example 51A, 120 mg, 221 µmol) in N,N-dimethylformamide (1.2 ml) was treated with HATU (126 mg, 331 µmol) and stirred 3 h at room temperature. 4,4-difluoro-L-prolinamide hydrochloride (1:1) (61.8 mg, 331 µmol) was added followed by N,N-diisopropylethylamine (150 µl, 880 µmol). The resulting mixture was stirred overnight at room temperature. Purification by preparative HPLC (Method 4) afforded 39.1 mg (25% of th.) of the title compound.

LC-MS (Method 2): $R_t$=1.70 min; MS (ESIpos): m/z=675.1 [M+H]$^+$ $^1$H-NMR (400 MHz, DMSO-d6) δ [ppm]: 8.91 (d, 1H), 7.91-7.18 (m, 9H), 6.92 (dd, 1H), 5.19-4.92 (m, 2H), 4.45-4.23 (m, 2H), 4.07-3.60 (m, 4H), 2.94-2.59 (m, 1H), 2.47-2.27 (m, 1H, overlap with DMSO peak).

Example 373

3-Chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-[2-fluorocyclopropyl]benzamide (Diastereomeric Mixture)

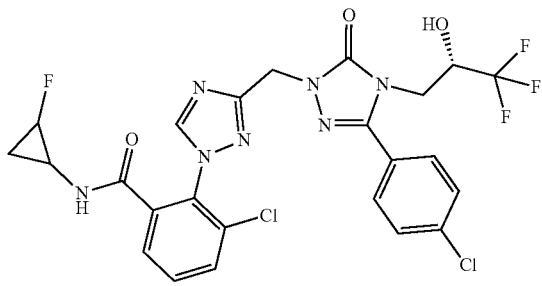 [SMILES: O=C(NC1CC1F)c1cccc(Cl)c1-n1cnc(Cn2nc(-c3ccc(Cl)cc3)n(C[C@H](O)C(F)(F)F)c2=O)n1]

A solution of 3-chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoic acid (Example 51A, 120 mg, 221 µmol) in N,N-dimethylformamide (1.2 ml) was treated with HATU (126 mg, 331 µmol) and stirred 3 h at room temperature. 2-Fluorocyclopropanamine 4-methylbenzenesulfonate (1:1) (cis configured, 81.9 mg, 331 µmol) was added followed by N,N-diisopropylethylamine (150 µl, 880 µmol). The resulting mixture was stirred overnight at room temperature. Purification by preparative HPLC (Method 4) afforded 45.6 mg (34% of th.) of the title compound.

LC-MS (Method 2): $R_t$=1.70 min; MS (ESIpos): m/z=600.1 [M+H]$^+$ $^1$H-NMR (400 MHz, DMSO-d6) δ [ppm]: 8.69 (s, 1H), 8.54 (d, 1H), 7.88-7.49 (m, 7H), 6.92 (d, 1H), 5.11-4.96 (m, 2H), 4.71-4.21 (m, 2H), 4.06-3.77 (m, 2H), 2.77-2.21 (m, 1H, overlap with DMSO peak), 0.99-0.70 (m, 2H).

Example 374

2-[(1-{2-Chloro-6-[(3,3-difluoropyrrolidin-1-yl)carbonyl]phenyl}-1H-1,2,4-triazol-3-yl)methyl]-5-(4-chlorophenyl)-4-[(2S)-3,3,3-trifluoro-2-hydroxypropyl]-2,4-dihydro-3H-1,2,4-triazol-3-one

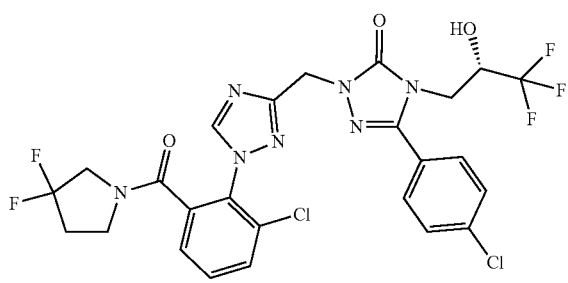 [SMILES: O=C(c1cccc(Cl)c1-n1cnc(Cn2nc(-c3ccc(Cl)cc3)n(C[C@H](O)C(F)(F)F)c2=O)n1)N1CCC(F)(F)C1]

A solution of 3-chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoic acid (Example 51A, 120 mg, 221 µmol) in N,N-dimethylformamide (1.2 ml) was treated with HATU (126 mg, 331 µmol) and stirred 3 h at room temperature. 3,3-difluoropyrrolidine hydrochloride (1:1) (47.6 mg, 331 µmol) was added followed by N,N-diisopropylethylamine (150 µl, 880 µmol). The resulting mixture was stirred overnight at room temperature. Purification by preparative HPLC (Method 4) afforded 44.0 mg (28% of th.) of the title compound.

LC-MS (Method 2): $R_t$=1.90 min; MS (ESIpos): m/z=632.1 [M+H]$^+$ $^1$H-NMR (400 MHz, DMSO-d6) δ [ppm]: 8.93-8.84 (m, 1H), 7.88-7.51 (m, 7H), 6.91 (d, 1H), 5.13-4.99 (m, 2H), 4.39-4.20 (m, 1H), 4.04-3.40 (m, 6H), 2.44-2.21 (m, 2H).

Example 375

2-[(1-{2-Chloro-6-[(2,2-dimethylmorpholin-4-yl)carbonyl]phenyl}-1H-1,2,4-triazol-3-yl)methyl]-5-(4-chlorophenyl)-4-[(2S)-3,3,3-trifluoro-2-hydroxypropyl]-2,4-dihydro-3H-1,2,4-triazol-3-one

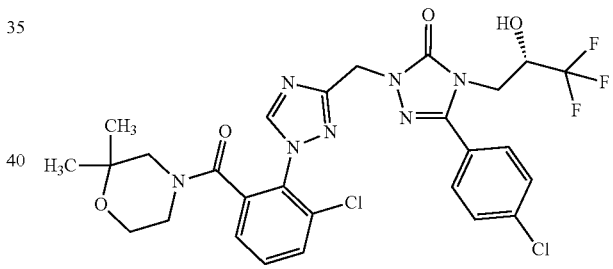

A solution of 3-chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoic acid (Example 51A, 120 mg, 221 µmol) in N,N-dimethylformamide (1.2 ml) was treated with HATU (126 mg, 331 µmol) and stirred 3 h at room temperature. 2,2-dimethylmorpholine (38.2 mg, 331 µmol) was added followed by N,N-diisopropylethylamine (120 µl, 660 µmol). The resulting mixture was stirred overnight at room temperature. Purification by preparative HPLC (Method 4) afforded 57.1 mg (40% of th.) of the title compound.

LC-MS (Method 2): $R_t$=1.86 min; MS (ESIpos): m/z=640. [M+H]$^+$ $^1$H-NMR (400 MHz, DMSO-d6) δ [ppm]: 8.83 (s, 1H), 7.85-7.42 (m, 7H), 6.91 (dd, 1H), 5.08 (s, 2H), 4.39-4.22 (br m, 1H), 4.09-2.59 (m, 8H, overlap with HDO peak), 1.20-0.73 (m, 6H).

Example 376

3-Chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(3,3-difluorocyclobutyl)benzamide

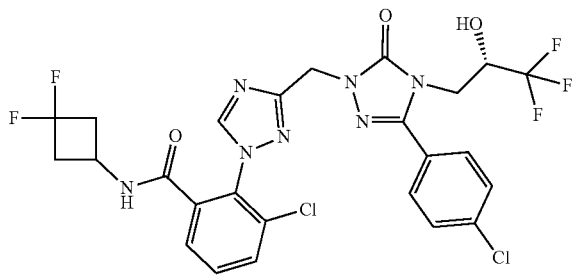 [SMILES: O=C(NC1CC(F)(F)C1)c1cccc(Cl)c1-n1cnc(Cn2nc(-c3ccc(Cl)cc3)n(C[C@H](O)C(F)(F)F)c2=O)n1]

A solution of 3-chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoic acid (Example 51A, 120 mg, 221 μmol) in N,N-dimethylformamide (1.2 ml) was treated with HATU (126 mg, 331 μmol) and stirred 3 h at room temperature. 3,3-Difluorocyclobutanamine hydrochloride (1:1) (47.6 mg, 331 μmol) was added followed by N,N-diisopropylethylamine (150 μl, 880 μmol). The resulting mixture was stirred overnight at room temperature. Purification by preparative HPLC (Method 4) afforded 56.5 mg (40% of th.) of the title compound.

LC-MS (Method 2): $R_t$=1.83 min; MS (ESIpos): m/z=632.1 [M+H]$^+$ $^1$H-NMR (400 MHz, DMSO-d6) δ [ppm]: 8.86-8.72 (m, 2H), 7.88-7.54 (m, 7H), 6.92 (d, 1H), 5.14-4.99 (m, 2H), 4.39-4.21 (br m, 1H), 4.06-3.77 (m, 3H), 2.83-2.64 (m, 2H), 2.48-2.27 (m, 2H, overlap with DMSO peak).

Example 377

2-{[1-(2-Chloro-6-{[2-methylmorpholin-4-yl]carbonyl}phenyl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Diastereomeric Mixture)

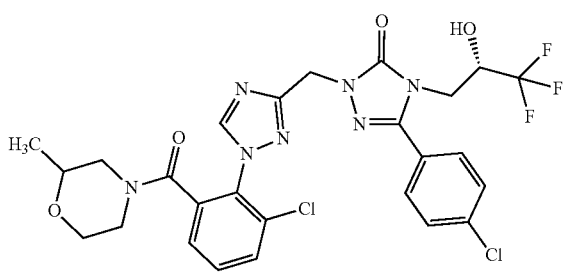 [SMILES: CC1CN(C(=O)c2cccc(Cl)c2-n2cnc(Cn3nc(-c4ccc(Cl)cc4)n(C[C@H](O)C(F)(F)F)c3=O)n2)CCO1]

A solution of 3-chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoic acid (Example 51A, 120 mg, 221 μmol) in N,N-dimethylformamide (1.2 ml) was treated with HATU (126 mg, 331 μmol) and stirred 3 h at room temperature. 2-Methylmorpholine (33.5 mg, 331 μmol) was added followed by N,N-diisopropylethylamine (120 μl, 660 μmol). The resulting mixture was stirred overnight at room temperature. Purification by preparative HPLC (Method 4) afforded 50.5 mg (36% of th.) of the title compound.

LC-MS (Method 2): $R_t$=1.81 min; MS (ESIpos): m/z=626.1 [M+H]$^+$ $^1$H-NMR (400 MHz, DMSO-d6) δ [ppm]: 8.85 (s, 1H), 7.89-7.38 (m, 7H), 6.91 (br d, 1H), 5.23-4.93 (m, 2H), 4.39-4.22 (br m, 1H), 4.18-2.00 (m, 9H, overlap with HDO and DMSO peak), 0.87 (br s, 3H).

Example 378

1-{3-Chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl}-prolinamide (Diastereomeric Mixture)

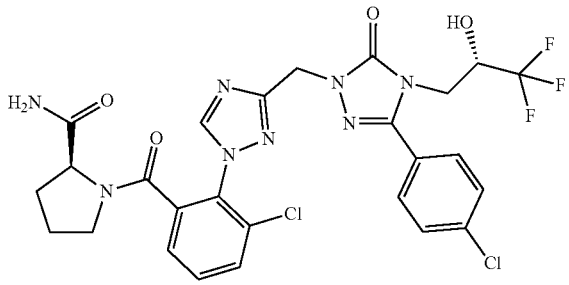 [SMILES: NC(=O)[C@@H]1CCCN1C(=O)c1cccc(Cl)c1-n1cnc(Cn2nc(-c3ccc(Cl)cc3)n(C[C@H](O)C(F)(F)F)c2=O)n1]

A solution of 3-chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoic acid (Example 51A, 120 mg, 221 μmol) in N,N-dimethylformamide (1.2 ml) was treated with HATU (126 mg, 331 μmol) and stirred 3 h at room temperature. Prolinamide (37.8 mg, 331 μmol) was added followed by N,N-diisopropylethylamine (120 μl, 660 μmol). The resulting mixture was stirred overnight at room temperature. Purification by preparative HPLC (Method 4) afforded 44.2 mg (31% of th.) of the title compound.

LC-MS (Method 2): $R_t$=1.60 min; MS (ESIpos): m/z=639.1 [M+H]$^+$ $^1$H-NMR (400 MHz, DMSO-d6) δ [ppm]: 8.84 (s, 1H), 7.90-7.09 (m, 8H), 7.06-6.83 (m, 2H), 5.18-4.97 (m, 2H), 4.39-3.76 (m, 4H), 3.30-3.04 (m, 2H, overlap with HDO peak), 2.10-1.41 (m, 4H).

Example 379

2-{[1-(2-Chloro-6-{[hydroxy-3-(trifluoromethyl)pyrrolidin-1-yl]carbonyl}phenyl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Diastereomeric Mixture)

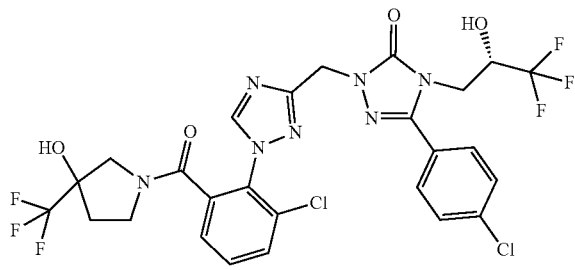 [SMILES: O=C(c1cccc(Cl)c1-n1cnc(Cn2nc(-c3ccc(Cl)cc3)n(C[C@H](O)C(F)(F)F)c2=O)n1)N1CCC(O)(C(F)(F)F)C1]

A solution of 3-chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoic acid (Example 51A, 120 mg, 221 μmol) in N,N-dimethylformamide (1.2 ml) was treated with HATU (126 mg, 331 μmol) and stirred 3 h at room temperature. 3-(Trifluoromethyl)pyrrolidin-3-ol hydrochloride (1:1) (63.5 mg, 331 μmol) was added followed by N,N-diisopropylethylamine (150 μl, 880 μmol). The resulting mixture was stirred overnight at room temperature. Purification by preparative HPLC (Method 4) afforded 49.0 mg (29% of th.) of the title compound.

LC-MS (Method 2): $R_t$=1.85 min; MS (ESIpos): m/z=680.1 [M+H]$^+$ $^1$H-NMR (400 MHz, DMSO-d6) δ [ppm]: 8.93-8.78 (m, 1H), 7.88-7.48 (m, 7H), 6.97-6.84 (m, 1H), 6.49 (d, 1H), 5.15-4.94 (m, 2H), 4.39-4.20 (br m, 1H), 4.08-3.77 (m, 2H), 3.59-3.34 (m, 4H, overlap with HDO peak), 2.19-1.78 (m 2H).

Example 380

5-(4-Chlorophenyl)-2-{[1-(2-chloro-6-{[2-(trifluoromethyl)morpholin-4-yl]carbonyl}phenyl)-1H-1,2,4-triazol-3-yl]methyl}-4-[(2S)-3,3,3-trifluoro-2-hydroxypropyl]-2,4-dihydro-3H-1,2,4-triazol-3-one (Diastereomeric Mixture)

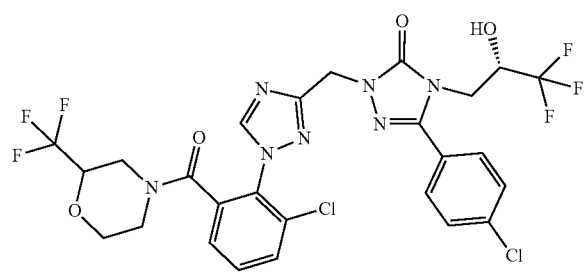 [SMILES: O=C(c1cccc(Cl)c1-n1cnc(Cn2nc(-c3ccc(Cl)cc3)n(C[C@H](O)C(F)(F)F)c2=O)n1)N1CCOC(C(F)(F)F)C1]

A solution of 3-chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoic acid (Example 51A, 120 mg, 221 μmol) in N,N-dimethylformamide DMF (1.2 ml, 16 mmol) was treated with HATU (126 mg, 331 μmol) and stirred 3 h at room temperature. 2-(Trifluoromethyl)morpholine hydrochloride (1:1) (63.5 mg, 331 μmol) was added followed by N,N-diisopropylethylamine (150 μl, 880 μmol). The resulting mixture was stirred overnight at room temperature. Purification by preparative HPLC (Method 4) afforded 47.2 mg (31% of th.) of the title compound.

LC-MS (Method 2): $R_t$=1.99 min; MS (ESIpos): m/z=680.1 [M+H]$^+$ $^1$H-NMR (400 MHz, DMSO-d6) δ [ppm]: 9.01-8.81 (m, 1H), 7.91-7.42 (m, 7H), 6.99-6.78 (br m, 1H), 5.27-4.96 (m, 2H), 4.45-2.60 (m, 10H, overlap with HDO peak).

Example 381

5-(4-Chlorophenyl)-2-({1-[2-chloro-6-(piperidin-1-ylcarbonyl)phenyl]-1H-1,2,4-triazol-3-yl}methyl)-4-[(2S)-3,3,3-trifluoro-2-hydroxypropyl]-2,4-dihydro-3H-1,2,4-triazol-3-one

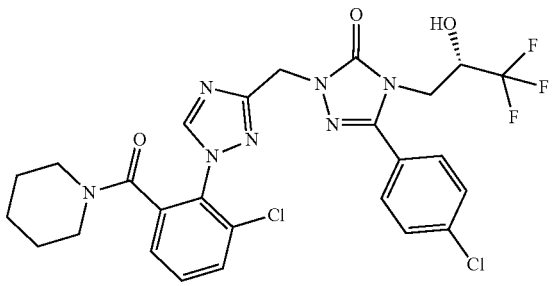 [SMILES: O=C(c1cccc(Cl)c1-n1cnc(Cn2nc(-c3ccc(Cl)cc3)n(C[C@H](O)C(F)(F)F)c2=O)n1)N1CCCCC1]

A solution of 3-chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoic acid (Example 51A, 120 mg, 221 μmol) in N,N-dimethylformamide (1.2 m was treated with HATU (126 mg, 331 μmol) and stirred 3 h at room temperature. Piperidine (33 μl, 330 μmol) was added followed by N,N-diisopropylethylamine (120 μl, 660 μmol). The resulting mixture was stirred overnight at room temperature. Purification by preparative HPLC (Method 4) afforded 56.8 mg (42% of th.) of the title compound.

LC-MS (Method 2): $R_t$=1.93 min; MS (ESIpos): m/z=610.1 [M+H]$^+$ $^1$H-NMR (400 MHz, DMSO-d6) δ [ppm]: 8.77 (d, 1H), 7.83-7.37 (m, 7H), 6.90 (br t, 1H), 5.17-4.95 (m, 2H), 4.28 (br s, 1H), 4.07-3.74 (m, 2H), 3.33-2.81 (m, 4H, overlap with HDO peak), 1.48-1.04 (m, 6H).

Example 382

2-({1-[2-Chloro-6-(morpholin-4-ylcarbonyl)phenyl]-1H-1,2,4-triazol-3-yl}methyl)-5-(4-chlorophenyl)-4-[(2S)-3,3,3-trifluoro-2-hydroxypropyl]-2,4-dihydro-3H-1,2,4-triazol-3-one

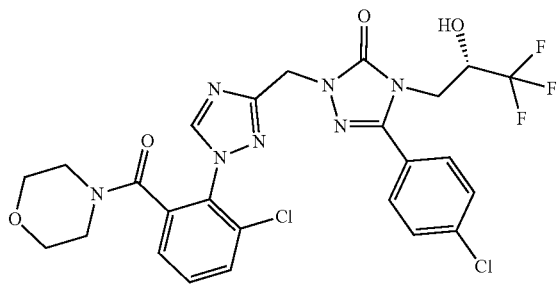 [SMILES: O=C(c1cccc(Cl)c1-n1cnc(Cn2nc(-c3ccc(Cl)cc3)n(C[C@H](O)C(F)(F)F)c2=O)n1)N1CCOCC1]

A solution of 3-chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoic acid (Example 51A, 120 mg, 221 μmol) in N,N-dimethylformamide (1.2 ml) was treated with HATU (126 mg, 331 μmol) and stirred 3 h at room temperature. Morpholine (29 μl, 330 μmol) was added followed by N,N-diisopropylethylamine (120 μl, 660 μmol). The resulting mixture was stirred overnight at room temperature. Purification by preparative HPLC (Method 4) afforded 60.0 mg (44% of th.) of the title compound.

LC-MS (Method 2): $R_t$=1.73 min; MS (ESIpos): m/z=612.1 [M+H]$^+$ $^1$H-NMR (400 MHz, DMSO-d6) δ [ppm]: 8.85 (s, 1H), 7.87-7.44 (m, 7H), 6.90 (d, 1H), 5.20-5.01 (m, 2H), 4.39-4.22 (br m, 1H), 4.09-3.75 (m, 2H), 3.55-2.88 (m, 8H, overlap with HDO peak).

Example 383

5-(4-Chlorophenyl)-2-{[1-(2-chloro-6-{[(2S)-2-(trifluoromethyl)pyrrolidin-1-yl]carbonyl}phenyl)-1H-1,2,4-triazol-3-yl]methyl}-4-[(2S)-3,3,3-trifluoro-2-hydroxypropyl]-2,4-dihydro-3H-1,2,4-triazol-3-one

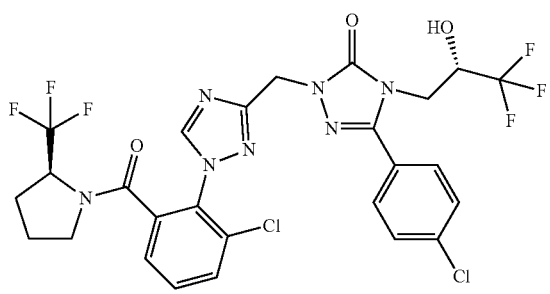 [SMILES: O=C(c1cccc(Cl)c1-n1cnc(Cn2nc(-c3ccc(Cl)cc3)n(C[C@H](O)C(F)(F)F)c2=O)n1)N1CCC[C@H]1C(F)(F)F]

A solution of 3-chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoic acid (Example 51A, 120 mg, 221 μmol) in N,N-dimethylformamide DMF (1.2 ml, 16 mmol) was treated with HATU (126 mg, 331 μmol) and stirred 3 h at room temperature. (2S)-2-(trifluoromethyl)pyrrolidine (46.1 mg, 331 μmol) was added followed by N,N-diisopropylethylamine (120 μl, 660 μmol). The resulting mixture was stirred overnight at room temperature. Purification by preparative HPLC (Method 4) afforded 55.1 mg (38% of th.) of the title compound.

LC-MS (Method 2): $R_t$=2.05 min; MS (ESIpos): m/z=664.1 [M+H]$^+$ $^1$H-NMR (400 MHz, DMSO-d6) δ [ppm]: 8.97-8.84 (m, 1H), 7.92-7.46 (m, 7H), 6.91 (d, 1H), 5.14-4.94 (m, 2H), 4.63 (br t, 1H), 4.39-4.22 (br m, 1H), 4.05-3.78 (m, 2H), 3.44-3.23 (m, 2H, overlap with HDO peak), 2.21-1.72 (m, 4H).

Example 384

5-(4-Chlorophenyl)-2-{[1-(2-chloro-6-{[(2R)-2-(trifluoromethyl)pyrrolidin-1-yl]carbonyl}phenyl)-1H-1,2,4-triazol-3-yl]methyl}-4-[(2S)-3,3,3-trifluoro-2-hydroxypropyl]-2,4-dihydro-3H-1,2,4-triazol-3-one

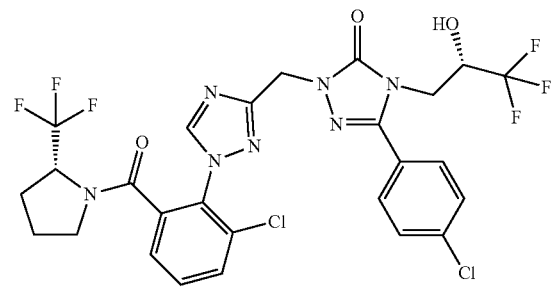 [SMILES: O=C(c1cccc(Cl)c1-n1cnc(Cn2nc(-c3ccc(Cl)cc3)n(C[C@H](O)C(F)(F)F)c2=O)n1)N1CCC[C@@H]1C(F)(F)F]

A solution of 3-chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoic acid (Example 51A, 120 mg, 221 μmol) in N,N-dimethylformamide (1.2 ml) was treated with HATU (126 mg, 331 μmol) and stirred 3 h at room temperature. (2R)-2-(trifluoromethyl)pyrrolidine (46.1 mg, 331 μmol) was added followed by N,N-diisopropylethylamine (120 μl, 660 μmol). The resulting mixture was stirred overnight at room temperature. Purification by preparative HPLC (Method 4) afforded 54.4 mg (37% of th.) of the title compound.

LC-MS (Method 2): $R_t$=2.06 min; MS (ESIpos): m/z=664.1 [M+H]$^+$ $^1$H-NMR (400 MHz, DMSO-d6) δ [ppm]: 8.97-8.86 (m, 1H), 7.90-7.46 (m, 7H), 6.91 (d, 1H), 5.17-4.93 (m, 2H), 4.74-4.58 (m, 1H), 4.39-4.20 (br m, 1H), 4.08-3.74 (m, 2H), 3.49-3.07 (m, 2H, overlap with HDO peak), 2.18-1.51 (m, 4H).

Example 385

2-[(1-{2-Chloro-6-[(1,1-dioxidothiomorpholin-4-yl)carbonyl]phenyl}-1H-1,2,4-triazol-3-yl)methyl]-5-(4-chlorophenyl)-4-[(2S)-3,3,3-trifluoro-2-hydroxypropyl]-2,4-dihydro-3H-1,2,4-triazol-3-one

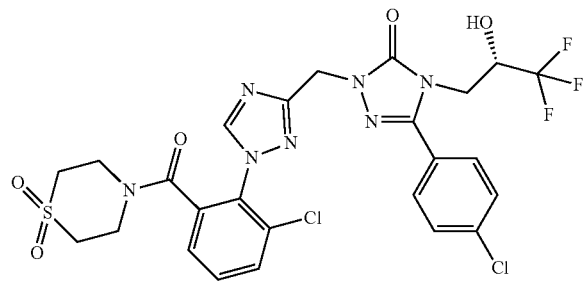 [SMILES: O=C(c1cccc(Cl)c1-n1cnc(Cn2nc(-c3ccc(Cl)cc3)n(C[C@H](O)C(F)(F)F)c2=O)n1)N1CCS(=O)(=O)CC1]

A solution of 3-chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoic acid (Example 51A, 120 mg, 221 µmol) in N,N-dimethylformamide (1.2 ml) was treated with HATU (126 mg, 331 µmol) and stirred 1.5 h at room temperature. Thiomorpholine 1,1-dioxide (44.8 mg, 331 µmol) was added followed by N,N-diisopropylethylamine (120 µl, 660 µmol). The resulting mixture was stirred overnight at room temperature. Purification by preparative HPLC (Method 4) afforded 55.7 mg (38% of th.) of the title compound.

LC-MS (Method 2): $R_t$=1.69 min; MS (ESIpos): m/z=660.1 [M+H]$^+$ $^1$H-NMR (400 MHz, DMSO-d6) δ [ppm]: 8.94 (d, 1H), 7.89-7.57 (m, 7H), 6.90 (br t, 1H), 5.21-4.96 (m, 2H), 4.39-4.20 (br m, 1H), 4.13-3.43 (m, 6H), 3.39-2.97 (m, 4H, overlap with HDO peak).

Example 386

5-(4-Chlorophenyl)-2-{[1-(2-chloro-6-{[3-(trifluoromethyl)pyrrolidin-1-yl]carbonyl}phenyl)-1H-1,2,4-triazol-3-yl]methyl}-4-[(2S)-3,3,3-trifluoro-2-hydroxypropyl]-2,4-dihydro-3H-1,2,4-triazol-3-one (Diastereomeric Mixture)

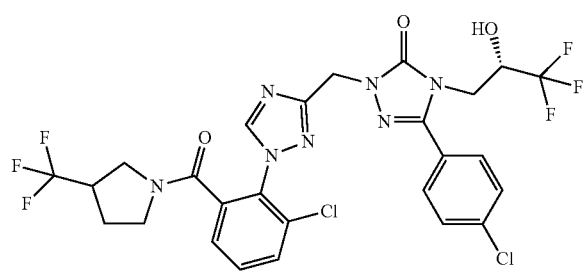 [SMILES: O=C(c1cccc(Cl)c1-n1cnc(Cn2nc(-c3ccc(Cl)cc3)n(C[C@H](O)C(F)(F)F)c2=O)n1)N1CCC(C(F)(F)F)C1]

A solution of 3-chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoic acid (Example 51A, 120 mg, 221 µmol) in N,N-dimethylformamide (1.2 ml) was treated with HATU (126 mg, 331 µmol) and stirred 3 h at room temperature. 3-(Trifluoromethyl)pyrrolidine (46.1 mg, 331 µmol) was added followed by N,N-diisopropylethylamine (120 µl, 660 µmol). The resulting mixture was stirred overnight at room temperature. Purification by preparative HPLC (Method 4) afforded 60.1 mg (41% of th.) of the title compound.

LC-MS (Method 2): $R_t$=2.00 min; MS (ESIpos): m/z=664.1 [M+H]$^+$ $^1$H-NMR (400 MHz, DMSO-d6) δ [ppm]: 8.86 (d, 1H), 7.88-7.47 (m, 7H), 6.95-6.86 (m, 1H), 5.14-4.96 (m, 2H), 4.38-4.20 (br m, 1H), 4.06-3.75 (m, 2H), 3.60-2.94 (m, 5H, overlap with HDO peak), 2.12-1.77 (m, 2H).

Example 387

3-Chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(cyclopropylmethyl)-N-methylbenzamide

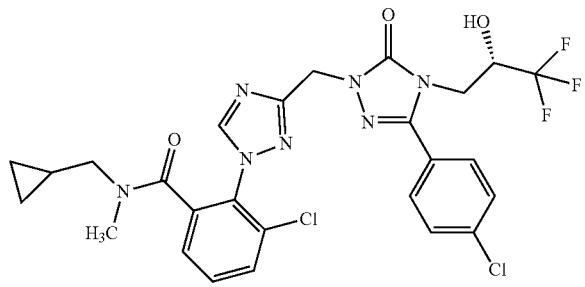 [SMILES: CN(CC1CC1)C(=O)c1cccc(Cl)c1-n1cnc(Cn2nc(-c3ccc(Cl)cc3)n(C[C@H](O)C(F)(F)F)c2=O)n1]

A solution of 3-chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoic acid (Example 51A, 120 mg, 221 µmol) in N,N-dimethylformamide (1.2 ml) was treated with HATU (126 mg, 331 µmol) and stirred 3 h at room temperature. 1-Cyclopropyl-N-methylmethanamine (28.2 mg, 331 µmol) was added followed by N,N-diisopropylethylamine (120 µl, 660 µmol). The resulting mixture was stirred overnight at room temperature. Purification by preparative HPLC (Method 4) afforded 28.4 mg (21% of th.) of the title compound.

LC-MS (Method 2): $R_t$=1.95 min; MS (ESIpos): m/z=610.1 [M+H]$^+$ $^1$H-NMR (400 MHz, DMSO-d6) δ [ppm]: 8.85-8.67 (m, 1H), 7.90-7.33 (m, 7H), 6.90 (d, 1H), 5.07 (s, 2H), 4.39-4.20 (br m, 1H), 4.11-3.73 (m, 2H), 3.19-2.60 (m, 5H), 0.92-0.54 (m, 1H), 0.47-0.16 (br m, 2H), 0.15-0.30 (m, 2H).

Example 388

3-Chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(1-methylcyclopropyl)benzamide

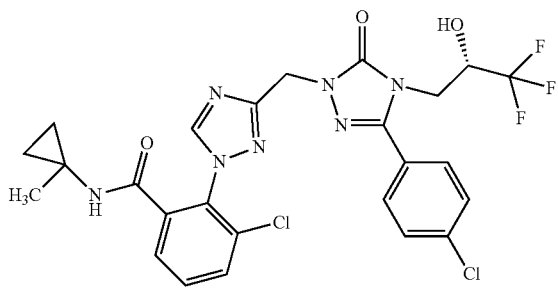 [SMILES: CC1(NC(=O)c2cccc(Cl)c2-n2cnc(Cn3nc(-c4ccc(Cl)cc4)n(C[C@H](O)C(F)(F)F)c3=O)n2)CC1]

A solution of 3-chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoic acid (Example 51A, 120 mg, 221 µmol) in N,N-dimethylformamide (1.2 ml) was treated with HATU (126 mg, 331 µmol) and stirred 3 h at room temperature. 1-Methylcyclopropanamine (23.6 mg, 331 µmol) was added followed by N,N-diisopropylethylamine (120 µl, 660 µmol). The resulting mixture was stirred overnight at room temperature. Purification by preparative HPLC (Method 4) afforded 54.7 mg (42% of th.) of the title compound.

LC-MS (Method 2): $R_t$=1.77 min; MS (ESIpos): m/z=596.1 [M+H]$^+$ $^1$H-NMR (400 MHz, DMSO-d6) δ [ppm]: 8.82-8.32 (m, 2H), 7.92-7.37 (m, 7H), 6.92 (d, 1H), 5.18-4.88 (m, 2H), 4.39-4.21 (br m, 1H), 4.08-3.72 (m, 2H), 1.12 (s, 3H), 0.53-0.24 (m, 4H).

Example 389

3-Chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-[2-fluorocyclopropyl]benzamide (Diastereomeric Mixture Cis Configured)

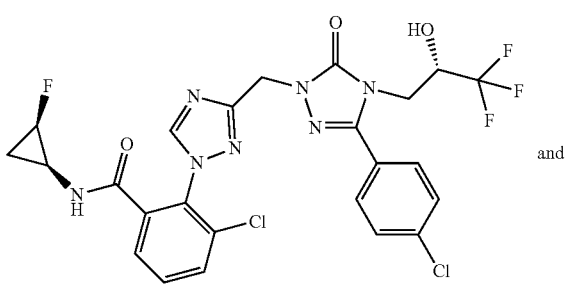

and

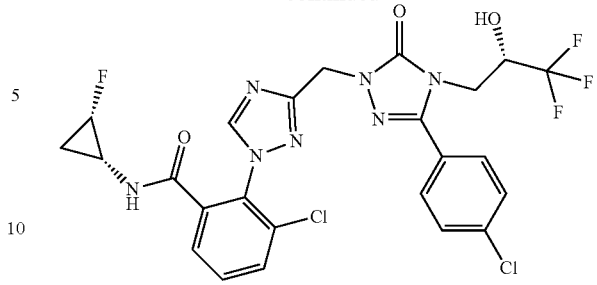

A solution of 3-chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoic acid (Example 51A, 120 mg, 221 µmol) in N,N-dimethylformamide (1.2 ml) was treated with HATU (126 mg, 331 µmol) and stirred 3 h at room temperature. 2-Fluorocyclopropanamine (cis configured, 24.9 mg, 331 µmol) was added followed by N,N-diisopropylethylamine (120 µl, 660 µmol). The resulting mixture was stirred overnight at room temperature. Purification by preparative HPLC (Method 4) afforded 46.5 mg (35% of th.) of the title compound.

LC-MS (Method 2): $R_t$=1.69 min; MS (ESIpos): m/z=600.1 [M+H]$^+$ $^1$H-NMR (400 MHz, DMSO-d6) δ [ppm]: 8.72-8.45 (m, 2H), 7.90-7.48 (m, 7H), 6.92 (d, 1H), 5.14-4.93 (m, 2H), 4.70-4.21 (m, 2H), 4.07-3.76 (m, 2H), 2.78-2.15 (m, 1H, overlap with HDO peak), 0.98-0.70 (m, 2H).

Example 390

N-[2-Amino-3,3,3-trifluoropropyl]-3-chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzamide (Diastereomeric Mixture)

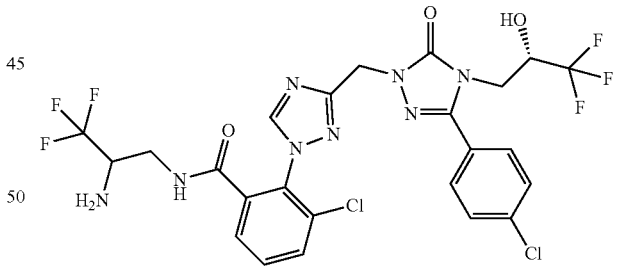

A solution of 3-chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoic acid (Example 51A, 120 mg, 221 µmol) in N,N-dimethylformamide (1.2 ml) was treated with HATU (126 mg, 331 µmol) and stirred 30 min at room temperature. 3,3,3-Trifluoropropane-1,2-diamine dihydrochloride (66.6 mg, 331 µmol) was added followed by N,N-diisopropylethylamine (190 µl, 1.1 mmol). The resulting mixture was stirred 2 h at room temperature. Purification by preparative HPLC (Method 4) afforded 72.9 mg (50% of th.) of the title compound.

LC-MS (Method 2): $R_t$=1.65 min; MS (ESIpos): m/z=653.1 [M+H]$^+$

¹H-NMR (400 MHz, DMSO-d6) δ [ppm]: 8.86-8.43 (m, 2H), 7.98-7.49 (m, 7H), 6.93 (dd, 1H), 5.20-4.90 (m, 2H), 4.39-4.21 (br m, 1H), 4.13-3.72 (m, 2H), 3.40-3.17-2.90 (m, 3H), 2.24-1.55 (m, 2H).

Example 391

1-{3-Chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl}-4,4-difluoro-D-prolinamide

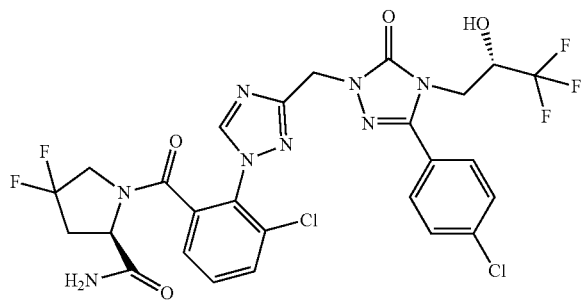 [SMILES: NC(=O)[C@H]1CC(F)(F)CN1C(=O)c1cccc(Cl)c1-n1cnc(Cn2nc(-c3ccc(Cl)cc3)n(C[C@H](O)C(F)(F)F)c2=O)n1]

A solution of 3-chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoic acid (Example 51A, 120 mg, 221 µmol) in N,N-dimethylformamide (1.2 ml) was treated with HATU (126 mg, 331 µmol) and stirred 3 h at room temperature. 4,4-Difluoro-D-prolinamide hydrochloride (1:1) (61.8 mg, 331 µmol) was added followed by N,N-diisopropylethylamine (150 µl, 880 µmol). The resulting mixture was stirred overnight at room temperature. Purification by preparative HPLC (Method 4) afforded 48.3 mg (32% of th.) of the title compound.

LC-MS (Method 2): R_t=1.72 min; MS (ESIpos): m/z=675.1 [M+H]⁺

¹H-NMR (400 MHz, DMSO-d6) δ [ppm]: 8.90 (d, 1H), 7.93-7.16 (m, 9H), 6.91 (t, 1H), 5.20-4.94 (m, 2H), 4.54-4.17 (m, 2H), 4.07-3.57 (m, 4H), 2.94-2.20 (m, 2H, overlap with DMSO peak).

Example 392

3-Chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(3,3,3-trifluoropropyl)benzamide

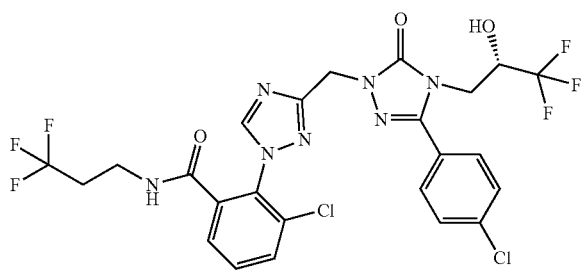 [SMILES: O=C(NCCC(F)(F)F)c1cccc(Cl)c1-n1cnc(Cn2nc(-c3ccc(Cl)cc3)n(C[C@H](O)C(F)(F)F)c2=O)n1]

A solution of 3-chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoic acid (Example 51A, 120 mg, 221 µmol) in N,N-dimethylformamide (1.2 ml) was treated with (126 mg, 331 µmol) and stirred 3 h at room temperature. 3,3,3-trifluoropropan-1-amine (37.5 mg, 331 µmol) was added followed by N,N-diisopropylethylamine (150 µl, 880 µmol). The resulting mixture was stirred overnight at room temperature. Purification by preparative HPLC (Method 4) afforded 53.7 mg (38% of th.) of the title compound.

LC-MS (Method 2): R_t=1.86 min; MS (ESIpos): m/z=638.1 [M+H]⁺

¹H-NMR (400 MHz, DMSO-d6) δ [ppm]: 8.81-8.50 (m, 2H), 7.88-7.49 (m, 7H), 6.91 (d, 1H), 5.15-4.95 (m, 2H), 4.39-4.21 (br m, 1H), 4.05-3.78 (m, 2H), 3.26-3.14 (m, 2H), 2.37-2.19 (m, 2H).

Example 393

3-Chloro-2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]-N-cyclopropylbenzamide

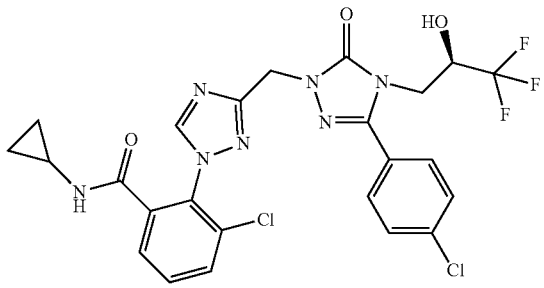 [SMILES: O=C(NC1CC1)c1cccc(Cl)c1-n1cnc(Cn2nc(-c3ccc(Cl)cc3)n(C[C@@H](O)C(F)(F)F)c2=O)n1]

A solution of 3-chloro-2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]benzoic acid (Example 61A, 120 mg, 221 µmol) in N,N-dimethylformamide (1.2 ml) was treated with HATU (126 mg, 331 µmol) and stirred 3 h at room temperature. Cyclopropanamine (23 µl, 330 µmol) was added followed by N,N-diisopropylethylamine (120 µl, 660 µmol). The resulting mixture was stirred overnight at room temperature. Purification by preparative HPLC (Method 4) afforded 54.9 mg (43% of th.) of the title compound.

LC-MS (Method 2): R_t=1.72 min; MS (ESIpos): m/z=582.1 [M+H]⁺

¹H-NMR (400 MHz, DMSO-d6) δ [ppm]: 8.69 (s, 1H), 8.35 (d, 1H), 7.84-7.48 (m, 7H), 6.92 (d, 1H), 5.07 (d, 2H), 4.39-4.22 (br m, 1H), 4.08-3.76 (m, 2H), 2.53-2.39 (m, 1H, overlap with DMSO peak), 0.51-0.16 (m, 4H).

Example 394

3-Chloro-2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]-N-(cyclopropylmethyl)benzamide

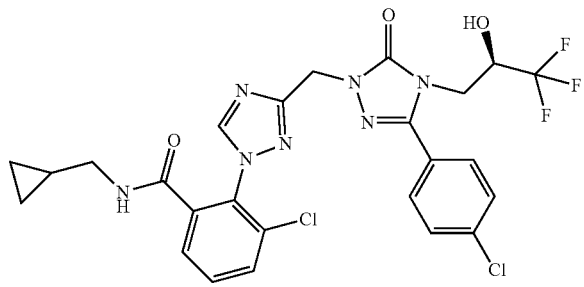 [SMILES: O=C(NCC1CC1)c1cccc(Cl)c1-n1cnc(Cn2nc(-c3ccc(Cl)cc3)n(C[C@@H](O)C(F)(F)F)c2=O)n1]

A solution of 3-chloro-2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]benzoic acid (Example 61A, 120 mg, 221 µmol) in N,N-dimethylformamide (1.2 ml) was treated with HATU (126 mg, 331 µmol) and stirred 3 h at room temperature. 1-Cyclopropylmethanamine (29 µl, 330 µmol) was added followed by N,N-diisopropylethylamine (120 µl, 660 µmol). The resulting mixture was stirred overnight at room temperature. Purification by preparative HPLC (Method 4) afforded 62.2 mg (47% of th.) of the title compound.

LC-MS (Method 2): $R_t$=1.82 min; MS (ESIpos): m/z=596.1 [M+H]$^+$ $^1$H-NMR (400 MHz, DMSO-d6) δ [ppm]: 8.70 (s, 1H), 8.34 (t, 1H), 7.85-7.49 (m, 7H), 6.91 (d, 1H), 5.13-4.98 (m, 2H), 4.41-4.20 (m, 1H), 4.07-3.76 (m, 2H), 2.84 (t, 2H), 0.79-0.64 (m, 1H), 0.31--0.09 (m, 4H).

Example 395

3-Chloro-2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]-N-[2,2-difluorocyclopropyl]benzamide (Diastereomeric Mixture)

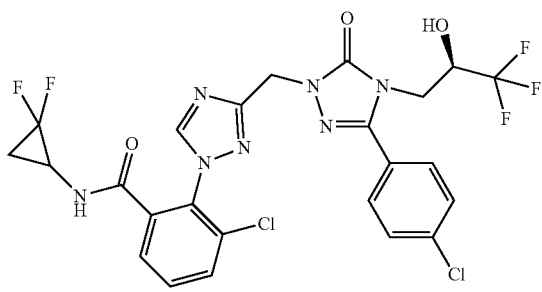 [SMILES: O=C(NC1CC1(F)F)c1cccc(Cl)c1-n1cnc(Cn2nc(-c3ccc(Cl)cc3)n(C[C@@H](O)C(F)(F)F)c2=O)n1]

A solution of 3-chloro-2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]benzoic acid (Example 61A, 120 mg, 221 µmol) in N,N-dimethylformamide (1.2 ml) was treated with HATU (126 mg, 331 µmol) and stirred 3 h at room temperature. 2,2-Difluorocyclopropanamine hydrochloride (1:1) (42.9 mg, 331 µmol) was added followed by N,N-diisopropylethylamine (150 µl. 880 µmol). The resulting mixture was stirred overnight at room temperature. Purification by preparative HPLC (Method 4) afforded 13.8 mg (10% of th.) of the title compound.

LC-MS (Method 1): $R_t$=0.94 min; MS (ESIpos): m/z=618.3 [M+H]$^+$ $^1$H-NMR (400 MHz, DMSO-d6) δ [ppm]: 8.90-8.66 (m, 2H), 7.87-7.50 (m, 7H), 6.92 (d, 1H), 5.13-4.97 (m, 2H), 4.39-4.21 (br m, 1H), 4.06-3.76 (m, 2H), 3.22-3.07 (br m, 1H), 1.81-1.57 (m, 1H), 1.46-1.22 (m, 1H).

Example 396

1-{3-Chloro-2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]benzoyl}-4,4-difluoro-L-prolinamide

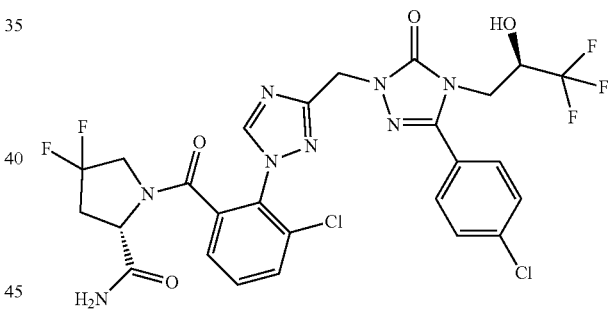

A solution of 3-chloro-2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]benzoic acid (Example 61A, 120 mg, 221 µmol) in N,N-dimethylformamide (1.2 ml) was treated with HATU (126 mg, 331 µmol) and stirred 3 h at room temperature. 4,4-Difluoro-L-prolinamide hydrochloride (1:1) (61.8 mg, 331 µmol) was added followed by N,N-diisopropylethylamine (150 µl, 880 µmol). The resulting mixture was stirred overnight at room temperature. Purification by preparative HPLC (Method 4) afforded 62.6 mg (42% of th.) of the title compound.

LC-MS (Method 1): $R_t$=0.91 min; MS (ESIpos): m/z=675.4 [M+H]$^+$ $^1$H-NMR (400 MHz, DMSO-d6) δ [ppm]: 8.90 (d, 1H), 7.91-7.16 (m, 9H), 6.91 (t, 1H), 5.16-4.96 (m, 2H), 4.50-4.22 (m, 2H), 4.07-3.57 (m, 4H), 2.96-2.22 (m, 2H, overlap with DMSO peak).

Example 397

3-Chloro-2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]-N-[2-fluorocyclopropyl]benzamide (Diastereomeric Mixture Cis Configured)

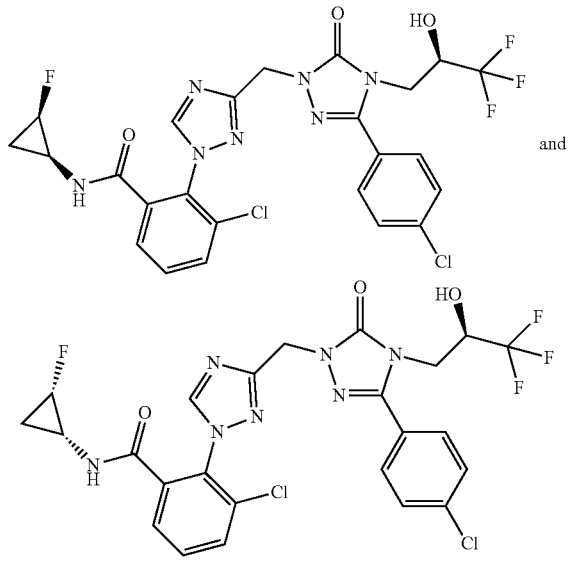

and

A solution of 3-chloro-2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]benzoic acid (Example 61A, 120 mg, 221 µmol) in N,N-dimethylformamide (1.2 ml) was treated with HATU (126 mg, 331 µmol) and stirred 3 h at room temperature. 2-Fluorocyclopropanamine 4-methylbenzenesulfonate (1:1) (cis configured, 81.9 mg, 331 µmol) was added followed by N,N-diisopropylethylamine (150 µl, 880 µmol). The resulting mixture was stirred overnight at room temperature. Purification by preparative HPLC (Method 4) afforded 63.4 mg (48% of th.) of the title compound.

LC-MS (Method 1): $R_t$=0.90 min; MS (ESIpos): m/z=600.3 [M+H]$^+$ $^1$H-NMR (400 MHz, DMSO-d6) δ [ppm]: 8.73-8.48 (m, 2H), 7.87-7.47 (m, 7H), 6.92 (d, 1H), 5.14-4.96 (m, 2H), 4.71-4.21 (m, 2H), 4.07-3.77 (m, 2H), 2.61-2.42 (m, 1H, overlap with DMSO peak), 0.99-0.68 (m, 2H).

Example 398

2-[(1-{2-Chloro-6-[(3,3-difluoropyrrolidin-1-yl)carbonyl]phenyl}-1H-1,2,4-triazol-3-yl)methyl]-5-(4-chlorophenyl)-4-[(2R)-3,3,3-trifluoro-2-hydroxypropyl]-2,4-dihydro-3H-1,2,4-triazol-3-one

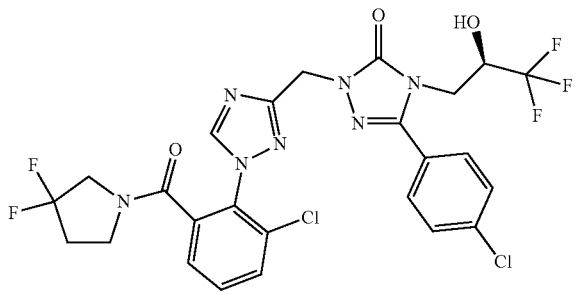 [SMILES: O=C(c1cccc(Cl)c1-n1cnc(Cn2nc(-c3ccc(Cl)cc3)n(C[C@@H](O)C(F)(F)F)c2=O)n1)N1CCC(F)(F)C1]

A solution of 3-chloro-2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]benzoic acid (Example 61A, 120 mg, 221 µmol) in N,N-dimethylformamide (1.2 ml) was treated with HATU (126 mg, 331 µmol) and stirred 3 h at room temperature. 3,3-Difluoropyrrolidine hydrochloride (1:1) (47.6 mg, 331 µmol) was added followed by N,N-diisopropylethylamine (150 µl, 880 µmol). The resulting mixture was stirred overnight at room temperature. Purification by preparative HPLC (Method 4) afforded 74.5 mg (53% of th.) of the title compound.

LC-MS (Method 1): $R_t$=1.00 min; MS (ESIpos): m/z=632.3 [M+H]$^+$ $^1$H-NMR (400 MHz, DMSO-d6) δ [ppm]: 8.89 (d, 1H), 7.89-7.52 (m, 7H), 6.91 (d, 1H), 5.13-5.00 (m, 2H), 4.38-4.20 (m, 1H), 4.07-3.37 (m, 6H), 2.44-2.19 (m, 2H).

Example 399

3-Chloro-2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]-N-(3,3-difluorocyclobutyl)benzamide

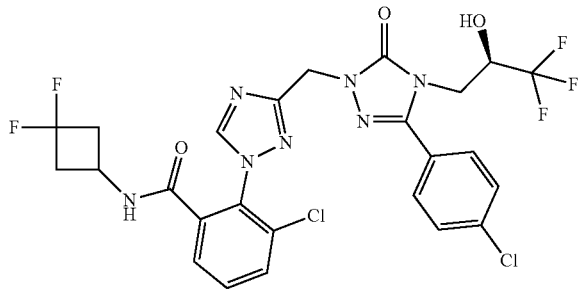 [SMILES: O=C(NC1CC(F)(F)C1)c1cccc(Cl)c1-n1cnc(Cn2nc(-c3ccc(Cl)cc3)n(C[C@@H](O)C(F)(F)F)c2=O)n1]

A solution of 3-chloro-2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]benzoic acid (Example 61A, 120 mg, 221 µmol) in N,N-dimethylformamide (1.2 ml) was treated with HATU (126 mg, 331 µmol) and stirred 3 h at room temperature. 3,3-Difluorocyclobutanamine hydrochloride (1:1) (47.6 mg, 331 µmol) was added followed by N,N-diisopropylethylamine (150 µl, 880 µmol). The resulting mixture was stirred overnight at room temperature. Purification by preparative HPLC (Method 4) afforded 66.7 mg (48% of th.) of the title compound.

LC-MS (Method 1): $R_t$=0.97 min; MS (ESIpos): m/z=632.3 [M+H]$^+$ $^1$H-NMR (400 MHz, DMSO-d6) δ [ppm]: 8.92-8.63 (m, 2H), 7.92-7.44 (m, 7H), 6.92 (d, 1H), 5.15-4.94 (m, 2H), 4.39-4.21 (br m, 1H), 4.08-3.72 (m, 3H), 2.89-2.23 (m, 4H, overlap with DMSO peak).

Example 400

1-{3-Chloro-2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]benzoyl}-prolinamide (Diastereomeric Mixture)

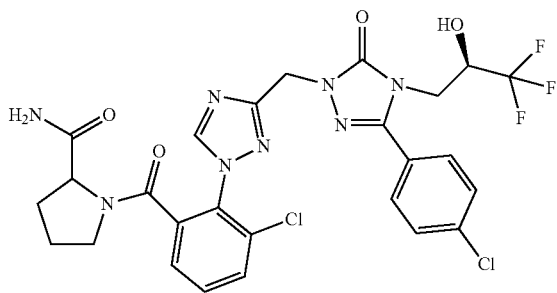 [SMILES: NC(=O)C1CCCN1C(=O)c1cccc(Cl)c1-n1cnc(Cn2nc(-c3ccc(Cl)cc3)n(C[C@@H](O)C(F)(F)F)c2=O)n1]

A solution of 3-chloro-2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]benzoic acid (Example 61A, 120 mg, 221 µmol) in N,N-dimethylformamide (1.2 ml) was treated with HATU (126 mg, 331 µmol) and stirred 3 h at room temperature. Prolinamide (37.8 mg, 331 µmol) was added followed by N,N-diisopropylethylamine (120 µl, 660 µmol). The resulting mixture was stirred overnight at room temperature. Purification by preparative HPLC (Method 4) afforded 59.8 mg (42% of th.) of the title compound.

LC-MS (Method 1): $R_t$=0.85 min; MS (ESIpos): m/z=639.1 [M+H]$^+$ $^1$H-NMR (400 MHz, DMSO-d6) δ [ppm]: 8.84 (d, 1H), 7.87-7.55 (m, 7H), 7.38-6.88 (m, 3H), 5.16-4.98 (m, 2H), 4.39-4.21 (br m, 1H), 4.14-3.77 (m, 3H), 3.29-2.97 (m, 2H, overlap with HDO peak), 2.13-1.42 (m, 4H).

Example 401

5-(4-Chlorophenyl)-2-({1-[2-chloro-6-(piperidin-1-ylcarbonyl)phenyl]-1H-1,2,4-triazol-3-yl}methyl)-4-[(2R)-3,3,3-trifluoro-2-hydroxypropyl]-2,4-dihydro-3H-1,2,4-triazol-3-one

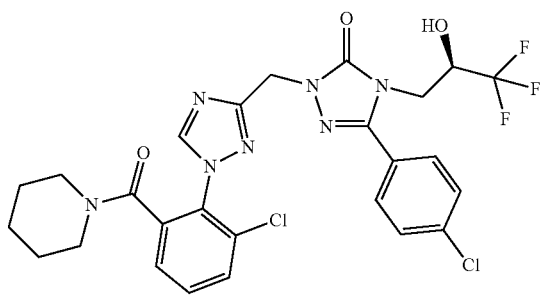 [SMILES: O=C(c1cccc(Cl)c1-n1cnc(Cn2nc(-c3ccc(Cl)cc3)n(C[C@@H](O)C(F)(F)F)c2=O)n1)N1CCCCC1]

A solution of 3-chloro-2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]benzoic acid (Example 61A, 120 mg, 221 µmol) in N,N-dimethylformamide (1.2 ml) was treated with HATU (126 mg, 331 µmol) and stirred 3 h at room temperature. Piperidine (33 µl, 330 µmol) was added followed by N,N-diisopropylethylamine (120 µl, 660 µmol). The resulting mixture was stirred overnight at room temperature. Purification by preparative HPLC (Method 4) afforded 74.7 mg (55% of th.) of the title compound.

LC-MS (Method 1): $R_t$=1.02 min; MS (ESIpos): m/z=610.2 [M+H]$^+$ $^1$H-NMR (400 MHz, DMSO-d6) δ [ppm]: 8.77 (d, 1H), 7.86-7.37 (m, 7H), 6.90 (t, 1H), 5.18-4.97 (m, 2H), 4.39-4.18 (br m, 1H), 4.08-3.76 (m, 2H), 3.24-2.86 (m, 4H), 1.53-1.01 (m, 6H).

Example 402

2-({1-[2-Chloro-6-(morpholin-4-ylcarbonyl)phenyl]-1H-1,2,4-triazol-3-yl}methyl)-5-(4-chlorophenyl)-4-[(2R)-3,3,3-trifluoro-2-hydroxypropyl]-2,4-dihydro-3H-1,2,4-triazol-3-one

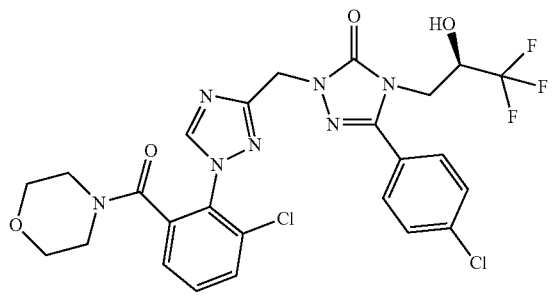 [SMILES: O=C(c1cccc(Cl)c1-n1cnc(Cn2nc(-c3ccc(Cl)cc3)n(C[C@@H](O)C(F)(F)F)c2=O)n1)N1CCOCC1]

A solution of 3-chloro-2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]benzoic acid (Example 61A, 120 mg, 221 µmol) in N,N-dimethylformamide (1.2 ml) was treated with HATU (126 mg, 331 µmol) and stirred 3 h at room temperature. Morpholine (29 µl, 330 µmol) was added followed by N,N-diisopropylethylamine (120 µl, 660 µmol). The resulting mixture was stirred overnight at room temperature. Purification by preparative HPLC (Method 4) afforded 73.3 mg (54% of th.) of the title compound.

LC-MS (Method 1): $R_t$=0.92 min; MS (ESIpos): m/z=612.1 [M+H]$^+$ $^1$H-NMR (400 MHz, DMSO-d6) δ [ppm]: 8.85 (s, 1H), 7.87-7.45 (m, 7H), 6.90 (d, 1H), 5.11 (s, 2H), 4.39-4.22 (br m, 1H), 4.07-3.76 (m, 2H), 3.56-2.91 (m, 8H).

Example 403

3-Chloro-2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]-N-[1-(trifluoromethyl)cyclopropyl]benzamide

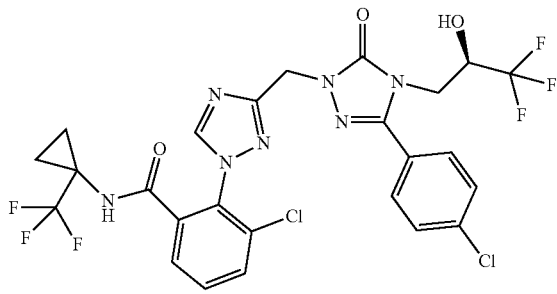 [SMILES: O=C(NC1(C(F)(F)F)CC1)c1cccc(Cl)c1-n1cnc(Cn2nc(-c3ccc(Cl)cc3)n(C[C@@H](O)C(F)(F)F)c2=O)n1]

A solution of 3-chloro-2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]benzoic acid (Example 61A, 120 mg, 221 µmol) in N,N-dimethylformamide (1.2 ml) was treated with HATU (126 mg, 331 µmol) and stirred 3 h at room temperature. 1-(Trifluoromethyl)cyclopropanaminium chloride (53.5 mg, 331 µmol) was added followed by N,N-diisopropylethylamine (120 µl, 660 µmol). The resulting mixture was stirred overnight at room temperature. Purification by preparative HPLC (Method 4) afforded 38.5 mg (26% of th.) of the title compound.

LC-MS (Method 1): $R_t$=0.99 min; MS (ESIpos): m/z=650.1 [M+H]$^+$ $^1$H-NMR (400 MHz, DMSO-d6) δ [ppm]: 9.12 (s, 1H), 8.74 (s, 1H), 7.87-7.51 (m, 7H), 6.92 (d, 1H), 5.04 (d, 2H), 4.39-4.21 (m, 1H), 4.05-3.77 (m, 2H), 1.16-0.66 (m, 4H).

Example 404

5-(4-Chlorophenyl)-2-{[1-(2-chloro-6-{[(2R)-2-(trifluoromethyl)pyrrolidin-1-yl]carbonyl}phenyl)-1H-1,2,4-triazol-3-yl]methyl}-4-[(2R)-3,3,3-trifluoro-2-hydroxypropyl]-2,4-dihydro-3H-1,2,4-triazol-3-one

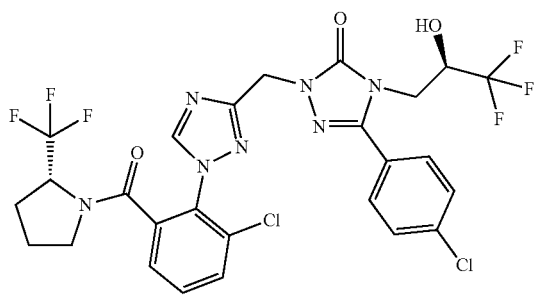 [SMILES: O=C(c1cccc(Cl)c1-n1cnc(Cn2nc(-c3ccc(Cl)cc3)n(C[C@@H](O)C(F)(F)F)c2=O)n1)N1CCC[C@@H]1C(F)(F)F]

A solution of 3-chloro-2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]benzoic acid (Example 61A, 120 mg, 221 µmol) in N,N-dimethylformamide (1.2 ml) was treated with HATU (126 mg, 331 µmol) and stirred 3 h at room temperature. (2R)-2-(trifluoromethyl)pyrrolidine (46.1 mg, 331 µmol) was added followed by N,N-diisopropylethylamine (120 µl, 660 µmol). The resulting mixture was stirred overnight at room temperature. Purification by preparative HPLC (Method 4) afforded 67.8 mg (46% of th.) of the title compound.

LC-MS (Method 2): $R_t$=2.07 min; MS (ESIpos): m/z=664.1 [M+H]$^+$ $^1$H-NMR (400 MHz, DMSO-d6) δ [ppm]: 8.96-8.84 (m, 1H), 7.89-7.44 (m, 7H), 6.91 (d, 1H), 5.16-4.91 (m, 2H), 4.64 (br t, 1H), 4.38-4.18 (br m, 1H), 4.07-3.76 (m, 2H), 3.52-3.09 (m, 2H, overlap with HDO peak), 2.19-1.67 (m 4H).

Example 405

3-Chloro-2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]-N-(1-methylcyclopropyl)benzamide

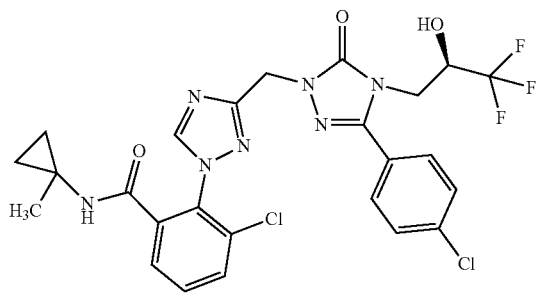 [SMILES: CC1(NC(=O)c2cccc(Cl)c2-n2cnc(Cn3nc(-c4ccc(Cl)cc4)n(C[C@@H](O)C(F)(F)F)c3=O)n2)CC1]

A solution of 3-chloro-2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]benzoic acid (Example 61A, 120 mg, 221 µmol) in N,N-dimethylformamide (1.2 ml) was treated with HATU (126 mg, 331 µmol) and stirred 3 h at room temperature. 1-Methylcyclopropanamine (23.6 mg, 331 µmol) was added followed by N,N-diisopropylethylamine (120 µl, 660 µmol). The resulting mixture was stirred overnight at room temperature. Purification by preparative HPLC (Method 4) afforded 68.0 mg (52% of th.) of the title compound.

LC-MS (Method 2): $R_t$=1.77 min; MS (ESIpos): m/z=596.1 [M+H]$^+$ $^1$H-NMR (400 MHz, DMSO-d6) δ [ppm]: 8.73-8.35 (m, 2H), 7.85-7.42 (m, 7H), 6.92 (d, 1H), 5.11-4.98 (m, 2H), 4.39-4.21 (br m, 1H), 4.07-3.77 (m, 2H), 1.12 (s, 3H), 0.49-0.28 (m, 4H).

Example 406

3-Chloro-2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]-N-[2-fluorocyclopropyl]benzamide (Diastereomeric Mixture)

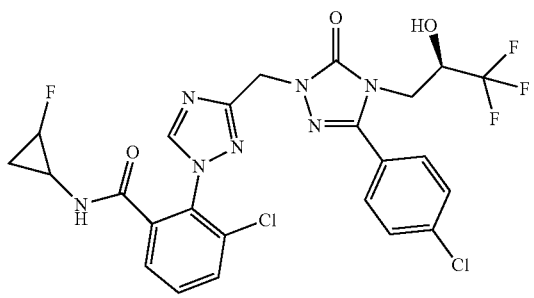 [SMILES: O=C(NC1CC1F)c1cccc(Cl)c1-n1cnc(Cn2nc(-c3ccc(Cl)cc3)n(C[C@@H](O)C(F)(F)F)c2=O)n1]

A solution of 3-chloro-2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]benzoic acid (Example 61A, 120 mg, 221 µmol) in N,N-dimethylformamide (1.2 ml) was treated with HATU (126 mg, 331 µmol) and stirred 3 h at room temperature. 2-Fluorocyclopropanamine (24.9 mg, 331 µmol) was added followed by N,N-diisopropylethylamine (120 µl, 660 µmol). The resulting mixture was stirred overnight at room temperature. Purification by preparative HPLC (Method 4) afforded 35.0 mg (26% of th.) of the title compound.

LC-MS (Method 1): $R_t$=0.91 min; MS (ESIpos): m/z=600.2 [M+H]$^+$ $^1$H-NMR (400 MHz, DMSO-d6) δ [ppm]: 8.75-8.46 (m, 2H), 7.90-7.47 (m, 7H), 6.92 (d, 1H), 5.12-4.97 (m, 2H), 4.70-4.21 (m, 2H), 4.06-3.77 (m, 2H), 2.74-2.28 (m, 1H, overlap with DMSO peak), 1.00-0.68 (m, 2H).

Example 407

2-[(1-{2-Chloro-6-[(3,3-dimethylmorpholin-4-yl)carbonyl]phenyl}-1H-1,2,4-triazol-3-yl)methyl]-5-(4-chlorophenyl)-4-[(2R)-3,3,3-trifluoro-2-hydroxypropyl]-2,4-dihydro-3H-1,2,4-triazol-3-one

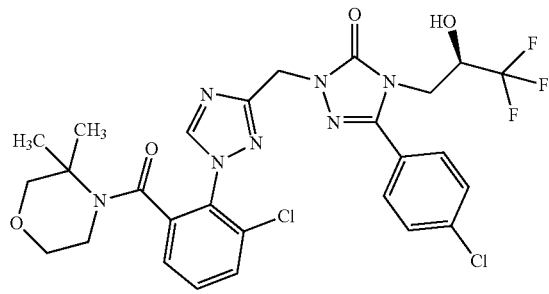 [SMILES: CC1(C)COCCN1C(=O)c1cccc(Cl)c1-n1cnc(Cn2nc(-c3ccc(Cl)cc3)n(C[C@@H](O)C(F)(F)F)c2=O)n1]

A solution of 3-chloro-2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]benzoic acid (Example 61A, 120 mg, 221 µmol) in N,N-dimethylformamide (1.2 ml) was treated with HATU (126 mg, 331 µmol) and stirred 3 h at room temperature. 3,3-Dimethylmorpholine hydrochloride (1:1) (50.2 mg, 331 µmol) was added followed by N,N-diisopropylethylamine (150 µl, 880 µmol). The resulting mixture was stirred overnight at room temperature. Purification by preparative HPLC (Method 4) afforded 56.2 mg (39% of th.) of the title compound.

LC-MS (Method 2): $R_t$=1.89 min; MS (ESIpos): m/z=640.1 [M+H]$^+$ $^1$H-NMR (400 MHz, DMSO-d6) δ [ppm]: 8.81 (s, 1H), 7.83-7.40 (m, 7H), 6.96-6.81 (br m, 1H), 5.10 (d, 2H), 4.39-4.21 (br m, 1H), 4.06-3.79 (m, 2H), 3.61-2.96 (m, 6H, overlap with HDO peak), 1.52-0.77 (m, 6H).

Example 408

N-[2-Amino-3,3,3-trifluoropropyl]-3-chloro-2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]benzamide (Diastereomeric Mixture)

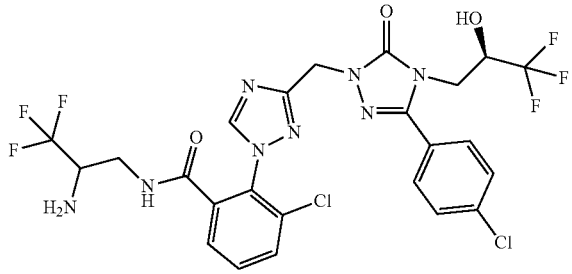 [SMILES: NC(CNC(=O)c1cccc(Cl)c1-n1cnc(Cn2nc(-c3ccc(Cl)cc3)n(C[C@@H](O)C(F)(F)F)c2=O)n1)C(F)(F)F]

A solution of 3-chloro-2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]benzoic acid (Example 61A, 120 mg, 221 µmol) in N,N-dimethylformamide (1.2 ml) was treated with HATU (126 mg, 331 µmol) and stirred 30 min at room temperature. 3,3,3-Trifluoropropane-1,2-diamine dihydrochloride (66.6 mg, 331 µmol) was added followed by N,N-diisopropylethylamine (190 µl, 1.1 mmol). The resulting mixture was stirred 2 h at room temperature. Purification by preparative HPLC (Method 4) afforded 93.0 mg (64% of th.) of the title compound.

LC-MS (Method 2): $R_t$=1.65 min; MS (ESIpos): m/z=653.1 [M+H]$^+$ $^1$H-NMR (400 MHz, DMSO-d6) δ [ppm]: 8.82-8.48 (m, 2H), 7.89-7.55 (m, 7H), 6.93 (dd, 1H), 5.16-4.98 (m, 2H), 4.41-4.23 (m, 1H), 4.06-3.77 (m, 2H), 3.45-3.18 (m, 2H, overlap with HDO peak), 3.15-2.95 (m, 1H), 2.42-1.61 (br s, 2H).

Example 409

1-{3-Chloro-2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]benzoyl}-4,4-difluoro-D-prolinamide

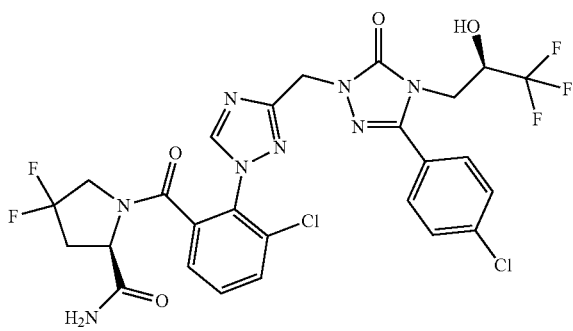 [SMILES: NC(=O)[C@H]1CC(F)(F)CN1C(=O)c1cccc(Cl)c1-n1cnc(Cn2nc(-c3ccc(Cl)cc3)n(C[C@@H](O)C(F)(F)F)c2=O)n1]

A solution of 3-chloro-2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]benzoic acid (Example 61A, 120 mg, 221 µmol) in N,N-dimethylformamide (1.2 ml) was treated with HATU (126 mg, 331 µmol) and stirred 3 h at room temperature. 4,4-Difluoro-D-prolinamide hydrochloride (1:1) (61.8 mg, 331 µmol) was added followed by N,N-diisopropylethylamine (150 µl, 880 µmol). The resulting mixture was stirred overnight at room temperature. Purification by preparative HPLC (Method 4) afforded 74.4 mg (50% of th.) of the title compound.

LC-MS (Method 2): $R_t$=1.69 min; MS (ESIpos): m/z=675.1 [M+H]$^+$ $^1$H-NMR (400 MHz, DMSO-d6) δ [ppm]: 8.91 (d, 1H), 7.92-7.11 (m, 9H), 6.92 (dd, 1H), 5.17-4.97 (m, 2H), 4.49-4.21 (m, 2H), 4.09-3.58 (m, 4H), 3.02-2.26 (m, 2H, overlap with DMSO peak).

Example 410

3-Chloro-2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]-N-(3,3,3-trifluoropropyl)benzamide

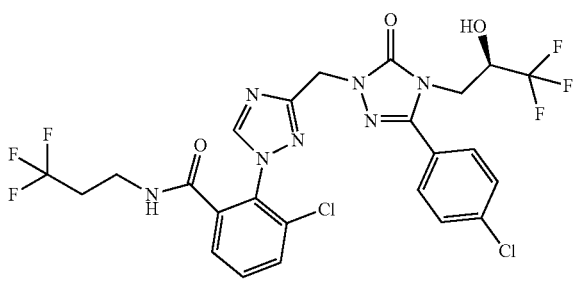 [SMILES: O=C(NCCC(F)(F)F)c1cccc(Cl)c1-n1cnc(Cn2nc(-c3ccc(Cl)cc3)n(C[C@@H](O)C(F)(F)F)c2=O)n1]

A solution of 3-chloro-2-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]benzoic acid (Example 61A, 120 mg, 221 µmol) in N,N-dimethylformamide (1.2 ml) was treated with HATU (126 mg, 331 µmol) and stirred 3 h at room temperature. 3,3,3-Trifluoropropan-1-amine (37.5 mg, 331 µmol) was added followed by N,N-diisopropylethylamine (150 µl, 880 µmol). The resulting mixture was stirred overnight at room temperature. Purification by preparative HPLC (Method 4) afforded 64.2 mg (46% of th.) of the title compound.

LC-MS (Method 2): $R_t$=1.86 min; MS (ESIpos): m/z=638.1 [M+H]$^+$ $^1$H-NMR (400 MHz, DMSO-d6) δ [ppm]: 8.78-8.52 (m, 2H), 7.88-7.48 (m, 7H), 6.92 (d, 1H), 5.15-4.96 (m, 2H), 4.39-4.1 (br m, 1H), 4.05-3.77 (m, 2H), 3.26-3.13 (m, 2H), 2.40-2.16 (m, 2H).

Example 411

2-({1-[2-Chloro-6-(2-oxa-6-azaspiro[3.3]hept-6-ylcarbonyl)phenyl]-1H-1,2,4-triazol-3-yl}methyl)-5-(4-chlorophenyl)-4-[(2S)-3,3,3-trifluoro-2-hydroxypropyl]-2,4-dihydro-3H-1,2,4-triazol-3-one

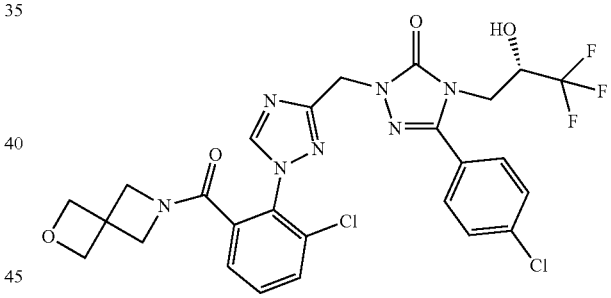

A solution of 3-chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoic acid (Example 51A, 120 mg, 221 µmol) in N,N-dimethylformamide (1.2 ml) was treated with HATU (126 mg, 331 µmol) and stirred 3 h at room temperature. 2-Oxa-6-azaspiro[3.3]heptane ethanedioate (2:1) (47.8 mg, 166 µmol) was added followed by N,N-diisopropylethylamine (190 µl, 1.1 mmol). The resulting mixture was stirred overnight at room temperature. Purification by preparative HPLC (Method 4) afforded 54.8 mg (40% of th.) of the title compound.

LC-MS (Method 2): $R_t$=1.64 min; MS (ESIpos): m/z=624.1 [M+H]$^+$ $^1$H-NMR (400 MHz, DMSO-d6) δ [ppm]: 8.85 (s, 1H), 7.91-7.44 (m, 7H), 6.93 (d, 1H), 5.06 (d, 2H), 4.75-4.52 (m, 4H), 4.43-3.74 (m, 7H).

Example 412

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(2,2,2-trifluoroethyl)-3-(trifluoromethyl)benzamide

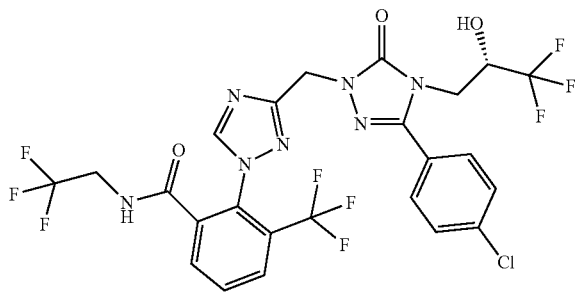 [SMILES: O=C(NCC(F)(F)F)c1cccc(C(F)(F)F)c1-n1cnc(Cn2nc(-c3ccc(Cl)cc3)n(C[C@H](O)C(F)(F)F)c2=O)n1]

A solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-3-(trifluoromethyl)benzoic acid (Example 54A, 70.0 mg, 121 µmol) in N,N-dimethylformamide (620 µl) was treated with HATU (69.2 mg, 182 µmol) and stirred 3 h at room temperature. 2,2,2-trifluoroethanamine (15 µl, 180 µmol) was added followed by N,N-diisopropylethylamine (63 µl, 360 µmol). The resulting mixture was stirred overnight at room temperature. Purification by preparative HPLC (Method 4) afforded 67.5 mg (85% of th.) of the title compound.

LC-MS (Method 2): R$_t$=1.84 min MS (ESIpos): m/z=658.1 [M+H]$^+$ $^1$H-NMR (400 MHz, DMSO-d6) δ [ppm]: 9.14 (t, 1H), 8.70 (s, 1H), 8.21-7.54 (m, 7H), 6.92 (d, 1H), 5.11-4.86 (m, 2H), 4.39-4.20 (br m, 1H), 4.09-3.67 (m, 4H).

Example 413

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-[2-fluorocyclopropyl]-3-(trifluoromethyl)benzamide (Diastereomeric Mixture Cis Configured)

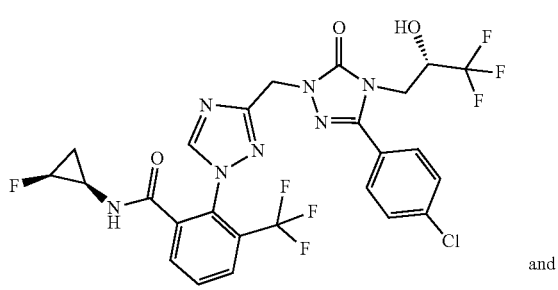

and

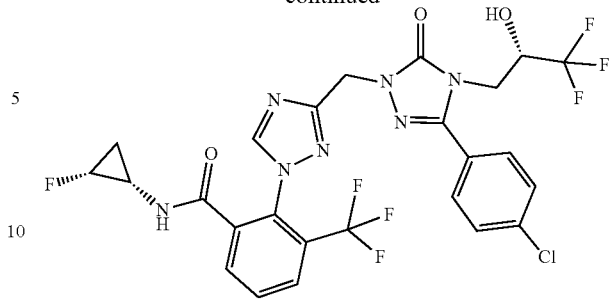

A solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-3-(trifluoromethyl)benzoic acid (Example 54A, 70.0 mg, 121 µmol) in N,N-dimethylformamide (620 µl) was treated with HATU (69.2 mg, 182 µmol) and stirred 1 h at room temperature. 2-Fluorocyclopropanamine 4-methylbenzenesulfonate (1:1) (cis configured, 45.0 mg, 182 µmol) was added followed by N,N-diisopropylethylamine (85 µl, 490 µmol). The resulting mixture was stirred overnight at room temperature. Purification by preparative HPLC (Method 4) afforded 67.3 mg (87% of th.) of the title compound.

LC-MS (Method 1): R$_t$=0.93 min; MS (ESIpos): m/z=634.1 [M+H]$^+$ $^1$H-NMR (400 MHz, DMSO-d6) δ [ppm]: 8.72-8.50 (m, 2H), 8.15-7.54 (m, 7H), 6.92 (d, 1H), 5.17-4.91 (m, 2H), 4.77-4.20 (m, 2H), 4.06-3.72 (m, 2H), 2.76-2.22 (m, 1H, overlap with DMSO peak), 1.02-0.64 (m, 2H).

Example 414

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(1-methylcyclopropyl)-3-(trifluoromethyl)benzamide

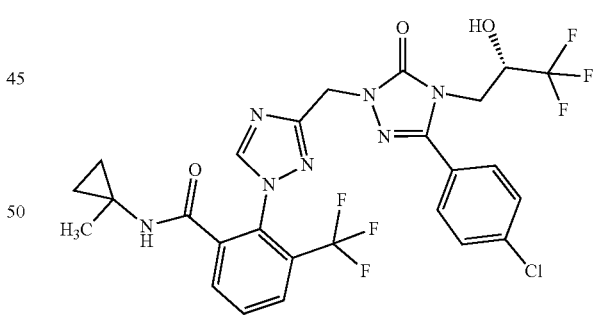

A solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-3-(trifluoromethyl)benzoic acid (Example 54A, 70.0 mg, 121 µmol) in N,N-dimethylformamide (620 µl) was treated with HATU (69.2 mg, 182 µmol) and stirred 1 h at room temperature. 1-Methylcyclopropanamine hydrochloride (1:1) (19.6 mg, 182 µmol) was added followed by N,N-diisopropylethylamine (85 µl, 490 µmol). The resulting mixture was stirred overnight at room temperature. Purification by preparative HPLC (Method 4) afforded 62.5 mg (82% of th.) of the title compound.

LC-MS (Method 1): $R_t$=0.97 min; MS (ESIpos): m/z=630.2 [M+H]$^+$ $^1$H-NMR (400 MHz, DMSO-d6) δ [ppm]: 8.73-8.41 (m, 2H), 8.13-7.54 (m, 7H), 6.92 (d, 1H), 5.16-4.90 (m, 2H), 4.39-4.21 (br m, 1H), 4.05-3.74 (m, 2H), 1.10 (s, 3H), 0.51-0.26 (m, 4H).

Example 415

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-cyclopropyl-3-(trifluoromethyl)benzamide

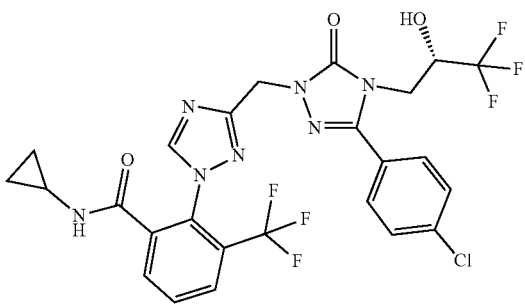

A solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-3-(trifluoromethyl)benzoic acid (Example 54A, 70.0 mg, 121 µmol) in N,N-dimethylformamide (620 µl) was treated with HATU (69.2 mg, 182 µmol) and stirred 1 h at room temperature. Cyclopropanamine (13 µl, 180 µmol) was added followed by N,N-diisopropylethylamine (63 µl, 360 µmol). The resulting mixture was stirred overnight at room temperature. Purification by preparative HPLC (Method 4) afforded 62.7 mg (75% of th.) of the title compound.

LC-MS (Method 1): $R_t$=0.92 min; MS (ESIpos): m/z=616.2 [M+H]$^+$ $^1$H-NMR (400 MHz, DMSO-d6) δ [ppm]: 8.78-7.40 (m, 9H), 6.92 (d, 1H), 5.16-4.92 (m, 2H), 4.39-4.21 (br m, 1H), 4.05-3.71 (m, 2H), 2.63-2.34 (m, 1H, overlap with DMSO peak), 0.51-0.05 (m, 4H).

Example 416

5-(4-Chlorophenyl)-2-({1-[2-{[(2R)-2-(methoxymethyl)pyrrolidin-1-yl]carbonyl}-6-(trifluoromethyl)phenyl]-1H-1,2,4-triazol-3-yl}methyl)-4-[(2S)-3,3,3-trifluoro-2-hydroxypropyl]-2,4-dihydro-3H-1,2,4-triazol-3-one

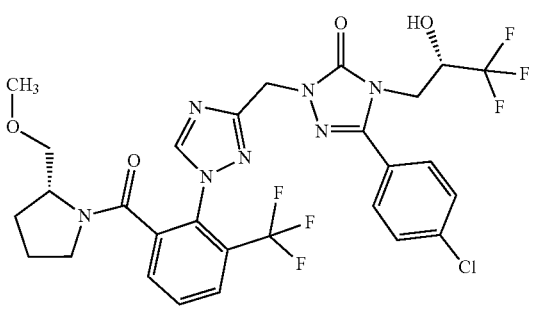

A solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-3-(trifluoromethyl)benzoic acid (Example 54A, 60.0 mg, 104 µmol) in N,N-dimethylformamide (530 µl) was treated with HATU (59.3 mg, 156 µmol) and stirred 1 h at room temperature. (2R)-2-(methoxymethyl)pyrrolidine (19 µl, 160 µmol) was added followed by N,N-diisopropylethylamine (54 µl, 310 µmol). The resulting mixture was stirred overnight at room temperature. Purification by preparative HPLC (Method 4) afforded 57.8 mg (76% of th.) of the title compound.

LC-MS (Method 1): $R_t$=1.03 min; MS (ESIpos): m/z=674.3 [M+H]$^+$ $^1$H-NMR (400 MHz, DMSO-d6) δ [ppm]: 8.88-8.65 (m, 1H), 8.13-7.45 (m, 7H), 6.98-6.81 (m, 1H), 5.21-4.94 (m, 2H), 4.39-4.18 (br m, 1H), 4.10-3.77 (m, 3H), 3.23-2.74 (m, 7H), 1.97-1.34 (m, 4H).

Example 417

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(3,3-difluorocyclobutyl)-3-(trifluoromethyl)benzamide

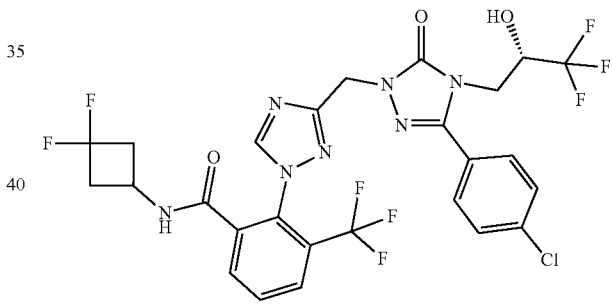

A solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-3-(trifluoromethyl)benzoic acid (Example 54A, 60.0 mg, 104 µmol) in N,N-dimethylformamide (530 µl) was treated with HATU (59.3 mg, 156 µmol) and stirred 1 h at room temperature. 3,3-Difluorocyclobutanamine hydrochloride (1:1) (22.4 mg, 156 µmol) was added followed by N,N-diisopropylethylamine (72 µl, 420 µmol). The resulting mixture was stirred overnight at room temperature. Purification by preparative HPLC (Method 4) afforded 68.4 mg (99% of th.) of the title compound.

LC-MS (Method 1): $R_t$=0.99 min; MS (ESIpos): m/z=666.2 [M+H]$^+$ $^1$H-NMR (400 MHz, DMSO-d6) δ [ppm]: 8.96-8.63 (m, 2H), 8.15-7.53 (m, 7H), 6.92 (d, 1H), 5.14-4.92 (m, 2H), 4.39-4.21 (br m, 1H), 4.08-3.76 (m, 3H), 2.85-2.60 (m, 2H), 2.48-2.22 (m, 2H).

Example 418

5-(4-Chlorophenyl)-2-[(1-{2-[(1,1-dioxidothiomorpholin-4-yl)carbonyl]-6-(trifluoromethyl)phenyl}-1H-1,2,4-triazol-3-yl)methyl]-4-[(2S)-3,3,3-trifluoro-2-hydroxypropyl]-2,4-dihydro-3H-1,2,4-triazol-3-one

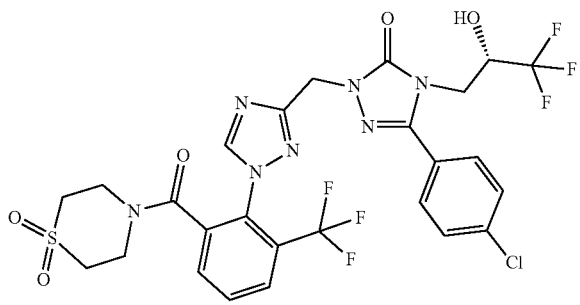

A solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-3-(trifluoromethyl)benzoic acid (Example 54A, 60.0 mg, 104 µmol) in N,N-dimethylformamide (530 µl) was treated with HATU (59.3 mg, 156 µmol) and stirred 1 h at room temperature. Thiomorpholine 1,1-dioxide (21.1 mg, 156 µmol) was added followed by N,N-diisopropylethylamine (54 µl, 310 µmol). The resulting mixture was stirred overnight at room temperature. Purification by preparative HPLC (Method 4) afforded 55.8 mg (77% of th.) of the title compound.

LC-MS (Method 1): $R_t$=0.92 min; MS (ESIpos): m/z=694.2 [M+H]$^+$ $^1$H-NMR (400 MHz, DMSO-d6) δ [ppm]: 8.83 (s, 1H), 8.17-7.53 (m, 7H), 6.90 (dd, 1H), 5.25-4.89 (m, 2H), 4.39-4.19 (m, 1H), 4.16-3.78 (m, 3H), 3.73-2.91 (m, 7H, overlap with HDO peak).

Example 419

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(cyclopropylmethyl)-3-(trifluoromethyl)benzamide

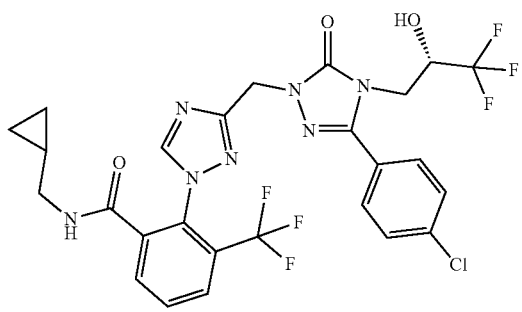 [SMILES: O=C(NCC1CC1)c1cccc(C(F)(F)F)c1-n1cnc(Cn2nc(-c3ccc(Cl)cc3)n(C[C@H](O)C(F)(F)F)c2=O)n1]

A solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-3-(trifluoromethyl)benzoic acid (Example 54A, 60.0 mg, 104 µmol) in N,N-dimethylformamide (530 µl) was treated with HATU (59.3 mg, 156 µmol) and stirred 1 h at room temperature. 1-Cyclopropylmethanamine (14 µl, 160 µmol) was added followed by N,N-diisopropylethylamine (54 µl, 310 µmol). The resulting mixture was stirred overnight at room temperature. Purification by preparative HPLC (Method 4) afforded 44.7 mg (68% of th.) of the title compound.

LC-MS (Method 1): $R_t$=0.98 min; MS (ESIpos): m/z=630.2 [M+H]$^+$ $^1$H-NMR (400 MHz, DMSO-d6) δ [ppm]: 8.74-8.31 (m, 2H), 8.10-7.55 (m, 7H), 6.91 (d, 1H), 5.12-4.96 (m, 2H), 4.39-4.20 (br m, 1H), 4.05-3.77 (m, 2H), 2.82 (t, 2H), 0.80-0.56 (m, 1H), 0.31-0.17 (m, 2H), 0.07-0.12 (m, 2H).

Example 420

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-[2,2-difluorocyclopropyl]-3-(trifluoromethyl)benzamide (Diastereomeric Mixture)

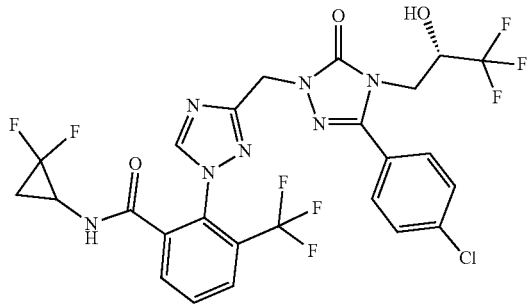 [SMILES: O=C(NC1CC1(F)F)c1cccc(C(F)(F)F)c1-n1cnc(Cn2nc(-c3ccc(Cl)cc3)n(C[C@H](O)C(F)(F)F)c2=O)n1]

A solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-3-(trifluoromethyl)benzoic acid (Example 54A, 60.0 mg, 104 µmol) in N,N-dimethylformamide (530 µl) was treated with HATU (59.3 mg, 156 µmol) and stirred 1 h at room temperature. 2,2-Difluorocyclopropanamine hydrochloride (1:1) (20.2 mg, 156 µmol) was added followed by N,N-diisopropylethylamine (82 µl, 470 µmol). The resulting mixture was stirred overnight at room temperature. Purification by preparative HPLC (Method 4) afforded 8.70 mg (13% of th.) of the title compound.

LC-MS (Method 1): $R_t$=0.96 min; MS (ESIpos): m/z=652.2 [M+H]$^+$ $^1$H-NMR (400 MHz, DMSO-d6) δ [ppm]: 8.99-8.58 (m, 2H), 8.15-7.52 (m, 7H), 6.92 (d, 1H), 5.22-4.85 (m, 2H), 4.39-4.20 (br m, 1H), 4.08-3.75 (m, 2H), 3.22-3.00 (br m, 1H), 1.81-1.20 (m, 2H).

Example 421

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-3-(trifluoromethyl)-N-(3,3,3-trifluoropropyl)benzamide

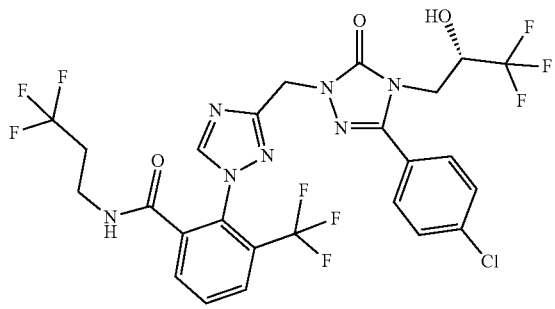 [SMILES: O=C(NCCC(F)(F)F)c1cccc(C(F)(F)F)c1-n1cnc(Cn2nc(-c3ccc(Cl)cc3)n(C[C@H](O)C(F)(F)F)c2=O)n1]

A solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-3-(trifluoromethyl)benzoic acid (Example 54A, 60.0 mg, 104 µmol) in N,N-dimethylformamide (530 µl) was treated with HATU (59.3 mg, 156 µmol) and stirred 1 h at room temperature. 3,3,3-Trifluoropropan-1-amine (17.6 mg, 156 µmol) was added followed by N,N-diisopropylethylamine (54 µl, 310 µmol). The resulting mixture was stirred overnight at room temperature. Purification by preparative HPLC (Method 4) afforded 49.0 mg (70% of th.) of the title compound.

LC-MS (Method 1): $R_t$=1.00 min; MS (ESIpos): m/z=672.2 [M+H]$^+$ $^1$H-NMR (400 MHz, DMSO-d6) δ [ppm]: 8.73-8.60 (m, 2H), 8.11-7.57 (m, 7H), 6.91 (d, 1H), 5.13-4.95 (m, 2H), 4.39-4.21 (br m, 1H), 4.05-3.78 (m, 2H), 3.23-3.07 (m, 2H), 2.38-2.13 (m, 2H).

Example 422

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-[2-fluorocyclopropyl]-3-(trifluoromethyl)benzamide (Diastereomeric Mixture Trans Configured)

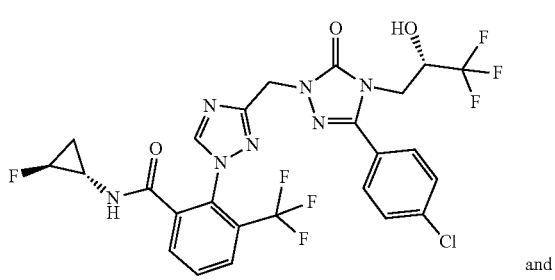

and

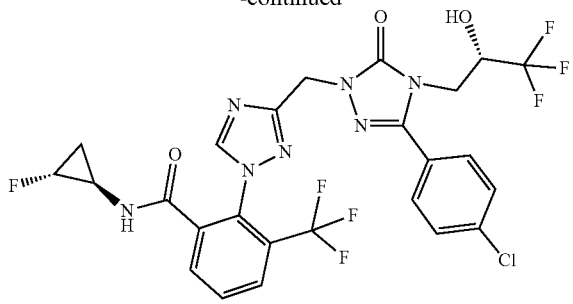

A solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-3-(trifluoromethyl)benzoic acid (Example 54A, 60.0 mg, 104 µmol) in N,N-dimethylformamide (530 µl) was treated with HATU (59.3 mg, 156 µmol) and stirred 1.5 h at room temperature. 2-Fluorocyclopropanamine hydrochloride (1:1) (trans configured, 17.4 mg, 156 µmol) was added followed by N,N-diisopropylethylamine (72 µl, 420 µmol). The resulting mixture was stirred 45 min at room temperature. Purification by preparative HPLC (Method 4) afforded 53.8 mg (78% of th.) of the title compound.

LC-MS (Method 1): $R_t$=0.93 min; MS (ESIpos): m/z=634.2 [M+H]$^+$ $^1$H-NMR (400 MHz, DMSO-d6) δ [ppm]: 8.71-8.50 (m, 2H), 8.15-7.43 (m, 7H), 6.92 (d, 1H), 5.15-4.86 (m, 2H), 4.75-4.21 (m, 2H), 4.08-3.72 (m, 2H), 2.71-2.32 (m, 1H, overlap with DMSO peak), 1.04-0.63 (m, 2H).

Example 423

5-(4-Chlorophenyl)-2-({1-[2-{[(2S)-2-(methoxymethyl)pyrrolidin-1-yl]carbonyl}-6-(trifluoromethyl)phenyl]-1H-1,2,4-triazol-3-yl}methyl)-4-[(2S)-3,3,3-trifluoro-2-hydroxypropyl]-2,4-dihydro-3H-1,2,4-triazol-3-one

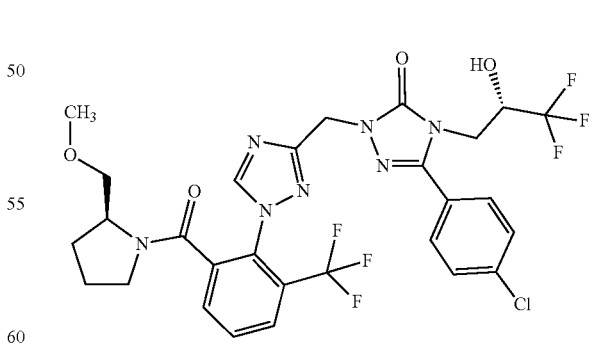

A solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-3-(trifluoromethyl)benzoic acid (Example 54A, 46.2 mg, 80.1 µmol) in N,N-dimethylformamide (410 µl) was treated with HATU (45.7 mg, 120 µmol) and stirred 1 h at room temperature. (2S)-2-(methoxymethyl)pyrrolidine (13.8 mg, 120 µmol) was added followed by N,N-diisopropylethylamine (42 µl, 240 µmol). The resulting mixture was stirred overnight at room temperature. Purification by preparative HPLC (Method 4) afforded 44.5 mg (82% of th.) of the title compound.

LC-MS (Method 2): $R_t$=1.96 min; MS (ESIpos): m/z=674.2 [M+H]$^+$ $^1$H-NMR (400 MHz, DMSO-d6) δ [ppm]: 8.81-8.65 (m, 1H), 8.14-7.54 (m, 7H), 6.91 (d, 1H), 5.22-4.90 (m, 2H), 4.38-4.19 (br m, 1H), 4.08-3.76 (m, 3H), 3.24-2.82 (m, 7H), 1.89-1.39 (m, 4H).

Example 424

N-(2-Amino-2-methylpropyl)-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-5-fluorobenzamide

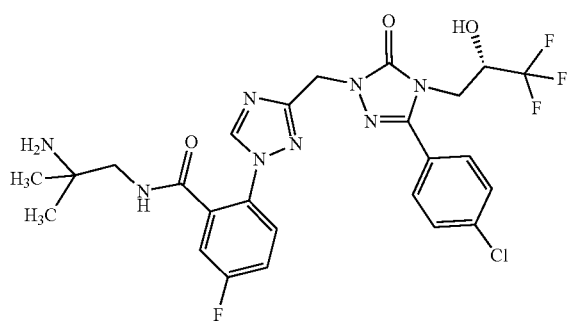

2-Methylpropane-1,2-diamine (49 µl, 470 µmol) and N,N-diisopropylethylamine (50 µl, 280 µmol) were added to a solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-5-fluorobenzoyl chloride (Example 60A, 104 mg, 190 µmol) in dichloromethane (2.5 ml). This reaction mixture was stirred for 30 min at room temperature. The crude product was purified by preparative HPLC (Method 4). Lyophilisation of the product containing fractions afforded 102 mg (88% of th.) of the title compound.

LC-MS (Method 1): $R_t$=0.68 min; MS (ESIpos): m/z=597 [M+H]$^+$ $^1$H-NMR (400 MHz, DMSO-d6) δ [ppm]: 1.014 (16.00), 1.038 (14.91), 2.254 (0.85), 3.128 (3.69), 3.806 (1.59), 3.830 (1.78), 3.843 (2.03), 3.867 (2.09), 3.965 (2.33), 3.973 (2.38), 4.001 (1.62), 4.009 (1.39), 4.299 (1.12), 4.315 (1.33), 4.332 (0.86), 4.989 (0.94), 5.029 (6.57), 5.037 (6.04), 5.076 (0.69), 7.481 (0.89), 7.489 (1.20), 7.503 (1.81), 7.510 (2.33), 7.524 (1.19), 7.531 (1.51), 7.551 (2.40), 7.559 (2.13), 7.573 (2.47), 7.580 (2.04), 7.603 (1.29), 7.610 (6.26), 7.614 (3.12), 7.626 (3.22), 7.631 (8.38), 7.637 (1.93), 7.651 (2.39), 7.663 (2.42), 7.673 (2.00), 7.685 (1.83), 7.755 (1.81), 7.761 (8.76), 7.766 (3.40), 7.778 (2.90), 7.783 (6.72), 7.789 (1.30), 8.322 (3.67), 8.751 (9.43), 8.798 (1.26).

Example 425

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-5-fluoro-N-methylbenzamide

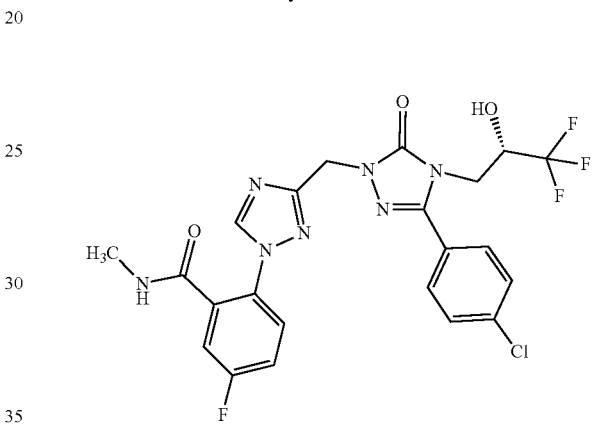

Methanamine (240 µl, 2.0 M, 470 µmol) and N,N-diisopropylethylamine (50 µl, 280 µmol) were added to a solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-5-fluorobenzoyl chloride (Example 60A, 104 mg, 190 µmol) in dichloromethane (2.5 ml). This reaction mixture was stirred for 30 min at room temperature. The crude product was purified by preparative HPLC (Method 4). Lyophilisation of the product containing fractions afforded 76.4 mg (75% of th.) of the title compound.

LC-MS (Method 2): $R_t$=1.57 min; MS (ESIpos): m/z=540 [M+H]$^+$ $^1$H-NMR (400 MHz, DMSO-d6) δ [ppm]: 2.234 (1.04), 2.576 (16.00), 2.588 (15.49), 3.291 (1.86), 3.814 (1.54), 3.838 (1.80), 3.851 (2.23), 3.875 (2.39), 3.974 (2.26), 3.983 (2.41), 4.011 (1.57), 4.019 (1.44), 4.304 (1.29), 4.322 (1.23), 5.063 (14.37), 6.909 (4.31), 6.924 (4.21), 7.426 (2.66), 7.433 (3.64), 7.447 (2.72), 7.455 (3.63), 7.462 (1.95), 7.469 (1.43), 7.483 (3.19), 7.491 (2.47), 7.504 (2.05), 7.511 (1.62), 7.603 (1.75), 7.609 (8.42), 7.614 (3.38), 7.625 (4.16), 7.630 (11.03), 7.636 (2.07), 7.642 (3.39), 7.654 (3.30), 7.664 (2.73), 7.676 (2.51), 7.743 (2.34), 7.749 (11.12), 7.754 (3.58), 7.766 (3.40), 7.771 (7.81), 7.777 (1.04), 8.314 (2.64), 8.326 (2.50), 8.338 (0.84), 8.695 (12.71).

Example 426

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-5-fluoro-N-(2,2,2-trifluoroethyl)benzamide

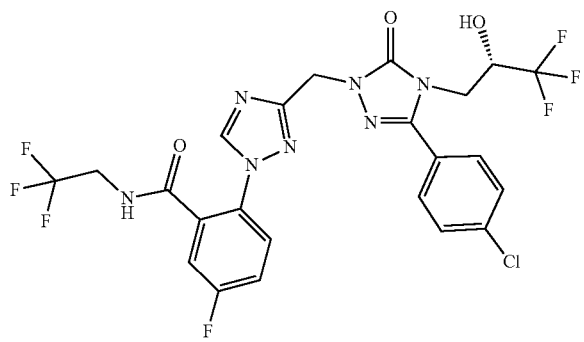

2,2,2-Trifluoroethanamine (37 µl, 470 µmol) and N,N-diisopropylethylamine (50 µl, 280 µmol) were added to a solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-5-fluorobenzoyl chloride (Example 60A, 104 mg, 190 µmol) in dichloromethane (2.5 ml). This reaction mixture was stirred for 30 min at room temperature. The crude product was purified by preparative HPLC (§ HTS). Lyophilisation of the product containing fractions afforded 72.6 mg (63% of th.) of the title compound.

LC-MS (Method 5): $R_t$=1.78 min; MS (ESIpos): m/z=608 [M+H]$^+$ $^1$H-NMR (400 MHz, DMSO-d6) δ [ppm]: 2.259 (1.11), 3.812 (1.92), 3.836 (2.71), 3.849 (4.09), 3.855 (3.75), 3.872 (5.84), 3.879 (3.56), 3.895 (2.99), 3.919 (0.94), 3.972 (2.70), 3.980 (2.89), 4.008 (1.83), 4.017 (1.63), 4.300 (1.44), 5.022 (16.00), 6.908 (3.95), 6.924 (3.82), 7.431 (3.09), 7.438 (3.67), 7.452 (3.12), 7.460 (3.46), 7.523 (1.78), 7.530 (1.68), 7.544 (3.26), 7.552 (2.91), 7.566 (2.15), 7.573 (1.98), 7.594 (1.71), 7.601 (9.05), 7.605 (3.89), 7.617 (4.36), 7.622 (12.03), 7.628 (2.05), 7.703 (3.72), 7.715 (3.84), 7.725 (3.49), 7.740 (13.07), 7.745 (4.67), 7.757 (3.72), 7.762 (8.81), 7.768 (1.50), 8.730 (14.14), 9.040 (1.93), 9.056 (3.79), 9.072 (1.75).

Example 427

5-Chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(2,2,2-trifluoroethyl)benzamide

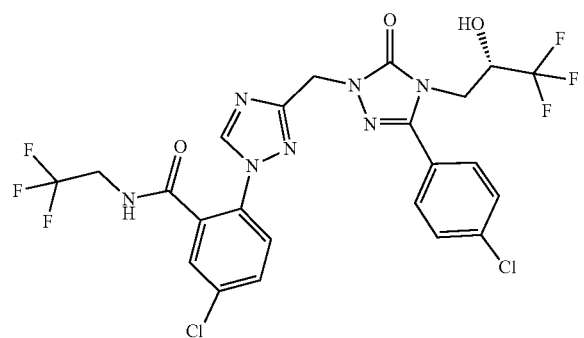

2,2,2-Trifluoroethanamine (36 µl, 460 µmol) and N,N-diisopropylethylamine (48 µl, 280 µmol) were added to a solution of 5-chloro-2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]benzoyl chloride (Example 59A, 103 mg, 184 µmol) in dichloromethane (3.0 ml). This reaction mixture was stirred for 30 min at room temperature. The crude product was purified by preparative HPLC (Method 4). Lyophilisation of the product containing fractions afforded 93.8 mg (82% of th.) of the title compound.

LC-MS (Method 2): $R_t$=1.89 min: MS (ESIpos): m/z=624 [M+H]$^+$ $^1$H-NMR (400 MHz, DMSO-d6) δ [ppm]: −0.008 (1.16), 0.008 (0.98), 3.812 (1.67), 3.836 (1.98), 3.848 (3.24), 3.863 (1.56), 3.872 (5.33), 3.888 (3.21), 3.896 (2.91), 3.912 (2.85), 3.936 (0.87), 3.972 (2.38), 3.981 (2.69), 4.009 (1.67), 4.017 (1.61), 4.299 (1.24), 4.315 (1.19), 5.028 (16.00), 6.907 (4.13), 6.923 (4.13), 7.594 (1.21), 7.600 (9.14), 7.605 (3.35), 7.621 (15.90), 7.625 (10.14), 7.698 (4.57), 7.719 (9.84), 7.733 (1.95), 7.739 (12.76), 7.744 (4.23), 7.750 (6.65), 7.756 (8.37), 7.761 (9.48), 7.767 (1.50), 7.771 (2.89), 7.777 (2.65), 8.774 (15.40), 9.086 (1.92), 9.102 (4.07), 9.118 (1.84).

Example 428

3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(2,2,2-trifluoroethyl)pyridine-2-carboxamide

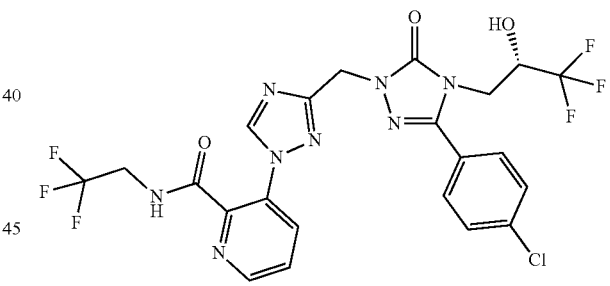

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 11A, 105 mg, 206 µmol) in N,N-dimethylformamide (1.0 ml, 13 mmol) was treated with HATU (117 mg, 309 µmol) and stirred 45 min at room temperature. 2,2,2-trifluoroethanamine (25 µl, 310 µmol) was then added followed by and N,N-diisopropylethylamine (110 µl, 620 µmol). The resulting mixture was stirred overnight at room temperature, diluted with methanol and purified by preparative HPLC (Method 4) affording 101 mg (83% of th.) of the title compound.

LC-MS (Method 1): $R_t$=0.91 min; MS (ESIpos): m/z=591.2 [M+H]$^+$ $^1$H-NMR (400 MHz, DMSO-d6) δ [ppm]: 9.34 (t, 1H), 8.90-8.64 (m, 2H), 8.15 (dd, 1H), 7.88-7.48 (m, 5H), 6.92 (d, 1H), 5.14-4.96 (m, 2H), 4.44-4.20 (m, 1H), 4.11-3.73 (m, 4H).

Example 429

N-[(2R)-2-Amino-3,3,3-trifluoropropyl]-3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-2-carboxamide (Diastereomeric Mixture)

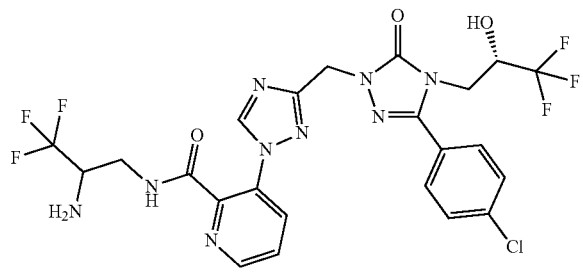 [SMILES: NC(CNC(=O)c1ncccc1-n1cnc(Cn2nc(-c3ccc(Cl)cc3)n(C[C@H](O)C(F)(F)F)c2=O)n1)C(F)(F)F]

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 11A, 100 mg, 196 µmol) in N,N-dimethylformamide (1.0 ml, 13 mmol) was treated with HATU (112 mg, 294 µmol) and stirred 1 h at room temperature. 3,3,3-Trifluoropropane-1,2-diamine dihydrochloride (59.1 mg, 294 µmol) was then added followed by and N,N-diisopropylethylamine (170 µl, 980 µmol). The resulting mixture was stirred overnight at room temperature, diluted with methanol and purified by preparative HPLC (Method 4) affording 78.5 mg (65% of th.) of the title compound.

LC-MS (Method 2): $R_t$=1.42 min; MS (ESIpos): m/z=620.1 [M+H]$^+$ $^1$H-NMR (400 MHz, DMSO-d6) δ [ppm]: 9.12-8.62 (m, 3H), 8.12 (dd, 1H), 7.90-7.50 (m, 5H), 6.92 (d, 1H), 5.23-4.94 (m, 2H), 4.41-4.20 (m, 1H), 4.11-3.73 (m, 2H), 3.62-3.13 (m, 2H), 3.35-3.13 (br m, 1H, overlapping with HDO peak), NH$_2$ not visible.

Example 430

3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-[3,3,3-trifluoro-2-hydroxypropyl]pyridine-2-carboxamide (Diastereomeric Mixture)

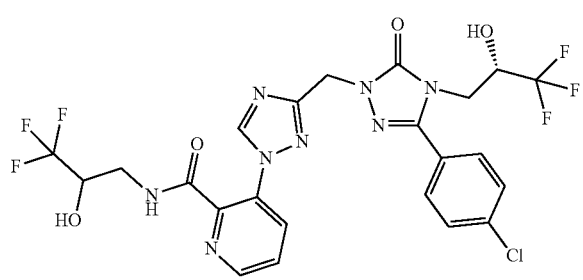 [SMILES: O=C(NCC(O)C(F)(F)F)c1ncccc1-n1cnc(Cn2nc(-c3ccc(Cl)cc3)n(C[C@H](O)C(F)(F)F)c2=O)n1]

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 11, 100 mg, 196 µmol) in N,N-dimethylformamide (1.0 ml, 13 mmol) was treated with HATU (112 mg, 294 µmol) and stirred 1 h at room temperature. 3-Amino-1,1,1-trifluoropropan-2-ol hydrochloride (1:1) (48.7 mg, 294 µmol) was then added followed by and N,N-diisopropylethylamine (140 µl, 780 µmol). The resulting mixture was stirred overnight at room temperature, diluted with methanol and purified by preparative HPLC (Method 4) affording 81.1 mg (67% of th.) of the title compound.

LC-MS (Method 2): $R_t$=1.59 min; MS (ESIpos): m/z=621.1 [M+H]$^+$ $^1$H-NMR (400 MHz, DMSO-d6) δ [ppm]: 9.06-8.60 (m, 3H), 8.11 (dd, 1H), 7.92-7.46 (m, 5H), 6.92 (d, 1H), 6.47 (d, 1H), 5.30-4.94 (m, 2H), 4.43-4.06 (m, 2H), 4.05-3.72 (m, 2H), 3.59-3.44 (m, 1H), 3.39-3.19 (m, 1H, overlapping with HDO peak).

Example 431

3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-cyclopropylpyridine-2-carboxamide

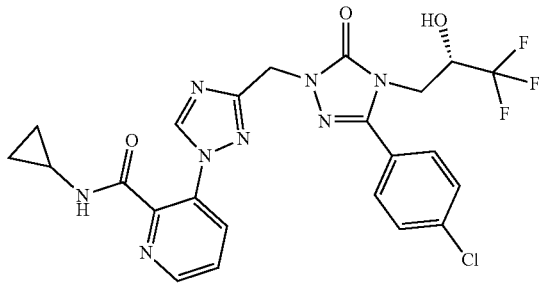 [SMILES: O=C(NC1CC1)c1ncccc1-n1cnc(Cn2nc(-c3ccc(Cl)cc3)n(C[C@H](O)C(F)(F)F)c2=O)n1]

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 11A, 100 mg, 196 µmol) in N,N-dimethylformamide (950 µl, 12 mmol) was treated with HATU (112 mg, 294 µmol) and stirred 1 h at room temperature. Cyclopropanamine (20 µl, 290 µmol) was then added followed by and N,N-diisopropylethylamine (100 µl, 590 µmol). The resulting mixture was stirred overnight at room temperature, diluted with methanol and purified by preparative HPLC (Method 4) affording 66.9 mg (61% of th.) of the title compound.

LC-MS (Method 2): $R_t$=1.54 min; MS (ESIpos): m/z=549.1 [M+H]$^+$ $^1$H-NMR (400 MHz, DMSO-d6) δ [ppm]: 8.84-8.60 (m, 3H), 8.09 (dd, 1H), 7.78-7.50 (m, 5H), 6.93 (d, 1H), 5.09 (s, 2H), 4.40-4.22 (br m, 1H), 4.10-3.72 (m, 2H), 2.81-2.60 (m, 1H), 0.70-0.39 (m, 4H).

Example 432

3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(cyclopropylmethyl)pyridine-2-carboxamide

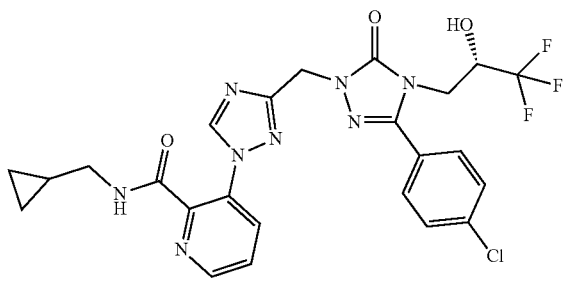 [SMILES: O=C(NCC1CC1)c1ncccc1-n1cnc(Cn2nc(-c3ccc(Cl)cc3)n(C[C@H](O)C(F)(F)F)c2=O)n1]

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 11A, 100 mg, 196 μmol) in N,N-dimethylformamide (1.0 ml, 13 mmol) was treated with HATU (112 mg, 294 μmol) and stirred 1 h at room temperature. 1-Cyclopropylmethanamine (26 μl, 290 μmol) was then added followed by and N,N-diisopropylethylamine (100 μl, 590 μmol). The resulting mixture was stirred overnight at room temperature, diluted with water and purified by preparative HPLC (Method 4) affording 80.2 mg (73% of th.) of the title compound.

LC-MS (Method 2): $R_t$=1.66 min; MS (ESIpos): m/z=563.2 [M+H]$^+$ $^1$H-NMR (400 MHz, DMSO-d6) δ [ppm]: 8.84-8.66 (m, 3H), 8.16-7.99 (m, 1H), 7.85-7.49 (m, 5H), 6.92 (d, 1H), 5.08 (s, 2H), 4.31 (br d, 1H), 4.09-3.75 (m, 2H), 3.03 (t, 2H), 1.03-0.74 (m, 1H), 0.46-0.25 (m, 2H), 0.23-0.05 (m, 2H).

Example 433

1-({3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}carbonyl)-4,4-difluoro-D-prolinamide

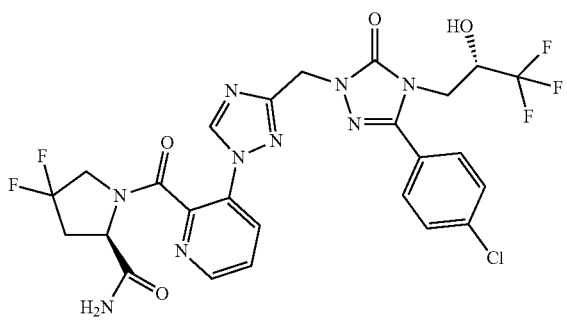 [SMILES: NC(=O)[C@H]1CC(F)(F)CN1C(=O)c1ncccc1-n1cnc(Cn2nc(-c3ccc(Cl)cc3)n(C[C@H](O)C(F)(F)F)c2=O)n1]

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 11A, 100 mg, 196 μmol) in N,N-dimethylformamide (1 ml, 13 mmol) was treated with HATU (112 mg, 294 μmol) and stirred 1 h at room temperature. 4,4-Difluoro-D-prolinamide hydrochloride (1:1) (54.9 mg, 294 μmol) was then added followed by and N,N-diisopropylethylamine (140 μl, 780 μmol). The resulting mixture was stirred overnight at room temperature, diluted with methanol and purified by preparative HPLC (Method 4) affording 91.3 mg (73% of th.) of the title compound.

Mixture of Rotamers

LC-MS (Method 2): $R_t$=1.50 min; MS (ESIpos): m/z=642.1 [M+H]$^+$ $^1$H-NMR (400 MHz, DMSO-d6) δ [ppm]: 9.22-8.93 (2 s, 1H), 8.82-8.54 (m, 1H), 8.37-8.12 (m, 1H), 7.89-7.57 (m, 5H), 7.49 (2 s, 1H), 7.36-7.06 (m, 1H), 6.92 (2 d, 1H), 5.25-5.01 (m, 2H), 5.04-4.57 (m, 1H), 4.4-4.21 (br m, 1H), 4.16-3.71 (m, 4H), 3.10-2.77 (m, 1H), 2.61-2.39 (m, 1H, overlap with DMSO peak).

Example 434

1-({3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}carbonyl)-4,4-difluoro-L-prolinamide

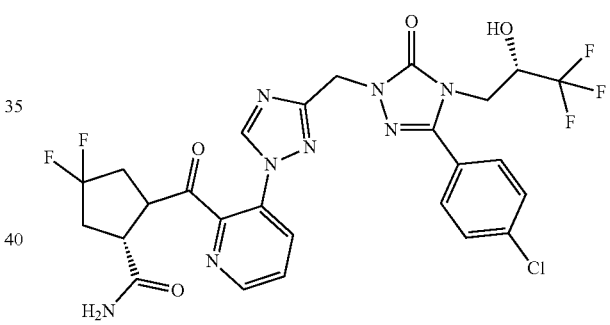

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 11A, 100 mg, 196 μmol) in N,N-dimethylformamide (1 ml, 13 mmol) was treated with HATU (112 mg, 294 μmol) and stirred 1 h at room temperature. 4,4-difluoro-L-prolinamide hydrochloride (1:1) (54.9 mg, 294 μmol) was then added followed by and N,N-diisopropylethylamine (140 μl, 780 μmol). The resulting mixture was stirred overnight at room temperature, diluted with methanol and purified by preparative HPLC (Method 4) affording 86.5 mg (69% of th.) of the title compound.

LC-MS (Method 2): $R_t$=1.49 min; MS (ESIpos): m/z=642.1 [M+H]$^+$ $^1$H-NMR (400 MHz, DMSO-d6) δ [ppm]: 9.20-8.91 (2 s, 1H), 8.77-8.56 (m, 1H), 8.33-8.09 (m, 1H), 7.85-7.56 (m, 5H), 7.56-7.41 (2 s, 1H), 7.37-7.08 (2 s, 1H), 6.92 (2 d, 1H), 5.23-5.04 (m, 2H), 5.02-4.57 (m, 1H), 4.40-4.20 (br m, 1H), 4.15-3.69 (m, 4H), 3.12-2.74 (m, 1H), 2H not visible.

Example 435

3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-[2-fluorocyclopropyl]pyridine-2-carboxamide
(Diastereomeric Mixture Cis Configured)

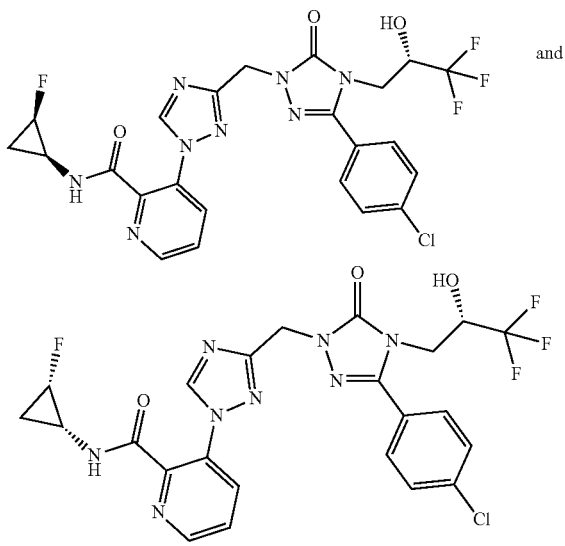

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 11A, 100 mg, 196 μmol) in N,N-dimethylformamide (1.0 ml, 13 mmol) was treated with HATU (112 mg, 294 μmol) and stirred 1 h at room temperature. 2-Fluorocyclopropanamine 4-methylbenzenesulfonate (1:1) (cis configured, 72.8 mg, 294 μmol) was then added followed by and N,N-diisopropylethylamine (140 μl, 780 μmol). The resulting mixture was stirred overnight at room temperature, diluted with methanol and purified by preparative HPLC (Method 4) affording 78.9 mg (68% of th.) of the title compound.

LC-MS (Method 2): $R_t$=1.55 min; MS (ESIpos): m/z=567.1 [M+H]$^+$ $^1$H-NMR (400 MHz, DMSO-d6) δ [ppm]: 8.86 (d, 1H), 8.76-8.68 (m, 2H), 8.11 (dd, 1H), 7.82-7.56 (m, 5H), 6.92 (d, 1H), 5.09 (s, 2H), 4.87-4.53 (m, 1H), 4.40-4.21 (br m, 1H), 4.07-3.78 (m, 2H), 2.81-2.70 (m, 1H), 1.20-0.95 (m, 2H).

Example 436

3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-[2,2-difluorocyclopropyl]pyridine-2-carboxamide
(Diastereomeric Mixture)

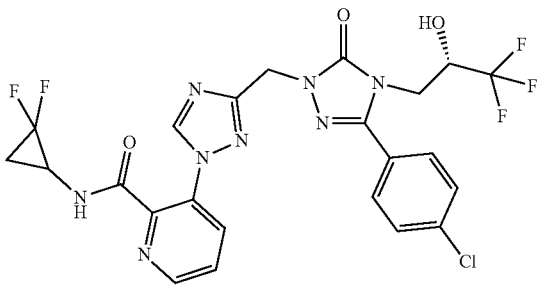 [SMILES: O=C(NC1CC1(F)F)c1ncccc1-n1cnc(Cn2nc(-c3ccc(Cl)cc3)n(C[C@H](O)C(F)(F)F)c2=O)n1]

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 11A, 100 mg, 196 μmol) in N,N-dimethylformamide (1.0 ml, 13 mmol) was treated with HATU (112 mg, 294 μmol) and stirred 1 h at room temperature. 2,2-Difluorocyclopropanamine hydrochloride (1:1) (38.1 mg, 294 μmol) was then added followed by and N,N-diisopropylethylamine (140 μl, 780 μmol). The resulting mixture was stirred overnight at room temperature, diluted with methanol and purified by preparative HPLC (Method 4) affording 15.5 mg (14% of th.) of the title compound.

LC-MS (Method 2): $R_t$=1.66 min; MS (ESIpos): m/z=585.1 [M+H]$^+$ $^1$H-NMR (400 MHz, DMSO-d6) δ [ppm]: 9.16 (br s, 1H), 8.87-8.65 (m, 2H), 8.13 (dd, 1H), 7.87-7.46 (m, 5H), 6.92 (d, 1H), 5.18-4.95 (m, 2H), 4.40-4.21 (br m, 1H), 4.10-3.68 (m, 2H), 3.48-3.30 (m, 1H, overlapping with HDO peak), 2.01-1.53 (m, 2H).

Example 437

5-(4-Chlorophenyl)-2-[(1-{2-[(3,3-difluoropyrrolidin-1-yl)carbonyl]pyridin-3-yl}-1H-1,2,4-triazol-3-yl)methyl]-4-[(2S)-3,3,3-trifluoro-2-hydroxypropyl]-2,4-dihydro-3H-1,2,4-triazol-3-one

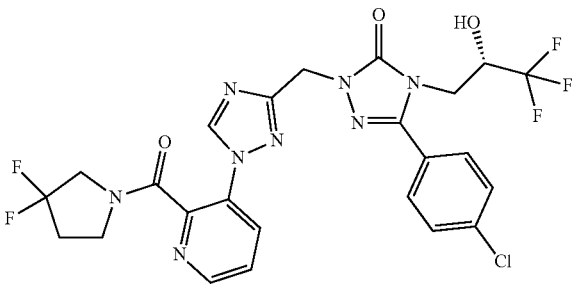 [SMILES: O=C(c1ncccc1-n1cnc(Cn2nc(-c3ccc(Cl)cc3)n(C[C@H](O)C(F)(F)F)c2=O)n1)N1CCC(F)(F)C1]

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 11A, 100 mg, 196 μmol) in N,N-dimethylformamide (1.0 ml, 13 mmol) was treated with HATU (112 mg, 294 μmol) and stirred 1 h at room temperature. 3,3-Difluoropyrrolidine hydrochloride (1:1) (42.2 mg, 294 μmol) was then added followed by and N,N-diisopropylethylamine (140 μl, 780 μmol). The resulting mixture was stirred overnight at room temperature, diluted with water and purified by preparative HPLC (Method 4) affording 69.2 mg (59% of th.) of the title compound as mixture of rotamers.

Rotamer Mixture

LC-MS (Method 2): $R_t$=1.67 min; MS (ESIpos): m/z=599.1 [M+H]$^+$ $^1$H-NMR (400 MHz, DMSO-d6) δ [ppm]: 9.01 (2 s, 1H), 8.70 (2 d, 1H), 8.27 (2 d, 1H), 7.81-7.56 (m, 5H), 6.91 (d, 1H), 5.18-4.95 (m, 2H), 4.40-4.20 (br m, 1H), 4.08-3.93 (m, 1H), 3.91-3.46 (m, 5H), 2.53-2.32 (br m, 2H).

Example 438

5-(4-Chlorophenyl)-2-[(1-{2-[(2,2-dimethylmorpholin-4-yl)carbonyl]pyridin-3-yl}-1H-1,2,4-triazol-3-yl)methyl]-4-[(2S)-3,3,3-trifluoro-2-hydroxypropyl]-2,4-dihydro-3H-1,2,4-triazol-3-one

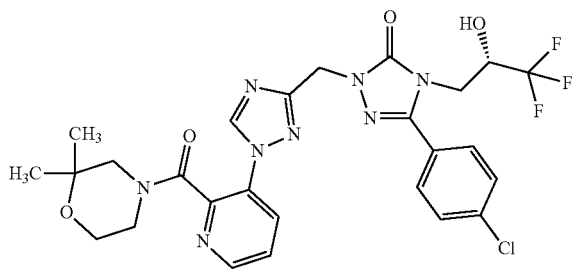 [SMILES: CC1(C)CN(C(=O)c2ncccc2-n2cnc(Cn3nc(-c4ccc(Cl)cc4)n(C[C@H](O)C(F)(F)F)c3=O)n2)CCO1]

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 11A, 100 mg, 196 µmol) in N,N-dimethylformamide (1.0 ml, 13 mmol) was treated with HATU (112 mg, 294 µmol) and stirred 1 h at room temperature. 2,2-Dimethylmorpholine (33.9 mg, 294 µmol) was then added followed by and N,N-diisopropylethylamine (100 µl, 590 µmol). The resulting mixture was stirred overnight at room temperature, diluted with water and purified by preparative HPLC (Method 4) affording 75.1 mg (63% of th.) of the title compound.
Mixture of Rotamers
LC-MS (Method 2): R$_t$=1.61 min; MS (ESIpos): m/z=607.1 [M+H]$^+$
$^1$H-NMR (400 MHz, DMSO-d6) δ [ppm]: 9.04-8.93 (m, 1H), 8.76-8.61 (m, 1H), 8.28-8.17 (m, 1H), 7.83-7.55 (m, 5H), 6.96-6.85 (m, 1H), 5.16-5.01 (m, 2H), 4.41-4.22 (br m, 1H), 4.04-3.78 (m, 2H), 3.63-3.48 (m, 2H), 3.47-3.18 (m, 2H, overlap with HDO peak), 3.13-2.82 (m, 2H), 1.20-0.88 (m, 6H).

Example 439

3-[3-({3-(4-Chlorophenyl)-5-oxo-4-[(2S)-3,3,3-trifluoro-2-hydroxypropyl]-4,5-dihydro-1H-1,2,4-triazol-1-yl}methy)-1H-1,2,4-triazol-1-yl]-N-(3,3-difluorocyclobutyl)pyridine-2-carboxamide

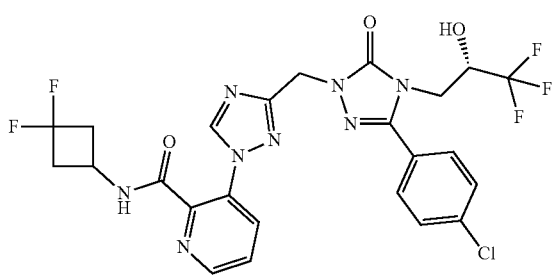 [SMILES: O=C(NC1CC(F)(F)C1)c1ncccc1-n1cnc(Cn2nc(-c3ccc(Cl)cc3)n(C[C@H](O)C(F)(F)F)c2=O)n1]

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 11A, 100 mg, 196 µmol) in N,N-dimethylformamide (1.0 ml, 13 mmol) was treated with HATU (112 mg, 294 µmol) and stirred 1 h at room temperature. 3,3-difluorocyclobutanamine hydrochloride (1:1) (42.2 mg, 294 µmol) was then added followed by and N,N-diisopropylethylamine (140 µl, 780 µmol). The resulting mixture was stirred overnight at room temperature, diluted with water and purified by preparative HPLC (Method 4) affording 66.1 mg (56% of th.) of the title compound.
LC-MS (Method 2): R$_t$=1.69 min; MS (ESIpos): m/z=599.1 [M+H]$^+$
$^1$H-NMR (400 MHz, DMSO-d6) δ [ppm]: 9.22 (d, 1H), 8.91-8.66 (m, 2H), 8.20-8.06 (m, 1H), 7.87-7.53 (m, 5H), 6.92 (d, 1H), 5.08 (s, 2H), 4.40-4.21 (br m, 1H), 4.20-3.72 (m, 3H), 2.98-2.59 (m, 4H).

Example 440

5-(4-Chlorophenyl)-2-{[1-(2-{[2-methylmorpholin-4-yl]carbonyl}pyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Diastereomeric Mixture)

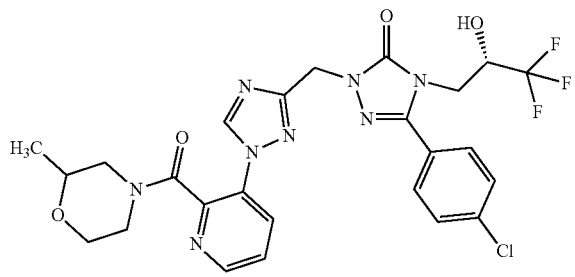 [SMILES: CC1CN(C(=O)c2ncccc2-n2cnc(Cn3nc(-c4ccc(Cl)cc4)n(C[C@H](O)C(F)(F)F)c3=O)n2)CCO1]

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 11A, 100 mg, 196 µmol) in N,N-dimethylformamide (1.0 ml, 13 mmol) was treated with HATU (112 mg, 294 µmol) and stirred 1 h at room temperature. 2-Methylmorpholine (29.8 mg, 294 µmol) was then added followed by and N,N-diisopropylethylamine (100 µl, 590 µmol). The resulting mixture was stirred overnight at room temperature, diluted with water and purified by preparative HPLC (Method 4) affording 61.4 mg (51% of th.) of the title compound as a mixture of rotamers.
LC-MS (Method 2): R$_t$=1.55 min; MS (ESIpos): m/z=593.2 [M+H]$^+$
$^1$H-NMR (400 MHz, DMSO-d6) δ [ppm]: 9.05-8.94 (m, 1H), 8.69 (dd, 1H), 8.28-8.15 (m, 1H), 7.83-7.53 (m, 5H), 6.98-6.85 (m, 1H), 5.22-5.00 (m, 2H), 4.40-3.24 (m, 7H, overlap with HDO peak), 3.23-2.39 (m, 3H, overlap with DMSO peak), 1.10-0.76 (m, 3H).

Example 441

1-({3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}carbonyl)-prolinamide (Diastereomeric Mixture)

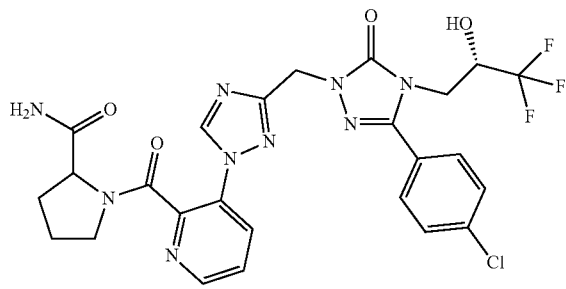 [SMILES: NC(=O)C1CCCN1C(=O)c1ncccc1-n1cnc(Cn2nc(-c3ccc(Cl)cc3)n(C[C@H](O)C(F)(F)F)c2=O)n1]

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 11A, 100 mg, 196 µmol) in N,N-dimethylformamide (1 ml, 13 mmol) was treated with HATU (112 mg, 294 µmol) and stirred 1 h at room temperature. Prolinamide (33.6 mg, 294 µmol) was then added followed by and N,N-diisopropylethylamine (100 µl, 590 µmol). The resulting mixture was stirred overnight at room temperature, diluted with water and purified by preparative HPLC (Method 4) affording 79.1 mg (67% of th.) of the title compound as a mixture of rotamers.

LC-MS (Method 2): $R_t$=1.40 min; MS (ESIpos): m/z=606.2 [M+H]$^+$ $^1$H-NMR (400 MHz, DMSO-d6) δ [ppm]: 9.17-8.96 (m, 1H), 8.78-8.53 (m, 1H), 8.35-8.09 (m, 1H), 7.84-7.54 (m, 5H), 7.46-6.82 (m, 3H), 5.28-4.97 (m, 2H), 4.72-3.34 (m, 6H, overlap with HDO peak), 2.31-2.02 (m, 1H), 1.98-1.68 (m, 3H).

Example 442

5-(4-Chlorophenyl)-2-{[1-(2-{[3-hydroxy-3-(trifluoromethyl)pyrrolidin-1-yl]carbonyl}pyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Diastereomeric Mixture)

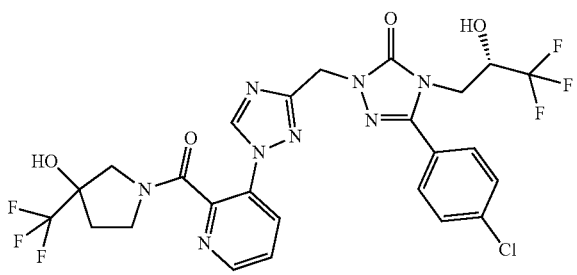 [SMILES: O=C(c1ncccc1-n1cnc(Cn2nc(-c3ccc(Cl)cc3)n(C[C@H](O)C(F)(F)F)c2=O)n1)N1CCC(O)(C(F)(F)F)C1]

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 11A, 100 mg, 196 µmol) in N,N-dimethylformamide (1 ml, 13 mmol) was treated with HATU (112 mg, 294 µmol) and stirred 1 h at room temperature. 3-(Trifluoromethyl)pyrrolidin-3-ol hydrochloride (1:1) (56.4 mg, 294 µmol) was then added followed by and N,N-diisopropylethylamine (140 µl. 780 µmol). The resulting mixture was stirred overnight at room temperature, diluted with water and purified by preparative HPLC (Method 4) affording 68.5 mg (54% of th.) of the title compound.

LC-MS (Method 2): $R_t$=1.64 min; MS (ESIpos): m/z=647.1 [M+H]$^+$ $^1$H-NMR (400 MHz, DMSO-d6) δ [ppm]: 9.05-8.84 (m, 1H), 8.71 (d, 1H), 8.24 (t, 1H), 7.82-7.50 (m, 5H), 6.91 (br d, 1H), 6.57 (s, 1H), 5.16-4.94 (m, 2H), 4.40-421 (br m, 1H), 4.13-3.37 (m, 6H), 2.29-1.85 (m, 2H).

Example 443

4-({3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridin-2-yl}carbonyl)piperazin-2-one

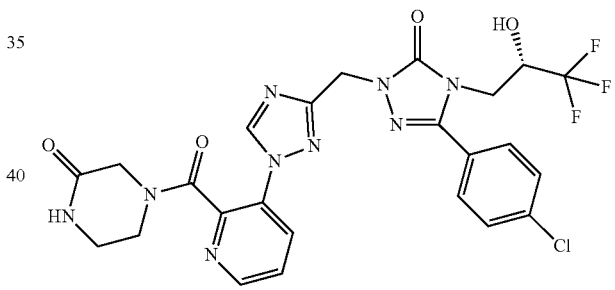

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 11A, 100 mg, 196 µmol) in N,N-dimethylformamide (1 ml, 13 mmol) was treated with HATU (112 mg, 294 µmol) and stirred 1 h at room temperature. Piperazin-2-one (29.5 mg, 294 µmol) was then added followed by and N,N-diisopropylethylamine (100 µl, 590 µmol). The resulting mixture was stirred overnight at room temperature, diluted with water and purified by preparative HPLC (Method 4) affording 40.4 mg (35% of th.) of the title compound as mixture of rotamers.

LC-MS (Method 2): $R_t$=1.28 min; MS (ESIpos): m/z=592.1 [M+H]$^+$ $^1$H-NMR (400 MHz, DMSO-d6) δ [ppm]: 9.06 (s, 1H), 8.75-8.60 (m, 1H), 8.36-8.01 (m, 2H), 7.86-7.51 (m, 5H), 6.90 (2 d, 1H), 5.20-4.95 (m, 2H), 4.40-4.20 (br m, 1H), 4.13-3.56 (m, 5H), 3.41-2.98 (m, 3H, overlap with HDO peak).

Example 444

5-(4-Chlorophenyl)-4-[(2S)-3,3,3-trifluoro-2-hydroxypropyl]-2-{[1-(2-{[2-(trifluoromethyl)morpholin-4-yl]carbonyl}pyridin-3-yl)-1H-1,2,4-triazol-3-yl]methyl}-2,4-dihydro-3H-1,2,4-triazol-3-one (Diastereomeric Mixture)

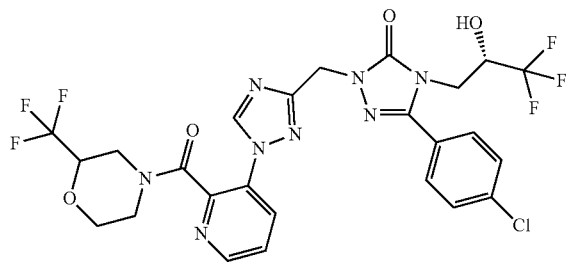 [SMILES: O=C(c1ncccc1-n1cnc(Cn2nc(-c3ccc(Cl)cc3)n(C[C@H](O)C(F)(F)F)c2=O)n1)N1CCOC(C(F)(F)F)C1]

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 11A, 100 mg, 196 μmol) in N,N-dimethylformamide (1 ml, 13 mmol) was treated with HATU (112 mg, 294 μmol) and stirred 1 h at room temperature. 2-(Trifluoromethyl)morpholine hydrochloride (1:1) (56.4 mg, 294 μmol) was then added followed by and N,N-diisopropylethylamine (140 μl, 780 μmol). The resulting mixture was stirred overnight at room temperature, diluted with water and purified by preparative HPLC (Method 4) affording 74.0 mg (58% of th.) of the title compound.

LC-MS (Method 2): $R_t$=1.78 min; MS (ESIpos): m/z=647.1 [M+H]$^+$ $^1$H-NMR (400 MHz, DMSO-d6) δ [ppm]: 9.07 (s, 1H), 8.82-8.62 (m, 1H), 8.45-8.14 (m, 1H), 7.86-7.47 (m, 5H), 7.03-6.75 (m, 1H), 5.30-4.94 (m, 2H), 4.52-2.82 (m, 10H, overlap with HDO peak).

Example 445

5-(4-Chlorophenyl)-2-({1-[2-(piperidin-1-ylcarbonyl)pyridin-3-yl]-1H-1,2,4-triazol-3-yl}methyl)-4-[(2S)-3,3,3-trifluoro-2-hydroxypropyl]-2,4-dihydro-3H-1,2,4-triazol-3-one

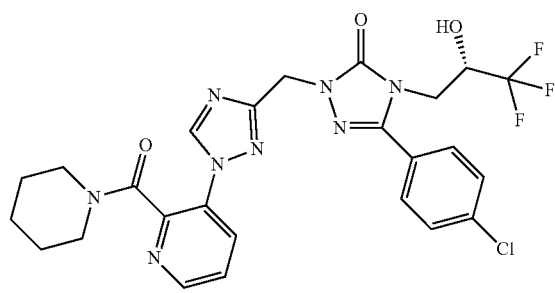 [SMILES: O=C(c1ncccc1-n1cnc(Cn2nc(-c3ccc(Cl)cc3)n(C[C@H](O)C(F)(F)F)c2=O)n1)N1CCCCC1]

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 11A, 100 mg, 196 μmol) in N,N-dimethylformamide (1 ml, 13 mmol) was treated with HATU (112 mg, 294 μmol) and stirred 1 h at room temperature. Piperidine (29 μl, 290 μmol) was then added followed by and N,N-diisopropylethylamine (100 μl, 590 μmol). The resulting mixture was stirred overnight at room temperature, diluted with water and purified by preparative HPLC (Method 4) affording 61.3 mg (54% of th.) of the title compound.

LC-MS (Method 2): $R_t$=1.68 min: MS (ESIpos): m/z=577.2 [M+H]$^+$ $^1$H-NMR (400 MHz, DMSO-d6) δ [ppm]: 8.90 (s, 1H), 8.68 (dd, 1H), 8.19 (dd, 1H), 7.87-7.51 (m, 5H), 6.91 (d, 1H), 5.09 (s, 2H), 4.40-4.19 (br m, 1H), 4.13-3.71 (m, 2H), 3.54-3.38 (br m, 2H), 3.10-2.92 (m, 2H), 1.55-1.19 (m, 6H).

Example 446

5-(4-Chlorophenyl)-2-({1-[2-(morpholin-4-ylcarbonyl)pyridin-3-yl]-1H-1,2,4-triazol-3-yl}methyl)-4-[(2S)-3,3,3-trifluoro-2-hydroxypropyl]-2,4-dihydro-3H-1,2,4-triazol-3-one

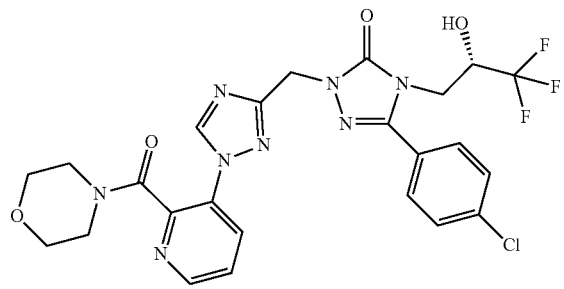 [SMILES: O=C(c1ncccc1-n1cnc(Cn2nc(-c3ccc(Cl)cc3)n(C[C@H](O)C(F)(F)F)c2=O)n1)N1CCOCC1]

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 11A, 100 mg, 196 μmol) in N,N-dimethylformamide (1 ml, 13 mmol) was treated with HATU (112 mg, 294 μmol) and stirred 1 h at room temperature. Morpholine (26 μl, 290 μmol) was then added followed by and N,N-diisopropylethylamine (100 μl, 590 μmol). The resulting mixture was stirred overnight at room temperature, diluted with water and purified by preparative HPLC (Method 4) affording 67.0 mg (59% of th.) of the title compound.

LC-MS (Method 2): $R_t$=1.47 min; MS (ESIpos): m/z=579.1 [M+H]$^+$ $^1$H-NMR (400 MHz, DMSO-d6) δ [ppm]: 9.00 (s, 1H), 8.69 (dd, 1H), 8.33-8.16 (m, 1H), 7.88-7.48 (m, 5H), 6.90 (d, 1H), 5.20-5.02 (m, 2H), 4.40-4.22 (br m, 1H), 4.13-3.75 (m, 2H), 3.66-3.38 (m, 6H), 3.12 (t, 2H).

Example 447

3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-[1-(trifluoromethyl)cyclopropyl]pyridine-2-carboxamide

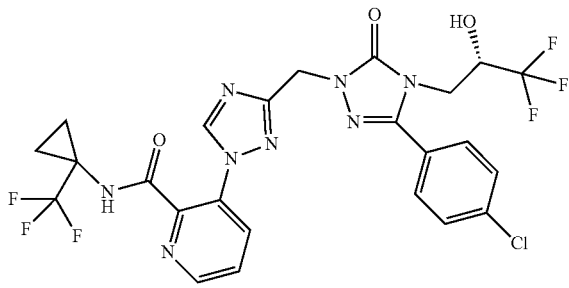 [SMILES: O=C(NC1(C(F)(F)F)CC1)c1ncccc1-n1cnc(Cn2nc(-c3ccc(Cl)cc3)n(C[C@H](O)C(F)(F)F)c2=O)n1]

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 11A, 100 mg, 196 µmol) in N,N-dimethylformamide (1 ml, 13 mmol) was treated with HATU (112 mg, 294 µmol) and stirred 1 h at room temperature. 1-(Trifluoromethyl)cyclopropanaminium chloride (47.5 mg, 294 µmol) was then added followed by and N,N-diisopropylethylamine (100 µl, 590 µmol). The resulting mixture was stirred overnight at room temperature, diluted with water and purified by preparative HPLC (Method 4) affording 65.5 mg (54% of th.) of the title compound.

LC-MS (Method 2): $R_t$=1.79 min; MS (ESIpos): m/z=617.1 [M+H]$^+$ $^1$H-NMR (400 MHz, DMSO-d6) δ [ppm]: 9.38 (s, 1H), 8.95-8.61 (m, 2H), 8.15 (dd, 1H), 7.89-7.41 (m, 5H), 6.92 (d, 1H), 5.06 (s, 2H), 4.40-4.21 (br m, 1H), 4.14-3.69 (m, 2H), 1.35-0.84 (m, 4H).

Example 448

5-(4-Chlorophenyl)-4-[(2S)-3,3,3-trifluoro-2-hydroxypropyl]-2-{[1-(2-{[3-(trifluoromethyl)piperazin-1-yl]carbonyl}pyridin-3-yl)-1H-1,2,4-triazol-3-yl]methyl}-2,4-dihydro-3H-1,2,4-triazol-3-one
(Diastereomeric Mixture)

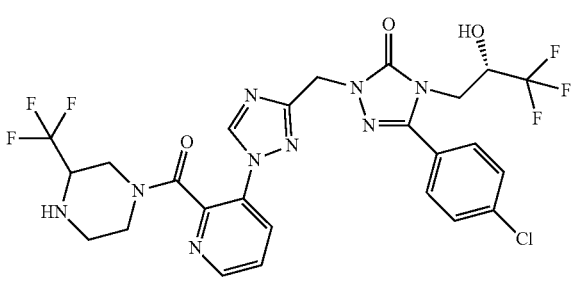 [SMILES: O=C(c1ncccc1-n1cnc(Cn2nc(-c3ccc(Cl)cc3)n(C[C@H](O)C(F)(F)F)c2=O)n1)N1CCNC(C(F)(F)F)C1]

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 11A, 100 mg, 196 µmol) in N,N-dimethylformamide (1 ml, 13 mmol) was treated with HATU (112 mg, 294 µmol) and stirred 1 h at room temperature. 2-(Trifluoromethyl)piperazine (45.3 mg, 294 µmol) was then added followed by and N,N-diisopropylethylamine (100 µl, 590 µmol). The resulting mixture was stirred overnight at room temperature, diluted with water and purified by preparative HPLC (Method 4) affording 72.2 mg (54% of th.) of the title compound as a mixture of rotamers.

LC-MS (Method 2): $R_t$=1.61 min; MS (ESIpos): m/z=646.1 [M+H]$^+$ $^1$H-NMR (400 MHz, DMSO-d6) δ [ppm]: 9.07-8.96 (m, 1H), 8.81-8.62 (m, 1H), 8.35-8.14 (m, 1H), 7.87-7.49 (m, 5H), 7.03-6.83 (m, 1H), 5.23-4.99 (m, 2H), 4.48-3.69 (m, 4H), 3.59-2.39 (m, 7H, overlap with HDO peak and DMSO peak).

Example 449

5-(4-Chlorophenyl)-4-[(2S)-3,3,3-trifluoro-2-hydroxypropyl]-2-{[1-(2-{[3-(trifluoromethyl)pyrrolidin-1-yl]carbonyl}pyridin-3-yl)-1H-1,2,4-triazol-3-yl]methyl}-2,4-dihydro-3H-1,2,4-triazol-3-one
(Diastereomeric Mixture)

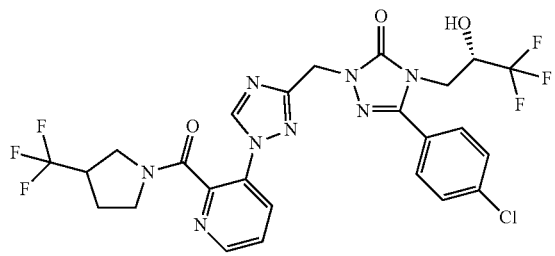 [SMILES: O=C(c1ncccc1-n1cnc(Cn2nc(-c3ccc(Cl)cc3)n(C[C@H](O)C(F)(F)F)c2=O)n1)N1CCC(C(F)(F)F)C1]

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 11A, 100 mg, 196 µmol) in N,N-dimethylformamide (1 ml, 13 mmol) was treated with HATU (112 mg, 294 µmol) and stirred 1 h at room temperature. Trifluoromethyl)pyrrolidine (40.9 mg, 294 µmol) was then added followed by and N,N-diisopropylethylamine (100 µl, 590 µmol). The resulting mixture was stirred overnight at room temperature, diluted with water and purified by preparative HPLC (Method 4) affording 66.8 mg (54% of th.) of the title compound.

LC-MS (Method 2): $R_t$=1.80 min; MS (ESIpos): m/z=631 [M+H]$^+$ $^1$H-NMR (400 MHz, DMSO-d6) δ [ppm]: 8.97 (s, 1H), 8.74-8.66 (m, 1H), 8.24 (d, 1H), 7.82-7.53 (m, 5H), 6.91 (d, 1H), 5.16-4.96 (m, 2H), 4.30 (br d, 1H), 4.10-3.09 (m, 7H, overlap with HDO peak), 2.25-1.88 (m, 2H).

Example 450

5-(4-Chlorophenyl)-4-[(2S)-3,3,3-trifluoro-2-hydroxypropyl]-2-{[1-(2-{[(2S)-2-(trifluoromethyl)pyrrolidin-1-yl]carbonyl}pyridin-3-yl)-1H-1,2,4-triazol-3-yl]methyl}-2,4-dihydro-3H-1,2,4-triazol-3-one

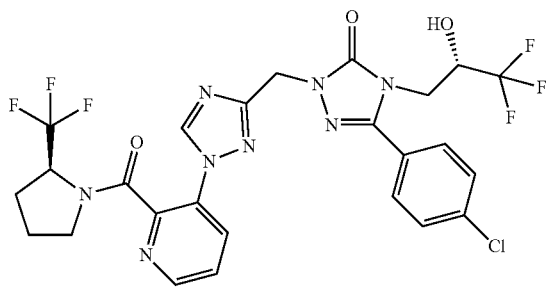 [SMILES: O=C(c1ncccc1-n1cnc(Cn2nc(-c3ccc(Cl)cc3)n(C[C@H](O)C(F)(F)F)c2=O)n1)N1CCC[C@H]1C(F)(F)F]

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 11A, 100 mg, 196 µmol) in N,N-dimethylformamide (1 ml, 13 mmol) was treated with HATU (112 mg, 294 µmol) and stirred 1 h at room temperature. (2S)-2-(Trifluoromethyl)pyrrolidine (40.9 mg, 294 µmol) was then added followed by and N,N-diisopropylethylamine (100 µl, 590 µmol). The resulting mixture was stirred overnight at room temperature, diluted with water and purified by preparative HPLC (Method 4) affording 71.4 mg (58% of th.) of the title compound.

LC-MS (Method 2): $R_t$=1.87 min; MS (ESIpos): m/z=631.1 [M+H]$^+$ $^1$H-NMR (400 MHz, DMSO-d6) δ [ppm]: 9.05 (s, 1H), 8.79-8.60 (m, 1H), 8.29 (d, 1H), 7.89-7.52 (m, 5H), 6.91 (d, 1H), 5.18-4.94 (m, 2H), 4.90-4.68 (br m, 1H), 4.40-4.20 (br m, 1H), 4.07-3.75 (m, 2H), 3.51-3.30 (m, 1H, overlap with HDO peak), 2.39-1.74 (m, 5H).

Example 451

5-(4-Chlorophenyl)-4-[(2S)-3,3,3-trifluoro-2-hydroxypropyl]-2-{[1-(2-{[(2R)-2-(trifluoromethyl)pyrrolidin-1-yl]carbonyl}pyridin-3-yl)-1H-1,2,4-triazol-3-yl]methyl}-2,4-dihydro-3H-1,2,4-triazol-3-one

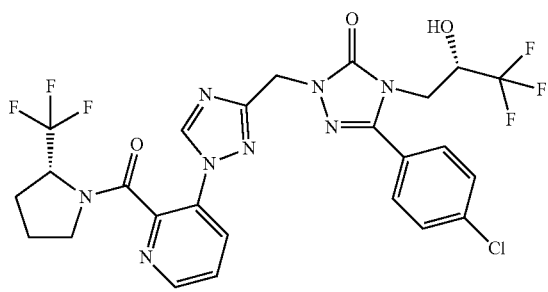 [SMILES: O=C(c1ncccc1-n1cnc(Cn2nc(-c3ccc(Cl)cc3)n(C[C@H](O)C(F)(F)F)c2=O)n1)N1CCC[C@@H]1C(F)(F)F]

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 11A, 100 mg, 196 µmol) in N,N-dimethylformamide (1 ml, 13 mmol) was treated with HATU (112 mg, 294 µmol) and stirred 1 h at room temperature. (2R)-2-(Trifluoromethyl)pyrrolidine (40.9 mg, 294 µmol) was then added followed by and N,N-diisopropylethylamine (100 µl. 590 µmol). The resulting mixture was stirred overnight at room temperature, diluted with water and purified by preparative HPLC (Method 4) affording 67.6 mg (55% of th.) of the title compound.

LC-MS (Method 2): $R_t$=1.87 min; MS (ESIpos): m/z=631.1 [M+H]$^+$ $^1$H-NMR (400 MHz, DMSO-d6) δ [ppm]: 9.13-8.99 (m, 1H), 8.80-8.59 (m, 1H), 8.29 (dd, 1H), 7.86-7.52 (m, 5H), 6.98-6.82 (m, 1H), 5.20-4.97 (m, 2H), 4.95-4.78 (m, 1H), 4.29 (br d, 1H), 4.06-3.77 (m, 2H), 3.50-3.31 (m, 3H), 2.33-2.14 (m, 1H), 2.04-1.70 (m, 3H).

Example 452

5-(4-Chlorophenyl)-2-[(1-{2-[(1,1-dioxidothiomorpholin-4-yl)carbonyl]pyridin-3-yl}-1H-1,2,4-triazol-3-yl)methyl]-4-[(2S)-3,3,3-trifluoro-2-hydroxypropyl]-2,4-dihydro-3H-1,2,4-triazol-3-one

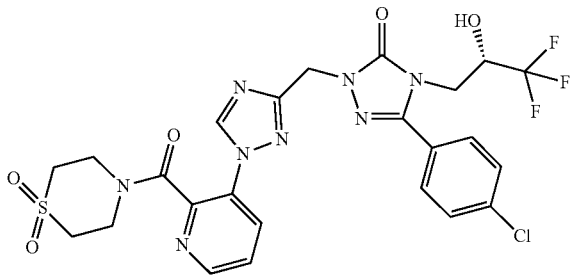 [SMILES: O=C(c1ncccc1-n1cnc(Cn2nc(-c3ccc(Cl)cc3)n(C[C@H](O)C(F)(F)F)c2=O)n1)N1CCS(=O)(=O)CC1]

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 11A, 100 mg, 196 µmol) in N,N-dimethylformamide (1 ml, 13 mmol) was treated with HATU (112 mg, 294 µmol) and stirred 1 h at room temperature. Thiomorpholine 1,1-dioxide (39.8 mg, 294 µmol) was then added followed by and N,N-diisopropylethylamine (100 µl, 590 µmol). The resulting mixture was stirred overnight at room temperature, diluted with water and purified by preparative HPLC (Method 4) affording 59.0 mg (48% of th.) of the title compound.

LC-MS (Method 2): $R_t$=1.49 min; MS (ESIpos): m/z=627.1 [M+H]$^+$ $^1$H-NMR (400 MHz, DMSO-d6) δ [ppm]: 9.20-9.03 (m, 1H), 8.71 (d, 1H), 8.30 (d, 1H), 7.82-7.53 (m, 5H), 6.92 (d, 1H), 5.23-4.92 (m, 2H), 4.40-4.21 (br m, 1H), 4.12-3.63 (m, 6H), 3.48-3.20 (m, 4H, overlap with HDO peak).

Example 453

5-(4-Chlorophenyl)-2-[(1-{2-[(2,2-dimethylpiper-azin-1-yl)carbonyl]pyridin-3-yl}-1H-1,2,4-triazol-3-yl)methyl]-4-[(2S)-3,3,3-trifluoro-2-hydroxypropyl]-2,4-dihydro-3H-1,2,4-triazol-3-one-Hydrochloric Acid Salt

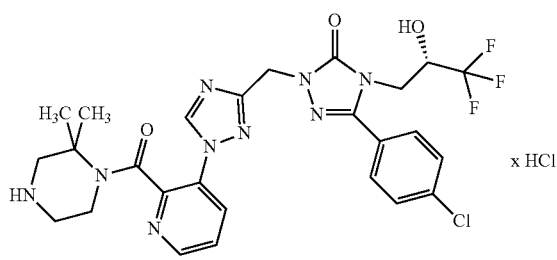 [SMILES: CC1(C)CNCCN1C(=O)c1ncccc1-n1cnc(Cn2nc(-c3ccc(Cl)cc3)n(C[C@H](O)C(F)(F)F)c2=O)n1]

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 11A, 100 mg, 196 µmol) in N,N-dimethylformamide (1 ml, 13 mmol) was treated with HATU (112 mg, 294 µmol) and stirred 1 h at room temperature. 2,2-Dimethylpiperazine (33.6 mg, 294 µmol) was then added followed by and N,N-diisopropylethylamine (100 µl, 590 µmol). The resulting mixture was stirred overnight at room temperature, diluted with water and purified by preparative HPLC (Method 4) affording 72.0 mg (61% of th.) of the title compound.

LC-MS (Method 2): $R_t$=1.07 min; MS (ESIpos): m/z=606.2 [M+H]$^+$ $^1$H-NMR (400 MHz, DMSO-d6) δ [ppm]: 9.23-8.56 (m, 4H), 8.37-8.19 (m, 1H), 7.85-7.51 (m, 5H), 6.92 (br d, 1H), 5.21-4.92 (m, 2H), 4.40-4.18 (br m, 1H), 4.11-3.08 (m, 8H, overlap with HDO peak), 1.49-1.12 (m, 6H).

Example 454

3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(cyclopropylmethyl)-N-methylpyridine-2-carboxamide

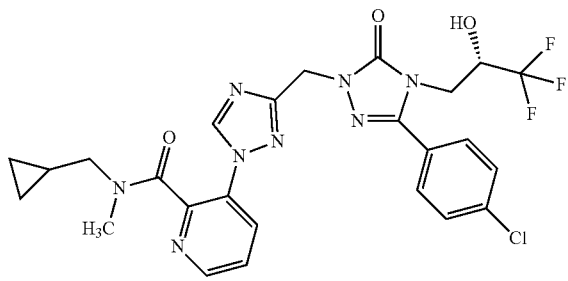 [SMILES: CN(CC1CC1)C(=O)c1ncccc1-n1cnc(Cn2nc(-c3ccc(Cl)cc3)n(C[C@H](O)C(F)(F)F)c2=O)n1]

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 11A, 100 mg, 196 µmol) in N,N-dimethylformamide (1 ml, 13 mmol) was treated with HATU (112 mg, 294 µmol) and stirred 1 h at room temperature. 1-Cyclopropyl-N-methylmethanamine (25.1 mg, 294 µmol) was then added followed by and N,N-diisopropylethylamine (100 µl, 590 µmol). The resulting mixture was stirred overnight at room temperature, diluted with water and purified by preparative HPLC (Method 4) affording 56.8 mg (50% of th.) of the title compound.

LC-MS (Method 2): $R_t$=1.73 min; MS (ESIpos): m/z=577.2 [M+H]$^+$ $^1$H-NMR (400 MHz, DMSO-d6) δ [ppm]: 9.01-8.54 (m, 2H), 8.20 (d, 1H), 7.86-7.43 (m, 5H), 6.90 (d, 1H), 5.08 (d, 2H), 4.40-4.20 (br m, 1H), 4.11-3.69 (m, 2H), 3.50-2.26 (m, 6H, overlap with HDO peak and DMSO peak), 1.06-0.73 (m, 1H), 0.53-0.24 (m, 2H), 0.13 (q, 1H).

Example 455

3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(1-methylcyclopropyl)pyridine-2-carboxamide

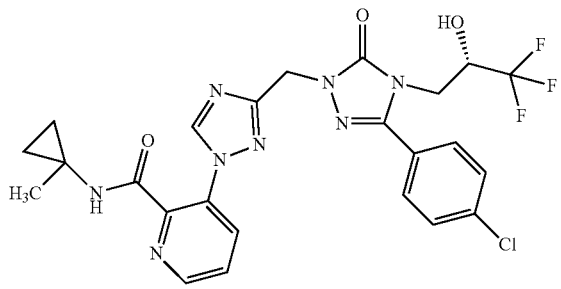 [SMILES: CC1(NC(=O)c2ncccc2-n2cnc(Cn3nc(-c4ccc(Cl)cc4)n(C[C@H](O)C(F)(F)F)c3=O)n2)CC1]

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 11A, 100 mg, 196 µmol) in N,N-dimethylformamide (1 ml, 13 mmol) was treated with HATU (112 mg, 294 µmol) and stirred 1 h at room temperature. 1-Methylcyclopropanamine (20.9 mg, 294 µmol) was then added followed by and N,N-diisopropylethylamine (100 µl, 590 µmol). The resulting mixture was stirred overnight at room temperature, diluted with water and purified by preparative HPLC (Method 4) affording 53.6 mg (49% of th.) of the title compound.

LC-MS (Method 2): $R_t$=1.67 min; MS (ESIpos): m/z=563.2 [M+H]$^+$ $^1$H-NMR (400 MHz, DMSO-d6) δ [ppm]: 8.92-8.54 (m, 3H), 8.09 (d, 1H), 7.88-7.50 (m, 5H), 6.92 (d, 1H), 5.21-4.96 (m, 2H), 4.40-4.21 (br m, 1H), 4.11-3.65 (m, 2H), 1.27 (s, 3H), 0.76-0.41 (m, 4H).

Example 456

3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-[2-fluorocyclopropyl]pyridine-2-carboxamide
(Diastereomeric Mixture Cis Configured)

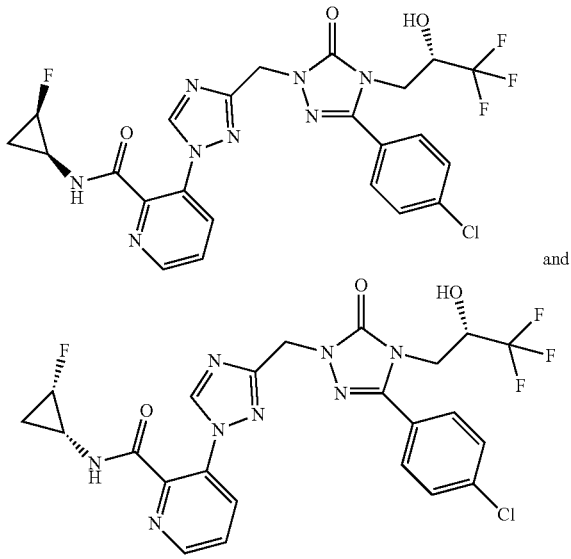

and

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 11A, 100 mg, 196 µmol) in N,N-dimethylformamide (1 ml, 13 mmol) was treated with HATU (112 mg, 294 µmol) and stirred 1 h at room temperature. 2-Fluorocyclopropanamine (cis configured, 22.1 mg, 294 µmol) was then added followed by and N,N-diisopropylethylamine (100 µl, 590 µmol). The resulting mixture was stirred overnight at room temperature, diluted with water and purified by preparative HPLC (Method 4) affording 14.3 mg (13% of th.) of the title compound.

LC-MS (Method 2): $R_t$=1.60 min; MS (ESIpos): m/z=567.1 [M+H]$^+$ $^1$H-NMR (400 MHz, DMSO-d6) δ [ppm]: 9.01-8.61 (m, 3H), 8.11 (dd, 1H), 7.82-7.50 (m, 5H), 6.92 (d, 1H), 5.09 (s, 2H), 4.90-4.53 (m, 1H), 4.40-4.21 (br m, 1H), 4.08-3.75 (m, 2H), 2.87-2.66 (m, 1H), 1.25-0.91 (m, 2H).

Example 457

3-[3-({3-(4-Chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]-N-(2,2,2-trifluoroethyl)pyridine-2-carboxamide

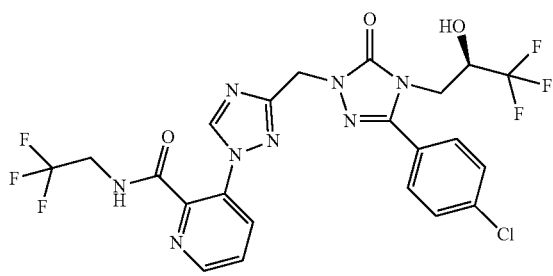 [SMILES: O=C(NCC(F)(F)F)c1ncccc1-n1cnc(Cn2nc(-c3ccc(Cl)cc3)n(C[C@@H](O)C(F)(F)F)c2=O)n1]

A solution of 3-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 12A, 100 mg, 196 µmol) in N,N-dimethylformamide (1.0 ml, 13 mmol) was treated with HATU (112 mg, 294 µmol) and stirred 1 h at room temperature. 2,2,2-Trifluoroethanamine (24 µl, 290 µmol) was then added followed by and N,N-diisopropylethylamine (100 µl, 590 µmol). The resulting mixture was stirred overnight at room temperature, diluted with water and purified by preparative HPLC (Method 4) affording 37.6 mg (32% of th.) of the title compound.

LC-MS (Method 2): $R_t$=1.73 min: MS (ESIpos): m/z=591.1 [M+H]$^+$ $^1$H-NMR (400 MHz, DMSO-d6) δ [ppm]: 9.34 (t, 1H), 8.91-8.68 (m, 2H), 8.15 (dd, 1H), 7.88-7.52 (m, 5H), 6.92 (d, 1H), 5.08 (s, 2H), 4.46-4.15 (m, 1H), 4.09-3.72 (m, 4H).

Example 458

3-[3-({3-(4-Chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]-N-cyclopropylpyridine-2-carboxamide

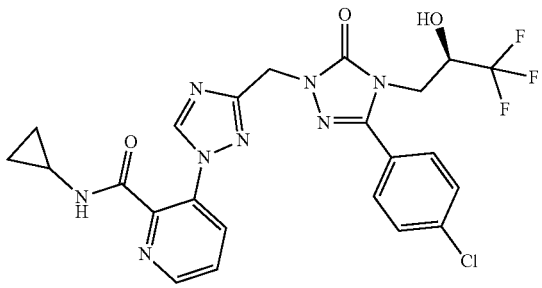

A solution of 3-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 12A, 100 mg, 196 µmol) in N,N-dimethylformamide (950 µl, 12 mmol) was treated with HATU (112 mg, 294 µmol) and stirred 1 h at room temperature. Cyclopropanamine (20 µl, 290 µmol) was then added followed by and N,N-diisopropylethylamine (100 µl, 590 µmol). The resulting mixture was stirred overnight at room temperature, diluted with water and purified by preparative HPLC (Method 4) affording 38.1 mg (32% of th.) of the title compound.

LC-MS (Method 2): $R_t$=1.59 min; MS (ESIpos): m/z=549.1 [M+H]$^+$ $^1$H-NMR (400 MHz, DMSO-d6) δ [ppm]: 8.90-8.60 (m, 3H), 8.09 (dd, 1H), 7.84-7.46 (m, 5H), 6.93 (d, 1H), 5.09 (s, 2H), 4.40-4.22 (br m, 1H), 4.08-3.73 (m, 2H), 2.81-2.62 (m, 1H), 0.72-0.36 (m, 4H).

Example 459

3-[3-({3-(4-Chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]-N-(cyclopropylmethyl)pyridine-2-carboxamide

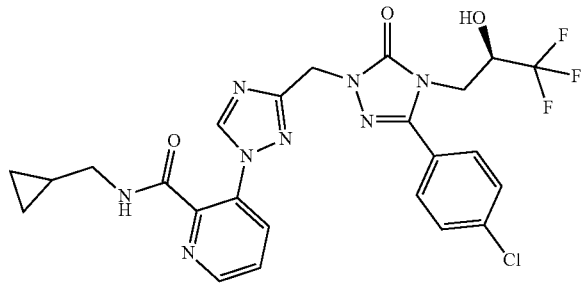

A solution of 3-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 12 A, 100 mg, 196 µmol) in N,N-dimethylformamide (1.0 ml, 13 mmol) was treated with HATU (112 mg, 294 µmol) and stirred 1 h at room temperature. 1-Cyclopropylmethanamine (26 µl, 290 µmol) was then added followed by and N,N-diisopropylethylamine (100 µl, 590 µmol). The resulting mixture was stirred overnight at room temperature, diluted with water and purified by preparative HPLC (Method 4) affording 30.4 mg (28% of th.) of the title compound.

LC-MS (Method 2): $R_t$=1.70 min; MS (ESIpos): m/z=563.2 [M+H]$^+$ $^1$H-NMR (400 MHz, DMSO-d6) δ [ppm]: 8.91-8.61 (m, 3H), 8.09 (dd, 1H), 7.89-7.48 (m, 5H), 6.92 (d, 1H), 5.08 (s, 2H), 4.40-4.21 (br m, 1H), 4.10-3.70 (m, 2H), 3.03 (t, 2H), 1.06-0.80 (m, 1H), 0.48-0.05 (m, 4H).

Example 460

3-[3-({3-(4-Chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]-N-[2,2-difluorocyclopropyl]pyridine-2-carboxamide
(Diastereomeric Mixture)

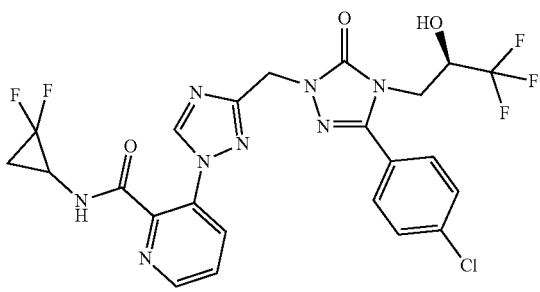

A solution of 3-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 12A, 100 mg, 196 µmol) in N,N-dimethylformamide (1.0 ml, 13 mmol) was treated with HATU (112 mg, 294 µmol) and stirred 1 h at room temperature. 2,2-Difluorocyclopropanamine hydrochloride (1:1) (38.1 mg, 294 µmol) was then added followed by and N,N-diisopropylethylamine (140 µl, 780 µmol). The resulting mixture was stirred overnight at room temperature, diluted with water and purified by preparative HPLC (Method 4) affording 23.1 mg (20% of th.) of the title compound.

LC-MS (Method 2): $R_t$=1.69 min; MS (ESIpos): m/z=585.1 [M+H]$^+$ $^1$H-NMR (400 MHz, DMSO-d6) δ [ppm]: 9.16 (br s, 1H), 8.89-8.63 (m, 2H), 8.13 (dd, 1H), 7.92-7.52 (m, 5H), 6.92 (d, 1H), 5.25-4.93 (m, 2H), 4.40-4.21 (br m, 1H), 4.15-3.70 (m, 2H), 3.50-3.20 (br m, 1H, overlapping with HDO peak), 2.04-1.52 (m 2H).

Example 461

1-({3-[3-({3-(4-Chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridin-2-yl}carbonyl)-4,4-difluoro-L-prolinamide

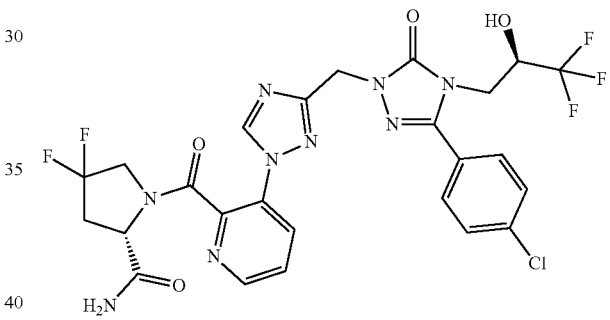

A solution of 3-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 12A, 100 mg, 196 µmol) in N,N-dimethylformamide (1 ml, 13 mmol) was treated with HATU (112 mg, 294 µmol) and stirred 1 h at room temperature. 4,4-Difluoro-L-prolinamide hydrochloride (1:1) (54.9 mg, 294 µmol) was then added followed by and N,N-diisopropylethylamine (140 µl, 780 µmol). The resulting mixture was stirred overnight at room temperature, diluted with water and purified by preparative HPLC (Method 4) affording 35.4 mg (26% of th.) of the title compound.

Mixture of Rotamers

LC-MS (Method 2): $R_t$=1.55 min; MS (ESIpos): m/z=642.1 [M+H]$^+$ $^1$H-NMR (400 MHz, DMSO-d6) δ [ppm]: 9.14-8.99 (2 s, 1H), 8.73-8.61 (m, 1H), 8.30-8.16 (m, 1H), 7.79-7.58 (m, 5H), 7.55-7.08 (4 s, 2H), 6.92 (2 d, 1H), 5.18-5.04 (m, 2H), 5.02-4.60 (m, 1H), 4.39-4.20 (br m, 1H), 4.16-3.59 (m, 4H), 3.08-2.76 (m, 1H), 2.59-2.41 (m, 1H, overlap with DMSO peak).

Example 462

3-[3-({3-(4-Chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]-N-[2-fluorocyclopropyl]pyridine-2-carboxamide
(Diastereomeric Mixture Cis Configured)

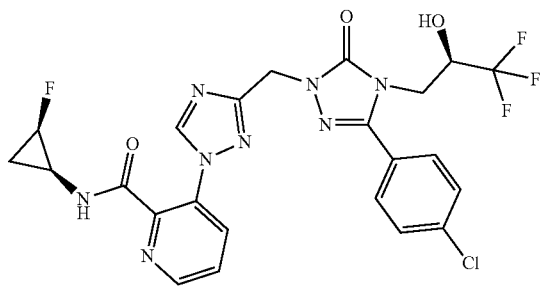

and

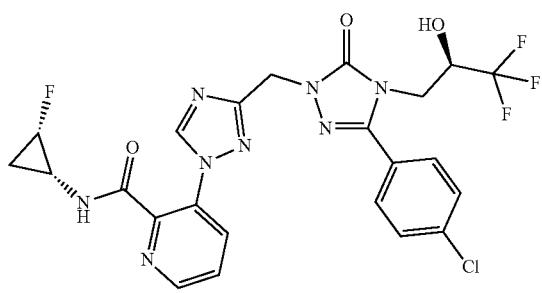

A solution of 3-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 12A, 100 mg, 196 µmol) in N,N-dimethylformamide (1.0 ml, 13 mmol) was treated with HATU (112 mg, 294 µmol) and stirred 1 h at room temperature. 2-Fluorocyclopropanamine 4-methylbenzenesulfonate (1:1) (cis configured, 72.8 mg, 294 µmol) was then added followed by and N,N-diisopropylethylamine (140 µl, 780 µmol). The resulting mixture was stirred overnight at room temperature, diluted with water and purified by preparative HPLC (Method 4) affording 30.0 mg (24% of th.) of the title compound.

LC-MS (Method 2): $R_t$=1.60 min; MS (ESIpos): m/z=567.1 [M+H]$^+$ $^1$H-NMR (400 MHz, DMSO-d6) δ [ppm]: 8.98-8.64 (m, 3H), 8.11 (dd, 1H), 7.84-7.50 (m, 5H), 6.92 (d, 1H), 5.09 (s, 2H), 4.92-4.52 (m, 1H), 4.40-4.21 (br m, 1H), 4.11-3.77 (m, 2H), 2.73 (dt, 1H), 1.25-0.86 (m, 2H).

Example 463

5-(4-Chlorophenyl)-2-[(1-{2-[(3,3-difluoropyrrolidin-1-yl)carbonyl]pyridin-3-yl}-1H-1,2,4-triazol-3-yl)methyl]-4-[(2R)-3,3,3-trifluoro-2-hydroxypropyl]-2,4-dihydro-3H-1,2,4-triazol-3-one

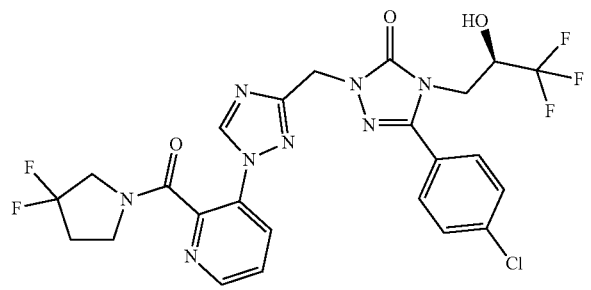

A solution of 3-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 12A, 100 mg, 196 µmol) in N,N-dimethylformamide (1.0 ml, 13 mmol) was treated with HATU (112 mg, 294 µmol) and stirred 1 h at room temperature. 3,3-Difluoropyrrolidine hydrochloride (1:1) (42.2 mg, 294 µmol) was then added followed by and N,N-diisopropylethylamine (140 µl, 780 µmol). The resulting mixture was stirred overnight at room temperature, diluted with water and purified by preparative HPLC (Method 4) affording 2.50 mg (2% of th.) of the title compound.

Mixture of Rotamers

LC-MS (Method 2): $R_t$=1.71 min; MS (ESIpos): m/z=599.1 [M+H]$^+$ $^1$H-NMR (400 MHz, DMSO-d6) δ [ppm]: 9.01 (2 s, 1H), 8.70 (2 d, 1H), 8.27 (2d, 1H), 7.86-7.47 (m, 5H), 6.91 (d, 1H), 5.17-4.91 (m, 2H), 4.38-4.19 (br s, 1H), 4.11-3.45 (m, 6H), 2.54-2.36 (m, 2H, overlap with DMSO peak).

Example 464

5-(4-Chlorophenyl)-2-[(1-{2-[(2,2-dimethylmorpholin-4-yl)carbonyl]pyridin-3-yl}-1H-1,2,4-triazol-3-yl)methyl]-4-[(2R)-3,3,3-trifluoro-2-hydroxypropyl]-2,4-dihydro-3H-1,2,4-triazol-3-one

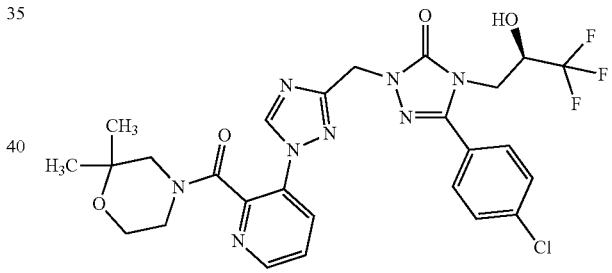

A solution of 3-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 12A, 100 mg, 196 µmol) in N,N-dimethylformamide (1 ml, 13 mmol) was treated with HATU (112 mg, 294 µmol) and stirred 1 h at room temperature. 2,2-Dimethylmorpholine (33.9 mg, 294 µmol) was then added followed by and N,N-diisopropylethylamine (100 µl, 590 µmol). The resulting mixture was stirred overnight at room temperature, diluted with water and purified by preparative HPLC (Method 4) affording 38.0 mg (29% of th.) of the title compound.

LC-MS (Method 2): $R_t$=1.65 min; MS (ESIpos): m/z=607.2 [M+H]$^+$ $^1$H-NMR (400 MHz, DMSO-d6) δ [ppm]: 9.06-8.90 (m, 1H), 8.80-8.64 (m, 1H), 8.29-8.15 (m, 1H), 7.81-7.51 (m, 5H), 6.99-6.78 (m, 1H), 5.16-4.99 (m, 2H), 4.42-4.21 (m, 1H), 4.10-3.78 (m, 2H), 3.73-3.48 (m, 2H), 3.45-3.22 (m, 2H, overlap with HDO peak), 3.13-2.79 (m, 2H), 1.22-0.88 (m, 6H).

Example 465

3-[3-({3-(4-Chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]-N-(3,3-difluorocyclobutyl)pyridine-2-carboxamide

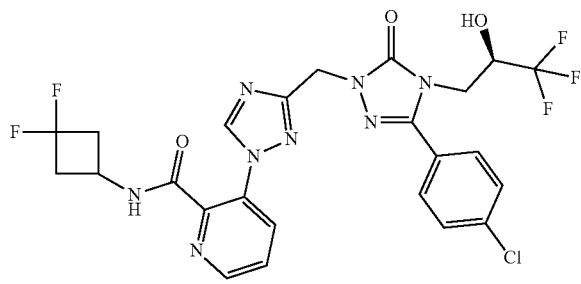

A solution of 3-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 12 A, 100 mg, 196 µmol) in N,N-dimethylformamide (1.0 ml, 13 mmol) was treated with HATU (112 mg, 294 µmol) and stirred 1 h at room temperature. 3,3-Difluorocyclobutanamine hydrochloride (1:1) (42.2 mg, 294 µmol) was then added followed by and N,N-diisopropylethylamine (140 µl, 780 µmol). The resulting mixture was stirred overnight at room temperature, diluted with water and purified by preparative HPLC (Method 4) affording 31.2 mg (27% of th.) of the title compound.

LC-MS (Method 2): $R_t$=1.73 min; MS (ESIpos): m/z=599.1 [M+H]$^+$ $^1$H-NMR (400 MHz, DMSO-d6) δ [ppm]: 9.22 (d, 1H), 8.89-8.67 (m, 2H), 8.12 (dd, 1H), 7.84-7.50 (m, 5H), 6.92 (d, 1H), 5.08 (s, 2H), 4.40-3.76 (m, 4H), 2.97-2.59 (m, 4H).

Example 466

5-(4-Chlorophenyl)-2-{[1-(2-{[2-methylmorpholin-4-yl]carbonyl}pyridin-3-yl)-1H-1,2,4-triazol-3-yl]methyl}-4-[(2R)-3,3,3-trifluoro-2-hydroxypropyl]-2,4-dihydro-3H-1,2,4-triazol-3-one (Diastereomeric Mixture)

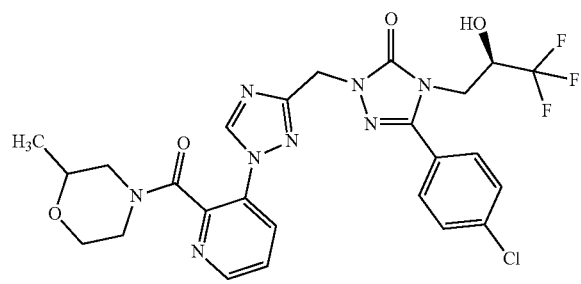

A solution of 3-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 12A, 100 mg, 196 µmol) in N,N-dimethylformamide (1 ml, 13 mmol) was treated with HATU (112 mg, 294 µmol) and stirred 1 h at room temperature. 2-Methylmorpholine (29.8 mg, 294 µmol) was then added followed by and N,N-diisopropylethylamine (100 µl, 590 µmol). The resulting mixture was stirred overnight at room temperature, diluted with water and purified by preparative HPLC (Method 4) affording 31.1 mg (27% of th.) of the title compound.

LC-MS (Method 2): $R_t$=1.59 min; MS (ESIpos): m/z=593.2 [M+H]$^+$ $^1$H-NMR (400 MHz, DMSO-d6) δ [ppm]: 8.99 (s, 1H), 8.69 (d, 1H), 8.23 (br d, 1H), 7.81-7.56 (m, 5H), 6.90 (br 2 d, 1H), 5.22-5.02 (m, 2H), 4.46-3.23 (m, 7H, overlap with HDO peak), 3.24-2.40 (m, 3H, overlap with DMSO peak), 1.08-0.74 (m, 3H).

Example 467

1-({3-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridin-2-yl}carbonyl)-prolinamide (Diastereomeric Mixture)

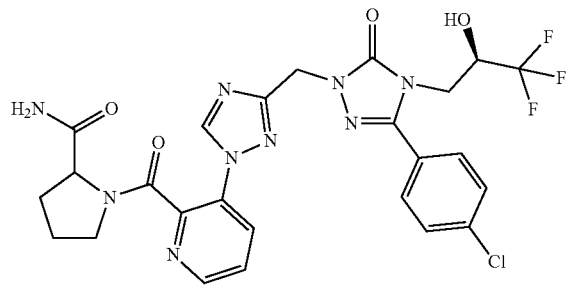

A solution of 3-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 12A, 100 mg, 196 µmol) in N,N-dimethylformamide (1 ml, 13 mmol) was treated with HATU (112 mg, 294 µmol) and stirred 1 h at room temperature. Prolinamide (33.6 mg, 294 µmol) was then added followed by and N,N-diisopropylethylamine (100 µl, 590 µmol). The resulting mixture was stirred overnight at room temperature, diluted with water and purified by preparative HPLC (Method 4) affording 32.2 mg (27% of th.) of the title compound.

LC-MS (Method 2): $R_t$=1.44 min; MS (ESIpos): m/z=606.2 [M+H]$^+$ $^1$H-NMR (400 MHz, DMSO-d6) δ [ppm]: 9.16-8.96 (m, 1H), 8.75-8.54 (m, 1H), 8.33-8.00 (m, 1H), 7.83-7.50 (m, 5H), 7.45-6.78 (m, 3H), 5.22-4.97 (m, 2H), 4.76-4.18 (m, 2H), 4.08-3.75 (m, 2H), 3.64-3.34 (m, 2H), 2.35-1.64 (m, 4H).

Example 468

5-(4-Chlorophenyl)-2-{[1-(2-{[3-hydroxy-3-(trifluoromethyl)pyrrolidin-1-yl]carbonyl}pyridin-3-yl)-1H-1,2,4-triazol-3-yl]methyl}-4-[(2R)-3,3,3-trifluoro-2-hydroxypropyl]-2,4-dihydro-3H-1,2,4-triazol-3-one
(Diastereomeric Mixture)

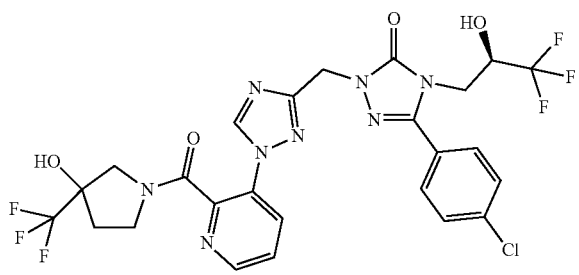

A solution of 3-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 12A, 100 mg, 196 μmol) in N,N-dimethylformamide (1 ml, 13 mmol) was treated with HATU (112 mg, 294 μmol) and stirred 1 h at room temperature. 3-(Trifluoromethyl)pyrrolidin-3-ol hydrochloride (1:1) (56.4 mg, 294 μmol) was then added followed by and N,N-diisopropylethylamine (140 μl, 780 μmol). The resulting mixture was stirred overnight at room temperature, diluted with water and purified by preparative HPLC (Method 4) affording 24.7 mg (19% of th.) of the title compound.

LC-MS (Method 2): $R_t$=1.67 min; MS (ESIpos): m/z=647.1 [M+H]$^+$ $^1$H-NMR (400 MHz, DMSO-d6) δ [ppm]: 9.03-8.86 (m, 1H), 8.71 (d, 1H), 8.24 (2d, 1H), 7.84-7.50 (m, 5H), 6.91 (d, 1H), 6.57 (s, 1H), 5.24-4.93 (m, 2H), 4.39-4.21 (br m, 1H), 4.12-3.38 (m, 6H), 2.30-1.85 (m, 2H).

Example 469

4-({3-[3-({3-(4-Chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridin-2-yl}carbonyl)piperazin-2-one

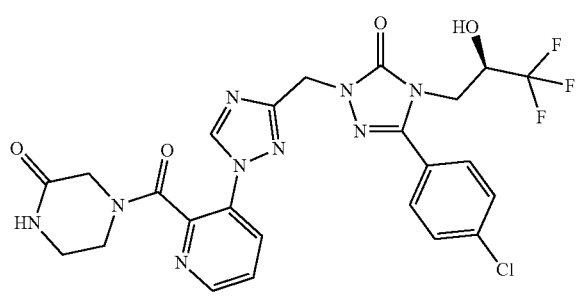

A solution of 3-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 12A, 100 mg, 196 μmol) in N,N-dimethylformamide (1 ml, 13 mmol) was treated with HATU (112 mg, 294 μmol) and stirred 1 h at room temperature. Piperazin-2-one (29.5 mg, 294 μmol) was then added followed by and N,N-diisopropylethylamine (100 μl, 590 μmol). The resulting mixture was stirred overnight at room temperature, diluted with water and purified by preparative HPLC (Method 4) affording 40.6 mg (35% of th.) of the title compound.

LC-MS (Method 2): $R_t$=1.31 min; MS (ESIpos): m/z=592.1 [M+H]$^+$ $^1$H-NMR (400 MHz, DMSO-d6) δ [ppm]: 9.06 (s, 1H), 8.75-8.62 (m, 1H), 8.34-8.07 (m, 2H), 7.84-7.49 (m, 5H), 6.95-6.83 (m, 1H), 5.18-4.99 (m, 2H), 4.40-4.21 (m, 1H), 4.06-3.04 (m, 8H, overlap with HDO peak).

Example 470

5-(4-Chlorophenyl)-4-[(2R)-3,3,3-trifluoro-2-hydroxypropyl]-2-{[1-(2-{[2-(trifluoromethyl)morpholin-4-yl]carbonyl}pyridin-3-yl)-1H-1,2,4-triazol-3-yl]methyl}-2,4-dihydro-3H-1,2,4-triazol-3-one
(Diastereomeric Mixture)

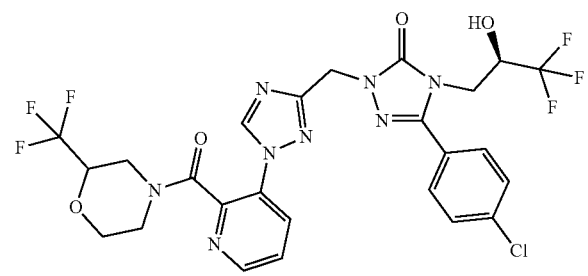

A solution of 3-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 12A, 100 mg, 196 μmol) in N,N-dimethylformamide (1 ml, 13 mmol) was treated with HATU (112 mg, 294 μmol) and stirred 1 h at room temperature. 2-(Trifluoromethyl)morpholine hydrochloride (1:1) (56.4 mg, 294 μmol) was then added followed by and N,N-diisopropylethylamine (140 μl, 780 μmol). The resulting mixture was stirred overnight at room temperature, diluted with water and purified by preparative HPLC (Method 4) affording 37.6 mg (30% of th.) of the title compound.

LC-MS (Method 2): $R_t$=1.81 min; MS (ESIpos): m/z=647.1 [M+H]$^+$ $^1$H-NMR (400 MHz, DMSO-d6) δ [ppm]: 9.15-8.97 (m, 1H), 8.81-8.62 (m, 1H), 8.35-8.20 (m, 1H), 7.83-7.51 (m, 5H), 6.89 (dd, 1H), 5.26-4.92 (m, 2H), 4.48-4.13 (m, 3H), 4.07-3.75 (m, 3H), 3.73-2.80 (m, 4H, overlap with HDO peak).

Example 471

5-(4-chlorophenyl)-2-({1-[2-(piperidin-1-ylcarbonyl)pyridin-3-yl]-1H-1,2,4-triazol-3-yl}methyl)-4-[(2R)-3,3,3-trifluoro-2-hydroxypropyl]-2,4-dihydro-3H-1,2,4-triazol-3-one

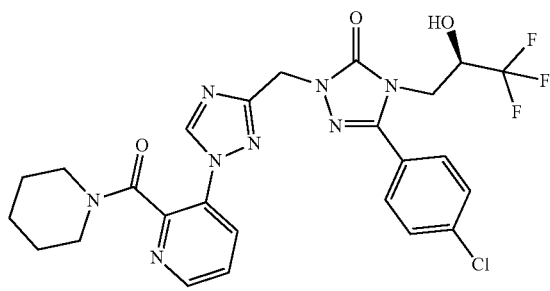

A solution of 3-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 12A, 100 mg, 196 µmol) in N,N-dimethylformamide (1 ml, 13 mmol) was treated with HATU (112 mg, 294 µmol) and stirred 1 h at room temperature. Piperidine (29 µl, 290 µmol) was then added followed by and N,N-diisopropylethylamine (100 µl, 590 µmol). The resulting mixture was stirred overnight at room temperature, diluted with water and purified by preparative HPLC (Method 4) affording 36.1 mg (32% of th.) of the title compound.

LC-MS (Method 2): $R_t$=1.71 min; MS (ESIpos): m/z=577.2 [M+H]$^+$ $^1$H-NMR (400 MHz, DMSO-d6) δ [ppm]: 8.90 (s, 1H), 8.68 (dd, 1H), 8.19 (dd, 1H), 7.80-7.57 (m, 5H), 6.91 (d, 1H), 5.09 (s, 2H), 4.39-4.21 (br m, 1H), 4.08-3.78 (m, 2H), 3.44 (br s, 2H), 3.09-2.88 (m, 2H), 1.51-1.16 (m, 6H).

Example 472

5-(4-Chlorophenyl)-2-({1-[2-(morpholin-4-ylcarbonyl)pyridin-3-yl]-1H-1,2,4-triazol-3-yl}methyl)-4-[(2R)-3,3,3-trifluoro-2-hydroxypropyl]-2,4-dihydro-3H-1,2,4-triazol-3-one

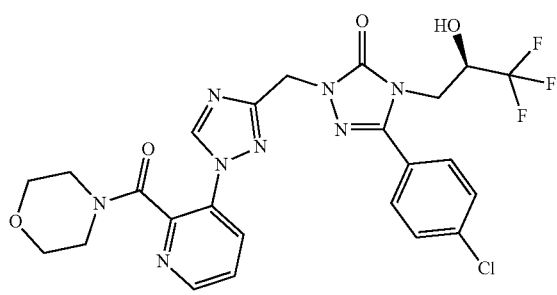

A solution of 3-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 12A, 100 mg, 196 µmol) in N,N-dimethylformamide (1 ml, 13 mmol) was treated with HATU (112 mg, 294 µmol) and stirred 1 h at room temperature. Morpholine (26 µl, 290 µmol) was then added followed by and N,N-diisopropylethylamine (100 µl, 590 µmol). The resulting mixture was stirred overnight at room temperature, diluted with water and purified by preparative HPLC (Method 4) affording 38.3 mg (34% of th.) of the title compound.

LC-MS (Method 2): $R_t$=1.50 min; MS (ESIpos): m/z=579.1 [M+H]$^+$ $^1$H-NMR (400 MHz, DMSO-d6) δ [ppm]: 9.00 (s, 1H), 8.69 (dd, 1H), 8.23 (dd, 1H), 7.86-7.48 (m, 5H), 6.90 (d, 1H), 5.22-4.98 (m, 2H), 4.40-4.22 (br m, 1H), 4.09-3.75 (m, 2H), 3.69-3.37 (m, 6H), 3.21-3.02 (br m, 2H).

Example 473

3-[3-({3-(4-Chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]-N-[1-(trifluoromethyl)cyclopropyl]pyridine-2-carboxamide

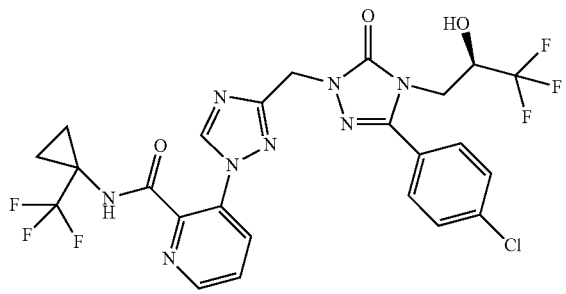 [SMILES: O=C(NC1(C(F)(F)F)CC1)c1ncccc1-n1cnc(Cn2nc(-c3ccc(Cl)cc3)n(C[C@@H](O)C(F)(F)F)c2=O)n1]

A solution of 3-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 12A, 100 mg, 196 µmol) in N,N-dimethylformamide (1 ml, 13 mmol) was treated with HATU (112 mg, 294 µmol) and stirred 1 h at room temperature. 1-(Trifluoromethyl)cyclopropanaminium chloride (47.5 mg, 294 µmol) was then added followed by and N,N-diisopropylethylamine (100 µl, 590 µmol). The resulting mixture was stirred overnight at room temperature, diluted with water and purified by preparative HPLC (Method 4) affording 33.2 mg (27% of th.) of the title compound.

LC-MS (Method 2): $R_t$=1.79 min; MS (ESIpos): m/z=617.1 [M+H]$^+$ $^1$H-NMR (400 MHz, DMSO-d6) δ [ppm]: 9.38 (s, 1H), 8.89-8.66 (m, 2H), 8.15 (d, 1H), 7.84-7.53 (m, 5H), 6.92 (d, 1H), 5.06 (s, 2H), 4.40-4.21 (br m, 1H), 4.10-3.69 (m, 2H), 1.41-0.85 (m, 4H).

Example 474

5-(4-Chlorophenyl)-2-[(1-{2-[(3,3-dimethylmorpholin-4-yl)carbonyl]pyridin-3-yl}-1H-1,2,4-triazol-3-yl)methyl]-4-[(2S)-3,3,3-trifluoro-2-hydroxypropyl]-2,4-dihydro-3H-1,2,4-triazol-3-one

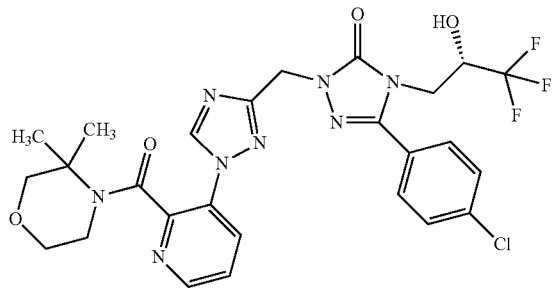 [SMILES: CC1(C)COCCN1C(=O)c1ncccc1-n1cnc(Cn2nc(-c3ccc(Cl)cc3)n(C[C@H](O)C(F)(F)F)c2=O)n1]

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 12A, 100 mg, 196 µmol) in N,N-dimethylformamide (1 ml, 13 mmol) was treated with HATU (112 mg, 294 µmol) and stirred 1 h at room temperature. 3,3-Dimethylmorpholine hydrochloride (1:1) (44.6 mg, 294 µmol) was then added followed by and N,N-diisopropylethylamine (140 µl, 780 µmol). The resulting mixture was stirred overnight at room temperature, diluted with water and purified by preparative HPLC (Method 4) affording 57.6 mg (48% of th.) of the title compound.

LC-MS (Method 2): $R_t$=1.63 min MS (ESIpos): m/z=607.2 [M+H]$^+$ $^1$H-NMR (400 MHz, DMSO-d6) δ [ppm]: 8.98 (s, 1H), 8.66 (dd, 1H), 8.21 (d, 1H), 7.84-7.51 (m, 5H), 6.91 (d, 1H), 5.21-4.95 (m, 2H), 4.31 (br d, 1H), 4.10-3.74 (m, 2H), 3.52 (t, 2H), 3.40-3.21 (s, 2H, overlap with HDO peak), 3.17 (br t, 2H), 1.59-1.11 (m, 6H).

Example 475

5-(4-Chlorophenyl)-2-[(1-{2-[(3,3-dimethylmorpholin-4-yl)carbonyl]pyridin-3-yl}-1H-1,2,4-triazol-3-yl)methyl]-4-[(2R)-3,3,3-trifluoro-2-hydroxypropyl]-2,4-dihydro-3H-1,2,4-triazol-3-one

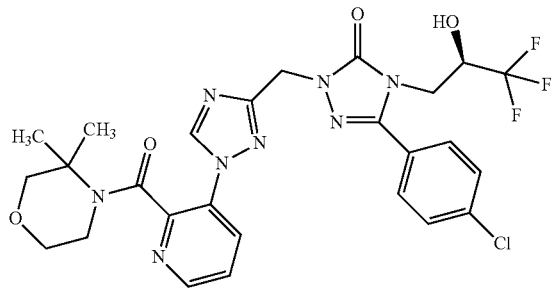 [SMILES: CC1(C)COCCN1C(=O)c1ncccc1-n1cnc(Cn2nc(-c3ccc(Cl)cc3)n(C[C@@H](O)C(F)(F)F)c2=O)n1]

A solution of 3-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 12A, 100 mg, 196 µmol) in N,N-dimethylformamide (1 ml, 13 mmol) was treated with HATU (112 mg, 294 µmol) and stirred 1 h at room temperature. 3,3-Dimethylmorpholine hydrochloride (1:1) (44.6 mg, 294 µmol) was then added followed by and N,N-diisopropylethylamine (140 µl, 780 µmol). The resulting mixture was stirred overnight at room temperature, diluted with water and purified by preparative HPLC (Method 4) affording 30.0 mg (25% of th.) of the title compound.

LC-MS (Method 2): $R_t$=1.66 min; MS (ESIpos): m/z=607.2 [M+H]$^+$ $^1$H-NMR (400 MHz, DMSO-d6) δ [ppm]: 8.98 (s, 1H), 8.66 (d, 1H), 8.21 (d, 1H), 7.83-7.53 (m, 5H), 6.90 (d, 1H), 5.18-4.93 (m, 2H), 4.40-4.21 (br m, 1H), 4.07-3.74 (m, 2H), 3.52 (t, 2H), 3.39-3.23 (s, 2H, overlap with HDO peak), 3.17 (br t, 2H), 1.38 (s, 6H).

Example 476

5-(4-Chlorophenyl)-4-[(2R)-3,3,3-trifluoro-2-hydroxypropyl]-2-{[1-(2-{[3-(trifluoromethyl)piperazin-1-yl]carbonyl}pyridin-3-yl)-1H-1,2,4-triazol-3-yl]methyl}-2,4-dihydro-3H-1,2,4-triazol-3-one
(Diastereomeric Mixture)

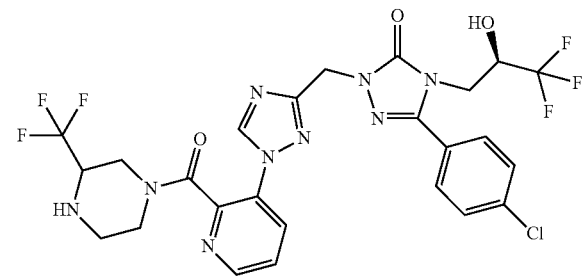 [SMILES: O=C(c1ncccc1-n1cnc(Cn2nc(-c3ccc(Cl)cc3)n(C[C@@H](O)C(F)(F)F)c2=O)n1)N1CCNC(C(F)(F)F)C1]

A solution of 3-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 12A, 100 mg, 196 µmol) in N,N-dimethylformamide (1 ml, 13 mmol) was treated with HATU (112 mg, 294 µmol) and stirred 1 h at room temperature. 2-(Trifluoromethyl)piperazine (45.3 mg, 294 µmol) was then added followed by and N,N-diisopropylethylamine (100 µl, 590 µmol). The resulting mixture was stirred overnight at room temperature, diluted with water and purified by preparative HPLC (Method 4) affording 43.1 mg (34% of th.) of the title compound.

LC-MS (Method 2): $R_t$=1.61 min; MS (ESIpos): m/z=646.2 [M+H]$^+$ $^1$H-NMR (400 MHz, DMSO-d6) δ [ppm]: 9.10-8.89 (m, 1H), 8.80-8.60 (m, 1H), 8.35-8.16 (m, 1H), 7.84-7.51 (m, 5H), 7.04-6.82 (m, 1H), 5.23-5.00 (m, 2H), 4.48-3.72 (m, 4H), 3.62-2.43 (m, 7H, overlap with HDO and DMSO peak).

Example 477

5-(4-Chlorophenyl)-4-[(2R)-3,3,3-trifluoro-2-hydroxypropyl]-2-{[1-(2-{[(2S)-2-(trifluoromethyl)pyrrolidin-1-yl]carbonyl}pyridin-3-yl)-1H-1,2,4-triazol-3-yl]methyl}-2,4-dihydro-3H-1,2,4-triazol-3-one

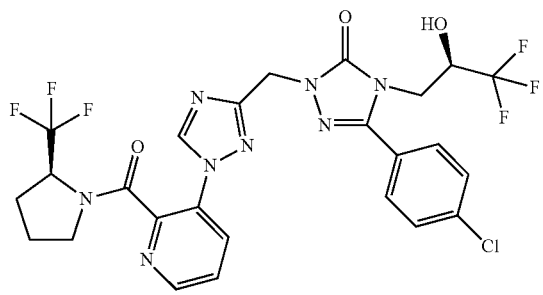 [SMILES: O=C(c1ncccc1-n1cnc(Cn2nc(-c3ccc(Cl)cc3)n(C[C@@H](O)C(F)(F)F)c2=O)n1)N1CCC[C@H]1C(F)(F)F]

A solution of 3-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 12A, 100 mg, 196 µmol) in N,N-dimethylformamide (1 mpl, 13 mmol) was treated with HATU (112 mg, 294 µmol) and stirred 1 h at room temperature. (2S)-2-(Trifluoromethyl)pyrrolidine (40.9 mg, 294 µmol) was then added followed by and N,N-diisopropylethylamine (100 µl, 590 µmol). The resulting mixture was stirred overnight at room temperature, diluted with water and purified by preparative HPLC (Method 4) affording 39.8 mg (32% of th.) of the title compound.

LC-MS (Method 2): R$_t$=1.87 min; MS (ESIpos): m/z=631.1 [M+H]$^+$ $^1$H-NMR (400 MHz, DMSO-d6) δ [ppm]: 9.19-8.91 (m, 1H), 8.82-8.60 (m, 1H), 8.29 (d, 1H), 7.89-7.49 (m, 5H), 6.99-6.80 (m, 1H), 5.24-4.72 (m, 3H), 4.38-4.19 (br m, 1H), 4.08-3.74 (m, 2H), 3.54-3.20 (m, 2H, overlap with HDO peak), 2.37-1.70 (m, 4H).

Example 478

5-(4-Chlorophenyl)-4-[(2R)-3,3,3-trifluoro-2-hydroxypropyl]-2-{[1-(2-{[(2R)-2-(trifluoromethyl)pyrrolidin-1-yl]carbonyl}pyridin-3-yl)-1H-1,2,4-triazol-3-yl]methyl}-2,4-dihydro-3H-1,2,4-triazol-3-one

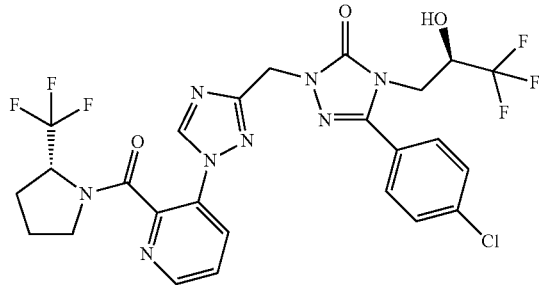 [SMILES: O=C(c1ncccc1-n1cnc(Cn2nc(-c3ccc(Cl)cc3)n(C[C@@H](O)C(F)(F)F)c2=O)n1)N1CCC[C@@H]1C(F)(F)F]

A solution of 3-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 12A, 100 mg, 196 µmol) in N,N-dimethylformamide (1 ml, 13 mmol) was treated with HATU (112 mg, 294 µmol) and stirred 1 h at room temperature. (2R)-2-(Trifluoromethyl)pyrrolidine (40.9 mg, 294 µmol) was then added followed by and N,N-diisopropylethylamine (100 µl, 590 µmol). The resulting mixture was stirred overnight at room temperature, diluted with water and purified by preparative HPLC (Method 4) affording 41.5 mg (34% of th.) of the title compound.

LC-MS (Method 2): R$_t$=1.87 min; MS (ESIpos): m/z=631.1 [M+H]$^+$ $^1$H-NMR (400 MHz, DMSO-d6) δ [ppm]: 9.05 (s, 1H), 8.77-8.62 (m, 1H), 8.35-8.24 (m, 1H), 7.83-7.53 (m, 5H), 6.91 (d, 1H), 5.21-4.98 (m, 2H), 4.91-4.72 (m, 1H), 4.39 4.20 (br m, 1H), 4.05-3.76 (m, 2H), 3.53-3.25 (m, 2H, overlap with HDO peak), 2.38-2.16 (m, 1H), 2.06-1.78 (m, 3H).

Example 479

5-(4-Chlorophenyl)-2-[(1-{2-[(1,1-dioxidothiomorpholin-4-yl)carbonyl]pyridin-3-yl}-1H-1,2,4-triazol-3-yl)methyl]-4-[(2R)-3,3,3-trifluoro-2-hydroxypropyl]-2,4-dihydro-3H-1,2,4-triazol-3-one

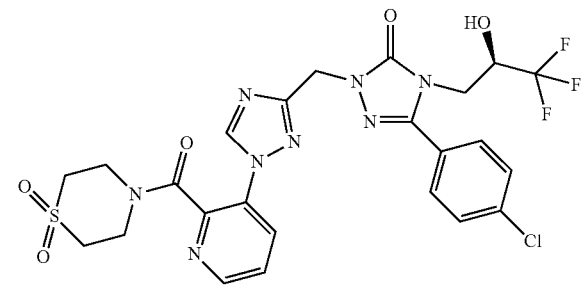 [SMILES: O=C(c1ncccc1-n1cnc(Cn2nc(-c3ccc(Cl)cc3)n(C[C@@H](O)C(F)(F)F)c2=O)n1)N1CCS(=O)(=O)CC1]

A solution of 3-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 12A, 100 mg, 196 µmol) in N,N-dimethylformamide (1 ml, 13 mmol) was treated with HATU (112 mg, 294 µmol) and stirred 1 h atroom temperature. Thiomorpholine 1,1-dioxide (39.8 mg, 294 µmol) was then added followed by and N,N-diisopropylethylamine (100 µl, 590 µmol). The resulting mixture was stirred overnight at room temperature, diluted with water and purified by preparative HPLC (Method 4) affording 35.7 mg (29% of th.) of the title compound.

LC-MS (Method 2): R$_t$=1.49 min; MS (ESIpos): m/z=627.1 [M+H]$^+$ $^1$H-NMR (400 MHz, DMSO-d6) δ [ppm]: 9.11 (s, 1H), 8.71 (dd, 1H), 8.30 (dd, 1H), 7.87-7.53 (m, 5H), 6.92 (d, 1H), 5.23-4.95 (m, 2H), 4.40-4.21 (br m, 1H), 4.12-3.60 (m, 6H), 3.40-3.21 (m, 4H, overlap with HDO peak).

Example 480

5-(4-Chlorophenyl)-4-[(2R)-3,3,3-trifluoro-2-hydroxypropyl]-2-{[1-(2-{[3-(trifluoromethyl)pyrrolidin-1-yl]carbonyl}pyridin-3-yl)-1H-1,2,4-triazol-3-yl]methyl}-2,4-dihydro-3H-1,2,4-triazol-3-one (Diastereomeric Mixture)

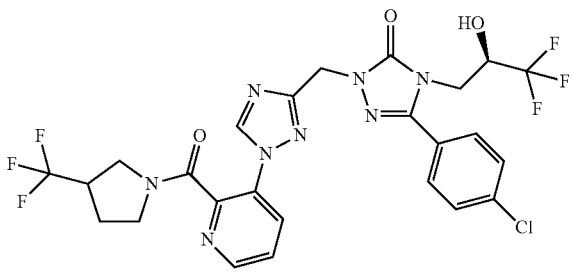 [SMILES: O=C(c1ncccc1-n1cnc(Cn2nc(-c3ccc(Cl)cc3)n(C[C@@H](O)C(F)(F)F)c2=O)n1)N1CCC(C(F)(F)F)C1]

A solution of 3-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 12A, 100 mg, 196 µmol) in N,N-dimethylformamide (1 ml, 13 mmol) was treated with HATU (112 mg, 294 µmol) and stirred 1 h at room temperature. 3-(Trifluoromethyl)pyrrolidine (40.9 mg, 294 µmol) was then added followed by and N,N-diisopropylethylamine (100 µl, 590 µmol). The resulting mixture was stirred overnight at room temperature, diluted with water and purified by preparative HPLC (Method 4) affording 40.3 mg (33% of th.) of the title compound.

LC-MS (Method 2): $R_t$=1.76 min; MS (ESIpos): m/z=631.1 [M+H]$^+$ $^1$H-NMR (400 MHz, DMSO-d6) δ [ppm]: 8.97 (s, 1H), 8.78-8.63 (m, 1H), 8.24 (d, 1H), 7.87-7.54 (m, 5H), 6.91 (d, 1H), 5.15-4.97 (m, 2H), 4.41-4.16 (m, 1H), 4.09-3.09 (m, 7H, overlap with HDO peak), 2.21-1.84 (m, 2H).

Example 481

5-(4-Chlorophenyl)-2-[(1-{2-[(2,2-dimethylpiperazin-1-yl)carbonyl]pyridin-3-yl}-1H-1,2,4-triazol-3-yl)methyl]-4-[(2R)-3,3,3-trifluoro-2-hydroxypropyl]-2,4-dihydro-3H-1,2,4-triazol-3-one

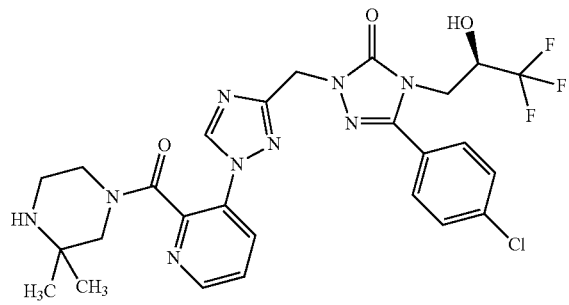 [SMILES: CC1(C)CN(C(=O)c2ncccc2-n2cnc(Cn3nc(-c4ccc(Cl)cc4)n(C[C@@H](O)C(F)(F)F)c3=O)n2)CCN1]

A solution of 3-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 12A, 100 mg, 196 µmol) in N,N-dimethylformamide (1 ml, 13 mmol) was treated with HATU (112 mg, 294 µmol) and stirred 1 h at room temperature. 2,2-Dimethylpiperazine (33.6 mg, 294 µmol) was then added followed by and N,N-diisopropylethylamine (100 µl, 590 µmol). The resulting mixture was stirred overnight at room temperature, diluted with water and purified by preparative HPLC (Method 4) affording 42.0 mg (35% of th.) of the title compound.

LC-MS (Method 1): $R_t$=0.64 min; MS (ESIpos): m/z=606.2 [M+H]$^+$ $^1$H-NMR (400 MHz, DMSO-d6) δ [ppm]: 9.19-8.57 (m, 3H), 8.36-8.19 (m, 1H), 7.88-7.57 (m, 5H), 6.94 (br s, 1H), 5.23-4.97 (m, 2H), 4.38-4.19 (br m, 1H), 4.10-2.99 (m, 8H, overlap with HDO peak), 1.45-1.08 (m, 6H).

Example 482

3-[3-({3-(4-Chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]-N-(cyclopropylmethyl)-N-methylpyridine-2-carboxamide

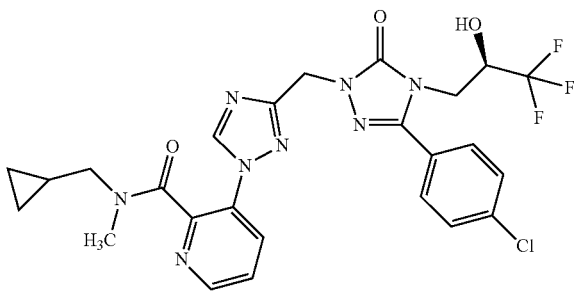 [SMILES: CN(CC1CC1)C(=O)c1ncccc1-n1cnc(Cn2nc(-c3ccc(Cl)cc3)n(C[C@@H](O)C(F)(F)F)c2=O)n1]

A solution of 3-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 12A, 100 mg, 196 µmol) in N,N-dimethylformamide (1 ml, 13 mmol) was treated with HATU (112 mg, 294 µmol) and stirred 1 h at room temperature. 1-Cyclopropyl-N-methylmethanamine (25.1 mg, 294 µmol) was then added followed by and N,N-diisopropylethylamine (100 µl, 590 µmol). The resulting mixture was stirred overnight at room temperature, diluted with water and purified by preparative HPLC (Method 4) affording 34.7 mg (31% of th.) of the title compound.

LC-MS (Method 1): $R_t$=0.91 min; MS (ESIpos): m/z=577.1 [M+H]$^+$ $^1$H-NMR (400 MHz, DMSO-d6) δ [ppm]: 8.90 (s, 1H), 8.69 (dd, 1H), 8.20 (d, 1H), 7.83-7.51 (m, 5H), 6.90 (d, 1H), 5.08 (d, 2H), 4.38-4.19 (br m, 1H), 4.12-3.69 (m, 2H), 3.25-3.06 (m, 1H), 2.94-2.75 (m, 4H), 1.06-0.72 (m, 1H), 0.53-0.23 (m, 2H), 0.22-0.06 (m, 1H), 0.03--0.06 (m, 1H, overlap with TMS peak).

Example 483

3-[3-({3-(4-Chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]-N-(1-methylcyclopropyl)pyridine-2-carboxamide

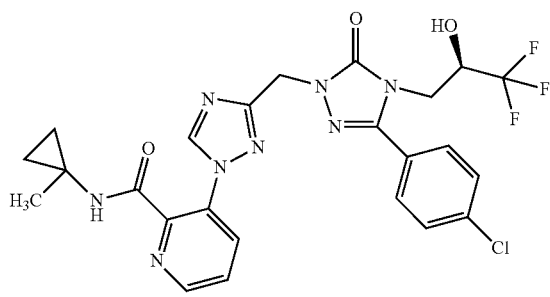 [SMILES: CC1(NC(=O)c2ncccc2-n2cnc(Cn3nc(-c4ccc(Cl)cc4)n(C[C@@H](O)C(F)(F)F)c3=O)n2)CC1]

A solution of 3-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 12A, 100 mg, 196 µmol) in N,N-dimethylformamide (1 ml, 13 mmol) was treated with HATU (112 mg, 294 µmol) and stirred 1 h at room temperature. 1-Methylcyclopropanamine (20.9 mg, 294 µmol) was then added followed by and N,N-diisopropylethylamine (100 µl, 590 µmol). The resulting mixture was stirred overnight at room temperature, diluted with water and purified by preparative HPLC (Method 4) affording 36.9 mg (30% of th.) of the title compound.

LC-MS (Method 1): $R_t$=0.88 min; MS (ESIpos): m/z=563.1 $[M+H]^+$ $^1$H-NMR (400 MHz, DMSO-d6) δ [ppm]: 8.85-8.61 (m, 3H), 8.09 (dd, 1H), 7.88-7.52 (m, 5H), 6.92 (d, 1H), 5.08 (s, 2H), 4.40-4.21 (br m, 1H), 4.09-3.76 (m, 2H), 1.27 (s, 3H), 0.79-0.40 (m, 4H).

Example 484

N-[2-Amino-3,3,3-trifluoropropyl]-3-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridine-2-carboxamide (Diastereomeric Mixture)

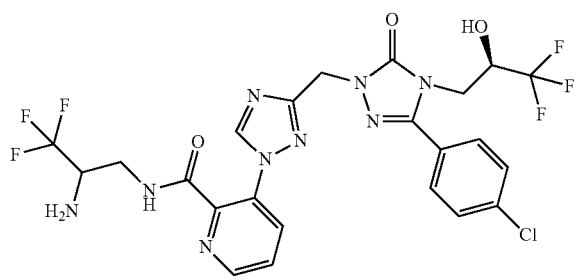 [SMILES: NC(CNC(=O)c1ncccc1-n1cnc(Cn2nc(-c3ccc(Cl)cc3)n(C[C@@H](O)C(F)(F)F)c2=O)n1)C(F)(F)F]

A solution of 3-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 12A, 100 mg, 196 µmol) in N,N-dimethylformamide (1.0 ml, 13 mmol) was treated with HATU (112 mg, 294 µmol) and stirred 1 h at room temperature. 3,3,3-Trifluoropropane-1,2-diamine dihydrochloride (59.1 mg, 294 µmol) was then added followed by and N,N-diisopropylethylamine (170 µl, 980 µmol). The resulting mixture was stirred overnight at room temperature, diluted with water and purified by preparative HPLC (Method 4) affording 25.4 mg (21% of th.) of the title compound.

LC-MS (Method 2): $R_t$=1.44 min; MS (ESIpos): m/z=620.1 $[M+H]^+$ $^1$H-NMR (400 MHz, DMSO-d6) δ [ppm]: 9.17-9.02 (m, 1H), 8.87-8.70 (m, 2H), 8.13 (dd, 1H), 7.90-7.56 (m, 5H), 6.94-6.86 (m, 1H), 5.10 (s, 2H), 4.39-4.21 (br m, 1H), 4.11-3.80 (m, 3H), 3.71-3.40 (m, 2H), NH$_2$ not visible.

Example 485

3-[3-({3-(4-Chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]-N-[3,3,3-trifluoro-2-hydroxypropyl]pyridine-2-carboxamide (Diastereomeric Mixture)

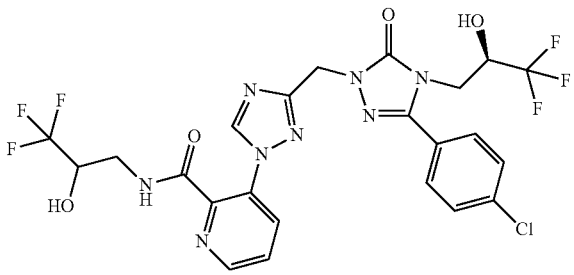 [SMILES: O=C(NCC(O)C(F)(F)F)c1ncccc1-n1cnc(Cn2nc(-c3ccc(Cl)cc3)n(C[C@@H](O)C(F)(F)F)c2=O)n1]

A solution of 3-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 12A, 100 mg, 196 µmol) in N,N-dimethylformamide (1.0 ml, 13 mmol) was treated with HATU (112 mg, 294 µmol) and stirred 1 h at room temperature. 3-Amino-1,1,1-trifluoropropan-2-ol hydrochloride (1:1) (48.7 mg, 294 µmol) was then added followed by and N,N-diisopropylethylamine (140 µl, 780 µmol). The resulting mixture was stirred overnight at room temperature, diluted with water and purified by preparative HPLC (Method 4) affording 33.6 mg (28% of th.) of the title compound.

LC-MS (Method 2): $R_t$=1.62 min; MS (ESIpos): m/z=621.1 $[M+H]^+$ $^1$H-NMR (400 MHz, DMSO-d6) δ [ppm]: 9.06-8.61 (m, 3H), 8.11 (dd, 1H), 7.90-7.48 (m, 5H), 6.92 (d, 1H), 6.47 (d, 1H), 5.24-4.97 (m, 2H), 4.45-3.69 (m, 4H), 3.60-3.20 (m, 2H, overlap with HDO peak).

Example 486

1-({3-[3-({3-(4-Chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridin-2-yl}carbonyl)-4,4-difluoro-D-prolinamide

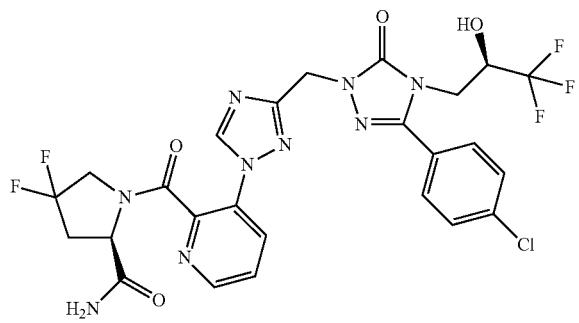 [SMILES: NC(=O)[C@H]1CC(F)(F)CN1C(=O)c1ncccc1-n1cnc(Cn2nc(-c3ccc(Cl)cc3)n(C[C@@H](O)C(F)(F)F)c2=O)n1]

A solution of 3-[3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]pyridine-2-carboxylic acid (Example 12A, 100 mg, 196 µmol) in N,N-dimethylformamide (1.0 ml, 13 mmol) was treated with HATU (112 mg, 294 µmol) and stirred 30 min at room temperature. 4,4-Difluoro-D-prolinamide hydrochloride (1:1) (54.9 mg, 294 µmol) was then added followed by and N,N-diisopropylethylamine (140 µl, 780 µmol). The resulting mixture was stirred overnight at room temperature, diluted with water and purified by preparative HPLC (Method 4) affording 24.2 mg (19% of th.) of the title compound.

LC-MS (Method 2): $R_t$=1.51 min; MS (ESIpos): m/z=642.1 [M+H]$^+$ $^1$H-NMR (400 MHz, DMSO-d6) δ [ppm]: 9.18-8.98 (m, 1H), 8.77-8.60 (m, 1H), 8.34-8.14 (m, 1H), 7.86-7.55 (m, 5H), 7.54-7.05 (m, 2H), 6.92 (dd, 1H), 5.10 (d, 2H), 5.01-4.60 (m, 1H), 4.43-3.72 (m, 5H), 3.17-2.77 (m, 1H), 2.63-2.38 (m, 1H, overlap with DMSO peak).

Example 487

3-[3-({3-(4-Chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-1-yl]-5-(1,1-dioxidothiomorpholin-4-yl)-1H-1,2,4-triazol-1-yl]-N-[2-fluorocyclopropyl]pyridine-2-carboxamide (Diastereomeric Mixture Trans Configured)

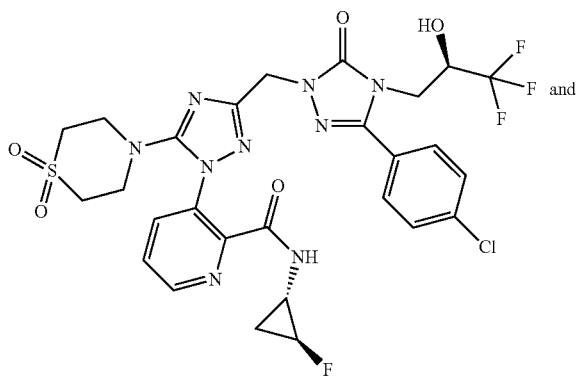
and

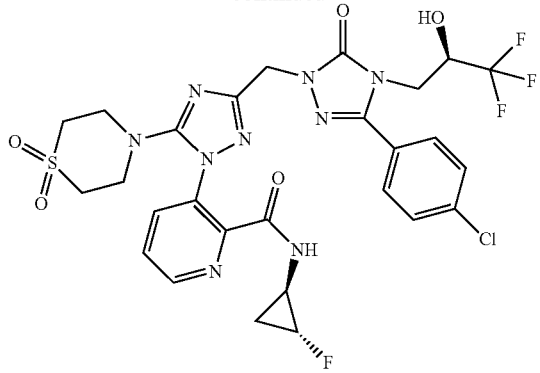

A solution of 3-[3-({3-(4-chlorophenyl)-5-oxo-4-[(2R)-3,3,3-trifluoro-2-hydroxypropyl]-4,5-dihydro-1H-1,2,4-triazol-1-yl}methyl)-5-(1,1-dioxidothiomorpholin-4-yl)-1H-1,2,4-triazol-1-yl]pyridine-2-carboxylic acid (Example 16A, 30.0 mg, 46.7 µmol) in N,N-dimethylformamide (240 µl, 3.1 mmol) was treated with HATU (26.6 mg, 70.0 µmol) and stirred 30 min at room temperature. 2-Fluorocyclopropanamine hydrochloride (1:1) (trans configured, 7.81 mg, 70.0 µmol) was then added followed by and N,N-diisopropylethylamine (33 µl, 190 µmol). The resulting mixture was stirred overnight at room temperature, diluted with water and purified by preparative HPLC (Method 4) affording 21.7 mg (66% of th.) of the title compound.

LC-MS (Method 2): $R_t$=1.63 min; MS (ESIpos): m/z=700.1 [M+H]$^+$ $^1$H-NMR (400 MHz, DMSO-d6) δ [ppm]: 8.96-8.63 (m, 2H), 8.14 (dd, 1H), 7.86-7.51 (m, 5H), 6.91 (br d, 1H), 5.01-4.84 (m, 2H), 4.82-4.52 (m, 1H), 4.38-4.19 (br m, 1H), 4.10-3.70 (m, 2H), 3.63-3.38 (m 4H), 3.18-3.033 (br m, 4H), 2.88-2.60 (m 1H), 1.26-0.91 (m 2H).

Example 488

3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-cyclopropylpyridine-4-carboxamide

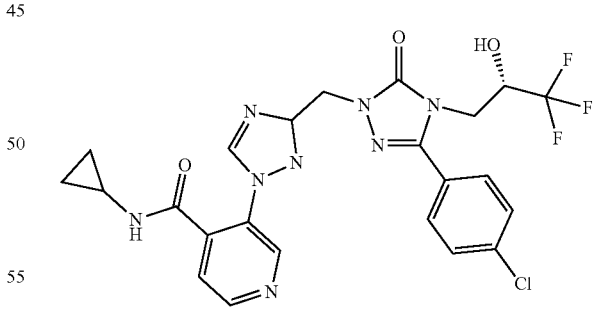

A solution of cyclopropanamine (10 µl, 150 µmol) in dichloromethane (2 ml) was treated with a solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-4-carbonyl chloride in dichloromethane (Example 24A, 1 ml, 59 µmol). N,N-diisopropylethylamine (15 µl, 89 µmol) was then added and the resulting mixture was stirred overnight at room temperature. The reaction mixture was evaporated and the residue was purified by preparative HPLC (Method 4) affording 20.1 mg (61% of th.) of the title compound.

LC-MS (Method 1): $R_t$=0.86 min; MS (ESIpos): m/z=549.1 [M+H]$^+$ $^1$H-NMR (400 MHz, DMSO-d6) δ [ppm]: 8.91-8.46 (m, 4H), 7.86-7.43 (m, 5H), 6.93 (d, 1H), 5.09 (s, 2H), 4.41-4.22 (br m, 1H), 4.11-3.73 (m, 2H), 2.70-2.55 (m, 1H), 0.64-0.29 (m, 4H).

Example 489

3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(2,2,2-trifluoroethyl)pyridine-4-carboxamide

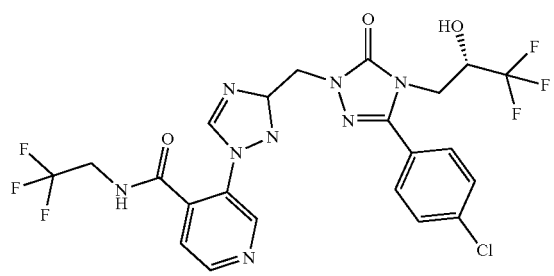

A solution of 2,2,2-trifluoroethanamine (12 µl, 150 µmol) in dichloromethane (2 ml) was treated with a solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-4-carbonyl chloride in dichloromethane (Example 24A, 1 ml, 59 µmol). N,N-diisopropylethylamine (15 µl, 89 µmol) was then added and the resulting mixture was stirred 30 min at room temperature. The reaction mixture was evaporated and the residue was purified by preparative HPLC (Method 4) affording 22.1 mg (63% of th.) of the title compound.

LC-MS (Method 1): $R_t$=0.89 min; MS (ESIpos): m/z=591.1 [M+H]$^+$ $^1$H-NMR (400 MHz, DMSO-d6) δ [ppm]: 9.27-8.69 (m, 4H), 7.83-7.49 (m, 5H), 6.92 (d, 1H), 5.05 (s, 2H), 4.42-4.18 (m, 1H), 4.07-3.73 (m, 4H).

Example 490

3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-[(1R,2S)-2-fluorocyclopropyl]pyridine-4-carboxamide
(Mixture of Diastereoisomers Cis Configured)

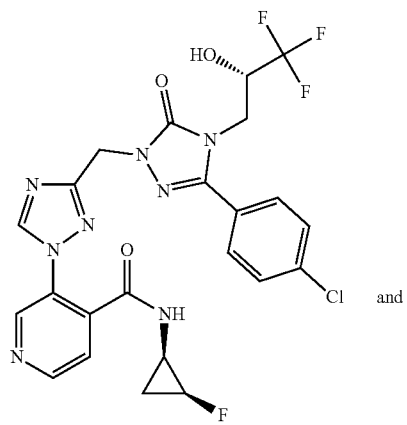

and

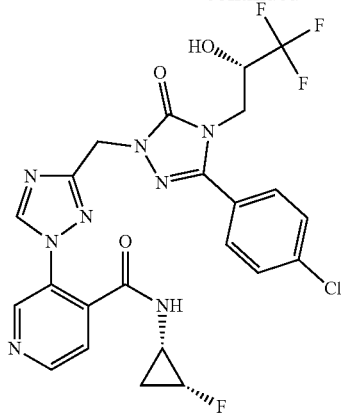

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-4-carboxylic acid (Example 24A, 60.0 mg, 118 µmol) in N,N-dimethylformamide (1.0 ml) was treated with HATU (67.1 mg, 177 µmol) and stirred 2 h at room temperature. 2-Fluorocyclopropanamine hydrochloride (1:1) (cis configured, 19.7 mg, 177 µmol) was then added followed by and N,N-diisopropylethylamine (100 µl, 590 µmol). The resulting mixture was stirred overnight at room temperature. Purification by preparative HPLC (Method 4) afforded 38.0 mg (57% of th.) of the title compound.

LC-MS (Method 1): $R_t$=0.80 min; MS (ESIpos): m/z=567.1 [M+H]$^+$ $^1$H-NMR (600 MHz, DMSO-d$_6$) δ [ppm] 8.95-8.64 (m, 4H), 7.83-7.45 (m, 5H), 6.91 (d, 1H), 5.08 (s, 2H), 4.82-4.51 (m, 1H), 4.39-4.25 (m, 1H), 4.07-3.77 (m, 2H), 2.75-2.59 (m, 1H), 1.09-0.81 (m, 2H)

Example 491

3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(3,3,3-trifluoropropyl)pyridine-4-carboxamide

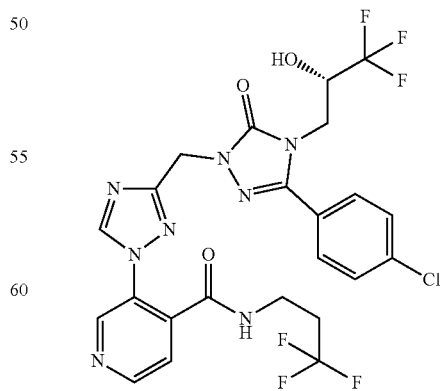

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-4-carboxylic acid (Example 24A, 60.0 mg, 118 µmol) in N,N-dimethylformamide (1 ml) was treated with HATU (67.1 mg, 177 µmol) and stirred 2 h at room temperature. 3,3,3-Trifluoropropan-1-amine (14 µl, 180 µmol) was then added followed by and N,N-diisopropylethylamine (61 µl, 350 µmol). The resulting mixture was stirred overnight at room temperature. Purification by preparative HPLC (Method 4) afforded 53.0 mg (74% of th.) of the title compound.

LC-MS (Method 1): $R_t$=0.88 min; MS (ESIpos): m/z=605.1 [M+H]$^+$ $^1$H-NMR (400 MHz, DMSO-d6) δ [ppm]: 8.96-8.70 (m, 4H), 7.82-7.46 (m, 5H), 7.02-6.81 (m, 1H), 5.15-4.96 (m, 2H), 4.40-4.21 (m, 1H), 4.07-3.74 (m, 2H), 3.44-3.18 (m, 2H, overlap with HDO peak), 2.51-2.22 (m, 2H, overlap with DMSO peak).

Example 492

3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(1-methylcyclopropyl)pyridine-4-carboxamide

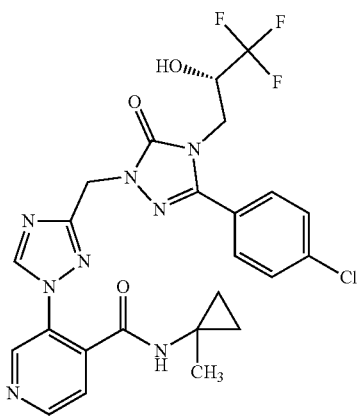 [SMILES: CC1(NC(=O)c2ccncc2-n2cnc(Cn3nc(-c4ccc(Cl)cc4)n(C[C@H](O)C(F)(F)F)c3=O)n2)CC1]

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-4-carboxylic acid (Example 24A, 60.0 mg, 118 µmol) in N,N-dimethylformamide (1.0 ml) was treated with HATU (67.1 mg, 177 µmol) and stirred 2 h at room temperature. 1-Methylcyclopropanamine hydrochloride (1:1) (19.0 mg, 177 µmol) was then added followed by and N,N-diisopropylethylamine (100 µl, 590 µmol). The resulting mixture was stirred overnight at room temperature. Purification by preparative HPLC (Method 4) afforded 49.0 mg (74% of th.) of the title compound.

LC-MS (Method 1): $R_t$=0.84 min; MS (ESIpos): m/z=563.2 [M+H]$^+$ $^1$H-NMR (400 MHz, DMSO-d6) δ [ppm]: 8.90-8.55 (m, 4H), 7.83-7.45 (m, 5H), 6.93 (d, 1H), 5.06 (s, 2H), 4.39-4.20 (m, 1H), 4.09-3.75 (m, 2H), 1.25 (s, 3H), 0.69-0.38 (m, 4H).

Example 493

5-(4-Chlorophenyl)-2-{[1-(4-{[2-(methoxymethyl)pyrrolidin-1-yl]carbonyl}pyridin-3-yl)-1H-1,2,4-triazol-3-yl]methyl}-4-[(2S)-3,3,3-trifluoro-2-hydroxypropyl]-2,4-dihydro-3H-1,2,4-triazol-3-one (Diastereomeric Mixture)

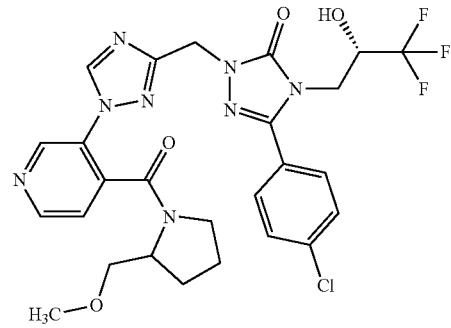 [SMILES: COCC1CCCN1C(=O)c1ccncc1-n1cnc(Cn2nc(-c3ccc(Cl)cc3)n(C[C@H](O)C(F)(F)F)c2=O)n1]

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-4-carboxylic acid (Example 24A, 100 mg, 196 µmol) in N,N-dimethylformamide (2.0 ml) was treated with HATU (112 mg, 294 µmol) and stirred 2 h at room temperature. 2-(Methoxymethyl)pyrrolidine hydrochloride (1:1) (44.6 mg, 294 µmol) was then added followed by and N,N-diisopropylethylamine (170 µl, 980 µmol). The resulting mixture was stirred overnight at room temperature. Purification by preparative HPLC (Method 4) afforded 95.4 mg (80% of th.) of the title compound.

LC-MS (Method 2): $R_t$=1.64 min; MS (ESIpos): m/z=607.2 [M+H]$^+$ $^1$H-NMR (400 MHz, DMSO-d6) δ [ppm]: 9.11-8.91 (m, 2H), 8.80-8.68 (m, 1H), 7.81-7.43 (m, 5H), 6.98-6.83 (m, 1H), 5.24-4.95 (m, 2H), 4.40-4.20 (m, 1H), 4.14-3.73 (m, 3H), 3.66-3.16 (m, 4H), 3.14-2.89 (m, 3H), 1.99-1.46 (m, 4H).

Example 494

2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(2,2,2-trifluoroethyl)pyridine-3-carboxamide

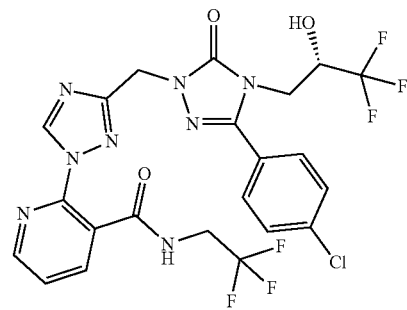

A solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-3-carboxylic acid (Example 24A, 42.8 mg, 84.0 µmol) in dichloromethane (2.0 ml) was treated with 1-Chloro-1- dimethylamino-2-methyl-1-propen (13.5 mg, 101 µmol) and stirred 1 h at room temperature. 2,2,2-trifluoroethanamine (12.5 mg, 126 µmol) was then added. The resulting mixture was stirred 1 h at room temperature and evaporated. The residue was purified by preparative HPLC (Method 4) affording 8.50 mg (17% of th.) of the title compound.

LC-MS (OpenAccess): $R_t$=1.20 min; MS (ESIpos): m/z=591.0 [M+H]$^+$ $^1$H-NMR (400 MHz, DMSO-d6) δ [ppm]: 9.15 (s, 1H), 8.96 (t, 1H), 8.64 (dd, 1H), 8.03 (dd, 1H), 7.82-7.52 (m, 5H), 6.95 (br d, 1H), 5.04 (s, 2H), 4.40-4.21 (br m, 1H), 4.09-3.69 (m, 4H).

Example 495

2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-methylpyridine-3-carboxamide

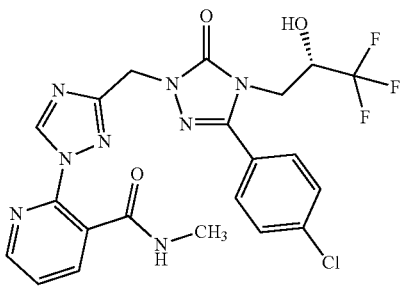

A solution of methanamine (2.0 ml, 2.0 M, 4.0 mmol) in dichloromethane (2 ml) was treated with a solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-3-carbonyl chloride in dichloromethane (Example 34A, 2 ml, 189 µmol) and stirred 30 min at room temperature. The reaction mixture was evaporated and the residue was purified by preparative HPLC (Method 4) affording 90.4 mg (91% of th.) of the title compound.

LC-MS (Method 2): $R_t$=1.45 min; MS (ESIpos): m/z=523.1 [M+H]$^+$ $^1$H-NMR (400 MHz, DMSO-d6) δ [ppm]: 9.14-9.08 (m, 1H), 8.60 (dd, 1H), 8.21 (q, 1H), 8.01 (dd, 1H), 7.80-7.53 (m, 5H), 6.93 (d, 1H), 5.08 (s, 2H), 4.45-4.23 (m, 1H), 4.08-3.76 (m, 2H), 2.61 (d, 3H).

Example 496

2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-cyclopropylpyridine-3-carboxamide

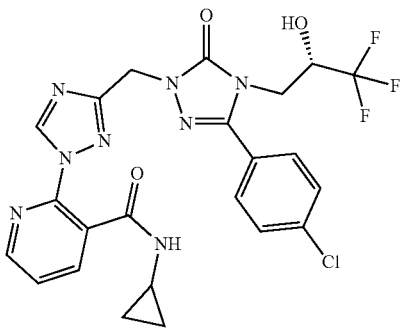

A solution of cyclopropanamine (66 µl, 950 µmol) in dichloromethane (2 ml) was treated with a solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-3-carbonyl chloride in dichloromethane (Example 34A, 2 ml, 189 µmol) and stirred 30 min at room temperature. The reaction mixture was evaporated and the residue was purified by preparative HPLC (Method 4) affording 79.1 mg (76% of th.) of the title compound.

LC-MS (Method 2): $R_t$=1.56 min; MS (ESIpos): m/z=549.1 [M+H]$^+$ $^1$H-NMR (400 MHz, DMSO-d6) δ [ppm]: 9.18-8.94 (m, 1H), 8.69-8.26 (m, 2H), 8.08-7.47 (m, 6H), 6.95 (d, 1H), 5.08 (s, 2H), 4.42-4.24 (m, 1H), 4.10-3.74 (m, 2H), 2.69-2.55 (m, 1H), 0.67-0.31 (m, 4H).

Example 497

2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(3,3,3-trifluoropropyl)pyridine-3-carboxamide

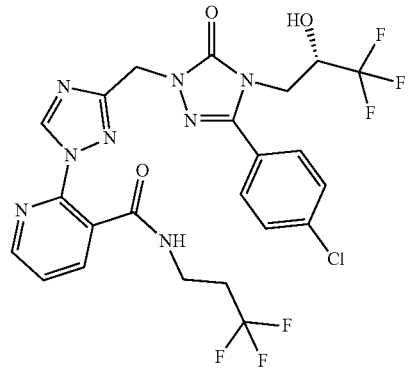

A solution of 3,3,3-trifluoropropan-1-amine (107 mg, 946 µmol) in dichloromethane (2 ml) was treated with a solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-3-carbonyl chloride in dichloromethane (Example 34A, 2 ml, 189 µmol) and stirred 30 min at room temperature. The reaction mixture was evaporated and the residue was purified by preparative HPLC (Method 4) affording 69.4 mg (61% of th.) of the title compound.

LC-MS (Method 2): $R_t$=1.74 min; MS (ESIpos): m/z=605.1 [M+H]$^+$ $^1$H-NMR (400 MHz, DMSO-d6) δ [ppm]: 9.15 (s, 1H), 8.67-8.55 (m, 2H), 8.00 (dd, 1H), 7.86-7.49 (m, 5H), 6.92 (d, 1H), 5.13-4.96 (m, 2H), 4.39-4.20 (m, 1H), 4.06-3.75 (m, 2H), 3.38-3.28 (m, 2H, overlap with HDO peak), 2.60-2.39 (m, 2H, overlap with DMSO peak).

Example 498

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(3,3-difluorocyclobutyl)pyridine-3-carboxamide

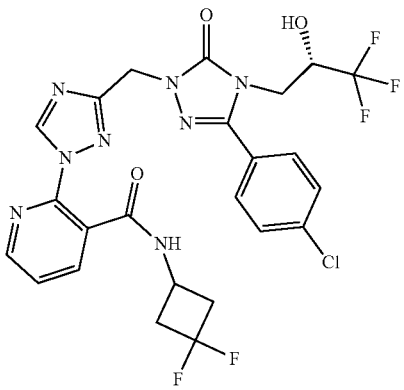

A solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-3-carboxylic acid (Example 33A; 80.0 mg, 157 µmol) in N,N-dimethylformamide (1.0 ml) was treated with HATU (89.5 mg, 235 µmol) and stirred 30 min at room temperature. 3,3-Difluorocyclobutanamine hydrochloride (89.5 mg, 235 µmol) was then added followed by N,N-diisopropylethylamine (120 µl, 710 µmol). The resulting mixture was stirred 2 h at room temperature and diluted with methanol. Purification by preparative HPLC (Method 4) afforded 84.4 mg (90% of th.) of the title compound.

LC-MS (Method 1): $R_t$=0.92 min; MS (ESIpos): m/z=599.1 [M+H]$^+$ $^1$H-NMR (400 MHz, DMSO-d6) δ [ppm]: 9.17 (s, 1H), 8.79 (d, 1H), 8.62 (dd, 1H), 8.05 (dd, 1H), 7.82-7.54 (m, 5H), 6.92 (d, 1H), 5.06 (s, 2H), 4.39-4.24 (m, 1H), 4.19-3.77 (m, 3H), 2.98-2.79 (m, 2H), 2.70-2.44 (m, 2H, overlap with DMSO peak).

Example 499

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(cyclopropylmethyl)pyridine-3-carboxamide

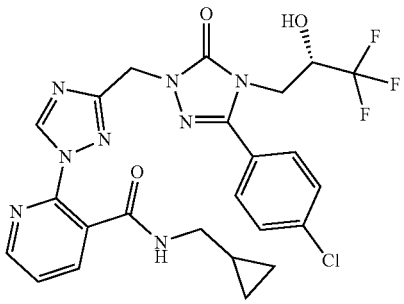

A solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-3-carboxylic acid (Example 33A, 80.0 mg, 157 µmol) in N,N-dimethylformamide (1 ml) was treated with HATU (89.5 mg, 235 µmol) and stirred 30 min at room temperature. Cyclopropylmethanamine (20 µl, 240 µmol) was then added followed by N,N-diisopropylethylamine (82 µl, 470 µmol). The resulting mixture was stirred overnight at room temperature. Purification by preparative HPLC (Method 4) afforded 70.6 mg (80% of th.) of the title compound.

LC-MS (Method 2): $R_t$=1.71 min; MS (ESIpos): m/z=563.2 [M+H]$^+$ $^1$H-NMR (400 MHz, DMSO-d6) δ [ppm]: 9.08 (s, 1H), 8.60 (dd, 1H), 8.39 (t, 1H), 8.01 (dd, 1H), 7.82-7.53 (m, 5H), 6.94 (d, 1H), 5.05 (s, 2H), 4.38-4.25 (m, 1H), 4.04-3.73 (m, 2H), 3.02-2.93 (m, 2H), 0.97-0.79 (m, 1H), 0.41-0.27 (m, 2H), 0.11-0.03 (m, 2H).

Example 500

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(2,2-difluorocyclopropyl)pyridine-3-carboxamide

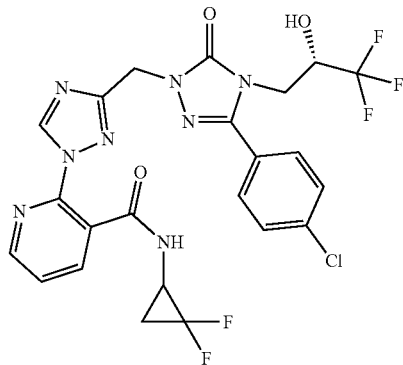

A solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-3-carboxylic acid (Example 33A, 80.0 mg, 157 µmol) in N,N-dimethylformamide (1.0 ml) was treated with HATU (89.5 mg, 235 µmol) and stirred 30 min at room temperature. 2,2-Difluorocyclopropanamine hydrochloride (1:1) (30.5 mg, 235 pmo) was then added followed by and N,N-diisopropylethylamine (120 µl, 710 µmol). The resulting mixture was stirred 5 h at room temperature. Purification by preparative HPLC (Method 4) afforded 4.4 mg (5% of th.) of the title compound.

LC-MS (Method 1): $R_t$=0.89 min; MS (ESIpos): m/z=585.0 [M+H]$^+$ $^1$H-NMR (400 MHz, DMSO-d6) δ [ppm]: 9.15 (s, 1H), 8.89-8.55 (m, 2H), 8.02 (dd, 1H), 7.83-7.50 (m, 5H), 6.91 (d, 1H), 5.08 (s, 2H), 4.41-4.23 (m, 1H), 4.09-3.75 (m, 2H), 1.94-1.34 (m, 2H), 1H not visible.

Example 501

5-(4-Chlorophenyl)-2-{[1-(3-{[(2R)-2-(methoxymethyl)pyrrolidin-1-yl]carbonyl}pyridin-2-yl)-1H-1,2,4-triazol-3-yl]methyl}-4-[(2S)-3,3,3-trifluoro-2-hydroxypropyl]-2,4-dihydro-3H-1,2,4-triazol-3-one

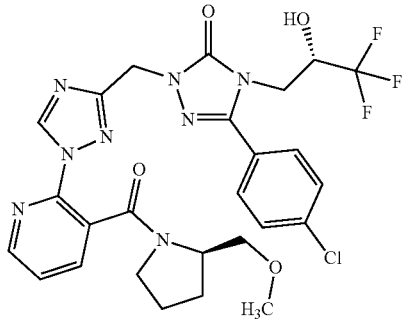

A solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-3-carboxylic acid (Example 33A, 80.0 mg, 157 µmol) in N,N-dimethylformamide (1.0 ml) was treated with HATU (89.5 mg, 235 µmol) and stirred 30 min at room temperature. (2R)-2-(methoxymethyl)pyrrolidine (27.1 mg, 235 µmol) was then added followed by and N,N-diisopropylethylamine (82 µl, 470 µmol). The resulting mixture was stirred 2 h at room temperature. Purification by preparative HPLC (Method 4) afforded 87.9 mg (92% of th.) of the title compound.

LC-MS (Method 1): R$_t$=0.94 min; MS (ESIpos): m/z=607.1 [M+H]$^+$ $^1$H-NMR (400 MHz, DMSO-d6) δ [ppm]: 9.24 (s, 1H), 8.60 (dd, 1H), 8.12-7.89 (m, 1H), 7.85-7.48 (m, 5H), 6.90 (d, 1H), 5.22-4.93 (m, 2H), 4.45-4.09 (m, 2H), 4.08-3.76 (m, 2H), 3.74-3.21 (m, 4H, overlap with HDO peak), 3.15-2.85 (m, 3H), 2.07-1.42 (m, 4H).

Example 502

5-(4-Chlorophenyl)-2-{[1-(3-{[(2S)-2-(methoxymethyl)pyrrolidin-1-yl]carbonyl}pyridin-2-yl)-1H-1,2,4-triazol-3-yl]methyl}-4-[(2S)-3,3,3-trifluoro-2-hydroxypropyl]-2,4-dihydro-3H-1,2,4-triazol-3-one

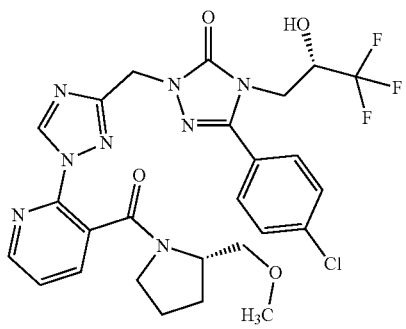

A solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-3-carboxylic acid (Example 33A, 80.0 mg, 157 µmol) in N,N-dimethylformamide (1.0 ml) was treated with HATU (89.5 mg, 235 µmol) and stirred 30 min at room temperature. (2S)-2-(methoxymethyl)pyrrolidine (27.1 mg, 235 µmol) was then added followed by and N,N-diisopropylethylamine (82 µl, 470 µmol). The resulting mixture was stirred 5 h at room temperature. Purification by preparative HPLC (Method 4) afforded 69.9 mg (73% of th.) of the title compound.

LC-MS (Method 2): R$_t$=1.78 min; MS (ESIpos): m/z=607.2 [M+H]$^+$ $^1$H-NMR (400 MHz, DMSO-d6) δ [ppm]: 9.25 (s, 1H), 8.60 (dd, 1H), 8.08-7.94 (m, 1H), 7.83-7.53 (m, 5H), 6.94 (d, 1H), 5.20-4.96 (m, 2H), 4.40-4.24 (m, 1H), 4.20-3.44 (m, 4H), 3.28-3.21 (m, 3H, overlap with HDO peak), 3.08-2.88 (m 3H), 2.03-1.46 (m 4H).

Example 503

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-[(2-fluorocyclopropyl)]pyridine-3-carboxamide
(Diastereomeric Mixture Trans Configured)

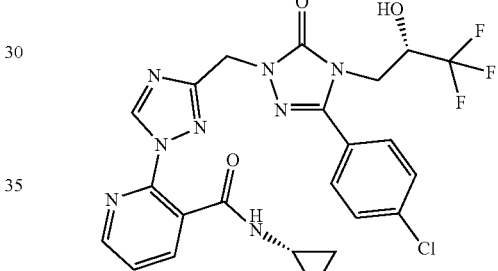
and
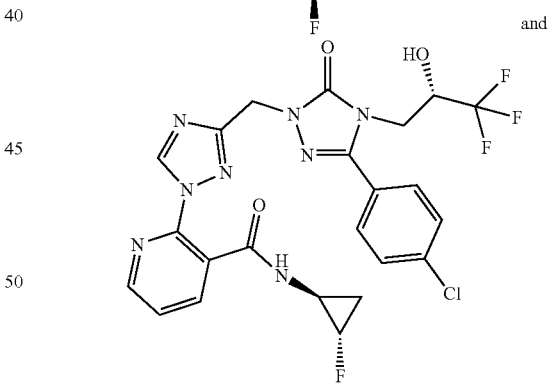

A solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-3-carboxylic acid (Example 33A, 80.0 mg, 157 µmol) in N,N-dimethylformamide (1.0 ml) was treated with HATU (89.5 mg, 235 µmol) and stirred 30 min at room temperature. 2-Fluorocyclopropanamine hydrochloride (1:1) (trans configured, 26.3 mg, 235 µmol) was then added followed by and N,N-diisopropylethylamine (120 µl, 710 µmol). The resulting mixture was stirred 2 h at room temperature. Purification by preparative HPLC (Method 4) afforded 52.9 mg (59% of th.) of the title compound.

LC-MS (Method 1): $R_t$=0.84 min; MS (ESIpos): m/z=567.0 [M+H]$^+$ $^1$H-NMR (400 MHz, DMSO-d6) δ [ppm]: 9.09 (s, 1H), 8.65-8.49 (m, 2H), 7.98 (dd, 1H), 7.83-7.53 (m, 5H), 6.93 (dd, 1H), 5.06 (s, 2H), 4.78-4.49 (m, 1H), 4.39-4.25 (m, 1H), 4.07-3.76 (m, 2H), 2.75-2.60 (m, 1H), 1.04-0.80 (m, 2H).

Example 504

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-[2-fluorocyclopropyl]pyridine-3-carboxamide (Diastereomeric Mixture Cis Configured)

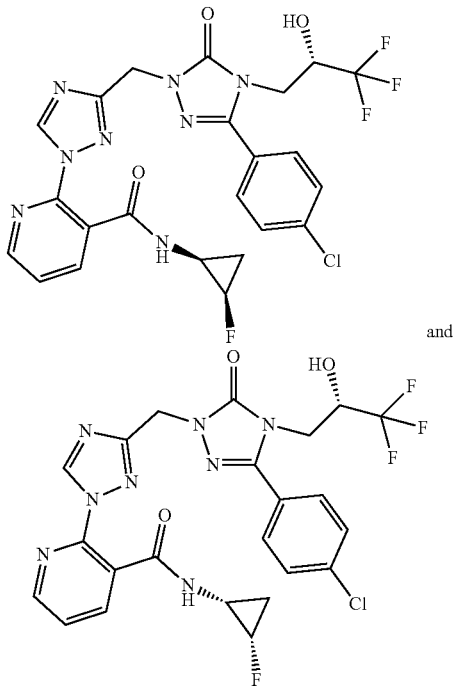

and

A solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-3-carboxylic acid (Example 33A, 80.0 mg, 157 μmol) in N,N-dimethylformamide (1.0 ml) was treated with HATU (89.5 mg, 235 μmol) and stirred 30 min at room temperature. 2-Fluorocyclopropanamine 4-methylbenzenesulfonate (1:1) (cis configured, 58.2 mg, 235 μmol) was then added followed by and N,N-diisopropylethylamine (120 μl, 710 μmol). The resulting mixture was stirred 2 h at room temperature. Purification by preparative HPLC (Method 4) afforded 69.6 mg (75% of th.) of the title compound.

LC-MS (Method 1): $R_t$=0.84 min; MS (ESIpos): m/z=567.0 [M+H]$^+$ $^1$H-NMR (400 MHz, DMSO-d6) δ [ppm]: 9.09 (s, 1H), 8.67-8.48 (m, 2H), 7.98 (dd, 1H), 7.84-7.49 (m, 5H), 6.93 (d, 1H), 5.06 (s, 2H), 4.79-4.49 (m, 1H), 4.42-4.23 (m, 1H), 4.10-3.74 (m, 2H), 2.76-2.59 (m, 1H), 1.08-0.79 (m, 2H).

Example 505

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(1-methylcyclopropyl)pyridine-3-carboxamide

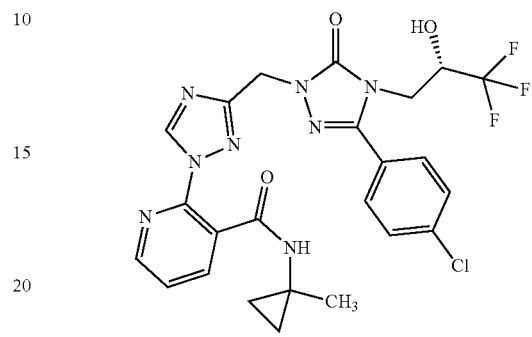

A solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-3-carboxylic acid (Example 33A, 80.0 mg, 157 μmol) in N,N-dimethylformamide (1.0 ml) was treated with HATU (89.5 mg, 235 μmol) and stirred 30 min at room temperature. 1-Methylcyclopropanamine hydrochloride (1:1) (25.3 mg, 235 μmol) was then added followed by and N,N-diisopropylethylamine (120 μl, 710 μmol). The resulting mixture was stirred 2 h at room temperature. Purification by preparative HPLC (Method 4) afforded 72.1 mg (82% of th.) of the title compound.

LC-MS (Method 2): $R_t$=1.66 min; MS (ESIpos): m/z=563.2 [M+H]$^+$ $^1$H-NMR (400 MHz, DMSO-d6) δ [ppm]: 9.08 (s, 1H), 8.65-8.43 (m, 2H), 7.97 (dd, 1H), 7.86-7.45 (m, 5H), 6.93 (d, 1H), 5.05 (s, 2H), 4.41-4.20 (m, 1H), 4.07-3.73 (m, 2H), 1.32 (s, 3H), 0.77-0.37 (m 4H).

Example 506

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]-N-(1-cyanocyclopropyl)pyridine-3-carboxamide

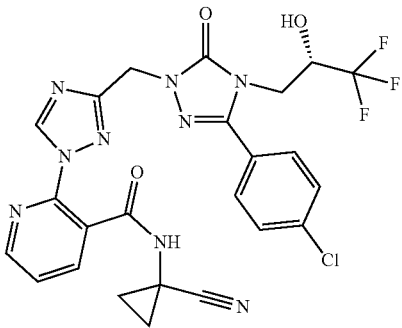 [SMILES: N#CC1(NC(=O)c2cccnc2-n2cnc(Cn3nc(-c4ccc(Cl)cc4)n(C[C@H](O)C(F)(F)F)c3=O)n2)CC1]

A solution of 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]pyridine-3-carboxylic acid (Example 33A, 80.0 mg, 157 µmol) in N,N-dimethylformamide (1.0 ml) was treated with HATU (89.5 mg, 235 µmol) and stirred 30 min at room temperature. 1-Aminocyclopropanecarbonitrile hydrochloride (1:1) (27.9 mg, 235 µmol) was then added followed by and N,N-diisopropylethylamine (120 µl, 710 µmol). The resulting mixture was stirred 2 h at room temperature. Purification by preparative HPLC (Method 4) afforded 72.0 mg (80% of th.) of the title compound.

LC-MS (Method 2): $R_t$=1.60 min; MS (ESIpos): m/z=574.1 [M+H]$^+$ $^1$H-NMR (400 MHz, DMSO-d6) δ [ppm]: 9.23 (d, 2H), 8.64 (dd, 1H), 8.08 (dd, 1H), 7.83-7.53 (m, 5H), 6.92 (d, 1H), 5.08 (s, 2H), 4.41-4.21 (m, 1H), 4.08-3.75 (m, 2H), 1.60-1.11 (m, 4H).

Example 507

3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-5-(3-oxopiperazin-1-yl)-1H-1,2,4-triazol-1-yl]-N-[2-fluorocyclopropyl]pyridine-2-carboxamide (Diastereomeric Mixture Trans Configured)

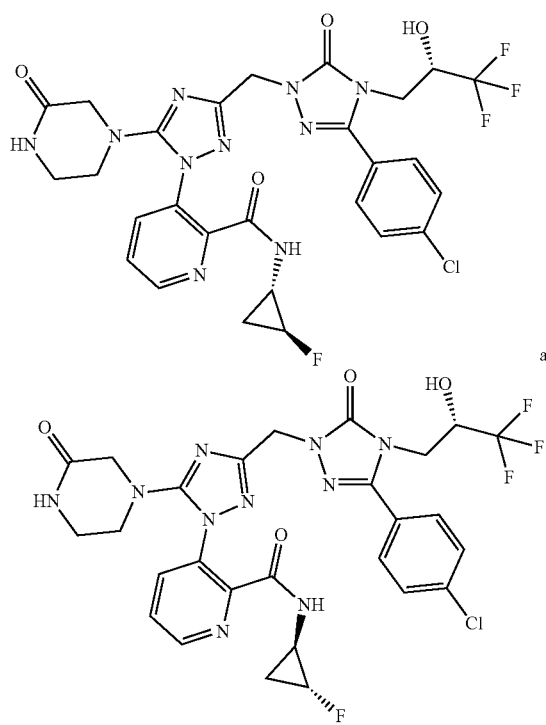

and

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-5-(3-oxopiperazin-1-yl)-1H-1,2,4-triazol-1-yl]pyridine-2-carboxylic acid (Example 20A, 33.0 mg, 54.3 µmol) in N,N-dimethylformamide (280 µl) was treated with HATU (31.0 mg, 81.4 µmol) and stirred 30 min at room temperature. 2-fluorocyclopropanamine hydrochloride (1:1) (trans configured, 9.08 mg, 81.4 µmol) was then added followed by N,N-diisopropylethylamine (38 µl, 220 µmol). The resulting mixture was stirred overnight at room temperature. Purification by preparative HPLC (Method 4) afforded 30.8 mg (85% of th.) of the title compound.

LC-MS (Method 1): $R_t$=0.78 min; MS (ESIpos): m/z=665.2 [M+H]$^+$ $^1$H-NMR (400 MHz, DMSO-d6) δ [ppm]: 8.85-8.68 (m, 2H), 8.17-7.89 (m, 2H), 7.82-7.55 (m, 5H), 6.90 (d, 1H), 4.99-4.83 (m, 2H), 4.80-4.54 (m, 1H), 4.37-4.22 (m, 1H), 4.05-3.77 (m, 2H), 3.65-3.45 (m, 2H), 3.23-3.04 (m, 4H), 2.76-2.62 (m, 1H), 1.26-0.91 (m, 2H)

Example 508

3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-5-(3-oxopiperazin-1-yl)-1H-1,2,4-triazol-1-yl]-N-[2-fluorocyclopropyl]pyridine-2-carboxamide (Diastereomeric Mixture Cis Configured)

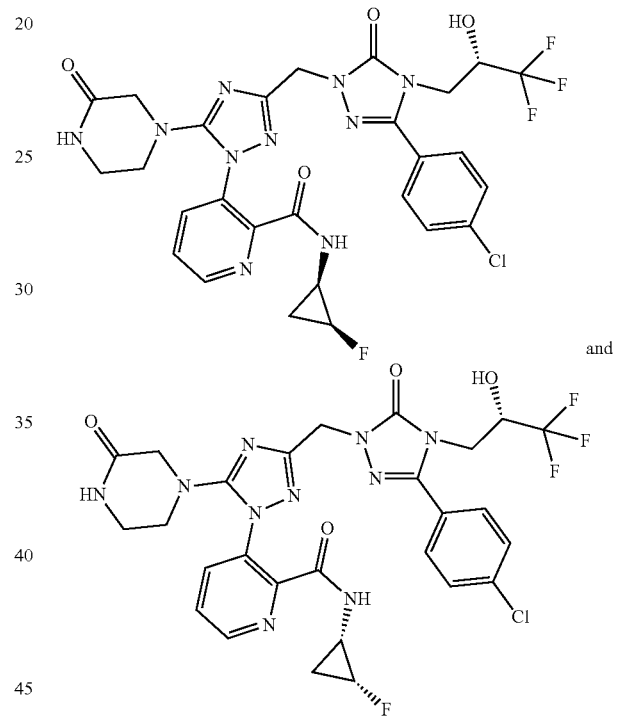

and

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-5-(3-oxopiperazin-1-yl)-1H-1,2,4-triazol-1-yl]pyridine-2-carboxylic acid (Example 20A, 33.0 mg, 54.3 µmol) in N,N-dimethylformamide (280 µl) was treated with HATU (31.0 mg, 81.4 µmol) and stirred 30 min at room temperature. 2-fluorocyclopropanamine 4-methylbenzenesulfonate (1:1) (cis configured, 20.1 mg, 81.4 µmol) was then added followed by N,N-diisopropylethylamine (38 µl, 220 µmol). The resulting mixture was stirred overnight at room temperature. Purification by preparative HPLC (Method 4) afforded 20.3 mg (56% of th.) of the title compound.

LC-MS (Method 1): $R_t$=0.78 min: MS (ESIpos): m/z=665.2 [M+H]$^+$ $^1$H-NMR (400 MHz, DMSO-d6) δ [ppm]: 8.87-8.60 (m, 2H), 8.21-7.88 (m, 2H), 7.85-7.49 (m, 5H), 6.90 (d, 1H), 4.90 (s, 2H), 4.78-4.51 (m, 1H), 4.39-4.19 (m, 1H), 4.08-3.74 (m, 2H), 3.56 (s, 2H), 3.22-2.99 (m, 4H), 2.79-2.60 (m, 1H), 1.25-0.92 (m, 2H).

Example 509

3-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-5-(3-oxopiperazin-1-yl)-1H-1,2,4-triazol-1-yl]-N-(2,2,2-trifluoroethyl)pyridine-2-carboxamide

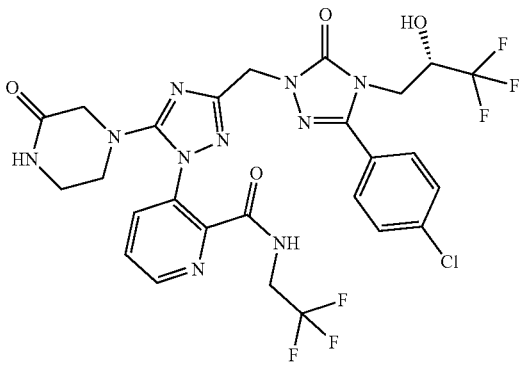 [SMILES: O=C1CN(c2nc(Cn3nc(-c4ccc(Cl)cc4)n(C[C@H](O)C(F)(F)F)c3=O)nn2-c2cccnc2C(=O)NCC(F)(F)F)CCN1]

A solution of 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-5-(3-oxopiperazin-1-yl)-1H-1,2,4-triazol-1-yl]pyridine-2-carboxylic acid (Example 20A, 33.0 mg, 54.3 µmol) in N,N-dimethylformamide (280 µl) was treated with HATU (31.0 mg, 81.4 µmol) and stirred 30 min at room temperature. 2,2,2-trifluoroethanamine (8.07 mg, 81.4 µmol) was then added followed by and N,N-diisopropylethylamine (38 µl, 220 µmol). The resulting mixture was stirred overnight at room temperature. Purification by preparative HPLC (Method 4) afforded 33.0 mg (88% of th.) of the title compound.

LC-MS (§ ESI pos): $R_t$=0.82 min; MS (ESIpos): m/z=689.2 [M+H]$^+$ $^1$H-NMR (400 MHz, DMSO-d6) δ [ppm]: 9.34 (t, 1H), 8.78 (dd, 1H), 8.15 (dd, 1H), 8.02-7.91 (m, 1H), 7.86-7.52 (m, 5H), 6.89 (d, 1H), 5.00-4.79 (m, 2H), 4.39-4.20 (m, 1H), 4.08-3.75 (m, 4H), 3.61-3.46 (m, 2H), 3.23-3.00 (m, 4H).

Example 510

3-{3-({3-(4-Chlorophenyl)-5-oxo-4-[(2S)-3,3,3-trifluoro-2-hydroxypropyl]-4,5-dihydro-1H-1,2,4-triazol-1-yl}methyl)-5-[(3-oxopiperazin-1-yl)carbonyl]-1H-1,2,4-triazol-1-yl}-N-(2,2,2-trifluoroethyl)pyridine-4-carboxamide

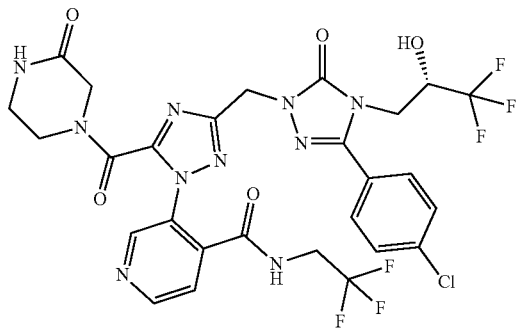 [SMILES: O=C1CN(C(=O)c2nc(Cn3nc(-c4ccc(Cl)cc4)n(C[C@H](O)C(F)(F)F)c3=O)nn2-c2cnccc2C(=O)NCC(F)(F)F)CCN1]

A solution of 3-{3-({3-(4-chlorophenyl)-5-oxo-4-[(2S)-3,3,3-trifluoro-2-hydroxypropyl]-4,5-dihydro-1H-1,2,4-triazol-1-yl}methyl)-5-[(3-oxopiperazin-1-yl)carbonyl]-1H-1,2,4-triazol-1-yl}pyridine-4-carboxylic acid (Example 26A, 60.0 mg, 94.3 µmol) in N,N-dimethylformamide (1.0 ml) was treated with HATU (53.8 mg, 142 µmol) and stirred 10 min at room temperature. 2,2,2-Trifluoroethanamine (11 µl, 140 µmol) was then added followed by and N,N-diisopropylethylamine (49 µl, 280 µmol). The resulting mixture was stirred 1 h at room temperature. Purification by preparative HPLC (Method 4) afforded 44.8 mg (66% of th.) of the title compound.

Mixture of 2 Conformers

LC-MS (Method 1): $R_t$=0.82 min; MS (ESIpos): m/z=717.1 [M+H]$^+$ $^1$H-NMR (400 MHz, DMSO-d6) δ [ppm]: 9.53-9.31 (m, 1H), 8.95-8.74 (m, 2H), 8.27-8.04 (m, 1H), 7.87-7.51 (m, 5H), 7.03-6.81 (m, 1H), 5.22-5.00 (m, 2H), 4.50-4.23 (m, 2H), 4.08-3.54 (m, 7H), 3.30-3.06 (m, 2H).

Example 511

3-{3-({3-(4-Chlorophenyl)-5-oxo-4-[(2S)-3,3,3-trifluoro-2-hydroxypropyl]-4,5-dihydro-1H-1,2,4-triazol-1-yl}methyl)-5-[(3-oxopiperazin-1-yl)carbonyl]-1H-1,2,4-triazol-1-yl}-N-(3,3,3-trifluoropropyl)pyridine-4-carboxamide

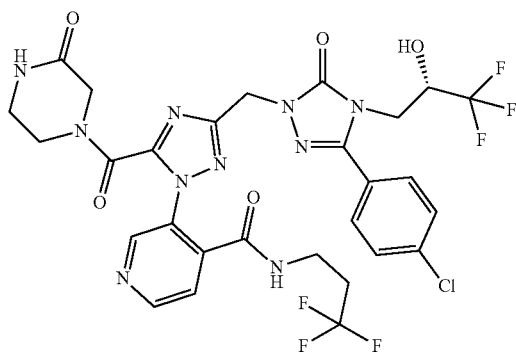 [SMILES: O=C1CN(C(=O)c2nc(Cn3nc(-c4ccc(Cl)cc4)n(C[C@H](O)C(F)(F)F)c3=O)nn2-c2cnccc2C(=O)NCCC(F)(F)F)CCN1]

A solution of 3-{3-({3-(4-chlorophenyl)-5-oxo-4-[(2S)-3,3,3-trifluoro-2-hydroxypropyl]-4,5-dihydro-1H-1,2,4-triazol-1-yl}methyl)-5-[(3-oxopiperazin-1-yl)carbonyl]-1H-1,2,4-triazol-1-yl}pyridine-4-carboxylic acid (Example 26A, 47.0 mg, 73.9 µmol) in N,N-dimethylformamide (780 µl) was treated with HATU (42.2 mg, 111 µmol) and stirred 10 min at room temperature. 3,3,3-Trifluoropropan-1-aminium chloride (16.6 mg, 111 µmol) was then added followed by and N,N-diisopropylethylamine (64 µl, 370 µmol). The resulting mixture was stirred 1 h at room temperature. Purification by preparative HPLC (Method 4) afforded 35.5 mg (66% of th.) of the title compound.

LC-MS (Method 1): $R_t$=0.84 min; MS (ESIpos): m/z=731.1 [M+H]$^+$ $^1$H-NMR (400 MHz, DMSO-d6) δ [ppm]: 9.04-8.72 (m, 3H), 8.28-8.03 (m, 1H), 7.87-7.53 (m, 5H), 7.03-6.82 (m, 1H), 5.28-5.01 (m, 2H), 4.49-4.17 (m, 2H), 4.08-3.55 (m, 5H), 3.40-3.08 (m, 4H, overlap with HDO peak), 2.48-2.23 (m, 2H, overlap with DMSO peak).

Example 512

2-{3-({3-(4-Chlorophenyl)-5-oxo-4-[(2S)-3,3,3-trifluoro-2-hydroxypropyl]-4,5-dihydro-1H-1,2,4-triazol-1-yl}methyl)-5-[(3-oxopiperazin-1-yl)carbonyl]-1H-1,2,4-triazol-1-yl}-N-(3,3,3-trifluoropropyl)pyridine-3-carboxamide

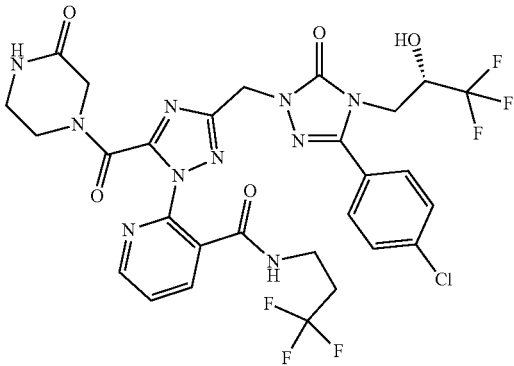 [SMILES: O=C1CN(C(=O)c2nc(Cn3nc(-c4ccc(Cl)cc4)n(C[C@H](O)C(F)(F)F)c3=O)nn2-c2ncccc2C(=O)NCCC(F)(F)F)CCN1]

A solution of 2-{3-({3-(4-chlorophenyl)-5-oxo-4-[(2S)-3,3,3-trifluoro-2-hydroxypropyl]-4,5-dihydro-1H-1,2,4-triazol-1-yl}methyl)-5-[(3-oxopiperazin-1-yl)carbonyl]-1H-1,2,4-triazol-1-yl}pyridine-3-carboxylic acid (Example 36A, 50.0 mg, 78.6 µmol) in N,N-dimethylformamide (830 µl) was treated with HATU (44.8 mg, 118 µmol) and stirred 10 min at room temperature. 3,3,3-Trifluoropropan-1-aminium chloride (17.6 mg, 118 µmol) was then added followed by and N,N-diisopropylethylamine (68 µl, 390 µmol). The resulting mixture was stirred 1 h at room temperature. Purification by preparative HPLC (Method 4) afforded 37.4 mg (65% of th.) of the title compound.

Mixture of Conformers

LC-MS (Method 2): $R_t$=1.61 min; MS (ESIpos): m/z=731.2 [M+H]$^+$ $^1$H-NMR (500 MHz, DMSO-d6) δ [ppm]: 8.86-8.73 (m, 1H), 8.66-8.49 (m, 1H), 8.22-8.01 (m, 2H), 7.81-7.56 (m, 5H), 6.99-6.85 (m, 1H), 5.22-4.98 (m, 2H), 4.42-4.22 (m, 1H), 4.14-3.64 (m, 6H), 3.43-3.08 (m 4H, overlap with HDO peak), 2.58-2.38 (m 2H, overlap with DMSO peak).

Example 513

2-{3-({3-(4-Chlorophenyl)-5-oxo-4-[(2S)-3,3,3-trifluoro-2-hydroxypropyl]-4,5-dihydro-1H-1,2,4-triazol-1-yl}methyl)-5-[(3-oxopiperazin-1-yl)carbonyl]-1H-1,2,4-triazol-1-yl}-N-cyclopropylpyridine-3-carboxamide

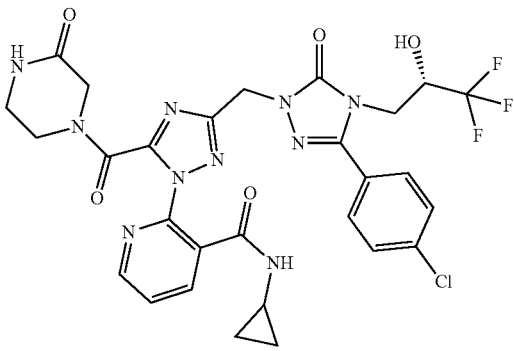 [SMILES: O=C1CN(C(=O)c2nc(Cn3nc(-c4ccc(Cl)cc4)n(C[C@H](O)C(F)(F)F)c3=O)nn2-c2ncccc2C(=O)NC2CC2)CCN1]

A solution of 2-{3-({3-(4-chlorophenyl)-5-oxo-4-[(2S)-3,3,3-trifluoro-2-hydroxypropyl]-4,5-dihydro-1H-1,2,4-triazol-1-yl}methyl)-5-[(3-oxopiperazin-1-yl)carbonyl]-1H-1,2,4-triazol-1-yl}pyridine-3-carboxylic acid (Example 36A, 50.0 mg, 78.6 µmol) in N,N-dimethylformamide (830 µl) was treated with HATU (44.8 mg, 118 µmol) and stirred 10 min at room temperature. Cyclopropanamine (8.2 µl, 120 µmol) was then added followed by and N,N-diisopropylethylamine (41 µl, 240 µmol). The resulting mixture was stirred 1 h at room temperature. Purification by preparative HPLC (Method 4) afforded 32.1 mg (60% of th.) of the title compound.

Mixture of Conformers

LC-MS (Method 2): $R_t$=1.47 min; MS (ESIpos): m/z=675.2 [M+H]$^+$ $^1$H-NMR (500 MHz, DMSO-d6) δ [ppm]: 8.70-8.42 (m, 2H), 8.27-7.95 (m, 2H), 7.82-7.53 (m, 5H), 6.99-6.84 (m, 1H), 5.23-5.03 (m, 2H), 4.41-4.24 (m, 1H), 4.19-3.65 (m, 6H), 3.29-3.06 (m, 2H), 2.68-2.59 (m, 1H), 0.70-0.34 (m, 4H).

Example 514

3-{3-({3-(4-Chlorophenyl)-5-oxo-4-[(2S)-3,3,3-trifluoro-2-hydroxypropyl]-4,5-dihydro-1H-1,2,4-triazol-1-yl}methyl)-5-[(3-oxopiperazin-1-yl)carbonyl]-1H-1,2,4-triazol-1-yl}-N-cyclopropylpyridine-4-carboxamide

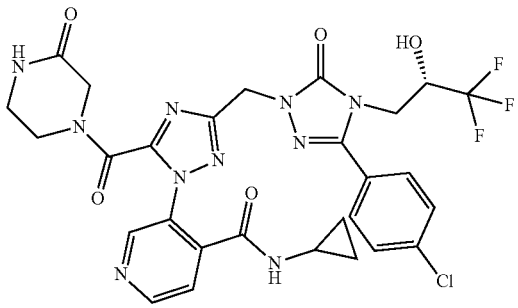 [SMILES: O=C1CN(C(=O)c2nc(Cn3nc(-c4ccc(Cl)cc4)n(C[C@H](O)C(F)(F)F)c3=O)nn2-c2cnccc2C(=O)NC2CC2)CCN1]

A solution of 3-{3-({3-(4-chlorophenyl)-5-oxo-4-[(2S)-3,3,3-trifluoro-2-hydroxypropyl]-4,5-dihydro-1H-1,2,4-triazol-1-yl}methyl)-5-[(3-oxopiperazin-1-yl)carbonyl]-1H-1,2,4-triazol-1-yl}pyridine-4-carboxylic acid (Example 26A, 70.0 mg, 110 µmol) in N,N-dimethylformamide (1.2 ml) was treated with HATU (62.8 mg, 165 µmol) and stirred 10 min at room temperature. Cyclopropanamine (11 µl, 170 µmol) was then added followed by and N,N-diisopropylethylamine (58 µl, 330 µmol). The resulting mixture was stirred overnight at room temperature. Purification by preparative HPLC (Method 4) afforded 48.4 mg (65% of th.) of the title compound.

Mixture of Conformers

LC-MS (Method 2): $R_t$=1.44 min; MS (ESIneg): m/z=673.2 [M-H]$^-$ $^1$H-NMR (400 MHz, DMSO-d6) δ [ppm]: 8.90-8.59 (m, 3H), 8.30-8.06 (m, 1H), 7.88-7.48 (m, 5H), 7.04-6.75 (m, 1H), 5.26-5.04 (m, 2H), 4.48-4.21 (m, 2H), 4.10-3.58 (m, 5H), 3.44-3.11 (m, 2H, overlap with HDO peak), 2.75-2.54 (m, 1H, overlap with DMSO peak), 0.66-0.28 (m, 4H).

Example 515

3-{3-({3-(4-Chlorophenyl)-5-oxo-4-[(2S)-3,3,3-trifluoro-2-hydroxypropyl]-4,5-dihydro-1H-1,2,4-triazol-1-yl}methyl)-5-[(3-oxopiperazin-1-yl)carbonyl]-1H-1,2,4-triazol-1-yl}-N-(1-methylcyclopropyl)pyridine-4-carboxamide

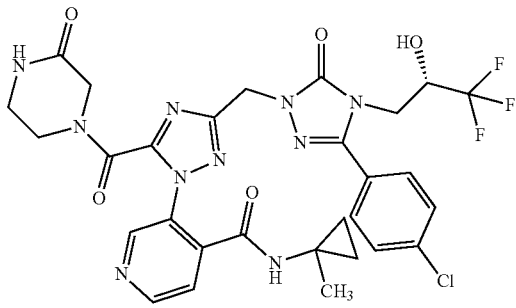 [SMILES: CC1(NC(=O)c2ccncc2-n2nc(Cn3nc(-c4ccc(Cl)cc4)n(C[C@H](O)C(F)(F)F)c3=O)nc2C(=O)N2CCNC(=O)C2)CC1]

A solution of 3-{3-({3-(4-chlorophenyl)-5-oxo-4-[(2S)-3,3,3-trifluoro-2-hydroxypropyl]-4,5-dihydro-1H-1,2,4-triazol-1-yl}methyl)-5-[(3-oxopiperazin-1-yl)carbonyl]-1H-1,2,4-triazol-1-yl}pyridine-4-carboxylic acid (Example 26A, 70.0 mg, 110 µmol) in N,N-dimethylformamide (1.2 ml) was treated with HATU (62.8 mg, 165 µmol) and stirred 10 min at room temperature. 1-Methylcyclopropanamine hydrochloride (1:1) (17.8 mg, 165 µmol) was then added followed by and N,N-diisopropylethylamine (96 µl, 550 µmol). The resulting mixture was stirred overnight at room temperature. Purification by preparative HPLC (Method 4) afforded 55.6 mg (73% of th.) of the title compound.
Mixture of Conformers LC-MS (Method 2): $R_t$=1.52 min; MS (ESIneg): m/z=687.2 [M−H]⁻

¹H-NMR (400 MHz, DMSO-d6) δ [ppm]: 8.84-8.67 (m, 3H), 8.28-8.05 (m, 1H), 7.82-7.51 (m, 5H), 7.04-6.84 (m, 1H), 5.21-5.04 (m, 2H), 4.52-4.23 (m, 2H), 4.06-3.60 (m, 5H), 3.28-3.11 (m, 2H, overlap with HDO peak), 1.22-1.05 (m, 3H), 0.58-0.36 (m, 4H).

Example 516

4-{[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1-(4-{[2-(methoxymethyl)pyrrolidin-1-yl]carbonyl}pyridin-3-yl)-1H-1,2,4-triazol-5-yl]carbonyl}piperazin-2-one (Diastereomeric Mixture)

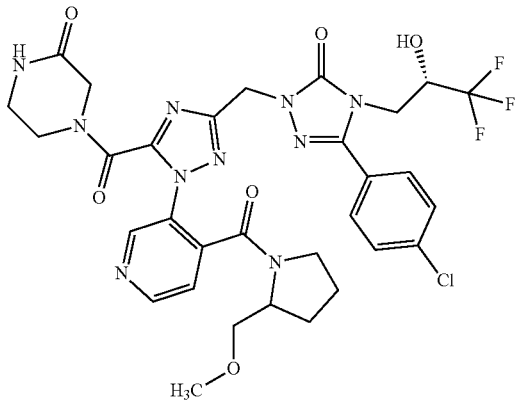 [SMILES: COCC1CCCN1C(=O)c1ccncc1-n1nc(Cn2nc(-c3ccc(Cl)cc3)n(C[C@H](O)C(F)(F)F)c2=O)nc1C(=O)N1CCNC(=O)C1]

A solution of 3-{3-({3-(4-chlorophenyl)-5-oxo-4-[(2S)-3,3,3-trifluoro-2-hydroxypropyl]-4,5-dihydro-1H-1,2,4-triazol-1-yl}methyl)-5-[(3-oxopiperazin-1-yl)carbonyl]-1H-1,2,4-triazol-1-yl}pyridine-4-carboxylic acid (Example 26A, 70.0 mg, 110 µmol) in N,N-dimethylformamide (1.2 ml) was treated with HATU (62.8 mg, 165 µmol) and stirred 10 min at room temperature. 2-(Methoxymethyl)pyrrolidine hydrochloride (1:1) (25.0 mg, 165 µmol) was then added followed by and N,N-diisopropylethylamine (96 µl, 550 µmol). The resulting mixture was stirred overnight at room temperature. Purification by preparative HPLC (Method 4) afforded 57.8 mg (72% of th.) of the title compound.

LC-MS (Method 2): $R_t$=1.58 min; MS (ESIpos): m/z=733.2 [M+H]⁺

¹H-NMR (400 MHz, DMSO-d6) δ [ppm]: 8.90-8.66 (m, 2H), 8.30-8.04 (m, 1H), 7.89-7.43 (m, 5H), 7.03-6.82 (m, 1H), 5.24-5.06 (m, 2H), 4.49-4.15 (m, 2H), 4.11-3.47 (m, 6H), 3.44-2.87 (m, 9H, overlap with HDO peak), 1.95-1.32 (m 4H).

Example 517

3-{3-({3-(4-Chlorophenyl)-5-oxo-4-[(2S)-3,3,3-trifluoro-2-hydroxypropyl]-4,5-dihydro-1H-1,2,4-triazol-1-yl}methyl)-5-[(3-oxopiperazin-1-yl)carbonyl]-1H-1,2,4-triazol-1-yl}-N-[2-fluorocyclopropyl]pyridine-4-carboxamide (Diastereomeric Mixture Cis Configured)

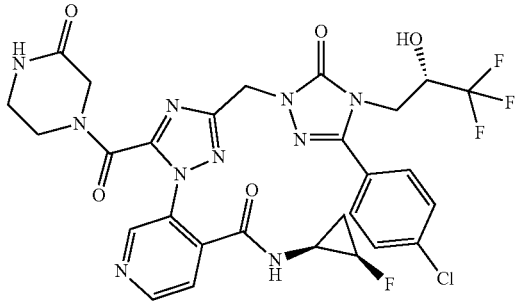

and

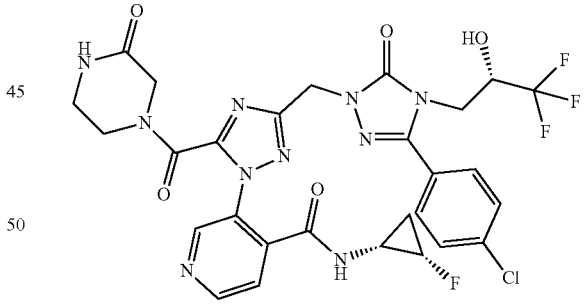

A solution of 3-{3-({3-(4-chlorophenyl)-5-oxo-4-[(2S)-3,3,3-trifluoro-2-hydroxypropyl]-4,5-dihydro-1H-1,2,4-triazol-1-yl}methyl)-5-[(3-oxopiperazin-1-yl)carbonyl]-1H-1,2,4-triazol-1-yl}pyridine-4-carboxylic acid (Example 26A, 70.0 mg, 110 µmol) in N,N-dimethylformamide (1.2 ml) was treated with HATU (62.8 mg, 165 µmol) and stirred 10 min at room temperature. 2-Fluorocyclopropanamine 4-methylbenzenesulfonate (1:1) (cis configured, 40.8 mg, 165 µmol) was then added followed by and N,N-diisopropylethylamine (58 µl, 330 µmol). The resulting mixture was stirred overnight at room temperature. Purification by preparative HPLC (Method 4) afforded 35.0 mg (46% of th.) of the title compound.

Mixture of Conformers

LC-MS (Method 2): R$_t$=1.39 min; MS (ESIpos): m/z=693.2 [M+H]$^+$ $^1$H-NMR (400 MHz, DMSO-d6) δ [ppm]: 8.97-8.68 (m, 3H), 8.27-8.08 (m, 1H), 7.87-7.51 (m, 5H), 7.04-6.83 (m, 1H), 5.31-5.01 (m, 2H), 4.84-4.14 (m, 3H), 4.09-3.53 (m, 5H), 3.32-3.12 (m, 2H, overlap with HDO peak), 2.79-2.57 (m, 1H), 1.15-0.79 (m, 2H).

Example 518

3-{3-({3-(4-Chlorophenyl)-5-oxo-4-[(2S)-3,3,3-trifluoro-2-hydroxypropyl]-4,5-dihydro-1H-1,2,4-triazol-1-yl}methyl)-5-[(1,1-dioxidothiomorpholin-4-yl)carbonyl]-1H-1,2,4-triazol-1-yl}-N-(2,2,2-trifluoroethyl)pyridine-4-carboxamide

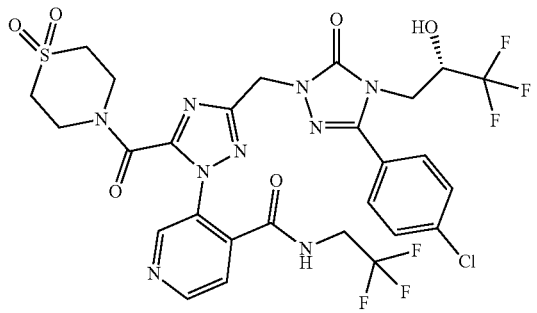 [SMILES: O=C(NCC(F)(F)F)c1ccncc1-n1nc(Cn2nc(-c3ccc(Cl)cc3)n(C[C@H](O)C(F)(F)F)c2=O)nc1C(=O)N1CCS(=O)(=O)CC1]

A solution of 3-{3-({3-(4-chlorophenyl)-5-oxo-4-[(2S)-3,3,3-trifluoro-2-hydroxypropyl]-4,5-dihydro-1H-1,2,4-triazol-1-yl}methyl)-5-[(1,1-dioxidothiomorpholin-4-yl)carbonyl]-1H-1,2,4-triazol-1-yl}pyridine-4-carboxylic acid (Example 28A, 70.0 mg, 104 μmol) in N,N-dimethylformamide (1.2 ml) was treated with HATU (59.5 mg, 156 μmol) and stirred 10 min at room temperature. 2,2,2-Trifluoroethanamine (12 μl, 160 μmol) was then added followed by and N,N-diisopropylethylamine (55 μl, 310 μmol). The resulting mixture was stirred overnight at room temperature. Purification by preparative HPLC (Method 4) afforded 66.5 mg (85% of th.) of the title compound.

LC-MS (Method 2): R$_t$=1.66 min; MS (ESIneg): m/z=750.1 [M−H]$^−$ $^1$H-NMR (400 MHz, DMSO-d6) δ [ppm]: 9.55-9.40 (m, 1H), 8.92-8.78 (m, 2H), 7.86-7.53 (m, 5H), 6.99-6.76 (m, 1H), 5.25-5.00 (m, 2H), 4.41-4.18 (m, 3H), 4.09-3.77 (m, 6H), 3.46-3.07 (m, 4H, overlap with HDO peak).

Example 519

3-{3-({3-(4-Chlorophenyl)-5-oxo-4-[(2S)-3,3,3-trifluoro-2-hydroxypropyl]-4,5-dihydro-1H-1,2,4-triazol-1-yl}methyl)-5-[(1,1-dioxidothiomorpholin-4-yl)carbonyl]-1H-1,2,4-triazol-1-yl}-N-(3,3,3-trifluoropropyl)pyridine-4-carboxamide

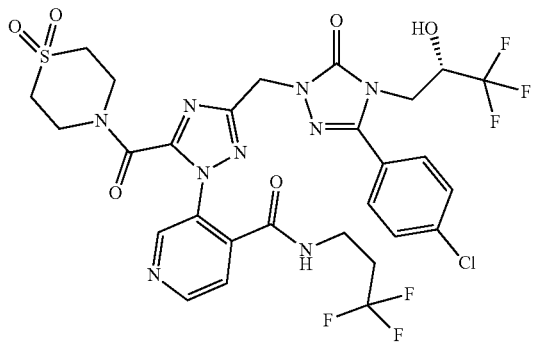 [SMILES: O=C(NCCC(F)(F)F)c1ccncc1-n1nc(Cn2nc(-c3ccc(Cl)cc3)n(C[C@H](O)C(F)(F)F)c2=O)nc1C(=O)N1CCS(=O)(=O)CC1]

A solution of 3-{3-({3-(4-chlorophenyl)-5-oxo-4-[(2S)-3,3,3-trifluoro-2-hydroxypropyl]-4,5-dihydro-1H-1,2,4-triazol-1-yl}methyl)-5-[(1,1-dioxidothiomorpholin-4-yl)carbonyl]-1H-1,2,4-triazol-1-yl}pyridine-4-carboxylic acid (Example 28A, 70.0 mg, 104 μmol) in N,N-dimethylformamide (1.2 ml) was treated with HATU (59.5 mg, 156 μmol) and stirred 10 min at room temperature. 3,3,3-Trifluoropropan-1-aminium chloride (23.4 mg, 156 μmol) was then added followed by and N,N-diisopropylethylamine (91 μl, 520 μmol). The resulting mixture was stirred overnight at room temperature. Purification by preparative HPLC (Method 4) afforded 42.1 mg (53% of th.) of the title compound.

LC-MS (Method 2): R$_t$=1.71 min; MS (ESIneg): m/z=764.1 [M−H]$^−$ $^1$H-NMR (400 MHz, DMSO-d6) δ [ppm]: 9.14-8.71 (m, 3H), 7.86-7.51 (m, 5H), 6.97-6.80 (m, 1H), 5.24-5.04 (m, 2H), 4.40-4.14 (m, 3H), 4.10-3.74 (m, 4H), 3.41-3.08 (m, 6H, overlap with HDO peak), 2.52-2.27 (m, 2H, overlap with DMSO peak).

Example 520

3-{3-({3-(4-Chlorophenyl)-5-oxo-4-[(2S)-3,3,3-trifluoro-2-hydroxypropyl]-4,5-dihydro-1H-1,2,4-triazol-1-yl}methyl)-5-[(1,1-dioxidothiomorpholin-4-yl)carbonyl]-1H-1,2,4-triazol-1-yl}-N-cyclopropylpyridine-4-carboxamide

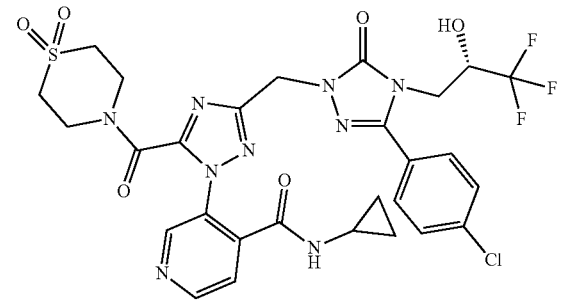 [SMILES: O=C(NC1CC1)c1ccncc1-n1nc(Cn2nc(-c3ccc(Cl)cc3)n(C[C@H](O)C(F)(F)F)c2=O)nc1C(=O)N1CCS(=O)(=O)CC1]

A solution of 3-{3-({3-(4-chlorophenyl)-5-oxo-4-[(2S)-3,3,3-trifluoro-2-hydroxypropyl]-4,5-dihydro-1H-1,2,4-triazol-1-yl}methyl)-5-[(1,1-dioxidothiomorpholin-4-yl)carbonyl]-1H-1,2,4-triazol-1-yl}pyridine-4-carboxylic acid (Example 28A, 70.0 mg, 104 μmol) in N,N-dimethylformamide (1.2 ml) was treated with HATU (59.5 mg, 156 μmol) and stirred 10 min at room temperature. Cyclopropanamine (11 μl, 160 μmol) was then added followed by and N,N-diisopropylethylamine (55 μl, 310 μmol). The resulting mixture was stirred overnight at room temperature. Purification by preparative HPLC (Method 4) afforded 46.4 mg (63% of th.) of the title compound.

LC-MS (Method 2): R$_t$=1.58 min; MS (ESIneg): m/z=708.1 [M−H]$^−$ $^1$H-NMR (400 MHz, DMSO-d6) δ [ppm]: 8.90-8.65 (m, 3H), 7.89-7.50 (m, 5H), 6.99-6.76 (m, 1H), 5.27-5.03 (m, 2H), 4.46-4.13 (m, 3H), 4.08-3.71 (m, 4H), 3.52-3.09 (m, 4H, overlap with HDO peak), 2.76-2.54 (m 1H, overlap with DMSO peak), 0.74-0.25 (m 4H).

Example 521

3-{3-({3-(4-Chlorophenyl)-5-oxo-4-[(2S)-3,3,3-trifluoro-2-hydroxypropyl]-4,5-dihydro-1H-1,2,4-triazol-1-yl}methyl)-5-[(1,1-dioxidothiomorpholin-4-yl)carbonyl]-1H-1,2,4-triazol-1-yl}-N-(1-methylcyclopropyl)pyridine-4-carboxamide

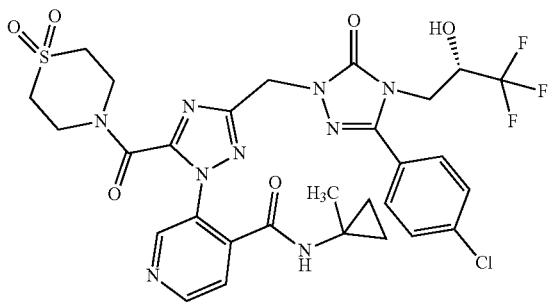 [SMILES: CC1(NC(=O)c2ccncc2-n2nc(Cn3nc(-c4ccc(Cl)cc4)n(C[C@H](O)C(F)(F)F)c3=O)nc2C(=O)N2CCS(=O)(=O)CC2)CC1]

A solution of 3-{3-({3-(4-chlorophenyl)-5-oxo-4-[(2S)-3,3,3-trifluoro-2-hydroxypropyl]-4,5-dihydro-1H-1,2,4-triazol-1-yl}methyl)-5-[(1,1-dioxidothiomorpholin-4-yl)carbonyl]-1H-1,2,4-triazol-1-yl}pyridine-4-carboxylic acid (Example 28A, 70.0 mg, 104 µmol) in N,N-dimethylformamide (1.2 ml) was treated with HATU (59.5 mg, 156 µmol) and stirred 10 min at room temperature. 1-Methylcyclopropanamine hydrochloride (1:1) (16.8 mg, 156 µmol) was then added followed by and N,N-diisopropylethylamine (91 µl, 520 µmol). The resulting mixture was stirred overnight at room temperature. Purification by preparative HPLC (Method 4) afforded 63.0 mg (83% of th.) of the title compound.

LC-MS (Method 2): R_t=1.66 min; MS (ESIneg): m/z=722.2 [M−H]⁻

¹H-NMR (400 MHz, DMSO-d6) δ [ppm]: 9.01-8.70 (m, 3H), 7.88-7.43 (m, 5H), 6.98-6.79 (m, 1H), 5.25-5.00 (m, 2H), 4.46-4.18 (m, 3H), 4.08-3.73 (m, 4H), 3.52-3.03 (m, 4H, overlap with HDO peak), 1.25-0.99 (m, 3H), 0.59-0.33 (m, 4H).

Example 522

5-(4-Chlorophenyl)-2-({5-[(1,1-dioxidothiomorpholin-4-yl)carbonyl]-1-(4-{[2-(methoxymethyl)pyrrolidin-1-yl]carbonyl}pyridin-3-yl)-1H-1,2,4-triazol-3-yl}methyl)-4-[(2S)-3,3,3-trifluoro-2-hydroxypropyl]-2,4-dihydro-3H-1,2,4-triazol-3-one
(Diastereomeric Mixture)

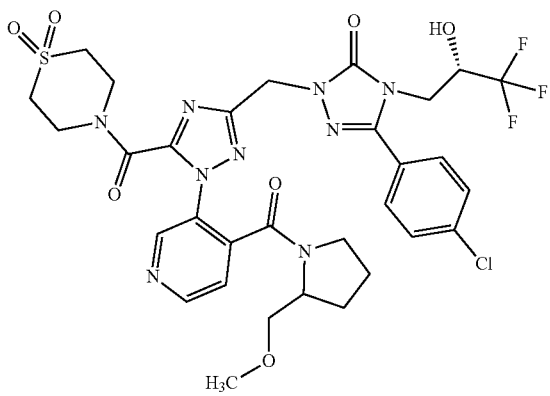 [SMILES: COCC1CCCN1C(=O)c1ccncc1-n1nc(Cn2nc(-c3ccc(Cl)cc3)n(C[C@H](O)C(F)(F)F)c2=O)nc1C(=O)N1CCS(=O)(=O)CC1]

A solution of 3-{3-({3-(4-chlorophenyl)-5-oxo-4-[(2S)-3,3,3-trifluoro-2-hydroxypropyl]-4,5-dihydro-1H-1,2,4-triazol-1-yl}methyl)-5-[(1,1-dioxidothiomorpholin-4-yl)carbonyl]-1H-1,2,4-triazol-1-yl}pyridine-4-carboxylic acid (Example 28A, 70.0 mg, 104 µmol) in N,N-dimethylformamide (1.2 ml) was treated with HATU (59.5 mg, 156 µmol) and stirred 10 min at room temperature. 2-(Methoxymethyl)pyrrolidine hydrochloride (1:1) (23.7 mg, 156 µmol) was then added followed by and N,N-diisopropylethylamine (91 µl, 520 µmol). The resulting mixture was stirred overnight at room temperature. Purification by preparative HPLC (Method 4) afforded 68.9 mg (86% of th.) of the title compound.

LC-MS (Method 2): R_t=1.72 min; MS (ESIpos): m/z=768.2 [M+H]⁺

¹H-NMR (400 MHz, DMSO-d6) δ [ppm]: 8.96-8.64 (m, 2H), 7.85-7.48 (m, 5H), 6.97-6.79 (m, 1H), 5.28-5.01 (m, 2H), 4.44-3.59 (m, 8H), 3.50-2.88 (m, 11H, overlap with HDO peak), 1.95-1.37 (m, 4H).

Example 523

3-{3-({3-(4-Chlorophenyl)-5-oxo-4-[(2S)-3,3,3-trifluoro-2-hydroxypropyl]-4,5-dihydro-1H-1,2,4-triazol-1-yl}methyl)-5-[(1,1-dioxidothiomorpholin-4-yl)carbonyl]-1H-1,2,4-triazol-1-yl}-N-[2-fluorocyclopropyl]pyridine-4-carboxamide
(Diastereomeric Mixture Cis Configured)

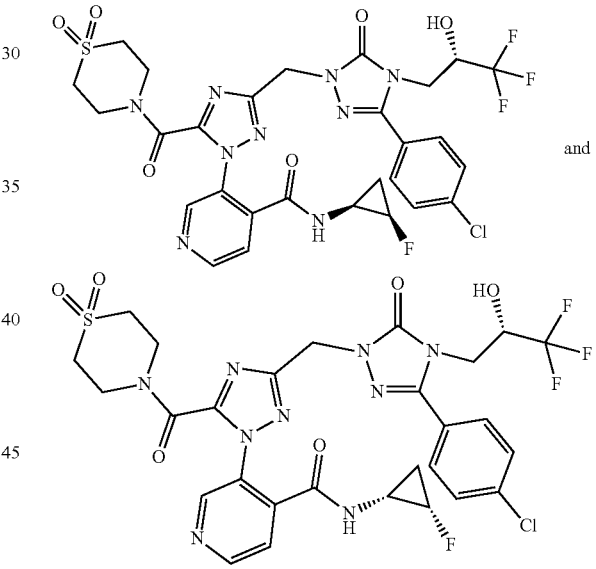

A solution of 3-{3-({3-(4-chlorophenyl)-5-oxo-4-[(2S)-3,3,3-trifluoro-2-hydroxypropyl]-4,5-dihydro-1H-1,2,4-triazol-1-yl}methyl)-5-[(1,1-dioxidothiomorpholin-4-yl)carbonyl]-1H-1,2,4-triazol-1-yl}pyridine-4-carboxylic acid (Example 28A, 70.0 mg, 104 µmol) in N,N-dimethylformamide (1.2 ml) was treated with HATU (59.5 mg, 156 µmol) and stirred 10 min at room temperature. 2-Fluorocyclopropanamine 4-methylbenzenesulfonate (1:1) (cis configured, 38.7 mg, 156 µmol) was then added followed by and N,N-diisopropylethylamine (55 µl, 310 µmol). The resulting mixture was stirred overnight at room temperature. Purification by preparative HPLC (Method 4) afforded 33.6 mg (44% of th.) of the title compound.

LC-MS (Method 2): R_t=1.53 min; MS (ESIpos): m/z=728.1 [M+H]⁺

¹H-NMR (400 MHz, DMSO-d6) δ [ppm]: 9.09-8.65 (m, 3H), 7.91-7.49 (m, 5H), 6.97-6.80 (m, 1H), 5.26-5.00 (m, 2H), 4.83-4.50 (m, 1H), 4.41-3.75 (m, 7H), 3.49-3.10 (m, 4H, overlap with HDO peak), 2.75-2.57 (m 1H, overlap with DMSO peak), 1.16-0.79 (m 2H).

Example 524

2-{3-({3-(4-Chlorophenyl)-5-oxo-4-[(2S)-3,3,3-trifluoro-2-hydroxypropyl]-4,5-dihydro-1H-1,2,4-triazol-1-yl}methyl)-5-[(3-oxopiperazin-1-yl)carbonyl]-1H-1,2,4-triazol-1-yl}-N-(2,2,2-trifluoroethyl)pyridine-3-carboxamide

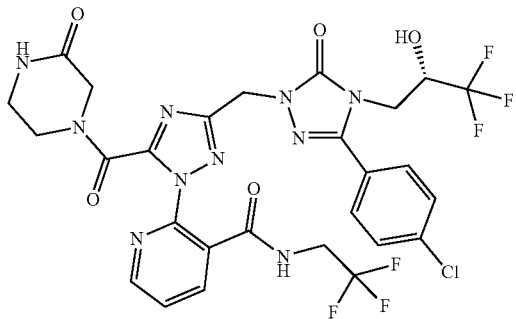 [SMILES: O=C1CN(C(=O)c2nc(Cn3nc(-c4ccc(Cl)cc4)n(C[C@H](O)C(F)(F)F)c3=O)nn2-c2ncccc2C(=O)NCC(F)(F)F)CCN1]

A solution of 2-{3-({3-(4-chlorophenyl)-5-oxo-4-[(2S)-3,3,3-trifluoro-2-hydroxypropyl]-4,5-dihydro-1H-1,2,4-triazol-1-yl}methyl)-5-[(3-oxopiperazin-1-yl)carbonyl]-1H-1,2,4-triazol-1-yl}pyridine-3-carboxylic acid (Example 36A, 50.0 mg, 78.6 µmol) in N,N-dimethylformamide (830 µl) was treated with HATU (44.8 mg, 118 µmol) and stirred 10 min at room temperature. 2,2,2-Trifluoroethanamine (9.4 µl, 120 µmol) was then added followed by and N,N-diisopropylethylamine (41 µl, 240 µmol). The resulting mixture was stirred 1 h at room temperature. Purification by preparative HPLC (Method 4) afforded 35.6 mg (63% of th.) of the title compound.
Mixture of 2 Conformers
LC-MS (Method 2): R$_f$=1.57 min; MS (ESIpos): m/z=717.2 [M+H]$^+$
$^1$H-NMR (500 MHz, DMSO-d6) δ [ppm]: 9.36-9.13 (m, 1H), 8.69-8.51 (m, 1H), 8.26-8.01 (m, 2H), 7.85-7.52 (m, 5H), 6.92 (dd, 1H), 5.19-5.00 (m, 2H), 4.43-4.22 (m, 1H), 4.17-3.65 (m, 8H), 3.28-3.07 (m, 2H, overlap with HDO peak).

Example 525

2-{3-({3-(4-Chlorophenyl)-5-oxo-4-[(2S)-3,3,3-trifluoro-2-hydroxypropyl]-4,5-dihydro-1H-1,2,4-triazol-1-yl}methyl)-5-[(3-oxopiperazin-1-yl)carbonyl]-1H-1,2,4-triazol-1-yl}-N-(1-methylcyclopropyl)pyridine-3-carboxamide

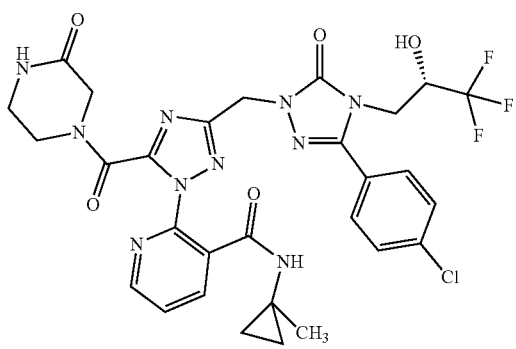 [SMILES: CC1(NC(=O)c2cccnc2-n2nc(Cn3nc(-c4ccc(Cl)cc4)n(C[C@H](O)C(F)(F)F)c3=O)nc2C(=O)N2CCNC(=O)C2)CC1]

A solution of 2-{3-({3-(4-chlorophenyl)-5-oxo-4-[(2S)-3,3,3-trifluoro-2-hydroxypropyl]-4,5-dihydro-1H-1,2,4-triazol-1-yl}methyl)-5-[(3-oxopiperazin-1-yl)carbonyl]-1H-1,2,4-triazol-1-yl}pyridine-3-carboxylic acid (Example 36A, 50.0 mg, 78.6 µmol) in N,N-dimethylformamide (1.0 ml) was treated with HATU (44.8 mg, 118 µmol) and stirred to 0 min at room temperature. 1-Methylcyclopropanamine hydrochloride (1:1) (12.7 mg, 118 µmol) was then added followed by and N,N-diisopropylethylamine (68 µl, 390 µmol). The resulting mixture was stirred overnight at room temperature. Purification by preparative HPLC (Method 4) afforded 32.7 mg (60% of th.) of the title compound.
Mixture of Conformers
LC-MS (Method 1): R$_f$=0.84 min; MS (ESIpos): m/z=689.1 [M+H]$^+$
$^1$H-NMR (400 MHz, DMSO-d6) δ [ppm]: 8.72-8.41 (m, 2H), 8.27-7.90 (m, 2H), 7.85-7.49 (m, 5H), 7.04-6.80 (m, 1H), 5.25-4.96 (m, 2H), 4.42-4.19 (m, 1H), 4.15-3.63 (m, 6H), 3.30-2.99 (m, 2H, overlap with HDO peak), 1.40-1.15 (m, 3H), 0.81-0.37 (m, 4H).

Example 526

4-{[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1-(3-{[2-(methoxymethyl)pyrrolidin-1-yl]carbonyl}pyridin-2-yl)-1H-1,2,4-triazol-5-yl]carbonyl}piperazin-2-one (Diastereomeric Mixture)

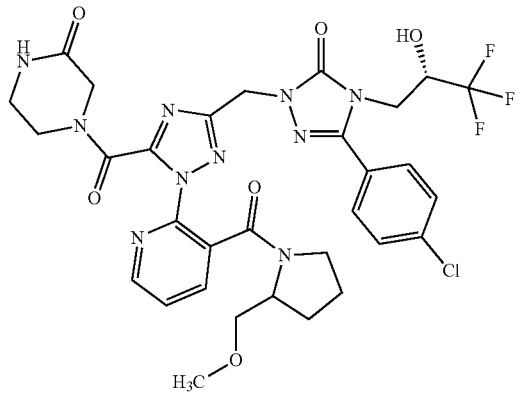 [SMILES: COCC1CCCN1C(=O)c1cccnc1-n1nc(Cn2nc(-c3ccc(Cl)cc3)n(C[C@H](O)C(F)(F)F)c2=O)nc1C(=O)N1CCNC(=O)C1]

A solution of 2-{3-({3-(4-chlorophenyl)-5-oxo-4-[(2S)-3,3,3-trifluoro-2-hydroxypropyl]-4,5-dihydro-1H-1,2,4-triazol-1-yl}methyl)-5-[(3-oxopiperazin-1-yl)carbonyl]-1H-1,2,4-triazol-1-yl}pyridine-3-carboxylic acid (Example 36A, 50.0 mg, 78.6 µmol) in N,N-dimethylformamide (1.0 ml) was treated with HATU (44.8 mg, 118 µmol) and stirred 10 min at room temperature. 2-(Methoxymethyl)pyrrolidine hydrochloride (1:1) (17.9 mg, 118 µmol) was then added followed by and N,N-diisopropylethylamine (68 µl, 390 µmol). The resulting mixture was stirred overnight at room temperature. Purification by preparative HPLC (Method 4) afforded 37.7 mg (65% of th.) of the title compound.

Mixture of Conformers

LC-MS (Method 1): $R_t$=0.87 min; MS (ESIpos): m/z=733.1 [M+H]$^+$ $^1$H-NMR (400 MHz, DMSO-d6) δ [ppm]: 8.61-8.40 (m, 1H), 8.28-7.97 (m, 2H), 7.87-7.52 (m, 5H), 7.02-6.81 (m, 1H), 5.23-5.01 (m, 2H), 4.42-4.21 (m, 1H), 4.17-3.39 (m, 8H), 3.37-2.82 (m, 8H, overlap with HDO peak), 1.99-1.32 (m, 4H).

Example 527

2-{3-({3-(4-chlorophenyl)-5-oxo-4-[(2S)-3,3,3-trifluoro-2-hydroxypropyl]-4,5-dihydro-1H-1,2,4-triazol-1-yl}methyl)-5-[(3-oxopiperazin-1-yl)carbonyl]-1H-1,2,4-triazol-1-yl}-N-[2-fluorocyclopropyl]pyridine-3-carboxamide (Diastereomeric Mixture Cis Configured)

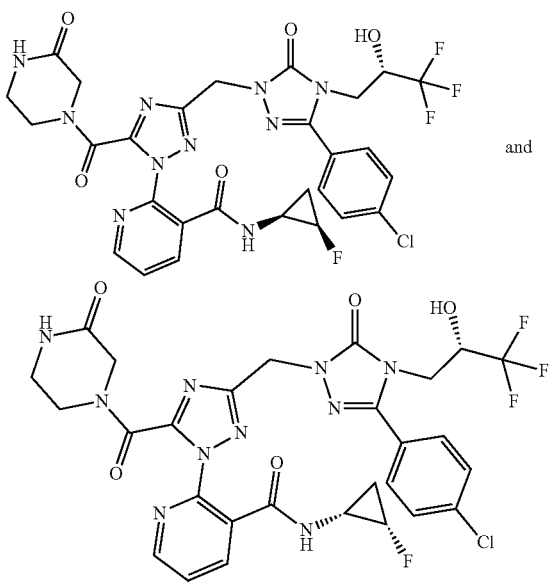

and

A solution of 2-{3-({3-(4-chlorophenyl)-5-oxo-4-[(2S)-3,3,3-trifluoro-2-hydroxypropyl]-4,5-dihydro-1H-1,2,4-triazol-1-yl}methyl)-5-[(3-oxopiperazin-1-yl)carbonyl]-1H-1,2,4-triazol-1-yl}pyridine-3-carboxylic acid (Example 36A; 70.0 mg, 110 μmol) in N,N-dimethylformamide DMF (1.2 ml, 16 mmol) was treated with HATU (62.8 mg, 165 μmol) and stirred 10 min at room temperature. 2-Fluorocyclopropanamine 4-methylbenzenesulfonate (1:1) (cis configured, 40.8 mg, 165 μmol) was then added followed by and N,N-diisopropylethylamine (96 μl, 550 μmol). The resulting mixture was stirred overnight at room temperature. Purification by preparative HPLC (Method 4) afforded 40.2 mg (48% of th.) of the title compound.

Mixture of Conformers

LC-MS (Method 2): $R_t$=1.42 min MS (ESIpos): m/z=693.2 [M+H]$^+$ $^1$H-NMR (400 MHz, DMSO-d6) δ [ppm]: 8.89-8.44 (m, 2H), 8.31-7.97 (m, 2H), 7.91-7.51 (m, 5H), 7.07-6.78 (m, 1H), 5.13 (s, 2H), 4.80-4.49 (m, 1H), 4.45-4.23 (m, 1H), 4.21-3.57 (m, 6H), 3.29-3.02 (m, 2H), 2.77-2.61 (m, 1H), 1.11-0.88 (m, 2H).

Example 528

2-{3-({3-(4-Chlorophenyl)-5-oxo-4-[(2S)-3,3,3-trifluoro-2-hydroxypropyl]-4,5-dihydro-1H-1,2,4-triazol-1-yl}methyl)-5-[(1,1-dioxidothiomorpholin-4-yl)carbonyl]-1H-1,2,4-triazol-1-yl}-N-(2,2,2-trifluoroethyl)pyridine-3-carboxamide

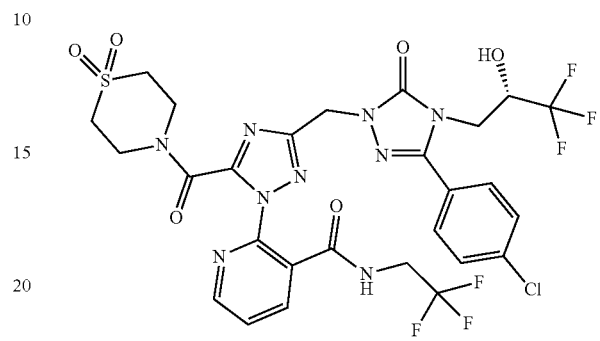

A solution of 2-{3-({3-(4-chlorophenyl)-5-oxo-4-[(2S)-3,3,3-trifluoro-2-hydroxypropyl]-4,5-dihydro-1H-1,2,4-triazol-1-yl}methyl)-5-[(1,1-dioxidothiomorpholin-4-yl)carbonyl]-1H-1,2,4-triazol-1-yl}pyridine-3-carboxylic acid (Example 38A, 70.0 mg, 104 μmol) in N,N-dimethylformamide (1.2 ml) was treated with HATU (59.5 mg, 156 μmol) and stirred 10 min at room temperature. 2,2,2-Trifluoroethanamine (12 μl, 160 μmol) was then added followed by and N,N-diisopropylethylamine (55 μl, 310 μmol). The resulting mixture was stirred overnight at room temperature. Purification by preparative HPLC (Method 4) afforded 65.3 mg (83% of th.) of the title compound.

LC-MS (Method 1): $R_t$=0.94 min; MS (ESIpos): m/z=752.0 [M+H]$^+$ $^1$H-NMR (400 MHz, DMSO-d6) δ [ppm]: 9.41-9.24 (m, 1H), 8.70-8.56 (m, 1H), 8.16-8.07 (m, 1H), 7.85-7.55 (m, 5H), 6.98-6.79 (m, 1H), 5.20-4.97 (m, 2H), 4.41-4.20 (m, 1H), 4.13-3.69 (m, 8H), 3.30-3.11 (m, 4H, overlap with HDO peak).

Example 529

2-{3-({3-(4-Chlorophenyl)-5-oxo-4-[(2S)-3,3,3-trifluoro-2-hydroxypropyl]-4,5-dihydro-1H-1,2,4-triazol-1-yl}methyl)-5-[(1,1-dioxidothiomorpholin-4-yl)carbonyl]-1H-1,2,4-triazol-1-yl}-N-(3,3,3-trifluoropropyl)pyridine-3-carboxamide

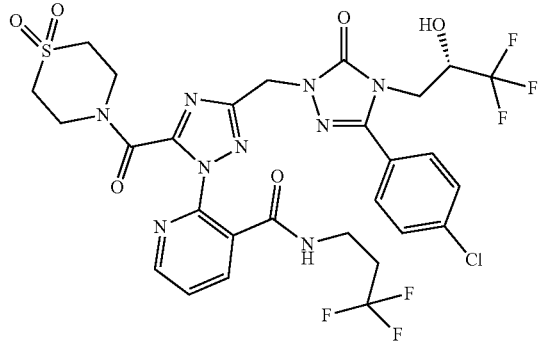 [SMILES: O=C(NCCC(F)(F)F)c1cccnc1-n1nc(Cn2nc(-c3ccc(Cl)cc3)n(C[C@H](O)C(F)(F)F)c2=O)nc1C(=O)N1CCS(=O)(=O)CC1]

A solution of 2-{3-({3-(4-chlorophenyl)-5-oxo-4-[(2S)-3,3,3-trifluoro-2-hydroxypropyl]-4,5-dihydro-1H-1,2,4-triazol-1-yl}methyl)-5-[(1,1-dioxidothiomorpholin-4-yl)carbonyl]-1H-1,2,4-triazol-1-yl}pyridine-3-carboxylic acid (Example 38A, 70.0 mg, 104 μmol) in N,N-dimethylformamide (1.2 ml) was treated with HATU (59.5 mg, 156 μmol) and stirred 10 min at room temperature. 3,3,3-Trifluoropropan-1-aminium chloride (23.4 mg, 156 μmol) was then added followed by and N,N-diisopropylethylamine (91 μl, 520 μmol). The resulting mixture was stirred overnight at room temperature. Purification by preparative HPLC (Method 4) afforded 59.8 mg (75% of th.) of the title compound.

LC-MS (Method 1): $R_t$=0.96 min; MS (ESIpos): m/z=766.0 [M+H]$^+$ $^1$H-NMR (400 MHz, DMSO-d6) δ [ppm]: 8.95-8.76 (m, 1H), 8.67-8.54 (m, 1H), 8.15-8.02 (m, 1H), 7.81-7.53 (m, 5H), 7.02-6.80 (m, 1H), 5.21-4.99 (m, 2H), 4.40-4.20 (m, 1H), 4.14-3.73 (m, 6H), 3.47-3.10 (m, 6H, overlap with HDO peak), 2.62-2.39 (m, 2H, overlap with DMSO peak).

Example 530

2-{3-({3-(4-Chlorophenyl)-5-oxo-4-[(2S)-3,3,3-trifluoro-2-hydroxypropyl]-4,5-dihydro-1H-1,2,4-triazol-1-yl}methyl)-5-[(1,1-dioxidothiomorpholin-4-yl)carbonyl]-1H-1,2,4-triazol-1-yl}-N-cyclopropylpyridine-3-carboxamide

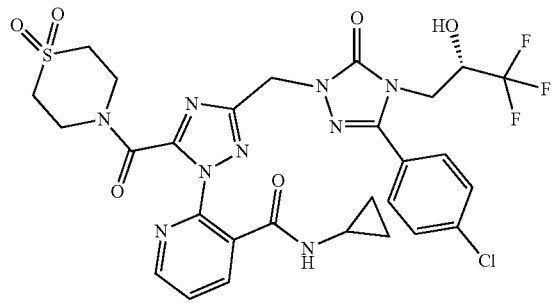 [SMILES: O=C(NC1CC1)c1cccnc1-n1nc(Cn2nc(-c3ccc(Cl)cc3)n(C[C@H](O)C(F)(F)F)c2=O)nc1C(=O)N1CCS(=O)(=O)CC1]

A solution of 2-{3-({3-(4-chlorophenyl)-5-oxo-4-[(2S)-3,3,3-trifluoro-2-hydroxypropyl]-4,5-dihydro-1H-1,2,4-triazol-1-yl}methyl)-5-[(1,1-dioxidothiomorpholin-4-yl)carbonyl]-1H-1,2,4-triazol-1-yl}pyridine-3-carboxylic acid (Example 38A, 70.0 mg, 104 μmol) in N,N-dimethylformamide (1.2 ml) was treated with HATU (59.5 mg, 156 μmol) and stirred 10 min at room temperature. Cyclopropanamine (11 μl, 160 μmol) was then added followed by and N,N-diisopropylethylamine (55 μl, 310 μmol). The resulting mixture was stirred overnight at room temperature. Purification by preparative HPLC (Method 4) afforded 38.6 mg (52% of th.) of the title compound.

LC-MS (Method 1): $R_t$=0.89 min; MS (ESIpos): m/z=710.0 [M+H]$^+$ $^1$H-NMR (400 MHz, DMSO-d6) δ [ppm]: 8.77-8.49 (m, 2H), 8.12-7.95 (m, 1H), 7.88-7.52 (m, 5H), 7.00-6.81 (m, 1H), 5.28-4.95 (m, 2H), 4.45-4.21 (m, 1H), 4.17-3.70 (m, 6H), 3.46-3.10 (m, 4H, overlap with HDO peak), 2.78-2.56 (m, 1H), 0.68-0.34 (m, 4H).

Example 531

2-{3-({3-(4-Chlorophenyl)-5-oxo-4-[(2S)-3,3,3-trifluoro-2-hydroxypropyl]-4,5-dihydro-1H-1,2,4-triazol-1-yl}methyl)-5-[(1,1-dioxidothiomorpholin-4-yl)carbonyl]-1H-1,2,4-triazol-1-yl}-N-(1-methylcyclopropyl)pyridine-3-carboxamide

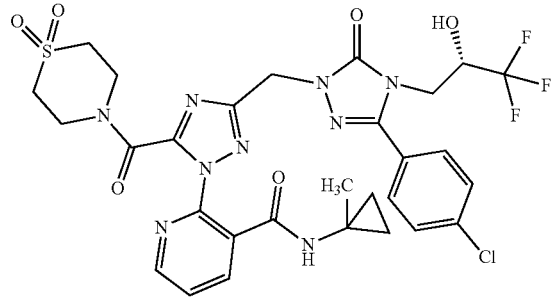 [SMILES: CC1(NC(=O)c2cccnc2-n2nc(Cn3nc(-c4ccc(Cl)cc4)n(C[C@H](O)C(F)(F)F)c3=O)nc2C(=O)N2CCS(=O)(=O)CC2)CC1]

A solution of 2-{3-({3-(4-chlorophenyl)-5-oxo-4-[(2S)-3,3,3-trifluoro-2-hydroxypropyl]-4,5-dihydro-1H-1,2,4-triazol-1-yl}methyl)-5-[(1,1-dioxidothiomorpholin-4-yl)carbonyl]-1H-1,2,4-triazol-1-yl}pyridine-3-carboxylic acid (Example 38A, 70.0 mg, 104 μmol) in N,N-dimethylformamide (1.2 ml) was treated with HATU (59.5 mg, 156 μmol) and stirred 10 min at room temperature. 1-Methylcyclopropanamine hydrochloride (1:1) (16.8 mg, 156 μmol) was then added followed by and N,N-diisopropylethylamine (91 μl, 520 μmol). The resulting mixture was stirred overnight at room temperature. Purification by preparative HPLC (Method 4) afforded 54.5 mg (72% of th.) of the title compound.

LC-MS (Method 1): $R_t$=0.92 min; MS (ESIpos): m/z=724.0 [M+H]$^+$ $^1$H-NMR (400 MHz, DMSO-d6) δ [ppm]: 8.85-8.71 (m, 1H), 8.63-8.48 (m, 1H), 8.09-7.91 (m, 1H), 7.81-7.52 (m, 5H), 6.99-6.82 (m, 1H), 5.23-4.98 (m, 2H), 4.42-4.17 (m, 1H), 4.13-3.73 (m, 6H), 3.30-3.10 (m 4H, overlap with HDO peak), 1.27 (s, 3H), 0.79-0.37 (m 4H).

Example 532

5-(4-Chlorophenyl)-2-({5-[(1,1-dioxidothiomorpholin-4-yl)carbonyl]-1-(3-{[2-(methoxymethyl)pyrrolidin-1-yl]carbonyl}pyridin-2-yl)-1H-1,2,4-triazol-3-yl}methyl)-4-[(2S)-3,3,3-trifluoro-2-hydroxypropyl]-2,4-dihydro-3H-1,2,4-triazol-3-one (Diastereomeric Mixture)

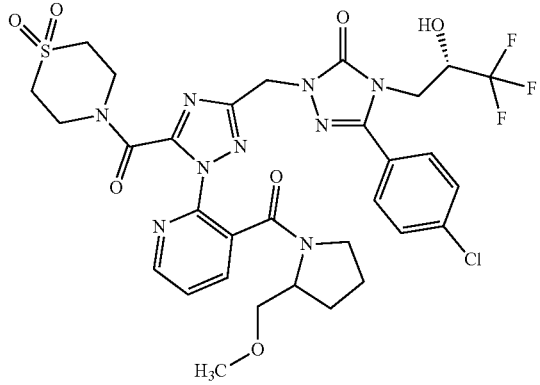 [SMILES: COCC1CCCN1C(=O)c1cccnc1-n1nc(Cn2nc(-c3ccc(Cl)cc3)n(C[C@H](O)C(F)(F)F)c2=O)nc1C(=O)N1CCS(=O)(=O)CC1]

A solution of 2-{3-({3-(4-chlorophenyl)-5-oxo-4-[(2S)-3,3,3-trifluoro-2-hydroxypropyl]-4,5-dihydro-1H-1,2,4-triazol-1-yl}methyl)-5-[(1,1-dioxidothiomorpholin-4-yl)carbonyl]-1H-1,2,4-triazol-1-yl}pyridine-3-carboxylic acid (Example 38A, 70.0 mg, 104 µmol) in N,N-dimethylformamide (1.2 ml) was treated with HATU (59.5 mg, 156 µmol) and stirred 10 min at room temperature. 2-(Methoxymethyl)pyrrolidine hydrochloride (1:1) (23.7 mg, 156 µmol) was then added followed by and N,N-diisopropylethylamine (91 µl, 520 µmol). The resulting mixture was stirred overnight at room temperature. Purification by preparative HPLC (Method 4) afforded 65.2 mg (81% of th.) of the title compound.

LC-MS (Method 1): $R_t$=0.95 min; MS (ESIpos): m/z=768.0 [M+H]$^+$ $^1$H-NMR (400 MHz, DMSO-d6) δ [ppm]: 8.58-8.50 (m, 1H), 8.16-8.00 (m, 1H), 7.80-7.51 (m, 5H), 7.04-6.77 (m, 1H), 5.24-5.02 (m, 2H), 4.46-4.21 (m, 1H), 4.20-3.74 (m, 6H), 3.65-2.85 (m, 12H, overlap with HDO peak), 2.05-1.38 (m, 4H).

Example 533

2-{3-({3-(4-Chlorophenyl)-5-oxo-4-[(2S)-3,3,3-trifluoro-2-hydroxypropyl]-4,5-dihydro-1H-1,2,4-triazol-1-yl}methyl)-5-[(1,1-dioxidothiomorpholin-4-yl)carbonyl]-1H-1,2,4-triazol-1-yl}-N-[2-fluorocyclopropyl]pyridine-3-carboxamide (Diastereomeric Mixture Cis Configured)

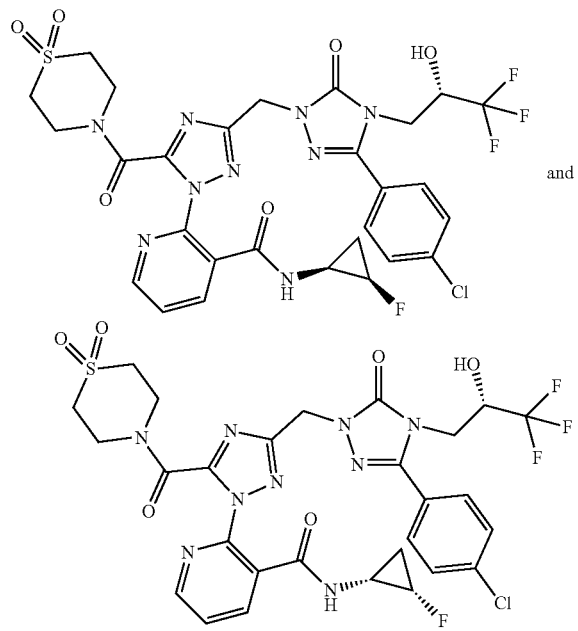

A solution of 2-{3-({3-(4-chlorophenyl)-5-oxo-4-[(2S)-3,3,3-trifluoro-2-hydroxypropyl]-4,5-dihydro-1H-1,2,4-triazol-1-yl}methyl)-5-[(1,1-dioxidothiomorpholin-4-yl)carbonyl]-1H-1,2,4-triazol-1-yl}pyridine-3-carboxylic acid (Example 38A, 70.0 mg, 104 µmol) in N,N-dimethylformamide (1.2 ml) was treated with HATU (59.5 mg, 156 µmol) and stirred 10 min at room temperature. 2-Fluorocyclopropanamine 4-methylbenzenesulfonate (1:1) (cis configured, 38.7 mg, 156 µmol) was then added followed by and N,N-diisopropylethylamine (91 µl, 520 µmol). The resulting mixture was stirred overnight at room temperature. Purification by preparative HPLC (Method 4) afforded 30.8 mg (41% of th.) of the title compound.

LC-MS (Method 2): $R_t$=1.57 min; MS (ESIpos): m/z=728.1 [M+H]$^+$ $^1$H-NMR (400 MHz, DMSO-d6) δ [ppm]: 8.84 (br d, 1H), 8.63 (dd, 1H), 8.08 (dd, 1H), 7.82-7.54 (m, 5H), 6.90 (d, 1H), 5.22-4.98 (m, 2H), 4.82-4.49 (m, 1H), 4.43-4.22 (m, 1H), 4.19-3.72 (m, 6H), 3.34-3.12 (m, 4H, overlap with HDO peak), 2.73-2.58 (m, 1H), 1.16-0.83 (m, 2H).

Example 534

3-{5-[(2-Amino-2-methylpropyl)carbamoyl]-3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl}-N-(2,2,2-trifluoroethyl)pyridine-4-carboxamide

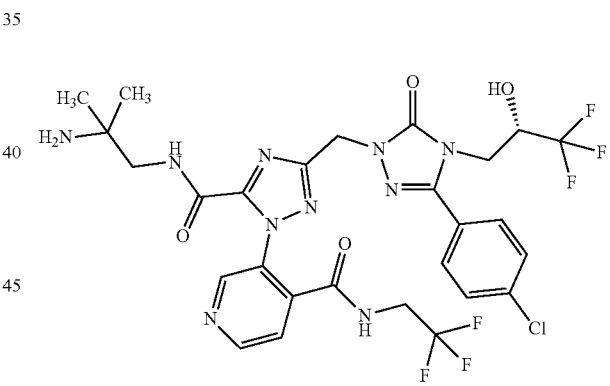

A solution of 3-{5-[(2-amino-2-methylpropyl)carbamoyl]-3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl}pyridine-4-carboxylic acid (Example 30A, 70.0 mg, 112 µmol) in N,N-dimethylformamide (750 µl) was treated with HATU (64.0 mg, 168 µmol) and stirred 10 min at room temperature. 2,2,2-trifluoroethanamine (13 µl, 170 µmol) was then added followed by and N,N-diisopropylethylamine (59 µl, 340 µmol). The resulting mixture was stirred overnight at room temperature. Purification by preparative HPLC (Method 4) afforded 20.0 mg (25% of th.) of the title compound.

LC-MS (Method 2): $R_t$=1.23 min; MS (ESIpos): m/z=705.2 [M+H]$^+$

¹H-NMR (400 MHz, DMSO-d6) δ [ppm]: 9.19-8.54 (m, 3H), 7.84-7.53 (m, 5H), 7.05 (br s, 1H), 5.11 (s, 2H), 4.40-4.20 (m, 1H), 4.09-3.71 (m, 4H), 3.16 (s, 2H), 1.19-0.93 (m, 6H), 3 hydrogens not visible.

Example 535

3-{5-[(2-amino-2-methylpropyl)carbamoyl]-3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl}-N-[2-fluorocyclopropyl]pyridine-4-carboxamide
(Diastereomeric Mixture Cis Configured)

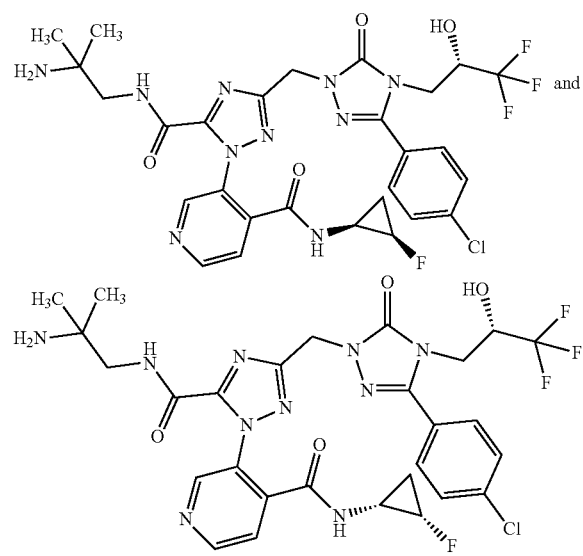

A solution of 3-{5-[(2-amino-2-methylpropyl)carbamoyl]-3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl}pyridine-4-carboxylic acid (Example 30A, 70.0 mg, 112 µmol) in N,N-dimethylformamide (750 µl) was treated with HATU (64.0 mg, 168 µmol) and stirred 10 min at room temperature. 2-Fluorocyclopropanamine 4-methylbenzenesulfonate (1:1) (cis configured, 41.6 mg, 168 µmol) was then added followed by and N,N-diisopropylethylamine (98 µl, 560 µmol). The resulting mixture was stirred overnight at room temperature. Purification by preparative HPLC (Method 4) afforded 24.6 mg (32% of th.) of the title compound.

LC-MS (Method 2): $R_t$=1.14 min; MS (ESIpos): m/z=681.2 [M+H]⁺

¹H-NMR (400 MHz, DMSO-d6) δ [ppm]: 9.24-8.54 (m, 3H), 7.92-7.45 (m, 5H), 7.02 (br s, 1H), 5.29-4.98 (m, 2H), 4.80-4.43 (m, 1H), 4.38-4.17 (m, 1H), 4.07-3.73 (m, 2H), 3.15 (s, 2H), 2.73-2.41 (m, 1H, overlap with DMSO peak), 1.19-0.79 (m, 8H), 3 hydrogens not visible.

Example 536

N-(2-amino-2-methylpropyl)-3-({3-(4-chlorophenyl)-5-oxo-4-[(2S)-3,3,3-trifluoro-2-hydroxypropyl]-4,5-dihydro-1H-1,2,4-triazol-1-yl}methyl)-1-(4-{[2-(methoxymethyl)pyrrolidin-1-yl]carbonyl}pyridin-3-yl)-1H-1,2,4-triazole-5-carboxamide
(Diastereomeric Mixture)

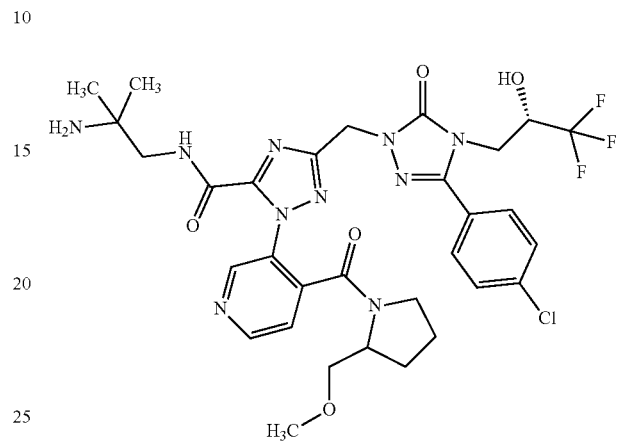

A solution of 3-{5-[(2-amino-2-methylpropyl)carbamoyl]-3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl}pyridine-4-carboxylic acid (Example 30A, 70.0 mg, 112 µmol) in N,N-dimethylformamide (750 µl) was treated with HATU (64.0 mg, 168 µmol) and stirred 10 min at room temperature. 2-(Methoxymethyl)pyrrolidine hydrochloride (1:1) (25.5 mg, 168 µmol) was then added followed by and N,N-diisopropylethylamine (98 µl, 560 µmol). The resulting mixture was stirred overnight at room temperature. Purification by preparative HPLC (Method 4) afforded 41.6 mg (51% of th.) of the title compound.

LC-MS (Method 2): $R_t$=1.28 min; MS (ESIpos): m/z=721.3 [M+H]⁺

¹H-NMR (400 MHz, DMSO-d6) δ [ppm]: 9.21-8.54 (m, 3H), 7.87-7.44 (m, 5H), 7.30-6.77 (m, 1H), 5.30-4.94 (m, 2H), 4.44-4.21 (m, 1H), 4.10-3.75 (m, 3H), 3.72-2.83 (m, 15H, overlap with HDO peak), 1.95-1.36 (m 4H), NH₂ not visible.

Experimental Section—Biological Assays

Abbreviations and Acronyms:
Acc. No. accession number
AVP arginine vasopressin
$B_{max}$ maximal ligand binding capacity
BSA bovine serum albumin
cAMP cyclic adenosine monophosphate
Cat. No. catalogue number
cDNA complementary deoxyribonucleic acid
CHO chinese hamster ovary
CRE cAMP response element
Ct cycle threshold
DMEM/F12 Dulbecco's modified Eagle's medium/Ham's F12 medium (1:1)
DNA deoxyribonucleic acid
DMSO dimethylsulfoxide
DTT dithiothreitol
$EC_{50}$ half-maximal effective concentration EDTA ethylenediamine-tetraacetic acid
FAM carboxyfluorescein succinimidyl ester
f.c. final concentration
FCS fetal calf serum
HEPES 4-(2-hydroxyethyl)piperazine-1-ethanesulfonic acid
$IC_{50}$ half-maximal inhibitory concentration
$K_d$ dissociation constant
$K_i$ dissociation constant of an inhibitor
mRNA messenger ribonucleic acid
PBS phosphate buffered saline
PEG polyethylene glycol
p.o. per os, peroral
RNA ribonucleic acid
RTPCR real-time polymerase chain reaction
SPA scintillation proximity assay
TAMRA carboxytetramethylrhodamine
TRIS; Tris 2-amino-2-hydroxymethylpropane-1,3-diol Demonstration of the activity of the compounds of the present invention may be accomplished through in vitro, ex vivo, and in vivo assays that are well known in the art. For example, to demonstrate the activity of the compounds of the present invention, the following assays may be used.

B-1. Cellular In Vitro Assay for Determining Vasopressin Receptor Activity

The identification of agonists and antagonists of the V1a and V2 vasopressin receptors from humans, rats and dogs as well as the quantification of the activity of the compounds of the invention is carried out using recombinant cell lines. These cell lines originally derive from a hamster's ovary epithelial cell (Chinese Hamster Ovary, CHO K1, ATCC: American Type Culture Collection, Manassas, Va. 20108, USA). The test cell lines constitutively express the human, rat or dog V1a or V2 receptors. In case of the $G_{\alpha q}$-coupled V1a receptors, cells are also stably transfected with a modified form of the calcium-sensitive photoproteins aequorin (human and rat V1a) or obelin (dog V1a), which, after reconstitution with the cofactor coelenterazine, emit light when there are increases in free calcium concentrations [Rizzuto R, Simpson A W, Brini M, Pozzan T, *Nature* 358, 325-327 (1992); Illarionov B A, Bondar V S, Illarionova V A, Vysotski E S, *Gene* 153 (2), 273-274 (1995)]. The resulting vasopressin receptor cells react to stimulation of the recombinantly expressed V1a receptors by intracellular release of calcium ions, which can be quantified by the resulting photoprotein luminescence. The $G_s$-coupled V2 receptors are stably transfected into cell lines expressing the gene for firefly luciferase under control of a CRE-responsible promoter. Activation of V2 receptors induces the activation of the CRE-responsive promoter via cAMP increase, thereby inducing the expression of firefly luciferase. The light emitted by photoproteins of V1a cell lines as well as the light emitted by firefly luciferase of V2 cell lines corresponds to the activation or inhibition of the respective vasopressin receptor. The bioluminescence of the cell lines is detected using a suitable luminometer [Milligan G, Marshall F, Rees S, *Trends in Pharmacological Sciences* 17, 235-237 (1996)].

Test Procedure:
Vasopressin V1a Receptor Cell Lines:
On the day before the assay, the cells are plated out in culture medium (DMEM/F12, 2% FCS, 2 mM glutamine, 10 mM HEPES, 5 µg/ml coelenterazine) in 384-well microtiter plates and kept in a cell incubator (96% humidity, 5% v/v $CO_2$, 37° C.). On the day of the assay, test compounds in various concentrations are placed for 10 minutes in the wells of the microtiter plate before the agonist [Arg]-vasopressin at $EC_{50}$ concentration is added. The resulting light signal is measured immediately in a luminometer.

Vasopressin V2 Receptor Cell Lines:
On the day before the assay, the cells are plated out in culture medium (DMEM/F12, 2% FCS, 2 mM glutamine, 10 mM HEPES) in 384-well microtiter plates and kept in a cell incubator (96% humidity, 5% v/v $CO_2$, 37° C.). On the day of the assay, test compounds in various concentrations and the agonist [$Arg^8$]-vasopressin at $EC_{50}$ concentration are added together to the wells, and plates are incubated for 3 hours in a cell incubator. Upon addition of the cell lysis reagent Triton™ and the substrate luciferin, luminescence of firefly luciferase is measured in a luminometer.

Table 1A below lists individual $IC_{50}$ values for the compounds of the invention (including racemic mixtures as well as separated enantiomers) that were obtained from cell lines transfected with the human V1a or V2 receptor:

TABLE 1A

| Example No. | $IC_{50}$ hV1a [µM] | $IC_{50}$ hV2 [µM] | ratio $IC_{50}$ hV2/hV1a |
|---|---|---|---|
| 1 | 1.95000 | 7.87500 | 4.0 |
| 2 | 0.58500 | 0.21000 | 0.4 |
| 3 | 1.21750 | 0.73000 | 0.6 |
| 4 | 0.11500 | 0.12500 | 1.1 |
| 5 | 0.18000 | 3.00000 | 16.7 |
| 6 | 0.07150 | 2.50000 | 35.0 |
| 7 | 1.75000 | 3.85000 | 2.2 |
| 8 | 0.58500 | 3.00000 | 5.1 |
| 9 | 0.00650 | 0.28500 | 43.8 |
| 10 | 0.23500 | 0.44500 | 1.9 |
| 11 | 0.95750 | 0.41000 | 0.4 |
| 12 | 0.72750 | 0.37000 | 0.5 |
| 13 | 0.57500 | 0.09060 | 0.2 |
| 14 | 0.27750 | 5.33333 | 19.2 |
| 15 | 0.01925 | 0.78500 | 40.8 |
| 16 | 0.07950 | 1.55000 | 19.5 |
| 17 | 2.25000 | 2.85000 | 1.3 |
| 18 | 0.02370 | 1.95000 | 82.3 |
| 19 | 0.43000 | 2.25000 | 5.2 |
| 20 | 4.35000 | 5.92500 | 1.4 |
| 21 | 0.84000 | 1.47667 | 1.8 |
| 22 | 0.25000 | 0.69000 | 2.8 |
| 23 | 0.71000 | 4.25000 | 6.0 |
| 24 | 0.33000 | 4.67500 | 14.2 |
| 25 | 1.97500 | 4.90000 | 2.5 |
| 26 | 0.05800 | 0.32333 | 5.6 |
| 27 | 0.00405 | 0.28250 | 69.8 |
| 28 | 0.01100 | 0.39500 | 35.9 |
| 29 | 0.01650 | 0.36500 | 22.1 |
| 30 | 0.01285 | 0.78333 | 61.0 |
| 31 | 0.01835 | 1.66667 | 90.8 |
| 32 | 0.00500 | 0.75333 | 150.7 |
| 34 | 0.01350 | 1.24333 | 92.1 |
| 35 | 0.01050 | 0.55333 | 52.7 |
| 36 | 0.06750 | 0.23250 | 3.4 |
| 37 | 0.00750 | 0.57750 | 77.0 |
| 38 | 0.00420 | 0.22000 | 52.4 |
| 39 | 0.02300 | 0.36000 | 15.7 |
| 40 | 0.02550 | 0.35000 | 13.7 |
| 41 | 0.00350 | 0.22540 | 64.4 |
| 42 | 0.02300 | 0.62000 | 27.0 |
| 43 | 0.00585 | 0.21333 | 36.5 |
| 44 | 0.00425 | 0.36000 | 84.7 |
| 45 | 0.03300 | 0.69333 | 21.0 |
| 46 | 0.03200 | 1.56667 | 49.0 |
| 47 | 0.00700 | 0.28333 | 40.5 |
| 48 | 0.00705 | 0.55667 | 79.0 |
| 49 | 0.00480 | 1.10500 | 230.2 |
| 50 | 0.02050 | 4.36667 | 213.0 |
| 51 | 0.00500 | 0.76500 | 153.0 |
| 52 | 0.01150 | 2.00000 | 173.9 |
| 53 | 0.03150 | 2.25000 | 71.4 |
| 54 | 0.00450 | 0.40667 | 90.4 |
| 55 | 0.00365 | 0.69500 | 190.4 |

TABLE 1A-continued

| Example No. | IC$_{50}$ hV1a [μM] | IC$_{50}$ hV2 [μM] | ratio IC$_{50}$ hV2/hV1a |
|---|---|---|---|
| 56 | 0.00440 | 0.40500 | 92.0 |
| 57 | 0.01300 | 0.50333 | 38.7 |
| 58 | 0.01950 | 1.13667 | 58.3 |
| 59 | 0.00513 | 0.95000 | 185.4 |
| 60 | 0.00425 | 0.88500 | 208.2 |
| 61 | 0.00435 | 0.48500 | 111.5 |
| 62 | 0.01950 | 0.95667 | 49.1 |
| 63 | 0.00315 | 1.15333 | 366.1 |
| 64 | 0.01600 | 0.53500 | 33.4 |
| 65 | 0.19000 | 0.38000 | 2.0 |
| 66 | 0.04350 | 0.36333 | 8.4 |
| 67 | 0.07650 | 0.15667 | 2.0 |
| 68 | 0.06350 | 0.43667 | 6.9 |
| 69 | 0.23500 | 0.32000 | 1.4 |
| 70 | 0.15000 | 0.69000 | 4.6 |
| 71 | 0.15000 | 0.24000 | 1.6 |
| 72 | 2.05000 | 32.00000 | 15.6 |
| 73 | 0.05300 | 0.71000 | 13.4 |
| 74 | 0.0056 | 0.86500 | 154.5 |
| 75 | 0.00660 | 1.30000 | 197.0 |
| 76 | 0.00645 | 2.33750 | 362.4 |
| 77 | 0.01200 | 2.35000 | 195.8 |
| 78 | 0.01950 | 3.65000 | 187.2 |
| 79 | 0.10200 | 10.50000 | 102.9 |
| 80 | 0.00665 | 1.80000 | 270.7 |
| 81 | 0.00205 | 1.35000 | 658.5 |
| 82 | 0.03300 | 0.33500 | 10.2 |
| 83 | 0.00535 | 0.57000 | 106.5 |
| 84 | 0.00995 | 3.20000 | 321.6 |
| 85 | 0.00735 | 4.95000 | 673.5 |
| 86 | 0.00450 | 1.40000 | 311.1 |
| 87 | 0.00480 | 1.09500 | 228.1 |
| 88 | 0.04100 | 1.17500 | 28.7 |
| 89 | 0.03600 | 1.85000 | 51.4 |
| 90 | 0.09000 | 1.55000 | 17.2 |
| 91 | 0.19500 | 1.25000 | 6.4 |
| 92 | 0.24000 | 1.75000 | 7.3 |
| 93 | 0.00765 | 0.50500 | 66.0 |
| 94 | 0.01600 | 2.25000 | 140.6 |
| 95 | 0.09200 | 2.15000 | 23.4 |
| 96 | 0.00210 | 0.56000 | 266.7 |
| 97 | 0.13500 | 2.05000 | 15.2 |
| 98 | 0.12500 | 0.94500 | 7.6 |
| 99 | 0.04000 | 4.00000 | 100.0 |
| 100 | 0.02650 | 1.06500 | 40.2 |
| 101 | 0.11000 | 1.95000 | 17.7 |
| 102 | 0.08000 | 1.15000 | 14.4 |
| 103 | 0.15500 | 2.40000 | 15.5 |
| 104 | 0.00825 | 1.60000 | 193.9 |
| 105 | 0.13000 | 1.10000 | 8.5 |
| 106 | 0.00235 | 1.20000 | 510.6 |
| 107 | 0.00565 | 0.71000 | 125.7 |
| 108 | 0.03150 | 0.70000 | 22.2 |
| 109 | 0.11500 | 6.75000 | 58.7 |
| 110 | 0.00630 | 0.52500 | 83.3 |
| 111 | 0.00470 | 1.30000 | 276.6 |
| 112 | 0.17000 | 66.00000 | 388.2 |
| 113 | 0.09100 | 0.83500 | 9.2 |
| 114 | 0.01900 | 0.24000 | 12.6 |
| 115 | 0.03100 | 0.49000 | 15.8 |
| 116 | 0.07800 | 1.15000 | 14.7 |
| 117 | 0.06550 | 1.04500 | 16.0 |
| 118 | 0.14000 | 1.15000 | 8.2 |
| 119 | 0.03500 | 0.27000 | 7.7 |
| 120 | 0.02700 | 0.42500 | 15.7 |
| 121 | 0.05200 | 1.50000 | 28.8 |
| 122 | 0.12000 | 1.65000 | 13.8 |
| 123 | 0.10500 | 2.30000 | 21.9 |
| 124 | 0.31500 | 3.80000 | 12.1 |
| 125 | 0.02950 | 0.36000 | 12.2 |
| 126 | 0.03600 | 0.25000 | 6.9 |
| 127 | 0.16000 | 1.05000 | 6.6 |
| 128 | 0.01350 | 1.50000 | 111.1 |
| 129 | 0.67000 | 3.65000 | 5.4 |
| 130 | 0.18850 | 4.50000 | 23.9 |
| 131 | 0.01250 | 1.95000 | 156.0 |
| 132 | 0.04550 | 5.15000 | 113.2 |
| 133 | 0.00490 | 1.45000 | 295.9 |
| 134 | 0.11700 | 1.25000 | 10.7 |
| 135 | 0.06650 | 0.93000 | 14.0 |
| 136 | 0.02350 | 0.34000 | 14.5 |
| 137 | 0.14600 | 1.35000 | 9.2 |
| 138 | 0.03850 | 2.35000 | 61.0 |
| 139 | 0.02050 | 0.46500 | 22.7 |
| 140 | 0.03350 | 1.00500 | 30.0 |
| 141 | 0.03200 | 1.06500 | 33.3 |
| 142 | 0.10000 | 2.40000 | 24.0 |
| 143 | 0.01500 | 1.12000 | 74.7 |
| 144 | 0.18500 | 1.90000 | 10.3 |
| 145 | 0.12500 | 1.01000 | 8.1 |
| 146 | 0.05600 | 0.55500 | 9.9 |
| 147 | 0.30500 | 0.94000 | 3.1 |
| 148 | 0.01900 | 0.25500 | 13.4 |
| 149 | 0.01240 | 1.90000 | 153.2 |
| 150 | 0.05450 | 2.40000 | 44.0 |
| 151 | 0.09800 | 0.66500 | 6.8 |
| 152 | 0.06500 | 1.35000 | 20.8 |
| 153 | 0.41000 | 17.30000 | 42.2 |
| 154 | 0.00675 | 2.20000 | 325.9 |
| 155 | 0.03900 | 1.95000 | 50.0 |
| 156 | 0.06600 | 1.35000 | 20.5 |
| 157 | 0.00355 | 3.05000 | 859.2 |
| 158 | 0.01055 | 3.80000 | 360.2 |
| 159 | 0.05250 | 1.85000 | 35.2 |
| 160 | 0.02700 | 1.35000 | 50.0 |
| 161 | 0.02650 | 0.50000 | 18.9 |
| 162 | 0.30000 | 7.20000 | 24.0 |
| 163 | 0.02800 | 1.30000 | 46.4 |
| 164 | 0.66000 | 1.30000 | 2.0 |
| 165 | 0.06600 | 0.63500 | 9.6 |
| 166 | 0.03900 | 2.00000 | 51.3 |
| 167 | 0.01933 | 1.25000 | 64.7 |
| 168 | 0.02850 | 1.54250 | 54.1 |
| 169 | 0.00236 | 0.28000 | 118.5 |
| 171 | 0.13925 | 7.35000 | 52.8 |
| 172 | 0.00325 | 2.11750 | 651.5 |
| 173 | 0.00428 | 2.60500 | 608.2 |
| 174 | 0.00501 | 0.25759 | 51.4 |
| 175 | 0.01025 | 1.54500 | 150.7 |
| 176 | 0.01500 | 1.25000 | 83.3 |
| 177 | 0.00990 | 0.69000 | 69.7 |
| 178 | 0.01850 | 1.80000 | 97.3 |
| 179 | 0.00610 | 1.70000 | 278.7 |
| 180 | 0.06800 | 2.95000 | 43.4 |
| 181 | 0.19500 | 18.65000 | 95.6 |
| 182 | 0.02400 | 2.05000 | 85.4 |
| 183 | 0.08800 | 3.50000 | 39.8 |
| 184 | 0.02850 | 3.10000 | 108.8 |
| 185 | 0.00900 | 1.79500 | 199.4 |
| 186 | 0.00525 | 0.24250 | 46.2 |
| 187 | 0.01235 | 0.04850 | 3.9 |
| 188 | 0.00683 | 0.56750 | 83.2 |
| 189 | 0.06075 | 3.65000 | 60.1 |
| 190 | 0.30000 | 7.05000 | 23.5 |
| 191 | 0.01950 | 3.75000 | 192.3 |
| 192 | 0.07450 | 7.35000 | 98.7 |
| 193 | 0.08000 | 3.10000 | 38.8 |
| 194 | 0.06350 | 2.95000 | 46.5 |
| 195 | 0.10400 | 2.39250 | 23.0 |
| 196 | 0.02200 | 0.85500 | 38.9 |
| 197 | 0.04950 | 6.95000 | 140.4 |
| 198 | 0.02200 | 5.40000 | 245.5 |
| 199 | 0.03650 | 2.42500 | 66.4 |
| 200 | 0.01125 | 1.72500 | 153.3 |
| 201 | 0.00120 | 3.75000 | 3125.0 |
| 202 | 0.00430 | 0.00405 | 0.9 |
| 203 | 0.00835 | 0.22500 | 26.9 |
| 204 | 0.00125 | 0.11500 | 92.0 |
| 205 | 0.00058 | 0.18500 | 321.7 |
| 206 | 0.00145 | 0.83500 | 575.9 |
| 207 | 0.00535 | 0.30500 | 57.0 |
| 208 | 0.00240 | 0.09550 | 39.8 |
| 209 | 0.00565 | 0.13000 | 23.0 |
| 210 | 0.00165 | 0.75500 | 457.6 |

TABLE 1A-continued

| Example No. | IC$_{50}$ hV1a [μM] | IC$_{50}$ hV2 [μM] | ratio IC$_{50}$ hV2/hV1a |
|---|---|---|---|
| 211 | 0.00665 | 0.17000 | 25.6 |
| 212 | 0.02350 | 0.57500 | 24.5 |
| 213 | 0.00755 | 1.34500 | 178.1 |
| 214 | 0.00165 | 1.41000 | 854.5 |
| 215 | 0.01175 | 1.20000 | 102.1 |
| 216 | 0.01200 | 0.17000 | 14.2 |
| 217 | 0.00395 | 0.09350 | 23.7 |
| 218 | 0.00032 | 0.00780 | 24.4 |
| 219 | 0.02100 | 0.04150 | 2.0 |
| 220 | 0.00365 | 0.21500 | 58.9 |
| 221 | 0.00495 | 0.46000 | 92.9 |
| 222 | 0.00485 | 0.18500 | 38.1 |
| 223 | 0.00150 | 0.00115 | 0.8 |
| 224 | 0.01260 | 0.14500 | 11.5 |
| 225 | 0.00550 | 0.21000 | 38.2 |
| 226 | 0.00130 | 0.00745 | 5.7 |
| 227 | 0.00121 | 0.06750 | 55.8 |
| 228 | 0.00565 | 0.15000 | 26.5 |
| 229 | 0.00235 | 0.04950 | 21.1 |
| 230 | 0.00850 | 0.05650 | 6.6 |
| 231 | 0.00305 | 0.77500 | 254.1 |
| 232 | 0.00220 | 0.53500 | 243.2 |
| 233 | 0.01445 | 6.70000 | 463.7 |
| 234 | 0.00695 | 2.90000 | 417.3 |
| 235 | 0.00870 | 0.35500 | 40.8 |
| 236 | 0.00705 | 0.34000 | 48.2 |
| 237 | 0.01550 | 0.44500 | 28.7 |
| 238 | 0.01350 | 0.04450 | 3.3 |
| 239 | 0.00735 | 0.24000 | 32.7 |
| 240 | 0.01250 | 0.30000 | 24.0 |
| 241 | 0.00220 | 0.07350 | 33.4 |
| 242 | 0.00570 | 0.12650 | 22.2 |
| 243 | 0.02250 | 0.54000 | 24.0 |
| 244 | 0.00730 | 0.23000 | 31.5 |
| 245 | 0.00645 | 0.81000 | 125.6 |
| 246 | 0.00455 | 1.20000 | 263.7 |
| 247 | 0.00240 | 0.01045 | 4.4 |
| 248 | 0.00120 | 0.06500 | 54.2 |
| 249 | 0.00280 | 0.13600 | 48.6 |
| 250 | 0.00445 | 0.08700 | 19.6 |
| 251 | 0.00885 | 0.08150 | 9.2 |
| 252 | 0.00760 | 0.25500 | 33.6 |
| 253 | 0.00570 | 0.36500 | 64.0 |
| 254 | 0.00225 | 0.67000 | 297.8 |
| 255 | 0.00133 | 0.22500 | 169.8 |
| 256 | 0.00360 | 0.01300 | 3.6 |
| 257 | 0.00605 | 0.15000 | 24.8 |
| 258 | 0.00190 | 0.08150 | 42.9 |
| 259 | 0.00250 | 0.05500 | 22.0 |
| 260 | 0.02550 | 0.76000 | 29.8 |
| 261 | 0.00145 | 0.45000 | 310.3 |
| 262 | 0.00340 | 0.88000 | 258.8 |
| 263 | 0.03250 | 8.35000 | 256.9 |
| 264 | 0.00245 | 1.25500 | 512.2 |
| 265 | 0.03450 | 8.80000 | 255.1 |
| 266 | 0.00385 | 0.86000 | 223.4 |
| 267 | 0.03350 | 4.00000 | 119.4 |
| 268 | 0.00365 | 0.97000 | 265.8 |
| 269 | 0.00250 | 1.05500 | 422.0 |
| 270 | 0.00210 | 1.44000 | 685.7 |
| 271 | 0.01450 | 3.50000 | 241.4 |
| 272 | 0.00585 | 1.75000 | 299.1 |
| 273 | 0.01300 | 6.20000 | 476.9 |
| 274 | 0.02200 | 9.65000 | 438.6 |
| 275 | 0.00255 | 1.23500 | 484.3 |
| 276 | 0.00270 | 1.15000 | 425.9 |
| 277 | 0.00530 | 1.80000 | 339.6 |
| 278 | 0.00160 | 0.40500 | 253.1 |
| 279 | 0.02750 | 2.70000 | 98.2 |
| 280 | 0.07850 | 10.15000 | 129.3 |
| 281 | 0.00112 | 2.80000 | 2500.0 |
| 282 | 0.00235 | 2.35000 | 1000.0 |
| 283 | 0.00605 | 7.50000 | 1239.7 |
| 284 | 0.00200 | 0.97000 | 485.0 |
| 285 | 0.00190 | 0.44000 | 231.6 |
| 286 | 0.01450 | 2.50000 | 172.4 |
| 287 | 0.00570 | 2.20000 | 386.0 |
| 288 | 0.04600 | 4.25000 | 92.4 |
| 289 | 0.00083 | 0.44500 | 536.1 |
| 290 | 0.00910 | 0.84500 | 92.9 |
| 291 | 0.00660 | 1.15000 | 174.2 |
| 292 | 0.00295 | 0.06450 | 21.9 |
| 293 | 0.00470 | 0.84000 | 178.7 |
| 294 | 0.00210 | 1.54500 | 735.7 |
| 295 | 0.00250 | 0.07700 | 30.8 |
| 296 | 0.00395 | 0.50000 | 126.6 |
| 297 | 0.00505 | 1.40000 | 277.2 |
| 298 | 0.00330 | 1.54500 | 468.2 |
| 299 | 0.00440 | 0.26500 | 60.2 |
| 300 | 0.00102 | 0.67000 | 656.9 |
| 301 | 0.00875 | 0.61000 | 69.7 |
| 302 | 0.00375 | 3.30000 | 880.0 |
| 303 | 0.00215 | 0.50500 | 234.9 |
| 304 | 0.00225 | 0.06550 | 29.1 |
| 305 | 0.00097 | 0.05400 | 55.7 |
| 306 | 0.00160 | 0.12350 | 77.2 |
| 307 | 0.00165 | 0.17500 | 106.1 |
| 308 | 0.01750 | 3.30000 | 188.6 |
| 309 | 0.00190 | 0.11650 | 61.3 |
| 310 | 0.00260 | 0.21500 | 82.7 |
| 311 | 0.00185 | 1.25000 | 675.7 |
| 312 | 0.00685 | 0.13500 | 19.7 |
| 313 | 0.00415 | 0.91500 | 220.5 |
| 314 | 0.00215 | 0.51000 | 237.2 |
| 315 | 0.00415 | 0.15500 | 37.3 |
| 316 | 0.00175 | 0.25500 | 145.7 |
| 317 | 0.00230 | 0.28500 | 123.9 |
| 318 | 0.01450 | 0.92000 | 63.4 |
| 319 | 0.00355 | 0.32500 | 91.5 |
| 320 | 0.00135 | 0.10250 | 75.9 |
| 321 | 0.01300 | 0.57000 | 43.8 |
| 322 | 0.00265 | 0.27500 | 103.8 |
| 323 | 0.00205 | 0.07050 | 34.4 |
| 324 | 0.01400 | 1.65000 | 117.9 |
| 325 | 0.00101 | 0.12000 | 118.8 |
| 326 | 0.00830 | 1.50000 | 180.7 |
| 327 | 0.00440 | 0.49500 | 112.5 |
| 328 | 0.00795 | 2.15000 | 270.4 |
| 329 | 0.01105 | 1.90000 | 171.9 |
| 330 | 0.00995 | 1.35000 | 135.7 |
| 331 | 0.03300 | 7.70000 | 233.3 |
| 332 | 0.02050 | 10.45000 | 509.8 |
| 333 | 0.00555 | 8.95000 | 1612.6 |
| 334 | 0.00295 | 0.85500 | 289.8 |
| 335 | 0.01550 | 1.10500 | 71.3 |
| 336 | 0.00280 | 1.27000 | 453.6 |
| 337 | 0.02350 | 1.08500 | 46.2 |
| 338 | 0.00160 | 0.96000 | 600.0 |
| 339 | 0.00275 | 3.65000 | 1327.3 |
| 340 | 0.00850 | 0.39000 | 45.9 |
| 341 | 0.00155 | 0.20500 | 132.3 |
| 342 | 0.00615 | 0.36500 | 59.3 |
| 343 | 0.00087 | 0.10300 | 118.4 |
| 344 | 0.00093 | 0.00470 | 5.0 |
| 345 | 0.00320 | 0.11900 | 37.2 |
| 346 | 0.00175 | 0.11850 | 67.7 |
| 347 | 0.00755 | 1.06500 | 141.1 |
| 348 | 0.00385 | 0.97000 | 251.9 |
| 349 | 0.00470 | 0.74000 | 157.4 |
| 350 | 0.00180 | 0.26500 | 147.2 |
| 351 | 0.00270 | 0.95000 | 351.9 |
| 352 | 0.00084 | 0.32000 | 383.2 |
| 353 | 0.00094 | 0.28000 | 299.5 |
| 354 | 0.00225 | 0.15000 | 66.7 |
| 355 | 0.00175 | 0.63500 | 362.9 |
| 356 | 0.00245 | 1.89000 | 771.4 |
| 357 | 0.03300 | 2.45000 | 74.2 |
| 358 | 0.01800 | 2.75000 | 152.8 |
| 359 | 0.00650 | 0.90000 | 138.5 |
| 360 | 0.00074 | 0.01490 | 20.1 |
| 361 | 0.00255 | 0.09750 | 38.2 |
| 362 | 0.00485 | 2.50000 | 515.5 |
| 363 | 0.00550 | 0.34500 | 62.7 |
| 364 | 0.00047 | 0.15500 | 329.8 |

TABLE 1A-continued

| Example No. | IC$_{50}$ hV1a [μM] | IC$_{50}$ hV2 [μM] | ratio IC$_{50}$ hV2/hV1a |
|---|---|---|---|
| 365 | 0.03000 | 0.92000 | 30.7 |
| 366 | 0.19500 | 3.70000 | 19.0 |
| 367 | 0.04500 | 0.26000 | 5.8 |
| 368 | 0.35000 | 2.10000 | 6.0 |
| 369 | 0.00280 | 0.47000 | 167.9 |
| 370 | 0.03300 | 0.42000 | 12.7 |
| 371 | 0.01500 | 0.71000 | 47.3 |
| 372 | 0.05250 | 3.40000 | 64.8 |
| 373 | 0.00475 | 1.03000 | 216.8 |
| 374 | 0.04750 | 1.45000 | 30.5 |
| 375 | 0.71000 | 21.00000 | 29.6 |
| 376 | 0.07350 | 0.57000 | 7.8 |
| 377 | 0.29500 | 8.60000 | 29.2 |
| 378 | 0.12000 | 2.05000 | 17.1 |
| 379 | 0.07050 | 0.84500 | 12.0 |
| 380 | 0.09550 | 4.00000 | 41.9 |
| 381 | 0.01700 | 2.25000 | 132.4 |
| 382 | 0.07800 | 6.25000 | 80.1 |
| 383 | 0.43500 | 7.75000 | 17.8 |
| 384 | 0.11150 | 2.00000 | 17.9 |
| 385 | 0.43500 | 9.55000 | 22.0 |
| 386 | 0.17000 | 4.15000 | 24.4 |
| 387 | 0.09250 | 3.40000 | 36.8 |
| 388 | 0.00715 | 1.55000 | 216.8 |
| 389 | 0.00265 | 0.83500 | 315.1 |
| 390 | 0.06900 | 0.53000 | 7.7 |
| 391 | 0.05200 | 3.40000 | 65.4 |
| 392 | 0.02250 | 0.28000 | 12.4 |
| 393 | 0.01650 | 6.10000 | 369.7 |
| 394 | 0.29500 | 4.40000 | 14.9 |
| 395 | 0.08200 | 5.15000 | 62.8 |
| 396 | 0.30100 | 32.00000 | 106.3 |
| 397 | 0.07200 | 6.95000 | 96.5 |
| 398 | 0.44000 | 22.00000 | 50.0 |
| 399 | 0.19000 | 3.15000 | 16.6 |
| 400 | 0.57000 | 32.00000 | 56.1 |
| 401 | 0.24000 | 9.95000 | 41.5 |
| 402 | 0.43500 | 32.00000 | 73.6 |
| 403 | 0.07450 | 5.80000 | 77.9 |
| 404 | 0.31500 | 11.50000 | 36.5 |
| 405 | 0.01650 | 10.15000 | 615.2 |
| 406 | 0.02600 | 10.15000 | 390.4 |
| 407 | 0.42500 | 32.00000 | 75.3 |
| 408 | 0.40000 | 8.50000 | 21.3 |
| 409 | 0.18000 | 32.00000 | 177.8 |
| 410 | 0.32500 | 3.30000 | 10.2 |
| 411 | 0.36500 | 4.85000 | 13.3 |
| 412 | 0.14000 | 2.00000 | 14.3 |
| 413 | 0.03450 | 2.05000 | 59.4 |
| 414 | 0.04450 | 3.60000 | 80.9 |
| 415 | 0.05350 | 1.50000 | 28.0 |
| 416 | 0.05150 | 5.85000 | 113.6 |
| 417 | 0.03750 | 0.31500 | 8.4 |
| 418 | 0.63500 | 32.00000 | 50.4 |
| 419 | 0.09600 | 1.02500 | 10.7 |
| 420 | 0.05850 | 1.15000 | 19.7 |
| 421 | 0.02200 | 0.37000 | 16.8 |
| 422 | 0.03000 | 2.80000 | 93.3 |
| 423 | 0.04000 | 18.90000 | 472.5 |
| 424 | 0.01150 | 2.65000 | 230.4 |
| 425 | 0.00985 | 0.10000 | 10.2 |
| 426 | 0.01900 | 0.12500 | 6.6 |
| 427 | 0.02100 | 0.07275 | 3.5 |
| 428 | 0.04100 | 1.29000 | 31.5 |
| 429 | 0.05100 | 1.40000 | 27.5 |
| 430 | 0.04450 | 0.71000 | 16.0 |
| 431 | 0.01650 | 1.10000 | 66.7 |
| 432 | 0.04450 | 0.94500 | 21.2 |
| 433 | 0.07100 | 2.20000 | 31.0 |
| 434 | 0.08200 | 2.70000 | 32.9 |
| 435 | 0.02450 | 1.06500 | 43.5 |
| 436 | 0.02500 | 0.82500 | 33.0 |
| 437 | 0.04050 | 3.70000 | 91.4 |
| 438 | 0.08600 | 8.90000 | 103.5 |
| 439 | 0.05350 | 1.28500 | 24.0 |
| 440 | 0.10000 | 4.55000 | 45.5 |
| 441 | 0.17500 | 6.05000 | 34.6 |
| 442 | 0.19000 | 4.65000 | 24.5 |
| 443 | 0.22000 | 22.50000 | 102.3 |
| 444 | 0.12000 | 7.85000 | 65.4 |
| 445 | 0.02000 | 3.65000 | 182.5 |
| 446 | 0.04700 | 21.50000 | 457.4 |
| 447 | 0.02950 | 0.81500 | 27.6 |
| 448 | 0.16500 | 2.70000 | 16.4 |
| 449 | 0.20000 | 3.35000 | 16.8 |
| 450 | 0.03950 | 1.25000 | 31.6 |
| 451 | 0.11000 | 1.02500 | 9.3 |
| 452 | 0.26500 | 5.90000 | 22.3 |
| 453 | 0.17500 | 32.00000 | 182.9 |
| 454 | 0.01200 | 4.05000 | 337.5 |
| 455 | 0.00440 | 1.20000 | 272.7 |
| 456 | 0.01200 | 0.78500 | 65.4 |
| 457 | 0.21000 | 5.30000 | 25.2 |
| 458 | 0.10000 | 6.05000 | 60.5 |
| 459 | 0.21000 | 4.40000 | 21.0 |
| 460 | 0.13000 | 3.95000 | 30.4 |
| 461 | 1.10000 | 22.00000 | 20.0 |
| 462 | 0.09700 | 5.95000 | 61.3 |
| 463 | 0.23500 | 32.00000 | 136.2 |
| 464 | 0.06000 | 32.00000 | 533.3 |
| 465 | 0.17000 | 3.60000 | 21.2 |
| 466 | 0.71000 | 66.00000 | 93.0 |
| 467 | 0.62000 | 32.00000 | 51.6 |
| 468 | 0.42000 | 32.00000 | 76.2 |
| 469 | 0.56000 | 100.00000 | 178.6 |
| 470 | 0.75000 | 32.00000 | 42.7 |
| 471 | 0.15000 | 20.90000 | 139.3 |
| 472 | 0.32000 | 66.00000 | 206.3 |
| 473 | 0.09200 | 1.80000 | 19.6 |
| 474 | 0.02400 | 22.50000 | 937.5 |
| 475 | 0.09000 | 66.00000 | 733.3 |
| 476 | 0.75000 | 100.00000 | 133.3 |
| 477 | 0.46000 | 11.00000 | 23.9 |
| 478 | 0.29000 | 7.80000 | 26.9 |
| 479 | 1.40000 | 32.00000 | 22.9 |
| 480 | 0.46000 | 32.00000 | 69.6 |
| 481 | 0.86000 | 100.00000 | 116.3 |
| 482 | 0.09900 | 32.00000 | 323.2 |
| 483 | 0.03700 | 3.95000 | 106.8 |
| 484 | 0.21000 | 9.40000 | 44.8 |
| 485 | 0.23000 | 5.00000 | 21.7 |
| 486 | 0.11000 | 32.00000 | 290.9 |
| 487 | 5.30000 | 100.00000 | 18.9 |
| 488 | 0.02900 | 2.00000 | 69.0 |
| 489 | 0.05000 | 1.70000 | 34.0 |
| 490 | 0.01600 | 0.38000 | 23.8 |
| 491 | 0.02100 | 1.30000 | 61.9 |
| 492 | 0.00180 | 0.44000 | 244.4 |
| 493 | 0.01350 | 7.30000 | 540.7 |
| 494 | 0.02450 | 0.13000 | 5.3 |
| 495 | 0.02000 | 0.52000 | 26.0 |
| 496 | 0.00720 | 0.17000 | 23.6 |
| 497 | 0.02650 | 0.49000 | 18.5 |
| 498 | 0.01050 | 0.47000 | 44.8 |
| 499 | 0.01500 | 0.50500 | 33.7 |
| 500 | 0.00680 | 0.30500 | 44.9 |
| 501 | 0.03050 | 0.53000 | 17.4 |
| 502 | 0.02950 | 2.00000 | 67.8 |
| 503 | 0.00555 | 0.21500 | 38.7 |
| 504 | 0.00310 | 0.15500 | 50.0 |
| 505 | 0.00105 | 0.05500 | 52.6 |
| 506 | 0.01400 | 0.90500 | 64.6 |
| 507 | 4.50000 | 32.00000 | 7.1 |
| 508 | 5.15000 | 23.50000 | 4.6 |
| 509 | 2.65000 | 32.00000 | 12.1 |
| 510 | 9.95000 | 8.90000 | 0.9 |
| 511 | 1.65000 | 1.45000 | 0.9 |
| 512 | 3.60000 | 1.25000 | 0.3 |
| 513 | 2.40000 | 5.45000 | 2.3 |
| 514 | 0.34000 | 1.25000 | 3.7 |
| 515 | 2.00000 | 2.25000 | 1.1 |
| 516 | 5.70000 | 55.00000 | 9.6 |
| 517 | 0.49000 | 1.84333 | 3.8 |
| 518 | 0.95500 | 0.48000 | 0.5 |

TABLE 1A-continued

| Example No. | IC$_{50}$ hV1a [µM] | IC$_{50}$ hV2 [µM] | ratio IC$_{50}$ hV2/hV1a |
|---|---|---|---|
| 519 | 1.35000 | 0.92500 | 0.7 |
| 520 | 0.29500 | 0.66500 | 2.3 |
| 521 | 6.25000 | 0.88500 | 0.1 |
| 522 | 3.00000 | 15.00000 | 5.0 |
| 523 | 0.36500 | 1.09667 | 3.0 |
| 524 | 4.65000 | 3.45000 | 0.7 |
| 525 | 9.40000 | 6.55000 | 0.7 |
| 526 | 8.65000 | 20.00000 | 2.3 |
| 527 | 1.08000 | 1.53333 | 1.4 |
| 528 | 0.07550 | 0.78000 | 10.3 |
| 529 | 0.09750 | 2.90000 | 29.7 |
| 530 | 0.53000 | 5.25000 | 9.9 |
| 531 | 0.09650 | 2.85000 | 29.5 |
| 532 | 0.27500 | 4.85000 | 17.6 |
| 533 | 0.14600 | 3.18333 | 21.8 |
| 534 | 0.18000 | 3.61667 | 20.1 |
| 535 | 0.08250 | 4.61667 | 56.0 |
| 536 | 0.28000 | 83.33333 | 297.6 |

B-2. Radioactive Binding Assay

IC$_{50}$ and K$_i$ values can be determined in radioactive binding assays using membrane fractions of recombinant human embryonic kidney cell line 293 (HEK293) or CHO-K1 cell lines expressing the respective human vasopressin V1a and V2 receptors.

Human recombinant vasopressin V1a receptors expressed in HEK293 cells are used in 50 mM Tris-HCl buffer, pH 7.4, 5 mM MgCl$_2$, 0.1% BSA using standard techniques. Aliquots of prepared membranes are incubated with test compounds in various concentrations in duplicates and 0.03 nM [$^{125}$I]Phenylacetyl-D-Tyr(Me)-Phe-Gln-Asn-Arg-Pro-Arg-Tyr-NH$_2$ for 120 minutes at 25° C. Non-specific binding is estimated in the presence of 1 M [Arg$^8$]Vasopressin. Receptors are filtered and washed, the filters are then counted to determine [$^{125}$I]Phenylacetyl-D-Tyr(Me)-Phe-Gln-Asn-Arg-Pro-Arg-Tyr-NH$_2$ specifically bound.

CHO-K1 cells stably transfected with a plasmid encoding human vasopressin V2 receptor are used to prepare membranes in 50 mM Tris-HCl buffer, pH 7.4, 10 mM MgCl$_2$, 0.1% BSA using standard techniques. Aliquots of prepared membrane are incubated with test compounds in various concentrations in duplicates and 4 nM [$^3$H](Arg$^8$)-Vasopressin for 120 minutes at 25° C. Non-specific binding is estimated in the presence of 1 mM (Arg$^8$)-vasopressin. Membranes are filtered and washed 3 times and the filters are counted to determine [$^3$H](Arg)-Vasopressin specifically bound.

IC$_{50}$ values are determined by a non-linear, least squares regression analysis using MathIQ™ (ID Business Solutions Ltd., UK). The inhibition constant K$_i$ is calculated using the equation of Cheng and Prusoff (Cheng, Y., Prusoff, W. H., Biochem. Pharmacol. 22:3099-3108, 1973).

B-3. Cellular In Vitro Assay for Detecting the Action of Vasopressin V1a Receptor Antagonists on the Regulation of Pro-Fibrotic Genes The cell line H9C2 (American Type Culture Collection ATCC No. CRL-1446), described as a cardiomyocyte type isolated from rat cardiac tissue, endogenously expresses the vasopressin V1a receptor AVPR1 A in high copy number, whereas AVPR2 expression cannot be detected. Likewise, the cell line NRK49F (ATCC No. CRL1570) isolated from rat kidney tissue, shows similar expression pattern of high AVPR1 A mRNA expression and diminishing AVPR2 expression. For cell assays detecting the inhibition of AVPR1 A receptor-dependent regulation of gene expression by receptor antagonists, the procedure is as follows:

H9C2 cells or NRK49F cells are seeded in 6-well microtiter plates for cell culture at a cell density of 50 000 cells/well in 2.0 ml of Opti-MEM medium (Invitrogen Corp., Carlsbad, Calif., USA, Cat. No. 11058-021) and held in a cell incubator (96% humidity, 8% v/v CO$_2$, 37° C.). After 24 hours, sets of three wells (triplicate) are charged with vehicle solution (negative control) and vasopressin solution ([Arg8]-vasopressin acetate, Sigma, Cat. No. V9879), or test compound (dissolved in vehicle: water with 20% v/v ethanol) and vasopressin solution. In the cell culture, the final vasopressin concentration is 1 nM. The test compound solution is added to the cell culture in small volumes, so that a final concentration of 0.03% of ethanol in the cell assay is not exceeded. After an incubation time of 5 hours, the culture supernatant is drawn off under suction, the adherent cells are lysed in 350 µl of RLT buffer (Qiagen, Cat. No. 79216), and the RNA is isolated from the lysate using the RNeasy kit (Qiagen, Cat. No. 74104). This is followed by DNAse digestion (Invitrogen, Cat. No. 18068-015), cDNA synthesis (Promaga, ImProm-II Reverse Transcription System, Cat. No. A3800) and Reverse Transcription Polymerase Chain Reaction (RTPCR) (pPCR MasterMix RT-QP2X-03-075, Eurogentec, Seraing, Belgium). All procedures take place in accordance with the working protocols of the test reagents' manufacturers. The primer sets for the RTPCR are selected on the basis of the mRNA gene sequences (NCBI GenBank Entrez Nucleotide Data Base) using the Primer3Plus program with 6-FAM TAMRA-labelled probes. The RTPCR for determining the relative mRNA expression in the cells of the various assay batches is carried out using the Applied Biosystems ABI Prism 7700 Sequence Detector in 384-well microtiter plate format in accordance with the instrument operating instructions. The relative gene expression is represented by the delta-delta Ct value [Applied Biosystems, User Bulletin No. 2 ABI Prism 7700 SDS, Dec. 11, 1997 (updated October 2001)] with reference to the level of expression of the ribosomal protein L-32 gene (GenBank Acc. No. NM_013226) and the threshold Ct value of Ct=35.

B-4. Inhibition of Vasopressin Induced Aggregation of Human Platelets

Human platelets endogenously express the V1a receptor. It was found that relatively high vasopressin concentrations (ca. 50-100 nM) stimulate platelet aggregation ex vivo. Therefore, platelets enriched from human blood may serve as a V1a expressing tissue for pharmacological studies with corresponding high concentrations of vasopressin antagonists.

Human blood is collected in a 10 mM trisodium citrate solution by venous puncture from nonsmoking healthy volunteers (n=4-8) who were drug free for at least 1 week. Platelet-rich plasma (PRP) is obtained by centrifuging the blood sample at 140 g for 20 min at 4° C. The resulting pellet is further centrifuged (15,000 rpm, 2 min) to produce platelet-poor plasma (PPP). Platelet aggregation is measured turbidimetrically using an aggregometer (APACT 4). The reaction is followed by monitoring changes in light transmission on 178 µL PRP aliquots, under continuous stirring at 37° C., against PPP control. Various concentrations of vasopressin antagonists (in 2 µL) are added to PRP 5 min before the addition of 20 µL Arg-vasopressin (final concentration 100 nM. The inhibitory effects of the compounds are determined by measuring the height of the aggregation wave from the bottom of the shape change compared with the control response. IC50 values are calculated a dose-response inhibition curve by an iterative nonlinear regression program B-5. Effects on the Contraction of Isolated Rat Vessel Rings Isolated Aorta Test compounds can be investigated on isolated aortic rings from male Wistar rats endogenously expressing the V1a receptor. Male Wistar rats are euthanized using carbon dioxide. The aorta is removed and placed in ice-cold Krebs-Henseleit buffer of following composition (in mmol/l): NaCl 112, KCl 5.9, $CaCl_2$ 2.0, $MgCl_2$ 1.2, $NaH_2PO_4$ 1.2, $NaHCO_3$ 25, glucose 11.5. The aorta is cut into 3 mm rings and transferred to 20 ml organ baths containing Krebs-Henseleit solution equilibrated with 95% $O_2$, 5% $CO_2$ at 37° C. For recording of isometric tension the rings are mounted between two hooks. The resting tension is adjusted to 3 g. After an equilibration period, each experiment is started by exposing the preparation to K+ (50 mM) Krebs-Henseleit solution. The aortic rings are than pre-contracted using 1 nmol/l Arg-vasopressin. After a stable contraction is established, a cumulative dose response curve of the test compound is constructed. The stabilized contraction induced by Arg-vasopressin is defined as 100% tension. The relaxation is expressed as percentage tension.

Isolated *A. renalis*

Male Wistar rats (200-250 g) are euthanized using carbon dioxide. The *A. renalis* is removed and placed in ice-cold Krebs-Henseleit buffer of following composition (in mmol/l): NaCl 112, KCl 5.9, $CaCl_2$ 2.0, $MgCl_2$ 1.2, $NaH_2PO_4$ 1.2, $NaHCO_3$ 25, glucose 11.5. For measurement of isometric tension, ring segments, 2 mm in length, are mounted in a small vessel chamber myograph (Danish Myo Technology A/S, Denmark) using two tungsten wires fixed to mounting jaws. One mounting jaw is attached to a micrometer, allowing control of vessel circumference. The other mounting jaw is attached to a force transducer for measurement of tension development. The whole preparation is kept in a chamber with physiological salt solution at 37° C., bubbled with oxygen. After a 30 min equilibration period, the vessels are stretched to their optimal lumen diameter for active tension development which is determined based on the internal circumference-wall tension ratio. The internal circumference is set to 90% of what the vessels would have if they are exposed to a passive tension equivalent to that produced by a transmural pressure of 100 mmHg.

Afterwards, the vessels are washed three times with Krebs-Henseleit buffer and left to equilibrate for 30 min. The contractility is then tested by a twofold exposure to a high $K^+$ solution (50 mmol/l KCl). After washing with Krebs-Henseleit buffer the vessels are then pre-contracted using 1 nmol/l Arg-vasopressin. After a stable contraction is established, a cumulative dose response curve of the test compound is constructed. The stabilized contraction induced by Arg-vasopressin is defined as 100% tension. The relaxation is expressed as percentage tension.

B-6. In Vivo Assay for Detecting Cardiovascular Effects: Blood Pressure Measurement in Anaesthetized Rats (Vasopressin 'Challenge' Model)

Male Sprague-Dawley rats (250-350 g body weight) are used under ketamine/xylazine/pentobarbital injection anaesthesia. Polyethylene tubes (PE-50, Intramedic®), prefilled with heparin-containing (500 IU/ml) isotonic sodium chloride solution, are introduced into the jugular vein and the femoral vein and then tied in. Arg-vasopressin (SIGMA) is injected via one venous access, with the aid of a syringe; the test substance is administered via the second venous access. For determination of the systolic blood pressure, a pressure catheter (Millar SPR-320 2F) is tied into the carotid artery. The arterial catheter is connected to a pressure transducer which feeds its signals to a recording computer equipped with suitable recording software. In a typical experiment, the experimental animal is administered 3-4 successive bolus injections at intervals of 10-15 min with a defined amount of Arg-vasopressin (30 ng/kg) in isotonic sodium chloride solution. When the blood pressure has reached initial levels again, the test substance is administered as a bolus, with subsequent continuous infusion, in a suitable solvent. After this, at defined intervals (10-15 min), the same amount of Arg-vasopressin as at the start is administered again. On the basis of the blood pressure values, a determination is made of the extent to which the test substance counteracts the hypertensive effect of Arg-vasopressin. Control animals only receive solvent instead of the test substance.

Following intravenous administration, the compounds of the invention, in comparison to the solvent controls, bring about an inhibition of the blood pressure increase caused by Arg-vasopressin.

B-7. In Vivo Assay for Detecting Cardiovascular Effects: Diuresis Investigations in Conscious Rats Kept in Metabolism Cages Wistar rats (220-450 g body weight) are kept with free access to feed (Altromin) and drinking water. During the experiment, the animals are kept with free access to drinking water for 4 to 8 or up to 24 hours individually in metabolism cages suitable for rats of this weight class (Tecniplast Deutschland GmbH, D-82383 Hohenpeißenberg). At the beginning of the experiment, the animals are administered the test substance in a volume of 1 to 3 ml/kg body weight of a suitable solvent by means of gavage into the stomach. Control animals only receive solvent. Controls and substance tests are carried out in parallel on the same day. Control groups and substance-dose groups each consist of 4 to 8 animals. During the experiment, the urine excreted by the animals is collected continuously in a receiver at the base of the cage. The volume of urine per time unit is determined separately for each animal, and the concentration of urinary electrolytes is measured by standard methods of flame photometry. Before the beginning of the experiment, the body weight of the individual animals is determined.

B-8. In Vivo Assay for Detecting Protective Renal Effects: Acute Ischemia/Reperfusion Injury Model in Rodents Laboratory bred male C57B/6J mice 6-8 weeks old are obtained from Taconic Biosciences, male 6-8 weeks old Sprague Dawley® rat are obtained from Charles River. Both rats and mice are maintained under standard laboratory conditions, 12 hour light-dark cycles with access to normal chow and drinking water at libitum. For the ischemia reperfusion injury model a total of 10-12 rats or mice is used in each control and experimental group.

Animals are anesthetized with continuous inhaled isoflurane. A right nephrectomy is performed through a right flank incision 7 days before the ischemic procedures in the contralateral kidneys. For renal ischemia a left flank incision is made. Renal vessels are exposed by dissection of the left renal pedicle. Non-traumatic vascular clamps are used to stop blood flow (artery and vein) during 45 min (rats) or 25 min (mice) of ischemia. Reperfusion is established by removing the clamps. The abdominal wall (muscular layer and skin) is closed with 5.0 polypropylene sutures. Temgesic® (Buprenorphin, 0.025 mg/kg s.c.) is applied as an analgesic.

Urine of each animal is collected in metabolic cages over night before sacrifice at 24 h post ischemia. Upon sacrifice, blood samples are obtained under terminal anesthesia. After centrifugation of the blood samples, serum is isolated. Both serum creatinine and serum urea are measured via clinical biochemistry analyzer (Pentra 400). For the assessment of serum and urinary kidney injury biomarkers (Neutrophil gelatinase-associated lipocalin [NGAL], kidney injury molecule-1 [KIM-1] and Osteopontin) ELiSA's are performed according to the manufacturers protocol. Both urinary creatinine and albumin are measured to determine the albumin/creatinine ratio.

Total RNA is isolated from kidneys. Left kidneys are snap-frozen in liquid nitrogen at sacrifice. Kidney tissue is then homogenized and RNA is obtained. Total RNA is transcribed to cDNA. Using TaqMan real-time PCR renal NGAL, Osteopontin, KIM-1, Nephrin and Podocin mRNA expression is analyzed in whole kidney tissue.

Differences between groups are analyzed by one-way ANOVA with Dunnett's corrections for multiple comparisons. Statistical significance is defined as p<0.05. All statistical analyses are done using GraphPad Prism 6.

B-9. In Vivo Assay for Detecting Cardiovascular Effects: Hemodynamic Investigations in Anaesthetized Dogs Male beagle dogs (Beagle, Marshall BioResources, USA) with a weight of between 10 and 15 kg are anesthetized with pentobarbital (30 mg/kg iv, Narcoren®, Merial, Germany) for the surgical interventions and the hemodynamic and functional investigation termini. Pancuroniumbromide (Pancuronium Inresa, Inresa, Germany, 2-4 mg/animal i.v.) serves additionally as a muscle relaxant. The dogs are intubated and ventilated with an oxygen/ambient air mixture (30/70%), about 2.5-4 L/min. Ventilation takes place using a ventilator from GE Healthcare (Avance, Germany) and is monitored using a carbon dioxide analyzer (Datex Ohmeda). The anesthesia is maintained by continual infusion of pentobarbital (50 µg/kg/min); fentanyl is used as an analgesic (10 µg/kg/h).

In preparatory interventions, the dogs are fitted with a cardiac pacemaker. At start of experiment, a cardiac pacemaker from Biotronik (Logos®, Germany) is implanted into a subcutaneous skin pocket and is contacted with the heart via a pacemaker electrode (Siello S60®, Biotronik, Germany) which is advanced through the external jugular vein, with illumination, into the right ventricle.

Thereafter accesses are removed and the dog wakes spontaneously from the anesthesia. After a further 7 days, the above-described pacemaker is activated and the heart is stimulated at a frequency of 220 beats per minute.

The actual drug testing experiments take place 28 days after the beginning of pacemaker stimulation, using the following instrumentation:
- Introduction of a bladder catheter for bladder relief and for measuring the flow of urine
- Attachment of electrocardiography (ECG) leads to the extremities for ECG measurement
- Introduction of a sheath introducer filled with sodium chloride solution into the femoral artery. This tube is connected to a pressure sensor (Braun Melsungen, Melsungen, Germany) for measuring the systemic blood pressure
- Introduction of a Millar Tip catheter (type 350 PC, Millar Instruments, Houston, USA) through a port secured in the carotid artery, for measuring cardiac hemodynamics.
- Introduction of a Swan-Ganz catheter (CCOmbo 7.5F, Edwards, Irvine, USA) via the jugular vein into the pulmonary artery, for measuring the cardiac output, oxygen saturation, pulmonary arterial pressures and central venous pressure
- Siting of a venous catheter in the cephalic vein, for infusing pentobarbital, for liquid replacement and for blood sampling (determination of the plasma levels of substance or other clinical blood values)
- Siting of a venous catheter in the saphenous vein, for infusing fentanyl and for administration of substance
- Infusion of vasopressin (Sigma) in increasing dosage, up to a dose of 4 mU/kg/min. The pharmacological substances are then tested with this dosage.

The primary signals are amplified if necessary (ACQ7700, Data Sciences International, USA or Edwards-Vigilance-Monitor, Edwards, Irvine, USA) and subsequently fed into the Ponemah system (Data Sciences International, USA) for evaluation. The signals are recorded continuously throughout the experimental period, and are further processed digitally by said software, and averaged over 30 seconds.

Although the invention has been disclosed with reference to specific embodiments, it is apparent that other embodiments and variations of the invention may be devised by others skilled in the art without departing from the true spirit and scope of the invention. The claims are intended to be construed to include all such embodiments and equivalent variations.

C) Working Examples of Pharmaceutical Compositions

The substances according to the invention can be converted to pharmaceutical preparations as follows:

Tablet:
Composition:
100 mg of the compound of Example 1, 50 mg of lactose (monohydrate), 50 mg of maize starch, 10 mg of polyvinylpyrrolidone (PVP 25) (from BASF, Germany) and 2 mg of magnesium stearate.

Tablet weight 212 mg. Diameter 8 mm, radius of curvature 12 mm.

Production:
The mixture of the compound of Example 1, lactose and starch is granulated with a 5% strength solution (m/m) of the PVP in water. After drying, the granules are mixed with the magnesium stearate for 5 min. This mixture is compressed in a conventional tabletting press (see above for format of the tablet).

Oral Suspension:
Composition:
1000 mg of the compound of Example 1, 1000 mg of ethanol (96%), 400 mg of Rhodigel (xanthan gum) (from FMC, USA) and 99 g of water.

10 ml of oral suspension correspond to a single dose of 100 mg of the compound of the invention.

Production:
The Rhodigel is suspended in ethanol, and the compound of Example 1 is added to the suspension. The water is added while stirring. The mixture is stirred for about 6 h until swelling of the Rhodigel is complete.

Sterile i.v. Solution:
The compound according to the invention is dissolved at a concentration below saturation solubility in a physiologically acceptable solvent (for example isotonic sodium chloride solution, glucose solution 5% and/or PEG 400 solution 30%). The solution is sterilized by filtration and filled into sterile and pyrogen-free injection containers.

The invention claimed is:
1. A compound of general formula (I)

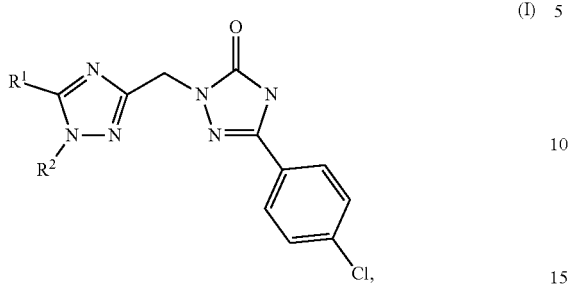

in which
R¹ represents hydrogen, 1,1-dioxidothiomorpholin-4-yl, 3-oxopiperazin-1-yl, (1,1-dioxidothiomorpholin-4-yl)carbonyl, (3-oxopiperazin-1-yl)carbonyl or 2-amino-2-methyl-propylaminocarbonyl,
R² represents a group of formula

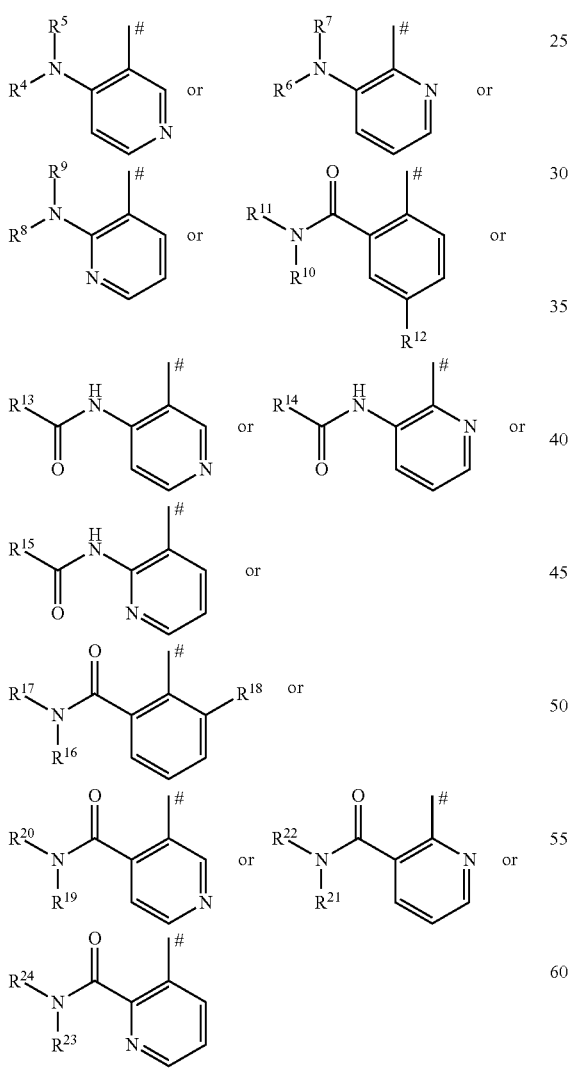

in which
# represents the point of attachment to the 1,2,4-triazolyl-ring,
R⁴ represents hydrogen,
R⁵ represents $C_1$-$C_5$-alkyl or $C_3$-$C_6$-cycloalkyl,
  where alkyl may be substituted by 1 to 2 substituents independently of one another selected from the group consisting of fluorine, hydroxy, amino, hydroxycarbonyl, aminocarbonyl, trifluoromethyl, $C_3$-$C_6$-cycloalkyl, 4- to 7-membered heterocyclyl and $C_1$-$C_4$-alkoxycarbonyl,
    wherein cycloalkyl may be substituted by one substituent hydroxy and amino,
    and
    wherein heterocyclyl may be substituted by 1 to 3 substituents independently of one another selected from the group consisting of oxo, chlorine, fluorine, hydroxy, aminocarbonyl, trifluoromethyl, methyl and methoxy,
  where cycloalkyl may be substituted by 1 to 3 substituents independently of one another selected from the group consisting of fluorine, cyano, hydroxy, amino, trifluoromethyl and methyl,
or
R⁴ and R⁵ together with the nitrogen atom to which they are attached form a 4- to 6-membered heterocyclyl,
  where heterocyclyl may be substituted by 1 to 3 substituents independently of one another selected from the group consisting of oxo, chlorine, fluorine, hydroxy, aminocarbonyl, trifluoromethyl, methyl, methoxy and methoxymethyl,
R⁶ represents hydrogen,
R⁷ represents $C_1$-$C_5$-alkyl or $C_3$-$C_6$-cycloalkyl,
  where alkyl may be substituted by 1 to 2 substituents independently of one another selected from the group consisting of fluorine, hydroxy, amino, hydroxycarbonyl, aminocarbonyl, trifluoromethyl, $C_3$-$C_6$-cycloalkyl, 4- to 7-membered heterocyclyl and $C_1$-$C_4$-alkoxycarbonyl,
    wherein cycloalkyl may be substituted by one substituent hydroxy and amino,
    and
    wherein heterocyclyl may be substituted by 1 to 3 substituents independently of one another selected from the group consisting of oxo, chlorine, fluorine, hydroxy, aminocarbonyl, trifluoromethyl, methyl and methoxy,
  where cycloalkyl may be substituted by 1 to 3 substituents independently of one another selected from the group consisting of fluorine, cyano, hydroxy, amino, trifluoromethyl and methyl,
or
R⁶ and R⁷ together with the nitrogen atom to which they are attached form a 4- to 6-membered heterocyclyl,
  where heterocyclyl may be substituted by 1 to 3 substituents independently of one another selected from the group consisting of oxo, chlorine, fluorine, hydroxy, aminocarbonyl, trifluoromethyl, methyl, methoxy and methoxymethyl,
R⁸ represents hydrogen,
R⁹ represents $C_1$-$C_5$-alkyl or $C_3$-$C_6$-cycloalkyl,
  where alkyl may be substituted by 1 to 2 substituents independently of one another selected from the group consisting of fluorine, hydroxy, amino, hydroxycarbonyl, aminocarbonyl, trifluoromethyl, $C_3$-$C_6$-cycloalkyl, 4- to 7-membered heterocyclyl and $C_1$-$C_4$-alkoxycarbonyl, wherein cycloalkyl may be substituted by one substituent fluorine, hydroxy and amino,
and
wherein heterocyclyl may be substituted by 1 to 3 substituents independently of one another selected from the group consisting of oxo, chlorine, fluorine, hydroxy, aminocarbonyl, trifluoromethyl, methyl and methoxy,
where cycloalkyl may be substituted by 1 to 3 substituents independently of one another selected from the group consisting of fluorine, cyano, hydroxy, amino, trifluoromethyl and methyl,
or
$R^8$ and $R^9$ together with the nitrogen atom to which they are attached form a 4- to 6-membered heterocyclyl,
where heterocyclyl may be substituted by 1 to 3 substituents independently of one another selected from the group consisting of oxo, chlorine, fluorine, hydroxy, aminocarbonyl, trifluoromethyl, methyl, methoxy and methoxymethyl,
$R^{10}$ represents hydrogen, methyl, ethyl or propan-2-yl,
$R^{11}$ represents $C_1$-$C_5$-alkyl, prop-2-en-1-yl, 3-methylbut-2-en-1-yl, methoxy, $C_3$-$C_7$-cycloalkyl, phenyl, 4- to 6-membered heterocyclyl or 5- or 6-membered heteroaryl,
where alkyl may be substituted by 1 to 2 substituents independently of one another selected from the group consisting of fluorine, cyano, hydroxy, amino, aminocarbonyl, trifluoromethyl, 1,1,2,2-tetrafluoroethyl, $C_3$-$C_6$-cycloalkyl, phenyl, 4- to 7-membered heterocyclyl, 5- or 6-membered heteroaryl and $C_1$-$C_4$-alkoxycarbonyl,
wherein cycloalkyl may be substituted by 1 to 3 substituents independently of one another selected from the group consisting of fluorine, cyano, hydroxyl and methyl,
and
wherein phenyl may be substituted by 1 to 3 substituents independently of one another selected from the group consisting of fluorine, cyano, hydroxyl and methyl,
and
wherein heterocyclyl may be substituted by 1 to 3 substituents independently of one another selected from the group consisting of oxo, chlorine, fluorine, hydroxy, aminocarbonyl, trifluoromethyl, methyl and methoxy,
and
wherein heteroaryl may be substituted by 1 to 3 substituents independently of one another selected from the group consisting of fluorine, trifluoromethyl and methyl,
where cycloalkyl may be substituted by 1 to 3 substituents independently of one another selected from the group consisting of fluorine, cyano, hydroxy, amino and methyl,
and
where phenyl may be substituted by 1 to 3 substituents independently of one another selected from the group consisting of chlorine, fluorine, cyano, hydroxy, amino and methyl,
and
where heterocyclyl may be substituted by 1 to 3 substituents of oxo,
and
where heteroaryl may be substituted by 1 to 3 substituents independently of one another selected from the group consisting of chlorine, fluorine, hydroxy, amino, trifluoromethyl, methyl and ethyl,
or
$R^{10}$ and $R^{11}$ together with the nitrogen atom to which they are attached form a 4- to 7-membered heterocyclyl, 6-oxo-2,5,7-triazaspiro[3.4]octan-2-yl, 2-oxa-5-azabicyclo[2.2.1]hept-5-yl or 5-methyl-2,5-diazabicyclo[2.2.1]hept-2-yl,
where heterocyclyl may be substituted by 1 to 3 substituents independently of one another selected from the group consisting of oxo, chlorine, fluorine, hydroxy, formyl, aminocarbonyl, trifluoromethyl, methyl, ethyl, methoxy, methoxymethyl, dimethylamino and methylcarbonylamino,
$R^{12}$ represents hydrogen, chlorine or fluorine,
$R^{13}$ represents methyl, methoxy or $C_3$-$C_6$-cycloalkyl,
where methyl and methoxy may be substituted by one substituent independently of one another selected from the group consisting of fluorine, hydroxy, trifluoromethyl, methoxy, $C_3$-$C_6$-cycloalkyl, 4- to 7-membered heterocyclyl, methylsulfonyl and methylsulfonylamino,
and
where cycloalkyl may be substituted by 1 to 3 substituents independently of one another selected from the group consisting of fluorine and trifluoromethyl,
$R^{14}$ represents trifluoromethyl, methyl, methoxy, 2,2,2-trifluoroethylamino, $C_3$-$C_6$-cycloalkyl or 4- to 6-membered heterocyclyl,
where methyl and methoxy may be substituted by one substituent independently of one another selected from the group consisting of fluorine, hydroxy, trifluoromethyl, methoxy, $C_3$-$C_6$-cycloalkyl, 4- to 7-membered heterocyclyl, methylsulfonyl and methylsulfonylamino,
and
where cycloalkyl may be substituted by 1 to 3 substituents independently of one another selected from the group consisting of fluorine and trifluoromethyl,
and
where heterocyclyl may be substituted by 1 to 3 substituents of oxo,
$R^{15}$ represents $C_1$-$C_5$-alkyl, methoxy, 2,2,2-trifluoroethoxy, prop-2-en-1-yl, but-3-en-2-yl, $C_3$-$C_7$-cycloalkyl, phenyl, 4- to 6-membered heterocyclyl or 5- or 6-membered heteroaryl,
where alkyl and methoxy may be substituted by one substituent independently of one another selected from the group consisting of fluorine, hydroxy, trifluoromethyl, methoxy, methylsulfanyl, methylamino, $C_3$-$C_6$-cycloalkyl, phenyl, 4- to 7-membered heterocyclyl, 5- or 6-membered heteroaryl, methylsulfonyl and methylsulfonylamino,
wherein heterocyclyl may be substituted by 1 to 3 substituents independently of one another selected from the group consisting of oxo and methyl,
and
wherein heteroaryl may be substituted by 1 to 3 substituents independently of one another selected from the group consisting of fluorine, trifluoromethyl and methyl,
and
where cycloalkyl may be substituted by 1 to 3 substituents independently of one another selected from the group consisting of fluorine, aminocarbonyl, trifluoromethyl and methyl,
and
where phenyl may be substituted by 1 to 3 substituents independently of one another selected from the group consisting of fluorine, cyano, hydroxyl and methyl,
and
where heterocyclyl may be substituted by 1 to 3 substituents independently of one another selected from the group consisting of oxo and methyl,
and
where heteroaryl may be substituted by 1 to 3 substituents independently of one another selected from the group consisting of fluorine, trifluoromethyl, methyl and ethyl, $R^{16}$ represents hydrogen or methyl, $R^{17}$ represents $C_1$-$C_5$-alkyl, prop-2-en-1-yl, 3-methylbut-2-en-1-yl or $C_3$-$C_7$-cycloalkyl,
where alkyl may be substituted by 1 to 2 substituents independently of one another selected from the group consisting of fluorine, cyano, hydroxy, amino, aminocarbonyl, trifluoromethyl, 1,1,2,2-tetrafluoroethyl, $C_3$-$C_6$-cycloalkyl and $C_1$-$C_4$-alkoxycarbonyl,
wherein cycloalkyl may be substituted by 1 to 3 substituents independently of one another selected from the group consisting of fluorine, cyano, hydroxyl and methyl,
and
where cycloalkyl may be substituted by 1 to 3 substituents independently of one another selected from the group consisting of fluorine, cyano, hydroxy, amino, trifluoromethyl and methyl,
or
$R^{16}$ and $R^{17}$ together with the nitrogen atom to which they are attached form a 4- to 7-membered heterocyclyl or 2-oxa-6-azaspiro[3.3]hept-6-yl,
where heterocyclyl may be substituted by 1 to 3 substituents independently of one another selected from the group consisting of oxo, chlorine, fluorine, hydroxy, formyl, aminocarbonyl, trifluoromethyl, methyl, ethyl, methoxy, methoxymethyl, dimethylamino and methylcarbonylamino, $R^{18}$ represents chlorine or trifluoromethyl, $R^{19}$ represents hydrogen or methyl, $R^{20}$ represents $C_1$-$C_5$-alkyl or $C_3$-$C_6$-cycloalkyl,
where alkyl may be substituted by 1 to 2 substituents independently of one another selected from the group consisting of fluorine, hydroxy, amino, trifluoromethyl and $C_3$-$C_6$-cycloalkyl,
wherein cycloalkyl may be substituted by one substituent fluorine, hydroxy and amino,
and
where cycloalkyl may be substituted by 1 to 3 substituents independently of one another selected from the group consisting of fluorine, cyano, hydroxy, amino, trifluoromethyl and methyl,
or
$R^{19}$ and $R^{20}$ together with the nitrogen atom to which they are attached form a 4- to 6-membered heterocyclyl,
where heterocyclyl may be substituted by 1 to 3 substituents independently of one another selected from the group consisting of oxo, chlorine, fluorine, hydroxy, aminocarbonyl, trifluoromethyl, methyl, methoxy and methoxymethyl, $R^{21}$ represents hydrogen or methyl, $R^{22}$ represents $C_1$-$C_5$-alkyl or $C_3$-$C_6$-cycloalkyl,
where alkyl may be substituted by 1 to 2 substituents independently of one another selected from the group consisting of fluorine, hydroxy, amino, trifluoromethyl and $C_3$-$C_6$-cycloalkyl,
wherein cycloalkyl may be substituted by one substituent fluorine, hydroxy and amino,
and
where cycloalkyl may be substituted by 1 to 3 substituents independently of one another selected from the group consisting of fluorine, cyano, hydroxy, amino, trifluoromethyl and methyl,
or
$R^{21}$ and $R^{22}$ together with the nitrogen atom to which they are attached form a 4- to 6-membered heterocyclyl,
where heterocyclyl may be substituted by 1 to 3 substituents independently of one another selected from the group consisting of oxo, chlorine, fluorine, hydroxy, aminocarbonyl, trifluoromethyl, methyl, methoxy and methoxymethyl, $R^{23}$ represents hydrogen or methyl, $R^{24}$ represents $C_1$-$C_5$-alkyl or $C_3$-$C_6$-cycloalkyl,
where alkyl may be substituted by 1 to 2 substituents independently of one another selected from the group consisting of fluorine, hydroxy, amino,

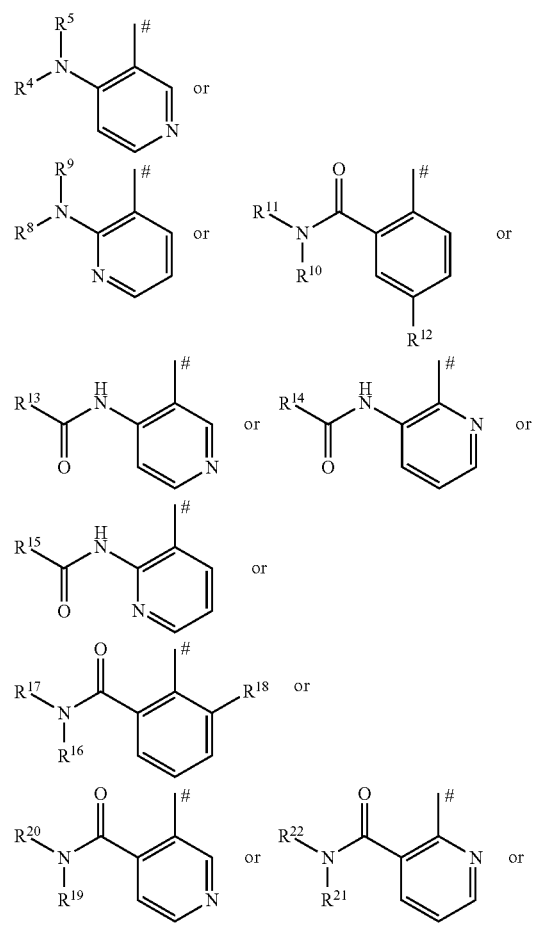

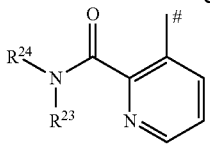

in which
# represents the point of attachment to the 1,2,4-triazolyl-ring, $R^4$ represents hydrogen, $R^5$ represents $C_1$-$C_5$-alkyl,
where alkyl may be substituted by 1 to 2 substituents independently of one another selected from the group consisting of fluorine, hydroxy, amino, hydroxycarbonyl, aminocarbonyl, trifluoromethyl, $C_3$-$C_6$-cycloalkyl, 4- to 7-membered heterocyclyl and $C_1$-$C_4$-alkoxycarbonyl,
wherein cycloalkyl may be substituted by one substituent hydroxy and amino,
and
wherein heterocyclyl may be substituted by 1 to 3 substituents of oxo, or $R^4$ and $R^5$ together with the nitrogen atom to which they are attached form a 4- to 6-membered heterocyclyl,
where heterocyclyl may be substituted by 1 to 3 substituents independently trifluoromethyl and $C_3$-$C_6$-cycloalkyl,
wherein cycloalkyl may be substituted by one substituent fluorine, hydroxy and amino,
and
where cycloalkyl may be substituted by 1 to 3 substituents independently of one another selected from the group consisting of fluorine, cyano, hydroxy, amino, trifluoromethyl and methyl, or $R^{23}$ and $R^{24}$ together with the nitrogen atom to which they are attached form a 4- to 6-membered heterocyclyl,
where heterocyclyl may be substituted by 1 to 3 substituents independently of one another selected from the group consisting of oxo, chlorine, fluorine, hydroxy, aminocarbonyl, trifluoromethyl, methyl, methoxy and methoxymethyl, $R^3$ represents a group of formula

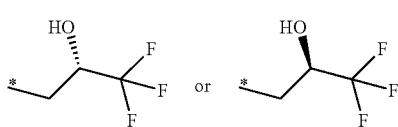

in which
* represents the point of attachment to the 2,4-dihydro-3H-1,2,4-triazolyl-ring, and/or a pharmaceutically acceptable salt thereof, solvate thereof or solvate of a salt thereof.

2. A compound of formula (I) according to claim 1, wherein
$R^1$ represents hydrogen, 1,1-dioxidothiomorpholin-4-yl, 3-oxopiperazin-1-yl, (1,1-dioxidothiomorpholin-4-yl) carbonyl, (3-oxopiperazin-1-yl)carbonyl or 2-amino-2-methyl-propylaminocarbonyl, $R^2$ represents a group of formula of one another selected from the group consisting of oxo, chlorine, fluorine, hydroxy, aminocarbonyl and methyl, $R^8$ represents hydrogen, $R^9$ represents $C_1$-$C_5$-alkyl or $C_3$-$C_6$-cycloalkyl,
where alkyl may be substituted by 1 to 2 substituents independently of one another selected from the group consisting of fluorine, hydroxy, amino, trifluoromethyl, $C_3$-$C_6$-cycloalkyl and 4- to 7-membered heterocyclyl,
wherein heterocyclyl may be substituted by 1 to 3 substituents of oxo,
where cycloalkyl may be substituted by 1 to 3 substituents independently of one another selected from the group consisting of fluorine, trifluoromethyl and methyl, or $R^8$ and $R^9$ together with the nitrogen atom to which they are attached form a 4- to 6-membered heterocyclyl,
where heterocyclyl may be substituted by 1 to 3 substituents independently of one another selected from the group consisting of oxo, chlorine, fluorine, hydroxy, aminocarbonyl, trifluoromethyl and methyl, $R^{10}$ represents hydrogen, methyl, ethyl or propan-2-yl, $R^{11}$ represents $C_1$-$C_5$-alkyl, prop-2-en-1-yl, 3-methyl-but-2-en-1-yl, methoxy, $C_3$-$C_7$-cycloalkyl, phenyl, 4- to 6-membered heterocyclyl or 5- or 6-membered heteroaryl,
where alkyl may be substituted by 1 to 2 substituents independently of one another selected from the group consisting of fluorine, cyano, hydroxy, amino, aminocarbonyl, trifluoromethyl, 1,1,2,2-tetrafluoroethyl, $C_3$-$C_6$-cycloalkyl, phenyl, 4- to 7-membered heterocyclyl and 5- or 6-membered heteroaryl,
wherein phenyl may be substituted by 1 to 3 of fluorine,
and
wherein heterocyclyl may be substituted by 1 to 3 substituents independently of one another selected from the group consisting of oxo and methyl,
and
wherein heteroaryl may be substituted by 1 to 3 substituents of methyl,
where cycloalkyl may be substituted by 1 to 3 substituents independently of one another selected from the group consisting of fluorine, hydroxy, amino and methyl,
and
where phenyl may be substituted by 1 to 3 substituents independently of one another selected from the group consisting of chlorine, fluorine, hydroxy, amino and methyl,
and
where heterocyclyl may be substituted by 1 to 3 substituents of oxo,
and
where heteroaryl may be substituted by 1 to 3 substituents independently of one another selected from the group consisting of chlorine, fluorine, hydroxy, amino, methyl and ethyl, or $R^{10}$ and $R^{11}$ together with the nitrogen atom to which they are attached form a 4- to 7-membered heterocyclyl, 6-oxo-2,5,7-triazaspiro[3.4]octan-2-yl, 2-oxa-5-azabicyclo[2.2.1]hept-5-yl or 5-methyl-2,5-diazabicyclo[2.2.1]hept-2-yl,
   where heterocyclyl may be substituted by 1 to 3 substituents independently of one another selected from the group consisting of oxo, chlorine, fluorine, hydroxy, formyl, aminocarbonyl, methyl, ethyl, methoxy, methoxymethyl, dimethylamino and methylcarbonylamino, $R^{12}$ represents hydrogen, chlorine or fluorine,
$R^{13}$ represents methyl, methoxy or $C_3$-$C_6$-cycloalkyl,
   where methyl and methoxy may be substituted by one substituent independently of one another selected from the group consisting of trifluoromethyl and $C_3$-$C_6$-cycloalkyl,
   and
   where cycloalkyl may be substituted by 1 to 3 substituents independently of one another selected from the group consisting of fluorine and trifluoromethyl, $R^{14}$ represents trifluoromethyl, methyl, methoxy, 2,2,2-trifluoroethylamino, $C_3$-$C_6$-cycloalkyl or 4- to 6-membered heterocyclyl,
   where methyl and methoxy may be substituted by one substituent independently of one another selected from the group consisting of fluorine, trifluoromethyl, methoxy, $C_3$-$C_6$-cycloalkyl, methylsulfonyl and methylsulfonylamino,
   and
   where cycloalkyl may be substituted by 1 to 3 substituents independently of one another selected from the group consisting of fluorine and trifluoromethyl,
   and
   where heterocyclyl may be substituted by 1 to 3 substituents of oxo, $R^{15}$ represents $C_1$-$C_5$-alkyl, 2,2,2-trifluoroethoxy, prop-2-en-1-yl, but-3-en-2-yl, $C_3$-$C_7$-cycloalkyl, phenyl, 4- to 6-membered heterocyclyl or 5- or 6-membered heteroaryl,
   where alkyl may be substituted by one substituent selected from the group consisting of hydroxy, trifluoromethyl, methoxy, methylsulfanyl, methylamino, $C_3$-$C_6$-cycloalkyl, phenyl, 4- to 7-membered heterocyclyl and 5- or 6-membered heteroaryl,
      wherein heterocyclyl may be substituted by 1 to 3 substituents of oxo,
      and
      wherein heteroaryl may be substituted by 1 to 3 substituents of methyl,
   and
   where cycloalkyl may be substituted by 1 to 3 substituents independently of one another selected from the group consisting of fluorine, aminocarbonyl, trifluoromethyl and methyl,
   and
   where phenyl may be substituted by 1 to 3 substituents independently of one another selected from the group consisting of fluorine, cyano, hydroxyl and methyl,
   and
   where heterocyclyl may be substituted by 1 to 3 substituents independently of one another selected from the group consisting of oxo and methyl,
   and
   where heteroaryl may be substituted by 1 to 3 substituents independently of one another selected from the group consisting of fluorine, methyl and ethyl, $R^{16}$ represents hydrogen or methyl,
$R^{17}$ represents $C_1$-$C_5$-alkyl or $C_3$-$C_7$-cycloalkyl,
   where alkyl may be substituted by 1 to 2 substituents independently of one another selected from the group consisting of hydroxy, amino, trifluoromethyl and $C_3$-$C_6$-cycloalkyl,
   and
   where cycloalkyl may be substituted by 1 to 3 substituents independently of one another selected from the group consisting of fluorine, trifluoromethyl and methyl,
or
$R^{16}$ and $R^{17}$ together with the nitrogen atom to which they are attached form a 4- to 7-membered heterocyclyl or 2-oxa-6-azaspiro[3.3]hept-6-yl,
   where heterocyclyl may be substituted by 1 to 3 substituents independently of one another selected from the group consisting of oxo, chlorine, fluorine, hydroxy, aminocarbonyl, trifluoromethyl, methyl, ethyl and methoxymethyl, $R^{18}$ represents chlorine or trifluoromethyl,
$R^{19}$ represents hydrogen,
$R^{20}$ represents $C_1$-$C_5$-alkyl or $C_3$-$C_6$-cycloalkyl,
   where alkyl may be substituted by 1 to 2 substituents of trifluoromethyl,
   and
   where cycloalkyl may be substituted by 1 to 3 substituents independently of one another selected from the group consisting of fluorine and methyl,
or
$R^{19}$ and $R^{20}$ together with the nitrogen atom to which they are attached form a 4- to 6-membered heterocyclyl,
   where heterocyclyl may be substituted by one substituent of methoxymethyl, $R^{21}$ represents hydrogen,
$R^{22}$ represents $C_1$-$C_5$-alkyl or $C_3$-$C_6$-cycloalkyl,
   where alkyl may be substituted by 1 to 2 substituents independently of one another selected from the group consisting of trifluoromethyl and $C_3$-$C_6$-cycloalkyl,
   and
   where cycloalkyl may be substituted by 1 to 3 substituents independently of one another selected from the group consisting of fluorine, cyano and methyl,
or
$R^{21}$ and $R^{22}$ together with the nitrogen atom to which they are attached form a 4- to 6-membered heterocyclyl,
   where heterocyclyl may be substituted by one substituent of methoxymethyl, $R^{23}$ represents hydrogen or methyl,
$R^{24}$ represents $C_1$-$C_5$-alkyl or $C_3$-$C_6$-cycloalkyl,
   where alkyl may be substituted by 1 to 2 substituents independently of one another selected from the group consisting of hydroxy, amino, trifluoromethyl and $C_3$-$C_6$-cycloalkyl,
   and
   where cycloalkyl may be substituted by 1 to 3 substituents independently of one another selected from the group consisting of fluorine, trifluoromethyl and methyl,
or
$R^{23}$ and $R^{24}$ together with the nitrogen atom to which they are attached form a 4- to 6-membered heterocyclyl, where heterocyclyl may be substituted by 1 to 3 substituents independently of one another selected from the group consisting of oxo, chlorine, fluorine, hydroxy, aminocarbonyl, trifluoromethyl and methyl, R³ represents a group of formula

[chemical structures showing two stereoisomers with HO, F, F, F groups]

in which
* represents the point of attachment to the 2,4-dihydro-3H-1,2,4-triazolyl-ring, And/or a pharmaceutically acceptable salt thereof, solvate thereof or solvate of a salt thereof.

3. A compound of formula (I) according to claim 1, wherein
$R^1$ represents hydrogen,
$R^2$ represents a group of formula

[chemical structures showing eight different pyridine/benzamide variants with R¹⁰-R²⁴ substituents]

in which
# represents the point of attachment to the 1,2,4-triazolyl-ring,
$R^{10}$ represents hydrogen, methyl, ethyl or propan-2-yl,
$R^{11}$ represents $C_1$-$C_5$-alkyl, prop-2-en-1-yl, 3-methylbut-2-en-1-yl, methoxy, $C_3$-$C_7$-cycloalkyl, phenyl, 4- to 6-membered heterocyclyl or 5- or 6-membered heteroaryl,
where alkyl may be substituted by 1 to 2 substituents independently of one another selected from the group consisting of fluorine, cyano, hydroxy, amino, aminocarbonyl, trifluoromethyl, 1,1,2,2-tetrafluoroethyl, $C_3$-$C_6$-cycloalkyl, phenyl, 4- to 7-membered heterocyclyl and 5- or 6-membered heteroaryl,
wherein phenyl may be substituted by 1 to 3 of fluorine,
and
wherein heterocyclyl may be substituted by 1 to 3 substituents independently of one another selected from the group consisting of oxo and methyl,
and
wherein heteroaryl may be substituted by 1 to 3 substituents of methyl,
where cycloalkyl may be substituted by 1 to 3 substituents independently of one another selected from the group consisting of fluorine, hydroxy, amino and methyl,
and
where phenyl may be substituted by 1 to 3 substituents independently of one another selected from the group consisting of chlorine, fluorine, hydroxy, amino and methyl,
and
where heterocyclyl may be substituted by 1 to 3 substituents of oxo,
and
where heteroaryl may be substituted by 1 to 3 substituents independently of one another selected from the group consisting of chlorine, fluorine, hydroxy, amino, methyl and ethyl,
or
$R^{10}$ and $R^{11}$ together with the nitrogen atom to which they are attached form a 4- to 7-membered heterocyclyl, 6-oxo-2,5,7-triazaspiro[3.4]octan-2-yl, 2-oxa-5-azabicyclo[2.2.1]hept-5-yl or 5-methyl-2,5-diazabicyclo[2.2.1]hept-2-yl,
where heterocyclyl may be substituted by 1 to 3 substituents independently of one another selected from the group consisting of oxo, chlorine, fluorine, hydroxy, formyl, aminocarbonyl, methyl, ethyl, methoxy, methoxymethyl, dimethylamino and methylcarbonylamino,
$R^{12}$ represents hydrogen, chlorine or fluorine,
$R^{13}$ represents methyl, methoxy or $C_3$-$C_6$-cycloalkyl,
where methyl and methoxy may be substituted by one substituent independently of one another selected from the group consisting of trifluoromethyl and $C_3$-$C_6$-cycloalkyl,
and
where cycloalkyl may be substituted by 1 to 3 substituents independently of one another selected from the group consisting of fluorine and trifluoromethyl,
$R^{14}$ represents trifluoromethyl, methyl, methoxy, 2,2,2-trifluoroethylamino, $C_3$-$C_6$-cycloalkyl or 4- to 6-membered heterocyclyl,
where methyl and methoxy may be substituted by one substituent independently of one another selected from the group consisting of fluorine, trifluoromethyl, methoxy, $C_3$-$C_6$-cycloalkyl, methylsulfonyl and methylsulfonylamino,
and
where cycloalkyl may be substituted by 1 to 3 substituents independently of one another selected from the group consisting of fluorine and trifluoromethyl,
and
where heterocyclyl may be substituted by 1 to 3 substituents of oxo,
$R^{15}$ represents $C_1$-$C_5$-alkyl, 2,2,2-trifluoroethoxy, prop-2-en-1-yl, but-3-en-2-yl, $C_3$-$C_7$-cycloalkyl, phenyl, 4- to 6-membered heterocyclyl or 5- or 6-membered heteroaryl,
where alkyl may be substituted by one substituent selected from the group consisting of hydroxy, trifluoromethyl, methoxy, methylsulfanyl, methylamino, $C_3$-$C_6$-cycloalkyl, phenyl, 4- to 7-membered heterocyclyl and 5- or 6-membered heteroaryl,
wherein heterocyclyl may be substituted by 1 to 3 substituents of oxo,
and
wherein heteroaryl may be substituted by 1 to 3 substituents of methyl,
and
where cycloalkyl may be substituted by 1 to 3 substituents independently of one another selected from the group consisting of fluorine, aminocarbonyl, trifluoromethyl and methyl,
and
where phenyl may be substituted by 1 to 3 substituents independently of one another selected from the group consisting of fluorine, cyano, hydroxyl and methyl,
and
where heterocyclyl may be substituted by 1 to 3 substituents independently of one another selected from the group consisting of oxo and methyl,
and
where heteroaryl may be substituted by 1 to 3 substituents independently of one another selected from the group consisting of fluorine, methyl and ethyl,
$R^{16}$ represents hydrogen or methyl,
$R^{17}$ represents $C_1$-$C_5$-alkyl or $C_3$-$C_7$-cycloalkyl,
where alkyl may be substituted by 1 to 2 substituents independently of one another selected from the group consisting of hydroxy, amino, trifluoromethyl and $C_3$-$C_6$-cycloalkyl,
and
where cycloalkyl may be substituted by 1 to 3 substituents independently of one another selected from the group consisting of fluorine, trifluoromethyl and methyl,
or
$R^{16}$ and $R^{17}$ together with the nitrogen atom to which they are attached form a 4- to 7-membered heterocyclyl or 2-oxa-6-azaspiro[3.3]hept-6-yl,
where heterocyclyl may be substituted by 1 to 3 substituents independently of one another selected from the group consisting of oxo, chlorine, fluorine, hydroxy, aminocarbonyl, trifluoromethyl, methyl, ethyl and methoxymethyl,
$R^{18}$ represents chlorine or trifluoromethyl,
$R^{19}$ represents hydrogen,
$R^{20}$ represents $C_1$-$C_5$-alkyl or $C_3$-$C_6$-cycloalkyl,
where alkyl may be substituted by 1 to 2 substituents of trifluoromethyl,
and
where cycloalkyl may be substituted by 1 to 3 substituents independently of one another selected from the group consisting of fluorine and methyl,
or
$R^{19}$ and $R^{20}$ together with the nitrogen atom to which they are attached form a 4- to 6-membered heterocyclyl,
where heterocyclyl may be substituted by one substituent of methoxymethyl,
$R^{21}$ represents hydrogen,
$R^{22}$ represents $C_1$-$C_5$-alkyl or $C_3$-$C_6$-cycloalkyl,
where alkyl may be substituted by 1 to 2 substituents independently of one another selected from the group consisting of trifluoromethyl and $C_3$-$C_6$-cycloalkyl,
and
where cycloalkyl may be substituted by 1 to 3 substituents independently of one another selected from the group consisting of fluorine, cyano and methyl,
or
$R^{21}$ and $R^{22}$ together with the nitrogen atom to which they are attached form a 4- to 6-membered heterocyclyl,
where heterocyclyl may be substituted by one substituent of methoxymethyl,
$R^{23}$ represents hydrogen or methyl,
$R^{24}$ represents $C_1$-$C_5$-alkyl or $C_3$-$C_6$-cycloalkyl,
where alkyl may be substituted by 1 to 2 substituents independently of one another selected from the group consisting of hydroxy, amino, trifluoromethyl and $C_3$-$C_6$-cycloalkyl,
and
where cycloalkyl may be substituted by 1 to 3 substituents independently of one another selected from the group consisting of fluorine, trifluoromethyl and methyl,
or
$R^{23}$ and $R^{24}$ together with the nitrogen atom to which they are attached form a 4- to 6-membered heterocyclyl,
where heterocyclyl may be substituted by 1 to 3 substituents independently of one another selected from the group consisting of oxo, chlorine, fluorine, hydroxy, aminocarbonyl, trifluoromethyl and methyl,
$R^3$ represents a group of formula

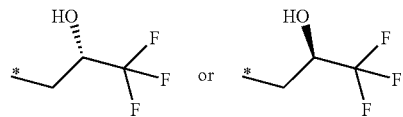

in which
* represents the point of attachment to the 2,4-dihydro-3H-1,2,4-triazolyl-ring,
and/or a pharmaceutically acceptable salt thereof, solvate thereof or solvate of a salt thereof.

4. The compound of formula (I) according to claim 1, wherein
$R^1$ represents hydrogen,
$R^2$ represents a group of formula

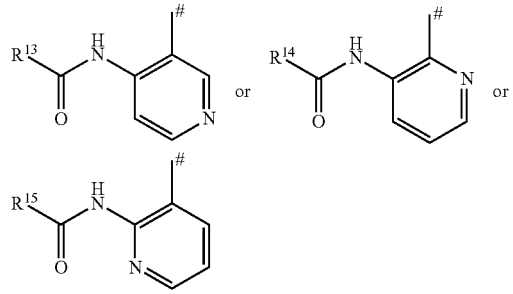

in which
# represents the point of attachment to the 1,2,4-triazolyl-ring,
$R^{13}$ represents methyl, methoxy or $C_3$-$C_6$-cycloalkyl, where methyl and methoxy may be substituted by one substituent independently of one another selected from the group consisting of trifluoromethyl and $C_3$-$C_6$-cycloalkyl,
and
where cycloalkyl may be substituted by 1 to 3 substituents independently of one another selected from the group consisting of fluorine and trifluoromethyl, $R^{14}$ represents trifluoromethyl, methyl, methoxy, 2,2,2-trifluoroethylamino, $C_3$-$C_6$-cycloalkyl or 4- to 6-membered heterocyclyl,
where methyl and methoxy may be substituted by one substituent independently of one another selected from the group consisting of fluorine, trifluoromethyl, methoxy, $C_3$-$C_6$-cycloalkyl, methylsulfonyl and methylsulfonylamino,
and
where cycloalkyl may be substituted by 1 to 3 substituents independently of one another selected from the group consisting of fluorine and trifluoromethyl,
and
where heterocyclyl may be substituted by 1 to 3 substituents of oxo, $R^{15}$ represents $C_1$-$C_5$-alkyl, 2,2,2-trifluoroethoxy, prop-2-en-1-yl, but-3-en-2-yl, $C_3$-$C_7$-cycloalkyl, phenyl, 4- to 6-membered heterocyclyl or 5- or 6-membered heteroaryl,
where alkyl may be substituted by one substituent selected from the group consisting of hydroxy, trifluoromethyl, methoxy, methylsulfanyl, methylamino, $C_3$-$C_6$-cycloalkyl, phenyl, 4- to 7-membered heterocyclyl and 5- or 6-membered heteroaryl,
wherein heterocyclyl may be substituted by 1 to 3 substituents of oxo,
and
wherein heteroaryl may be substituted by 1 to 3 substituents of methyl,
and
where cycloalkyl may be substituted by 1 to 3 substituents independently of one another selected from the group consisting of fluorine, aminocarbonyl, trifluoromethyl and methyl,
and
where phenyl may be substituted by 1 to 3 substituents independently of one another selected from the group consisting of fluorine, cyano, hydroxyl and methyl,
and
where heterocyclyl may be substituted by 1 to 3 substituents independently of one another selected from the group consisting of oxo and methyl,
and
where heteroaryl may be substituted by 1 to 3 substituents independently of one another selected from the group consisting of fluorine, methyl and ethyl, $R^3$ represents a group of formula

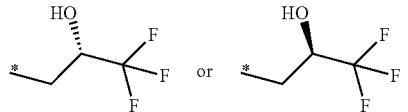

in which
* represents the point of attachment to the 2,4-dihydro-3H-1,2,4-triazolyl-ring,
and/or a pharmaceutically acceptable salt thereof, solvate thereof or solvate of a salt thereof.

5. The compound of the formula (I) according to claim 1, wherein
$R^1$ represents hydrogen,
$R^2$ represents a group of formula

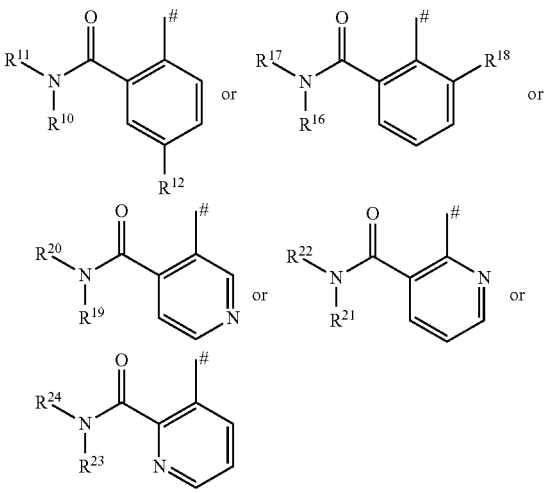

in which
# represents the point of attachment to the 1,2,4-triazolyl-ring,
$R^{10}$ represents hydrogen, methyl, ethyl or propan-2-yl,
$R^{11}$ represents $C_1$-$C_5$-alkyl, prop-2-en-1-yl, 3-methylbut-2-en-1-yl, methoxy, $C_3$-$C_7$-cycloalkyl, phenyl, 4- to 6-membered heterocyclyl or 5- or 6-membered heteroaryl,
where alkyl may be substituted by 1 to 2 substituents independently of one another selected from the group consisting of fluorine, cyano, hydroxy, amino, aminocarbonyl, trifluoromethyl, 1,1,2,2-tetrafluoroethyl, $C_3$-$C_6$-cycloalkyl, phenyl, 4- to 7-membered heterocyclyl and 5- or 6-membered heteroaryl,
wherein phenyl may be substituted by 1 to 3 of fluorine,
and
wherein heterocyclyl may be substituted by 1 to 3 substituents independently of one another selected from the group consisting of oxo and methyl,
and
wherein heteroaryl may be substituted by 1 to 3 substituents of methyl,
where cycloalkyl may be substituted by 1 to 3 substituents independently of one another selected from the group consisting of fluorine, hydroxy, amino and methyl,
and
where phenyl may be substituted by 1 to 3 substituents independently of one another selected from the group consisting of chlorine, fluorine, hydroxy, amino and methyl,
and
where heterocyclyl may be substituted by 1 to 3 substituents of oxo,
and
where heteroaryl may be substituted by 1 to 3 substituents independently of one another selected from the group consisting of chlorine, fluorine, hydroxy, amino, methyl and ethyl, or $R^{10}$ and $R^{11}$ together with the nitrogen atom to which they are attached form a 4- to 7-membered heterocyclyl, 6-oxo-2,5,7-triazaspiro[3.4]octan-2-yl, 2-oxa-5-azabicyclo[2.2.1]hept-5-yl or 5-methyl-2,5-diazabicyclo[2.2.1]hept-2-yl, where heterocyclyl may be substituted by 1 to 3 substituents independently of one another selected from the group consisting of oxo, chlorine, fluorine, hydroxy, formyl, aminocarbonyl, methyl, ethyl, methoxy, methoxymethyl, dimethylamino and methylcarbonylamino, $R^{12}$ represents hydrogen, chlorine or fluorine, $R^{16}$ represents hydrogen or methyl, $R^{17}$ represents $C_1$-$C_5$-alkyl or $C_3$-$C_7$-cycloalkyl, where alkyl may be substituted by 1 to 2 substituents independently of one another selected from the group consisting of hydroxy, amino, trifluoromethyl and $C_3$-$C_6$-cycloalkyl, and where cycloalkyl may be substituted by 1 to 3 substituents independently of one another selected from the group consisting of fluorine, trifluoromethyl and methyl, or $R^{16}$ and $R^{17}$ together with the nitrogen atom to which they are attached form a 4- to 7-membered heterocyclyl or 2-oxa-6-azaspiro[3.3]hept-6-yl, where heterocyclyl may be substituted by 1 to 3 substituents independently of one another selected from the group consisting of oxo, chlorine, fluorine, hydroxy, aminocarbonyl, trifluoromethyl, methyl, ethyl and methoxymethyl, $R^{18}$ represents chlorine or trifluoromethyl, $R^{19}$ represents hydrogen, $R^{20}$ represents $C_1$-$C_5$-alkyl or $C_3$-$C_6$-cycloalkyl, where alkyl may be substituted by 1 to 2 substituents of trifluoromethyl, and where cycloalkyl may be substituted by 1 to 3 substituents independently of one another selected from the group consisting of fluorine and methyl, or $R^{19}$ and $R^{20}$ together with the nitrogen atom to which they are attached form a 4- to 6-membered heterocyclyl, where heterocyclyl may be substituted by one substituent of methoxymethyl, $R^{21}$ represents hydrogen, $R^{22}$ represents $C_1$-$C_5$-alkyl or $C_3$-$C_6$-cycloalkyl, where alkyl may be substituted by 1 to 2 substituents independently of one another selected from the group consisting of trifluoromethyl and $C_3$-$C_6$-cycloalkyl, and where cycloalkyl may be substituted by 1 to 3 substituents independently of one another selected from the group consisting of fluorine, cyano and methyl, or $R^{21}$ and $R^{22}$ together with the nitrogen atom to which they are attached form a 4- to 6-membered heterocyclyl, where heterocyclyl may be substituted by one substituent of methoxymethyl, $R^{23}$ represents hydrogen or methyl, $R^{24}$ represents $C_1$-$C_5$-alkyl or $C_3$-$C_6$-cycloalkyl, where alkyl may be substituted by 1 to 2 substituents independently of one another selected from the group consisting of hydroxy, amino, trifluoromethyl and $C_3$-$C_6$-cycloalkyl, and where cycloalkyl may be substituted by 1 to 3 substituents independently of one another selected from the group consisting of fluorine, trifluoromethyl and methyl, or $R^{23}$ and $R^{24}$ together with the nitrogen atom to which they are attached form a 4- to 6-membered heterocyclyl, where heterocyclyl may be substituted by 1 to 3 substituents independently of one another selected from the group consisting of oxo, chlorine, fluorine, hydroxy, aminocarbonyl, trifluoromethyl and methyl, $R^3$ represents a group of formula

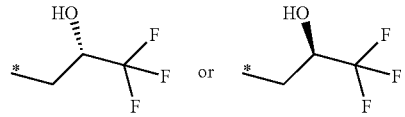

in which

* represents the point of attachment to the 2,4-dihydro-3H-1,2,4-triazolyl-ring, and/or a pharmaceutically acceptable salt thereof, solvate thereof or solvate of a salt thereof.

6. The compound of formula (I) according to claim 1, wherein $R^1$ represents hydrogen, $R^2$ represents a group of the formula

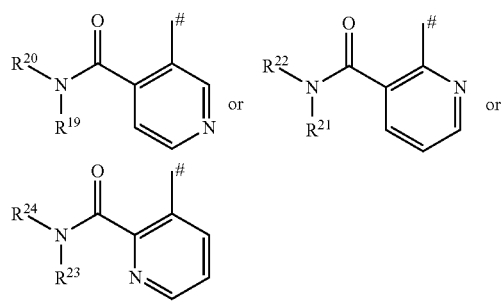

in which # represents the point of attachment to the 1,2,4-triazolyl-ring, $R^{19}$ represents hydrogen, $R^{20}$ represents methyl, ethyl, 2-methyl-prop-1-yl or cyclopropyl, where methyl and ethyl may be substituted by one substituent of trifluoromethyl, and where cyclopropyl may be substituted by 1 to 3 substituents independently of one another selected from the group consisting of fluorine and methyl, or $R^{19}$ and $R^{20}$ together with the nitrogen atom to which they are attached form a pyrrolidinyl, where pyrrolidinyl may be substituted by one substituent of methoxymethyl, $R^{21}$ represents hydrogen, $R^{22}$ represents methyl, ethyl, 2-methyl-prop-1-yl, cyclopropyl, cyclobutyl or cyclopentyl, where methyl and ethyl may be substituted by one substituent from the group consisting of trifluoromethyl and cyclopropyl, and where cyclopropyl and cyclobutyl may be substituted by 1 to 3 substituents independently of one another selected from the group consisting of fluorine, cyano and methyl, or $R^{21}$ and $R^{22}$ together with the nitrogen atom to which they are attached form a pyrrolidinyl, where pyrrolidinyl may be substituted by one substituent of methoxymethyl, $R^{23}$ represents hydrogen or methyl, $R^{24}$ represents represents methyl, ethyl, 2-methyl-prop-1-yl, 2-amino-2-methyl-prop-1-yl, cyclopropyl, cyclobutyl or cyclopentyl, where methyl and ethyl may be substituted by one substituent selected from the group consisting of trifluoromethyl and cyclopropyl, and where cyclopropyl and cyclobutyl may be substituted by 1 to 3 substituents independently of one another selected from the group consisting of fluorine, trifluoromethyl and methyl, or $R^{23}$ and $R^{24}$ together with the nitrogen atom to which they are attached form a pyrrolidinyl, piperidinyl and morpholinyl, where pyrrolidinyl, piperidinyl and morpholinyl may be substituted by 1 to 3 substituents independently of one another selected from the group consisting of fluorine, hydroxyl and methyl, $R^3$ represents a group of formula

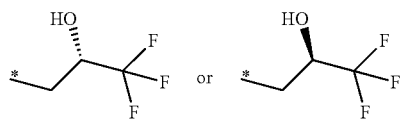

in which
* represents the point of attachment to the 2,4-dihydro-3H-1,2,4-triazolyl-ring, and/or a pharmaceutically acceptable salt thereof, solvate thereof or solvate of a salt thereof.

7. The compound as defined in claim 1 for treatment and/or prevention of one or more diseases.

8. The compound as defined in claim 1 for treatment and/or prevention of acute and chronic kidney disease comprising one or more of diabetic nephropathy, acute and chronic heart failure, preeclampsia, peripheral arterial disease (PAD), coronary microvascular dysfunction (CMD), Raynaud's syndrome, dysmenorrhea, cardiorenal syndrome, hypervolemic and euvolemic hyponatremia, liver cirrhosis, ascites, edema and the syndrome of inadequate ADH secretion (SIADH).

9. The Use of a compound as defined in claim 1 for manufacture of a pharmaceutical composition for treatment and/or prevention of acute and chronic kidney disease comprising one or more of diabetic nephropathy, acute and chronic heart failure, preeclampsia, peripheral arterial disease (PAD), coronary microvascular dysfunction (CMD), Raynaud's syndrome dysmenorrhea, cardiorenal syndrome, hypervolemic and euvolemic hyponatremia, liver cirrhosis, ascites, edema and the syndrome of inadequate ADH secretion (SIADH).

10. Pharmaceutical composition comprising a compound as defined in claim 1 and one or more pharmaceutically acceptable excipients.

11. Pharmaceutical composition of claim 10 comprising one or more first active ingredients, optionally a compound of formula (I), and one or more further active ingredients, optionally one or more additional therapeutic agents selected from the group consisting of diuretics, angiotensin AII antagonists, ACE inhibitors, beta-receptor blockers, mineralocorticoid receptor antagonists, organic nitrates, NO donors, activators and stimulators of the soluble guanylate cyclase, and positive-inotropic agents, antiinflammatory agents, immunosuppressive agents, phosphate binders and/or compounds which modulate vitamin D metabolism.

12. The pharmaceutical composition as defined in claim 10 for treatment and/or prevention of acute and chronic kidney disease comprising one or more of diabetic nephropathy, acute and chronic heart failure, preeclampsia, peripheral arterial disease (PAD), coronary microvascular dysfunction (CMD), Raynaud's syndrome, dysmenorrhea, cardiorenal syndrome, hypervolemic and euvolemic hyponatremia, liver cirrhosis, ascites, edema and the syndrome of inadequate ADH secretion (SIADH).

13. Method for treatment and/or prevention of acute and chronic kidney disease comprising one or more of diabetic nephropathy, acute and chronic heart failure, preeclampsia, peripheral arterial disease (PAD) and coronary microvascular dysfunction (CMD), Raynaud's syndrome dysmenorrhea, cardiorenal syndrome, hypervolemic and euvolemic hyponatremia, liver cirrhosis, ascites, edema and the syndrome of inadequate ADH secretion (SIADH) in a human or other mammal, comprising administering to a human or other mammal in need thereof a therapeutically effective amount of one or more compounds as defined in claim 1, or of a pharmaceutical composition thereof.

* * * * *